(12) United States Patent
Demont et al.

(10) Patent No.: US 7,253,198 B2
(45) Date of Patent: Aug. 7, 2007

(54) HYDROXYETHYLAMINE DERIVATIVES FOR THE TREATMENT OF ALZHEIMER'S DISEASE

(75) Inventors: Emmanuel H Demont, Welwyn (GB); Andrew Faller, Windlesham (GB); David Timothy MacPherson, Harlow (GB); Peter Henry Milner, Harlow (GB); Alan Naylor, Harlow (GB); Sally Redshaw, Welwyn (GB); Steven James Stanway, Harlow (GB); David R Vesey, Welwyn (GB); Daryl S Walter, Welwyn (GB)

(73) Assignee: Glaxo Group Limited, Greenford, Middlesex (GB)

( * ) Notice: Subject to any disclaimer, the term of this patent is extended or adjusted under 35 U.S.C. 154(b) by 237 days.

(21) Appl. No.: 10/536,303

(22) PCT Filed: Dec. 3, 2003

(86) PCT No.: PCT/EP03/13806

§ 371 (c)(1),
(2), (4) Date: May 25, 2005

(87) PCT Pub. No.: WO2004/050619

PCT Pub. Date: Jun. 17, 2004

(65) Prior Publication Data

US 2006/0025459 A1 Feb. 2, 2006

(30) Foreign Application Priority Data

Dec. 5, 2002 (GB) ................. 0228410.7

(51) Int. Cl.
C07D 275/03 (2006.01)
C07D 207/12 (2006.01)
A61K 31/425 (2006.01)
A61K 31/4015 (2006.01)

(52) U.S. Cl. ............... 514/372; 514/424; 548/213; 548/551

(58) Field of Classification Search ................ 548/213, 548/551; 514/372, 424
See application file for complete search history.

(56) References Cited

U.S. PATENT DOCUMENTS

| 5,545,640 A | 8/1996 | Beaulieu et al. |
| 5,811,581 A | 9/1998 | Piva et al. |
| 5,866,100 A | 2/1999 | Tournier et al. |
| 5,968,942 A | 10/1999 | Vazquez et al. |
| 6,248,775 B1 | 6/2001 | Vazquez et al. |
| 2003/0004360 A1 | 1/2003 | Reeder |
| 2004/0171881 A1 | 9/2004 | John et al. |

FOREIGN PATENT DOCUMENTS

| DE | 4109169 C2 | 9/1992 |
| DE | 19817461 A1 | 10/1999 |
| DE | 19818614 A1 | 10/1999 |
| EP | 0663391 B1 | 4/1997 |
| SE | 511087 C2 | 8/1999 |
| SE | 9801901 | 8/1999 |
| WO | 9206691 A1 | 5/1992 |
| WO | 9404492 A1 | 3/1994 |
| WO | 9414478 A1 | 7/1994 |
| WO | 9506030 A1 | 3/1995 |
| WO | 9619437 A1 | 6/1996 |
| WO | 9722365 A1 | 6/1997 |
| WO | 9730788 A1 | 8/1997 |
| WO | 9825883 A1 | 6/1998 |
| WO | 9833795 A1 | 8/1998 |
| WO | 9925686 A1 | 5/1999 |
| WO | 9954305 A1 | 10/1999 |
| WO | 0144213 A1 | 6/2001 |
| WO | 0170672 A2 | 9/2001 |
| WO | 0202505 A2 | 1/2002 |
| WO | 0202512 A2 | 1/2002 |
| WO | 0202518 A2 | 1/2002 |
| WO | WO02/02506 | 1/2002 |
| WO | 03040096 A2 | 5/2003 |

OTHER PUBLICATIONS

Alker et al., Application of Enantiopure Templated Azomethine Ylids to β-Hydroxy-α-amino Acid Synthesis, Tetrahedron 54:6089-6098 (1998).
Berg et al., Acylation of 2,2,2,6,6-Tetramethylpiperidine and 2,2,5,5-Tetramethylpyrrolidine, J. Chem. Soc. C 1654-1658 (1971).
Berge et al., Pharmaceutical Salts, Journal of Pharmaceutical Sciences 66(1):1-19 (1977).
Bertus et al., New and easy route to primary cyclopropylamines from nitriles, Chem. Commun. 16:1792-1973 (2001).
Cai et al., BACE1 is the major β-sectetase for generation of Aβ peptides by neurons, Nature *Neuroscience* 4(3):233-234 (2001).
Connor, Cathepsin D, Handbook of Proteolytic Enzymes pp. 828-836 (1998).
Dalla Croce et al., Stereoselective synthesis of 3-heteroaromatic-substituted alanines, Tetrahedron: *Asymmetry* 11:2635-2642 (2000).
De Strooper et al., A firm base for drug development, Nature 402:471-472 (1999).
Fleisher et al., Improved oral drug delivery: solubility limitation overcome by the use of prodrugs, Advanced Drug Delivery Reviews 19:115-130 (1996).

(Continued)

*Primary Examiner*—Kamal A. Saeed
*Assistant Examiner*—Michael P. Barker
(74) *Attorney, Agent, or Firm*—Bonnie L. Deppenbrock

(57) ABSTRACT

The present invention relates to novel hydroxyethylamine compounds having Asp2 (β-secretase, BACE1 or Memapsin) inhibitory activity, processes for their preparation, to compositions containing them and to their use in the treatment of diseases characterised by elevated β-amyloid levels or β-amyloid deposits, particularly Alzheimer's disease.

16 Claims, No Drawings

OTHER PUBLICATIONS

Greene et al., The Role of Protective Groups in Organic Synthesis, Protective Groups in Organic Synthesis, 3rd ed., 1-16 (1999).

Higuchi et al., Pro-drugs as Novel Drug Delivery Systems, ACS Symposium Series 14, American Chemical Society pp. 14-15 (1975).

Jacquier et al., Bulletin de la Societe Chimique de France (Mousseron) 596600 (1957) (FR).

Koelsch, A Synthesis of 3-Phenylpiperidines, J. of Am. Chem. Soc. 65:2093-2095 (1943).

Luo et al., Mice deficient in BACE1, the Alzheimer's β-secretase, have normal phenotype and abolished β-amyloid generation, Nature Neuroscience 4(3):231-232 (2001).

Kerins et al., Generation of Substituted Styrenes via Suzuki Cross-Coupling of Aryl Halides with 2,4,6-Trivinylcyclotriboroxane, J. Org. Chem. 67:4968-4971 (2002).

Morris et al., Vinyl Sulfonyl Esters and Amides in the Synthesis of Substituted δ-Sultams and δ-Sultones, J. Org. Chem. 56:3549-3556 (1991).

Roberds et al., BACE knockout mice are healthy despite lacking the primary β-secretase activity in brain: implications for Alzheimer's disease therapeutics, Human Molecular Genetics 10(12):1317-1324 (2001).

Naslund et al., Correlation Between Elevated Levels of Amyloid β-Peptide in the Brain and Cognitive Decline, JAMA 283(12):1571-1577 (2000).

Selkoe, Alzheimer's Disease: Genes, Proteins, and Therapy, Physiological Reviews 81(2):741-766 (2001).

Tani et al., Development of a Highly Selective EP2-Receptor Agonist. Part 1: Identification of 16-hydroxy-17,17-trimethylene $PGE_2$ Derivatives, Bioorganic & Medicinal Chemistry 10:1093-1106 (2002).

Tsuri et al., A Novel Class of Platelet Activating Factor (PAF) Antagonists. I. Synthesis and Structure-Activity Studies on PAF-Sulfonamide Isosteres, Chem Pharm. Bull. 40(1):75-84 (1992).

Vassar et al., Aβ-Generating Enzymes: Recent Advances in β- and γ-Secretase Research, Neuron 27:419-422 (2000).

Younkin, Amyloid β vaccination: reduced plaques and improved cognition, Nature Medicine 7(1):18-19 (2001).

HYDROXYETHYLAMINE DERIVATIVES FOR THE TREATMENT OF ALZHEIMER'S DISEASE

CROSS-REFERENCE TO RELATED APPLICATIONS

This application is filed pursuant to 35 U.S.C. § 371 as a United States National Phase Application of International Application No. PCT/EP2003/013806 filed Dec. 3, 2003, which claims priority from GB0228410.7 filed Dec. 5, 2002.

FIELD OF THE INVENTION

The present invention relates to novel hydroxyethylamine compounds having Asp2 (β-secretase, BACE1 or Memapsin) inhibitory activity, processes for their preparation, to compositions containing them and to their use in the treatment of diseases characterised by elevated β-amyloid levels or β-amyloid deposits, particularly Alzheimer's disease.

BACKGROUND OF THE INVENTION

Alzheimer's disease is a degenerative brain disorder in which extracellular deposition of Aβ in the form of senile plaques represents a key pathological hallmark of the disease (Selkoe, D. J. (2001) Physiological Reviews 81: 741-766). The presence of senile plaques is accompanied by a prominent inflammatory response and neuronal loss. β-amyloid (Aβ) exists in soluble and insoluble, fibrillar forms and a specific fibrillar form has been identified as the predominant neurotoxic species (Vassar, R. and Citron, M. (2000) Neuron 27: 419422). In addition it has been reported that dementia correlates more closely with the levels of soluble amyloid rather than plaque burden (Naslund, J. et al., (2000) J. Am. Med. Assoc. 12: 1571-1577; Younkin, S. (2001) Nat. Med. 1: 8-19). AP is known to be produced through the cleavage of the beta amyloid precursor protein (also known as APP) by an aspartyl protease enzyme known as Asp2 (also known as 13-secretase, BACE1 or Memapsin) (De Strooper, B. and Konig, G. (1999) Nature 402: 471-472).

Therefore, it has been proposed that inhibition of the Asp2 enzyme would reduce the level of APP processing and consequently reduce the levels of Aβ peptides found within the brain. Therefore, it is also thought that inhibition of the Asp2 enzyme would be an effective therapeutic target in the treatment of Alzheimer's disease.

APP is cleaved by a variety of proteolytic enzymes (De Strooper, B. and Konig, G. (1999) Nature 402: 471-472). The key enzymes in the amyloidogenic pathway are Asp2 (β-secretase) and γ-secretase both of which are aspartic proteinases and cleavage of APP by these enzymes generates Aβ. The non-amyloidogenic, α-secretase pathway, which precludes Aβ formation, has been shown to be catalysed by a number of proteinases, the best candidate being ADAM10, a disintegrin and metalloproteinase. Asp1 has been claimed to show both α- and β-secretase activity in vitro. The pattern of expression of Asp1 and Asp2 are quite different, Asp2 is most highly expressed in the pancreas and brain while Asp1 expression occurs in many other peripheral tissues. The Asp2 knockout mouse indicates that lack of Asp2 abolished Aβ production and also shows that in this animal model endogenous Asp1 cannot substitute for the Asp2 deficiency (Luo, Y. et al. (2001) Nat Neurosci. 4: 231-232; Cai, H. et. al. (2001) Nat Neurosci. 4: 233-234; Roberds, S. L. et al. (2001) Hum. Mol. Genet. 10: 1317-1324).

For an agent to be therapeutically useful in the treatment of Alzheimer's disease it is preferable that said agent is a potent inhibitor of the Asp2 enzyme, but should ideally also be selective for Asp2 over other enzymes of the aspartyl proteinase family, e.g Cathepsin D (Connor, G. E. (1998) Cathepsin D in Handbook of Proteolytic Enzymes, Barrett, A. J., Rawlings, N. D., & Woesner, J. F. (Eds) Academic Press London. pp 828-836).

WO 01/70672, WO 02/02512, WO 02/02505, WO 02/02506 and WO 03/040096 (Elan Pharmaceuticals Inc.) describe a series of hydroxyethylamine compounds having β-secretase activity which are implicated to be useful in the treatment of Alzheimer's disease.

SUMMARY OF THE INVENTION

We have found a novel series of compounds which are potent inhibitors of the Asp2 enzyme, thereby indicating the potential for these compounds to be effective in the treatment of Alzheimer's disease.

Thus, according to a first aspect of the present invention we provide a compound of formula (I):

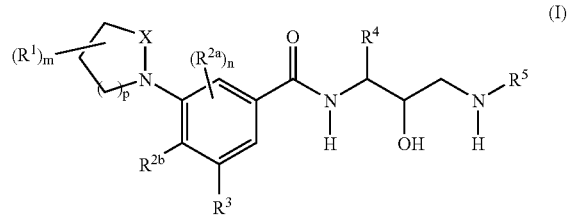

wherein $R^1$ represents $C_{1-6}$ alkyl, $C_{2-6}$ alkenyl, halogen, $C_{-1-6}$ alkoxy, amino, cyano, hydroxy, aryl, heteroaryl or heterocyclyl;

$R^{2a}$ represents hydrogen, $C_{1-3}$ alkyl, $C_{1-3}$ alkoxy or halogen;

m and n independently represent 0, 1 or 2;

X represents CO, SO or $SO_2$;

p represents an integer from 1 to 3;

$R^{2b}$ represents hydrogen, $C_{1-6}$ alkyl, $C_{2-6}$ alkenyl, halogen, $C_{1-6}$ alkoxy, amino, cyano, hydroxy, aryl, heteroaryl or heterocyclyl;

$R^3$ represents halogen, $C_{1-6}$ alkyl, $C_{2-6}$ alkenyl, aryl, heteroaryl, heterocyclyl, —$C_{1-6}$ alkyl-aryl, —$C_{1-6}$ alkyl-heteroaryl, —$C_{1-6}$ alkyl-heterocyclyl, —$C_{2-6}$ alkenyl-aryl, —$C_{2-6}$ alkenyl-heteroaryl, —$C_{2-6}$ alkenyl-heterocyclyl, $C_{3-8}$ cycloalkyl, —$C_{1-6}$ alkyl-$C_{3-8}$ cycloalkyl, cyano, azido, nitro, —$NR^7R^8$, —$NR^9COR^{10}$, —$NR^{11}SO_2R^{12}$, —$OR^{13}$, —$SO_2R^{14}$, —$SR^{15}$, —$C\equiv CR^{16}$, —$C_{1-6}$ alkyl-$(CF_2)_qCF_3$, —$CONR^{17}R^{18}$, $COOR^{19}$, —$C_{1-6}$ alkyl-$NR^{20}R^{21}$ or —$C_{1-6}$ alkyl-$N_3$, or $R^3$ and $R^{2b}$ together with the phenyl group to which they are attached form a naphthyl or benzofused heterocyclic or heteroaryl ring optionally substituted by one or two $C_{1-6}$ alkyl groups;

$R^4$ represents —$C_{2-6}$ alkynyl, —$C_{1-6}$ alkyl-aryl, —$C_{1-6}$ alkyl-heteroaryl or —$C_{1-6}$ alkyl-heterocyclyl;

$R^5$ represents hydrogen, —$C_{1-10}$ alkyl, —$C_{3-10}$ cycloalkyl, —$C_{3-10}$ cycloalkenyl, aryl, heteroaryl, heterocyclyl, —$C_{1-6}$ alkyl-$C_{3-10}$ cycloalkyl, —$C_{3-10}$ cycloalkyl-$C_{1-10}$ alkyl, —$C_{3-10}$ cycloalkyl-$C_{1-6}$ alkyl-aryl, —$C_{3-10}$ cycloalkyl-aryl, —$C_{1-6}$ alkyl-aryl-heteroaryl, —$C(R^cR^b)$—CONH—$C_{1-6}$ alkyl, —$C(R^cR^d)$—CONH—$C_{3-10}$ cycloalkyl, —$C_{1-6}$ alkyl-S—$C_{1-6}$ alkyl, —$C_{1-6}$ alkyl-$NR^eR^f$, —$C_{1-6}$ alkyl-aryl, —$C_{1-6}$ alkyl-heteroaryl, —$C_{1-6}$alkyl-heterocyclyl —$C_{1-6}$ alkyl-$C_{1-6}$alkoxy-aryl, —$C_{1-6}$ alkyl-$C_{1-6}$ alkoxy-heteroaryl or —$C_{1-6}$alkyl-$C_{1-6}$ alkoxy-heterocyclyl;

$R^7$, $R^8$, $R^9$, $R^{10}$, $R^{13}$, $R^{14}$, $R^{15}$, $R^{16}$, $R^{17}$, $R^{18}$, $R^{19}$, $R^{20}$ and $R^{21}$ independently represent hydrogen, $C_{1-6}$ alkyl, $C_{2-6}$ alkenyl, $C_{3-8}$ cycloalkyl, aryl, heteroaryl, heterocyclyl, —$C_{1-6}$ alkyl-$C_{3-8}$ cycloalkyl, —$C_{1-6}$ alkyl-aryl, —$C_{1-6}$ alkyl-heteroaryl, —$C_{1-6}$ alkyl-heterocyclyl or —CO—$C_{1-6}$ alkyl;

$R^{11}$, $R^{12}$, $R^a$, $R^c$, $R^e$ and $R^f$ independently represent hydrogen, $C_{1-6}$ alkyl or $C_{3-8}$ cycloalkyl;

$R^b$ and $R^d$ independently represent hydrogen, $C_{1-6}$ alkyl, $C_{3-8}$ cycloalkyl or —$C_{1-6}$ alkyl-$SO_2$—$C_{1-6}$ alkyl;

q represents 1 to 3;

wherein said alkyl groups may be optionally substituted by one or more (eg. 1, 2 or 3) halogen, $C_{1-6}$ alkyl, $C_{1-6}$ alkoxy, $C_{2-6}$ alkenoxy, $C_{3-8}$ cycloalkyl, amino, cyano or hydroxy groups;

and wherein said cycloalkyl, aryl, heteroaryl or heterocyclyl groups may be optionally substituted by one or more (eg. 1, 2 or 3) $C_{1-6}$ alkyl, $C_{2-6}$ alkenyl, $C_{2-6}$ alkynyl, halogen, halo$C_{1-6}$ alkyl, —$OCF_3$, oxo, $C_{1-6}$ alkoxy, —$C_{1-6}$ alkoxy-CN, amino, cyano, nitro, —$NR^{22}COR^{23}$, —$CONR^{22}R^{23}$, —$COOR^{22}$, —$SO_2R^{22}$, —$C_{1-6}$ alkyl-$NR^{22}R^{23}$ (wherein $R^{22}$ and $R^{23}$ independently represent hydrogen or $C_{1-6}$ alkyl), —$C_{1-6}$ alkyl-$C_{1-6}$ alkoxy, —$C_{1-6}$ alkanol or hydroxy groups;

or a pharmaceutically acceptable salt or solvate thereof.

In one particular aspect of the present invention, there is provided a compound of formula (I) as defined above wherein:

X represents CO or $SO_2$; and $R^{2a}$ represents hydrogen, $C_{1-3}$ alkyl or halogen; and $R^3$ and $R^{2b}$ together with the phenyl group which they are attached form an unsubstituted benzofused heterocyclic or heteroaryl ring; and $R^4$ represents —$C_{1-6}$ alkyl-aryl, —$C_{1-6}$ alkyl-heteroaryl or —$C_{1-6}$ alkyl-heterocyclyl; and $R^5$ represents hydrogen, —$C_{1-10}$ alkyl, —$C_{3-8}$ cycloalkyl, —$C_{3-8}$ cycloalkenyl, aryl, heteroaryl, heterocyclyl, —$C_{1-6}$ alkyl-$C_{3-8}$ cycloalkyl, —$C_{1-6}$ alkyl-aryl-heteroaryl, —$C(R_cR^b)$—CONH—$C_{1-6}$ alkyl, —$C(R_cR^d)$—CONH—$C_{3-8}$ cycloalkyl, —$C_{1-6}$ alkyl-S—$C_{1-6}$ alkyl, —$C_{1-6}$ alkyl-$NR^eR^f$, —$C_{1-6}$ alkyl-aryl, —$C_{1-6}$ alkyl-heteroaryl, —$C_{1-6}$ alkyl-heterocyclyl —$C_{1-6}$ alkyl-$C_{1-6}$ alkoxy-aryl, —$C_{1-6}$ alkyl-$C_{1-6}$ alkoxy-heteroaryl or —$C_{1-6}$ alkyl-$C_{1-6}$ alkoxy-heterocyclyl; and said alkyl groups may be optionally substituted by one or more (eg. 1, 2 or 3) halogen, $C_{1-6}$ alkoxy, amino, cyano or hydroxy groups; and wherein said aryl, heteroaryl or heterocyclyl groups may be optionally substituted by one or more (eg. 1, 2 or 3) $C_{1-6}$ alkyl, halogen, —$OCF_3$, oxo, $C_{1-6}$ alkoxy, amino, cyano, nitro, —$NR^{22}COR^{23}$, —$C_{1-6}$ alkyl-$NR^{22}R^{23}$ (wherein $R^{22}$ and $R^{23}$ independently represent hydrogen or $C_{1-6}$ alkyl), —$C_{1-6}$ alkyl-$C_{1-6}$ alkoxy, —$C_{1-6}$ alkanol or hydroxy groups.

DETAILED DESCRIPTION

References to alkyl include references to both straight chain and branched chain aliphatic isomers of the corresponding alkyl. It will be appreciated that references to alkenyl and alkenoxy shall be interpreted similarly. It will also be appreciated that when an alkenyl or alkenoxy group is attached to an O, N or S atom the double bond is not at the alpha position relative to said O, N or S atom.

References to cycloalkyl include references to all alicyclic (including branched) isomers of the corresponding alkyl. When a cycloalkyl group is substituted by two or more $C_{1-6}$ alkyl groups, said cycloalkyl groups together with any two alkyl groups may form a bridged cycloalkyl group which includes bicycloheptyl, adamantyl, bicyclo-octyl and the like.

References to 'aryl' include references to monocyclic carbocyclic aromatic rings (eg. phenyl) and bicyclic carbocyclic aromatic rings (e.g. naphthyl) or carbocyclic benzofused rings (eg. $C_{3-8}$ cycloalkyl fused to a phenyl ring, such as dihydroindenyl or tetrahydronaphthalenyl).

References to 'heteroaryl' include references to mono- and bicyclic heterocyclic aromatic rings containing 1-4 hetero atoms selected from nitrogen, oxygen and sulphur. Examples of monocyclic heterocyclic aromatic rings include e.g. thienyl, furyl, pyrrolyl, triazolyl, imidazolyl, oxazolyl, thiazolyl, oxadiazolyl, isothiazolyl, isoxazolyl, thiadiazolyl, pyrazolyl, pyrimidyl, pyridazinyl, pyrazinyl, pyridyl, tetrazolyl and the like. Examples of bicyclic heterocyclic aromatic rings include eg. quinolinyl, isoquinolinyl, quinazolinyl, quinoxalinyl, cinnolinyl, naphthyridinyl, indolyl, indazolyl, pyrrolopyridinyl, benzofuranyl, benzothienyl, benzimidazolyl, benzoxazolyl, benzisoxazolyl, benzothiazolyl, benzisothiazolyl, benzoxadiazolyl, benzothiadiazolyl and the like.

References to 'heterocyclyl' include references to a 5-7 membered non-aromatic monocyclic ring containing 1 to 3 heteroatoms selected from nitrogen, sulphur or oxygen. Examples of heterocyclic non-aromatic rings include e.g. morpholinyl, piperidinyl, piperazinyl, thiomorpholinyl, oxathianyl, dithianyl, dioxanyl, pyrrolidinyl, dioxolanyl, oxathiolanyl, imidazolidinyl, pyrazolidinyl and the like.

References to 'benzofused heterocyclyl or heteroaryl ring' include quinolinyl, isoquinolinyl, indolyl, indazolyl, dihydroindolyl, benzofuranyl, benzothienyl, benzimidazolyl, benzoxazolyl, benzisoxazolyl, benzothiazolyl, benzisothiazolyl, benzoxadiazolyl, benzothiadiazolyl, dihydrochromene, benzotriazolyl, tetrahydroquinoxalinyl and the like.

Preferably, m is 0 or 1, preferably 0. When m represents 1, $R^1$ is preferably aryl (eg. phenyl).

Preferably, n is 0 or 1, more preferably 1.

When n represents 1, $R^{2a}$ is preferably $C_{1-3}$ alkoxy (eg. methoxy) or halogen (eg. fluorine), more preferably halogen (eg. fluorine).

When n represents 1, $R^{2a}$ is preferably in the ortho position of the phenyl ring.

When X represents $SO_2$, p is preferably 2 or 3, more preferably 2 and when X represents CO, p is preferably 1 or 2, more preferably 1.

Preferably, $R^{2b}$ is:

hydrogen;

halogen (eg. chlorine or fluorine);

$C_{1-6}$ alkyl (eg. methyl);

$C_{1-6}$alkoxy (eg. methoxy); or heterocyclyl (eg. pyrrolidinyl) optionally substituted by an oxo group (eg. 2-oxopyrrolidin-1-yl).

More preferably, $R^{2b}$ is hydrogen or halogen (eg. fluorine), most preferably hydrogen.

Preferably, $R^3$ represents:

$C_{1-6}$ alkyl (eg. methyl, ethyl, n-propyl, i-propyl, n-butyl, i-butyl, sec-butyl or t-butyl) optionally substituted by one or more (eg. 1, 2 or 3) hydroxy, halogen (eg. fluorine) or $C_{1-6}$ alkoxy groups (eg. methoxy or ethoxy);

$C_{2-6}$ alkenyl (eg. propenyl);

$C_{3-8}$ cycloalkyl (eg. cyclopentyl or cyclohexyl);

cyano;

heterocyclyl (eg. piperidinyl, pyrrolidinyl or isothiazolidinyl) optionally substituted by one or two oxo groups;

—$NR^7R^8$;

—$OR^{13}$;

—$SR^{15}$; or

—$CONR^{17}R^{18}$.

Also preferably, $R^3$ and $R^{2b}$ together with the phenyl group which they are attached represent indolyl, indazolyl, dihydroindolyl, benzofuranyl, dihydrochromenyl, benzotriazolyl, benzimidazolyl or tetrahydroquinoxalinyl, optionally substituted by one or two $C_{1-6}$ alkyl (eg. methyl, ethyl, n-propyl, i-propyl, n-butyl, i-butyl, sec-butyl, t-butyl or pentyl) groups. More preferably $R^3$ and $R^{2b}$ together with the phenyl group which they are attached represent benzimidazolyl or indolyl substituted by a $C_{1-6}$ alkyl group (eg. ethyl).

More preferably, $R^3$ represents:

$C_{1-6}$ alkyl (eg. n-propyl);

—$NR^7R^8$;

$C_{3-8}$ cycloalkyl (eg. cyclopentyl or cyclohexyl);

—$OR^{13}$; or

—$CONR^{17}R^{18}$.

Preferably, $R^7$ and $R^8$ independently represent:

hydrogen;

$C_{1-6}$ alkyl (eg. methyl, ethyl, n-propyl, i-propyl, n-butyl, i-butyl, sec-butyl, t-butyl, pentyl, i-propyl, i-butyl, —$CH_2C(CH_3)_3$, —$CH(CH_2CH_3)CH_2CH_3$ or —$(CH_2)_2CH(CH_3)_2$);

$C_{3-8}$ cycloalkyl (eg. cyclopentyl or cyclohexyl);

aryl (eg. phenyl);

—$C_{1-6}$ alkyl-$C_{3-8}$ cycloalkyl (eg. —$CH_2$-cyclopropyl);

—$C_{1-6}$ alkyl-aryl (eg. —$CH_2$-phenyl or —$(CH_2)_2$-phenyl); or

—CO—$C_{1-6}$ alkyl (eg. —$COCH_3$).

More preferably, $R^7$ represents hydrogen and $R^8$ represents $C_{1-6}$ alkyl (particularly ethyl or isopropyl, especially ethyl).

Preferably, $R^{13}$ represents $C_{1-6}$ alkyl (eg. methyl, ethyl, n-propyl, i-propyl, n-butyl, i-butyl, sec-butyl or t-butyl or pentyl) optionally substituted by a hydroxy or $C_{1-6}$ alkoxy (eg. methoxy) group, more preferably $R^{13}$ represents ethyl or i-propyl.

Preferably, $R^{15}$ represents $C_{1-6}$ alkyl (eg. methyl or ethyl).

Preferably, $R^{17}$ and $R^{18}$ both represent $C_{1-6}$ alkyl (eg. both represent propyl or one represents propyl and the other represents methyl).

Preferably, $R^4$ represents —$C_{1-6}$ alkyl-aryl (eg. benzyl) or —$C_{1-6}$ alkyl-heteroaryl (eg. —$CH_2$-pyridinyl, —$CH_2$-thiazolyl, —$CH_2$-furanyl, —$CH_2$-thienyl or —$CH_2$-pyrazolyl) optionally substituted by one or two halogen atoms (eg. chlorine or fluorine). More preferably, $R^4$ represents —$C_{1-6}$ alkyl-aryl (eg. benzyl) optionally substituted by one or two halogen atoms (eg. chlorine or fluorine), most preferably $R^4$ represents unsubstituted benzyl.

Preferably, $R^5$ represents

—$C_{1-10}$ alkyl (eg. methyl, ethyl, n-propyl, n-butyl, n-pentyl or n-hexyl) optionally substituted by one or more $C_{1-6}$ alkyl (eg. methyl), $C_{1-6}$ alkoxy (eg. methoxy or —$OCH_2CH(CH_3)_2$) or $C_{2-6}$ alkenoxy (eg. —$OCH_2C(CH_3)=CH_2$) groups;

—$C_{3-10}$ cycloalkyl (eg. cyclopropyl, cyclobutyl, cyclopentyl, cyclohexyl, cycloheptyl, bicycloheptyl, adamantyl or bicyclo-octyl) optionally substituted by one or more $C_{1-6}$ alkyl (eg. methyl, ethyl or propyl) or halogen (eg. fluorine) groups;

—$C_{1-6}$ alkyl-$C_{3-10}$ cycloalkyl (eg. —$CH_2$-cyclohexyl or —$CH_2$-cyclopropyl);

-aryl (eg. phenyl, dihydroindenyl or tetrahydronaphthalenyl) optionally substituted by one or more hydroxy or $C_{1-6}$ alkoxy (eg. methoxy) groups;

—$C_{1-6}$ alkyl-aryl (eg. benzyl, -ethyl-phenyl, -ethyl-naphthyl, -propyl-phenyl, —C(H)(Me)-phenyl, —C(H)(Et)-phenyl —C(Me)(Me)-benzyl or —C(Me)(Me)-phenyl) optionally substituted by one or more halogen (eg. chlorine, bromine or fluorine), hydroxy, —$OCF_3$, halo$C_{1-6}$ alkyl (eg. —$CH_2CF_3$ or —$CF_3$), $C_{1-6}$ alkyl (eg. methyl, ethyl, n-propyl, i-propyl, n-butyl, i-butyl, sec-butyl or t-butyl), $C_{2-6}$ alkenyl (eg. ethenyl), $C_{2-6}$ alkynyl, $C_{1-6}$ alkoxy (eg. methoxy, ethoxy, propoxy, isopropoxy or methylethoxy), cyano, nitro, —$COOR^{22}$ (eg. COOH or COOMe), —$SO_2R^{22}$ (eg. —$SO_2Me$), —$NR^{22}COR^{23}$ (eg. $NHCOCH_3$), —$C_{1-6}$ alkyl-$NR^{22}R^{23}$ (eg. —$CH_2N(CH_3)_2$), —$C_{1-6}$ alkyl-$C_{1-6}$ alkoxy (eg. —$CH_2OC(CH_3)_3$), —$C_{1-6}$ alkanol (eg. —$CH_2OH$) or —$C_{1-6}$ alkoxy-CN (eg. $OCH_2CN$) groups;

—$C_{1-6}$ alkyl-heteroaryl (eg. —$CH_2$-furanyl, —$CH_2$-quinolinyl, —$CH_2$-thiophenyl, —$CH_2$-indolyl, —$CH_2$-benzoimidazolyl, —$CH_2$-imidazolyl, —$CH_2$-benzofuranyl, —$CH_2$-thiazolyl, —$CH_2$-pyridinyl, —$CH_2$-benzothiazolyl, —$CH_2$-pyrazolyl, —$CH_2$-isoxazolyl, —$CH_2$-oxazolyl, —$CH_2$-pyrrolyl, —$CH_2$-dihydrobenzofuranyl, —$CH_2$-dihydrobenzodioxinyl or —$CH_2$-dihydrochromenyl) optionally substituted by one or more $C_{1-6}$ alkyl (eg. methyl, ethyl, n-propyl, i-propyl, n-butyl, i-butyl, sec-butyl or t-butyl), $C_{2-6}$ alkenyl (eg. ethenyl or propenyl), $C_{2-6}$ alkynyl, halogen (eg. bromine or chlorine), halo$C_{1-6}$ alkyl (eg. fluoroethyl or trifluoroethyl), cyano, $C_{1-6}$ alkoxy (eg. methoxy), —$CONR^{22}R^{23}$ (eg. —CONHMe) or —$COOR^{22}$ (eg. —COOMe) groups;

-heterocyclyl (eg. tetrahydropyranyl or tetrahydrothiopyranyl);

—$C_{1-6}$ alkyl-heterocyclyl (eg. —$CH_2$-tetrahydropyranyl);

—$C_{3-10}$ cycloalkyl-$C_{1-10}$ alkyl (eg. -cyclobutyl-isopropyl, -cyclobutyl-ethyl, -cyclobutyl-propyl, -cyclopropyl-ethyl, -cyclopropyl-propyl, -cyclopropyl-isopropyl, -cyclopropyl-t-butyl, -cyclopropyl-$CH_2CH(CH_3)_2$, -cyclopropyl-$(CH_2)_2CH(CH_3)_2$, -cyclopropyl-$(CH_2)_2CH(CH_3)_2$ or -cyclopropyl-$(CH_2)_3CH(CH_3)_2$);

—$C_{3-10}$ cycloalkyl-$C_{1-6}$ alkyl-aryl (eg. -cyclopropyl-$CH_2$-phenyl) optionally substituted by one or more halogen (eg. chlorine) atoms;

—$C_{3-10}$ cycloalkyl-aryl (eg. -cyclopropyl-phenyl) optionally substituted by one or more halogen (eg. chlorine, bromine or fluorine), hydroxy, —$OCF_3$, halo$C_{1-6}$ alkyl (eg. —$CH_2CF_3$ or —$CF_3$), $C_{1-6}$ alkyl (eg. methyl, ethyl, n-propyl, i-propyl, n-butyl, i-butyl, sec-butyl or t-butyl), $C_{2-6}$ alkenyl (eg. ethenyl), $C_{2-6}$ alkynyl, $C_{1-6}$ alkoxy (eg. methoxy, ethoxy, propoxy, isopropoxy or methylethoxy), cyano, nitro, —$COOR^{22}$ (eg. COOH or COOMe), —$SO_2R^{22}$ (eg. —$SO_2Me$), —$NR^{22}COR^{23}$ (eg. $NHCOCH_3$), —$C_{1-6}$ alkyl-$NR^{22}R^{23}$ (eg. —$CH_2N(CH_3)_2$), —$C_{1-6}$ alkyl-$C_{1-6}$ alkoxy (eg. —$CH_2OC(CH_3)_3$), —$C_{1-6}$ alkanol (eg. —$CH_2OH$) or —$C_{1-6}$ alkoxy-CN (eg. $OCH_2CN$) groups;

—$C(R^aR^b)$—CONH—$C_{1-6}$ alkyl (eg. —$C(R^aR^b)$—CONH-i-butyl);

—C(R$^c$R$^d$)—CONH—C$_{3-10}$ cycloalkyl (eg. C(R$^c$R$^d$)—CONH-cyclohexyl);

—C$_{1-6}$ alkyl-S—C$_{1-6}$ alkyl (eg. -propyl-5-methyl or -dimethylethyl-5-isobutyl); or —C$_{1-6}$ alkyl-NR$^e$R$^f$ (eg. -dimethylpropyl-NR$^e$R$^f$).

More preferably R$^5$ represents:

—C$_{3-10}$ cycloalkyl (eg. cyclohexyl);

—C$_{1-6}$ alkyl-aryl (eg. benzyl) optionally substituted by one or more halogen (eg. chlorine, bromine or fluorine), —OCF$_3$ or haloC$_{1-6}$ alkyl (eg. —CF$_3$) groups;

—C$_{1-6}$ alkyl-heteroaryl (eg. —CH$_2$-thienyl, —CH$_2$-pyrazolyl or —CH$_2$-isoxazolyl) optionally substituted by one or more C$_{1-6}$ alkyl (eg. methyl, ethyl, isopropyl, propyl or butyl) or haloC$_{1-6}$ alkyl (eg. CH$_2$CF$_3$) groups; or -heterocyclyl (eg. tetrahydropyranyl).

Preferably, q represents 1 or 2.

Preferably, R$^a$ represents hydrogen or C$_{1-6}$ alkyl (methyl).

Preferably, R$^b$ and R$^d$ independently represent C$_{1-6}$ alkyl (eg. methyl, ethyl, propyl or butyl) or —C$_{1-6}$ alkyl-SO$_2$—C$_{1-6}$ alkyl (eg. —CH$_2$CH$_2$SO$_2$CH$_3$) optionally substituted by one or more hydroxy groups.

Preferably, R$^c$ represents hydrogen or C$_{1-6}$ alkyl (methyl).

Preferably, R$^e$ and R$^f$ both represent C$_{1-6}$ alkyl (eg. methyl).

Preferred compounds according to the invention includes examples E1-E744 as shown below, or a pharmaceutically acceptable salt thereof.

More preferred compounds according to the invention include:

formic acid-5-cyclopentyl-3-(1,1-dioxidotetrahydro-2H-1,2-thiazin-2-yl)-N-[(1S,2R)-3-{[(1-ethyl-1H-pyrazol-4-yl)methyl]amino}-2-hydroxy-1-(phenylmethyl)propyl]-2-fluorobenzamide (1:1);

formic acid-3-(1,1-dioxidotetrahydro-2H-1,2-thiazin-2-yl)-2-fluoro-N-[(1S,2R)-2-hydroxy-1-(phenylmethyl)-3-({[3-(trifluoromethyl)phenyl]methyl}amino)propyl]-5-[(1-methylethyl)amino]benzamide (1:1);

formic acid-3-(1,1-dioxidotetrahydro-2H-1,2-thiazin-2-yl)-N-[(1S,2R)-3-{[(1-ethyl-1H-pyrazol-4-yl)methyl]amino}-2-hydroxy-1-(phenylmethyl)propyl]-2-fluoro-5-[(1-methylethyl)amino]benzamide (1:1);

formic acid-3-(1,1-dioxidotetrahydro-2H-1,2-thiazin-2-yl)-2-fluoro-N-[(1S,2R)-2-hydroxy-1-(phenylmethyl)-3-[({3-[(trifluoromethyl)oxy]phenyl}methyl)amino]propyl}-5-[(1-methylethyl)amino]benzamide (1:1);

formic acid-N-((1S,2R)-1-benzyl-3-{[4-fluoro-3-(trifluoromethyl)benzyl] amino}-2-hydroxypropyl)-3-(1,1-dioxido-1,2-thiazinan-2-yl)-5-(ethylamino)-2-fluorobenzamide (1:1);

3-(1,1-dioxidotetrahydro-2H-1,2-thiazin-2-yl)-5-(ethylamino)-2-fluoro-N-[(1S,2R)-2-hydroxy-1-(phenylmethyl)-3-({[3-(trifluoromethyl)phenyl] methyl}amino) propyl] benzamide;

formic acid-3-(1,1-dioxidotetrahydro-2H-1,2-thiazin-2-yl)-5-(ethylamino)-N-[(1S,2R)-3-{[(5-ethyl-3-thienyl)methyl]amino}-2-hydroxy-1-(phenylmethyl)propyl] benzamide (1:1); and formic acid-3-(1,1-dioxidotetrahydro-2H-1,2-thiazin-2-yl)-5-(ethylamino)-2-fluoro-N-{(1S,2R)-2-hydroxy-1-(phenylmethyl)-3-[({3-[(trifluoromethyl)oxy] phenyl}methyl)amino]propyl}benzamide (1:1)

or a pharmaceutically acceptable salt thereof.

The compounds of formula (I) can form acid addition salts thereof. It will be appreciated that for use in medicine the salts of the compounds of formula (I) should be pharmaceutically acceptable. Suitable pharmaceutically acceptable salts will be apparent to those skilled in the art and include those described in J. Pharm. Sci., 1977, 66, 1-19, such as acid addition salts formed with inorganic or organic acids e.g. hydrochlorides, hydrobromides, sulphates, phosphates, acetates, benzoates, citrates, nitrates, succinates, lactates, tartrates, fumarates, maleates, 1-hydroxy-2-naphthoates, palmoates, methanesulphonates, p-toluenesulphonates, naphthalenesulphonates, formates or trifluoroacetates. The present invention includes within its scope all possible stoichiometric and non-stoichiometric forms.

The present invention also includes within its scope prodrugs of compounds of formula (I). As used herein, the term "prodrug" means a compound which is converted within the body, e.g. by hydrolysis in the blood, into its active form that has medical effects. Pharmaceutically acceptable prodrugs are described in T. Higuchi and V. Stella, Prodrugs as Novel Delivery Systems, Vol. 14 of the A.C.S. Symposium Series, Edward B. Roche, ed., Bioreversible Carriers in Drug Design, American Pharmaceutical Association and Pergamon Press, 1987, and in D. Fleisher, S. Ramon and H. Barbra "Improved oral drug delivery: solubility limitations overcome by the use of prodrugs", Advanced Drug Delivery Reviews (1996) 19(2) 115-130, each of which are incorporated herein by reference. Esters may be active in their own right and/or be hydrolysable under in vivo conditions in the human body. Suitable pharmaceutically acceptable in vivo hydrolysable ester groups include those which break down readily in the human body to leave the parent acid or its salt.

The compounds of formula (I) may be prepared in crystalline or non-crystalline form, and, if crystalline, may optionally be solvated, eg. as the hydrate. This invention includes within its scope stoichiometric solvates (eg. hydrates) as well as compounds containing variable amounts of solvent (eg. water).

Certain compounds of formula (I) are capable of existing in stereoisomeric forms (e.g. diastereomers and enantiomers) and the invention extends to each of these stereoisomeric forms and to mixtures thereof including racemates. The different stereoisomeric forms may be separated one from the other by the usual methods, or any given isomer may be obtained by stereospecific or asymmetric synthesis. The invention also extends to any tautomeric forms and mixtures thereof. Preferably, compounds of formula (I) are in the form of a single enantiomer of formula (Ia):

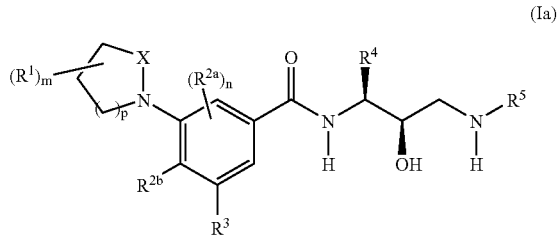

(Ia)

The compounds of formula (I) and salts and solvates thereof may be prepared by the methodology described hereinafter, constituting a further aspect of this invention.

A process according to the invention for preparing a compound of formula (I) which comprises:
(a) reacting a compound of formula (II)

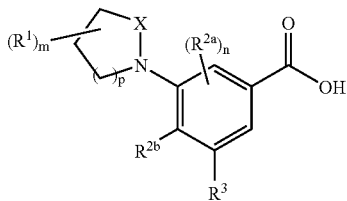
(II)

or an activated and optionally protected derivative thereof wherein $R^1$, m, X, p, $R^a$, n, $R^{2b}$ and $R^3$ are as defined above, with a compound of formula (III)

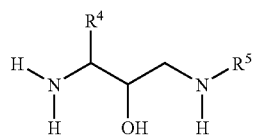
(III)

wherein $R^4$ and $R^5$ are as defined above; or
(b) preparing a compound of formula (I) which comprises reductive amination of a compound of formula (IV)

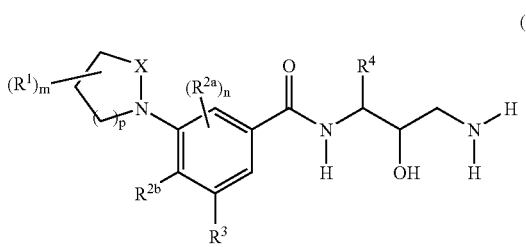
(IV)

wherein $R^1$, m, X, p, $R^{2a}$, n, $R^{2b}$, $R^3$ and $R^4$ are as defined above, with an appropriate aldehyde or ketone; or
(c) deprotecting a compound of formula (I) which is protected; and optionally thereafter
(d) interconversion of compounds of formula (I) to other compounds of formula (I).

Process (a) typically comprises the use of water soluble carbodiimide, HOBT and a suitable base such as tertiary alkylamine or pyridine in a suitable solvent such as DMF and at a suitable temperature, eg. between 0° C. and room temperature.

Process (b) typically comprises the use of sodium borohydride triacetate in the presence of a suitable solvent, such as ethanol and dichloromethane and at a suitable temperature, e.g. between 0° C. and room temperature.

In process (c), examples of protecting groups and the means for their removal can be found in T. W. Greene and P. G. M. Wuts 'Protective Groups in Organic Synthesis' (J. Wiley and Sons, 3rd Ed. 1999). Suitable amine protecting groups include aryl sulphonyl (e.g. tosyl), acyl (e.g. acetyl), carbamoyl (e.g. benzyloxycarbonyl or t-butoxycarbonyl) and arylalkyl (e.g. benzyl), which may be removed by hydrolysis or hydrogenolysis as appropriate. Other suitable amine protecting groups include trifluoroacetyl (—COCF$_3$) which may be removed by base catalysed hydrolysis. Suitable hydroxy protecting groups would be silyl based groups such as t-butyldimethylsilyl, which may be removed using standard methods, for example use of an acid such as trifluoroacetic or hydrochloric acid or a fluoride source such as tetra n-butylammonium fluoride.

Process (d) may be performed using conventional interconversion procedures such as epimerisation, oxidation, reduction, alkylation, aromatic substitution, ester hydrolysis, amide bond formation or removal and sulphonylation. An example of such an interconversion reaction may include interconversion of a compound of formula (I) wherein $R^3$ represents a $C_{2-6}$ alkenyl containing group to a corresponding compound of formula (I) wherein $R^3$ represents a $C_{1-6}$ alkyl containing group, using standard hydrogenation or reductive conditions. A further example of such an interconversion reaction may include interconversion of a compound of formula (I) wherein $R^3$ represents —$C_{1-6}$ alkyl-$N_3$ to a corresponding compound of formula (I) wherein $R^3$ represents —$C_{1-6}$ alkyl-$NH_2$, using standard hydrogenation or reductive conditions. A yet further example of such an interconversion reaction may include interconversion of a compound of formula (I) wherein $R^3$ represents a nitro group to a corresponding compound of formula (I) wherein $R^3$ represents $NH_2$, using standard hydrogenation or reductive conditions.

Compounds of formula (II) or activated and optionally protected derivatives thereof may be prepared in accordance with the following process:

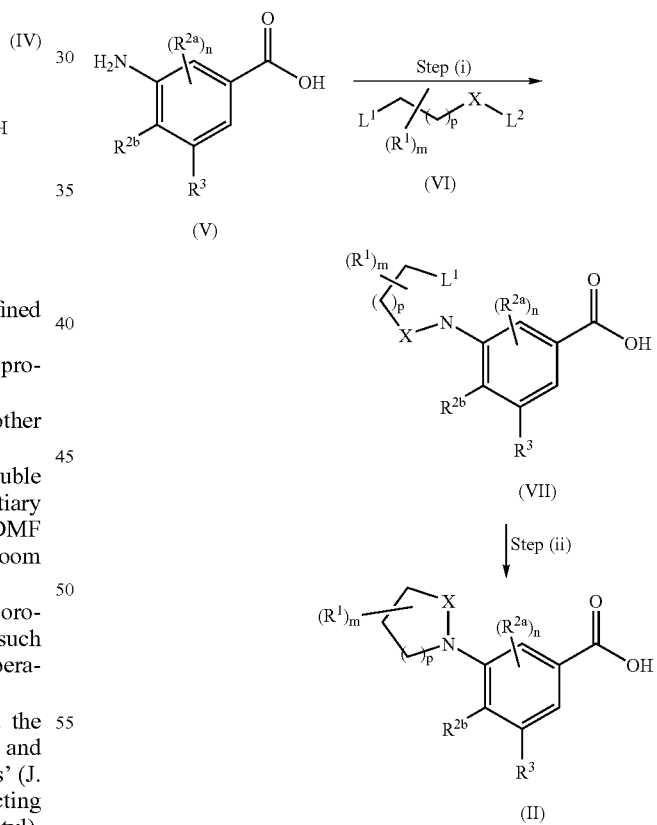

wherein $R^{2a}$, n, $R^{2b}$, $R^3$, p, X, $R^4$ and m are as defined above and $L^1$ and $L^2$ independently represent a suitable leaving group such as a halogen atom (eg. iodine, chlorine or bromine).

Step (i) typically comprises the use of a suitable solvent such as dichloromethane and a suitable base such as triethylamine.

Step (ii) typically comprises the use of sodium hydride in the presence of a suitable solvent such as tetrahydrofuran under nitrogen.

Compounds of formula (II) or activated and optionally protected derivatives thereof may also be prepared in accordance with the following process:

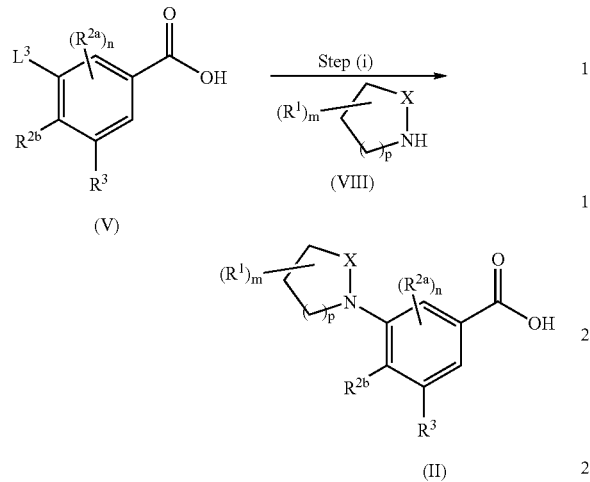

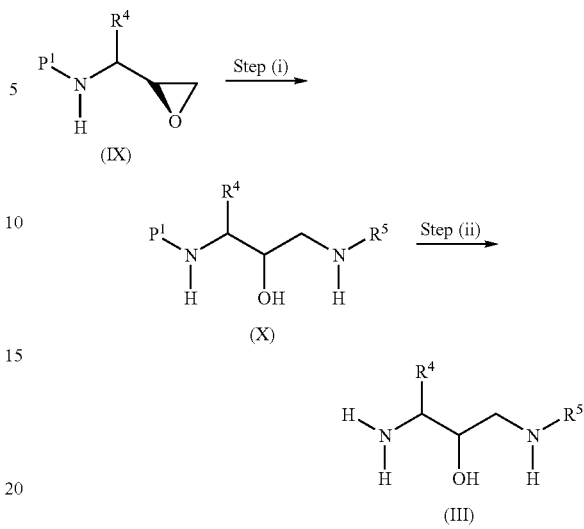

wherein $R^{2a}$, n, $R^{2b}$, $R^3$, p, X, $R^1$ and m are as defined above and $L^3$ represents a suitable leaving group such as a halogen atom (eg. iodine, chlorine or bromine).

Step (i) typically comprises the use of caesium carbonate, 4,5-bis(diphenylphosphino)-9,9-dimethylxanthene and a suitable catalyst such as tris(dibenzylideneacetone)dipalladium(0) under suitable conditions such as reflux under argon in the presence of a suitable solvent such as dioxan.

Compounds of formula (III) may be prepared in accordance with the following process:

wherein $R^4$ and $R^5$ are as defined above and $P^1$ represents a suitable amine protecting group, such as t-butoxycarbonyl.

Step (i) typically comprises the reaction of a compound of formula (IX) with a compound of formula $NH_2R^5$ in the presence of a suitable solvent, e.g. ethanol at a suitable temperature, e.g. reflux.

Step (ii) typically comprises the use of suitable deprotection reactions as described above for process (c), eg. when $P^1$ represents t-butoxycarbonyl, deprotection typically comprises the use of trifluoroacetic acid in the presence of a suitable solvent, such as dichloromethane at a suitable temperature, e.g. between 0° C. and room temperature.

Compounds of formula (IV) may be prepared in accordance with the following process:

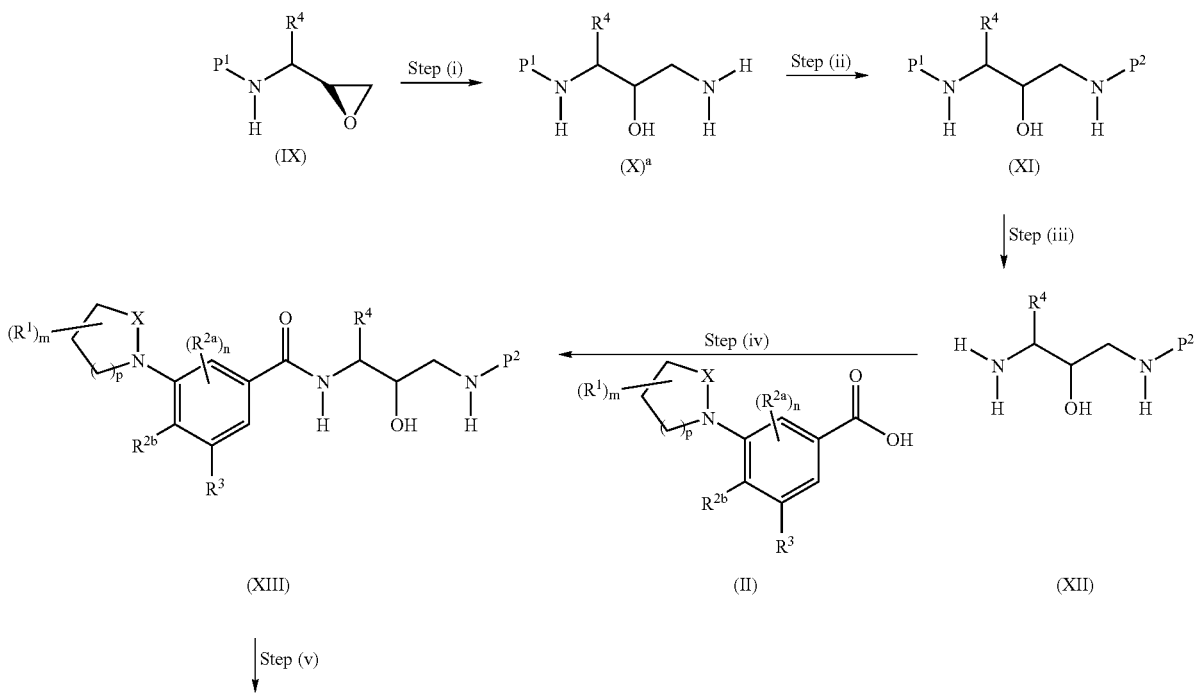

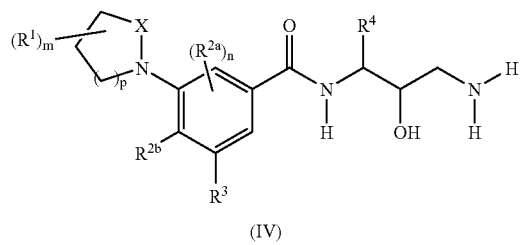

(IV)

wherein $R^1$, m, X, p, $R^{2a}$, n, $R^{2b}$, $R^3$, $R^4$ and $P^1$ are as defined above and $P^2$ represents a suitable amine protecting group different to $P^1$, such as —COOCH$_2$-phenyl.

Step (i) typically comprises the reaction of a compound of formula (IX) in aqueous ammonia in the presence of a suitable solvent, e.g. ethanol at a suitable temperature, e.g. reflux.

When $P^2$ represents —COOCH$_2$-phenyl, step (ii) typically comprises the use of ClCOOCH$_2$-phenyl in the presence of a suitable base, e.g. triethylamine, a suitable solvent, e.g. dimethylformamide at a suitable temperature, e.g. between 0° C. and room temperature.

Step (iii) typically comprises the use of suitable deprotection reactions as described above for process (c), eg. when $P^1$ represents t-butoxycarbonyl, deprotection typically comprises the use of trifluoroacetic acid in the presence of a suitable solvent, such as dichloromethane at a suitable temperature, e.g. between 0° C. and room temperature.

Step (iv) typically comprises reacting a compound of formula (XII) with a compound of formula (II) in the presence of water soluble carbodiimide and HOBT.

Step (iv) typically comprises the use of suitable deprotection reactions as described above for process (c), eg. when $p^2$ represents —COOCH$_2$-phenyl, deprotection typically comprises the use of a suitable catalyst, eg. palladium in the presence of a suitable solvent, e.g. water and ethanol and in the presence of a suitable hydrogen source, e.g. ammonium formate at a suitable temperature, eg. 60° C.

Compounds of formula (V) are either commercially available or may be prepared by interconversion of commercially available compounds of formula (V).

Compounds of formula (VI), (VIII) and (IX) are either known or may be prepared in accordance with known procedures.

As a further aspect of the invention there is thus provided a compound of formula (I) or a pharmaceutically acceptable salt or solvate thereof for use as a pharmaceutical, particularly in the treatment of patients with diseases characterised by elevated β-amyloid levels or β-amyloid deposits.

According to another aspect of the invention, there is provided the use of a compound of formula (I) or a physiologically acceptable salt or solvate thereof for the manufacture of a medicament for the treatment of patients with diseases characterised by elevated β-amyloid levels or β-amyloid deposits.

In a further or alternative aspect there is provided a method for the treatment of a human or animal subject with diseases characterised by elevated β-amyloid levels or β-amyloid deposits, which method comprises administering to said human or animal subject an effective amount of a compound of formula (I) or a physiologically acceptable salt or solvate thereof.

As a further aspect of the invention there is thus provided a pharmaceutical composition comprising a compound of formula (I) or a pharmaceutically acceptable salt or solvate thereof for use in the treatment of diseases characterised by elevated β-amyloid levels or β-amyloid deposits.

It will be appreciated by those skilled in the art that reference herein to treatment extends to prophylaxis as well as the treatment of diseases characterised by elevated β-amyloid levels or β-amyloid deposits.

The compounds according to the invention may be formulated for administration in any convenient way, and the invention therefore also includes within its scope pharmaceutical compositions for use in the therapy of diseases characterised by elevated β-amyloid levels or β-amyloid deposits, comprising a compound of formula (I) or a physiologically acceptable salt or solvate thereof together, if desirable, with one or more physiologically acceptable diluents or carriers.

It will be appreciated that diseases characterised by elevated β-amyloid levels or β-amyloid deposits include Alzheimer's disease, mild cognitive impairment, Down's syndrome, hereditary cerebral haemorrhage with β-amyloidosis of the Dutch type, cerebral β-amyloid angiopathy and various types of degenerative dementias, such as those associated with Parkinson's disease, progressive supranuclear palsy, cortical basal degeneration and diffuse Lewis body type of Alzheimer's disease.

Most preferably, the disease characterised by elevated β-amyloid levels or β-amyloid deposits is Alzheimer's disease.

There is also provided a process for preparing such a pharmaceutical formulation which comprises mixing the ingredients.

Compounds of formula (I) may be used in combination with other therapeutic agents. Suitable examples of such other therapeutic agents may be acetylcholine esterase inhibitors (such as tetrahydroaminoacridine, donepezil hydrochloride and rivastigmine), gamma secretase inhibitors, anti-inflammatory agents (such as cyclooxygenase II inhibitors), antioxidants (such as Vitamin E and ginkolidesor), statins or p-glycoprotein (P-gp) inhibitors (such as cyclosporin A, verapamil, tamoxifen, quinidine, Vitamin E-TGPS, ritonavir, megestrol acetate, progesterone, rapamycin, 10,11-methanodibenzosuberane, phenothiazines, acridine derivatives such as GF120918, FK506, VX-710, LY335979, PSC-833, GF-102 and 918).

When the compounds are used in combination with other therapeutic agents, the compounds may be administered either sequentially or simultaneously by any convenient route.

The compounds according to the invention may, for example, be formulated for oral, inhaled, intranasal, buccal, enteral, parenteral, topical, sublingual, intrathecal or rectal administration, preferably for oral administration.

Tablets and capsules for oral administration may contain conventional excipients such as binding agents, for example syrup, acacia, gelatin, sorbitol, tragacanth, mucilage of starch, cellulose or polyvinyl pyrrolidone; fillers, for example, lactose, microcrystalline cellulose, sugar, maize-starch, calcium phosphate or sorbitol; lubricants, for example, magnesium stearate, stearic acid, talc, polyethylene glycol or silica; disintegrants, for example, potato starch, croscarmellose sodium or sodium starch glycollate; or wetting agents such as sodium lauryl sulphate. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, for example, sorbitol syrup, methyl cellulose, glucose/sugar syrup, gelatin, hydroxymethyl cellulose, carboxymethyl cellulose, aluminium stearate gel or hydrogenated edible fats; emulsifying agents, for example, lecithin, sorbitan mono-oleate or acacia; non-aqueous vehicles (which may include edible oils), for example almond oil, fractionated coconut oil, oily esters, propylene glycol or ethyl alcohol; or preservatives, for example, methyl or propyl p-hydroxybenzoates or sorbic acid. The preparations may also contain buffer salts, flavouring, colouring and/or sweetening agents (e.g. mannitol) as appropriate.

For buccal administration the compositions may take the form of tablets or lozenges formulated in conventional manner.

The compounds may also be formulated as suppositories, e.g. containing conventional suppository bases such as cocoa butter or other glycerides.

The compounds according to the invention may also be formulated for parenteral administration by bolus injection or continuous infusion and may be presented in unit dose form, for instance as ampoules, vials, small volume infusions or pre-filled syringes, or in multi-dose containers with an added preservative. The compositions may take such forms as solutions, suspensions, or emulsions in aqueous or non-aqueous vehicles, and may contain formulatory agents such as anti-oxidants, buffers, antimicrobial agents and/or tonicity adjusting agents. Alternatively, the active ingredient may be in powder form for constitution with a suitable vehicle, e.g. sterile, pyrogen-free water, before use. The dry solid presentation may be prepared by filling a sterile powder aseptically into individual sterile containers or by filling a sterile solution aseptically into each container and freeze-drying.

When the compounds of the invention are administered topically they may be presented as a cream, ointment or patch.

The composition may contain from 0.1% to 99% by weight, preferably from 10 to 60% by weight, of the active material, depending on the method of administration.

The dose of the compound used in the treatment of the aforementioned disorders will vary in the usual way with the seriousness of the disorders, the weight of the sufferer, and other similar factors. However, as a general guide suitable unit doses may be 0.05 to 3000 mg; and such unit doses may be administered more than once a day, for example one, two, three or four times per day (preferably once or twice); and such therapy may extend for a number of weeks, months or years.

All publications, including but not limited to patents and patent applications, cited in this specification are herein incorporated by reference as if each individual publication were specifically and individually indicated to be incorporated by reference herein as though fully set forth.

EXAMPLES

Preparation of Intermediates

Description 1

3-Amino-5-nitro-benzoic acid methyl ester (D1)

To a solution of 3-amino-5-nitro-benzoic acid (65 g, 357 mmol, 1 equiv) in MeOH (650 ml) at 0° C. was added $SOCl_2$ dropwise (39 ml, 536 mmol, 1.5 equiv). The resulting solution was allowed to warm to room temperature and stirred for 16 h. A further portion of $SOCl_2$ (10 ml, 137 mmol, 0.4 equiv) was added dropwise and the solution was stirred at room temperature for 5 h, at 50° C. for 2 h and then cooled to room temperature and concentrated in vacuo. The residue was dissolved in AcOEt and the organic phase washed with saturated aqueous $NaHCO_3$ solution, dried over $MgSO_4$ and concentrated in vacuo. The solid residue was triturated with AcOEt/iso-hexane to give 3-amino-5-nitro-benzoic acid methyl ester (D1) (55 g, 78%) as a pale yellow solid.

Description 2

3-(4-Chloro-butanoylamino)-5-nitro-benzoic acid methyl ester (D2)

To a solution of 3-amino-5-nitro-benzoic acid methyl ester (D1) (38 g, 194 mmol, 1 equiv) in $CH_2Cl_2$ (350 ml) was added $NEt_3$ (32 ml, 230 mmol, 1.2 equiv) followed by 4-chlorobutyryl chloride (24.7 ml, 220 mmol, 1.13 equiv) dropwise over 20 nm. The resulting mixture was allowed to warm to room temperature and stirred for 30 min. The organic phase was then washed with 2N aqueous HCl solution, dried over $MgSO_4$ and concentrated in vacuo. The residue was triturated with iso-hexane and $Et_2O$ to give 3-(4-chloro-butanoylamino)-5-nitro-benzoic acid methyl ester D2 (56 g, 96%) as a brown solid.

Description 3

3-(5-Chloro-pentanoylamino)-5-nitro-benzoic acid methyl ester (D3)

5-Chlorovaleryl chloride (2.64 g, 17 mmol, 1.1 equiv) in $CH_2Cl_2$ (5 ml) was added over 2 min to a stirred solution of 3-amino-5-nitro-benzoic acid methyl ester (D1) (3 g, 15.3 mmol, 1 equiv) and $NEt_3$ (2.6 ml, 18 mmol, 1.2 equiv) in $CH_2Cl_2$ (30 ml). The resulting mixture was stirred for 1 h at room temperature then washed with 2N aqueous HCl solution, dried over $MgSO_4$ and concentrated in vacuo. The residue was triturated with $CH_2Cl_2$ to give 3-(5-Chloro-pentanoylamino)-5-nitro-benzoic acid methyl ester D3 (6 g, 112%) as a brown oil.

Description 4a

3-Amino-5-(2-oxo-pyrrolidin-1-yl)-benzoic acid methyl ester (D4a)

A flask was charged with 3-nitro-5-(2-oxo-pyrrolidin-1-yl)-benzoic acid methyl ester (B27) (5 g, 19 mmol, 1 equiv), 10% palladium on charcoal (50% wet, 750 mg, 7.5% w/w), $NH_4COOH$ (11.9 g, 190 mmol, 10 equiv) $H_2O$ (30 ml) and MeOH (60 ml). The resulting mixture was stirred at 50° C.

for 1.5 h, cooled to room temperature and the catalyst was filtered off through a pad of celite. Most of the MeOH was removed in vacuo and the residue diluted with saturated aqueous NaHCO$_3$ solution. The aqueous phase was extracted twice with AcOEt. The combined organic phases were dried over MgSO$_4$ and concentrated in vacuo to give an off white solid. The catalyst was then washed three times with DMF and the combined organic phases concentrated in vacuo. The residue was combined with the material obtained previously and was triturated with Et$_2$O to give amino-5-(2-oxo-pyrrolidin-1-yl)-benzoic acid methyl ester (D4a) (3.9 g, 88%) as a white solid which was used in the next step without further purification.

Description 4a (Alternative Procedure)

3-Amino-5-(2-oxo-pyrrolidin-1-yl)-benzoic acid methyl ester (D4a)

To a solution of 3-amino-5-(2-oxo-pyrrolidin-1-yl)-benzoic acid (D6) (2.2 g, 10 mmol, 1 equiv) in MeOH/Et$_2$O (1:1, 20 ml) was added 1-(3-dimethylaminopropyl)-3-ethyl-carbodiimide hydrochloride (2.3 g, 12 mmol, 1.2 equiv), DMAP (112 mg, 1 mmol, 0.1 equiv) and the resulting mixture was stirred at room temperature for 16 h then diluted with AcOEt. The organic phase was washed with saturated aqueous NaHCO$_3$ solution, dried over MgSO$_4$ and concentrated in vacuo. The residue was triturated with Et$_2$O to give 3-amino-5-(2-oxo pyrrolidin-1-yl)-benzoic acid methyl ester (D4a) (1.6 g, 68%) as a white solid.

Description 4b

3-Amino-5-(2-oxo-piperidin-1-yl)-benzoic acid methyl ester (D4b)

Description 4b was prepared in an analogous manner to Description 4a from 3-nitro-5-(2-oxo-piperidin-1-yl)-benzoic acid methyl ester (B82).

Description 5

3-Bromo-5-nitro-benzoic acid (D5)

To a solution of 3-amino-5-nitro-benzoic acid (17.6 g, 96.6 mmol, 1 equiv) in 48% aqueous HBr solution (180 ml) at 0° C. was added portionwise NaNO$_2$ (8.67 g, 126 mmol, 1.3 equiv) over 20 min. The temperature was kept below 8° C. during this addition. The resulting mixture was then added to a suspension of CuBr (9.7 g, 67.6 mmol, 0.7 equiv) in 48% aqueous HBr solution (50 ml) at 65° C. over 40 min. The temperature was kept above 60° C. during the addition. The resulting mixture was stirred at 70° C. for 45 min, cooled to room temperature and diluted with 1 L of water. The aqueous phase was extracted three times with Et$_2$O. The combined organic layers were washed twice with H$_2$O, dried over MgSO$_4$ and concentrated in vacuo to give 3-bromo-5-nitro-benzoic acid (D5) (21 g, 88%) as a brown solid. [M–H]$^-$=245.7, RT=2.82 min Description 6

3-Amino-5-(2-oxo-pyrrolidin-1-yl)-benzoic acid (D6)

To a solution of 3-nitro-5-(2-oxo-pyrrolidin-1-yl)-benzoic acid (A27) (4 g, 16 mmol, 1 equiv) in MeOH/H$_2$O (9:1, 40 ml) was added 10% palladium on charcoal (50% wet, 800 mg, 0.1 equiv w/w). The resulting mixture was stirred for 6 h at atmospheric pressure under an atmosphere of hydrogen. The catalyst was removed by filtration through a pad of celite and the solvent was removed in vacuo. The residue was dried at 60° C. under vacuum for 16 h to give 3-amino-5-(2-oxo-pyrrolidin-1-yl)-benzoic acid (D6) (3.34 g, 15.2 mmol, 95%) as a pale brown solid. [M–H]$^-$=218.8, RT=1.86 min Description 7

3-Bromo-5-iodo-benzoic acid (D7)

Description 7 is commercially available from Avocado Research Chemicals Ltd.

Description 8a

3-Bromo-5-iodo-benzoic acid methyl ester (D8a)

To a solution of 3-bromo-5-iodo-benzoic acid (D7) (14.6 g, 44.7 mmol, 1 equiv) in MeOH (150 ml) at 0° C. was added SOCl$_2$ (3.9 ml, 53.6 mmol, 1.2 equiv). The resulting solution was refluxed for 2 h, cooled to room temperature and concentrated in vacuo. The residue was diluted with AcOEt and washed twice with 2N aqueous NaOH solution then brine, dried over MgSO$_4$ and concentrated in vacuo to give 3-bromo-5-iodo-benzoic acid methyl ester (D8a) (14.8 g, 97%) as a pale brown solid.

Description 8b

3-Bromo-5-iodo-benzoic acid tert-butyl ester (D8b)

To a solution of 3-bromo-5-iodo-benzoic acid (D7) (50 g, 153 mmol, 1 equiv) in CH$_2$Cl$_2$ (500 ml) was added 1-(3-dimethylaminopropyl)-3-ethyl-carbodiimide hydrochloride (30.8 g, 160 mmol, 1.05 equiv), DMAP (14 g, 114 mmol, 0.75 equiv) and tert-butanol (90 ml, 917 mmol, 6 equiv). The resulting mixture was stirred at room temperature for 48 h. DMAP (4.67 g, 38 mmol, 0.25 equiv) was then added and the solution was stirred for another 24 h then concentrated in vacuo. The residue was dissolved in AcOEt and washed sequentially with 2N aqueous HCl solution, 1N aqueous NaOH solution and brine, dried over MgSO$_4$ and concentrated in vacuo to give 3-bromo-5-iodo-benzoic acid tert-butyl ester (D8b) (50.6 g, 86%) as a brown solid.

Description 8b (Alternative Procedure)

3-Bromo-5-iodo-benzoic acid tert-butyl ester (D8b)

To a solution of 3-bromo-5-iodo-benzoic acid (D7) (50 g, 153 mmol, 1 equiv) in CH$_2$Cl$_2$ (500 ml) was added 1-(3-dimethylaminopropyl)-3-ethyl-carbodiimide hydrochloride (30.8 g, 160 mmol, 1.05 equiv), DMAP (14 g, 114 mmol, 0.75 equiv) and tert-butanol (90 ml, 917 mmol, 6 equiv). The resulting mixture was stirred at room temperature for 48 h then DMAP (4.67 g, 38 mmol, 0.25 equiv) was added, and the solution was stirred for another 24 h then concentrated in vacuo. The residue was diluted with AcOEt and washed sequentially with 2N aqueous HCl solution, 1N aqueous NaOH solution and brine, dried over MgSO$_4$ and concentrated in vacuo to give 3-bromo-5-iodo-benzoic acid tert-butyl ester (D8b) (50.6 g, 86%) as a brown solid.

Description 9a

3-Bromo-5-(2-oxo-pyrrolidin-1-yl)-benzoic acid methyl ester D9a

A flask was charged under nitrogen with 3-bromo-5-iodo-benzoic acid methyl ester (D8a) (14.8 g, 43.4 mmol, 1 equiv), $Cs_2CO_3$ (21 g, 65 mmol, 1.5 equiv), tris(dibenzylideneacetone)dipalladium(0) (794 mg, 0.87 mmol, 0.02 equiv), Xantphos (1.5 g, 2.6 mmol, 0.06 equiv) and dioxan (150 ml). Pyrrolidin-2-one (5 ml, 5.54 mmol, 1.5 equiv) was then added via syringe and the resulting mixture was stirred at 55° C. for 5 days then cooled to room temperature and concentrated in vacuo. The residue was partitioned between $H_2O$ and AcOEt and the aqueous phase was re-extracted with AcOEt. The combined organic solutions were dried over $MgSO_4$ and concentrated in vacuo to give a solid residue. Purification of the residue by flash chromatography on silica gel (iso-hexane/AcOEt: 4/1 to 1/1) gave 3-bromo-5-(2-oxo-pyrrolidin-1-yl)-benzoic acid methyl ester (D9a) (6.4 g, 50%) as a white solid. $[M+H]^+$=299.9, RT=2.95 min Description 9a (Alternative Procedure)

3-Bromo-5-(2-oxo-pyrrolidin-1-yl)-benzoic acid methyl ester (D9a)

To a solution of 3-bromo-5-(4-chloro-butanoylamino)-benzoic acid methyl ester (D13) (530 mg, 1.6 mmol, 1 equiv) in THF (5 ml) at room temperature was added NaH (60% in mineral oil, 64 mg, 1.7 mmol, 1.1 equiv) and the resulting mixture was stirred at room temperature for 2 h. $H_2O$ was then added and the resulting mixture was diluted with AcOEt. The two layers were separated and the organic phase dried over $MgSO_4$ and concentrated in vacuo to give 3-bromo-5-(2-oxo-pyrrolidin-1-yl)-benzoic acid methyl ester (D9a) (361 mg, 76%) as a yellow solid. [M−H]-296.3, RT=2.49.

Description 9b

3-Bromo-5-(2-oxo-pyrrolidin-1-yl)-benzoic acid tert-butyl ester (D9b)

A flask was charged under nitrogen with bromo-5-iodobenzoic acid tert-butyl ester (D8b) (11.5 g, 30 mmol, 1 equiv), $Cs_2CO_3$ (13.7 g, 42 mmol, 1.5 equiv), tris(dibenzylideneacetone)dipalladium(0) (549 mg, 0.6 mmol, 0.02 equiv), Xantphos (1.04 g, 1.8 mmol, 0.06 equiv) and dioxan (100 ml). Pyrrolidin-2-one (2.5 ml, 33 mmol, 1.1 equiv) was then added via syringe and the resulting mixture was stirred at 60° C. for 60 h then cooled to room temperature and concentrated in vacuo. The residue was partitioned between $H_2O$ and AcOEt and the aqueous phase re-extracted with AcOEt. The combined organic solutions were dried over $MgSO_4$ and concentrated in vacuo to give a solid residue which was triturated with $Et_2O$ to give 3-bromo-5-(2-oxo-pyrrolidin-1-yl)-benzoic acid tert-butyl ester (D9b) (6.63 g, 65%) as an off white solid. The filtrate was concentrated in vacuo. Purification of the residue by flash chromatography on silica gel (iso-hexane/AcOEt: 4/1 to 1/1) gave a further 1.46 g (14%) of 3-bromo-5-(2-oxo-pyrrolidin-1-yl)-benzoic acid tert-butyl ester (D9b) as a white solid. [M+H-tBu)]+=285.9, RT=3.46 min Description 10

3-Bromo-5-(2-oxo-piperidin-1-yl)-benzoic acid tert-butyl ester (D10)

A flask was charged under nitrogen with 3-bromo-5-iodobenzoic acid tert-butyl ester (D8b) (6.42 g, 16.7 mmol, 1 equiv), $Cs_2CO_3$ (7.6 g, 23.4 mmol, 1.4 equiv), tris(dibenzylideneacetone)dipalladium(0) (307 mg, 0.33 mmol, 0.02 equiv), Xantphos (578 mg, 1 mmol, 0.06 equiv) and dioxan (120 ml). δ-Valerolactam (1.9 ml, 20 mmol, 1.2 equiv) was then added via syringe and the resulting mixture was stirred at 60° C. for 40 h then cooled to room temperature and concentrated in vacuo. The residue was partitioned between $H_2O$ and AcOEt and the aqueous phase was re-extracted with AcOEt. The combined organic solutions were dried over $MgSO_4$ and concentrated in vacuo Purification by flash chromatography on silica gel (iso-hexane/AcOEt: 3/1 to 1/1) gave 3-bromo-5-(2-oxo-piperidin-1-yl)-benzoic acid tert-butyl ester (D10) (4 g, 68%) as a white solid. RT=2.88 min Description 11

3-Bromo-5-nitro-benzoic acid methyl ester (D11)

To a solution of 3-bromo-5-nitro-benzoic acid (D5) (22.3 g, 90.6 mmol, 1 equiv) in MeOH (300 ml) at 0° C. was added $SOCl_2$ (7.9 ml, 108 mmol, 1.2 equiv) dropwise. The resulting solution was stirred at reflux for 4 hours then cooled to room temperature and concentrated in vacuo. The residue was diluted with AcOEt, washed twice with 2N aqueous NaOH solution and once with brine, dried over $MgSO_4$ and concentrated in vacuo to give 3-bromo-5-nitro-benzoic acid methyl ester (D11) (22.1 g, 94%) as a pale brown solid. RT=3.18 min Description 11 (Alternative Procedure)

3-Bromo-5-nitro-benzoic acid methyl ester (D11)

To an ice cold solution of 3-bromo-5-nitro-benzoic acid (D5) (2.5 g, 10 mmol, 1 equiv) in MeOH (25 ml) was added $SOCl_2$ (1 ml, 15 mmol, 1.5 equiv) dropwise. The resulting solution was allowed to warm to room temperature and was then stirred at 60° C. for 3 h, cooled to room temperature and concentrated in vacuo. The residue was dissolved in AcOEt and the organic layer was washed with saturated aqueous $NaHCO_3$ solution, dried over $MgSO_4$ and concentrated in vacuo to give 3-bromo-5-nitro-benzoic acid methyl ester (D11) (2.6 g, 100%) as a yellow solid. RT=3.22 min Description 12

3-Amino-5-bromo-benzoic acid methyl ester (D12)

To a solution of 3-bromo-5-nitro-benzoic acid methyl ester (D11) (12.1 g, 46.5 mmol, 1 equiv) in MeOH (200 ml) was added $SnCl_2$ (44 g, 233 mmol, 5 equiv). The resulting mixture was stirred at reflux for 4 h, cooled to room temperature and concentrated in vacuo. The residue was partitioned between ice-cold AcOEt and $H_2O$. The aqueous phase was basified with 2N aqueous NaOH solution until a white precipitate appeared, then slowly with 12.5N aqueous NaOH solution until this precipitate disappeared. The temperature was kept below 10° C. during this addition. The two layers were separated and the aqueous phase extracted with AcOEt. The combined organic layers were washed with brine, dried over $MgSO_4$ and concentrated in vacuo to give 3-amino-5-bromo-benzoic acid methyl ester (D12) (9.9 g, 93%) as a brown solid.

Description 13

3-bromo-5-(4-chloro-butanoylamino)-benzoic acid methyl ester (D13)

To a solution of 3-amino-5-bromo-benzoic acid methyl ester (D12) (460 mg, 2.0 mmol, 1 equiv) in $CH_2Cl_2$ (10 ml) at room temperature was added $NEt_3$ (306 µl, 2.2 mmol, 1.1 equiv) then 4-chlorobutyrylchloride (247 µl, 2.2 mmol, 1.1 equiv). The resulting mixture was stirred at room temperature for 16 h and then diluted with AcOEt. The organic phase was washed with 2N aqueous HCl solution, dried over $MgSO_4$ and concentrated in vacuo to give 3-bromo-5-(4-chloro-butanoylamino)-benzoic acid methyl ester (D13) (530 mg, 79%) as a pale yellow oil. RT=2.88 s Description 14

3-(3-Chloro-propane-1-sulfonylamino)-5-nitro-benzoic acid methyl ester (D14)

To a solution of 3-amino-5-nitro-benzoic acid methyl ester (D1) (45 g, 229 mmol, 1 equiv) in $CH_2Cl_2$ (450 ml) was added pyridine (18.5 ml, 229 mmol, 1 equiv), DMAP (100 mg, 0.8 mmol, catalytic) and 3-chloropropanesulfonyl chloride (28 ml, 230 mmol, 1 equiv). The resulting mixture was stirred for 40 h then diluted with AcOEt. The organic phase was diluted with 2N aqueous HCl solution. The resulting solid was filtered to give 3-(3-chloro-propane-1-sulfonylamino)-5-nitro-benzoic acid methyl ester (23 g, 32%). The filtrate was separated and the organic phase was washed with saturated aqueous $NaHCO_3$ solution, dried over $MgSO_4$ and concentrated in vacuo. The residue was triturated with AcOEt and isohexane to give a further 50 g (65%) of 3-(3-chloro-propane-1-sulfonylamino)-5-nitro-benzoic acid methyl ester (D14) as a pale brown solid. $[M-H]^-$=334.9, RT=3.11 min Description 15

3-(1,1-Dioxo-1/$^6$-isothiazolidin-2-yl)-5-nitro-benzoic acid methyl ester (D15)

To a solution of 3-(3-chloro-propane-1-sulfonylamino)-5-nitro-benzoic acid methyl ester (D14) (73 g, 217 mmol, 1 equiv) in EtOH (600 ml) was added E % N (60 ml, 430 mmol, 2 equiv) and the resulting mixture was refluxed for 3 h, cooled to room temperature and concentrated in vacuo. The residue was dissolved in AcOEt, washed with 2N aqueous HCl solution, dried over $MgSO_4$ and concentrated in vacuo. The residue was triturated with iso-hexane and AcOEt to give 3-(1,1-dioxo-1/$^6$-isothiazolidin-2-yl)-5-nitro-benzoic acid methyl ester (D15) (58 g, 88%) as a pale brown solid. $[M+H+NH_3]^+$=318.0, RT=2.78 min Description 15 (Alternative Procedure)

3-(1,1-Dioxo-1/$^6$-isothiazolidin-2-yl)-5-nitro-benzoic acid methyl ester (D15)

A 50 ml flask was charged under nitrogen with 3-bromo-5-nitro-benzoic acid methyl ester (D11) (1 g, 3.8 mmol, 1 equiv), $CS_2CO_3$ (536 mg, 4.4 mmol, 1.2 equiv) tris(dibenzylideneacetone)dipalladium(0) (5 mg, 0.0055 mmol, 0.0154 equiv), Xantphos (10 mg, 0.014 mmol, 0.04 equiv) and toluene (15 ml). Isothiazolidine 1,1-dioxide (D22a) (536 mg, 4.4 mmol, 1.1 equiv) was then added and the resulting mixture was stirred at 90° C. for 16 hours then cooled to room temperature and diluted with $H_2O$ and AcOEt. The layers were separated, the aqueous phase diluted with a saturated aqueous $NaHCO_3$ solution and extracted with AcOEt. The combined organic phases were dried over $MgSO_4$ and concentrated in vacuo to give 3-(1,1-dioxo-1/$^6$-isothiazolidin-2-yl)-5-nitro-benzoic acid methyl ester (D15) (187 mg, 16%) as a yellow solid. $[M+H+NH_3]^+$=318.0, RT=2.81 min Description 16

3-Amino-5-(1,1-dioxo-1/$^6$-isothiazolidin-2-yl)-benzoic acid methyl ester (D16)

A flask was charged with 3-(1,1-dioxo-1/$^6$-isothiazolidin-2-yl)-5-nitro-benzoic acid methyl ester (D15) (25 g, 83 mmol, 1 equiv) and 10% palladium (0) on charcoal (50% wet, 5 g, 10% w/w) and EtOH (500 ml). The resulting suspension was stirred under an atmosphere of hydrogen (atmospheric pressure) for 4 h and the catalyst was filtered off through a pad of celite. The catalyst was washed three times with DMF and the combined organic layers were concentrated in vacuo. The residue was dissolved in AcOEt and filtered again through celite in order to remove residual catalyst. The organic phase was concentrated in vacuo. The residue was triturated with $Et_2O$ to give 3-amino-5-(1,1-dioxo-1/$^6$-isothiazolidin-2-yl)-benzoic acid methyl ester (D16) (18 g, 80%) as a pale brown solid. $[M+H]^+$=271.0, RT=2.16 min Description 17

3-Bromo-5-(1,1-dioxo-1/$^6$-isothiazolidin-2-yl)-benzoic acid tert-butyl ester (D17)

A flask was charged under nitrogen with 3-bromo-5-iodo-benzoic acid tert-butyl ester D8b (1 g, 2.6 mmol, 1 equiv), $Cs_2CO_3$ (1.26 g, 3.9 mmol, 1.5 equiv), tris(dibenzylideneacetone)dipalladium(0) (12 mg, 0.013 mmol, 0.005 equiv), Xantphos (22 mg, 0.038 mmol, 0.015 equiv) and toluene (20 ml). Isothiazolidine 1,1-dioxide (D22a) (350 mg, 2.9 mmol, 1.1 equiv) was then added and the resulting mixture was stirred at 100° C. for 16 h then cooled to room temperature and diluted with AcOEt. The organic phase was washed with saturated aqueous $NaHCO_3$ solution, dried over $MgSO_4$ and concentrated in vacuo. The residue was triturated with $Et_2O$ to give 3-bromo-5-(1,1-dioxo-1/$^6$-isothiazolidin-2-yl)-benzoic acid tert-butyl ester (D17) (350 mg 38%) as a white solid.

Description 18

3-bromo-5-(1,1-dioxo-1/$^6$-[1,2]thiazinan-2-yl)-benzoic acid tert-butyl ester (D18)

Description 18 was prepared in an analogous manner to Description 17b from 3-bromo-5-iodo-benzoic acid tert-butyl ester (D8b) (5.2 g, 13.6 mmol) and [1,2] thiazinane 1,1-dioxide (D22b) which gave the title compound (D18) (1.8 g, 34%) as a pale yellow solid. $[M+H-tert-Bu]^+$=335.9, RT=3.26 min Description 19

3-Bromo-5-(3-chloro-propane-1-sulfonylamino)-benzoic acid methyl ester (D19)

To a solution of 3-amino-5-bromo-benzoic acid methyl ester (D12) (2.3 g, 10 mmol, 1 equiv) in $CH_2Cl_2$ (30 ml) was added pyridine (1.6 ml, 20 mmol, 2 equiv), DMAP (320 mg, 2.5 mmol, 2.5 equiv) and 3-chlorosulphonyl chloride (1.46 ml, 12 mmol, 1.2 equiv) dropwise. The resulting mixture was stirred at room temperature for 16 h then concentrated in vacuo. The residue was dissolved in AcOEt and the organic phase washed sequentially with 2N aqueous HCl solution, saturated aqueous NaHCO$_3$ solution and brine, dried over MgSO$_4$ and concentrated in vacuo to give 3-bromo-5-(3-chloro-propane-1-sulfonylamino)-benzoic acid methyl ester (D19) (3.36 g, 91%) as a red solid. [M–H]$^-$=369.9, RT=3.25 min Description 20

4-Chloro-1-butanesulfonyl chloride (D20)

To a mixture of [1,2]oxathiane 2,2-dioxide (D23) (50 g, 367 mmol, 1 equiv) and SOCl$_2$ (29 ml, 401 mmol, 1.1 equiv) was added DMF (4 ml, 51.6 mmol, 0.14 equiv). The resulting mixture was stirred under nitrogen at 70° C. for 3 days. A second portion of SOCl$_2$ (10 ml, 137 mmol, 0.37 equiv) was added. The mixture was stirred at 70° C. for another 3 days and then cooled to room temperature and concentrated in vacuo. The residue was diluted with toluene then concentrated in vacuo. This procedure was repeated and the residue was dried under vacuum for 16 h to give crude 4-chloro-1-butanesulfonyl chloride (D20) (63 g, 90%).

Description 21a

3-Chloro-1-propanesulfonamide (D21a)

To an ice-cooled solution of 3-chloro-1-propanesulfonyl chloride (Chem. Pharm. Bull, 40(1), 75-84, 1999) (30 ml, 250 mmol, 1 equiv) in CH$_2$Cl$_2$ (150 ml) was slowly added aqueous ammonia solution (32%, 30 ml). The resulting mixture was stirred at room temperature for 16 h and H$_2$O (20 ml) was added. The layers were separated and the organic layer was dried over MgSO$_4$ and concentrated in vacuo to give crude 3-chloro-1-propanesulfonamide (D21a) (27 g, 69%) as a white solid Chem. Pharm. Bull, 40(1), 75-84, 1999].

Description 21 b

3-Chloro-1-butanesulfonamide (D21b)

To an ice-cooled solution of 4-chloro-1-butanesulfonyl chloride (D20) (43 g, 225 mmol, 1 equiv) in CH$_2$Cl$_2$ (350 ml) was slowly added aqueous ammonia solution (25%, 140 ml). The resulting mixture was stirred at room temperature for 16 h then concentrated in vacuo. The residue was diluted with AcOEt and washed with brine. The organic phase was dried over MgSO$_4$ and concentrated in vacuo to give crude 3-chloro-1-butanesulfonamide (D21b) (31 g, 88%).

Description 22a

Isothiazolidine 1,1-dioxide (D22a)

To a solution of 3-chloro-1-propanesulfonamide (D21a) (27 g, 170 mmol, 1 equiv) in EtOH (250 ml) at room temperature was added NaOEt (11.7 g, 170 mmol, 1 equiv). The resulting mixture was refluxed for 5 h then cooled to room temperature and concentrated in vacuo. The residual solid was extracted thoroughly with CH$_2$Cl$_2$ and the extracts were concentrated in vacuo to give isothiazolidine 1,1-dioxide (D22a) (20 g, 100%).

Description 22b

[1,2] Thiazinane 1,1-dioxide (D22b)

To a solution of 3-chloro-1-butanesulfonamide (D21b) (31 g, 200 mmol, 1 equiv) in EtOH (500 ml) at room temperature was added NaOEt (14.9 g, 220 mmol, 1.1 equiv). The resulting mixture was refluxed for 5 h then cooled to room temperature and concentrated in vacuo. The residual solid was extracted thoroughly with CH$_2$Cl$_2$ and the extracts were concentrated in vacuo. The residual solid was triturated with Et$_2$O to give [1,2]thiazinane 1,1-dioxide (D22b) (18.7 g, 69%) as a pale brown solid.

Description 23

4-chloro-3,5-dinitrobenzoic acid (D23)

Description 23 is commercially available from Sigma-Aldrich Company.

Description 24

4-Methoxy-3,5-dinitro-benzoic acid (D24)

To a solution of KOH (1.12 g, 20 mmol, 1 equiv) in MeOH (20 ml) at 0° C. was added portionwise 4-chloro-3, 5-dinitrobenzoic acid (D23) (4.93 g, 20 mmol, 1 equiv). The resulting mixture was refluxed for 1 h then cooled to room temperature. A second portion of KOH (1.12 g, 20 mmol, 1 equiv) was added and the mixture refluxed for 90 min, cooled to room temperature and diluted with H$_2$O. The aqueous phase was acidified to pH 1 and extracted with AcOEt. The organic phase was dried over MgSO$_4$ and concentrated in vacuo to give crude 4-methoxy-3,5-dinitro-benzoic acid (D24) (4.49 g, 93%) as a light brown solid.

Description 25

4-Methoxy-3,5-dinitro-benzoic acid methyl ester (D25)

To a solution of crude 4-methoxy-3,5-dinitro-benzoic acid (D24) (4.43 g, 17.3 mmol, 1 equiv) in MeOH (60 ml) was added concentrated H$_2$SO$_4$ (4 ml). The resulting mixture was refluxed for 3 h, cooled to room temperature and concentrated in vacuo. The residue was partitioned between H$_2$O and AcOEt. The two layers were separated and the organic phase was washed with saturated aqueous NaHCO$_3$ solution, dried over MgSO$_4$ and concentrated in vacuo. Purification by flash chromatography on silica gel (iso-hexane/AcOEt: 85/15) gave 4-methoxy-3,5-dinitro-benzoic acid methyl ester (D25) (2.84 g, 65%) as an off white solid.

The following descriptions were prepared in an analogous manner to Description 25 from commercially available starting materials:

| Description | Starting material |
| --- | --- |
| 4-Chloro-3,5-dinitro-benzoic acid methyl ester (D25a) | D24a |
| 3-Amino-4-chloro-benzoic acid methyl ester (D27c) | D26 |

Description 27a

3,5-Diamino-4-chloro-benzoic acid methyl ester (D27a)

A mixture of 4-chloro-3,5-dinitro-benzoic acid methyl ester (D25a) (2.6 g, 10 mmol, 1 equiv) and $SnCl_2$ (18.95 g, 100 mmol, 10 equiv) in MeOH (80 ml) was refluxed for 1 h, cooled to room temperature and concentrated in vacuo. The residue was partitioned between AcOEt and 2N aqueous NaOH solution. The organic phase was dried over $MgSO_4$ and concentrated in vacuo. The residue was triturated with 1:1 $Et_2O$/iso-hexane to give 3,5-diamino-4-chloro-benzoic acid methyl ester (D27a) (1.56 g, 78%) as a light orange solid.

The following Description was prepared in an analogous manner to Description 27a (using 5 equivalents of $SnCl_2$ for nitroaryls and 10 equivalents for bis nitroaryls) from the starting material indicated in the below table:

| Description | Starting material |
|---|---|
| 3,5-Diamino-4-methoxy-benzoic acid methyl ester (D27b) | D25b |

Description 28c

4-Chloro-3-(4-chloro-butanoylamino)-benzoic acid methyl ester (D28c)

4-Chlorobutyryl chloride (2.82 g, 20 mmol, 2.0 equiv) in $CH_2Cl_2$ (5 ml) was added over 2 min to a stirred solution of 3-amino-4-chloro-benzoic acid methyl ester (D27c) (1.66 g, 10 mmol, 1 equiv) and $NEt_3$ (2.22 g, 22 mmol, 2.2 equiv) in $CH_2Cl_2$ (40 ml). The resulting mixture was stirred for 1 h at room temperature then washed with 2N aqueous HCl solution, dried over $MgSO_4$ and concentrated in vacuo. The residue was triturated with $CH_2Cl_2$ to give 4-chloro-3-(4-chloro-butanoylamino)-benzoic acid methyl ester (D28c) (1.81 g, 48%) as a pale pink solid.

The following Descriptions were prepared in an analogous manner to the process described in D28c from the starting material indicated in the below table:

| Description | Precursor |
|---|---|
| 4-Chloro-3,5-bis-(4-chloro-butanoylamino)-benzoic acid methyl ester (D28a) | D27a |
| 3,5-Bis-(4-chloro-butanoylamino)-4-methoxy-benzoic acid methyl ester (D28b) | D27b |

Description 30

(Benzyl-ethyl-amino)-(2-oxo-pyrrolidin-1-yl)-benzoic acid tert-butyl ester (D30)

A flask was charged under nitrogen with 3-bromo-5-(2-oxo-pyrrolidin-1-yl)-benzoic acid tert-butyl ester (D9b) (4.6 g, 13 mmol, 1 equiv), sodium tert-butoxide (1.9 g, 19.5 mmol, 1.5 equiv), tris(dibenzylideneacetone)dipalladium(0) (395 mg, 0.65 mmol, 0.05 equiv), 2-(dicyclohexylphosphino)biphenyl (341 mg, 0.97 mmol, 0.075 equiv) and toluene (100 ml). N-Ethylbenzylamine (2.9 ml, 19.5 mmol, 1.5 equiv) was then added via syringe and the resulting mixture was stirred at 90° C. for 2 h then cooled to room temperature, diluted with $H_2O$ and AcOEt. The layers were separated, the aqueous phase diluted with saturated aqueous $NaHCO_3$ solution and extracted with AcOEt. The combined organic phases were dried over $MgSO_4$ and concentrated in vacuo. Purification of the residue by flash chromatography on silica gel (iso-hexane/AcOEt: 1/2) gave (benzyl-ethyl-amino)-(2-oxo-pyrrolidin-1-yl)-benzoic acid tert-butyl ester (D30) (3 g, 60%) as a white solid. $[M+H]^+=395.0$, RT=3.70 min.

Descriptions 31-35 (D31-D35)

Descriptions 31-35 were prepared in an analogous manner to D30 from the appropriate aryl bromide and amine starting materials listed in the below table:

| Description | Aryl bromide | Amine | [M + H]⁺ | RT (mm) |
|---|---|---|---|---|
| (Benzyl-methyl-amino)-(2-oxo-pyrrolidin-1-yl)-benzoic acid tert-butyl ester (D31) | D9b | (structure) | 381.1 | 3.59 |
| (Benzyl-methyl-amino)-(2-oxopiperidin-1-yl)-benzoic acid tert-butyl ester (D32) | D10 | (structure) | 395.2 | 3.51 |

| Description | Aryl bromide | Amine | [M + H]+ | RT (min) |
|---|---|---|---|---|
| (Benzyl-ethyl-amino)-(2-oxopiperidin-1-yl)-benzoic acid tert-butyl ester (D33) | D10 | | | |
| (Benzyl-methyl-amino)-(1,1-dioxo-1l6-isothiazolidin-2-yl)-benzoic acid tert-butyl ester (D34) | D17 | | 417.1 | 3.51 |
| (Benzyl-ethyl-amino)-(1,1-dioxo-1l6-[1,2]thiazinan-2-yl)-benzoic acid tert-butyl ester (D35) | D18 | | 445.2 | 3.82 |

Description 36

3-Hydroxy-5-(2-oxo-pyrrolidin-1-yl)-benzoic acid (D36)

To a solution of 3-amino-5-(2-oxo-pyrrolidin-1-yl)-benzoic acid (D6) (280 mg, 1.25 mmol, 1 equiv) in a mixture of 2N aqueous HCl solution (2.5 ml) and MeOH (5 ml) at 0° C. was added NaN$_3$ (190 mg, 2.75 mmol, 2.2 equiv) portionwise over 20 min. H$_2$O (5 ml) was added and the resulting mixture was heated at 90° C. for 1 h then cooled to room temperature and diluted with AcOEt. The two layers were separated and the aqueous phase was extracted twice with AcOEt (20 ml). The combined organic layers were washed with brine (20 ml), dried over MgSO$_4$ and concentrated in vacuo to give a crude product which was triturated with Et$_2$O/MeOH to give 3-hydroxy-5-(2-oxo-pyrrolidin-1-yl)-benzoic acid (D36) (110 mg, 40%) as a light tan solid.

Description 37

3-Hydroxy-5-(2-oxo-pyrrolidin-1-yl)-benzoic acid methyl ester (D37)

3-Hydroxy-5-(2-oxo-pyrrolidin-1-yl)-benzoic acid (D36) (400 mg, 1.72 mmol, 1 equiv) was heated at reflux in a mixture of MeOH (20 ml) and concentrated H$_2$SO$_4$ (4 drops) for 7 h. The solution was then cooled to room temperature and concentrated in vacuo to give of 3-hydroxy-5-(2-oxo-pyrrolidin-1-yl)-benzoic acid methyl ester (D37) (300 mg, 74%) as a light brown solid.

Description 37 (Alternative Procedure)

3-Hydroxy-5-(2-oxo-pyrrolidin-1-yl)-benzoic acid methyl ester (D37)

3-Amino-5-(2-oxo-pyrrolidin-1-yl)-benzoic acid methyl ester (D4a) (1.50 g, 6.4 mmol, 1 equiv) was dissolved in a mixture of 2N aqueous HCl solution (25 ml) and MeOH (50 ml) at 0° C. and treated portionwise with NaN$_3$ (950 mg, 13.8 mmol, 2.2 equiv) over 20 min. H$_2$O (50 ml) was added and the resulting mixture was heated at 90° C. for 45 min then cooled to room temperature and diluted with Et$_2$O (300 ml). The two layers were separated and the organic phase was dried over MgSO$_4$ and concentrated in vacuo to give 3-hydroxy-5-(2-oxo-pyrrolidin-1-yl)-benzoic acid methyl ester (D37) (1.0 g, 67%) as a tan solid.

Description 38

3-(3-Benzyloxy-propoxy)-5-(2-oxo-pyrrolidin-1-yl)-benzoic acid methyl ester (D38)

A solution of 3-hydroxy-5-(2-oxopyrrolidin-1-yl)-benzoic acid methyl ester (D37) (300 mg, 1.28 mmol, 1 equiv), 3-benzyloxypropan-1-ol (0.28 ml, 1.79 mmol, 1.4 equiv) and triphenyl phosphine (470 mg, 1.79 mmol, 1.4 equiv) in THF (10 ml) at room temperature was treated dropwise with DEAD (0.282 ml, 1.79 mmol, 1.4 equiv). The mixture was stirred for 16 h at room temperature then concentrated in vacuo. Purification by flash chromatography on silica gel (ethyl acetate/iso-hexane: 1/4 to 1/1) gave 3-(3-benzyloxy-propoxy)-5-(2-oxo-pyrrolidin-1-yl)-benzoic acid methyl ester (D38).

Description 39

Description 39 was prepared in an analogous manner to Description 38 from Description 37 using the appropriate alcohol indicated in the table below:

| Description | Alcohol |
|---|---|
| 3-(2-Benzyloxy-ethoxy)-5-(2-oxo-pyrrolidin-1-yl)-benzoic acid methyl ester (D39) | 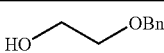 |

Description 40

3-(2-benzyloxy-ethoxy)-5-(2-oxo-pyrrolidin-1-yl)-benzoic acid (D40)

Description 40 was prepared by saponification of Description 39 in accordance with known procedures.

Description 41

3-(1,1-Dioxo-1/$^6$-isothiazolidin-2-yl)-5-hydroxy-benzoic acid methyl ester (D41)

1-[3-Amino-5-(1,1-dioxo-1/$^6$-isothiazolidin-2-yl)-phenyl]-propan-1-one (D16) (1.0 g, 3.7 mmol, 1 equiv) dissolved in a mixture of 2N aqueous HCl solution (15 ml) and MeOH (30 ml) was stirred at 0° C. and treated portionwise with sodium nitrite (550 mg, 8.0 mmol, 2.2 equiv) over 20 min. H$_2$O (50 ml) was added and the resulting mixture was heated at 90° C. for 45 min, cooled, and diluted with Et$_2$O (300 ml) The two layers were separated and the organic phase dried over MgSO$_4$ and concentrated in vacuo to give crude 3-(1,1-dioxo-1/$^6$-isothiazolidin-2-yl)-5-hydroxy-benzoic acid methyl ester (D41) (800 mg, 80%) as a brown oil.

Description 41 (Alternative Procedure)

3-(1,1-Dioxo-1/$^6$-isothiazolidin-2-yl)-5-hydroxy-benzoic acid methyl ester (D41)

A mixture of 3-benzyloxy-5-(1,1-dioxo-1/$^6$-isothiazolidin-2-yl)-benzoic acid methyl ester (D54) (4.5 g, 12.5 mmol, 1 equiv), NH$_4$COOH (7.7 g, 125 mmol, 10 equiv) and 10% Pd on charcoal (50% wet, 1.0 g, 11% w/w) in MeOH (150 ml) and H$_2$O (10 ml) was heated at 50° C. for 2 h. The cooled reaction mixture was filtered through a pad of celite and concentrated in vacuo. H$_2$O (100 ml) was added to the filtrate which was then extracted with AcOEt (150 ml). The organic solution was dried over MgSO$_4$ and concentrated in vacuo. The residue was crystallised from Et$_2$O to yield of 3-(1,1-dioxo-1/$^6$-isothiazolidin-2-yl)-5-hydroxy-benzoic acid methyl ester (D41) (2.6 g, 77%) as a white solid.

Description 42

5-hydroxy-isophthalic acid dimethyl ester (D42)

Description 42 is commercially available from Sigma-Aldrich Company.

Description 43

5-Ethoxy-isophthalic acid dimethyl ester (D43)

K$_2$CO$_3$ (31.6 g, 223 mmol, 2.23 equiv) and iodoethane (17.8 ml, 230 mmol, 2.3 equiv) were added to a solution of 5-hydroxy-isophthalic acid dimethyl ester (D42) (21 g, 100 mmol, 1 equiv) in acetone (500 ml) at room temperature. The resulting solution was refluxed for 16 h, then cooled to room temperature and concentrated in vacuo. The residue was partitioned between H$_2$O and AcOEt. The aqueous phase was extracted with AcOEt and the combined organic layers were washed with 2N aqueous NaOH solution and brine, dried over MgSO$_4$ and concentrated in vacuo to give 5-ethoxy-isophthalic acid dimethyl ester (D43) (23 g, 96%) as a white solid. RT=3.13 min Description 44

5-Benzyloxy-isophthalic acid dimethyl ester (D44)

K$_2$CO$_3$ (21 g, 153 mmol, 2 equiv) and benzyl bromide (11 ml, 92 mmol, 1.2 equiv) were added to a solution of 5-hydroxy-isophthalic acid dimethyl ester (D42) (16.1 g, 76.7 mmol, 1 equiv) in acetone (400 ml) at room temperature. The resulting solution was refluxed for 18 h, cooled to room temperature and concentrated in vacuo. The residue was partitioned between H$_2$O and AcOEt. The aqueous phase was extracted with AcOEt and the combined organic layers were washed with 2N aqueous NaOH solution and brine, dried over MgSO$_4$ and concentrated in vacuo to give 5-benzyloxy-isophthalic acid dimethyl ester (D44) (24.2 g, 105%) as a white solid. [M+H]$^+$=301.0, RT=3.50 min Description 45

5-Ethoxy-isophthalic acid monomethyl ester (D45)

To a solution of 5-ethoxy-isophthalic acid dimethyl ester (D43) (22 g, 92.4 mmol, 1 equiv) in MeOH (440 ml) was added 1N aqueous NaOH solution (87.8 ml, 87.8 mmol, 0.95 equiv) and the resulting solution was stirred at room temperature for 17 h. Most of the MeOH was removed in vacuo and the residue was partitioned between AcOEt and 1N aqueous NaOH solution. The aqueous layer was extracted with AcOEt, acidified to pH 1 and re-extracted with AcOEt. The second organic extract was dried over MgSO$_4$ and concentrated in vacuo to give 5-ethoxy-isophthalic acid monomethyl ester (D45) (17 g, 82%) as a white solid. [M+H+ NH$_3$]$^+$=242.0, RT=2.79 min Description 46

5-Benzyloxy-isophthalic acid monomethyl ester (D46)

To a solution of 5-benzyloxy-isophthalic acid dimethyl ester (D44) (24 g, 80 mmol, 1 equiv) in MeOH (300 ml) was added 1N aqueous NaOH solution (76 ml, 76 mmol, 0.95 equiv) and the resulting solution was stirred at room temperature for 17 h. A second portion of 1N aqueous NaOH solution (15 ml, 15 mmol, 0.2 equiv) was added and the solution stirred for another 6 h. Most of the MeOH was removed in vacuo and the residue was partitioned between AcOEt and 1N aqueous NaOH solution. The aqueous layer was extracted with AcOEt, acidified to pH 1 and re-extracted with AcOEt. The second organic extract was dried over MgSO$_4$ and concentrated in vacuo. The residue was triturated with Et$_2$O to give 5-benzyloxy-isophthalic acid monomethyl ester (D46) (15.5 g, 68%) as a white solid. [M+H]$^+$=2.86.0, RT=3.32 min Description 47

3-Benzyloxycarbonylamino-5-ethoxy-benzoic acid methyl ester (D47)

NEt$_3$ (14.2 ml, 102 mmol, 1.3 equiv) and diphenylphosphoryl azide (22 ml, 102 mmol, 1.3 equiv) were added to a suspension of 5-ethoxy-isophthalic acid monomethyl ester (D45) (17.6 g, 78.6 mmol, 1 equiv) in toluene (250 ml) and the mixture heated at 80° C. for 3 h. Benzyl alcohol (12 ml, 118 mmol, 1.5 equiv) was added and the resulting mixture was refluxed for 4 h, cooled to room temperature and concentrated in vacuo. The residue was dissolved in AcOEt (300 ml) and the resulting solution was washed with 2N aqueous HCl solution (100 ml) followed by saturated aqueous NaHCO$_3$ solution (100 ml), dried over MgSO$_4$ and concentrated in vacuo. The residue was triturated with Et$_2$O to give 3-benzyloxycarbonylamino-5-ethoxy-benzoic acid methyl ester (D47) (15 g, 62%) as a white solid. [M−H]$^-$=328.1, RT=3.46 min Description 48

3-Benzyloxy-5-(2-trimethylsilanyl-ethoxycarbonylamino)-benzoic acid methyl ester (D48)

NEt$_3$ (8.2 g, 81 mmol, 1.5 equiv) and diphenylphosphoryl azide (22.3 g, 81 mmol, 1.5 equiv) were added to a suspension of 5-benzyloxy-isophthalic acid monomethyl ester (D46) (15.5 g, 54.2 mmol, 1 equiv) in toluene (120 ml) and the resulting mixture heated at 80° C. for 3 h. 2-Trimethylsilylethanol (12.7 g, 108 mmol, 2 equiv) was added and the resulting mixture was refluxed for 4 h, cooled to room temperature and concentrated in vacuo. The residue was dissolved in EtOAc (300 ml) and the resulting solution was washed with 2N aqueous HCl solution (100 ml) followed by saturated aqueous NaHCO$_3$ solution (100 ml), dried over MgSO$_4$ and concentrated in vacuo. The residue was triturated with Et$_2$O and iso-hexane to give 3-benzyloxy-5-(2-trimethylsilanyl-ethoxycarbonylamino)-benzoic acid methyl ester (D48) (8.5 g, 40%) as a white solid.

Description 49

3-Amino-5-ethoxy-benzoic acid methyl ester (D49)

A mixture of 3-benzyloxycarbonylamino-5-ethoxy-benzoic acid methyl ester (D47) (15 g, 45.5 mmol, 1 equiv), 10% palladium on charcoal (50% wet, 1.5 g, 5% w/w) and NH$_4$COOH (15 g, 455 mmol, 10 equiv) H$_2$O (50 ml) and MeOH (200 ml) was stirred at 50° C. for 2 h. The mixture was cooled to room temperature and the catalyst was filtered off through a pad of celite. Most of the MeOH was removed in vacuo and the residue was partitioned between saturated aqueous NaHCO$_3$ solution and AcOEt. The aqueous phase was re-extracted with AcOEt. The combined organic phases were dried over MgSO$_4$ and concentrated in vacuo to give 3-amino-5-ethoxy-benzoic acid methyl ester (D49) (8.8 g, 99%) as a pale green solid which was used in the next step without further purification. [M+H]$^+$=196.1, RT=2.49 min Description 50

3-Amino-5-benzyloxy-benzoic acid methyl ester hydrochloride (D50)

3-Benzyloxy-5-(2-trimethylsilanyl-ethoxycarbonylamino)-benzoic acid methyl ester (D48) (8.5 g, 21.2 mmol, 1 equiv) in THF (40 ml) was treated with 1M tetrabutyl ammonium fluoride in THF (40 ml, 40 mmol, 1.9 equiv) and the resulting solution stirred at room temperature for 16 h then concentrated in vacuo. The residue was dissolved in AcOEt (200 ml) and washed with H$_2$O (200 ml) then dried over MgSO$_4$ and concentrated in vacuo. The residue was redissolved in Et$_2$O/EtOAc and treated with 2N HCl in Et$_2$O to give, after filtration, 3-amino-5-benzyloxy-benzoic acid methyl ester hydrochloride (D50) (5.0 g, 80%) as a white solid.

Description 51

3-(4-Chloro-butanoylamino)-5-ethoxy-benzoic acid methyl ester (D51)

3-Amino-5-ethoxy-benzoic acid methyl ester (D49) (4.0 g, 20.5 mmol, 1 equiv) was suspended in CH$_2$Cl$_2$ (40 ml) and treated at room temperature with NEt$_3$ (2.32 g, 23 mmol, 1.1 equiv). The resulting solution was cooled to 0° C. and 4-chlorobutyryl chloride (3.1 g, 22 mmol, 1.1 equiv) was added dropwise. The resulting mixture was stirred at 0° C. for 3 h then allowed to warm to room temperature. The solution was washed with 2N aqueous HCl solution, dried over MgSO$_4$ and concentrated in vacuo to give of 3-(4-chloro-butanoylamino)-5-ethoxy-benzoic acid methyl ester (D51) (7.0 g, 115%) as a brown oil.

Description 52

3-Benzyloxy-5-(3-chloro-propane-1-sulfonylamino)-benzoic acid methyl ester (D52)

A suspension of 3-amino-5-benzyloxy-benzoic acid methyl ester hydrochloride (D50) (5.0 g, 17 mmol, 1 equiv) in CH$_2$Cl$_2$ (100 ml) was treated with DMAP (400 mg, 3.2 mmol) and pyridine (3.5 g, 44 mmol, 2.6 equiv) followed by 3-chloropropanesulfonyl chloride (3.54 g, 20 mmol, 1.2 equiv) dropwise at room temperature. The resulting mixture was stirred for 16 h then concentrated in vacuo. The residue was dissolved in AcOEt (200 ml) and the resulting solution was washed with 2N aqueous HCl solution (100 ml) followed by saturated aqueous NaHCO$_3$ solution (100 ml), dried over MgSO$_4$ and concentrated in vacuo to give 3-benzyloxy-5-(3-chloro-propane-1-sulfonylamino)-benzoic acid methyl ester (D52) (6.0 g, 97%) as a pale pink solid. [M+H]$^+$=366.1, RT=2.34 min Description 53

3-(3-Chloro-propane-1-sulfonylamino)-5-ethoxy-benzoic acid methyl ester (D53)

A suspension of 3-amino-5-ethoxy-benzoic acid methyl ester (D49) (4.0 g, 20.5 mmol, 1 equiv) in CH$_2$Cl$_2$ (100 ml) was treated with DMAP (400 mg, 3.2 mmol,) and pyridine (1.74 g, 22 mmol, 1.1 equiv) followed by 3-chloropropanesulfonyl chloride (3.89 g, 22 mmol, 1.1 equiv) dropwise. The resulting mixture was stirred for 16 h then concentrated in vacuo. The residue was dissolved in AcOEt (200 ml) and the resulting solution was washed with 2N aqueous HCl solution (100 ml) followed by saturated aqueous NaHCO$_3$ solution (100 ml), then dried over MgSO$_4$ and concentrated in vacuo to give 3-(3-chloro-propane-1-sulfonylamino)-5-ethoxy-benzoic acid methyl ester (D53) (6.7 g, 98%) as a pale orange solid.

Description 54

3-Benzyloxy-5-(1,1-dioxo-1/$^6$-isothiazolidin-2-yl)-benzoic acid methyl ester (D54)

A solution of 3-benzyloxy-5-(3-chloro-propane-1-sulfonylamino)-benzoic acid methyl ester (D52) (6.0 g, 17 mmol, 1 equiv) in EtOH (80 ml) was treated with NEt$_3$ (3.4 g, 34 mmol, 2 equiv). The resulting mixture was refluxed for 6 h, cooled to room temperature and concentrated in vacuo to give 3-benzyloxy-5-(1,1-dioxo-1/$^6$-isothiazolidin-2-yl)-benzoic acid methyl ester (D54) (4.5 g, 74%) as a pale pink solid.

Description 55

5-Dimethylthiocarbamoyloxy-isophthalic acid dimethyl ester (D55)

o a solution of 5-hydroxy-isophthalic acid dimethyl ester (D42) (21 g, 100 mmol, 1 equiv) in DMF (300 ml) at room temperature was added DABCO (14.6 g, 130 mmol, 1.3 equiv) followed by dimethylthiocarbamoyl chloride (14.8 g, 120 mmol, 1.2 equiv). The resulting mixture was stirred at room temperature for 16 h and at 60° C. for 2 h, then cooled to room temperature and concentrated in vacuo. The residue was partitioned between AcOEt and H$_2$O and the aqueous phase re-extracted with AcOEt. The combined organic solution was washed sequentially with 5% aqueous citric acid solution, 2N aqueous NaOH solution and brine, then dried over MgSO$_4$ and concentrated in vacuo to give 5-dimethylthiocarbamoyloxy-isophthalic acid dimethyl ester (D55) (23.5 g, 79%) as a pale yellow oil. [M+H]$^+$=298.0, RT=3.06 min Description 56

5-Dimethylcarbamoylsulfanyl-isophthalic acid dimethyl ester (D56)

5-Dimethylthiocarbamoyloxy-isophthalic acid dimethyl ester (D55) (15.5 g, 52.2 mmol, 1 equiv) was stirred at 200° C. for 24 h under nitrogen then cooled to room temperature. Purification by flash chromatography on silica gel (iso-hexane/AcOEt: 4/1 then 3/1) gave 5-dimethylcarbamoylsulfanyl-isophthalic acid dimethyl ester (D56) (7.0 g, 45%) and recovered 5-dimethylthiocarbamoyloxy-isophthalic acid dimethyl ester (D55) (2.77 g, 18%), both as white solids. [M+H]$^+$=298.0, RT=2.92 min Description 57

5-Dimethylcarbamoylsulfanyl-isophthalic acid monomethyl ester (D57)

To a solution of 5-dimethylcarbamoylsulfanyl-isophthalic acid dimethyl ester (D56) (6 g, 20.2 mmol, 1 equiv) in THF (100 ml) at room temperature was added 2N aqueous NaOH solution (9.6 ml, 19.2 mmol, 0.95 equiv). The resulting mixture was stirred for 11 h and then partitioned between AcOEt and H$_2$O. The two layers were separated and the aqueous phase extracted with AcOEt. After acidification to pH 1, the aqueous phase was extracted twice with AcOEt. The organic solution was dried over MgSO$_4$ then concentrated in vacuo to give 5-dimethylcarbamoylsulfanyl-isophthalic acid monomethyl ester (D57) (4.54 g, 79%) as a white solid.

Description 58 tert-Butoxycarbonylamino-dimethylcarbamoylsulfanyl-benzoic acid methyl ester (D58)

To a solution of crude 5-dimethylcarbamoylsulfanyl-isophthalic acid monomethyl ester (D57) (4.56 g, 16.1 mmol, 1 equiv) in toluene (100 ml) was added triethylamine (6.7 ml, 48 mmol, 3 equiv) and diphenylphosphoryl azide (5.2 ml, 24 mmol, 1.5 equiv). The resulting mixture was stirred under nitrogen at 80° C. for 3 h and then tert-butanol (4.6 ml, 48 mmol, 3 equiv) was added. The solution was stirred at 80° C. for another 16 h then cooled to room temperature and concentrated in vacuo. The crude product was dissolved in AcOEt and the resulting solution washed sequentially with 2N aqueous NaOH solution, 2N aqueous HCl solution and brine, dried over MgSO$_4$ and concentrated in vacuo. Purification by flash chromatography on silica gel (isohexane/AcOEt: 3/1 to 6/4) gave tert-butoxycarbonylamino-dimethylcarbamoylsulfanyl-benzoic acid methyl ester (D58) (2.24 g, 40%) as a white solid.

Description 59

3-tert-Butoxycarbonylamino-5-mercapto-benzoic acid (D59)

To a solution of tert-butoxycarbonylamino-dimethylcarbamoylsulfanyl-benzoic acid methyl ester (D58) (2.24 g, 6.3 mmol, 1 equiv) in MeOH (30 ml) and H$_2$O (23 ml) was added 2N aqueous NaOH solution (7 ml, 14 mmol, 2.2 equiv). The resulting mixture was refluxed for 3 h and then cooled to room temperature and concentrated in vacuo. The residue was partitioned between AcOEt and 1N aqueous NaOH solution. The aqueous phase was acidified to pH 1 and extracted twice with AcOEt. The combined organic solutions were dried over MgSO$_4$ then concentrated in vacuo to give 3-tert-butoxycarbonylamino-5-mercapto-benzoic acid (D59) (1.54 g, 90%) as a white solid.

Description 60

3-tert-Butoxycarbonylamino-5-methylsulfanyl-benzoic acid methyl ester (D60)

To a solution of 3-tert-butoxycarbonylamino-5-mercapto-benzoic acid (D59) (0.68 g, 2.52 mmol, 1 equiv) in acetone (15 ml) was added K$_2$CO$_3$ (3.5 g, 25.3 mmol, 10 equiv) and iodomethane (473 μl, 7.59 mmol, 3 equiv). The resulting mixture was stirred at 50° C. for 2 h, cooled to room temperature and concentrated in vacuo. The residue was partitioned between AcOEt and H$_2$O. The organic layer was washed with H$_2$O and brine, dried over MgSO$_4$ and concentrated in vacuo. Purification by flash chromatography on silica gel (iso-hexane/AcOEt: 85/15) gave 3-tert-butoxycarbonylamino-5-methylsulfanyl-benzoic acid methyl ester (D60) (0.47 g, 63%) as a white solid. [M−H]$^-$=296.1, RT=3.51 min Description 61

3-tert-Butoxycarbonylamino-5-ethylsulfanyl-benzoic acid ethyl ester (D61)

Description 61 was obtained from 0.68 g (2.53 mmol) of 3-tert-butoxycarbonylamino-5-methylsulfanyl-benzoic acid methyl ester (D59) and iodoethane using the procedure described in Description 60, which yielded the title compound (D61) (0.58 g, 71%) as a white solid. [M−H]$^-$=324.2, RT=3.79 min Description 62

3-Amino-5-methylsulfanyl-benzoic acid methyl ester hydrochloride (D62)

3-tert-Butoxycarbonylamino-5-methylsulfanyl-benzoic acid methyl ester (D60) (0.54 g, 1.82 mmol, 1 equiv) was dissolved in dioxan (2 ml) and 4M HCl in dioxan (16 mmol, 4 ml, 8.8 equiv) was added. The solution was stirred at room temperature for 2 h allowing the hydrochloride salt of the amine to precipitate. This precipitate was filtered off, washed with Et$_2$O and dried giving 3-amino-5-methylsulfanyl-benzoic acid methyl ester hydrochloride (D62) (0.224 g, 52%). [M+H]$^+$=198.1, RT=2.68 min Description 63

3-Amino-5-ethylsulfanyl-benzoic acid ethyl ester hydrochloride (D63)

Description 63 was prepared from 0.57 g (1.75 mmol) of 3-tert-butoxycarbonylamino-5-ethylsulfanyl-benzoic acid ethyl (D61) in an analogous manner to that described in Description 62 which yielded 0.335 g (73%) of 3-amino-5-ethylsulfanyl-benzoic acid ethyl ester hydrochloride (D63) as a white solid. [M+H]$^+$=226.1, RT=3.13 min Description 64

3-(4-Chloro-butanoylamino)-5-methylsulfanyl-benzoic acid methyl ester (D64)

To a solution of 3-amino-5-methylsulfanyl-benzoic acid methyl ester hydrochloride (D62) (0.13 g, 0.556 mmol, 1 equiv) in dry CH$_2$Cl$_2$ (2 ml) at 0° C. was added NEt$_3$ (193 ml, 1.39 mmol, 2.5 equiv) then 4-chlorobutyryl chloride (69 ml, 0.612 mmol, 1.1 equiv), dropwise, over 2 min. The resulting solution was stirred at 0° C. for 15 min then at room temperature for 30 min. The solution was then diluted with AcOEt, washed sequentially with 2N aqueous HCl solution, saturated aqueous NaHCO$_3$ solution and brine, dried over Na$_2$SO$_4$ and concentrated in vacuo to give 3-(4-chloro-butanoylamino)-5-methylsulfanyl-benzoic acid methyl ester (D64) (173 mg, 103%) as pale yellow crystals. [M+H]$^+$=302.0, RT=3.20 min Description 65

3-(4-Chloro-butanoylamino)-5-ethylsulfanyl-benzoic acid ethyl ester (D65)

Description 65 was prepared from 140 mg (0.535 mmol) of 3-amino-5-ethylsulfanyl-benzoic acid ethyl ester hydrochloride (D63) in an analogous manner to that described in Description 64 which yielded 182 mg (103%) of 3-(4-chloro-butanoylamino)-5-ethylsulfanyl-benzoic acid ethyl ester (D65) as pale yellow crystals. [M+H]$^+$=330.0, RT=3.51 min Description 66

3-(3-Chloro-propane-1-sulfonylamino)-5-methylsulfanyl-benzoic acid methyl ester (D66)

To a solution of 3-amino-5-methylsulfanyl-benzoic acid methyl ester hydrochloride (D62) (130 mg, 0.556 mmol, 1 equiv) in CH$_2$Cl$_2$ (2 ml) was added pyridine (142 ml, 1.75 mmol, 3 equiv), DMAP (6.8 mg, 0.056 mmol, 0.1 equiv) and then 3-chloropropane sulfonyl chloride (71 µl, 0.584 mmol, 1.05 equiv) dropwise over 2 min. The resulting mixture was stirred at room temperature for 2 h, diluted with AcOEt, washed sequentially with 2N aqueous HCl solution, saturated aqueous NaHCO$_3$ solution and brine, dried over Na$_2$SO$_4$ and concentrated in vacuo to give 3-(3-chloropropane-1-sulfonylamino)-5-methylsulfanyl-benzoic acid methyl ester (D66) (196 mg, 104%) as light brown crystals. [M−H]$^−$=336.0 RT=3.20 min Description 67

3-(3-Chloro-propane-1-sulfonylamino)-5-ethylsulfanyl-benzoic acid ethyl ester (D67)

Description 67 was prepared from 140 mg (0.6 mmol) of 3-amino-5-ethylsulfanyl-benzoic acid ethyl ester hydrochloride (D63) in an analogous manner to that described in Description 66 which yielded 200 mg (102%) of crude 3-(3-chloro-propane-1-sulfonylamino)-5-ethylsulfanyl-benzoic acid ethyl ester (D67) as light brown crystals. [M−H]$^−$=364.0, RT=3.49 min Description 68

3-(2-Oxo-piperidin-1-yl)-5-(E/Z)-propenyl-benzoic acid tert-butyl ester (D68)

To a solution of 3-bromo-5-(2-oxo-piperidin-1-yl)-benzoic acid tert-butyl ester (D10) (500 mg, 1.4 mmol, 1 equiv) in DME (14 ml) and H$_2$O (4 ml) was added tetrakis(triphenylphosphine)-palladium(0) (81 mg, 0.07 mmol, 0.05 equiv), and the suspension was stirred for 10 min. 2,4,6 Tripropenylcyclotriboroxane-pyridine complex (394 mg, 1.4 mmol, 1 equiv) and K$_2$CO$_3$ (193 mg, 1.4 mmol, 1 equiv) were added and the resulting mixture was stirred at 90° C. for 1 h, cooled to room temperature and diluted with AcOEt. The organic phase was washed with H$_2$O, dried over MgSO$_4$ and concentrated in vacuo. Purification by flash chromatography on silica gel (iso-hexane/AcOEt: 4/1) gave 3-(2-oxopiperidin-1-yl)-5-(E/Z)-propenyl-benzoic acid tert-butyl ester (D68) (480 mg, 100%) of adduct as a pale yellow oil. [M+H]$^+$=316.2, RT=3.41 min Descriptions 69-72

Descriptions 69-72 were prepared in an analogous manner to that described for Description 68 from the appropriate aryl bromide starting material indicated in the below table using the appropriate 2,4,6 trialkenylcyclotriboroxane-pyridine complex as described by F. Kerins and D. F. O' Shea in *J. Org. Chem*, 2002, 67, 4968-4971:

| Description | Aryl bromide | [M + H]$^+$ | RT (min) |
| --- | --- | --- | --- |
| 3-(1,1-Dioxo-1/$^6$-[1,2]thiazinan-2-yl)-5-(E/Z)-propenyl-benzoic acid tert-butyl ester (D69) | D18 | (-tBu) 296.1 | 3.61 |
| 3-(2-Oxo-pyrrolidin-1-yl)-5-vinyl-benzoic acid methyl ester (D70) | D9a | | |
| 3-Isopropenyl-5-(2-oxo-pyrrolidin-1-yl)-benzoic acid methyl ester (D71) | D9a | 260.0 | 2.96 |
| 3-(2-Oxo-pyrrolidin-1-yl)-5-(E/Z)-propenyl-benzoic acid methyl ester (D72) | D9a | 260.0 | 2.97 |

Description 73

3-Cyclopent-2-enyl-5-(2-oxo-pyrrolidin-1-yl)-benzoic acid methyl ester;

3-Cyclopent-3-enyl-5-(2-oxo-pyrrolidin-1-yl)-benzoic acid methyl ester; and

3-Cyclopent-1-enyl-5-(2-oxo-pyrrolidin-1-yl)-benzoic acid methyl ester (D73)

To a solution of 3-bromo-5-(2-oxo-pyrrolidin-1-yl)-benzoic acid methyl ester (D9a) (686 mg, 2.3 mmol, 1 equiv) in DMF (3 ml) was added cyclopentene (409 µl, 4.6 mmol, 2 equiv), palladium(II)acetate (26 mg, 0.12 mmol, 0.05 equiv), tri(o-tolyl)phosphine (71 mg, 0.23 mmol, 0.1 equiv) and triethylamine (969 µl, 7 mmol, 3 equiv). The resulting mixture was stirred at 125° C. for 16 h then cooled to room temperature and partitioned between $H_2O$ and $Et_2O$. The two layers were separated and the organic phase was dried over $Na_2SO_4$ and concentrated in vacuo to give a mixture of 3-cyclopent-2-enyl-5-(2-oxo-pyrrolidin-1-yl)-benzoic acid methyl ester, 3-cyclopent-3-enyl-5-(2-oxo-pyrrolidin-1-yl)-benzoic acid methyl ester and 3-cyclopent-1-enyl-5-(2-oxo-pyrrolidin-1-yl)-benzoic acid methyl ester (D73) (562 mg, 85%) as a brown oil.

Description 74

3-Cyclohex-2-enyl-5-(2-oxo-pyrrolidin-1-yl)-benzoic acid methyl ester;

3-Cyclohex-3-enyl-5-(2-oxo-pyrrolidin-1-yl)-benzoic acid methyl ester; and

3-Cyclohex-1-enyl-5-(2-oxo-pyrrolidin-1-yl)-benzoic acid methyl ester (D74)

Description 74 was prepared in an analogous manner to that described for Description 73 from 686 mg (mmol) of 3-bromo-5-(2-oxo-pyrrolidin-1-yl)-benzoic acid methyl ester (D9a) and cyclohexene which yielded 207 mg (30%) of 3-cyclohex-2-enyl-5-(2-oxo-pyrrolidin-1-yl)-benzoic acid methyl ester, 3-cyclohex-3-enyl-5-(2-oxo-pyrrolidin-1-yl)-benzoic acid methyl ester and 3-cyclohex-1-enyl-5-(2-oxo-pyrrolidin-1-yl)-benzoic acid methyl ester (D74) after purification by flash chromatography on silica gel (iso-hexane/EtOAc: 5/1)

Description 75

3-(1,1-Dioxo-1/$^6$-isothiazolidin-2-yl)-5-(3-hydroxy-3-methyl-but-1-ynyl)-benzoic acid tert-butyl ester (D75)

To a solution of 3-bromo-5-(1,1-dioxo-1/$^6$-isothiazolidin-2-yl)-benzoic acid tert-butyl ester (D17) (376 mg, 1 mmol, 1 equiv) in DME (5 ml) and $H_2O$ (5 ml) were added $K_2CO_3$ (345 mg, 2.5 mmol, 2.5 equiv), CuI (8 mg, 0.04 mmol, 0.04 equiv), triphenyl phosphine (21 mg, 0.08 mmol, 0.08 equiv), 10% palladium on charcoal (21 mg, 0.02 mmol, 0.02 equiv) and the solution was stirred at room temperature for 15 min. 2-Methyl-3-butyne-2-ol (254 µl, 2.5 mmol, 2.5 equiv) was added and the resulting mixture was stirred at 80° C. for 16 h then cooled to room temperature. The catalyst was removed by filtration through a pad of celite and the filtrate was diluted with AcOEt. The organic phase was washed with 2N aqueous HCl solution, saturated aqueous $NaHCO_3$ solution, dried over $MgSO_4$ and concentrated in vacuo. Purification by flash chromatography on silica gel (iso-hexane/AcOEt: 4/1 to 2/1) gave 3-(1,1-dioxo-1/$^6$-isothiazolidin-2-yl)-5-(3-hydroxy-3-methyl-but-1-ynyl)-benzoic acid tert-butyl ester (D75) (142 mg, 37%) as a colorless oil which solidified on standing.

Description 76

3-(3-Hydroxy-3-methyl-but-1-ynyl)-5-(2-oxo-pyrrolidin-1-yl)-benzoic acid tert-butyl ester (D76)

Description 76 was prepared using an analogous process to that described for Description 75 from 390 mg of 3-bromo-5-(2-oxo-pyrrolidin-1-yl)-benzoic acid tert-butyl ester (D9b) which yielded 300 mg (76%) of 3-(3-hydroxy-3-methyl-but-1-ynyl)-5-(2-oxo-pyrrolidin-1-yl)-benzoic acid tert-butyl ester (D76) as a white foam.

Description 77

5-nitro-isophthalic acid monomethyl ester (D77)

Description 77 is commercially available from Sigma-Aldrich Company.

Description 78

5-Nitro-isophthalic acid 1-tert-butyl ester 3-methyl ester (D78)

A mixture of 5-nitro-isophthalic acid monomethyl ester (D77) (5.0 g, 22.2 mmol, 1 equiv), tert-BuOH (8.2 g, 111 mmol, 5 equiv), EDAC.HCl (4.8 g, 25 mmol, 1.1 equiv) and DMAP (205 mg, 1.68 mmol, 0.07 equiv) dissolved in $CH_2Cl_2$ (50 ml) was stirred for 1 h at room temperature The mixture was then diluted with $CH_2Cl_2$ (50 ml), washed with 2N aqueous HCl solution (50 ml) and saturated aqueous $NaHCO_3$ solution (50 ml), dried over $MgSO_4$ and concentrated in vacuo to give of 5-nitro-isophthalic acid 1-tert-butyl ester 3-methyl ester (D78) (5.3 g, 85%) as a pale yellow oil.

Description 79

5-Amino-isophthalic acid 1-tert-butyl ester 3-methyl ester (D79)

A mixture of 5-nitro-isophthalic acid 1-tert-butyl ester 3-methyl ester (D78) (5.3 g, 19 mmol, 1 equiv), $NH_4COOH$ (11.9 g, 190 mmol, 10 equiv) and 10% Palladium on charcoal (50% wet, 0.75 g, 7% w/w) in EtOH (50 ml) and $H_2O$ (25 ml) was heated at 50° C. for 30 min. MeOH (20 ml) was added and the resulting solution was heated at 50° C. for another hour then cooled to room temperature, filtered through a pad of celite and concentrated in vacuo. The residue was diluted with saturated aqueous $NaHCO_3$ solution (100 ml) and the aqueous phase was extracted with AcOEt (150 ml). The organic phase was dried over $MgSO_4$ and concentrated in vacuo. The residue was triturated with iso-hexane to give of 5-amino-isophthalic acid 1-tert-butyl ester 3-methyl ester (D79) (3.4 g, 71%) as a white solid.

Description 80

5-(4-Chloro-butanoylamino)-isophthalic acid 1-tert-butyl ester 3-methyl ester (D80)

A suspension of 5-amino-isophthalic acid 1-tert-butyl ester 3-methyl ester (D79) (3.4 g, 13.5 mmol, 1 equiv) in $CH_2Cl_2$ (25 ml) was treated with $NEt_3$ (2.32 g, 23 mmol, 1.1 equiv) and cooled to 0° C. 4-chlorobutyryl chloride (1.6 g, 15.7 mmol, 1.1 equiv) was added dropwise and the resulting solution was stirred at 0° C. for 3 h then allowed to warm to room temperature and washed with 2N aqueous HCl solution, dried over $MgSO_4$ and concentrated in vacuo. The residue was triturated with iso-hexane and $Et_2O$ to give 5-(4-chloro-butanoylamino)-isophthalic acid 1-tert-butyl ester 3-methyl ester (D80) (4.5 g, 94%) as a white solid.

Description 81

5-(3-Chloro-propane-1-sulfonylamino)-isophthalic acid 1-tert-butyl ester 3-methyl ester (D81)

To a solution of 5-amino-isophthalic acid 1-tert-butyl ester 3-methyl ester (D79) (5.0 g, 20 mmol, 1 equiv), DMAP (0.3 g, 2.46 mmol, 0.12 equiv) and pyridine (1.64 g, 20 mmol, 1 equiv) in $CH_2Cl_2$ (80 ml) was added 3-chloropropanesulfonyl chloride (2.4 ml, 20 mmol, 1 equiv) dropwise. The resulting mixture was stirred for 16 h then diluted with AcOEt (150 ml). The organic phase was washed with 2N aqueous HCl solution and saturated aqueous $NaHCO_3$ solution, dried over $MgSO_4$ and concentrated in vacuo to give 5-(3-chloro-propane-1-sulfonylamino)-isophthalic acid 1-tert-butyl ester 3-methyl ester (D81) (7.8 g, 99%) as a pale orange solid.

Description 82

5-(1,1-Dioxo-1/$^6$-isothiazolidin-2-yl)-isophthalic acid 1-tert-butyl ester 3-methyl ester (D82)

A mixture of 5-(3-chloro-propane-1-sulfonylamino)-isophthalic acid 1-tert-butyl ester 3-methyl ester (D81) (7.8 g, 20 mmol, 1 equiv) and $NEt_3$ (4.0 g, 40 mmol, 2 equiv) in EtOH (100 ml) was refluxed for 3 h, cooled to room temperature and concentrated in vacuo. The residue was diluted with AcOEt and the organic phase was washed with 2N aqueous HCl solution and saturated aqueous $NaHCO_3$ solution, dried over $MgSO_4$ and concentrated in vacuo to give 5-(1,1-dioxo-1/$^6$-isothiazolidin-2-yl)-isophthalic acid 1-tert-butyl ester 3-methyl ester (D82) (4.4 g, 62%) as a white solid.

Description 83

5-(1,1-Dioxo-1/$^6$-isothiazolidin-2-yl)-isophthalic acid monomethyl ester (D83)

A suspension of 5-(1,1-dioxo-1/$^6$-isothiazolidin-2-yl)-isophthalic acid 1-tert-butyl ester 3-methyl ester (D82) (4.4 g, 12.4 mmol, 1 equiv) in $CH_2Cl_2$ (10 ml) was treated with TFA (10 ml) and the resulting mixture was stirred for 2 h at room temperature. Toluene (10 ml) was added and the resulting mixture was concentrated in vacuo. The residue was triturated with $Et_2O$ to give 5-(1,1-dioxo-1/$^6$-isothiazolidin-2-yl)-isophthalic acid monomethyl ester (D83) (3.6 g, 97%) as a white solid.

Description 84

3-(1,1-Dioxo-1/$^6$-isothiazolidin-2-yl)-5-hydroxymethyl-benzoic acid methyl ester (D84)

A solution of 5-(1,1-dioxo-1/3-isothiazolidin-2-yl)-isophthalic acid monomethyl ester (D83) (500 mg, 1.67 mmol, 1 equiv) in THF (30 ml) was treated with $BH_3\text{-}Me_2S$ (2M solution in THF, 1.0 ml, 2 mmol, 1.2 equiv) and the mixture was refluxed for 30 min and then cooled to room temperature. MeOH (5 ml) was added dropwise and the resulting mixture was concentrated in vacuo. The residue was diluted with AcOEt (100 ml), and the resulting solution was washed with 2N aqueous HCl solution (100 ml) and saturated aqueous $NaHCO_3$ solution, dried over $MgSO_4$. and concentrated in vacuo to give 3-(1,1-dioxo-1/$^6$-isothiazolidin-2-yl)-5-hydroxymethyl-benzoic acid methyl ester (D84) (450 mg, 95%) as a clear, colourless oil.

Description 85

3-(1,1-Dioxo-1/$^6$-isothiazolidin-2-yl)-5-methanesulfonyloxymethyl-benzoic acid methyl ester (D85)

A solution of 3-(1,1-dioxo-1/$^6$-isothiazolidin-2-yl)-5-ethoxymethyl-benzoic acid (D84) (400 mg, 1.4 mmol, 1 equiv) in $CH_2Cl_2$ (20 ml) was treated with $NEt_3$ (303 mg, 3.0 mmol, 2.1 equiv) and methanesulfonic anhydride (261 mg, 1.5 mmol, 1.1 equiv) and stirred for 30 min at room temperature. The solution was then washed with 2N aqueous HCl solution (30 ml) and saturated aqueous $NaHCO_3$ solution (30 ml), dried over $MgSO_4$ and concentrated in vacuo. The residue was triturated in $Et_2O$ to give 3-(1,1-dioxo-1/$^6$-isothiazolidin-2-yl)-5-methanesulfonyloxymethyl-benzoic acid methyl ester (D85) (390 mg, 77%) as a white solid.

Description 86

3-(1,1-Dioxo-1/$^6$-isothiazolidin-2-yl)-5-formyl-benzoic acid methyl ester (D86)

A solution of 3-(1,1-dioxo-1/$^6$-isothiazolidin-2-yl)-5-hydroxymethyl-benzoic acid methyl ester (D84) (500 mg, 1.8 mmol, 1 equiv) in $CH_2Cl_2$ (20 ml) was treated with $MnO_2$ (763 mg, 8.8 mmol, 4.9 equiv) and the resulting mixture was stirred for 3 h at room temperature. A second portion of $MnO_2$ (500 mg, 5.8 mmol, 3.2 equiv) was added and the mixture stirred for 3 h when a third portion of $MnO_2$ (300 mg, 3.5 mmol, 1.9 equiv) was added. The mixture was stirred for 2 h and then filtered through a pad of celite. The filtrate was concentrated in vacuo to give 3-(1,1-dioxo-1/$^6$-isothiazolidin-2-yl)-5-formyl-benzoic acid methyl ester (D86) (450 mg, 88%) as a yellow waxy solid.

Description 87

5-Nitro-N,N-dipropyl-isophthalamic acid methyl ester (D87)

A suspension of 5-nitro-isophthalic acid monomethyl ester (D77) (1.0 g, 4.44 mmol, 1 equiv) in $CH_2Cl_2$ (40 ml) was treated with $(COCl)_2$ (655 mg, 5.2 mmol, 1.2 equiv) followed by a few drops of DMF. The resulting mixture was stirred for 1 h at room temperature and then dipropylamine (1.65 g, 15 mmol, 3.4 equiv) was added and the resulting solution stirred for a further 30 min. The solution was then washed with 2N aqueous HCl solution (50 ml), saturated aqueous $NaHCO_3$ solution (50 ml), dried over $MgSO_4$ and concentrated in vacuo to give 5-nitro-N,N-dipropyl-isophthalamic acid methyl ester (D87) (1.5 g, 110%) as a pale yellow oil.

Description 88

5-Amino-N,N-dipropyl-isophthalamic acid methyl ester (D88)

A mixture of 5-nitro-N,N-dipropyl-isophthalamic acid methyl ester (D87) (1.5 g, 4.9 mmol, 1 equiv), $NH_4COOH$ (3.0 g, 49 mmol, 10 equiv), 10% Pd on charcoal (50% wet, 250 mg, 0.082 equiv w/w), EtOH (20 ml) and $H_2O$ (10 ml) was heated at 50° C. for 90 min. The mixture was cooled to room temperature, filtered through a pad of celite and concentrated in vacuo. The residue was dissolved in AcOEt (200 ml) and the resulting solution was washed with saturated NaHCO$_3$ solution (100 ml), dried over MgSO$_4$ and concentrated in vacuo to give 5-amino-N,N-dipropyl-isophthalamic acid methyl ester (D88) (1.2 g, 88%) as a white waxy solid.

Description 89

5-(4-Chloro-butanoylamino)-N,N-dipropyl-isophthalamic acid methyl ester (D89)

A solution of 5-amino-N,N-dipropyl-isophthalamic acid methyl ester (D88) (1.2 g, 4.3 mmol, 1 equiv) in CH$_2$Cl$_2$ (10 ml) was treated with NEt$_3$ (525 mg, 5.2 mmol, 1.2 equiv). The solution was cooled to 0° C. and 4-chlorobutyryl chloride (733 mg, 5.0 mmol, 1.2 equiv) was added dropwise. The reaction mixture was then allowed to warm to room temperature and stirred for 1 h. The solution was washed with 2N aqueous HCl solution (20 ml), dried over MgSO$_4$ and concentrated in vacuo to give 5-(4-chloro-butanoylamino)-N,N-dipropyl-isophthalamic acid methyl ester (D89) (1.7 g, 104%) as a colourless oil.

Description 90

5-(5-Chloro-pentanoylamino)-N,N-dipropyl-isophthalamic acid methyl ester (D90)

Description 90 was prepared in an analogous manner to Description 89 from 5-amino-N,N-dipropyl-isophthalamic acid methyl ester (D88) and 5-chlorovaleryl chloride.

Description 91

5-(3-Chloro-propane-1-sulfonylamino)-N,N-dipropyl-isophthalamic acid methyl ester (D91)

A solution of 5-amino-N,N-dipropyl-isophthalamic acid methyl ester (D88) (1.4 g, 5.0 mmol, 1 equiv), DMAP (100 mg) and pyridine (392 mg, 5.0 mmol, 1.1 equiv) in CH$_2$Cl$_2$ (20 ml) was treated dropwise with 3-chloropropane-1-sulfonyl chloride (946 mg, 5.3 mmol, 1.1 equiv). The resulting mixture was stirred for 16 h at room temperature and then diluted with AcOEt (100 ml). The resulting solution was washed with 2N aqueous HCl solution (50 ml) followed by saturated aqueous NaHCO$_3$ solution (50 ml), dried over MgSO$_4$ and concentrated in vacuo. The residue was triturated with Et$_2$O to give 5-(3-chloro-propane-1-sulfonylamino)-N,N-dipropyl-isophthalamic acid methyl ester (D91) (1.8 g, 86%) as a pink solid.

Description 92

5-(4-Chloro-butane-1-sulfonylamino)-N,N-dipropyl-isophthalamic acid methyl ester (D92)

Description 92 was prepared in an analogous manner to Description 91 from 5-amino-N,N-dipropyl-isophthalamic acid methyl ester (D88) and 4-chloro-butane-1-sulfonyl chloride.

Description 93

(2S,3R)-3-Hydroxy-2-((S)-2-hydroxy-1-phenyl-ethylamino)-hexanoic acid methyl ester (D93)

Description 93 was obtained according to Alker, D.; Hamblett, G.; Harwood, L. M.; Robertson, S. M.; David, J.; Williams, C. E. *Tetrahedron*, 54 (22), 1998, 6089-6098.

Description 94

(2S,3R)-2-tert-Butoxycarbonylamino-3-hydroxy-hexanoic acid methyl ester (D94)

(2S,3R)-3-Hydroxy-2-((S>2-hydroxy-1-phenyl-ethylamino)-hexanoic acid methyl ester (D93) (2.88 g, 10.25 mmol, 1 equiv), 10% palladium on charcoal (50% wet, 2 g, 35% w/w), HCOOH (5 ml, excess) in MeOH (50 ml) were stirred at 60° C. for 1 h. The mixture was then cooled to room temperature, filtered through a pad of celite then concentrated in vacuo. The residue was dissolved in dioxan/water (1/1, 50 ml) and NaHCO$_3$ (10 g, excess) then di-tert-butyl dicarbonate (3.37 g, 15 mmol, 1.5 equiv) were added. The resulting mixture was stirred at room temperature for 2 h then concentrated in vacuo. The residue was dissolved in AcOEt and the organic phase was washed successively with 2N aqueous HCl solution and saturated aqueous NaHCO$_3$ solution, dried over MgSO$_4$ and concentrated in vacuo. Purification by flash chromatography on silica gel (CH$_2$Cl$_2$/MeOH 99/1) gave (2S,3R)-2-tert-Butoxycarbonylamino-3-hydroxy-hexanoic acid methyl ester (D94) (1.88 g, 70%) as a colourless gum.

Description 95

(S)-2-tert-butoxycarbonylamino-4-methylsulfanyl-butyric acid (D95)

Description 95 is commercially available from Sigma-Aldrich Company.

Description 96

((S)-1-Isobutylcarbamoyl-3-methylsulfanyl-propyl)-carbamic acid tert-butyl ester (D96)

(S)-2-tert-butoxycarbonylamino-4-methylsulfanyl-butyric acid (D95) (2.0 g, 8.0 mmol, 1 equiv), EDAC.HCl (1.84 g, 9.6 mmol, 1.2 equiv), HOBT (1.47 g, 9.6 mmol, 1.2 equiv), 4-ethylmorpholine (1.76 g, 16 mmol, 2 equiv) and iso-butylamine (952 ml, 9.6 mmol, 1.2 equiv) in CH$_2$Cl$_2$ (10 ml) were stirred at room temperature for 16 h. The solution was concentrated in vacuo and the residue dissolved in AcOEt. The organic phase was washed with 2N aqueous HCl solution, saturated aqueous NaHCO$_3$ solution and brine, dried over MgSO$_4$ and concentrated in vacuo to give ((S)-1-isobutylcarbamoyl-3-methylsulfanyl-propyl)-carbamic acid tert-butyl ester (D96) (2.38 g, 98%) as a colourless oil.

Description 97

(3-methoxy-phenyl)-acetic acid ethyl ester (D97)

Description 97 is commercially available from Sigma-Aldrich Company.

Description 98

2-(3-Methoxy-phenyl)-2-methyl-propionic acid ethyl ester (D98)

To a solution of (3-methoxy-phenyl)-acetic acid ethyl ester (D97) (19.72 g, 0.101 m, 1 equiv) in THF (200 ml) was added NaH (8.8 g, 0.222 mol, 2.2 equiv) then iodomethane (26 ml, 0.4 mol, 4 equiv). The resulting mixture was stirred at room temperature for 16 h then partitioned between AcOEt and a saturated NaHCO$_3$ aqueous solution. The two layers were separated and the organic phase washed with brine, dried over MgSO$_4$ and concentrated in vacuo to give 2-(3-methoxy-phenyl)-2-methyl-propionic acid ethyl ester (D98) (20.85 g, 98%) as an orange oil.

Description 99

2-(3-Methoxy-phenyl)-2-methyl-propionic acid (D99)

To a solution of 2-(3-methoxy-phenyl)-2-methyl-propionic acid ethyl ester (D98) (20.95 g, 94 mmol, 1 equiv) in EtOH (200 ml) was added 2N NaOH aqueous solution (90 ml, 180 mmol, 1.9 equiv) and the resulting mixture was stirred at 70° C. for 16 h then cooled to room temperature. Most of EtOH was removed in vacuo and the residue extracted with AcOEt then acidified to pH 1. The aqueous phase was then extracted with AcOEt and the organic phase dried over $MgSO_4$ and concentrated in vacuo to give 2-(3-methoxy-phenyl)-2-methyl-propionic acid (D99) (15 g, 82%) as a yellow oil.

Description 100

[1-(3-Methoxy-phenyl)-1-methyl-ethyl]-carbamic acid benzyl ester (D100)

To a solution of 2-(3-methoxy-phenyl)-2-methyl-propionic acid (D99) (1 g, 5.15 mmol, 1 equiv) in toluene (20 ml) at room temperature was added $NEt_3$ (1.07 ml, 7.72 mmol, 1.5 equiv) and then diphenylphosphoryl azide (2.2 ml, 10.3 mmol, 2 equiv). The resulting mixture was then heated at 80° C. for 2 h then benzyl alcohol (1.61 ml, 15.45 mmol, 3 equiv) was added and the solution heated for a further 2 h, cooled to room temperature and partitioned between EtOAc and a saturated $NaHCO_3$ aqueous solution. The two layers were separated and the aqueous phase dried over $MgSO_4$ and concentrated. in vacuo. Purification of the residue by flash chromatography on silica gel (iso-hexane/AcOEt: 9/1) gave [1-(3-methoxy-phenyl)-1-methyl-ethyl]-carbamic acid benzyl ester (D100) (1 g, 65%) a yellow gum.

Description 101

((S)-(S)-1-oxiranyl-2-phenyl-ethyl)-carbamic acid tert-butyl ester (D101)

Description 101 is commercially available from Chirex (ref 1819W94, lot#9924382).

Description 102

((1S,2R)-3-Amino-1-benzyl-2-hydroxy-propyl)-carbamic acid tert-butyl ester (D102)

To a solution of ((S)-(S)-1-oxiranyl-2-phenyl-ethyl)-carbamic acid tert-butyl ester (D101) (25 g, 95.1 mmol, 1 equiv)) in MeOH (350 ml) was added aqueous ammonia (32% w/w, 180 ml, 3.2 mol, 3.3 equiv). The resulting mixture was stirred at room temperature for 16 h then concentrated in vacuo to give ((1S,2R)-3-amino-1-benzyl-2-hydroxy-propyl)-carbamic acid tert-butyl ester (D102) (25.2 g, 95%) as a white solid.

Description 103

((2R,3S)-3-tert-Butoxycarbonylamino-2-hydroxy-4-phenyl-butyl)-carbamic acid benzyl ester (D103)

A solution of ((1S,2R)-3-amino-1-benzyl-2-hydroxy-propyl)-carbamic acid tert-butyl ester (D102) (25.6 g, 91.4 mmol, 1 equiv) in DMF (250 ml) at 0° C. was treated with $NEt_3$ (15 ml, 108 mmol, 1.2 equiv) and then with benzyl chloroformate (14 ml, 98 mmol, 1.1 equiv) in DMF (50 ml) dropwise. The resulting solution was stirred at 0° C. for 1 h and at room temperature for 16 h and then concentrated in vacuo. The residue was partitioned between AcOEt and saturated aqueous $NaHCO_3$ solution. The resulting precipitate was diluted with $H_2O$ and filtered to give ((2R,3S)-3-tert-butoxycarbonylamino-2-hydroxy-4-phenyl-butyl)-carbamic acid benzyl ester (D103) (31.5 g, 83%) as a white solid.

Description 104

((2R,3S)-3-Amino-2-hydroxy-4-phenyl-butyl)-carbamic acid benzyl ester (D104)

A solution of ((2R,3S)-3-tert-butoxycarbonylamino-2-hydroxy-4-phenyl-butyl)-carbamic acid benzyl ester (D103) (31.5 g, 76.1 mmol, 1 equiv) in THF (300 ml) was treated with 4N HCl solution in dioxan (40 ml, 160 mmol, 2.1 equiv). The resulting solution was stirred at room temperature for 2 h then concentrated in vacuo. The residue was triturated with $Et_2O$/iso-hexane to give ((2R,3S)-3-amino-2-hydroxy-4-phenyl-butyl)-carbamic acid benzyl ester hydrochloride (D104) (22.1 g, 83%) as a white solid.

Description 105

[(2R,3S)-2-Hydroxy-3-({1-[3-(2-oxo-pyrrolidin-1-yl)-5-pentyloxy-phenyl]-methanoyl}-amino)-4-phenyl-butyl]-carbamic acid benzyl ester (D105)

To a suspension of 3-(2-oxo-pyrrolidin-1-yl)-5-pentyloxy-benzoic acid (A13) (530 mg, 1.82 mmol, 1 equiv) in $CH_2Cl_2$ (20 ml) were added HOBT (300 mg, 2.2 mmol, 1.2 equiv) and EDAC.HCl (420 mg, 2.2 mmol, 1.2 equiv). After stirring for 5 min, 3-(2-oxo-pyrrolidin-1-yl)-5-pentyloxy-benzoic acid hydrochloride (D104) (570 mg, 1.82 mmol, 1 equiv) was added and the resulting mixture was stirred at room temperature for 16 h. The reaction mixture was then diluted with $CH_2Cl_2$ (20 ml) washed with saturated aqueous $NaHCO_3$ solution, dried over $MgSO_4$ and concentrated in vacuo to give [(2R,3S)-2-hydroxy-3-({1-[3-(2-oxo-pyrrolidin-1-yl)-5-pentyloxy-phenyl]-methanoyl}-amino)-4-phenyl-butyl]-carbamic acid benzyl ester (D105) (510 mg, 48%) as a white solid.

Description 106

[(2R,3S)-3-({1-[3-Ethylamino-5-(2-oxo-pyrrolidin-1-yl)-phenyl]-methanoyl}-amino)-2-hydroxy-4-phenyl-butyl]-carbamic acid benzyl ester (D106)

Description 106 was prepared in an analogous manner to Description 105 from 3-(2-oxo-pyrrolidin-1-yl)-5-pentyloxy-benzoic acid hydrochloride (D104) and 3-ethylamino-5-(2-oxo-pyrrolidin-1-yl)-benzoic acid (A31).

Description 107

[(2R,3S)-3-({1-[3-Isopropylamino-5-(2-oxo-pyrrolidin-1-yl)-phenyl]-methanoyl}-amino)-2-hydroxy-4-phenyl-butyl]-carbamic acid benzyl ester (D107)

Description 107 was prepared in an analogous manner to Description 105 from 3-(2-oxo-pyrrolidin-1-yl)-5-isopropylamino-benzoic acid hydrochloride (A44) and ((2R,3S)-3-amino-2-hydroxy-4-phenyl-butyl)-carbamic acid benzyl ester (D104).

Description 108-119

The following compounds (D108-D119) were prepared from Description 104 in an analogous manner to the process described for Description 105 using the appropriate acid.

| Description | Acid |
| --- | --- |
| Phenylmethyl [(2R,3S)-3-({[3-(1,1-dioxidotetrahydro-2H-1,2-thiazin-2-yl)-5-(ethylamino)phenyl]carbonyl}amino)-2-hydroxy-4-phenylbutyl]carbamate (D108) | A73 |
| Phenylmethyl [(2R,3S)-3-({[3-(1,1-dioxidotetrahydro-2H-1,2-thiazin-2-yl)-5-(ethylamino)-2-fluorophenyl]carbonyl}amino)-2-hydroxy-4-phenylbutyl]carbamate (D109) | A119 |
| Phenylmethyl [(2R,3S)-3-({[3-cyclopentyl-5-(2-oxo-1-pyrrolidinyl)phenyl]carbonyl}amino)-2-hydroxy-4-phenylbutyl]carbamate (D110) | A107 |
| Phenylmethyl [(2R,3S)-2-hydroxy-3-({[3-[(1-methylethyl)oxy]-5-(2-oxo-1-pyrrolidinyl)phenyl]carbonyl}amino)-4-phenylbutyl]carbamate (D111) | A12 |
| Phenylmethyl {(2R,3S)-3-[({3-(1,1-dioxidotetrahydro-2H-1,2-thiazin-2-yl)-5-[(1-methylethyl)oxy]phenyl}carbonyl)amino]-2-hydroxy-4-phenylbutyl}carbamate (D112) | A168 |
| Phenylmethyl [(2R,3S)-3-({[3-cyclopentyl-5-(1,1-dioxidotetrahydro-2H-1,2-thiazin-2-yl)phenyl]carbonyl}amino)-2-hydroxy-4-phenylbutyl]carbamate (D113) | A126 |
| Phenylmethyl [(2R,3S)-3-({[3-(ethyloxy)-5-(2-oxo-1-pyrrolidinyl)phenyl]carbonyl}amino)-2-hydroxy-4-phenylbutyl]carbamate (D114) | A11 |
| Phenylmethyl [(2R,3S)-3-({[3-(1,1-dioxido-2-isothiazolidinyl)-5-(ethyloxy)phenyl]carbonyl}amino)-2-hydroxy-4-phenylbutyl]carbamate (D115) | A18 |
| Phenylmethyl {(2R,3S)-3-[({3-(1,1-dioxido-2-isothiazolidinyl)-5-[(1-methylethyl)oxy]phenyl}carbonyl)amino]-2-hydroxy-4-phenylbutyl}carbamate (D116) | A19 |
| Phenylmethyl [(2R,3S)-3-({[3-cyclopentyl-5-(1,1-dioxido-2-isothiazolidinyl)phenyl]carbonyl}amino)-2-hydroxy-4-phenylbutyl]carbamate (D117) | A169 |
| Phenylmethyl [(2R,3S)-3-({[3-(1,1-dioxido-2-isothiazolidinyl)-5-(ethylamino)phenyl]carbonyl}amino)-2-hydroxy-4-phenylbutyl]carbamate (D118) | A70 |
| Phenylmethyl [(2R,3S)-3-({[3-(1,1-dioxidotetrahydro-2H-1,2-thiazin-2-yl)-5-(ethyloxy)phenyl]carbonyl}amino)-2-hydroxy-4-phenylbutyl]carbamate (D119) | A170 |

Description 120-131

The following compounds (D120-D131) were prepared in an analogous manner to the process described for Example 182 using the appropriate precursor:

| Description | Precursor |
| --- | --- |
| N-[(1S,2R)-3-Amino-2-hydroxy-1-(phenylmethyl)propyl]-3-(1,1-dioxidotetrahydro-2H-1,2-thiazin-2-yl)-5-(ethylamino)benzamide (D120) | D108 |
| N-[(1S,2R)-3-Amino-2-hydroxy-1-(phenylmethyl)propyl]-3-(1,1-dioxido tetrahydro-2H-1,2-thiazin-2-yl)-5-(ethylamino)-2-fluorobenzamide (D121) | D109 |
| N-[(1S,2R)-3-Amino-2-hydroxy-1-(phenylmethyl)propyl]-3-cyclopentyl-5-(2-oxo-1-pyrrolidinyl)benzamide (D122) | D110 |
| N-[(1S,2R)-3-Amino-2-hydroxy-1-(phenylmethyl)propyl]-3-[(1-methylethyl)oxy]-5-(2-oxo-1-pyrrolidinyl)benzamide (D123) | D111 |
| N-[(1S,2R)-3-Amino-2-hydroxy-1-(phenylmethyl)propyl]-3-(1,1-dioxidotetrahydro-2H-1,2-thiazin-2-yl)-5-[(1-methylethyl)oxy]benzamide (D124) | D112 |
| N-[(1S,2R)-3-Amino-2-hydroxy-1-(phenylmethyl)propyl]-3-cyclopentyl-5-(1,1-dioxidotetrahydro-2H-1,2-thiazin-2-yl)benzamide (D125) | D113 |
| N-[(1S,2R)-3-Amino-2-hydroxy-1-(phenylmethyl)propyl]-3-(ethyloxy)-5-(2-oxo-1-pyrrolidinyl)benzamide (D126) | D114 |
| N-[(1S,2R)-3-Amino-2-hydroxy-1-(phenylmethyl)propyl]-3-(1,1-dioxido-2-isothiazolidinyl)-5-(ethyloxy)benzamide (D127) | D115 |
| N-[(1S,2R)-3-Amino-2-hydroxy-1-(phenylmethyl)propyl]-3-(1,1-dioxido-2-isothiazolidinyl)-5-[(1-methylethyl)oxy]benzamide (D128) | D116 |
| N-[(1S,2R)-3-Amino-2-hydroxy-1-(phenylmethyl)propyl]-3-cyclopentyl-5-(1,1-dioxido-2-isothiazolidinyl)benzamide (D129) | D117 |
| N-[(1S,2R)-3-Amino-2-hydroxy-1-(phenylmethyl)propyl]-3-(1,1-dioxido-2-isothiazolidinyl)-5-(ethylamino)benzamide (D130) | D118 |
| N-[(1S,2R)-3-Amino-2-hydroxy-1-(phenylmethyl)propyl]-3-(1,1-dioxidotetrahydro-2H-1,2-thiazin-2-yl)-5-(ethyloxy)benzamide (D131) | D119 |

Description 132

Methyl 3-nitro-5-[(1E/Z)-1-propen-1-yl]benzoate (D132)

Methyl 3-nitro-5-[(1E/Z)-1-propen-1-yl]benzoate (D132) was prepared from methyl 3-bromo-5-nitrobenzoate (D11) in an analogous manner to that described for Description 68 (D68). No molecular ion. RT=3.42 min.

Description 133

Methyl 3-amino-5-propylbenzoate (D133)

Methyl 3-amino-5-propylbenzoate (D133) was prepared from methyl 3-nitro-5-[(1E/Z)-1-propen-1-yl]benzoate (D132) in an analogous manner to that described for Ester 116 (B116).

Description 134

Methyl 3-[(3-buten-1-ylsulfonyl)amino]-5-propylbenzoate (D134)

To a solution of methyl 3-amino-5-propylbenzoate (D133) (2.49 g, 12.9 mmol, 1 equiv) in $CH_2Cl_2$ (25 ml) were added pyridine (1.13 ml, 14 mmol, 1.1 equiv), 2-propene-1-sulfonyl chloride (2 g, 12.9 mmol, 1 equiv) and DMAP (350 mg, 2.9 mmol, 0.2 equiv) and the resulting mixture was stirred at room temperature for 4 days. The solution was diluted with AcOEt and the organic phase was washed with $H_2O$, dried over $MgSO_4$ and concentrated in vacuo. Purification of the residue by flash chromatography on silica gel (iso-hexane/AcOEt: 4:1) gave methyl 3-[(3-buten-1-ylsulfonyl)amino]-5-propylbenzoate (D134) (1.3 g, 32%) as a colourless oil. $[M-H]^-=310.0$, RT=3.39 min.

Description 135

Methyl 3-[(3-buten-1-ylsulfonyl)(2-propen-1-yl)amino]-5-propylbenzoate (D135)

To a solution of methyl 3-[(3-buten-1-ylsulfonyl)amino]-5-propylbenzoate (D134) (1.3 g, 4.2 mmol, 1 equiv), 2-propen-1-ol (280 μl, 4.2 mmol, 1 equiv) and triphenylphosphine (1.28 g, 4.9 mmol, 1.15 equiv) in toluene (20 ml) at room temperature was slowly added diisopropyl azodicarboxylate (964 ml, 4.9 mmol, 1.15 equiv). The resulting solution was stirred at this temperature for 30 min then concentrated in vacuo. Purification of the residue by flash chromatography on silica gel (iso-hexane/AcOEt: 4:1) gave methyl 3-[(3-buten-1-ylsulfonyl)(2-propen-1-yl)amino]-5-propylbenzoate (D135) (1.1 g, 75%) as a yellow oil. $[M+H]^+=352.1$, RT=3.63 min.

Description 136

2-Fluoro-3,5-dinitrobenzoic acid (D136)

A 70% aqueous $HNO_3$ solution (80 ml) was added dropwise to $H_2SO_4$ (160 ml). The temperature was kept below 10° C. using an ice-bath. 2-Fluoro benzoic acid (14 g, 0.1 mol, 1 equiv) was added portionwise over 5 min then the colorless suspension was slowly warmed to 90° C. and stirred at this temperature for 1 h then at 100° C. for 3 h. The solution was then cooled to room temperature and carefully poured into ice (1 l) diluted with $H_2O$ (1.5 l). The aqueous phase was extracted 3 times with AcOEt and the combined organic layers dried over $MgSO_4$ and concentrated in vacuo. The residue was triturated with $Et_2O$ to give 2-fluoro-3,5-dinitrobenzoic acid (D136) (13.6 g, 59%) as a pale yellow solid which was used in the next step without further purification. No molecular ion, RT=2.06 min.

Description 137

Methyl 2-fluoro-3,5-dinitrobenzoate (D137)

Methyl 2-fluoro-3,5-dinitrobenzoate (D137) was prepared in an analogous manner to Description 25 (D25) from 2-fluoro-3,5-dinitrobenzoic acid (D136).

Description 138

Methyl 3-amino-2-fluoro-5-nitrobenzoate (D138)

To a solution of methyl 2-fluoro-3,5-dinitrobenzoate (D137) (24.4 g, 0.1 mol, 1 equiv) in AcOH (1 l) was added iron (27.5 g, 0.5 mol, 5 equiv) and the resulting suspension was vigorously stirred for 1 h. The temperature was kept below 35° C. by small amount of cooling using an ice bath during that period. Toluene (200 ml) was added and the suspension filtered through a pad of celite. The remaining solution was concentrated in vacuo and the residue partitioned between AcOEt and a saturated aqueous $NaHCO_3$ solution. The two layers were separated and the aqueous phase was extracted twice with AcOEt. The combined organic phases were dried over $MgSO_4$ and concentrated in vacuo to give methyl 3-amino-2-fluoro-5-nitrobenzoate (D138) (17 g, 79%) as a yellow solid which was used in the next step without further purification. $[M-H]^-=212.9$, RT=2.68 min.

Description 139

Methyl 3-[(4-chlorobutanoyl)amino]-2-fluoro-5-nitrobenzoate (D139)

To a solution of methyl 3-amino-2-fluoro-5-nitrobenzoate (D138) (12 g, 56 mmol, 1 equiv) in $CH_2Cl_2$ (150 ml) at room temperature were added $NEt_3$ (11.7 ml, 84 mmol, 1.5 equiv) and 4-chlorobutanoyl chloride (6.9 ml, 61.6 mmol, 1.1 equiv) and the resulting mixture was stirred for 2 h then washed with a 2N aqueous HCl solution and a saturated aqueous $NaHCO_3$ solution, dried over $MgSO_4$ and concentrated in vacuo. Purification of the residue by flash chromatography on silica gel (iso-hexane/AcOEt: 4/1) gave methyl 3-[(4-chlorobutanoyl)amino]-2-fluoro-5-nitrobenzoate (D139) (16.2 g, 91%) as a yellow solid. $[M+H]^+=319.1$, RT=3.12 min.

Description 140

Methyl 2-fluoro-5-nitro-3-(2-oxo-1-pyrrolidinyl)benzoate (D140)

To a solution of methyl 3-[(4-chlorobutanoyl)amino]-2-fluoro-5-nitrobenzoate (D139) (8.5 g, 26.7 mmol, 1 equiv) in THF (100 ml) was added NaH (60% dispersion in mineral oil, 1.17 g, 29.4 mmol, 1.1 equiv) and the resulting mixture was stirred at room temperature for 1.5 h then diluted with AcOEt. The organic phase was washed with $H_2O$, dried over $MgSO_4$ and concentrated in vacuo. Purification of the residue by flash chromatography on silica gel (iso-hexane/AcOEt: 2/1) gave methyl 2-fluoro-5-nitro-3-(2-oxo-1-pyrrolidinyl)benzoate (D140) (3.3 g, 43%) as a yellow solid. $[M+H]^+=283.1$, RT=2.53 min.

Description 141

Methyl 3-{bis[(3-chloropropyl)sulfonyl]amino}-2-fluoro-5-nitrobenzoate (D141)

To a solution of methyl 3-amino-2-fluoro-5-nitrobenzoate (D138) (500 mg, 2.34 mmol, 1 equiv) in $CH_2Cl_2$ (50 ml) was added $NEt_3$ (840 μl, 6.0 mmol, 2.6 equiv) then 3-chloro-1-propanesulfonyl chloride (624 μl, 5.0 mmol, 2.1 equiv) and the resulting mixture was stirred for 1 h. The organic phase was then washed with a 2N aqueous HCl solution, dried over $MgSO_4$ and concentrated in vacuo to give methyl 3-{bis[(3-chloropropyl)sulfonyl]amino}-2-fluoro-5-nitrobenzoate (D141) (900 mg, 78%) as a brown foam which was used in the next step without further purification. No molecular ion, RT=3.51 min.

Description 142

Methyl 3-{bis[(4-chlorobutyl)sulfonyl]amino}-2-fluoro-5-nitrobenzoate (D142)

Methyl 3-{bis[(4-chlorobutyl)sulfonyl]amino}-2-fluoro-5-nitrobenzoate (D142) was obtained from methyl 3-amino-2-fluoro-5-nitrobenzoate (D138) in an analogous manner to that described for methyl 3-{bis[(3-chloropropyl)sulfonyl]amino}-2-fluoro-5-nitrobenzoate (D141) using 4-chloro-1-butanesulfonyl chloride (D20) instead of 3-chloro-1-propanesulfonyl chloride. $[M+H+ NH_3]^+$=540.1, RT=3.62 min.

Description 143

3-{[(3-Chloropropyl)sulfonyl]amino}-2-fluoro-5-nitrobenzoic acid (D143)

To a solution of crude methyl 3-{bis[(3-chloropropyl)sulfonyl]amino}-2-fluoro-5-nitrobenzoate (D141) (900 mg, 1.81 mmol, 1 equiv) in MeOH (25 ml) was added a 2N aqueous NaOH solution (15 ml, 30 mmol, excess) and the resulting mixture was stirred for 1 h. Most of MeOH was removed in vacuo and the residue partitioned between AcOEt and a 2N aqueous HCl solution. The two layers were separated and the aqueous phase was dried over $MgSO_4$ and concentrated in vacuo. The residue was triturated with $Et_2O$/iso-hexane to give 3-{[(3-chloropropyl)sulfonyl]amino}-2-fluoro-5-nitrobenzoic acid (D143) (600 mg, 97%) as a light tan solid which was used in the next step without further purification. No molecular ion, RT=3.05 min.

Description 144

3-{[(4-Chlorobutyl)sulfonyl]amino}-2-fluoro-5-nitrobenzoic acid (D144)

3-{[(4-Chlorobutyl)sulfonyl]amino}-2-fluoro-5-nitrobenzoic acid (D144) was obtained from methyl 3-{bis[(4-chlorobutyl)sulfonyl]amino}-2-fluoro-5-nitrobenzoate (D142) in an analogous manner to the process described for 3-{[(3-chloropropyl)sulfonyl]amino}-2-fluoro-5-nitrobenzoic acid (D143).

Description 145

Methyl 3-{[(3-chloropropyl)sulfonyl]amino}-2-fluoro-5-nitrobenzoate (D145)

Methyl 3-{[(3-chloropropyl)sulfonyl]amino}-2-fluoro-5-nitrobenzoate (D145) was prepared in an analogous manner to Description 25 from 3-{[(3-chloropropyl)sulfonyl]amino}-2-fluoro-5-nitrobenzoic acid (D143). $[M-H]^-$=353.0, RT=3.05 min.

Description 146

Methyl 3-{[(4-chlorobutyl)sulfonyl]amino}-2-fluoro-5-nitrobenzoate (D146)

Methyl 3-{[(4-chlorobutyl)sulfonyl]amino}-2-fluoro-5-nitrobenzoate (D146) was prepared in an analogous manner to Description 25 from 3-{[(4-chlorobutyl)sulfonyl]amino}-2-fluoro-5-nitrobenzoic acid (D144). $[M+H+ NH_3]^+$=386.1, RT=3.13 min.

Description 147

Methyl 3-(1,1-dioxido-2-isothiazolidinyl)-2-fluoro-5-nitrobenzoate (D147)

To a solution of methyl 3-{[(3-chloropropyl)sulfonyl]amino}-2-fluoro-5-nitrobenzoate (D145) (300 mg, 0.85 mmol, 1 equiv) in EtOH (30 ml) was added $NEt_3$ (280 μl, 2 mmol, 2.3 equiv) and the resulting solution was refluxed for 1.5 h then cooled to room temperature and concentrated in vacuo. The residue was dissolved in AcOEt and the organic phase was washed with a 2N aqueous HCl solution, dried over $MgSO_4$ and concentrated in vacuo. The residue was triturated with $AcOEt/Et_2O$ to give methyl 3-(1,1-dioxido-2-isothiazolidinyl)-2-fluoro-5-nitrobenzoate (D147) (150 mg, 55%) as a light tan solid which was used in the next step without further purification. $[M+H+ NH_3]^+$=336.3, RT=2.50 min.

Description 148

Methyl 3-(1,1-dioxidotetrahydro-2H-1,2-thiazin-2-yl)-2-fluoro-5-nitrobenzoate (D148)

Methyl 3-(1,1-dioxidotetrahydro-2H-1,2-thiazin-2-yl)-2-fluoro-5-nitrobenzoate (D148) was prepared in an analogous manner to the process for methyl 3-(1,1-dioxido-2-isothiazolidinyl)-2-fluoro-5-nitrobenzoate (D147) from methyl 3-{[(4-chlorobutyl)sulfonyl]amino}-2-fluoro-5-nitrobenzoate (D146). $[M+H+ NH_3]^+$=350.1, RT=2.79 min.

Description 149

Methyl 3-(1,1-dioxidotetrahydro-2H-1,2-thiazin-2-yl)-2-(methyloxy)-5-nitrobenzoate (D149)

To a solution of methyl 3-{[(4-chlorobutyl)sulfonyl]amino}-2-fluoro-5-nitrobenzoate (D146) (1.5 g, 4.1 mmol, 1 equiv) in MeOH (30 ml) was added $NEt_3$ (1.2 ml 8.6 mmol, 2.1 equiv) and the resulting solution was refluxed for 15 h then cooled to room temperature and concentrated in vacuo. The residue was dissolved in AcOEt and the organic phase was washed with a 2N aqueous HCl solution, dried over $MgSO_4$ and concentrated in vacuo. The residue was triturated with $AcOEt/Et_2O$ to give methyl 3-(1,1-dioxidotetrahydro-2H-1,2-thiazin-2-yl)-2-(methyloxy)-5-nitrobenzoate (D149) (1.2 g, 55%) as a light brown solid which was used in the next step without further purification. $[M+H]^+$=345.1, RT2.80 min.

Description 150

Methyl 5-amino-2-fluoro-3-(2-oxo-1-pyrrolidinyl)benzoate (D150)

To a solution of methyl 2-fluoro-5-nitro-3-(2-oxo-1-pyrrolidinyl)benzoate (D140) (3.3 g, 11.7 mmol, 1 equiv) in EtOH (100 ml) and H$_2$O (10 ml) were added NH$_4$COOH (7.4 g, 117 mmol, 10 equiv) and 10% palladium on charcoal (50% wet, 660 mg, 10% w/w) and the resulting mixture was refluxed for 2 h then cooled to room temperature. The catalyst was removed by filtration through a pad of celite and most of the solvent removed in vacuo. The residue was partitioned between AcOEt and H$_2$O and the two layers were separated. The organic phase was dried over MgSO$_4$ and concentrated in vacuo to give methyl 5-amino-2-fluoro-3-(2-oxo-1-pyrrolidinyl)benzoate (D150) (1.85 g, 63%) as a pale yellow solid which was used in the next step without further purification. [M+H]$^+$=253.0, RT=2.12 min.

Descriptions 151-153 (D151-153)

The following compounds have been made from the appropriate precursor in an analogous manner to the process described for methyl 5-amino-2-fluoro-3-(2-oxo-1-pyrrolidinyl)benzoate (D150).

| Description | Precursor | [M + H]$^+$ | RT (min) |
|---|---|---|---|
| Methyl 5-amino-3-(1,1-dioxido-2-isothiazolidinyl)-2-fluorobenzoate (D151) | D147 | 289.1 | 2.12 |
| Methyl 5-amino-3-(1,1-dioxidotetrahydro-2H-1,2-thiazin-2-yl)-2-fluorobenzoate (D152) | D148 | 303.1 | 2.33 |
| Methyl 5-amino-3-(1,1-dioxidotetrahydro-2H-1,2-thiazin-2-yl)-2-(methyloxy)benzoate (D153) | D149 | 315.1 | 2.18 |

Description 154

Methyl 2-fluoro-5-({[4-(methyloxy)phenyl]methyl}amino)-3-(2-oxo-1-pyrrolidinyl)benzoate (D154)

Methyl 2-fluoro-5-({[4-(methyloxy)phenyl]methyl}amino)-3-(2-oxo-1-pyrrolidinyl)benzoate (D154) was prepared from methyl 5-amino-2-fluoro-3-(2-oxo-1-pyrrolidinyl)benzoate (D150) in an analogous manner to the process described for Ester 35 (B35) using 4-(methyloxy)benzaldehyde instead of propionaldehyde. [M+H]$^+$=373.4, RT=2.85 min.

Description 155

Methyl 5-(ethyl{[4-(methyloxy)phenyl]methyl}amino)-2-fluoro-3-(2-oxo-1-pyrrolidinyl)benzoate (D155)

Methyl 5-(ethyl{[4-(methyloxy)phenyl]methyl}amino)-2-fluoro-3-(2-oxo-1-pyrrolidinyl)benzoate (D155) was prepared from methyl 2-fluoro-5-({[4-(methyloxy)phenyl]methyl}amino)-3-(2-oxo-1-pyrrolidinyl)benzoate (D154) in an analogous manner to the process described for Ester 35 (B35) using acetaldehyde instead of propionaldehyde. [M+H]$^+$=401.4, RT=3.11 min.

Description 156

Methyl 5-bromo-2-fluoro-3-(2-oxo-1-pyrrolidinyl)benzoate (D156)

To a solution of methyl 5-amino-2-fluoro-3-(2-oxo-1-pyrrolidinyl)benzoate (D150) (650 mg, 2.6 mmol, 1 equiv) in a 48% aqueous HBr solution at 0° C. was added NaNO$_2$ portionwise and the resulting mixture was stirred at 0° C. for 30 min. CuBr (260 mg, 1.82 mmol, 0.7 equiv) in a 48% aqueous HBr solution (1 ml) was added and the resulting mixture stirred at 90° C. for 1 h then cooled to room temperature and partitioned between H$_2$O and AcOEt. The two layers were separated and the organic phase was dried over MgSO$_4$ and concentrated in vacuo. Purification of the residue by flash chromatography on silica gel (iso-hexane/AcOEt: 2/1) gave methyl 5-bromo-2-fluoro-3-(2-oxo-1-pyrrolidinyl)benzoate (D156) (145 mg, 18%) as a white solid. [M+H]$^+$=318.1, RT=2.51 min.

Descriptions 157-158 (D157-158)

The following compounds were prepared in an analogous manner to the process described for Description 156 (D156) from the appropriate aniline:

| Description | Precursor | RT (min) |
|---|---|---|
| Methyl 5-bromo-3-(1,1-dioxido-2-isothiazolidinyl)-2-fluorobenzoate (D157) | D151 | 2.55 |
| Methyl 5-bromo-3-(1,1-dioxidotetrahydro-2H-1,2-thiazin-2-yl)-2-fluorobenzoate (D158) | D152 | |

Descriptions 159-161 (D159-161)

The following compounds were prepared in an analogous manner to the process described for Description 68 (D68) from the appropriate aryl bromide indicated in the below table:

| Description | Precursor | [M + H]$^+$ | RT (min) |
|---|---|---|---|
| Methyl 2-fluoro-3-(2-oxo-1-pyrrolidinyl)-5-[(1E/Z)-1-propen-1-yl]benzoate (D159) | D156 | 278.4 | 2.60 |
| Methyl 3-(1,1-dioxido-2-isothiazolidinyl)-2-fluoro-5-[(1E/Z)-1-propen-1-yl]benzoate (D160) | D157 | 314.2 | 2.67 |
| Methyl 3-(1,1-dioxidotetrahydro-2H-1,2-thiazin-2-yl)-2-fluoro-5-[(1E/Z)-1-propen-1-yl]benzoate (D161) | D158 | | |

Description 162

Methyl 4-methyl-3,5-dinitrobenzoate (D162)

Methyl 4-methyl-3,5-dinitrobenzoate (D162) was prepared in an analogous manner to Description 25 from commercially available 4-methyl-3,5-dinitrobenzoic acid. [M+H]$^+$=240.2, RT=3.07 min.

Description 163

Methyl 3-amino-4-(methyloxy)-5-nitrobenzoate (D163)

To a solution of methyl 4-(methyloxy)-3,5-dinitrobenzoate (D25) (5.0 g, 19.5 mmol, 1 equiv) in AcOH (150 ml) at room temperature was added iron powder (9.0 g, 161 mmol, 8.2 equiv) portionwise and the resulting mixture was stirred for 3 h. Toluene (500 ml) was added and the organic phase was filtered through a pad of celite then concentrated in vacuo. The residue was dissolved in AcOEt and the organic phase was washed with a saturated aqueous NaHCO$_3$ solution, dried over MgSO$_4$ and concentrated in vacuo. Trituration of the residue with Et$_2$O/iso-hexane gave methyl 3-amino-4-(methyloxy)-5-nitrobenzoate (D163) (3.65 g, 83%) as a yellow solid which was used in the next step without further purification. [M+H]$^+$=226.9, RT=2.76 min.

Description 164

Methyl 3-amino-4-methyl-5-nitrobenzoate (D164)

Methyl 3-amino-4-methyl-5-nitrobenzoate (D164) was obtained from methyl 4-methyl-3,5-dinitrobenzoate (D162) in an analogous manner to the process described for methyl 3-amino-4-(methyloxy)-5-nitrobenzoate (D163). [M+H]$^+$=211.0, RT=2.81 min.

Description 165

Methyl 3-iodo-4-(methyloxy)-5-nitrobenzoate (D165)

To a solution of methyl 3-amino-4-(methyloxy)-5-nitrobenzoate (D163) (370 mg, 1.64 mmol, 1 equiv) in toluene (20 ml) at 0° C. was added iodine (218 mg, 0.86 mmol, 0.5 equiv) then 1,1-dimethylethyl nitrite (200 mg, 1.75 mmol, 1.1 equiv) and the resulting mixture was stirred at room temperature for 15 h then partitioned between AcOEt and brine. The two layers were separated and the organic phase was dried over MgSO$_4$ and concentrated in vacuo. Purification of the residue by flash chromatography on silica gel gave methyl 3-iodo-4-(methyloxy)-5-nitrobenzoate (D165) (280 mg, 51%) as a light brown solid. No molecular ion. RT=3.33 min.

Description 166

Methyl 4-(methyloxy)-3-nitro-5-[(1E/Z)-1-propen-1-yl]benzoate (D166)

Methyl 4-(methyloxy)-3-nitro-5-[(1 E/Z)-1-propen-1-yl]benzoate (D166) was prepared from methyl 3-iodo-4-(methyloxy)-5-nitrobenzoate (D165) in an analogous manner to the process described for Description 68 (D68). No molecular ion. RT=3.46 min.

Description 167

Methyl 3-amino-4-(methyloxy)-5-[(1E/Z)-1-propen-1-yl]benzoate (D167)

To a solution of methyl 4-(methyloxy)-3-nitro-5-[(1E/Z)-1-propen-1-yl]benzoate (D166) (1.0 g, 4.0 mmol, 1 equiv) in AcOH (150 ml) at room temperature was added iron powder (1.4 g, 25 mmol, 6.25 equiv) portionwise and the resulting mixture was stirred for 3 h at room temperature. Iron powder (1 g, 17.9 mmol, 4.2 equiv) was added and the mixture stirred for another hour. Iron powder (1 g, 17.9 mmol, 4.2 equiv) was then added again and the mixture stirred at 45° C. for 3 h then cooled to room temperature and stirred at this temperature for 14 h. Toluene (200 ml) was added and the organic phase was filtered through a pad of celite then concentrated in vacuo. The residue was dissolved in AcOEt and the organic phase was washed with a saturated aqueous NaHCO$_3$ solution, dried over MgSO$_4$ and concentrated in vacuo to give methyl 3-amino-4-(methyloxy)-5-[(1E/Z)-1-propen-1-yl]benzoate (D167) (800 mg, 90%) as a brown oil which was used in the next step without further purification. [M+H]$^+$=222.1, RT=2.99 min.

Description 168

Methyl 3-{bis[(4-chlorobutyl)sulfonyl]amino}-4-(methyloxy)-5-[(1E/Z)-1-propen-1-yl]benzoate (D168)

To a solution of 3-amino-4-(methyloxy)-5-[(1 E/Z)-1-propen-1-yl]benzoate (D167) (800 mg, 3.6 mmol, 1 equiv) in CH$_2$Cl$_2$ (50 ml) was added NE % (1.5 ml, 10.8 mmol, 3.0 equiv) then 4-chloro-1-butanesulfonyl chloride (D20) (2 g, 10.8 mmol, 3.0 equiv) and the resulting mixture was stirred for 1 h. The organic phase was then washed with a 2N aqueous HCl solution and a saturated aqueous NaHCO$_3$ solution, dried over MgSO$_4$ and concentrated in vacuo. Purification of the residue by flash chromatography on silica gel (iso-hexane/AcOEt: 9/1 to 3/1) gave methyl 3-{bis[(4-chlorobutyl)sulfonyl]amino}-4-(methyloxy)-5-[(1E/Z)-1-propen-1-yl]benzoate (D168) (1.0 g, 52%) as a pale yellow oil.

Description 169

3-{[(4-Chlorobutyl)sulfonyl]amino}-4-(methyloxy)-5-[(1E/Z)-1-propen-1-yl]benzoic acid (D169)

To a solution of methyl 3-{bis[(4-chlorobutyl)sulfonyl]amino}-4-(methyloxy)-5-[(1E/Z)-1-propen-1-yl]benzoate (D168) (1.0 g, 1.88 mmol, 1 equiv) in MeOH (20 ml) was added a 2N aqueous NaOH solution (10 ml, 20 mmol, excess) and the resulting mixture was stirred for 1 h. Most of MeOH was removed in vacuo and the residue partitioned between AcOEt and a 2N aqueous HCl solution. The two layers were separated and the aqueous phase was dried over MgSO$_4$ and concentrated in vacuo. The residue was triturated with Et$_2$O/iso-hexane to give 3-{[(4-chlorobutyl)sulfonyl]amino}-4-(methyloxy)-5-[(1E/Z)-1-propen-1-yl]benzoic acid (D169) (470 mg, 69%) as a light cream solid which was used in the next step without further purification. [M−H]$^-$=360.0, RT=3.19 min.

Description 170

Methyl 3-{[(4-chlorobutyl)sulfonyl]amino}-4-(methyloxy)-5-[(1E)-1-propen-1-yl]benzoate (D170)

Methyl 3-{[(4-chlorobutyl)sulfonyl]amino}4-(methyloxy)-5-[(1E/Z)-1-propen-1-yl]benzoate (D170) was prepared from 3-{[(4-chlorobutyl)sulfonyl]amino}-4-(methyloxy)-5-[(1E/Z)-1-propen-1-yl]benzoic acid (D169) in an analogous manner to Description 25 (D25).

Descriptions 171-172 (D171-172)

The following compounds have been obtained from their corresponding precursors in an analogous manner to the process described for Description 2 (D2):

| Description | Precursor | [M + H]$^+$ | RT (min) |
| --- | --- | --- | --- |
| Methyl 3-[(4-chlorobutanoyl)amino]-4-(methyloxy)-5-nitrobenzoate (D171) | D163 | 331.0 | 3.13 |

-continued

| Description | Precursor | [M + H]⁺ | RT (min) |
|---|---|---|---|
| Methyl 3-[(4-chlorobutanoyl)amino]-4-methyl-5-nitrobenzoate (D172) | D164 | 315.1 | 3.02 |

Descriptions 173-174 (D173-174)

The following compounds have been obtained from their corresponding precursors in an analogous manner to the process described for Description 14 (D14):

| Description | Precursor | [M − H]⁻ | RT (min) |
|---|---|---|---|
| Methyl 3-{[(3-chloropropyl)sulfonyl]amino}-4-(methyloxy)-5-nitrobenzoate (D173) | D163 | 364.9 | 3.10 |
| Methyl 3-{[(3-chloropropyl)sulfonyl]amino}-4-methyl-5-nitrobenzoate (D174) | D164 | 349.0 | 3.12 |

Descriptions 175-176 (D175-176)

The following compounds have been obtained from their corresponding precursors in an analogous manner to the process described for Description 14 (D14) using 4-chloro-1-butanesulfonyl chloride (D20) instead of 3-chloro-1-propanesulfonyl chloride:

| Description | Precursor | [M − H]⁻ | RT (min) |
|---|---|---|---|
| Methyl 3-{[(4-chlorobutyl)sulfonyl]amino}-4-(methyloxy)-5-nitrobenzoate (D175) | D163 | | |
| Methyl 3-{[(4-chlorobutyl)sulfonyl]amino}-4-methyl-5-nitrobenzoate (D176) | D164 | 362.8 | 3.21 |

Descriptions 177-178 (D177-178)

The following compounds have been obtained from their corresponding precursors in an analogous manner to the process described for Ester 27 (B27):

| Description | Precursor | [M + H]⁺ | RT (min) |
|---|---|---|---|
| Methyl 4-(methyloxy)-3-nitro-5-(2-oxo-1-pyrrolidinyl)benzoate (D177) | D171 | 295.1 | 2.61 |
| Methyl 4-methyl-3-nitro-5-(2-oxo-1-pyrrolidinyl) benzoate (D178) | D172 | 279.0 | 2.60 |

Descriptions 179-182 (D179-182)

The following compounds have been obtained from their corresponding precursors in an analogous manner to the process described for Description 15 (D15):

| Description | Precursor | [M + H]⁺ | RT (min) |
|---|---|---|---|
| Methyl 3-(1,1-dioxido-2-isothiazolidinyl)-4-(methyloxy)-5-nitrobenzoate (D179) | D173 | 331.0 | 2.78 |
| Methyl 3-(1,1-dioxido-2-isothiazolidinyl)-4-methyl-5-nitrobenzoate (D180) | D174 | | |
| Methyl 3-(1,1-dioxidotetrahydro-2H-1,2-thiazin-2-yl)-4-(methyloxy)-5-nitrobenzoate (D181) | D175 | 345.0 | 2.90 |
| Methyl 3-(1,1-dioxidotetrahydro-2H-1,2-thiazin-2-yl)-4-methyl-5-nitrobenzoate (D182) | D176 | 329.0 | 2.93 |

Descriptions 183-188 (D183-188)

The following compounds have been obtained from their corresponding precursors in an analogous manner to the process described for the synthesis of Description 16 (D16) using the appropriate precursor indicated in the below table:

| Description | Precursor | [M + H]⁺ | RT (min) |
|---|---|---|---|
| methyl 3-amino-4-(methyloxy)-5-(2-oxo-1-pyrrolidinyl) benzoate (D183) | D177 | 265.1 | 2.18 |
| methyl 3-amino-4-methyl-5-(2-oxo-1-pyrrolidinyl) benzoate (D184) | D178 | 249.1 | 2.16 |
| methyl 3-amino-5-(1,1-dioxido-2-isothiazolidinyl)-4-(methyloxy) benzoate (D185) | D179 | 301.0 | 2.25 |
| methyl 3-amino-5-(1,1-dioxido-2-isothiazolidinyl)-4-methylbenzoate (D186) | D180 | 285.0 | 2.22 |
| methyl 3-amino-5-(1,1-dioxidotetrahydro-2H-1,2-thiazin-2-yl)-4-(methyloxy) benzoate (D187) | D181 | 315.1 | 2.40 |
| methyl 3-amino-5-(1,1-dioxidotetrahydro-2H-1,2-thiazin-2-yl)-4-methylbenzoate (D188) | D182 | 299.0 | 2.42 |

Description 189

4-((Z/E)-But-2-enylamino)-3,5-diiodo-benzoic acid ethyl ester (D189)

To a solution of 4-amino-3,5-diiodo-benzoic acid ethyl ester (commercially available from Maybridge) (72.6 g, 0.17 mmol, 1 equiv) in DMF (450 ml) at 0° C. under nitrogen was added NaH (60% in mineral oil, 7.3 g, 0.18 mmol, 1.05 equiv) portionwise over 2 min. After 10 min crotyl bromide (21.5 ml, 0.21 mmol, 1.2 equiv) in DMF (50 ml) was added via cannula over 5 min and the resulting mixture was allowed to warm to room temperature over 30 min. 5 Ml of EtOH were added and the mixture was concentrated in vacuo. The residue was dissolved in AcOEt and the organic phase was washed with H₂O. The aqueous phase was extracted with AcOEt and the combined organic phases were washed with brine, dried over MgSO₄ and concentrated in vacuo to give 4-((Z/E)-but-2-enylamino)-3,5-diiodo-benzoic acid ethyl ester (D189) (82 g, 100%) as a pink solid which was used in the next step without further purification. [M+H]⁺=472.0, RT=4.93 min.

Description 190

3-Ethyl-7-iodo-1H-indole-5-carboxylic acid ethyl ester (D190)

To a solution of 4-((Z/E)-but-2-enylamino)-3,5-diiodo-benzoic acid ethyl ester (D189) (15 g, 31.8 mmol, 1 equiv)

in DMF (150 ml) at room temperature under nitrogen were added Pd(OAc)$_2$ (357 mg, 1.6 mmol, 0.05 equiv), NaCOOH (6.5 g, 95.6 mmol, 3 equiv), Na$_2$CO$_3$ (8.4 g, 79.6 mmol, 2.5 equiv) and NBu$_4$Cl (8.0 g, 35.0 mmol, 1.1 equiv). The resulting suspension was stirred under nitrogen at 80° C. for 30 min then cooled to room temperature and concentrated in vacuo. The residue was partitioned between AcOEt and H$_2$O and the two phases were separated. The organic phase was dried over MgSO$_4$ and concentrated in vacuo. Purification of the residue by flash chromatography on silica gel (iso-hexane/AcOEt: 9/1) gave 3-ethyl-7-iodo-1H-indole-5-carboxylic acid ethyl ester (D190) (6.3 g, 58%) as a white solid. [M+H]$^+$=344.0, RT=3.86 min.

Description 191

1,1-Dimethylethyl 3-bromo-5-(2-oxo-5-phenyl-1-piperidinyl)benzoate (D191)

A flask was charged under nitrogen with 3-bromo-5-iodobenzoic acid methyl ester (D8b) (840 mg, 2.2 mmol, 1.1 equiv), Cs$_2$CO$_3$ (900 mg, 2.8 mmol, 1.4 equiv), tris(dibenzylideneacetone)dipalladium(0) (92 mg, 0.1 mmol, 0.05 equiv), Xantphos (120 mg, 0.2 mmol, 0.1 equiv) and toluene (40 ml). 5-Phenyl-2-piperidinone (Koelsch, *J. Am. Chem. Soc.* 1943, (65), 2093, 350 mg, 2 mmol, 1 equiv) was then added and the resulting mixture was stirred at 100° C. for 2.5 h then cooled to room temperature and concentrated in vacuo. The residue was partitioned between AcOEt and a saturated aqueous NaHCO$_3$ solution. The layers were separated and the organic phase was dried over MgSO$_4$ and concentrated in vacuo to give a solid residue. Purification of the residue by flash chromatography on silica gel (iso-hexane/AcOEt: 4/1 to 1/1) gave 1,1-dimethylethyl 3-bromo-5-(2-oxo-5-phenyl-1-piperidinyl)benzoate (D191) (480 mg, 51%) as a white solid. [M+H]$^+$=432.2, RT=3.82 min.

Description 192

1,1-Dimethylethyl 3-(2-oxo-5-phenyl-1-piperidinyl)-5-[(1E/Z)-1-propen-1-yl]benzoate (D192)

1,1-Dimethylethyl 3-(2-oxo-5-phenyl-1-piperidinyl)-5-[(1E/Z)-1-propen-1-yl]benzoate (D192) was prepared in an analogous manner to the process described for Description 68 (D68) from 1,1-dimethylethyl 3-bromo-5-(2-oxo-5-phenyl-1-piperidinyl)benzoate (D191). [M+H]$^+$=392.3, RT=3.83 min.

Description 193

Methyl 3-(1,1-dioxidotetrahydro-2H-1,2-thiazin-2-yl)-5-nitrobenzoate (D193)

Methyl 3-(1,1-dioxidotetrahydro-2H-1,2-thiazin-2-yl)-5-nitrobenzoate (D193) was obtained from methyl 3-bromo-5-nitrobenzoate (D11) in an analogous manner to the process described for Description 15 (D15) (alternative procedure) using tetrahydro-2H-1,2-thiazine 1,1-dioxide (D22b) instead of isothiazolidine 1,1-dioxide (D22a). [M+H+NH$_3$]$^+$=332.2, RT=2.75 min.

Description 194

Methyl 3-amino-5-(1,1-dioxidotetrahydro-2H-1,2-thiazin-2-yl)benzoate (D194)

Methyl 3-amino-5-(1,1-dioxidotetrahydro-2H-1,2-thiazin-2-yl)benzoate (D194) was obtained from methyl 3-(1,1-dioxidotetrahydro-2H-1,2-thiazin-2-yl)-5-nitrobenzoate (D193) in an analogous manner to the process described for Description 2 (D2). [M+H]$^+$=285.1, RT=2.12 min.

Description 195

Methyl 3-[(4-chlorobutanoyl)amino]-5-(1,1-dioxido-2-isothiazolidinyl)benzoate (D195)

Methyl 3-[(4-chlorobutanoyl)amino]-5-(1,1-dioxido-2-isothiazolidinyl)benzoate (D195) was obtained from methyl 3-amino-5-(1,1-dioxido-2-isothiazolidinyl)benzoate (D16) in an analogous manner to the process described for Description 13 (D13).

Description 196

Methyl 3-amino-4-methyl-5-nitrobenzoate (D196)

To a solution of methyl 4-methyl-3,5-dinitrobenzoate (D162) (30 g, 0.125 mmol, 1 equiv) in MeOH (150 ml) and cyclohexene (300 ml) was added 10% palladium on charcoal (50% wet, 3 g, 5% w/w) and the resulting suspension was refluxed for 7 h then cooled to room temperature. The catalyst was filtered off through a pad of celite and most of the solvent was removed in vacuo. The precipitate formed was filtered off to give methyl 3-amino-4-methyl-5-nitrobenzoate (D196) (22 g, 84%) as a yellow solid which was used in the next step without further purification. [M+H]$^+$=211.0, RT=2.81 min.

Description 197

Methyl 4-nitro-1H-indazole-6-carboxylate (D197)

To a suspension of 3-amino-4-methyl-5-nitrobenzoate (D196) (3.5 g, 16.7 mmol, 1 equiv) in H$_2$O (100 ml) at 0° C. was added 36% aqueous HCl solution (15 ml) and the resulting suspension was treated with NaNO$_2$ (1.35 g, 19.6 mmol, 1.2 equiv) then warmed to room temperature and stirred for 1.5 h. The insoluble material was removed by filtration and small amounts of urea were added to the mother liquors. The resulting solution was diluted with H$_2$O (500 ml) and treated with H$_2$SO$_4$ (17.5 ml) then heated at 50° C. for 15 min, cooled to room temperature and extracted with AcOEt. The organic phase was dried over MgSO$_4$ then concentrated in vacuo. The residue was triturated with MeOH to give methyl 4-nitro-1H-indazole-6-carboxylate (D197) (0.8 g, 22%) as a cream solid which was used in the next step without further purification. [M+H]$^+$=222.1, RT=2.84 min.

Description 198

Methyl 1-ethyl-4-nitro-1H-indazole-6-carboxylate (D198)

To a solution of methyl 4-nitro-1H-indazole-6-carboxylate (D197) (500 mg, 2.3 mmol, 1 equiv) in DMF (10 ml) at room temperature was added K$_2$CO$_3$ (346 mg, 2.5 mmol, 1.1 equiv) then ethyl iodide (200 μl, 2.5 mmol, 1.1 equiv). The resulting suspension was stirred at room temperature for 15 min then at 40° C. for 30 min, cooled to room temperature and partitioned between AcOEt and a 2N aqueous HCl solution. The two layers were separated and the organic phase dried over MgSO$_4$ and concentrated in vacuo. Purification of the residue by flash chromatography on silica gel (iso-hexane/AcOEt: 2/1) gave methyl 1-ethyl-4-nitro-1H- indazole-6-carboxylate (D198) (200 mg, 35%) as a pale yellow solid. [M+H]$^+$=250.1, RT=3.11 min.

Description 199

Methyl 4-amino-1-ethyl-1H-indazole-6-carboxylate (D199)

To a solution of methyl 1-ethyl-4-nitro-1H-indazole-6-carboxylate (D198) (2.2 g, 8.8 mmol, 1 equiv) in MeOH (100 ml) and H$_2$O (10 ml) was added 10% palladium on charcoal (50% wet, 700 mg, 16% w/w) and the resulting mixture was stirred at 60° C. for 30 min then cooled to room temperature. The catalyst was removed by filtration through a pad of celite and most of the solvent removed in vacuo. The residue was partitioned between AcOEt and a saturated aqueous NaHCO$_3$ solution and the two layers were separated. The organic phase was dried over MgSO$_4$ and concentrated in vacuo. The residue was triturated with isohexane to give methyl 4-amino-1-ethyl-1H-indazole-6-carboxylate (D199) (1.55 g, 80%) which was used in the next step without further purification. [M+H]$^+$=220.1, RT=3.31 min.

Description 200

Methyl 4-[(E)-2-(dimethylamino)ethenyl]-3,5-dinitrobenzoate (D200)

To a solution of methyl 4-methyl-3,5-dinitrobenzoate (D162) (20 g, 83.3 mmol, 1 equiv) in DMF (30 ml) was added N,N-dimethylformamide dimethylacetal (35 ml, excess) and the resulting solution was stirred at 45° C. for 30 min then cooled to room temperature and concentrated in vacuo. Trituration of the residue with Et$_2$O/iso-hexane gave methyl 4-[(E)-2-(dimethylamino)ethenyl]-3,5-dinitrobenzoate (D200) (20 g, 81%) as a dark red solid which was used in the next step without further purification.

Description 201

Methyl 4-amino-1H-indole-6-carboxylate (D201)

To a solution of methyl 4-[(E)-2-(dimethylamino)ethenyl]-3,5-dinitrobenzoate (D200) (10 g, 34 mmol, 1 equiv) in MeOH (250 ml) was added 10% palladium on charcoal (50% wet, 1.0 g, 5% w/w) and the resulting mixture was stirred under an atmosphere of hydrogen for 7 h. The catalyst was removed by filtration through a pad of celite and the solution concentrated in vacuo. The residue was triturated with AcOEt/iso-hexane to give methyl 4-amino-1H-indole-6-carboxylate (D201) (5 g, 77%) as a dark pink solid. [M+H]$^+$=191.0, RT=1.20 min.

Description 202

Methyl 4-amino-1-ethyl-1H-indole-6-carboxylate (D202)

To a solution of methyl 4-amino-1H-indole-6-carboxylate (D201) (900 mg, 4,74 mmol, 1 equiv) in DMF (25 ml) at room temperature was added NaH (60% dispersion in mineral oil, 200 mg, 5 mmol, 1.05 equiv) and after 15 min ethyl iodide (400 µl, 5 mmol, 1.05 equiv). The resulting mixture was stirred for 30 min then most of the solvent was removed in vacuo. The residue was diluted with AcOEt and the organic phase was washed with a 2N aqueous HCl solution, dried over MgSO$_4$ and concentrated in vacuo. Purification of the residue by flash chromatography on silica gel (iso-hexane/AcOEt: 1/1) gave an oil which was diluted with Et$_2$O and treated with a 4N HCl solution in Et$_2$O. The precipitate obtained was filtrated off to give methyl 4-amino-1-ethyl-1H-indole-6-carboxylate hydrochloride salt (D202) (800 mg, 66%) as a white solid. [M+H]$^+$=219.0, RT=2.50 min.

Description 203

Methyl 4-amino-3,5-dinitrobenzoate (D203)

Methyl 4-amino-3,5-dinitrobenzoate (D203) was prepared in an analogous manner to Description 25 from commercially available 4-amino-3,5-dinitrobenzoic acid. [M−H]$^-$=240.1, RT=2.42 min.

Description 204

Methyl 3,4-diamino-5-nitrobenzoate (D204)

To a solution of methyl 4-amino-3,5-dinitrobenzoate (D203) (3.0 g, 12.4 mmol, 1 equiv) in MeOH (40 ml) and cyclohexane (80 ml) was added 10% palladium on charcoal (50% wet, 2.0 g, 33% w/w) and the resulting mixture was refluxed for 30 min then cooled to room temperature. The catalyst was filtered off through a pad of celite and washed with DMF. The combined organic phases were concentrated in vacuo and the residue triturated with Et$_2$O/iso-hexane to give methyl 3,4-diamino-5-nitrobenzoate (D204) (2.1 g, 80%) as a red solid which was used in the next step without further purification. [M+H]$^+$=212.2, RT=2.46 min.

Description 205

Methyl 4-amino-3-(ethylamino)-5-nitrobenzoate (D205)

To a solution of methyl 3,4-diamino-5-nitrobenzoate (D204) (1.5 g, 7.1 mmol, 1 equiv) in DMF (30 ml) at room temperature was added K$_2$CO$_3$ (2.2 g, 16.0 mmol, 2.25 equiv) then ethyl iodide (1.28 ml, 16.0 mmol, 2.25 equiv). The resulting suspension was stirred at 60° C. for 2 h then ethyl iodide (1 ml, 12.5 mmol, 1.8 equiv) was added and the resulting mixture stirred for another 6 h then cooled to room temperature and partitioned between AcOEt and a saturated aqueous NaHCO$_3$ solution. The two layers were separated and the organic phase washed with H$_2$O, dried over MgSO$_4$ and concentrated in vacuo. The residue was triturated with Et$_2$O to give methyl 4-amino-3-(ethylamino)-5-nitrobenzoate (D205) (0.85 g, 50%) as a red solid which was used in the next step without further purification. [M+H]$^+$=240.2, RT=2.95 min.

Description 206

Methyl 1-ethyl-4-nitro-1H-benzimidazole-6-carboxylate (D206)

Methyl 4-amino-3-(ethylamino)-5-nitrobenzoate (D205) (850 mg, 3.55 mmol, 1 equiv) was dissolved in formic acid (20 ml) and the resulting solution was stirred at 100° C. for 45 min then cooled to room temperature and diluted with AcOEt (200 ml). The organic phase was washed with a 2N aqueous NaOH solution, dried over MgSO$_4$ and concentrated in vacuo to give methyl 1-ethyl-4-nitro-1H-benzimidazole-6-carboxylate (D206) (700 mg, 79%) as a tan solid which was used in the next step without further purification. [M+H]$^+$=250.1, RT=2.41 min.

Description 207

Methyl 4-amino-1-ethyl-1H-benzimidazole-6-carboxylate (D207)

To a solution of methyl 1-ethyl-4-nitro-1H-benzimidazole-6-carboxylate (D206) (700 mg, 2.81 mmol, 1 equiv) in MeOH (50 ml) and $H_2O$ (5 ml) was added 10% palladium on charcoal (50% wet, 400 mg, 28% w/w) and $NH_4COOH$ (1.77 g, 28.1 mmol, 10 equiv) and the resulting mixture was stirred at 70° C. for 30 min then cooled to room temperature. The catalyst was filtered off through a pad of celite and most of the MeOH was removed in vacuo. The residue was diluted with AcOEt and the organic layer was washed with a saturated aqueous $NaHCO_3$ solution, dried over $MgSO_4$ and concentrated in vacuo to give methyl 4-amino-1-ethyl-1H-benzimidazole-6-carboxylate (D207) (500 mg, 81%) as a white solid which was used in the next step without further purification. $[M+H]^+=220.2$, RT=2.17 min.

Description 208

Methyl 4-[(2-chloroethyl)amino]-3,5-dinitrobenzoate (D208)

To a solution of methyl 4-chloro-3,5-dinitrobenzoate (D25a) (5.0 g, 19.2 mmol, 1 equiv) in MeOH (300 ml) was added 2-chloroethylamine hydrochloride (4.64 mg, 40 mmol, 2.1 equiv) and $NEt_3$ (5.5 ml, 40 mmol, 2.1 equiv) and the resulting mixture was refluxed for 5 min then cooled to room temperature. Most of the solvent was evaporated in vacuo and the residue filtered off to give methyl 4-[(2-chloroethyl)amino]-3,5-dinitrobenzoate (D208) (9 g, 156%) as a yellow solid which was used in the next step without further purification. $[M+H]^+=304.1$, RT=3.06 min.

Description 209

Methyl 8-nitro-1,2,3,4-tetrahydro-6-quinoxalinecarboxylate (D209)

To a solution of crude methyl 4-[(2-chloroethyl)amino]-3,5-dinitrobenzoate (D208) (9 g, 19.2 mmol, 1 equiv) in MeOH (75 ml) and cyclohexene (150 ml) was added 10% palladium on charcoal (50% wet, 4.5 g, 25% w/w) and the resulting mixture was refluxed for 3 h then cooled to room temperature. The catalyst was filtered off through a pad of celite and most of the solvent was removed in vacuo. The residue was partitioned between AcOEt and a 2N aqueous HCl solution and the two layers were separated. The aqueous phase was extracted twice with AcOEt and the combined organic layers were washed with a saturated aqueous $NaHCO_3$ solution, dried over $MgSO_4$ and concentrated in vacuo. Purification of the residue by flash chromatography on silica gel (iso-hexane/AcOEt: 1/1) gave methyl 8-nitro-1,2,3,4-tetrahydro-6-quinoxalinecarboxylate (D209) (1.5 g, 34%) as a red solid. $[M-H]^-=236.2$, RT=2.65 min.

Description 210

Methyl 4-ethyl-8-nitro-1,2,3,4-tetrahydro-6-quinoxalinecarboxylate (D210)

Methyl 4-ethyl-8-nitro-1,2,3,4-tetrahydro-6-quinoxalinecarboxylate (D210) was prepared from methyl 8-nitro-1,2,3,4-tetrahydro-6-quinoxalinecarboxylate (D209) in an analogous manner to the process described for Ester 35 (B35) using acetaldehyde instead of propionaldehyde. $[M+H]^+=266.3$, RT=3.07 min.

Description 211

Methyl 8-amino-4-ethyl-1,2,3,4-tetrahydro-6-quinoxalinecarboxylate (D211)

Methyl 8-amino-4-ethyl-1,2,3,4-tetrahydro-6-quinoxalinecarboxylate (D211) was prepared from methyl 4-ethyl-8-nitro-1,2,3,4-tetrahydro-6-quinoxalinecarboxylate (D210) in an analogous manner to the process described for Description 207 (D207). $[M+H]^+=236.2$, RT=2.23 min.

Description 212

Ethyl 4-amino-3-nitrobenzoate (D212)

Ethyl 4-amino-3-nitrobenzoate (D212) was prepared in an analogous manner to Description from commercially available 4-amino-3-nitrobenzoic acid using EtOH as solvent instead of MeOH.

Description 213

Ethyl 4-amino-3-bromo-5-nitrobenzoate (D213)

To a solution of ethyl 4-amino-3-nitrobenzoate (D212) (21.0 g, 100 mmol, 1 equiv) in $CH_2Cl_2$ (500 ml) at room temperature was added bromine (6.7 ml, 130 mmol, 1.3 equiv) and the resulting mixture was refluxed for 4 h then bromine (2 ml, 40 mmol, 0.4 equiv) was added and the resulting mixture refluxed for another 3 h then cooled to room temperature. The organic phase was washed twice with a 10% aqueous $Na_2S_2O_3$ solution and twice with $H_2O$, dried over $MgSO_4$ and concentrated in vacuo to give ethyl 4-amino-3-bromo-5-nitrobenzoate (D213) (27.1 g, 94%) as a yellow solid which was used in the next step without further purification.

Description 214

Ethyl 3-bromo-5-nitro-4-[(trifluoroacetyl)amino]benzoate (D214)

To a solution of ethyl 4-amino-3-bromo-5-nitrobenzoate (D213) (27.1 g, 93.1 mmol, 1 equiv) in $CH_2Cl_2$ (500 ml) at room temperature was added N,N-diisopropylethylamine (22 ml, 130 mmol, 1.4 equiv) and trifluoroacetic acid anhydride (15.8 ml, 111.7 mmol, 1.2 equiv) and the resulting mixture was stirred for 2 h. N,N-diisopropylethylamine (22 ml, 130 mmol, 1.4 equiv) and trifluoroacetic acid anhydride (15.8 ml, 111.7 mmol, 1.2 equiv) were added and the resulting mixture was stirred for another 2 h. $H_2O$ was added and the two layers were separated. The organic phase was washed twice with a 2N aqueous HCl solution, $H_2O$, dried over $MgSO_4$ and concentrated in vacuo. Purification of the residue by flash chromatography on silica gel (iso-hexane/AcOEt: 9/1 to 3/1) gave ethyl 3-bromo-5-nitro-4-[(trifluoroacetyl)amino]benzoate (D214) (29.4 g, 82%) as a yellow solid.

Description 215

Ethyl 3-bromo-4-[(3-methyl-2-buten-1-yl)(trifluoroacetyl)amino]-5-nitrobenzoate (D215)

To a solution of ethyl 3-bromo-5-nitro-4-[(trifluoroacetyl)amino]benzoate (D214) (12.0 g, 31.3 mmol, 1 equiv) in $CH_3CN$ (100 ml) was added $K_2CO_3$ (5.6 g, 40 mmol, 1.3 equiv) and 1-bromo-3-methyl-2-butene (5.1 ml, 43.8 mmol, 1.4 equiv) and the resulting mixture was refluxed for 1 h then cooled to room temperature. The precipitate formed was filtered off through a pad of celite and washed with $CH_3CN$. The combined organic layers were concentrated in vacuo and the residue diluted with AcOEt. The organic layer was washed with brine, dried over $MgSO_4$ and concentrated in vacuo. Purification of the residue by flash chromatography on silica gel (iso-hexane/AcOEt: 9/1 to 4/1) gave ethyl 3-bromo-4-[(3-methyl-2-buten-1-yl)(trifluoroacetyl)amino]-5-nitrobenzoate (D215) (12.9 g, 91%) as an orange oil.

Descriptions 216-217 (D216-217)

The following compounds were obtained from ethyl 3-bromo-5-nitro-4-[(trifluoroacetyl)amino]benzoate (D214) in an analogous manner using the appropriate allyl bromide:

| Description | Allyl bromide |
| --- | --- |
| Ethyl 3-bromo-4-[(2E/Z)-2-buten-1-yl(trifluoroacetyl)amino]-5-nitrobenzoate (D216) | |
| Ethyl 3-bromo-5-nitro-4-[2-propen-1-yl(trifluoroacetyl)amino]benzoate (D217) | |

Description 218

Ethyl 3-(1-methylethyl)-7-nitro-1H-indole-5-carboxylate (D218)

To a solution of ethyl 3-bromo-4-[(3-methyl-2-buten-1-yl)(trifluoroacetyl)amino]-5-nitrobenzoate (D215) (12.9 g, 28.5 mmol, 1 equiv) in DMF (130 ml) were added HCOONa (1.94 g, 28.5 mmol, 1 equiv), $Na_2CO_3$ (7.54 g, 71.2 mmol, 2.5 equiv), $Bu_4NCl$ (8.7 g, 31.3 mmol, 1.1 equiv) and palladium (II) acetate (320 mg, 1.42 mmol, 0.05 equiv) and the resulting mixture was stirred under nitrogen for 1 h then cooled to room temperature and concentrated in vacuo. The residue was partitioned between AcOEt and $H_2O$ and the two layers were separated. The insoluble material in the aqueous phase was filtered off through a pad of celite and the aqueous layer extracted twice with AcOEt. The combined organic layers were washed with brine, dried over $MgSO_4$ and concentrated in vacuo to give methyl 3-(1-methylethyl)-7-nitro-1H-indole-5-carboxylate (D218) (10.1 g, 128%) as a black solid which was used in the next step without further purification.

Descriptions 219-220 (D219-220)

The following compounds were obtained in an analogous manner using the appropriate precursor:

| Description | Precursor |
| --- | --- |
| Ethyl 3-ethyl-7-nitro-1H-indole-5-carboxylate (D219) | D216 |
| Ethyl 3-methyl-7-nitro-1H-indole-5-carboxylate (D220) | D217 |

Description 221

Ethyl 7-amino-3-(1-methylethyl)-1H-indole-5-carboxylate (D221)

To a solution of crude ethyl 3-(1-methylethyl)-7-nitro-1H-indole-5-carboxylate (D218) (10.1 g, 28.5 mmol, 1 equiv) in MeOH (250 ml) and $H_2O$ (25 ml) was added 10% palladium on charcoal (50% wet, 1.5 g, 8% w/w) and $NH_4COOH$ (17 g, 280 mmol, 10 equiv) and the resulting mixture was stirred at 70° C. for 3 h then cooled to room temperature. The catalyst was filtered off through a pad of celite and most of the MeOH was removed in vacuo. The residue was diluted with AcOEt and the organic layer was washed with a saturated $NaHCO_3$ aqueous solution, dried over $MgSO_4$ and concentrated in vacuo. Purification of the residue by flash chromatography on silica gel (iso-hexane/AcOEt: 3/1 to 1/1) gave methyl 7-amino-3-(1-methylethyl)-1H-indole-5-carboxylate (D221) (1.47 g, 21%) as a white solid.

Descriptions 222-223 (D222-223)

The following compounds were obtained in an analogous manner to the process described for Description 221 using the appropriate precursor:

| Description | Precursor |
| --- | --- |
| Ethyl 7-amino-3-ethyl-1H-indole-5-carboxylate (D222) | D219 |
| Ethyl 7-amino-3-methyl-1H-indole-5-carboxylate (D223) | D220 |

Descriptions 224-230 (D224-230)

The following compounds have been obtained from their corresponding precursors in an analogous manner to the process described for Description 2 (D2):

| Description | Precursor | [M + H]⁺ | RT (min) |
| --- | --- | --- | --- |
| Ethyl 7-[(4-chlorobutanoyl)amino]-3-methyl-1H-indole-5-carboxylate (D224) | D223 | | |
| Ethyl 7-[(4-chlorobutanoyl)amino]-3-ethyl-1H-indole-5-carboxylate (D225) | D222 | | |
| Ethyl 7-[(4-chlorobutanoyl)amino]-3-(1-methylethyl)-1H-indole-5-carboxylate (D226) | D221 | | |

-continued

| Description | Precursor | [M + H]⁺ | RT (min) |
|---|---|---|---|
| Methyl 4-[(4-chlorobutanoyl)amino]-1-ethyl-1H-benzimidazole-6-carboxylate (D227) | D207 | | |
| Methyl 4-[(4-chlorobutanoyl)amino]-1H-indole-6-carboxylate (D228) | D201 | 295.0 | 2.63 |
| Methyl 4-[(4-chlorobutanoyl)amino]-1-ethyl-1H-indazole-6-carboxylate (D229) | D199 | 324.3 | 2.70 |
| Methyl 8-[(4-chlorobutanoyl)amino]-4-ethyl-1,2,3,4-tetrahydro-6-quinoxalinecarboxylate (D230) | D211 | 340.2 | 2.73 |

Description 231

Methyl 4-(1,1-dioxidotetrahydro-2H-1,2-thiazin-2-yl)-1H-indole-6-carboxylate (D231)

Methyl 4-(1,1-dioxidotetrahydro-2H-1,2-thiazin-2-yl)-1H-indole-6-carboxylate (D231) was obtained from 4-(1,1-dioxidotetrahydro-2H-1,2-thiazin-2-yl)-1H-indole-6-carboxylic acid (A155) in an analogous manner to Description 25 (D25).

Description 232

1-(1,1-Dimethylethyl) 6-methyl 4-(1,1-dioxidotetrahydro-2H-1,2-thiazin-2-yl)-1H-indole-1,6-dicarboxylate (D232)

To a solution of methyl 4-(1,1-dioxidotetrahydro-2H-1,2-thiazin-2-yl)-1H-indole-6-carboxylate (D231) (308 mg, 1.0 mmol, 1 equiv) in CH$_2$Cl$_2$ (10 ml) were added NEt$_3$ (166 pd, 1.2 mmol, 1.2 equiv), bis(1,1-dimethylethyl) dicarbonate (251 mg, 1.15 mmol, 1.15 equiv) and DMAP (12 mg, 0.1 mmol, 0.1 equiv) and the resulting mixture was stirred at room temperature for 30 min. The organic phase was washed with a 2N aqueous HCl solution and a saturated aqueous NaHCO$_3$ solution, dried over MgSO$_4$ and concentrated in vacuo. Trituration in Et$_2$O/iso-hexane gave 1-(1,1-dimethylethyl) 6-methyl 4-(1,1-dioxidotetrahydro-2H-1,2-thiazin-2-yl)-1H-indole-1,6-dicarboxylate (D232) (150 mg, 37%) as a white solid which was used in the next step without further purification. [M+H+ NH$_3$]⁺=426.2, RT=3.38 min.

Description 233

(1,1-Dimethylethyl) 6-methyl 4-(1,1-dioxidotetrahydro-2H-1,2-thiazin-2-yl)-2,3-dihydro-1H-indole-1,6-dicarboxylate (D233)

1-(1,1-Dimethylethyl) 6-methyl 4-(1,1-dioxidotetrahydro-2H-1,2-thiazin-2-yl)-2,3-dihydro-1H-indole-1,6-dicarboxylate (D233) was obtained from 1-(1,1-dimethylethyl) 6-methyl 4-(1,1-dioxidotetrahydro-2H-1,2-thiazin-2-yl)-1H-indole-1,6-dicarboxylate (D232) in an analogous manner to the process described for Ester 116 (B116). No molecular ion, RT=3.23 min.

Description 234

Methyl 4-(1,1-dioxidotetrahydro-2H-1,2-thiazin-2-yl)-2,3-dihydro-1H-indole-6-carboxylate hydrochloride salt (D234)

1-(1,1-Dimethylethyl) 6-methyl 4-(1,1-dioxidotetrahydro-2H-1,2-thiazin-2-yl)-2,3-dihydro-1H-indole-1,6-dicarboxylate (D233) (500 mg, 1.2 mmol, 1 equiv) was dissolved in a 4N HCl solution in Et$_2$O (10 ml, 40 mmol, excess) and the resulting solution was stirred at room temperature for 1 h then concentrated in vacuo. Trituration of the residue with Et$_2$O gave methyl 4-(1,1-dioxidotetrahydro-2H-1,2-thiazin-2-yl)-2,3-dihydro-1H-indole-6-carboxylate hydrochloride salt (D234) (430 mg, 100%) as a white solid which was used in the next step without further purification. [M+H]⁺=311.0, RT=2.16 min.

Description 235

Methyl 1-acetyl-4-(1,1-dioxidotetrahydro-2H-1,2-thiazin-2-yl)-2,3-dihydro-1H-indole-6-carboxylate (D235)

To a solution of methyl 4-(1,1-dioxidotetrahydro-2H-1,2-thiazin-2-yl)-2,3-dihydro-1H-indole-6-carboxylate hydrochloride salt (D234) (350 mg, 1.0 mmol, 1 equiv) in AcOEt (5 ml) were added NEt$_3$ (140 ml, 1.0 mmol, 1 equiv) and acetic anhydride (0.5 ml, 5.6 mmol, 5.6 equiv) and the resulting mixture was stirred at 50° C. for 30 min then cooled to room temperature and washed with a 2N aqueous HCl solution followed by a saturated aqueous NaHCO$_3$ solution, then dried over MgSO$_4$ and concentrated in vacuo to give methyl 1-acetyl-4-(1,1-dioxidotetrahydro-2H-1,2-thiazin-2-yl)-2,3-dihydro-1H-indole-6-carboxylate (D235) as a white solid which was used in the next step without further purification. [M+H]⁺=353.2, RT=2.24 min.

Description 236

Methyl 4-{bis[(3-chloropropyl)sulfonyl]amino}-1-ethyl-1H-indole-6-carboxylate (D236)

To a solution of methyl 4-amino-1-ethyl-1H-indole-6-carboxylate hydrochloride salt (D202) (1.7 g, 6.68 mmol, 1 equiv) in CH$_2$Cl$_2$ (50 ml) was added NEt$_3$ (4.2 ml, 30 mmol, 4.5 equiv) then 3-chloro-1-propanesulfonyl chloride (1.8 ml, 15.0 mmol, 2.2 equiv) and the resulting mixture was stirred for 2 h. The organic phase was washed with a 2N aqueous HCl solution and a saturated aqueous NaHCO$_3$ solution, dried over MgSO$_4$ and concentrated in vacuo. Purification of the residue by flash chromatography on silica gel (AcOEt/iso-hexane: 1/1) gave methyl 4-{bis[(3-chloropropyl)sulfonyl]amino}-1-ethyl-1H-indole-6-carboxylate (D236) (1.85 g, 55%) as a light tan solid. [M−H]⁻=498.1, RT=3.51 min.

Description 237

Methyl 4-{bis[(3-chloropropyl)sulfonyl]amino}-1-ethyl-1H-indazole-6-carboxylate (D237)

Methyl 4-{bis[(3-chloropropyl)sulfonyl]amino}-1-ethyl-1H-indazole-6-carboxylate (D237) was obtained from methyl 4-amino-1-ethyl-1H-indazole-6-carboxylate in an analogous manner to the process described for methyl 4-{bis[(3-chloropropyl)sulfonyl]amino}-1-ethyl-1H-indole-6-carboxylate (D236). [M+H]⁺=500.1, RT=3.50 min.

Description 238

Methyl 8-{bis[(3-chloropropyl)sulfonyl]amino}4-ethyl-1,2,3,4-tetrahydro-6-quinoxalinecarboxylate (D238)

Methyl 8-{bis[(3-chloropropyl)sulfonyl]amino}4-ethyl 1,2,3,4-tetrahydro-6-quinoxalinecarboxylate (D238) was obtained from methyl 8-amino-4-ethyl-1,2,3,4-tetrahydro-6- quinoxalinecarboxylate (D211) in an analogous manner to the process described for methyl 4-{bis[(3-chloropropyl)sulfonyl]amino}-1-ethyl-1H-indole-6-carboxylate (D236). [M+H]+=517.2, RT=3.32 min.

Description 239

Methyl 4-{bis[(3-chloropropyl)sulfonyl]amino})-1-ethyl-1H-benzimidazole-6-carboxylate (D239)

Methyl 4-{bis[(3-chloropropyl)sulfonyl]amino}-1-ethyl-H-benzimidazole-6-carboxylate (D239) was obtained from methyl 4-amino-1-ethyl-1H-benzimidazole-6-carboxylate (D207) in an analogous manner to the process described for methyl 4-{bis[(3-chloropropyl)sulfonyl]amino}-1-ethyl-1H-indole-6-carboxylate (D236). [M+H]+=500.3, RT=3.20 min.

Description 240

4-{[(3-Chloropropyl)sulfonyl]amino}-1-ethyl-1H-indole-6-carboxylic acid (D240)

To a solution of methyl 4-{bis[(3-chloropropyl)sulfonyl]amino}-1-ethyl-1H-indole-6-carboxylate (D236) (1.8 g, 3.6 mmol, 1 equiv) in MeOH (100 ml) was added a 2N aqueous NaOH solution (20 ml, 40 mmol, excess) and the resulting mixture was stirred for 1 h. Most of MeOH was removed in vacuo and the residue partitioned between AcOEt and a 2N aqueous HCl solution. The two layers were separated and the aqueous phase was dried over MgSO$_4$ and concentrated in vacuo to give 4-{[(3-chloropropyl)sulfonyl]amino}-1-ethyl-1H-indole-6-carboxylic acid (D240) (930 mg, 75%) as a brown oil which was used in the next step without further purification.

Description 241

Methyl 4-{[(3-chloropropyl)sulfonyl]amino}-1-ethyl-1H-indole-6-carboxylate (D241)

Methyl 4-{[(3-chloropropyl)sulfonyl]amino}-1-ethyl-1H-indole-6-carboxylate (D241) was obtained from 4-{[(3-chloropropyl)sulfonyl]amino}-1-ethyl-1H-indole-6-carboxylic acid (D240) in an analogous manner to Description 25 (D25). [M+H]+=359.2, RT=3.12 min.

Description 242

Ethyl 7-{[(4-chlorobutyl)sulfonyl]amino}-3-ethyl-1H-indole-5-carboxylate (D242)

To a solution of ethyl 7-amino-3-ethyl-1H-indole-5-carboxylate (D222) (150 mg, 0.65 mmol, 1 equiv) in CH$_2$Cl$_2$ (10 ml) at room temperature were added pyridine (115 μl, 1.42 mmol, 2.2 equiv), 4-chloro-1-butanesulfonyl chloride (D20) (259 mg, 1.36 mmol, 2.1 equiv) and DMAP (8 mg, 0.065 mmol, 0.1 equiv) and the resulting mixture was stirred for 1 h then diluted with AcOEt and washed with a 2N aqueous HCl solution and brine, then dried over MgSO$_4$ and concentrated in vacuo to give ethyl 7-{[(4-chlorobutyl)sulfonyl]amino}-3-ethyl-1H-indole-5-carboxylate (D242) (230 mg, 92%) as a purple oil which was used in the next step without further purification. [M+H]+=387.3, RT=3.35 min.

Description 243

Ethyl 7-{[(3-chloropropyl)sulfonyl]amino}-3-ethyl-1H-indole-5-carboxylate (D243)

Ethyl 7-{[(3-chloropropyl)sulfonyl]amino}-3-ethyl-1H-indole-5-carboxylate (D243) was obtained from ethyl 7-amino-3-ethyl-1H-indole-5-carboxylate (D222) in an analogous manner to the process described for Description 242 (D242) using 3-chloro-1-propanesulfonyl chloride instead of 4-chloro-1-butanesulfonyl chloride (D20). [M+H]+=373.0, RT=3.49 min.

Description 244

3,4-Diamino-5-nitrobenzoic acid (D244)

To a solution of 4-amino-3,5-dinitrobenzoic acid (10 g, 44 mmol, 1 equiv) in DME (100 ml) and CHCl$_3$ (10 ml) under nitrogen was added 10% palladium on charcoal (50% wet, 1 g, 5% w/w) and the resulting suspension was stirred under an atmosphere of nitrogen (35 psi) for 15 h. 10% Palladium on charcoal (50% wet, 1 g, 5% w/w) was added and the resulting suspension was stirred under an atmosphere of hydrogen (35 psi) for another 15 h. The catalyst was filtered off through a pad of celite and the solution was concentrated in vacuo to give 3,4-diamino-5-nitrobenzoic acid (D244) (9.85 g, 113%) as a red solid which was used in the next step without further purification. [M−H]−=196.1, RT=2.15 min Description 245

Methyl 3,4-diamino-5-nitrobenzoate (D245)

Methyl 3,4-diamino-5-nitrobenzoate (D245) was prepared in an analogous manner to Description 25 from 3,4-diamino-5-nitrobenzoic acid (D244) [M+H]+=212.2, RT=2.40 min.

Description 246

Methyl 4-nitro-1H-1,2,3-benzotriazole-6-carboxylate (D246)

To a solution of methyl 3,4-diamino-5-nitrobenzoate (D245) (2.5 g, 12 mmol, 1 equiv) in AcOH (10 ml) at room temperature was added NaNO$_2$ (900 mg, 13 mmol, 1.1 equiv) and the resulting mixture was stirred at 60° C. for 1 h, cooled to room temperature and concentrated in vacuo. the residue was partitioned between AcOEt and a 5% aqueous citric acid solution and the layers were separated. The organic phase was washed with brine, dried over MgSO$_4$ and concentrated in vacuo. Trituration of the residue in Et$_2$O/iso-hexane gave methyl 4-nitro-1H-1,2,3-benzotriazole-6-carboxylate (D246) (2.08 g, 78%) as an orange solid which was used in the next step without further purification. [M+H]+=223.3, RT=2.31 min.

Description 247

Methyl 4-amino-1H-1,2,3-benzotriazole-6-carboxylate (D247)

Methyl 4-amino-1H-1,2,3-benzotriazole-6-carboxylate (D247) was obtained from methyl 4-nitro-1H-1,2,3-benzotriazole-6-carboxylate (D246) in an analogous manner to the process described for methyl 5-amino-2-fluoro-3-(2-oxo-1-pyrrolidinyl)benzoate (D150). [M+H]$^+$=193.3, RT=2.01 min.

Description 248

Methyl 4-[(4-chlorobutanoyl)amino]-1H-1,2,3-benzotriazole-6-carboxylate (D248)

Methyl 4-[(4-chlorobutanoyl)amino]-1H-1,2,3-benzotriazole-6-carboxylate (D248) was obtained from methyl 4-amino-1H-1,2,3-benzotriazole-6-carboxylate (D247) in an analogous manner to the process described for Description 2 (D2). No molecular ion, RT=3.19 min.

Description 249

Methyl 4-(2-oxo-1-pyrrolidinyl)-1H-1,2,3-benzotriazole-6-carboxylate (D249)

Methyl 4-(2-oxo-1-pyrrolidinyl)-1H-1,2,3-benzotriazole-6-carboxylate (D249) was obtained from methyl 4-[(4-chlorobutanoyl)amino]-1H-1,2,3-benzotriazole-6-carboxylate (D248) in an analogous manner to the process described for Ester 27 (B27). [M+H]$^+$=261.2, RT=2.25 min.

Description 250

Methyl 4-nitro-1H-benzimidazole-6-carboxylate (D250)

A solution of methyl 3,4-diamino-5-nitrobenzoate (D245) (1.3 g, 6.16 mmol, 1 equiv) in HCOOH (20 ml) was stirred at 100° C. for 1 h then cooled to room temperature and concentrated in vacuo. The residue was partitioned between AcOEt and a 2N aqueous NaOH solution and the layers were separated. The organic phase was dried over MgSO$_4$ and concentrated in vacuo to give methyl 4-nitro-1H-benzimidazole-6-carboxylate (D250) (1.5 g, 110%) as a light brown solid which was used in the next step without further purification. [M+H]$^+$=222.3, RT=2.29 min.

Description 251

Methyl 4-amino-1H-benzimidazole-6-carboxylate (D251)

Methyl 4-amino-1H-benzimidazole-6-carboxylate (D251) was obtained from methyl 4-nitro-1H-benzimidazole-6-carboxylate (D250) in an analogous manner to the process described for methyl 5-amino-2-fluoro-3-(2-oxo-1-pyrrolidinyl)benzoate (D150). [M+H]$^+$=192.3, RT=1.55 min.

Description 252

Methyl 4-{[(4-chlorobutyl)sulfonyl]amino}-1H-benzimidazole-6-carboxylate (D252)

To a solution of methyl 4-amino-1H-benzimidazole-6-carboxylate (D251) (1.1 g, 5.76 mmol, 1 equiv) in CH$_2$Cl$_2$ (80 ml) at room temperature were added pyridine (1.02 ml, 12.67 mmol, 2.2 equiv), 4-chloro-1-butanesulfonyl chloride (D20) (2.31 g, 12.1 mmol, 2.1 equiv) and DMAP (704 mg, 5.76 mmol, 1 equiv) and the resulting mixture was stirred for 1 h then concentrated in vacuo. The residue was diluted with AcOEt and the organic phase was washed with a 2N aqueous HCl solution and brine, then dried over MgSO$_4$ and concentrated in vacuo. Purification of the residue by flash chromatography on silica gel (AcOEt/iso-hexane: 2/3) gave methyl 4-{[(4-chlorobutyl)sulfonyl]amino}-1H-benzimidazole-6-carboxylate (D252) (1 g, 50%) as a colorless oil. [M+H]$^+$=346.1, RT=2.97 min.

Description 253

Methyl 4-(1,1-dioxidotetrahydro-2H-1,2-thiazin-2-yl)-1H-benzimidazole-6-carboxylate (D253)

To a solution of methyl 4-{[(4-chlorobutyl)sulfonyl]amino}-1H-benzimidazole-6-carboxylate (D252) (1 g, 3.23 mmol, 1 equiv) in EtOH (50 ml) was added NEt$_3$ (2 ml, excess) and the resulting solution was stirred at 70° C. for 2 days. then cooled to room temperature and concentrated in vacuo. The residue was dissolved in AcOEt and the organic phase was washed with a 5% aqueous citric acid solution. The aqueous phase was saturated with NaCl and extracted twice with AcOEt. The combined organic phases were dried over MgSO$_4$ and concentrated in vacuo. Purification of the residue by flash chromatography on silica gel (CH$_2$Cl$_2$/MeOH: 96/4 to 90/10) gave methyl 4-(1,1-dioxidotetrahydro-2H-1,2-thiazin-2-yl)-1H-benzimidazole-6-carboxylate (D253) (250 mg, 25%) as a pale yellow solid. [M+H]$^+$=310.3, RT=2.11 min.

Description 254

Methyl 4-hydroxy-3,5-diiodobenzoate (D254)

Methyl 4-hydroxy-3,5-diiodobenzoate (D254) was prepared in an analogous manner to Description 25 (D25) from commercially available 4-hydroxy-3,5-diiodobenzoic acid.

Description 255

Methyl 4-[(2E/Z)-2-buten-1-yloxy]-3,5-diiodobenzoate (D255)

To a solution of methyl 4-hydroxy-3,5-diiodobenzoate (D254) (26.9 g, 66.7 mmol, 1 equiv) in acetone (250 ml) at room temperature were added K$_2$CO$_3$ (13.8 g, 100 mmol, 1.5 equiv) and 1-bromo-2-butene (8.25 ml, 80 mmol, 1.2 equiv) and the resulting suspension was stirred at 55° C. for 15 h then cooled to room temperature and concentrated in vacuo. The residue was partitioned between AcOEt and H$_2$O and the two layers were separated. The organic phase was washed with a 2N aqueous NaOH solution and brine, dried over MgSO$_4$ and concentrated in vacuo to give methyl 4-[(2E/Z)-2-buten-1-yloxy]-3,5-diiodobenzoate (D255) (28.6 g, 94%) as a white solid which was used in the next step without further purification.

Description 256

Methyl 3,5-diiodo-4-(2-propen-1-yloxy)benzoate (D256)

Methyl 3,5-diiodo-4-(2-propen-1-yloxy)benzoate (D256) was obtained from methyl 4-hydroxy-3,5-diiodobenzoate (D254) in an analogous manner to the process described for Description 255 (D255) using 3-bromo-1-propene instead of 1-bromo-2-butene.

Description 257

Methyl 4-(3-buten-1-yloxy)-3,5-diiodobenzoate (D257)

Methyl 4-(3-buten-1-yloxy)-3,5-diiodobenzoate (D257) was obtained from methyl 4-hydroxy-3,5-diiodobenzoate (D254) in an analogous manner to the process described for Description 255 (D255) using 4-bromo-1-butene instead of 1-bromo-2-butene. [M+H]$^+$=458.8, RT=4.05 min.

Description 258

Methyl 4-[(2E/Z)-2-buten-1-yloxy]-3-iodo-5-(2-oxo-1-pyrrolidinyl)benzoate (D258)

To a solution of methyl 4-[(2E/Z)-2-buten-1-yloxy]-3,5-diiodobenzoate (D255) (5 g, 11 mmol, 1 equiv) in toluene (50 ml) were added 2-pyrrolidinone (1.08 g, 13 mmol, 1.2 equiv), K$_3$PO$_4$ (4.46 g, 21 mmol, 2 equiv), CuI (105 mg, 0.55 mmol, 0.05 equiv) and dimethyl ethylene diamine (117 μl, 1.1 mmol, 0.1 equiv) and the resulting mixture was stirred at 100° C. for 15 h then cooled to room temperature and concentrated in vacuo. The residue was partitioned between AcOEt and H$_2$O and the layers were separated. The organic phase was dried under MgSO$_4$ and concentrated in vacuo. Purification of the residue by flash chromatography on silica gel (AcOEt/iso-hexane: 1/1) gave methyl 4-[(2E/Z)-2-buten-1-yloxy]-3-iodo-5-(2-oxo-1-pyrrolidinyl)benzoate (D258) (1.4 g, 31%) as a colorless oil. [M+H]$^+$=415.9, RT=3.27 min.

Description 259

Methyl 3-iodo-5-(2-oxo-1-pyrrolidinyl)-4-(2-propen-1-yloxy)benzoate (D259)

Methyl 3-iodo-5-(2-oxo-1-pyrrolidinyl)-4-(2-propen-1-yloxy)benzoate (D259) was obtained from methyl 3,5-diiodo-4-(2-propen-1-yloxy)benzoate (D256) in an analogous manner to the process described for Description 258 (D258).

Description 260

Methyl 4-(3-buten-1-yloxy)-3-Iodo-5-(2-oxo-1-pyrrolidinyl)benzoate (D260)

Methyl 4-(3-buten-1-yloxy)-3-iodo-5-(2-oxo-1-pyrrolidinyl)benzoate (D260) was obtained from methyl 4-(3-buten-1-yloxy)-3,5-diiodobenzoate (D257) in an analogous manner to the process described for Description 258 (D258). [M+H]$^+$=416.0, RT=3.02 min.

Description 261

Methyl 4-methyl-8-(2-oxo-1-pyrrolidinyl)-2H-chromene-6-carboxylate and methyl 4-(ethyloxy)-3-[ethyl(propanoyl)amino]-5-(1-methylethenyl)benzoate (D261)

Methyl 4-methyl-8-(2-oxo-1-pyrrolidinyl)-2H-chromene-6-carboxylate and methyl 4-(ethyloxy)-3-[ethyl(propanoyl)amino]-5-(1-methylethenyl)benzoate (D261) were obtained from methyl 4-(3-buten-1-yloxy)-3-iodo-5-(2-oxo-1-pyrrolidinyl)benzoate (D260) in an analogous manner to the process described for methyl 3-ethyl-7-(2-oxo-1-pyrrolidinyl)-1-benzofuran-5-carboxylate (B163). [M+H]$^+$=288.1, RT=min.

Description 262

Methyl 3-bromo-5-(1,1-dioxido-2-isothiazolidinyl)benzoate (D262)

Methyl 3-bromo-5-(1,1-dioxido-2-isothiazolidinyl)benzoate (D262) was obtained from methyl 3-bromo-5-iodobenzoate (D8a) in an analogous manner to the process described for Description 17 (D17) using D8a instead of D8b as starting material.

Description 263

Methyl 3-bromo-5-(1,1-dioxidotetrahydro-2H-1,2-thiazin-2-yl)benzoate (D263)

Methyl 3-bromo-5-(1,1-dioxidotetrahydro-2H-1,2-thiazin-2-yl)benzoate (D263) was obtained from methyl 3-bromo-5-iodobenzoate (D8a) in an analogous manner to the process described for Description 18 (D18) using D8a instead of D8b as starting material.

Description 264
Methyl 3-(3-cyclopenten-1-yl)-5-(1,1-dioxido-2-isothiazolidinyl)benzoate;
Methyl 3-(2-cyclopenten-1-yl)-5-(1,1-dioxido-2-isothiazolidinyl)benzoate;
Methyl 3-(1-cyclopenten-1-yl)-5-(1,1-dioxido-2-isothiazolidinyl)benzoate (D264)
Methyl 3-(3-cyclopenten-1-yl)-5-(1,1-dioxido-2-isothiazolidinyl)benzoate, methyl 3-(2-cyclopenten-1-yl)-5-(1,1-dioxido-2-isothiazolidinyl)benzoate and methyl 3-(1-cyclopenten-1-yl)-5-(1,1-dioxido-2-isothiazolidinyl)benzoate (D264) have been obtained from methyl 3-bromo-5-(1,1-dioxido-2-isothiazolidinyl)benzoate (D262) in an analogous manner to the process described for Description 73 (D73)

Description 265
Methyl 3-(1-cyclopenten-1-yl)-5-(1,1-dioxidotetrahydro-2H-1,2-thiazin-2-yl)benzoate;
Methyl 3-(2-cyclopenten-1-yl)-5-(1,1-dioxidotetrahydro-2H-1,2-thiazin-2-yl)benzoate;
Methyl 3-(3-cyclopenten-1-yl)-5-(1,1-dioxidotetrahydro-2H-1,2-thiazin-2-yl)benzoate (D265)
Methyl 3-(1-cyclopenten-1-yl)-5-(1,1-dioxidotetrahydro-2H-1,2-thiazin-2-yl)benzoate, methyl 3-(2-cyclopenten-1-yl)-5-(1,1-dioxidotetrahydro-2H-1,2-thiazin-2-yl)benzoate and methyl 3-(3-cyclopenten-1-yl)-5-(1,1-dioxidotetrahydro-2H-1,2-thiazin-2-yl)benzoate (D265) have been obtained from methyl 3-bromo-5-(1,1-dioxidotetrahydro-2H-1,2-thiazin-2-yl)benzoate (D263) in an analogous manner to the process described for Description 73 (D73).

Description 266

Methyl 3-(1,1-dioxidotetrahydro-2H-1,2-thiazin-2-yl)-5-nitrobenzoate (D266)

Methyl 3-(1,1-dioxidotetrahydro-2H-1,2-thiazin-2-yl)-5-nitrobenzoate (D266) was obtained from methyl 3-bromo-5-nitrobenzoate (D11) in an analogous manner to the process described for Description 15 (D15) using Description 22b (D22b) instead of Description D22a (D22a).

Description 267

Methyl 3-amino-5-(1,1-dioxidotetrahydro-2H-1,2-thiazin-2-yl)benzoate (D267)

Methyl 3-amino-5-(1,1-dioxidotetrahydro-2H-1,2-thiazin-2-yl)benzoate (D267) was obtained from methyl 3-(1,1-dioxidotetrahydro-2H-1,2-thiazin-2-yl)-5-nitrobenzoate (D266) in an analogous manner to the process described for Description 16 (D16).

Description 268

Methyl 3-(1,1-dioxidotetrahydro-2H-1,2-thiazin-2-yl)-5-hydroxybenzoate (D268)

To a solution of methyl 3-amino-5-(1,1-dioxidotetrahydro-2H-1,2-thiazin-2-yl)benzoate (D267) (7.5 g, 26.4 mol, 1 equiv) in a 2N aqueous HCl solution (75 ml) and MeOH (75 ml) at 0° C. was added $NaNO_2$ (4.0 g, 58.1 mmol, 2.2 equiv) portionwise over 20 min. MeOH (50 ml) and $H_2O$ (200 ml) were added and the resulting mixture was stirred at 95° C. for 1 h then cooled to room temperature. Most of the MeOH was removed in vacuo and the resulting aqueous phase was extracted with AcOEt. The insoluble material was filtered off to give methyl 3-(1,1-dioxidotetrahydro-2H-1,2-thiazin-2-yl)-5-hydroxybenzoate (D) (0.63 g, 8%). The organic phase was washed with brine, dried over $MgSO_4$ and concentrated in vacuo to give a brown residue which was redissolved in AcOEt. The organic phase was extracted with a saturated aqueous $Na_2CO_3$ solution and the aqueous phase was extracted three times with $Et_2O$ then acidified to pH 1 and re-extracted three times with AcOEt. The combined organic phases were washed with brine, dried over $MgSO_4$ and concentrated in vacuo to give methyl 3-(1,1-dioxidotetrahydro-2H-1,2-thiazin-2-yl)-5-hydroxybenzoate (D268) (2.2 g, 30%).

Description 269

Methyl 5-(1-cyclopenten-1-yl)-3-(1,1-dioxidotetrahydro-2H-1,2-thiazin-2-yl)-2-fluorobenzoate; methyl 5-(2-cyclopenten-1-yl)-3-(1,1-dioxidotetrahydro-2H-1,2-thiazin-2-yl)-2-fluorobenzoate; methyl 5-(3-cyclopenten-1-yl)-3-(1,1-dioxidotetrahydro-2H-1,2-thiazin-2-yl)-2-fluorobenzoate (D269)

Methyl 5-(1-cyclopenten-1-yl)-3-(1,1-dioxidotetrahydro-2H-1,2-thiazin-2-yl)-2-fluorobenzoate; methyl 5-(2-cyclopenten-1-yl)-3-(1,1-dioxidotetrahydro-2H-1,2-thiazin-2-yl)-2-fluorobenzoate; methyl 5-(3-cyclopenten-1-yl)-3-(1,1-dioxidotetrahydro-2H-1,2-thiazin-2-yl)-2-fluorobenzoate (D269) were obtained from Description 158 (D158) in an analogous manner to the process described for Description 73 (D73)

Description 270

Ethyl 2-methyl-2-[3-(trifluoromethyl)phenyl]propanoate (D270)

Ethyl 2-methyl-2-[3-(trifluoromethyl)phenyl]propanoate (D270) was obtained from ethyl [3-(trifluoromethyl)phenyl]acetate in an analogous manner to the process described for Description 98 (D98).

Description 271

2-Methyl-2-[3-(trifluoromethyl)phenyl]propanoic acid (D271)

2-Methyl-2-[3-(trifluoromethyl)phenyl]propanoic acid (D271) was obtained from ethyl 2-methyl-2-[3-(trifluoromethyl)phenyl]propanoate (D270) in an analogous manner to the process described for Description 99 (D99).

Description 272

Phenylmethyl {1-methyl-1-[3-(trifluoromethyl)phenyl]ethyl}carbamate (D272)

Phenylmethyl {1-methyl-1-[3-(trifluoromethyl)phenyl]ethyl}carbamate (D272) was obtained from 2-methyl-2-[3-(trifluoromethyl)phenyl]propanoic acid (D271) in an analogous manner to the process described for Description 100 (D100).

Description 273

2-({[(1,1-Dimethylethyl)oxy]carbonyl}amino)-2-methylpropyl methanesulfonate (D273)

To a solution of 1,1-dimethylethyl (2-hydroxy-1,1-dimethylethyl)carbamate (5.1 g, 27 mmol, 1 equiv) in $CH_2Cl_2$ (100 ml) at room temperature were added NEt3 (11.3 ml, 81 mmol, 3 equiv) and methanesulfonyl chloride (28.3 mmol, 2.2 ml, 1.05 equiv) and the resulting solution was stirred for 2 h then partitioned between AcOEt and a saturated aqueous $NaHCO_3$ solution. The two layers were separated and the organic phase dried over $MgSO_4$ and concentrated in vacuo to give 2-({[(1,1-dimethylethyl)oxy]carbonyl}amino)-2-methylpropyl methanesulfonate (D273) (7.8 g, 108%) as a yellow oil which was used in the next step without further purification.

Description 274

1,1-Dimethylethyl [1,1-dimethyl-2-(phenyloxy)ethyl]carbamate (D274)

To a solution of phenol (2.1 g, 22.4 mmol, 3 equiv) in DMF (10 ml) at room temperature were added NaH (60% dispersion in mineral oil, 360 mg, 9.0 mmol, 1.2 equiv) and after 10 min 2-({[(1,1-dimethylethyl)oxy]carbonyl}amino)-2-methylpropyl methanesulfonate (D273) (2 g, 7.5 mmol, 1 equiv) and the resulting solution was stirred at 50° C. for 2 h then cooled to room temperature and concentrated in vacuo. Purification of the residue by flash chromatography on silica gel (iso-hexane/AcOEt: 9/1 to 6/1) gave 1,1-dimethylethyl [1,1-dimethyl-2-(phenyloxy)ethyl]carbamate (D274) (180 mg, 9%) as a yellow oil.

Description 275

1,1-Dimethylethyl {1,1-dimethyl-2-[(phenylmethyl)oxy]ethyl}carbamate (D275)

1,1-Dimethylethyl {1,1-dimethyl-2-[(phenylmethyl)oxy]ethyl}carbamate (D275) was prepared from 2-({[(1,1-dimethylethyl)oxy]carbonyl}amino)-2-methylpropyl methanesulfonate (D273) in an analogous manner to 1,1-dimethylethyl [1,1-dimethyl-2-(phenyloxy)ethyl]carbamate (D274) using phenylmethanol instead of phenol.

Description 276

1,1-Dimethylethyl {1,1-dimethyl-2-[(2-methylpropyl)thio]ethyl}carbamate (D276)

1,1-Dimethylethyl {1,1-dimethyl-2-[(2-methylpropyl)thio]ethyl}carbamate (D276) was prepared from 2-({[(1,1-dimethylethyl)oxy]carbonyl}amino)-2-methylpropyl methanesulfonate (D273) in an analogous manner to 1,1-dimethylethyl [1,1-dimethyl-2-(phenyloxy)ethyl]carbamate (D274) using 2-methyl-1-propanethiol instead of phenol.

Description 277

1,1-Dimethylethyl (4,4-difluorocyclohexyl)carbamate (D277)

To a solution of 1,1-dimethylethyl (4-oxocyclohexyl) carbamate (1 g, 4.69 mmol, 1 equiv) in $CH_2Cl_2$ (15 ml) was added DAST (1.05 ml, 7.98 mmol, 1.7 equiv) and the resulting mixture was stirred for 15 h. A saturated aqueous $NaHCO_3$ solution was added and the resulting biphasic mixture was stirred vigorously for 1 h. The two layers were separated and the aqueous phase extracted with $CH_2Cl_2$. The combined organic phase were dried over $MgSO_4$ and concentrated in vacuo to give 1,1-dimethylethyl (4,4-difluorocyclohexyl)carbamate (D277) (1.03 g, 93%) as a beige solid which was used in the next step without further purification.

Descriptions 278-281 (D278-281)

The following acids have been obtained by alkylation of cyclobutanecarboxylic acid as described in: K. Tani, A. Naganawa, A. Ishida, K. Sagawa, H. Harada, M. Ogawa, T. Maruyama, S. Ohuchida, H. Nakai, K. Kondo, M. Toda *Bio. Med. Chem.* 2002, 10, 1093-1106:

| Description |
|---|
| 1-Ethylcyclobutanecarboxylic acid (D278) |
| 1-Propylcyclobutanecarboxylic acid (D279) |
| 1-(1-Methylethyl)cyclobutanecarboxylic acid (D280) |
| 1-[(3-Chlorophenyl)methyl] cyclobutanecarboxylic acid (D281) |

Descriptions 282-285 (D282-285)

The following compounds have been obtained from their precursors in an analogous manner to the process described for Description 100 (D100):

| Description | Precursor |
|---|---|
| Phenylmethyl (1-ethylcyclobutyl) carbamate (D282) | D278 |
| Phenylmethyl (1-propylcyclobutyl) carbamate (D283) | D279 |
| Phenylmethyl [1-(1-methylethyl)cyclobutyl] carbamate (D284) | D280 |
| Phenylmethyl {1-[(3-chlorophenyl)methyl] cyclobutyl}carbamate (D285) | D281 |

Descriptions 286-293 (D286-293)

The following amides were obtained via a Ritter reaction as described in: M. Mousseron Bull. Soc. Chim. Fr. 1957, 596.

| Description | Precursor |
|---|---|
| N-(1-Methylcyclohexyl) acetamide (D286) | 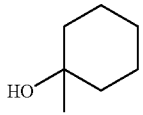 |
| N-(1-Ethylcyclohexyl) acetamide (D287) | 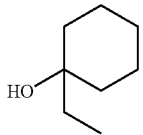 |
| N-(1-Methylcyclopentyl) acetamide (D288) | 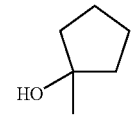 |
| N-(1-Propylcyclopentyl) acetamide (D289) | 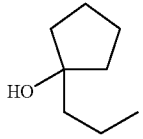 |
| N-(1-Propylcyclohexyl) acetamide (D290) | 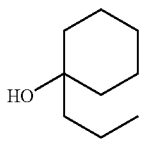 |

| Description | Precursor |
|---|---|
| N-(1,1-Dimethylhexyl) acetamide (D291) | |
| N-[2-(3-Chlorophenyl)-1,1-dimethylethyl] acetamide (D292) | |
| N-{1,1-Dimethyl-2-[3-(methyloxy)phenyl]ethyl}acetamide (D293) | |

Description 294

4,4-Dimethylcyclohexanone (D294)

4,4-Dimethylcyclohexanone (D294) was obtained from 4,4-dimethyl-2-cyclohexen-1-one in an analogous manner to the process described for ester 116 (B116).

Description 295

3,3-Dimethylcyclopentanone (D295)

3,3-Dimethylcyclopentanone (D295) was obtained from 4,4-dimethyl-2-cyclopenten-1-one in an analogous manner to the process described for 4,4-dimethylcyclohexanone (D294).

Description 296

4,4-Dimethylcyclohexanone oxime (D296)

To a solution of 4,4-dimethylcyclohexanone (D294) (9.2 g, 73 mmol, 1 equiv) in EtOH (50 ml) and $H_2O$ (50 ml) were added $NH_2OH \cdot HCl$ (6.6 g, 94.5 mmol, 1.3 equiv) and $Na_2CO_3$ (10.06 g, 94.5 mmol, 1.3 equiv) and the resulting cloudy solution was refluxed for 2 h then cooled to room temperature. Most of EtOH was removed in vacuo and the aqueous phase was extracted twice with AcOEt. The combined organic phases were dried over $MgSO_4$ and concentrated in vacuo to give 4,4-dimethylcyclohexanone oxime (D296) (10 g, 97%) as a colourless solid which was used in the next step without purification.

Descriptions 297-298 (D297-298)

The following oxime were obtained for their precursor in an analogous manner to the process described for Description (D296).

| Description | Precursor |
|---|---|
| (1E/Z)-2,2-Dimethylcyclohexanone oxime (D297) | D294 |
| (1E/Z)-3,3-Dimethylcyclopentanone oxime (D298) | D295 |

Descriptions 299-311 (D299-311)

The following compounds have been obtained from (2S)-2-(1-methylethyl)-3,6-bis(methyloxy)-2,5-dihydropyrazine according to the general procedure described in: P. dalla Croce, C. la Rosa, E. Pizzatti *Tetrahedron: Asymmetry* 2000, 11, 2635-2642:

| Description |
|---|
| 3,5-Difluoro-L-phenylalaninate (D299) |
| 3-Fluoro-L-phenylalaninate (D300) |
| 3,4-Difluoro-L-phenylalaninate (D301) |
| 2-Chloro-L-phenylalaninate (D302) |
| Methyl-3-chloro-L-phenylalaninate (D303) |
| Methyl 4-chloro-L-phenylalaninate (D304) |
| Methyl 3-(2-thienyl)-L-alaninate (D305) |
| Methyl 3-(3-thienyl)-L-alaninate (D306) |
| Methyl 3-(2-furanyl)-L-alaninate (D307) |
| Methyl 3-(2-pyridinyl)-L-alaninate (D308) |
| Methyl 3-(1,3-thiazol-2-yl)-L-alaninate (D309) |
| Methyl 3-(1H-pyrazol-1-yl)-L-alaninate (D310) |
| Methyl 3-(3-pyridinyl)-L-alaninate (D311) |

Descriptions 312-313 (D312-313)

Descriptions 312-313 were prepared in an analogous manner to Example 1 from the appropriate acid and amines indicated in the below table:

| Description | Acid | Amine | [M + H]+ | RT (min) |
|---|---|---|---|---|
| 3-(1,1-dioxido-6,7-dihydro-1,2-thiazepin-2(3H)-yl)-N-[(1S,2R)-2-hydroxy-1-(phenylmethyl)-3-({[3-(trifluoromethyl)phenyl]methyl}amino)propyl]-5-propylbenzamide (D312) | A117 | C16 | 630.4 | 2.89 |
| 3-(1,1-dioxido-6,7-dihydro-1,2-thiazepin-2(3H)-yl)-N-[(1S,2R)-2-hydroxy-3-({[3-(methyloxy)phenyl]methyl}amino)-1-(phenylmethyl)propyl]-5-propylbenzamide (D313) | A117 | C14 | 592.4 | 2.75 |

Description 314

1-[3-(Methyloxy)phenyl]cyclohexanol (D314)

To a solution of 3-methoxyphenylmagnesium bromide (1M in THF, 61 ml, 61 mmol, 1 equiv) at 0° C. was slowly added cyclohexanone (6 g, 61 mmol, 1 equiv) in $Et_2O$ (30 ml). The resulting mixture was stirred at room temperature for 4 h then poured in H₂O at 0° C. The two layers were separated and the aqueous phase was extracted three times with Et₂O. The combined organic phases were washed with brine, dried over MgSO₄ and concentrated in vacuo to give 1-[3-(methyloxy)phenyl]cyclohexanol (D314) (12.4 g, 100%) as a pale yellow oil which was used in the next step without further purification.

Description 315

1-(1-Azidocyclohexyl)-3-(methyloxy)benzene (D315)

To a solution of 1-[3-(methyloxy)phenyl]cyclohexanol (2.93 g, 14.22 mmol, 1 equiv) in CH₂Cl₂ (25 ml) under nitrogen at 0° C. was added sodium azide (1.85 g, 28.44 mmol, 2 equiv) then TFA (4.4 ml, 56.89 mmol, 4 equiv) slowly. 40 Ml of CH₂Cl₂ were then added and the resulting suspension was stirred at room temperature for 16 h then partitioned between Et₂O and H₂O. The two layers were separated and the organic phase was washed with H₂O and a 1N aqueous NaOH solution then dried over MgSO₄ and concentrated in vacuo to give 1-(1-azidocyclohexyl)-3-(methyloxy)benzene (D315) (2.78 g, 85%) as a clear oil which was used in the next step without further purification.

Description 316

(1E/Z)-Propanal oxime (D316)

(1E/Z)-Propanal oxime was obtained from propanal in a similar manner to the process described for Description 296 (D296).

Description 317

1,1-Dimethylethyl 2-propyn-1-ylcarbamate (D317)

To a solution of 2-propyn-1-amine (2 g, 36.4 mmol, 1 equiv) in CH₂Cl₂ (20 ml) were added NEt₃ (5.3 ml, 38.18 mmol, 1.05 equiv) and bis(1,1-dimethylethyl) dicarbonate (8.32 g, 38.18 mmol, 1.05 equiv). The resulting mixture was stirred at room temperature for 3 h then poured in a 2N aqueous HCl solution. The two layers were separated and the organic phase was washed with a saturated aqueous NaHCO₃ solution then dried over MgSO₄ and concentrated in vacuo to give 1,1-dimethylethyl 2-propyn-1-ylcarbamate (D317) (4.05 g, 72%) as a colourless crystal.

Description G33

((1S,2R)-2-hydroxy-1-isobutylcarbamoyl-pentyl)-carbamic acid tert-butyl ester (G33)

(2S,3R)-2-tert-Butoxycarbonylamino-3-hydroxy-hexanoic acid methyl ester (D94) (1.57 g, 6.02 mmol, 1 equiv) was refluxed in iso-butylamine (10 ml) for 2 h. The solution was concentrated in vacuo and the residue purified by flash chromatography on silica gel to give ((1S,2R)-2-hydroxy-1-isobutylcarbamoyl-pentyl)-carbamic acid tert-butyl ester (G33) (1.52 g, 84%) as a white solid.

The following compounds were obtained in an analogous manner to Description 96a using the appropriate (commercially available) acid and amine:

| Name |
| --- |
| ((S)-1-Cyclohexylcarbamoyl-3-methylsulfanyl-propyl)-carbamic acid tert-butyl ester (G6) |
| [(S)-1-(3,3-Dimethyl-butylcarbamoyl)-ethyl]-carbamic acid tert-butyl ester (G36) |

Description G38

((S)-1-Isobutylcarbamoyl-3-methanesulfonyl-propyl)-carbamic acid tert-butyl ester (G38)

To ((S)-1-isobutylcarbamoyl-3-methylsulfanyl-propyl)-carbamic acid tert-butyl ester (D96) (1.19 g, 3.9 mmol, 1 equiv) in CH₂Cl₂ (25 ml) at 0° C. was added m-chloroperbenzoic acid (50-55%, 4.0 g, 11.6 mmol, 3 equiv) portionwise. The resulting mixture was stirred 2 h at 0° C. then diluted with AcOEt and washed with saturated NaHCO₃ aqueous solution, dried over MgSO₄ and concentrated in vacuo to give ((S)-1-isobutylcarbamoyl-3-methanesulfonyl-propyl)-carbamic acid tert-butyl ester (G38) (1.06 g, 81%) as a colourless solid.

Description G157

1,1-Dimethylethyl [(3-ethyl-5-isoxazolyl)methyl]carbamate (G157)

To a solution of (1E/Z)-propanal oxime (D316) (49, 54.8 mmol, 1 equiv) in CH₂Cl₂ (200 ml) at room temperature was added N-chloro succinamide (7.44 g, 55.8 mmol, 1.02 equiv) and the resulting solution was stirred at this temperature for 2.5 h then NEt₃ (20 ml, excess) was added and the resulting mixture stirred for 2 h. DIPEA (9.52 mmol, 55.8 mmol, 1.02 equiv) and 1,1-dimethylethyl 2-propyn-1-ylcarbamate (0317) (1.34 g, 8.76 mmol, 0.16 equiv) were added and the solution stirred for 48 h then poured into a 1M aqueous HCl solution. The two layers were separated and the organic phase was washed with a saturated aqueous NaHCO₃ solution then dried over MgSO₄ and concentrated in vacuo. Purification of the residue by flash chromatography on silicagel (iso-hexane/AcOEt: 4/1 to 3/1) gave 1,1-dimethylethyl [(3-ethyl-5-isoxazolyl)methyl]carbamate (G157) (1.28 g, 63%).

Description F5

1,1,5-Trimethyl-hexylamine (F5)

Description F5 was obtained according to S. S. Berg and D. T. Cowling, *J. Chem. Soc.* (C) 1971, 1653-1658.

Description F33

(2S,3R)-2-Amino-3-hydroxy-hexanoic acid isobutyl-amide hydrochloride salt (F33)

(2S,3R)-2-tert-Butoxycarbonylamino-3-hydroxy-hexanoic acid methyl ester (G33) (235 mg, 0.86 mmol, 1 equiv) was dissolved in 4M HCl in dioxan (4 ml) and the solution was stirred for 1 h at room temperature then concentrated in vacuo. The residue was triturated with Et₂O to give (2S, 3R)-2-amino-3-hydroxy-hexanoic acid isobutyl-amide hydrochloride salt (F33) (176 mg, 95%) as a white solid.

The following compounds (as their hydrochloride salts) have been obtained from the appropriate precursors as

| Name | Precursor |
|---|---|
| (S)-2-Amino-N-cyclohexyl-propionamide (F6) | G6 |
| (S)-2-Amino-hexanoic acid isobutyl-amide (F36) | G36 |

Description F15

1-(3-Methoxy-phenyl)-1-methyl-ethylamine (F15)

A flask was charged with [1-(3-methoxy-phenyl)-1-methyl-ethyl]-carbamic acid benzyl ester (D100) (1 g, 3.34 mmol, 1 equiv), 10% palladium on charcoal (50% wet, 100 mg, 10% w/w), $NH_4COOH$ (2.1 g, 33 mmol, 10 equiv), EtOH (40 ml) and $H_2O$ (8 ml). The resulting mixture was stirred at 80° C. for 2 h, cooled to room temperature and the catalyst was filtered off using a pad of celite. Most of the EtOH was removed in vacuo and the residue was diluted with 1N HCl aqueous solution. The aqueous phase was extracted with AcOEt then basified to pH 13 and extracted twice with AcOEt. These combined organic layers were dried over $MgSO_4$ and concentrated in vacuo to yield 1-(3-methoxy-phenyl)-1-methyl-ethylamine (F15) (290 mg, 53%) as a yellow gum.

Description F40

2-[3-(Trifluoromethyl)phenyl]-2-propanamine (F40)

2-[3-(Trifluoromethyl)phenyl]-2-propanamine (F40) was obtained from phenylmethyl {1-methyl-1-[3-(trifluoromethyl)phenyl]ethyl}carbamate (D272) in an analogous manner to the process described for Description F15 (F15).

Description F41

{1-[3-(Methyloxy)phenyl]cyclohexyl}amine (F41)

To a solution of 1-(1-azidocyclohexyl)-3-(methyloxy) benzene (D315) (2.78 g, 12.0 mmol, 1 equiv) in THF (20 ml) at room temperature was added $LiAlH_4$ (1M in THF, 36 ml, 36 mmol, 3 equiv) and the resulting mixture was stirred at this temperature for 4 h. The mixture was then carefully quenched with a 1N aqueous NaOH solution (6 ml, 60 mmol, 1 equiv) then $H_2O$. The mixture was filtered through a pad of celite then acidified with a 2N aqueous HCl solution (50 ml). The two layers were separated and the pH of the aqueous phase adjusted to 9 using a 2N aqueous NaOH solution. The aqueous phase was extracted three times with $Et_2O$ and the combined organic phase were dried over $MgSO_4$ then concentrated in vacuo to give {1-[3-(methyloxy)phenyl]cyclohexyl}amine (F41) (1.55 g, 63%) as a clear oil which was used in the next step without further purification. $[M+H]^+=189.0$, RT=1.90 min.

Descriptions F48, F61, F81 and F110-114
The following amines were obtained from their corresponding amides in an analogous manner to the process described for Description F5 (F5):

| Description | Precursor |
|---|---|
| 2-Methyl-2-heptanamine (F48) | D291 |
| 2-Methyl-1-[3-(methyloxy)phenyl]-2-propanamine (F61) | D293 |
| 1-Methylcyclohexanamine (F81) | D286 |
| 1-Methylcyclohexanamine (F110) | D287 |
| 1-Methylcyclopentanamine (F111) | D288 |
| 1-Propylcyclopentanamine (F112) | D289 |
| 1-Propylcyclohexanamine (F113) | D290 |
| 1-(3-Chlorophenyl)-2-methyl-2-propanamine (F114) | D292 |

Description F52

7-(Methyloxy)-1,2,3,4-tetrahydro-1-naphthalenamine (F52)

7-(Methyloxy)-1,2,3,4-tetrahydro-1-naphthalenamine (F52) was obtained from 7-(methyloxy)-3,4-dihydro-1(2H)-naphthalenone in an analogous manner to the process described in U.S. Pat. No. 4,132,737.

Descriptions F54-56 and F155
The following amines were prepared from their precursor in an analogous manner to the process described for Amine 1 (C1):

| Description | Precursor |
|---|---|
| 2-Methyl-1-[(2-methylpropyl)thio]-2-propanamine hydrogen chloride (F54) | D276 |
| 2-Methyl-1-(phenyloxy)-2-propanamine hydrogen chloride (F55) | D274 |
| 2-Methyl-1-[(phenylmethyl)oxy]-2-propanamine hydrogen chloride (F56) | D275 |
| 4,4-Difluorocyclohexanamine hydrochloride (F155) | D277 |

Descriptions F63, F73-75 and F77-80
The following amines were prepared from their corresponding nitriles according to the general method described in: P. Bertus, J. Szymoniak Chem. Comm., 2001, 1792:

| Description | Precursor |
|---|---|
| 1-[3-(methyloxy)phenyl] cyclopropanamine (F63) | |
| 1-(4-methylpentyl) cyclopropanamine (F73) | |
| 1-ethylcyclopropanamine (F74) | |
| 1-(1-methylethyl) cyclopropanamine (F75) | |
| 1-propylcyclopropanamine (F77) | |

-continued

| Description | Precursor |
|---|---|
| 1-(3-methylbutyl) cyclopropanamine (F78) | [structure: N≡C-CH2-CH2-CH(CH3)2] |
| 1-(2-methylpropyl) cyclopropanamine (F79) | [structure: N≡C-CH2-CH(CH3)2] |
| 1-[(3-chlorophenyl)methyl] cyclopropanamine (F80) | [structure: N≡C-CH2-(3-chlorophenyl)] |

Descriptions F69 and F148-150

The following compounds have been obtained from their precursors in an analogous manner to the process described for Description F15 (F15):

| Description | Precursor |
|---|---|
| 1-Ethylcyclobutanamine (F69) | D282 |
| 1-Propylcyclobutanamine (F148) | D283 |
| 1-(1-Methylethyl) cyclobutanamine (F149) | D284 |
| 1-[(3-Chlorophenyl)methyl] cyclobutanamine (F150) | D285 |

Description F70

2-Methyl-1-[(2-methylpropyl)oxy]-2-propanamine (F70)

2-Methyl-1-[(2-methylpropyl)oxy]-2-propanamine (F70) was obtained from 2-Methyl-1-[(2-methyl-2-propen-1-yl)oxy]-2-propanamine (F71) in an analogous manner to the process described for Ester 166 (B116).

Description F71

2-Methyl-1-[(2-methyl-2-propen-1-yl)oxy]-2-propanamine (F71)

To a solution of NaH (60% dispersion in mineral oil, 2.0 g, 50 mmol, 1 equiv) in DMF at 0° C. was added 2-amino-2-methyl-1-propanol (4.8 ml, 50 mmol, 1 equiv) and after 1 h 3-bromo-2-methyl-1-propene (5.5 ml, 55 mmol, 1.1 equiv). The resulting solution was stirred at room temperature for 15 h then partitioned between AcOEt and $H_2O$. The two layers were separated and the organic phase was washed with $H_2O$ and brine, dried over $MgSO_4$ and distillated (45° C., P=150 mbar) to give 2-methyl-1-[(2-methyl-2-propen-1-yl)oxy]-2-propanamine (F71) as a light pink solid.

Description F83

4,4-Dimethylcyclohexanamine (F83)

4,4-Dimethylcyclohexanone oxime (D296) (10 g, 71 mmol, 1 equiv) in EtOH (100 ml) was stirred with Raney Ni (1 g, 10% w/w) under an atmosphere of $H_2$ (50 psi) for 4 days. The catalyst was filtered off through a pad of celite and HCl (1M in $Et_2O$, 100 ml, 100 mmol, 1.4 equiv) were added. The precipitate formed was filtered off and dissolved in water. The aqueous phase was washed with $Et_2O$ and made strongly basic with KOH pellets then extracted twice with $CH_2Cl_2$. The combined organic phases were dried over $MgSO_4$ and concentrated in vacuo to give 4,4-dimethylcyclohexanamine (F83) (8 g, 89%) as a clear oil which was used in the next step without further purification.

Descriptions F86 and F92

The following amines were obtained from their precursor in an analogous manner to the process described for 4,4-dimethylcyclohexanamine (F83):

| Amine | Precursor |
|---|---|
| 2,2-Dimethyl cyclohexanamine (F86) | D297 |
| 3,3-Dimethyl cyclopentanamine (F92) | D298 |

Description F157

[(3-Ethyl-5-isoxazolyl)methyl]amine (F157)

[(3-Ethyl-5-isoxazolyl)methyl]amine (F157) was obtained from 1,1-dimethylethyl [(3-ethyl-5-isoxazolyl)methyl]carbamate (G157) in an analogous manner to the process described in Description F33 (F33).

Preparation of Esters

Ester 1

3-Methylsulfanyl-5-(2-oxo-pyrrolidin-1-yl)-benzoic acid methyl ester (B1)

To a solution of crude 3-(4-chloro-butanoylamino)-5-methylsulfanyl-benzoic acid methyl ester (D64) (0.17 g, 0.56 mmol, 1 equiv) in THF (2 ml) at 0° C. was added portionwise NaH (60% in mineral oil, 24.6 mg, 0.616 mmol, 1.1 equiv) over 2 min. The resulting mixture was stirred at room temperature for 40 min and one drop of MeOH was added to destroy the remaining NaH. The resulting mixture was then diluted with AcOEt, washed sequentially with 2N aqueous HCl solution, saturated aqueous $NaHCO_3$ solution and brine, dried over $Na_2SO_4$ and concentrated in vacuo. Purification by flash chromatography on silica gel (iso-hexane/AcOEt: 1/1) gave 3-(4-chloro-butanoylamino)-5-methylsulfanyl-benzoic acid methyl ester (B1) (122 mg, 82%) as a white solid. $[M+H]^+=266.0$, RT=2.86 min Ester 2

3-Ethylsulfanyl-5-(2-oxo-pyrrolidin-1-yl)-benzoic acid ethyl ester (B2)

Ester 2 was prepared from 177 mg (0.54 mmol) of 3-(4-chloro-butanoylamino)-5-ethylsulfanyl-benzoic acid ethyl ester (D65) in an analogous manner to that described for Ester 1 which yielded 129 mg (82%) of 3-ethylsulfanyl-5-(2-oxo-pyrrolidin-1-yl)-benzoic acid ethyl ester (B2) as a clear colorless gum after purification by flash chromatography on silica gel (iso-hexane/AcOEt: 60/40). $[M+H]^+=294.1$, RT=3.23 min Ester 3

3-(1,1-Dioxo-1/⁶-isothiazolidin-2-yl)-5-methylsulfanyl-benzoic acid methyl ester (B3)

To a solution of 3-(3-chloro-propane-1-sulfonylamino)-5-methylsulfanyl-benzoic acid methyl ester (D66) (183 mg, 0.54 mmol, 1 equiv) in MeOH (3 ml) was added NEt₃ (150 μl, 1.08 mmol, 2 equiv). The resulting mixture was stirred at 70° C. for 2 h then left to cool to room temperature overnight. A further portion of NEt₃ (75 μl, 0.54 mmol, 1 equiv) was added and the mixture was stirred at 80° C. for 3 h when another portion of NEt₃ (75 μl, 0.54 mmol, 1 equiv) was added. After another 2 h at 80° C., the solution was cooled to room temperature and concentrated in vacuo. The residue was partitioned between AcOEt and 2N aqueous HCl solution. The organic layer was washed with brine, dried over Na₂SO₄ and concentrated in vacuo. Purification by flash chromatography on silica gel (iso-hexane/AcOEt: 60/40) gave 3-(1,1-dioxo-1/⁶-isothiazolidin-2-yl)-5-methylsulfanyl-benzoic acid methyl ester (B3) (150 mg, 92%). [M+H]⁺=302.0 RT=2.89 min Ester 4

3-(1,1-Dioxo-1/⁶-isothiazolidin-2-yl)-5-ethylsulfanyl-benzoic acid ethyl ester (B4)

Ester 4 was prepared from 190 mg (0.52 mmol) 3-(3-chloro-propane-1-sulfonylamino)-5-ethylsulfanyl-benzoic acid ethyl ester (D67) in an analogous manner to that described for Ester 3 which yielded 154 mg (90%) of 3-(1,1-dioxo-1/⁶-isothiazolidin-2-yl)-5-ethylsulfanyl-benzoic acid ethyl ester (B4) after purification by flash chromatography on silica gel (iso-hexane/AcOEt: 60/40). [M+H]⁺=330.0, RT=3.24 min Ester 11

3-Ethoxy-5-(2-oxo-pyrrolidin-1-yl)-benzoic acid methyl ester (B11)

To 3-hydroxy-5-(2-oxo-pyrrolidin-1-yl)-benzoic acid methyl ester (D37) (0.80 g, 3.4 mmol, 1 equiv) dissolved in DMF (10 ml) was added K₂CO₃ (0.94 g, 6.8 mmol, 2 equiv) and ethyl iodide (1.1 g, 6.8 mmol, 2 equiv). The resulting mixture was heated at 50° C. for 4 h, cooled to room temperature, diluted with 2N aqueous HCl solution (50 ml) and extracted with Et₂O (50 ml). The organic phase was then washed with water (50 ml), dried over MgSO₄ and concentrated in vacuo to give of 3-ethoxy-5-(2-oxo-pyrrolidin-1-yl)-benzoic acid methyl ester (B11) (0.85 g, 95%) as a brown oil which slowly solidified to a tan solid.

Ester 11 (Alternative Procedure)

3-Ethoxy-5-(2-oxo-pyrrolidin-1-yl)-benzoic acid methyl ester (B11)

3-(4-Chloro-butanoylamino)-5-ethoxy-benzoic acid methyl ester (D51) (7 g, 20 mmol, 1 equiv) in THF (50 ml) was treated portionwise with NaH (60% in mineral oil, 0.88 g, 22 mmol, 1.1 equiv) over 15 min at room temperature. The resulting mixture was stirred for 30 min and then diluted with AcOEt (300 ml). The resulting solution was washed with 2N aqueous HCl solution (200 ml), dried over MgSO₄ and concentrated in vacuo. Recrystallisation of the residue from Et₂O/hexane gave 3-ethoxy-5-(2-oxo-pyrrolidin-1-yl)-benzoic acid methyl ester (B11) (3.5 g, 66%) as white solid.

The following esters were prepared in an analogous manner to Ester 11 from D37 using an appropriate commercially available reagent:

| Ester |
| --- |
| 3-Methoxy-5-(2-oxo-pyrrolidin-1-yl)-benzoic acid methyl ester (B9) |
| 3-(2-Oxo-pyrrolidin-1-yl)-5-propoxy-benzoic acid methyl ester (B10) |
| 3-Isopropoxy-5-(2-oxo-pyrrolidin-1-yl)-benzoic acid methyl ester (B12) |
| 3-(2-Oxo-pyrrolidin-1-yl)-5-pentyloxy-benzoic acid methyl ester (B13) |

Ester 14

The following ester was prepared in an analogous manner to Description 38 from Description 37 using the appropriate alcohol indicated in the table below:

| Ester | Alcohol |
| --- | --- |
| 3-(2-Methoxy-ethoxy)-5-(2-oxo-pyrrolidin-1-yl)-benzoic acid methyl ester (B14) | 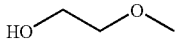 |

Ester 15

3-(3-Hydroxy-propoxy)-5-(2-oxo-pyrrolidin-1-yl)-benzoic acid methyl ester (B15)

3-(3-Benzyloxy-propoxy)-5-(2-oxo-pyrrolidin-1-yl)-benzoic acid methyl ester (D38) in MeOH (15 ml) was hydrogenolysed initially with 10% Pd on charcoal (50% wet, 0.25 g, 0.25 equiv w/w) at atmospheric pressure for 24 hrs and then a further 0.25 g of 10% Pd on charcoal (50% wet, 0.25 g, 0.25 equiv w/w) was added and the mixture hydrogenolysed at 50 psi for a further 48 hrs. The mixture was filtered through Celite and concentrated in vacuo. Purification by flash chromatography on silica gel (AcOEt/iso-hexane: 1/1) gave 3-(3-hydroxy-propoxy)-5-(2-oxo-pyrrolidin-1-yl)-benzoic acid methyl ester (B15) (260 mg, 69% over 2 steps). [M+H]⁺=294.0

Ester 17

3-(3-Methoxy-propoxy)-5-(2-oxo-pyrrolidin-1-yl)-benzoic acid methyl ester (B17)

3-(3-Hydroxy-propoxy)-5-(2-oxo-pyrrolidin-1-yl)-benzoic acid methyl ester (B15) (127 mg, 0.43 mmol, 1 equiv) in CH₂Cl₂ (2 ml) was treated with proton sponge (279 mg, 1.30 mmol, 3 equiv) and trimethyloxonium tetrafluoroborate (192 mg, 1.30 mmol, 3 equiv). After 3 hrs, further quantities of proton sponge (93 mg, 0.43 mmol, 1 equiv) and trimethyloxonium tetrafluoroborate (65 mg, 0.43 mmol, 1 equiv) were added and stirring was continued for a further 2 h. The mixture was then partitioned between AcOEt and 2N aqueous HCl solution. The two layers were separated and the aqueous phase extracted with AcOEt. The combined organic layers were washed with saturated aqueous NaHCO$_3$ solution, 2N aqueous HCl solution and brine and then dried over Na$_2$SO$_4$ and concentrated in vacuo. Purification by flash chromatography on silica gel (ethyl acetate/iso-hexane: 1/4 to 1/3) gave 3-(3-methoxy-propoxy)-5-(2-oxo-pyrrolidin-1-yl)-benzoic acid methyl ester (B17) (76 mg, 58%). [M+H]+=308.1

Ester 18

3-(1,1-Dioxo-1/$^6$-isothiazolidin-2-yl)-5-ethoxy-benzoic acid methyl ester (B18)

To 3-(1,1-dioxo-1/$^6$-isothiazolidin-2-yl)-5-hydroxy-benzoic acid methyl ester (D41) (0.80 g, 3.0 mmol, 1 equiv) dissolved in DMF (10 ml) was added K$_2$CO$_3$ (0.94 g, 6.8 mmol, 2 equiv) and ethyl iodide (1.1 g, 6.8 mmol, 2 equiv) and the resulting mixture was heated at 50° C. for 4 h then cooled to room temperature and diluted with 2N aqueous HCl solution (50 ml). The aqueous phase was extracted with Et$_2$O (50 ml). The organic phase was washed with H$_2$O (50 ml), dried over MgSO$_4$ and concentrated in vacuo. Purification by flash chromatography on silica gel (AcOEt/iso-hexane: 1/1) gave 3-(1,1-dioxo-1/$^6$-isothiazolidin-2-yl)-5-ethoxy-benzoic acid methyl ester (B18) (220 mg, 25%) as a pale yellow oil.

Ester 18 (Alternative Procedure)

3-(1,1-Dioxo-1/$^6$-isothiazolidin-2-yl)-5-ethoxy-benzoic acid methyl ester (B18)

A solution of 3-(3-chloro-propane-1-sulfonylamino)-5-ethoxy-benzoic acid methyl ester (D53) (6.7 g, 20 mmol, 1 equiv) in EtOH (100 ml) was treated with NEt$_3$ (4.0 g, 40 mmol, 2 equiv). The resulting mixture was refluxed for 4 h, cooled to room temperature and concentrated in vacuo. The residue was dissolved in AcOEt (200 ml) and the resulting solution was washed with 2N aqueous HCl solution (100 ml) followed by saturated aqueous NaHCO$_3$ solution (100 ml) then dried over MgSO$_4$ and concentrated in vacuo to give a brown oil. Crystallisation from Et$_2$O/hexane gave 3-(1,1-dioxo-1-isothiazolidin-2-yl)-5-ethoxy-benzoic acid methyl ester (B18) (4.7 g, 78%) as a light tan solid.

Ester 19

3-(1,1-Dioxo-1/$^6$-isothiazolidin-2-yl)-5-isopropoxy-benzoic acid methyl ester (B19)

To 3-(1,1-dioxo-1/$^6$-isothiazolidin-2-yl)-5-hydroxy-benzoic acid methyl ester (D41) (0.30 g, 1.1 mmol, 1 equiv) dissolved in DMF (5 ml) was added K$_2$CO$_3$ (0.306 g, 2.2 mmol, 2 equiv) and 2-iodopropane (374 mg, 2.2 mmol, 2 equiv) and the mixture heated at 50° C. for 4 h then cooled to room temperature and diluted with 2N aqueous HCl solution (50 ml). The aqueous phase was extracted with Et$_2$O (50 ml) and the organic phase was washed with H$_2$O (50 ml), dried over MgSO$_4$ and concentrated in vacuo to give 3-(1,1-dioxo-1/$^6$-isothiazolidin-2-yl)-5-isopropoxy-benzoic acid methyl ester (B19) (290 mg, 88%) as a pale yellow oil.

The following esters were prepared from Description 41 in an analogous manner to the process described for Ester 19 using the appropriate commercially available reagents:

| Ester |
| --- |
| 3-(1,1-Dioxo-1/$^6$-isothiazolidin-2-yl)-5-methoxy-benzoic acid methyl ester (B20) |
| 3-(1,1-Dioxo-1/$^6$-isothiazolidin-2-yl)-5-propoxy-benzoic acid methyl ester (B21) |
| 3-(1,1-Dioxo-1/$^6$-isothiazolidin-2-yl)-5-pentyloxy-benzoic acid methyl ester (B22) |

The following esters were prepared in an analogous manner to the process described in Description 30 from the appropriate aryl bromide and amine starting materials listed in the below table:

| Ester | Aryl bromide | Amine | [M + H]+ | RT (min) |
| --- | --- | --- | --- | --- |
| 3-(2-Oxo-pyrrolidin-1-yl)-5-pyrrolidin-1-yl-benzoic acid methyl ester (B113) | D9a |  | 289.1 | 3.03 |
| 3-Morpholin-4-yl-5-(2-oxo-pyrrolidin-1-yl)-benzoic acid methyl ester (B29) | D9a |  | 305.0 | 2.59 |
| 3-(4-Methyl-piperazin-1-yl)-5-(2-oxo-pyrrolidin-1-yl)-benzoic acid methyl ester (B115) | D9a | 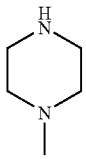 | 318.1 | 1.91 |

-continued

| Ester | Aryl bromide | Amine | [M + H]⁺ | RT (min) |
|---|---|---|---|---|
| 3-(2-Oxo-pyrrolidin-1-yl)-5-piperidin-1-yl-benzoic acid methyl ester (B28) | D9a | 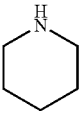 | 303.1 | 2.93 |
| 3-(2-Oxo-piperidin-1-yl)-5-pyrrolidin-1-yl-benzoic acid tert-butyl ester (B54) | D10 |  | 345.2 | 3.35 |
| 3-Morpholin-4-yl-5-(2-oxo-piperidin-1-yl)-benzoic acid tert-butyl ester (B56) | D10 | 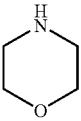 | 361.2 | 2.95 |
| 3-(2-Oxo-piperidin-1-yl)-5-piperidin-1-yl-benzoic acid tert-butyl ester (B55) | D10 |  | 359.2 | 3.35 |
| 3-(1,1-Dioxo-1l⁶-isothiazolidin-2-yl)-5-pyrrolidin-1-yl-benzoic acid tert-butyl ester (B114) | D17 |  | 67.1 | 3.43 |
| 3-(1,1-Dioxo-1l⁶-isothiazolidin-2-yl)-5-morpholin-4-yl-benzoic acid tert-butyl ester (B61) | D17 | 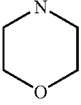 | 383.1 | 3.04 |

Ester 24

3,5-Bis-(2-oxo-pyrrolidin-1-yl)benzoic acid methyl ester (B24)

To a solution of 3-bromo-5-iodobenzoic acid methyl ester (D8a) (588 mg, 1.72 mmol, 1.5 equiv) in dioxan (10 ml) was added pyrrolidin-2-one (120 µl, 1.14 mmol, 1 equiv), Cs₂CO₃ (720 mg, 2.21 mmol, 2 equiv), Xantphos (51 mg, 0.09 mmol, 0.08 equiv) and tris(dibenzylideneacetone)dipalladium (0) (28 mg, 0.03 mmol, 0.026 equiv). The reaction mixture was stirred at 100° C. for 16 h, then cooled to room temperature and filtered through a pad of celite and concentrated in vacuo. Purification by column chromatography on silica gel (EtOAc) yielded 3,5-bis-(2-oxo-pyrrolidin-1-yl) benzoic acid methyl ester (B24) (411 mg, 79%) as light yellow solid. [M+H]⁺=303.2

The following esters were prepared in an analogous manner to Ester 23 from the appropriate starting materials indicated in the below table:

| Ester | Precursor |
|---|---|
| 4-Chloro-3,5-bis-(2-oxo-pyrrolidin-1-yl)-benzoic acid methyl ester (B25) | D28a |
| 4-Methoxy-3,5-bis-(2-oxo-pyrrolidin-1-yl)-benzoic acid methyl ester (B26) | D28b |

Ester 27

3-Nitro-5-(2-oxo-pyrrolidin-1-yl)-benzoic acid methyl ester (B27)

To a solution of 3-(4-chloro-butanoylamino)-5-nitro-benzoic acid methyl ester (D2) (56 g, 186 mmol, 1 equiv) in THF (500 ml) under nitrogen was added portionwise NaH (60% w/w in mineral oil, 8 g, 200 mmol, 1.07 equiv) over 10 min. The resulting mixture was stirred at room temperature for 1 h then cooled to 0° C. and MeOH was added dropwise until bubbling ceased.

The solution was concentrated in vacuo and the residue diluted with AcOEt. The organic phase was washed with H₂O, dried over MgSO₄ and concentrated in vacuo. The residue was triturated with iso-hexane to give 3-nitro-5-(2-oxo-pyrrolidin-1-yl)-benzoic acid methyl ester (B27) (38.5 g, 78%) as a light tan solid.

Ester 30

3-(2-Oxo-pyrrolidin-1-yl)-5-phenylamino-benzoic acid methyl ester (B30)

A flask was charged under nitrogen with 3-bromo-5-(2-oxo-pyrrolidin-1-yl)-benzoic acid methyl ester (D9a) (298 mg, 1 mmol, 1 equiv), Cs₂CO₃ (488 mg, 1.5 mmol, 1.5 equiv), tris(dibenzylideneacetone)dipalladium(0) (18.3 mg, 0.02 mmol, 0.02 equiv), 2-(di-tert-butylphosphino)biphenyl (18 mg, 0.06 mmol, 0.06 equiv) and DME (8 ml). Aniline (136 µl, 1.5 mmol, 1.5 equiv) was then added via syringe and the resulting mixture was stirred at 100° C. for 16 h then cooled to room temperature, diluted with H$_2$O and AcOEt. The layers were separated and the aqueous phase was extracted with AcOEt. The combined organic phases were dried over MgSO$_4$ and concentrated in vacuo. Purification of the residue by flash chromatography on silica gel (isohexane/AcOEt: 3/1 to 1/1) gave 3-(2-oxo-pyrrolidin-1-yl)-5-phenylamino-benzoic acid methyl ester (B30) (100 mg, 32%) as a white solid. [M+H]$^+$=311.0, RT=3.14 min Ester 31

3-Ethylamino-5-(2-oxo-pyrrolidin-1-yl)-benzoic acid tert-butyl ester (B31)

A flask was charged with (benzyl-ethyl-amino)-(2-oxo-pyrrolidin-1-yl)-benzoic acid tert-butyl ester (D30) (3 g, 7.6 mmol, 1 equiv), 10% Pd on charcoal (50% wet, 600 mg, 10% w/w), NH$_4$COOH (4.8 g, 76 mmol, 10 equiv), MeOH (30 ml) and H$_2$O (50 ml). The resulting mixture was stirred at 50° C. for 16 h, cooled to room temperature and the catalyst was filtered off using a pad of celite. Most of the MeOH was removed in vacuo and the residue was diluted with saturated aqueous NaHCO$_3$ solution. The aqueous phase was extracted twice with AcOEt. The combined organic phases were dried over MgSO$_4$ and concentrated in vacuo to give 3-ethylamino-5-(2-oxo-pyrrolidin-1-yl)-benzoic acid tert-butyl ester (B31) (2.2 g, 95%) as a yellow oil. [M+H]$^+$=305.2, RT=3.11 min The following esters were prepared in an analogous manner to the process described in Ester 31 (B31) from the appropriate benzyl aniline precursor listed in the below table:

| Ester | Precursor | [M + H]$^+$ | RT (min) |
|---|---|---|---|
| 3-Methylamino-5-(2-oxo-pyrrolidin-1-yl)-benzoic acid tert-butyl ester (B32) | D31 | 291.1 | 2.96 |
| 3-Methylamino-5-(2-oxo-piperidin-1-yl)-benzoic acid tert-butyl ester (B57) | D32 | 249.1 (-tBu) | 2.91 |
| 3-Ethylamino-5-(2-oxo-piperidin-1-yl)-benzoic acid tert-butyl ester (B59) | D33 | 319.2 | 3.10 |
| 3-(1,1-Dioxo-1/$^6$-isothiazolidin-2-yl)-5-methylamino-benzoic acid tert-butyl ester (B62) | D34 | | |
| 3-(1,1-Dioxo-1/$^6$-[1,2]thiazinan-2-yl)-5-ethylamino-benzoic acid tert-butyl ester (B73) | D35 | 355.2 | 3.32 |

Ester 33

Diethylamino-(2-oxo-pyrrolidin-1-yl)-benzoic acid methyl ester (B33)

To a solution of 3-amino-5-(2-oxo-pyrrolidin-1-yl)-benzoic acid methyl ester (D4a) (100 mg, 0.43 mmol, 1 equiv) in (CH$_2$Cl)$_2$ (1.5 ml) was added acetaldehyde (0.072 ml, 1.29 mmol, 3 equiv) and sodium triacetoxyborohydride (273 mg, 1.29 mmol, 3 equiv). The resulting solution was stirred at room temperature for 1 h, diluted with AcOEt (20 ml), washed with 2N aqueous NaOH solution (20 ml), dried over MgSO$_4$ and concentrated in vacuo to give diethylamino-(2-oxo-pyrrolidin-1-yl)-benzoic acid methyl ester (B33) (110 mg, 98%) as a pale yellow oil.

The following esters were prepared in an analogous manner to the process described in Ester 33 (B33) using the appropriate aldehyde and the appropriate aniline indicated in the below table:

| Ester | Aniline | [M + H]$^+$ | RT (min) |
|---|---|---|---|
| Dimethylamino-(2-oxo-pyrrolidin-1-yl)-benzoic acid methyl ester (B34) | D4a | 263.0 | 2.63 |
| Diethylamino-(1,1-dioxo-1/$^6$-isothiazolidin-2-yl)-benzoic acid methyl ester (B63) | D16 | 327.0 | 2.96 |
| Diethylamino-(2-oxo-piperidin-1-yl)-benzoic acid methyl ester (B60) | D4b | | |

Ester 35

3-(2-Oxo-pyrrolidin-1-yl)-5-propylamino-benzoic acid methyl ester (B35)

To a solution of 3-amino-5-(2-oxo-pyrrolidin-1-yl)-benzoic acid methyl ester (D4a) (500 mg, 2,14 mmol, 1 equiv) in (CH$_2$Cl)$_2$ (10 ml) was added sodium triacetoxyborohydride (640 mg, 3.02 mmol, 1.4 equiv), propionaldehyde (0.156 ml, 2.14 mmol, 1 equiv) and CH$_3$COOH (0.125 ml, 2.18 mmol, 1.02 equiv) The resulting mixture was stirred at room temperature for 2 h, diluted with CH$_2$Cl$_2$ (20 ml), washed with saturated aqueous NaHCO$_3$ solution (20 ml), dried over MgSO$_4$ and concentrated in vacuo. Purification of the residue by flash chromatography on silica gel (isohexane/AcOEt: 3/2) gave 3-(2-oxo-pyrrolidin-1-yl)-5-propylamino-benzoic acid methyl ester (B35) (250 mg, 42%) as a colourless oil.

The following esters were obtained in an analogous manner to the process described in Ester 35 (B35) using the appropriate aldehyde and the appropriate aniline indicated in the table below:

| Ester | Aniline | [M + H]$^+$ | RT (min) |
|---|---|---|---|
| 3-Benzylamino-5-(1,1-dioxo-1/$^6$-isothiazolidin-2-yl)-benzoic acid methyl ester (B64) | D16 | | |
| 3-Butylamino-5-(1,1-dioxo-1/$^6$-isothiazolidin-2-yl)-benzoic acid methyl ester (B65) | D16 | 327.0 | 3.10 |
| 3-(1,1-Dioxo-1/$^6$-isothiazolidin-2-yl)-5-(3-methyl-butylamino)-benzoic acid methyl ester (B66) | D16 | 341.1 | 3.26 |
| 3-(1,1-Dioxo-1/$^6$-isothiazolidin-2-yl)-5-phenethylamino-benzoic acid methyl ester (B67) | D16 | 375.0 | 3.23 |

-continued

| Ester | Aniline | [M + H]+ | RT (min) |
|---|---|---|---|
| 3-(1,1-Dioxo-1/6-isothiazolidin-2-yl)-5-pentylamino-benzoic acid methyl ester (B68) | D16 | 341.1 | 3.29 |
| 3-(1,1-Dioxo-1/6-isothiazolidin-2-yl)-5-propylamino-benzoic acid methyl ester (B69) | D16 | 313.0 | 2.90 |
| 3-(1,1-Dioxo-1/6-isothiazolidin-2-yl)-5-ethylamino-benzoic acid methyl ester (B70) | D16 | 299.0 | 2.91 |
| 3-(Cyclopropylmethyl-amino)-5-(1,1-dioxo-1/6-isothiazolidin-2-yl)-benzoic acid methyl ester (B71) | D16 | 325.0 | 2.91 |
| 3-Isobutylamino-5-(2-oxo-pyrrolidin-1-yl)-benzoic acid methyl ester (B36) | D4a | 291.1 | 3.03 |
| 3-Benzylamino-5-(2-oxo-pyrrolidin-1-yl)-benzoic acid methyl ester (B37) | D4a | | |
| 3-(3-Methyl-butylamino)-5-(2-oxo-pyrrolidin-1-yl)-benzoic acid methyl ester (B38) | D4a | | |
| 3-(2-Oxo-pyrrolidin-1-yl)-5-pentylamino-benzoic acid methyl ester (B39) | D4a | | |
| 3-Butylamino-5-(2-oxo-pyrrolidin-1-yl)-benzoic acid methyl ester (B40) | D4a | | |
| 3-(2,2-Dimethyl-propylamino)-5-(2-oxo-pyrrolidin-1-yl)-benzoic acid methyl ester (B41) | D4a | 305.0 | 3.22 |
| 3-(Cyclopropylmethyl-amino)-5-(2-oxo-pyrrolidin-1-yl)-benzoic acid methyl ester (B42) | D4a | | |
| 3-(2-Oxo-piperidin-1-yl)-5-propylamino-benzoic acid methyl ester (B58) | D4b | | |

Ester 43

3-(1-Ethyl-propylamino)-5-(2-oxo-pyrrolidin-1-yl)-benzoic acid methyl ester (B43)

To a solution of 3-amino-5-(2-oxo-pyrrolidin-1-yl)-benzoic acid methyl ester (D4a) (200 mg, 0.87 mmol, 1 equiv) in (CH$_2$Cl)$_2$ (5 ml) were added sodium triacetoxyborohydride (1.536 g, 5.22 mmol, 6 equiv), 3-pentanone (0.546 ml, 5.22 mmol, 6 equiv) and AcOH (0.050 ml, 0.87 mmol, 1 equiv). The resulting mixture was stirred at room temperature for 48 h, diluted with CH$_2$Cl$_2$ (20 ml), washed with saturated aqueous NaHCO$_3$ solution (20 ml), dried over MgSO$_4$ and concentrated in vacuo. Purification of the residue by flash chromatography on silica gel (iso-hexane/AcOH: 3/2) gave 3-(1-ethyl-propylamino)-5-(2-oxo-pyrrolidin-1-yl)-benzoic acid methyl ester (B43) (106 mg, 40%) as a colourless oil. [M+H]+=305.0 RT=3.19

The following esters were obtained in an analogous manner to Ester 43 (B43) using the appropriate ketone and the appropriate aniline indicated in the table below:

| Ester | Aniline | [M + H] | RT (min) |
|---|---|---|---|
| 3-(1,1-Dioxo-1/6-isothiazolidin-2-yl)-5-isopropylamino-benzoic acid methyl ester (B72) | D16 | 313.0 | 2.82 |
| 3-Isopropylamino-5-(2-oxo-pyrrolidin-1-yl)-benzoic acid methyl ester (B44) | D4a | 227.0 | 2.75 |
| 3-Cyclopentylamino-5-(2-oxo-pyrrolidin-1-yl)-benzoic acid methyl ester (B45) | D4a | | |
| 3-Cyclohexylamino-5-(2-oxo-pyrrolidin-1-yl)-benzoic acid methyl ester (B46) | D4a | | |

Ester 47

(Acetyl-methyl-amino)-(ethyl-propionyl-amino)-benzoic acid tert-butyl ester (B47)

To a solution of 3-methylamino-5-(2-oxo-pyrrolidin-1-yl)-benzoic acid tert-butyl ester (B32) (200 mg, 0.69 mmol, 1 equiv) in CH$_2$Cl$_2$ (5 ml) was added NEt$_3$ (278 µl, 2 mmol, 2.9 equiv) and acetic anhydride (195 µl, 2 mmol, 2.9 equiv). The resulting mixture was stirred at room temperature for 16 h, diluted with CH$_2$Cl$_2$, washed with saturated aqueous NaHCO$_3$ solution, dried over MgSO$_4$ and concentrated in vacuo to give (acetyl-methyl-amino)-(ethyl-propionyl-amino)-benzoic acid tert-butyl ester (B47) (203 mg, 89%) as a pale yellow oil which was used in the next step without further purification. [M+H]+=333.1 RT=2.76 min The following esters were prepared in an analogous manner to the process described in Ester 47 from the appropriate amine starting materials:

| Ester | Amine |
|---|---|
| (Acetyl-propyl-amino)-(2-oxo-pyrrolidin-1-yl)-benzoic acid methyl ester (B48) | B35 |
| (Acetyl-isopropyl-amino)-(2-oxo-pyrrolidin-1-yl)-benzoic acid methyl ester (B49) | B44 |

Ester 50

3-Acetylamino-5-(2-oxo-pyrrolidin-1-yl)-benzoic acid methyl ester (B50)

To a solution of 3-amino-5-(2-oxo-pyrrolidin-1-yl)-benzoic acid methyl ester (D4a) (80 mg, 0.34 mmol, 1 equiv) in CH$_2$Cl$_2$ (10 ml) was added NEt$_3$ (0.142 ml, 1.02 mmol, 2 equiv) and acetic anhydride (0.078 ml, 0.82 mmol, 2.4 equiv). The resulting mixture was stirred at room temperature for 16 h. The reaction was then diluted with AcOEt (20 ml), washed with 2N aqueous HCl solution (20 ml), dried over MgSO$_4$, and concentrated in vacuo to give 3-acetylamino-5-(2-oxo-pyrrolidin-1-yl)-benzoic acid methyl ester (B50) (67 mg, 71%) as a pale yellow foam.

Ester 51

(Methanesulfonyl-methyl-amino)-(2-oxo-pyrrolidin-1-yl)-benzoic acid tert-butyl ester (B51)

To a solution of 3-methylamino-5-(2-oxo-pyrrolidin-1-yl)-benzoic acid tert-butyl ester (B32) (200 mg, 0.69 mmol, 1 equiv) in CH$_2$Cl$_2$ (5 ml) was added NEt$_3$ (278 pd, 2 mmol, 2.9 equiv) and methanesulphonyl chloride (162 μl, 2 mmol, 2.9 equiv). The resulting mixture was stirred at room temperature for 16 h, diluted with CH$_2$Cl$_2$, washed with saturated aqueous NaHCO$_3$ solution, dried over MgSO$_4$ and concentrated in vacuo to give (methanesulfonyl-methylamino)-(2-oxo-pyrrolidin-1-yl)-benzoic acid tert-butyl ester (B51) (203 mg, 89%) as a pale yellow oil. [M+H]$^+$=313.0, RT=2.95 min Ester 52

(Methanesulfonyl-propyl-amino)-(2-oxo-pyrrolidin-1-yl)-benzoic acid methyl ester (B52)

Ester 52 was prepared from 3-(2-oxo-pyrrolidin-1-yl)-5-propylamino-benzoic acid methyl ester (B35) in an analogous manner to that described for Ester 51 (B51).

Ester 53

3-Methanesulfonylamino-5-(2-oxo-pyrrolidin-1-yl)-benzoic acid methyl ester (B53)

To a solution of 3-amino-5-(2-oxo-pyrrolidin-1-yl)-benzoic acid methyl ester (D4a) (200 mg, 0.85 mmol, 1 equiv) in CH$_2$Cl$_2$ (5 ml) and DMF (5 ml) was added NEt$_3$ (0.181 ml, 1.3 mmol, 1.5 equiv) and methanesulphonyl chloride (0.071 ml, 1 mmol, 1.2 equiv). The resultant mixture was stirred at room temperature for 1 h, diluted with AcOEt (30 ml), washed with 2N aqueous HCl solution (30 ml), dried over MgSO$_4$ and concentrated in vacuo. The residue was triturated with Et$_2$O and then filtered to give 3-methanesulfonylamino-5-(2-oxo-pyrrolidin-1-yl)-benzoic acid methyl ester (B53) as a pale yellow solid (100 mg, 38%).

Ester 74

5-(2-Oxo-pyrrolidin-1-yl)-isophthalic acid 1-tert-butyl ester 3-methyl ester (B74)

A solution of 1-tert-butyl ester 3-methyl ester (D80) (4.5 g, 12.7 mmol, 1 equiv) in THF (60 ml) was treated portionwise with NaH (60% suspension in mineral oil, 560 mg, 14 mmol, 1.1 equiv) over 5 min at room temperature. The resulting mixture was stirred for 1 h, then MeOH (5 ml) was added and the mixture was concentrated in vacuo. The residue was diluted with AcOEt (200 ml) and the organic phase was washed with H$_2$O (100 ml), dried over MgSO$_4$ and concentrated in vacuo to give 5-(2-oxo-pyrrolidin-1-yl)-isophthalic acid 1-tert-butyl ester 3-methyl ester (B74) (3.9 g, 97%) as a white solid.

Ester 76

3-Hydroxymethyl-5-(2-oxo-pyrrolidin-1-yl)-benzoic acid methyl ester (B76)

A suspension of 5-(2-oxo-pyrrolidin-1-yl)-isophthalic acid monomethyl ester (A75) (200 mg, 0.76 mmol, 1 equiv) in THF (20 ml) was cooled to 0° C. and treated with BH$_3$-Me$_2$S (2M solution in THF, 0.64 ml, 1.28 mmol, 1.3 equiv). The resulting mixture was refluxed for 1 h and then cooled to room temperature. MeOH (5 ml) was added and the resulting mixture was concentrated in vacuo. The residue was diluted with AcOEt (50 ml) and the resulting solution was washed with saturated aqueous NaHCO$_3$ solution (30 ml) and 2N aqueous HCl solution (30 ml), dried over MgSO$_4$ and concentrated in vacuo to give 3-hydroxymethyl-5-(2-oxo-pyrrolidin-1-yl)-benzoic acid methyl ester (B76) (70 mg, 37%) as a pale yellow oil.

Ester 77

5-(2-Oxo-pyrrolidin-1-yl)-N-propyl-isophthalamic acid methyl ester (B77)

A suspension of 5-(2-oxo-pyrrolidin-1-yl)-isophthalic acid monomethyl ester (A75) (200 mg, 76 mmol, 1 equiv) in CH$_2$Cl$_2$ (20 ml) at room temperature was treated with a few drops of DMF followed by (COCl)$_2$ (100 mg, 0.8 mmol, 1.1 equiv). The resulting mixture was stirred for 1 h and then propylamine (140 mg, 2.4 mmol, 3.3 equiv) was added and the resulting solution was stirred for 30 min. The solution was then washed with 2N aqueous HCl solution (30 ml), saturated aqueous NaHCO$_3$ solution (30 ml), dried over MgSO$_4$ and concentrated in vacuo to give 5-(2-oxo-pyrrolidin-1-yl)-N-propyl-isophthalamic acid methyl ester (B77) (127 mg, 55%) as a cream waxy solid.

The following compounds were prepared in an analogous manner to that described for Ester 77 from 5-(2-oxo-pyrrolidin-1-yl)-isophthalic acid monomethyl ester (A75) and the appropriate amine:

| Ester |
| --- |
| N,N-Dimethyl-5-(2-oxo-pyrrolidin-1-yl)-isophthalamic acid methyl ester (B78) |
| N-Methyl-5-(2-oxo-pyrrolidin-1-yl)-isophthalamic acid methyl ester (B79) |

Ester 80

5-(2-Oxo-pyrrolidin-1-yl)-N,N-dipropyl-isophthalamic acid methyl ester (B80)

A solution of 5-(4-chloro-butanoylamino)-N,N-dipropyl-isophthalamic acid methyl ester (D89) (1.7 g, 4.4 mmol, 1 equiv) THF (20 ml) was treated portionwise with NaH (60% dispersion in mineral oil, 180 mg, 4.5 mmol, 1.1 equiv) and the resulting mixture was stirred for 1 h and then was diluted with AcOEt (100 ml). The resulting solution was washed with 2N aqueous HCl solution (50 ml), dried over MgSO$_4$ and concentrated in vacuo to give 5-(2-oxo-pyrrolidin-1-yl)-N,N-dipropyl-isophthalamic acid methyl ester (B80) (1.38 g, 91%) as a colourless oil.

Ester 81

5-(2-Oxo-piperidin-1-yl)-N,N-dipropyl-isophthalamic acid methyl ester (B81)

Ester 81 was prepared in an analogous manner to Ester 80 from 5-(5-chloro-pentanoylamino)-N,N-dipropyl-isophthalamic acid methyl ester (D90).

Ester 82

3-Nitro-5-(2-oxo-piperidin-1-yl)-benzoic acid methyl ester (B82)

NaH (60% w/w in mineral oil, 680 mg, 17 mmol, 0.9 equiv) was added portionwise to a solution of 3-(5-chloropentanoylamino)-5-nitro-benzoic acid methyl ester (D3) (6 g, 19 mmol, 1 equiv) in THF (40 ml) under nitrogen. The resulting mixture was stirred at room temperature for 1 h and then MeOH was added dropwise. The solution was concentrated in vacuo and the residue diluted with AcOEt. The organic phase was washed with $H_2O$, dried over $MgSO_4$ and concentrated in vacuo. Purification by flash chromatography on silica gel (AcOEt/iso-hexane: 1/2) gave 3-nitro-5-(2-oxopiperidin-1-yl)-benzoic acid methyl ester (B82) (2.8 g, 53%) as a pale orange oil.

Ester 83

3-(1,1-Dioxo-1/6-isothiazolidin-2-yl)-5-fluoromethyl-benzoic acid methyl ester (B83)

A solution of 3-(1,1-dioxo-1/$^6$-isothiazolidin-2-yl)-5-hydroxymethyl-benzoic acid methyl ester (D84) (400 mg, 1.4 mmol, 1 equiv) in $CH_2Cl_2$ (40 ml) at 0° C. was treated with (diethylamino)sulfur trifluoride (240 mg, 1.5 mmol, 1.1 equiv). The mixture was stirred at 0° C. for 1 h and then allowed to warm to room temperature. The solution was washed with 2N aqueous HCl solution (40 ml), dried over $MgSO_4$ and concentrated in vacuo to give 3-(1,1-dioxo-1/$^6$-isothiazolidin-2-yl)-5-fluoromethyl-benzoic acid methyl ester (B83) (250 mg, 62%) as a white solid.

Ester 84

3-Dimethylaminomethyl-5-(dioxo-1/$^6$-isothiazolidin-2-yl)-benzoic acid methyl ester (B84)

A solution of 3-(1,1-dioxo-1/$^6$-isothiazolidin-2-yl)-5-methanesulfonyloxymethyl-benzoic acid methyl ester (D85) (200 mg, 0.55 mmol, 1 equiv) in EtOH (3 ml) was treated with dimethylamine (33% in EtOH, 3 ml, excess). The resulting mixture was stirred for 15 min and then concentrated in vacuo and reevaporated with toluene (5 ml). The residue was dissolved in AcOEt (50 ml) and the resulting solution was washed with saturated aqueous $NaHCO_3$ solution (50 ml), dried over $MgSO_4$ and concentrated in vacuo to give 3-dimethylaminomethyl-5-(dioxo-1/$^6$-isothiazolidin-2-yl)-benzoic acid methyl ester (B84) (170 mg, 99%) as a yellow waxy solid.

Ester 85

3-Azidomethyl-5-(1,1-dioxo-1/$^6$-isothiazolidin-2-yl)-benzoic acid methyl ester (B85)

A solution of 3-(1,1-dioxo-1/$^6$-isothiazolidin-2-yl)-5-methanesulfonyloxymethyl-benzoic acid methyl ester (D85) (200 mg, 0.55 mmol, 1 equiv) in DMF (2 ml) was treated with $NaN_3$ (39 mg, 0.6 mmol, 1.1 equiv) and the resulting mixture was stirred for 1 h at room temperature and then diluted with AcOEt (50 ml). The resulting solution was washed sequentially with 2N aqueous HCl solution (30 ml), saturated aqueous $NaHCO_3$ solution (30 ml) and $H_2O$ (50 ml), dried over $MgSO_4$ and concentrated in vacuo to give 3-azidomethyl-5-(1,1-dioxo-1/$^6$-isothiazolidin-2-yl)-benzoic acid methyl ester (B85) as a white solid (129 mg, 76%).

Ester 89

3-(1,1-Dioxo-1/$^6$-isothiazolidin-2-yl)-5-(Z)-propenyl-benzoic acid methyl ester (B89)

A suspension of (ethyl)triphenylphosphonium bromide (371 mg, 1.0 mmol, 1.4 equiv) in THF (20 ml) was treated with KO$^t$Bu (112 mg, 1.0 mmol, 1.4 equiv) and the resulting mixture was stirred for 15 min at room temperature. A solution of 3-(1,1-dioxo-1/$^6$-isothiazolidin-2-yl)-5-formyl-benzoic acid methyl ester (D86) (200 mg, 0.7 mmol, 1 equiv) in THF (10 ml) was added and the resulting mixture was stirred for 1 h at room temperature and then diluted with AcOEt (100 ml). The resulting solution was washed with 2N aqueous HCl solution (100 ml), dried over $MgSO_4$ and concentrated in vacuo. Purification by flash chromatography on silica gel (EtOAc/iso-hexane: 1/1) gave 3-(1,1-dioxo-1/$^6$-isothiazolidin-2-yl)-5-(E/Z)-propenyl-benzoic acid methyl ester (B89) (135 mg, 65%) as a colourless oil.

The following compounds were prepared in an analogous manner to the process described for Ester 89 from 3-(1,1-dioxo-1/$^6$-isothiazolidin-2-yl)-5-formyl-benzoic acid methyl ester (D86) and the appropriate commercially available starting material:

| Ester |
| --- |
| 3-(1,1-Dioxo-1/$^6$-isothiazolidin-2-yl)-5-vinyl-benzoic acid methyl ester (B88) |
| (Z/E)-But-1-enyl-(ethanesulfonyl-ethyl-amino)-benzoic acid methyl ester (B90) |
| 3-(1,1-Dioxo-1/$^6$-isothiazolidin-2-yl)-5-(2-methyl-propenyl)-benzoic acid methyl ester (B91) |

Ester 92

5-(1,1-Dioxo-1-isothiazolidin-2-yl)-isophthalamic acid methyl ester (B92)

A suspension of 5-(1,1-dioxo-1/$^6$-isothiazolidin-2-yl)-isophthalic acid monomethyl ester (D83) (750 mg, 2.5 mmol, 1 equiv) in $CH_2Cl_2$ (30 ml) was treated with 2M $(COCl)_2$ in $CH_2Cl_2$ (1.5 ml, 3.0 mmol, 1.2 equiv) followed by a few drops of DMF. The resulting mixture was stirred for 30 min and then 32% aqueous ammonia (5 ml, excess) was added. The resulting mixture was stirred for 15 min and then diluted with $CH_2Cl_2$ (50 ml) and washed with 2N aqueous HCl solution (50 ml). The resulting white precipitate was filtered to give 5-(1,1-dioxo-1/$^6$-isothiazolidin-2-yl)-isophthalamic acid methyl ester B92 (650 mg, 87%) as a white solid.

Ester 93

3-Cyano-5-(1,1-dioxo-1/$^6$-isothiazolidin-2-yl)-benzoic acid methyl ester (B93)

A suspension of 5-(1,1-dioxo-1/$^6$-isothiazolidin-2-yl)-isophthalamic acid methyl ester (B92) (500 mg, 1.68 mmol, 1 equiv) in $CH_2Cl_2$ (100 ml) was treated with $NEt_3$ (404 mg, 4.0 mmol, 2.4 equiv) and trifluoroacetic anhydride (378 mg, 1.8 mmol, 1.1 equiv). The resulting mixture was stirred for 1 h at room temperature and then treated with further portions of $NEt_3$ (404 mg, 4.0 mmol, 2.4 equiv) and trifluoroacetic anhydride (378 mg, 1.8 mmol, 1.1 equiv) and stirred for another 45 min. The resulting solution was washed with 2N aqueous HCl solution (50 ml), saturated aqueous NaHCO$_3$ solution (50 ml), dried over MgSO$_4$. and concentrated in vacuo. The residue was triturated with Et$_2$O to give 3-cyano-5-(1,1-dioxo-1/$^6$-isothiazolidin-2-yl)-benzoic acid methyl ester (B93) (350 mg, 75%) as a white solid.

Ester 94

5-(1,1-Dioxo-1/$^6$-isothiazolidin-2-yl)-N,N-dipropyl-isophthalamic acid methyl ester (B94)

A solution of 5-(3-chloro-propane-1-sulfonylamino)-N,N-dipropyl-isophthalamic acid methyl ester (D91) (1.7 g, 4.0 mmol, 1 equiv) in EtOH (20 ml) was treated with NEt$_3$ (799 mg, 7.9 mmol, 2 equiv) and the mixture was refluxed for 3 h and then cooled to room temperature and concentrated in vacuo. The residue was dissolved in AcOEt (100 ml) and the organic phase was washed with 2N aqueous HCl solution (50 ml), dried over MgSO$_4$ and concentrated in vacuo. The residue was triturated with Et$_2$O to give 5-(1,1-dioxo-1/$^6$-isothiazolidin-2-yl)-N,N-dipropyl-isophthalamic acid methyl ester (B94) (1.2 g, 78%) as a white solid.

Ester 95

5-(1,1-Dioxo-1/$^6$-[1,2]thiazinan-2-yl)-N,N-dipropyl-isophthalamic acid methyl ester (B95)

Ester 95 was prepared in an analogous manner to Ester 94 from 5-(4-chloro-butane-1-sulfonylamino)-N,N-dipropyl-isophthalamic acid methyl ester (D92).

Ester 100

Fluoro-(2-oxo-pyrrolidin-1-yl)-trifluoromethyl-benzoic acid methyl ester (B100)

3-Bromo-2-fluoro-5-trifluoromethylbenzoic acid methyl ester (D29a) (500 mg, 1.95 mmol, 1 equiv), Cs$_2$CO$_3$ (950 mg, 2.92 mmol, 1.5 equiv), pyrrolidin-2-one (248 mg, 2.92 mmol, 1.5 equiv), Xantphos (68 mg, 0.117 mmol, 0.06 equiv) and tris(dibenzylideneacetone)dipalladium (0) (36 mg, 0.039 mmol, 0.02 equiv) were refluxed under argon in dioxan (7 ml) for 18 h. After cooling, the mixture was filtered and evaporated in vacuo. Purification by flash chromatography on silica gel (AcOEt/iso-hexane: 1/4 to 1/2) gave fluoro-(2-oxo-pyrrolidin-1-yl)-trifluoromethyl-benzoic acid methyl ester (B100) (195 mg, 32%). [M+H]$^+$306.2.

The following compounds (Esters 101-102) were prepared in an analogous manner to that described for Description 68 from the appropriate aryl bromide starting material indicated in the below table using the appropriate 2,4,6 trialkenylcyclotriboroxane-pyridine complex as described by F. Kerins and D. F. O' Shea in *J. Org. Chem*, 2002, 67, 49684971:

| Description | Aryl bromide | [M + H]$^+$ | RT (min) |
|---|---|---|---|
| 3-(2-Methyl-propenyl)-5-(2-oxo-pyrrolidin-1-yl)-benzoic acid methyl ester (B101) | D9a | 274.1 | 3.14 |
| 3-(2-Oxo-pyrrolidin-1-yl)-5-((E)-styryl)-benzoic acid methyl ester (B102) | D9a | | |

The following compounds were prepared in an analogous manner to the process described for 3-(2-oxo-piperidin-1-yl)-5-propyl-benzoic acid tert-butyl ester (B116):

| Ester | Alkene | [M + H]$^+$ | RT (min) |
|---|---|---|---|
| 3-Isopropyl-5-(2-oxo-pyrrolidin-1-yl)-benzoic acid methyl ester (B104) | D71 | 248.1 | 2.77 |
| 3-(2-Oxo-pyrrolidin-1-yl)-5-propyl-benzoic acid methyl ester (B106) | D72 | 262.1 | 3.04 |
| 3-Cyclopentyl-5-(2-oxo-pyrrolidin-1-yl)-benzoic acid methyl ester (B107) | D74 | 288.1 | 3.26 |
| 3-Cyclohexyl-5-(2-oxo-pyrrolidin-1-yl)-benzoic acid methyl ester (B108) | D74 | | |
| 3-(1,1-Dioxo-1/$^6$-[1,2]thiazinan-2-yl)-5-propyl-benzoic acid tert-butyl ester (B112) | D69 | | |

Ester 109

3-Ethynyl-5-(2-oxo-pyrrolidin-1-yl)-benzoic acid tert-butyl ester (B109)

Ester 109 was prepared in an analogous manner to the process described for Ester 111 from 300 mg (mmol) of 3-(3-hydroxy-3-methyl-but-1-ynyl)-5-(2-oxo-pyrrolidin-1-yl)-benzoic acid tert-butyl ester (D76) which yielded 220 mg (88%) of 3-ethynyl-5-(2-oxo-pyrrolidin-1-yl)-benzoic acid tert-butyl ester (B109) as an off white solid.

Ester 111

3-(1,1-Dioxo-1/$^6$-isothiazolidin-2-yl)-5-ethynyl-benzoic acid tert-butyl ester (B111)

To a solution of 3-(1,1-dioxo-1/$^6$-isothiazolidin-2-yl)-5-(3-hydroxy-3-methyl-but-1-ynyl)-benzoic acid tert-butyl ester (D75) (142 mg, 0.37 mmol, 1 equiv) in toluene (20 ml) was added NaH (60% dispersion in mineral oil, 4 mg, 0.1 mmol, 0.3 equiv). The resulting mixture was stirred at 110° C. for 30 min, cooled to room temperature and diluted with AcOEt. The organic phase was washed with saturated aqueous NaHCO$_3$ solution, dried over MgSO$_4$ and concentrated in vacuo to give 3-(1,1-Dioxo-1/$^6$-isothiazolidin-2-yl)-5-ethynyl-benzoic acid tert-butyl ester (B111) (142 mg, 118%) as a pale yellow oil.

Ester 116

3-(2-Oxo-piperidin-1-yl)-5-propyl-benzoic acid tert-butyl ester (B116)

To a solution of 3-(2-oxo-piperidin-1-yl)-5-(E/Z)-propenyl-benzoic acid tert-butyl ester (D68) (485 mg, 1.5 mmol, 1 equiv) in EtOH (10 ml) and H$_2$O (2 ml) was added 10% palladium on charcoal (50% wet, 485 mg, 5% w/w) and NH$_4$COOH (945 mg, 15 mmol, 10 equiv). The resulting mixture was stirred at 65° C. for 1 h then cooled to room temperature. Most of the EtOH was removed in vacuo and the residue dissolved in AcOEt. The organic phase was washed with H$_2$O, dried over MgSO$_4$ and concentrated in vacuo to give 3-(2-oxo-piperidin-1-yl)-5-propyl-benzoic acid tert-butyl ester (B116) (300 mg, 70%) as a colorless oil.

Ester 117

Methyl 3-(1,1-dioxido-6,7-dihydro-1,2-thiazepin-2(3H)-yl)-5-propylbenzoate (B117)

To a solution of methyl 3-[(3-buten-1-ylsulfonyl)(2-propen-1-yl)amino]-5-propylbenzoate (D135) (1 g, 2.8 mmol, 1 equiv) in $CH_2Cl_2$ (200 ml) was added bis(tricyclohexylphosphino)benzylidene ruthenium (IV) dichloride (117 mg, 0.14 mmol, 0.05 equiv) and the resulting solution was stirred at room temperature for 48 h then concentrated in vacuo. Purification of the residue by flash chromatography on silica gel (iso-hexane/AcOEt: 9:1) gave methyl 3-(1,1-dioxido-6,7-dihydro-1,2-thiazepin-2 (3H)-yl)-5-propylbenzoate (B117) (700 mg, 76%) as a pale purple oil. $[M+H]^+=324.4$, RT=3.10 min.

Ester 118

Methyl 5-(ethylamino)-2-fluoro-3-(2-oxo-1-pyrrolidinyl)benzoate (B118)

To a solution of methyl 5-(ethyl{[4-(methyloxy)phenyl]methyl}amino)-2-fluoro-3-(2-oxo-1-pyrrolidinyl)benzoate (D155) (7 g, 17.5 mmol, 1 equiv) in EtOH (150 ml) was added 10% palladium on charcoal (50% wet, 1.4 g, 10% w/w) and the resulting mixture was stirred under an atmosphere of hydrogen (1 atm) for 3 h. The catalyst was filtered off through a pad of celite and the solution concentrated in vacuo. The residue was triturated with AcOEt/iso-hexane to give methyl 5-(ethylamino)-2-fluoro-3-(2-oxo-1-pyrrolidinyl)benzoate (B118) (4.8 g, 98%) as a pale greenish solid which was used in the next step without further purification. $[M+H]+=281.2$, RT=2.35 min.

The following esters have been obtained from the appropriate precursor in an analogous manner to the process described for Ester 35 (B35) using acetaldehyde instead of propionaldehyde.

| Ester | Precursor | $[M + H]^+$ | RT (min) |
|---|---|---|---|
| Methyl 3-(1,1-dioxidotetrahydro-2H-1,2-thiazin-2-yl)-5-(ethylamino)-2-fluorobenzoate (B119) | D152 | 331.2 | 2.80 |
| Methyl 3-(1,1-dioxido-2-isothiazolidinyl)-5-(ethylamino)-2-fluorobenzoate (B122) | D151 | 317.1 | 2.64 |
| Methyl 3-(1,1-dioxidotetrahydro-2H-1,2-thiazin-2-yl)-5-(ethylamino)-2-(methyloxy)benzoate (B139) | D153 | 343.2 | 2.64 |

The following compounds were prepared in an analogous manner to the process described for 3-(2-oxo-piperidin-1-yl)-5-propyl-benzoic-acid tert-butyl ester (B116) from their appropriate precursor:

| Ester | Precursor | $[M + H]^+$ | RT (min) |
|---|---|---|---|
| Methyl 2-fluoro-3-(2-oxo-1-pyrrolidinyl)-5-propylbenzoate (B120) | D159 | 280.2 | 2.73 |
| Methyl 3-(1,1-dioxidotetrahydro-2H-1,2-thiazin-2-yl)-2-fluoro-5-propylbenzoate (B173) | D161 | 330.2 | 2.91 |
| Methyl 3-(1,1-dioxido-2-isothiazolidinyl)-2-fluoro-5-propylbenzoate(B174) | D160 | — | 2.74 |

Ester 121

1,1-Dimethylethyl 3-(2-oxo-5-phenyl-1-piperidinyl)-5-propylbenzoate (B121)

1,1-Dimethylethyl 3-(2-oxo-5-phenyl-1-piperidinyl)-5-propylbenzoate (B121) was prepared from 1,1-dimethylethyl 3-(2-oxo-5-phenyl-1-piperidinyl)-5-[(1E/Z)-1-propen-1-yl]benzoate (D192) in an analogous manner to the process described for 3-(2-oxo-piperidin-1-yl)-5-propyl-benzoic acid tert-butyl ester (B116). $[M+H]^+=394.3$, RT=3.88 min.

Ester 123

Methyl 3-(1,1-dioxido-4-phenyltetrahydro-2H-1,2-thiazin-2-yl)-5-nitrobenzoate (B123)

A flask was charged under nitrogen with methyl 3-bromo-5-nitrobenzoate (D11) (136 mg, 0.52 mmol, 1,1 equiv), $Cs_2CO_3$ (216 mg, 0.66 mmol, 1.4 equiv), tris(dibenzylideneacetone)dipalladium(0) (22 mg, 0.023 mmol, 0.05 equiv), Xantphos (27 mg, 0.047 mmol, 0.1 equiv) and toluene (10 ml). 4-phenyltetrahydro-2H-1,2-thiazine 1,1-dioxide (J. Morris, D. G. Wishka *J. Org. Chem.* 1991, 56, 3549-3556, 100 mg, 0.47 mmol, 1 equiv) was then added and the resulting mixture was stirred at 120° C. for 5 h then cooled to room temperature and concentrated in vacuo. The residue was partitioned between $H_2O$ and AcOEt and the aqueous phase was re-extracted with AcOEt. The combined organic solutions were dried over $MgSO_4$ and concentrated in vacuo. Purification of the residue by flash chromatography on silica gel (iso-hexane/AcOEt: 7/3) gave methyl 3-(1,1-dioxido-4-phenyltetrahydro-2H-1,2-thiazin-2-yl)-5-nitrobenzoate (B123) (110 mg, 60%) as a yellow oil. $[M+H+NH_3]^+=408.3$, RT=3.24 min Ester 124

Methyl 3-amino-5-(1,1-dioxido-4-phenyltetrahydro-2H-1,2-thiazin-2-yl)benzoate (B124)

Methyl 3-amino-5-(1,1-dioxido-4-phenyltetrahydro-2H-1,2-thiazin-2-yl)benzoate (B124) was obtained from methyl 3-(1,1-dioxido-4-phenyltetrahydro-2H-1,2-thiazin-2-yl)-5-nitrobenzoate (B123) in an analogous manner to the process described for Description 16 (D16). $[M+H]^+=361.3$, RT=2.91 min Ester 125

Methyl 3-(1,1-dioxido-4-phenyltetrahydro-2H-1,2-thiazin-2-yl)-5-(ethylamino)benzoate (B125)

Methyl 3-(1,1-dioxido-4-phenyltetrahydro-2H-1,2-thiazin-2-yl)-5-(ethylamino)benzoate (B125) was obtained from methyl 3-amino-5-(1,1-dioxido-4-phenyltetrahydro-2H-1,2-thiazin-2-yl)benzoate (B124) in an analogous manner to the process described for Ester 35 (B35) using acetaldehyde instead of propionaldehyde. $[M+H]^+=389.4$, RT=3.23 min Ester 126

Methyl 3-cyclopentyl-5-(1,1-dioxidotetrahydro-2H-1,2-thiazin-2-yl)benzoate (B126)

Methyl 3-cyclopentyl-5-(1,1-dioxidotetrahydro-2H-1,2-thiazin-2-yl)benzoate (B126) was obtained from methyl 3-(1-cyclopenten-1-yl)-5-(1,1-dioxidotetrahydro-2H-1,2-thiazin-2-yl)benzoate, methyl 3-(2-cyclopenten-1-yl)-5-(1,1-dioxidotetrahydro-2H-1,2-thiazin-2-yl)benzoate and methyl 3-(3-cyclopenten-1-yl)-5-(1,1-dioxidotetrahydro-2H-1,2-thiazin-2-yl)benzoate (D265) in an analogous manner to the process described for Ester 107 (B107).

Ester 127

Methyl 3-(1,1-dioxidotetrahydro-2H-1,2-thiazin-2-yl)-5-[(1-methylethyl)amino]benzoate (B127)

Methyl 3-(1,1-dioxidotetrahydro-2H-1,2-thiazin-2-yl)-5-[(1-methylethyl)amino]benzoate (B127) was obtained from methyl 3-amino-5-(1,1-dioxidotetrahydro-2H-1,2-thiazin-2-yl)benzoate (D194) in an analogous manner to the process described for Ester 35 (B35) using acetone instead of propionaldehyde. $[M+H]^+=327.2$, RT=2.82 min.

Ester 128

1,1-Dimethylethyl 3-[ethyl(methyl)amino]-5-(2-oxo-1-pyrrolidinyl)benzoate (B128)

1,1-Dimethylethyl 3-[ethyl(methyl)amino]-5-(2-oxo-1-pyrrolidinyl)benzoate (B1128) was obtained from 1,1-dimethylethyl 3-(methylamino)-5-(2-oxo-1-pyrrolidinyl)benzoate (B32) in an analogous manner to the process described in Ester 35 (B35) using acetaldehyde instead of propionaldehyde. $[M+H]^+=319.4$, RT=3.17 min.

The following compounds have been obtained from their corresponding precursors in an analogous manner to the process described for Ester 35 (B35) using acetaldehyde instead of propionaldehyde and the appropriate precursor indicated in the below table.

| Ester | Precursor | $[M + H]^+$ | RT (min) |
|---|---|---|---|
| Methyl 3-(ethylamino)-4-methyl-5-(2-oxo-1-pyrrolidinyl) benzoate (B129) | D184 | 277.1 | 2.63 |
| Methyl 3-(1,1-dioxido-2-isothiazolidinyl)-5-(ethylamino)-4-methylbenzoate (B130) | D186 | 313.1 | 2.79 |
| Methyl 3-(1,1-dioxidotetrahydro-2H-1,2-thiazin-2-yl)-5-(ethylamino)-4-methylbenzoate (B131) | D188 | 327.1 | 2.93 |
| Methyl 3-(1,1-dioxidotetrahydro-2H-1,2-thiazin-2-yl)-5-(ethylamino)-4-(methyloxy) benzoate (B132) | D187 | 343.1 | 2.90 |
| Methyl 3-(ethylamino)-4-(methyloxy)-5-(2-oxo-1-pyrrolidinyl) benzoate (B133) | D183 | 293.1 | 2.64 |
| Methyl 3-(1,1-dioxido-2-isothiazolidinyl)-5-(ethylamino)-4-(methyloxy) benzoate (B134) | D185 | 329.1 | 2.79 |

Ester 135

Methyl 3-(diethylamino)-5-(1,1-dioxidotetrahydro-2H-1,2-thiazin-2-yl)-4-methylbenzoate (B135)

Methyl 3-(diethylamino)-5-(1,1-dioxidotetrahydro-2H-1,2-thiazin-2-yl)-4-methylbenzoate (B135) was obtained as a by-product during the synthesis of methyl 3-(1, 1-dioxidotetrahydro-2H-1,2-thiazin-2-yl)-5-(ethylamino)-4-methylbenzoate (B131) from methyl 3-amino-5-(1,1-dioxidotetrahydro-2H-1,2-thiazin-2-yl)-4-methylbenzoate (D188). $[M+H]^+=355.1$, RT=2.95 min.

Ester 136

Methyl 3-(1,1-dioxidotetrahydro-2H-1,2-thiazin-2-yl)-4-(methyloxy)-5-[(1E/Z)-1-propen-1-yl]benzoate (B136)

To a solution of methyl 3-{[(4-chlorobutyl)sulfonyl]amino}-4-(methyloxy)-5-[(1E/Z)-1-propen-1-yl]benzoate (D170) (650 mg, 1.72 mmol, 1 equiv) in EtOH (50 ml) was added $NEt_3$ (500 µl, 3.6 mmol, 2.1 equiv) and the resulting solution was refluxed for 6 h then cooled to room temperature and concentrated in vacuo. The residue was dissolved in AcOEt and the organic phase was washed with a 2N aqueous HCl solution and a saturated aqueous $NaHCO_3$ solution, dried over $MgSO_4$ and concentrated in vacuo. Purification of the residue by flash chromatography on silica gel (iso-hexane/AcOEt: 3/1) gave methyl 3-(1,1-dioxidotetrahydro-2H-1,2-thiazin-2-yl)-4-(methyloxy)-5-[(1E/Z)-1-propen-1-yl]benzoate (B136) (450 mg, 77%) as a pale yellow oil. $[M+H]^+=340.0$, RT=3.14 min.

Ester 138

Methyl 3-(1, 1-dioxido-2-isothiazolidinyl)-5-(2-oxo-1-pyrrolidinyl)benzoate (B138)

Methyl 3-(1,1-dioxido-2-isothiazolidinyl)-5-(2-oxo-1-pyrrolidinyl)benzoate (B138) was obtained from methyl 3-[(4-chlorobutanoyl)amino]-5-(1,1-dioxido-2-isothiazolidinyl)benzoate (D195) in an analogous manner to the process described for Ester 27 (B27). $[M+H]^+=339.0$, RT=2.41 min.

Ester 140

Methyl 1-ethyl-4-(2-oxo-1-pyrrolidinyl)-1H-indole-6-carboxylate (B140)

To a solution of methyl 4-(2-oxo-1-pyrrolidinyl)-1H-indole-6-carboxylate (B154) (500 mg, 1.94 mmol, 1 equiv) in DMF (10 ml) at room temperature was added NaH (60% dispersion in mineral oil, 84 mg, 2.1 mmol, 1.1 equiv) and the resulting mixture was stirred 15 min. Ethyl iodide (200 µl, 2.5 mmol, 1.3 equiv) was added and the resulting solution was stirred for 30 min then concentrated in vacuo. The residue was dissolved in AcOEt and the organic phase was washed with a 2N aqueous HCl solution, dried over $MgSO_4$ and concentrated in vacuo. Purification of the residue by flash chromatography on silica gel (AcOEt/iso-hexane: 1/4 to 1/1) gave methyl 1-ethyl-4-(2-oxo-1-pyrrolidinyl)-1H-indole-6-carboxylate (B140) (400 mg, 72%) as an off-white solid. $[M+H]^+=287.0$, RT=2.73 min.

The following compounds have been obtained from their corresponding precursors in an analogous manner to the process described for Description 2 (D2):

| Ester | Precursor | $[M + H]^+$ | RT (min) |
|---|---|---|---|
| Ethyl 3-ethyl-7-(2-oxo-1-pyrrolidinyl)-1H-indole-5-carboxylate (B141) | D225 | | |
| Methyl 1-ethyl-4-(2-oxo-1-pyrrolidinyl)-1H-benzimidazole-6-carboxylate (B149) | D227 | | |
| Methyl 1-ethyl-4-(2-oxo-1-pyrrolidinyl)-1H-indazole-6-carboxylate (B152) | D229 | 288.4 | 2.20 |
| Methyl 4-(2-oxo-1-pyrrolidinyl)-1H-indole-6-carboxylate (B154) | D228 | 259.0 | 2.22 |
| Ethyl 3-methyl-7-(2-oxo-1-pyrrolidinyl)-1H-indole-5-carboxylate (B160) | D224 | | |
| Ethyl 3-(1-methylethyl)-7-(2-oxo-1-pyrrolidinyl)-1H-indole-5-carboxylate (B161) | D226 | | |
| Methyl 4-ethyl-8-(2-oxo-1-pyrrolidinyl)-1,2,3,4-tetrahydro-6-quinoxalinecarboxylate (B171) | D230 | 304.3 | 2.52 |

Ester 142

Ethyl 3-ethyl-1-methyl-7-(2-oxo-1-pyrrolidinyl)-1H-indole-5-carboxylate (B142)

To a solution of ethyl 3-ethyl-7-(2-oxo-1-pyrrolidinyl)-1H-indole-5-carboxylate (B141) (658 mg, 2.3 mmol, 1 equiv) in DMF (10 ml) at room temperature was added NaH (60% dispersion in mineral oil, 120 mg, 3.0 mmol, 1.3 equiv) and the resulting mixture was stirred 15 min at this temperature. Ethyl iodide (187 μl, 3.0 mmol, 1.3 equiv) was added and the resulting solution was stirred for 30 min then concentrated in vacuo. The residue was dissolved in AcOEt and the organic phase was washed with H$_2$O, dried over MgSO$_4$ and concentrated in vacuo. The residue was triturated with iso-hexane to give ethyl 3-ethyl-1-methyl-7-(2-oxo-1-pyrrolidinyl)-1H-indole-5-carboxylate (620 mg, 90%) as a yellow solid which was used in the next step without further purification.

Ester 143

Methyl 4-(1,1-dioxido-2-isothiazolidinyl)-1-ethyl-1H-indole-6-carboxylate (B143)

To a solution of methyl 4-{[(3-chloropropyl)sulfonyl]amino)}-1-ethyl-1H-indole-6-carboxylate (D241) (900 mg, 2.5 mmol, 1 equiv) in EtOH (100 ml) was added NEt$_3$ (1 ml, 7.3 mmol, 3 equiv) and the resulting solution was refluxed for 1.5 h then cooled to room temperature and concentrated in vacuo. The residue was dissolved in AcOEt and the organic phase was washed with a 2N aqueous HCl solution, dried over MgSO$_4$ and concentrated in vacuo to give methyl 4-(1,1-dioxido-2-isothiazolidinyl)-1-ethyl-1H-indole-6-carboxylate (B143) (386 mg, 48%) as a brown oil which was used in the next step without further purification.

Ester 144

Ethyl 7-(1,1-dioxido-2-isothiazolidinyl)-3-ethyl-1H-indole-5-carboxylate (B144)

Ethyl 7-(1,1-dioxido-2-isothiazolidinyl)-3-ethyl-1H-indole-5-carboxylate (B144) was obtained from ethyl 7-{[(3-chloropropyl)sulfonyl]amino}-3-ethyl-1H-indole-5-carboxylate (D243) in an analogous manner to the process described for methyl 4-(1,1-dioxido-2-isothiazolidinyl)-1-ethyl-1H-indole-6-carboxylate (B143). [M+H]$^+$=337.1, RT=3.23 min Ester 145

Methyl 4-(1,1-dioxidotetrahydro-2H-1,2-thiazin-2-yl)-1-ethyl-2,3-dihydro-1H-indole-6-carboxylate (B145)

To a solution of methyl 1-acetyl-4-(1,1-dioxidotetrahydro-2H-1,2-thiazin-2-yl)-2,3-dihydro-1H-indole-6-carboxylate (D235) (300 mg, 0.85 mmol, 1 equiv) in THF (20 ml) at room temperature was added BH$_3$ (1.5 M in THF, 2 ml, 3 mmol, 3.5 equiv) and the resulting mixture was stirred at room temperature for 15 h. EtOH (5 ml) was added and the resulting mixture was concentrated in vacuo after 5 min. The residue was partitioned between a 2N aqueous HCl solution (20 ml) and CH$_2$Cl$_2$ (20 ml) and the biphasic mixture was vigorously stirred for 3 h. The two layers were separated and the organic phase was dried over MgSO$_4$ and concentrated in vacuo. Purification of the residue by flash chromatography on silica gel (AcOEt/iso-hexane: 1/2) gave methyl 4-(1,1-dioxidotetrahydro-2H-1,2-thiazin-2-yl)-1-ethyl-2,3-dihydro-1H-indole-6-carboxylate (B145) (200 mg, 70%) as a very pale yellow solid. [M+H]+=339.2, RT=2.92 min.

Ester 146

Ethyl 7-(1,1-dioxido-2-isothiazolidinyl)-3-ethyl-1-methyl-1H-indole-5-carboxylate (B146)

Ethyl 7-(1,1-dioxido-2-isothiazolidinyl)-3-ethyl-1-methyl-1H-indole-5-carboxylate (B146) was prepared from ethyl 7-(1,1-dioxido-2-isothiazolidinyl)-3-ethyl-1H-indole-5-carboxylate (B144) in an analogous manner to the process described for Ester 142 (B142).

Ester 147

Methyl 4-(1,1-dioxidotetrahydro-2H-1,2-thiazin-2-yl)-1-ethyl-1H-indole-6-carboxylate (B147)

To a solution of methyl 4-(1,1-dioxidotetrahydro-2H-1,2-thiazin-2-yl)-1H-indole-6-carboxylate (D231) (180 mg, 0.58 mmol, 1 equiv) in DMF (3 ml) at room temperature was added NaH (60% dispersion in mineral oil, 24 mg, 0.6 mmol, 1 equiv) and the resulting mixture was stirred 15 min at this temperature. Ethyl iodide (64 μl, 0.8 mmol, 1.4 equiv) was added and the resulting solution was stirred for 1 h then concentrated in vacuo. The residue was dissolved in AcOEt and the organic phase was washed with a 2N aqueous HCl solution, dried over MgSO$_4$ and concentrated in vacuo. Purification of the residue by flash chromatography on silica gel gave methyl 4-(1,1-dioxidotetrahydro-2H-1,2-thiazin-2-yl)-1-ethyl-1H-indole-6-carboxylate (B147) (110 mg, 51%) as a yellow solid which was used in the next step without further purification. [M+H]$^+$=337.0, RT=2.82 min.

Ester 148

Ethyl 7-(1,1-dioxidotetrahydro-2H-1,2-thiazin-2-yl)-3-ethyl-1H-indole-5-carboxylate (B148)

To a solution of ethyl 7-{[(4-chlorobutyl)sulfonyl]amino}-3-ethyl-1H-indole-5-carboxylate (D242) (230 mg, 0.59 mmol, 1 equiv) in EtOH (10 ml) was added NEt$_3$ (249 μl, 1.78 mmol, 3 equiv) and the resulting solution was stirred at 70° C. for 3 h. NEt$_3$ (1 ml, excess) was added and the solution was stirred at the same temperature for 15 h then cooled to room temperature and concentrated in vacuo. The residue was dissolved in AcOEt and the organic phase was washed with a 2N aqueous HCl solution, dried over MgSO$_4$ and concentrated in vacuo. Purification of the residue by flash chromatography on silica gel (AcOEt/iso-hexane: 3/7) gave ethyl 7-(1,1-dioxidotetrahydro-2H-1,2-thiazin-2-yl)-3-ethyl-1H-indole-5-carboxylate (B148) (150 mg, 72%) as a colorless oil. [M−H]$^−$=349.3, RT=3.10 min.

Ester 150

Methyl 4-(1,1-dioxido-2-isothiazolidinyl)-1-ethyl-1H-benzimidazole-6-carboxylate (B150)

Methyl 4-(1,1-dioxido-2-isothiazolidinyl)-1-ethyl-1H-benzimidazole-6-carboxylate (B150) was obtained from methyl 4-{bis[(3-chloropropyl)sulfonyl]amino}-1-ethyl-1H-benzimidazole-6-carboxylate (D239) in an analogous manner to the process described for methyl 4-(1,1-dioxido-2-isothiazolidinyl)-1-ethyl-1H-indazole-6-carboxylate (B153) [M+H]$^+$=324.5, RT=2.10 min.

Ester 151

Methyl 4-(1,1-dioxidotetrahydro-2H-1,2-thiazin-2-yl)-1-ethyl-1H-benzimidazole-6-carboxylate (B151)

To a solution of methyl 4-(1,1-dioxidotetrahydro-2H-1,2-thiazin-2-yl)-1H-benzimidazole-6-carboxylate (D253) (230 mg, 0.74 mmol, 1 equiv) in DMF (10 ml) at room temperature was added NaH (60% dispersion in mineral oil, 33 mg, 0.82 mmol, 1.1 equiv) and the resulting mixture was stirred 5 min at this temperature. Ethyl iodide (66 µl, 0.82 mmol, 1.1 equiv) was added and the resulting solution was stirred for 30 min at 60° C. then cooled to room temperature and concentrated in vacuo. The residue was partitioned between AcOEt and a 5% aqueous citric acid solution. The two layers were separated and the aqueous phase saturated with NaCl and extracted twice with AcOEt. The combined organic phases were dried over MgSO$_4$ and concentrated in vacuo to give methyl 4-(1,1-dioxidotetrahydro-2H-1,2-thiazin-2-yl)-1-ethyl-1H-benzimidazole-6-carboxylate (B151) (400 mg, 160%) as a pale yellow viscous oil which was used in the next step without further purification. [M+H]$^+$=338.1, RT=2.43 min.

Ester 153

Methyl 4-(1,1-dioxido-2-isothiazolidinyl)-1-ethyl-1H-indazole-6-carboxylate (B153)

To a solution of methyl 4-{bis[(3-chloropropyl)sulfonyl]amino}-1-ethyl-1H-indazole-6-carboxylate (D237) (1.5 g, 3 mmol, 1 equiv) in EtOH (20 ml) was added NEt$_3$ (920 µl, 6.6 mmol, 2.2 equiv) and the resulting solution was refluxed for 3 h then cooled to room temperature and concentrated in vacuo. The residue was dissolved in AcOEt and the organic phase was washed with a 2N aqueous HCl solution, dried over MgSO$_4$ and concentrated in vacuo. The residue was triturated with AcOEt/iso-hexane to give methyl 4-(1,1-dioxido-2-isothiazolidinyl)-1-ethyl-1H-indazole-6-carboxylate (B153) as a light brown solid which was used in the next step without further purification. [M+H]$^+$=324.5, RT=2.35 min.

The following compounds have been obtained from Ester 154 (B154) in an analogous manner to the process described for Ester 140 (B140) using the appropriate alkylating reagent:

Ester 162

Ethyl 1-methyl-3-(1-methylethyl)-7-(2-oxo-1-pyrrolidinyl)-1H-indole-5-carboxylate (B162)

Ethyl 1-methyl-3-(1-methylethyl)-7-(2-oxo-1-pyrrolidinyl)-1H-indole-5-carboxylate (B162) has been obtained from ethyl 3-(1-methylethyl)-7-(2-oxo-1-pyrrolidinyl)-1H-indole-5-carboxylate (B161) using an analogous procedure to the process described for ethyl 3-ethyl-1-methyl-7-(2-oxo-1-pyrrolidinyl)-1H-indole-5-carboxylate (B142).

Ester 163

Methyl 3-ethyl-7-(2-oxo-1-pyrrolidinyl)-1-benzofuran-5-carboxylate (B163)

To a solution of methyl 4-[(2E/Z)-2-buten-1-yloxy]-3-iodo-5-(2-oxo-1-pyrrolidinyl)benzoate (D258) (1.4 g, 3.37 mmol, 1 equiv) in DMF (20 ml) at room temperature under nitrogen were added Pd(OAc)$_2$ (38 mg, 0.17 mmol, 0.05 equiv), NaCOOH (688 mg, 10.1 mmol, 3 equiv), Na$_2$CO$_3$ (893 mg, 8.4 mmol, 2.5 equiv) and NBu$_4$Cl (845 mg, 3.71 mmol, 1.1 equiv). The resulting suspension was stirred under nitrogen at 120° C. for 1 h then cooled to room temperature and concentrated in vacuo. The residue was partitioned between AcOEt and H$_2$O and the two phases were separated. The organic phase was washed with brine, dried over MgSO$_4$ and concentrated in vacuo. Purification of the residue by flash chromatography on silica gel (iso-hexane/AcOEt: 1/1) gave methyl 3-ethyl-7-(2-oxo-1-pyrrolidinyl)-1-benzofuran-5-carboxylate (B163) (250 mg, 26%) as a white solid. [M+H]$^+$=288.1, RT=3.02 min.

Ester 164

Methyl 4-(ethyloxy)-3-[ethyl(propanoyl)amino]-5-(1-methylethyl)benzoate (B164)

Methyl 4-(ethyloxy)-3-[ethyl(propanoyl)amino]-5-(1-methylethyl)benzoate (B164) was obtained from methyl 4-methyl-8-(2-oxo-1-pyrrolidinyl)-2H-chromene-6-carboxylate and methyl 4-(ethyloxy)-3-[ethyl(propanoyl)amino]-5-(1-methylethenyl)benzoate (D261) in an analo-

| Ester | Alkylating reagent | [M + H]$^+$ | RT (min) |
|---|---|---|---|
| Methyl 1-methyl-4-(2-oxo-1-pyrrolidinyl)-1H-indole-6-carboxylate (B156) | I-Et | 273.0 | 2.52 |
| Methyl 1-butyl-4-(2-oxo-1-pyrrolidinyl)-1H-indole-6-carboxylate (B157) | butyl-I | 315.1 | 3.10 |
| Methyl 4-(2-oxo-1-pyrrolidinyl)-1-pentyl-1H-indole-6-carboxylate (B158) | pentyl-I | | |

Ester 159

Methyl 3-methyl-7-(2-oxo-1-pyrrolidinyl)-1-benzofuran-5-carboxylate (B159)

Methyl 3-methyl-7-(2-oxo-1-pyrrolidinyl)-1-benzofuran-5-carboxylate (B159) was obtained from methyl 3-iodo-5-(2-oxo-1-pyrrolidinyl)-4-(2-propen-1-yloxy)benzoate (D259) in an analogous manner to the process described for Ester 163 (B163). [M+H]$^+$=274.0, RT=2.97 min.

gous manner to the process described for 3-(2-oxo-piperidin-1-yl)-5-propyl-benzoic acid tert-butyl ester (B116).

Ester 165

Ethyl 3-ethyl-7-(2-oxo-1-piperidinyl)-1H-indole-5-carboxylate (B165)

To a solution of ethyl 3-ethyl-7-iodo-1H-indole-5-carboxylate (D190) (1 g, 2.91 mmol, 1 equiv) in toluene (10 ml)

were added 2-piperidinone (346 mg, 3.50 mmol, 1.2 equiv), $K_3PO_4$ (1.24 g, 5.83 mmol, 2 equiv), CuI (56 mg, 0.29 mmol, 0.1 equiv) and dimethyl ethylene diamine (62 μl, 0.58 mmol, 0.2 equiv) and the resulting mixture was stirred at 100° C. for 15 h then cooled to room temperature and concentrated in vacuo. The residue was partitioned between AcOEt and $H_2O$ and the layers were separated. The organic phase was dried under $MgSO_4$ and concentrated in vacuo. Purification of the residue by flash chromatography on silica gel (AcOEt/iso-hexane: 1/0) gave ethyl 3-ethyl-7-(2-oxo-1-piperidinyl)-1H-indole-5-carboxylate (B165) (250 mg, 27%) as an off-white solid. $[M+H]^+=315.4$, RT=2.98 min.

Ester 166

Ethyl 3-ethyl-7-(2-oxo-4-phenyl-1-pyrrolidinyl)-1H-indole-5-carboxylate (B166)

Ethyl 3-ethyl-7-(2-oxo-4-phenyl-1-pyrrolidinyl)-1H-indole-5-carboxylate (B166) was obtained from ethyl 3-ethyl-7-iodo-1H-indole-5-carboxylate (D166) in an analogous manner to the process described for 1,1-dimethylethyl 3-bromo-5-(2-oxo-5-phenyl-1-piperidinyl)benzoate (D190) using 4-phenyl-2-pyrrolidinone (Koelsch *J. Am. Chem. Soc.* 1943, (65), p 2093) instead of 5-phenyl-2-piperidinone. $[M+H]^+=377.2$, RT=3.60 min.

Ester 167

Methyl 1-ethyl-4-(2-oxo-1-pyrrolidinyl)-1H-1,2,3-benzotriazole-6-carboxylate (B167)

To a solution of ethyl methyl 4-(2-oxo-1-pyrrolidinyl)-1H-1,2,3-benzotriazole-6-carboxylate (D249) (400 mg, 1.54 mmol, 1 equiv) in DMF (10 ml) at room temperature was added NaH (60% dispersion in mineral oil, 68 mg, 1.69 mmol, 1.1 equiv) and the resulting mixture was stirred 5 min at this temperature. Ethyl iodide (135 μl, 1.69 mmol, 1.1 equiv) was added and the resulting solution was stirred for 2 h then concentrated in vacuo. The residue was dissolved in AcOEt and the organic phase was washed with $H_2O$, dried over $MgSO_4$ and concentrated in vacuo. Purification of the residue by flash chromatography on silica gel (AcOEt/iso-hexane: 100/0) gave methyl 1-ethyl-4-(2-oxo-1-pyrrolidinyl)-1H-1,2,3-benzotriazole-6-carboxylate (270 mg, 61%) as a pale yellow oil. $[M+H]^+=289.3$, RT=2.47 min.

Ester 168

Methyl 3-(1,1-dioxidotetrahydro-2H-1,2-thiazin-2-yl)-5-(ethyloxy)benzoate (B168)

Methyl 3-(1,1-dioxidotetrahydro-2H-1,2-thiazin-2-yl)-5-(ethyloxy)benzoate (B168) was obtained from methyl 3-(1,1-dioxidotetrahydro-2H-1,2-thiazin-2-yl)-5-hydroxybenzoate (D268) in an analogous manner to the process described for Ester 18 (B18) from Description 41 (D41).

Ester 169

Methyl 3-cyclopentyl-5-(1,1-dioxido-2-isothiazolidinyl)benzoate (B169)

Methyl 3-cyclopentyl-5-(1,1-dioxido-2-isothiazolidinyl)benzoate (B169) was obtained from methyl 3-(3-cyclopenten-1-yl)-5-(1,1-dioxido-2-isothiazolidinyl)benzoate, methyl 3-(2-cyclopenten-1-yl)-5-(1,1-dioxido-2-isothiazo-lidinyl)benzoate and methyl 3-(1-cyclopenten-1-yl)-5-(1,1-dioxido-2-isothiazolidinyl)benzoate (D264) in an analogous manner to the process described for Ester 107 (B107).

Ester 170

Methyl 3-(1,1-dioxidotetrahydro-2H-1,2-thiazin-2-yl)-5-[(1-methylethyl)oxy]benzoate (B170)

Methyl 3-(1,1-dioxidotetrahydro-2H-1,2-thiazin-2-yl)-5-[(1-methylethyl)oxy]benzoate (B170) was obtained from methyl 3-(1,1-dioxidotetrahydro-2H-1,2-thiazin-2-yl)-5-hydroxybenzoate (D268) in an analogous manner to the process described for Ester 18 (B18) from Description 41 (D41) using 2-iodopropane instead of iodoethane.

Ester 172

Methyl 8-(1,1-dioxido-2-isothiazolidinyl)-4-ethyl-1,2,3,4-tetrahydro-6-quinoxalinecarboxylate (B172)

Methyl 8-(1,1-dioxido-2-isothiazolidinyl)-4-ethyl-1,2,3,4-tetrahydro-6-quinoxalinecarboxylate (B172) was obtained from methyl 8-bis[(3-chloropropyl)sulfonyl]amino-4-ethyl-1,2,3,4-tetrahydro-6-quinoxalinecarboxylate (D238) in an analogous manner to the process described for methyl 4-(1,1-dioxido-2-isothiazolidinyl)-1-ethyl-1H-indazole-6-carboxylate (B153). $[M+H]^+=340.2$, RT=3.32 min.

Ester 175

Methyl 3-(1,1-dioxidotetrahydro-2H-1,2-thiazin-2-yl)-2-fluoro-5-[(1-methylethyl)amino]benzoate (B175)

Methyl 3-(1,1-dioxidotetrahydro-2H-1,2-thiazin-2-yl)-2-fluoro-5-[(1-methylethyl)amino]benzoate (B175) was obtained from Description 152 (D152) in an analogous manner to the process described for Ester 43 (B43) using acetone instead of 3-pentanone.

Ester 176

Methyl 5-cyclopentyl-3-(1,1-dioxidotetrahydro-2H-1,2-thiazin-2-yl)-2-fluorobenzoate (B176)

Methyl 5-cyclopentyl-3-(1,1-dioxidotetrahydro-2H-1,2-thiazin-2-yl)-2-fluorobenzoate (B176) was obtained from Description (D269) in an analogous manner to the process described for Ester B116 (B116).

Preparation of Epoxides

Epoxide K1

1,1-Dimethylethyl {(1S)-2-(3,5-difluorophenyl)-1-[(2S)-2-oxiranyl]ethyl}carbamate (K1)

1,1-Dimethylethyl {(1S)-2-(3,5-difluorophenyl)-1-[(2S)-2-oxiranyl]ethyl}carbamate (K1) was obtained from 3,5-difluoro-L-phenylalaninate (D299) according to the procedure described in Patent U.S. 2003/0004360 A1

The following epoxides were obtained in an analogous manner to the process described for epoxide K1 using the appropriate alaninate:

| Epoxide | Precursor |
|---|---|
| 1,1-dimethylethyl {(1S)-2-(3-fluorophenyl)-1-[(2S)-2-oxiranyl]ethyl}carbamate (K2) | D300 |
| 1,1-dimethylethyl {(1S)-2-(3,4-difluorophenyl)-1-[(2S)-2-oxiranyl]ethyl}carbamate (K3) | D301 |
| 1,1-dimethylethyl {(1S)-2-(2-chlorophenyl)-1-[(2S)-2-oxiranyl]ethyl}carbamate (K4) | D302 |
| 1,1-dimethylethyl {(1S)-2-(3-chlorophenyl)-1-[(2S)-2-oxiranyl]ethyl}carbamate (K5) | D303 |
| 1,1-dimethylethyl {(1S)-2-(4-chlorophenyl)-1-[(2S)-2-oxiranyl]ethyl}carbamate (K6) | D304 |
| 1,1-dimethylethyl [(1S)-1-[(2S)-2-oxiranyl]-2-(2-thienyl)ethyl]carbamate (K7) | D305 |
| 1,1-dimethylethyl [(1S)-1-[(2S)-2-oxiranyl]-2-(3-thienyl)ethyl]carbamate (K8) | D306 |
| 1,1-dimethylethyl {(1S)-2-(2-furanyl)-1-[(2S)-2-oxiranyl]ethyl}carbamate (K9) | D307 |
| 1,1-dimethlethyl [(1S)-1-[(2S)-2-oxiranyl]-2-(2-pyridinyl)ethyl]carbamate (K10) | D308 |
| 1,1-dimethylethyl [(1S)-1-[(2S)-2-oxiranyl]-2-(1,3-thiazol-2-yl)ethyl]carbamate (K11) | D309 |
| 1,1-dimethylethyl [(1S)-1-[(2S)-2-oxiranyl]-2-(1H-pyrazol-1-yl)ethyl]carbamate (K12) | D310 |
| 1,1-dimethylethyl [(1S)-1-[(2S)-2-oxiranyl]-2-(3-pyridinyl)ethyl]carbamate (K13) | D311 |

Preparation of BOC-protected Amines

BOC-Protected Amine 1 (H1)

((1S,2R)-1-Benzyl-3-cyclohexylamino-2-hydroxy-propyl)-carbamic acid tert-butyl ester (H1)

((S)-(S)-1-Oxiranyl-2-phenyl-ethyl)-carbamic acid tert-butyl ester (D101) (10 g, 38 mmol, 1 equiv) [Chirex 1819W94 Lot#9924382] was dissolved in EtOH (100 ml) and cyclohexylamine (13 ml, 114 mmol, 3 equiv) was added. The resulting mixture was heated, under an atmosphere of nitrogen, for 12 h at reflux temperature. The mixture was cooled and the solvent was removed by evaporation in vacuo. The resulting white solid was washed with $H_2O$ and then with $Et_2O$ before drying in vacuo to give ((1S,2R)-1-benzyl-3-cyclohexylamino-2-hydroxy-propyl)-carbamic acid tert-butyl ester (H1) (9.0 g, 66%). $[M+H]^+=363.2$ BOC-protected amines H2-H20, H24-H33 and H36 were prepared in an analogous manner to that described for BOC-protected amine H1, substituting cyclohexylamine with the amines indicated in the table below (unless amines are commercially available):

| BOC-protected amine | Precursor |
|---|---|
| ((1S,2R)-1-Benzyl-3-cyclobutylamino-2-hydroxy-propyl)-carbamic acid tert-butyl ester (H2) | — |
| ((1S,2R)-1-Benzyl-2-hydroxy-3-isobutylamino-propyl)-carbamic acid tert-butyl ester (H3) | — |
| ((1S,2R)-1-Benzyl-2-hydroxy-3-propylamino-propyl)-carbamic acid tert-butyl ester (H4) | — |
| [(1S,2R)-1-Benzyl-2-hydroxy-3-(1,1,5-trimethyl-hexylamino)-propyl]-carbamic acid tert-butyl ester (H5) | F5 |
| [(1S,2R)-1-Benzyl-3-((S)-1-cyclohexylcarbamoyl-ethylamino)-2-hydroxy-propyl]-carbamic acid tert-butyl ester (H6) | F6 |
| {(1S,2R)-1-Benzyl-2-hydroxy-3-[(R)-1-(3-methoxy-phenyl)-ethylamino]-propyl}-carbamic acid tert-butyl ester (H7) | — |
| [(1S,2R)-1-Benzyl-2-hydroxy-3-(1-methyl-1-phenyl-ethylamino)-propyl]-carbamic acid tert-butyl ester (H8) | — |
| [(1S,2R)-1-Benzyl-2-hydroxy-3-(3-methyl-butylamino)-propyl]-carbamic acid tert-butyl ester (H9) | — |
| ((1S,2R)-1-Benzyl-3-tert-butylamino-2-hydroxy-propyl)-carbamic acid tert-butyl ester (H10) | — |
| [(1S,2R)-1-Benzyl-2-hydroxy-3-(3-trifluoromethoxy-benzylamino)-propyl]-carbamic acid tert-butyl ester (H11) | — |
| [(1S,2R)-1-Benzyl-2-hydroxy-3-(2,2,3,3,3,-pentafluoro-propylamino)-propyl]-carbamic acid tert-butyl ester (H12) | — |
| [(1S,2R)-1-Benzyl-3-(2,2,3,3,4,4,4,-heptafluoro-butylamino)-2-hydroxy-propyl]-carbamic acid tert-butyl ester (H13) | — |
| [(1S,2R)-1-Benzyl-2-hydroxy-3-(3-methoxy-benzylamino)-propyl]-carbamic acid tert-butyl ester (H14) | — |
| {(1S,2R)-1-Benzyl-2-hydroxy-3-[1-(3-methoxy-phenyl)-1-methyl-ethylamino]-propyl}-carbamic acid tert-butyl ester (H15) | F15 |
| [(1S,2R)-1-Benzyl-2-hydroxy-3-(3-trifluoromethyl-benzylamino)-propyl]-carbamic acid tert-butyl ester (H16) | — |
| {(1S,2R)-1-Benzyl-2-hydroxy-3-[(S)-1-(3-methoxy-phenyl)-ethylamino]-propyl}-carbamic acid tert-butyl ester (H17) | — |

-continued

| BOC-protected amine | Precursor |
|---|---|
| {(1S,2R)-1-Benzyl-2-hydroxy-3-[(S)-1-(3-methoxy-phenyl)-ethylamino]-propyl}-carbamic acid tert-butyl ester (H18) | — |
| [(1S,2R)-1-Benzyl-2-hydroxy-3-(5-methyl-hexylamino)-propyl]-carbamic acid tert-butyl ester (H19) | — |
| [(1S,2R)-1-Benzyl-3-(1,5-dimethyl-hexylamino)-2-hydroxy-propyl]-carbamic acid tert-butyl ester (H20) | — |
| ((1S,2R)-1-Benzyl-3-ethylamino-2-hydroxy-propyl)-carbamic acid tert-butyl ester (H24) | — |
| [(1S,2R)-1-Benzyl-3-(bis-trifluoromethyl-benzylamino)-2-hydroxy-propyl]-carbamic acid tert-butyl ester (H25) | — |
| ((1S,2R)-1-Benzyl-3-cyclopropylamino-2-hydroxy-propyl)-carbamic acid tert-butyl ester (H26) | — |
| [(1S,2R)-1-Benzyl-2-hydroxy-3-(4-methoxy-benzylamino)-propyl]-carbamic acid tert-butyl ester (H27) | — |
| ((1S,2R)-1-Benzyl-2-hydroxy-3-isopropylamino-propyl)-carbamic acid tert-butyl ester (H28) | — |
| [(1S,2R)-1-Benzyl-2-hydroxy-3-(2-methoxy-benzylamino)-propyl]-carbamic acid tert-butyl ester (H29) | — |
| [(1S,2R)-1-Benzyl-2-hydroxy-3-((S)-1-phenyl-ethylamino)-propyl]-carbamic acid tert-butyl ester (H30) | — |
| [(1S,2R)-1-Benzyl-2-hydroxy-3-((R)-1-phenyl-ethylamino)-propyl]-carbamic acid tert butyl ester (H31) | — |
| [(1S,2R)-1-Benzyl-2-hydroxy-3-(4-methyl-pentylamino)-propyl]-carbamic acid tert-butyl ester (H32) | — |
| [(1S,2R)-1-Benzyl-2-hydroxy-3-((R)-2-hydroxy-1-isobutylcarbamoyl-pentylamino)-propyl]-carbamic acid tert-butyl ester (H33) | F33 |
| [(1S,2R)-1-Benzyl-2-hydroxy-3-((S)-1-isobutylcarbamoyl-pentylamino)-propyl]-carbamic acid tert-butyl ester (H36) | F36 |

BOC-protected amines H40-H114 were prepared in an analogous manner to that described for BOC-protected amine H1, substituting cyclohexylamine with the amines indicated in the table below (unless amines are commercially available):

| BOC-protected amine | Precursor |
|---|---|
| 1,1-dimethylethyl [(1S,2R)-2-hydroxy-1-(phenylmethyl)-3-({[3-(trifluoromethyl)phenyl]methyl} amino)propyl]carbamate (H40) | F40 |
| 1,1-dimethylethyl [(1S,2R)-2-hydroxy-3-({1-[3-(methyloxy)phenyl]cyclohexyl} amino)-1-(phenylmethyl)propyl]carbamate (H41) | F41 |
| 1,1-dimethylethyl [(1S,2R)-2-hydroxy-3-{[(1-methyl-1H-pyrazol-4-yl)methyl]amino}-1-(phenylmethyl)propyl]carbamate (H42) | |
| 1,1-dimethylethyl [(1S,2R)-2-hydroxy-1-(phenylmethyl)-3-(tetrahydro-2H-pyran-4-ylamino)propyl]carbamate (H43) | |
| 1,1-dimethylethyl [(1S,2R)-3-[(3,3-dimethylbutyl)amino]-2-hydroxy-1-(phenylmethyl)propyl]carbamate (H44) | |
| 1,1-dimethylethyl {(1S,2R)-2-hydroxy-1-(phenylmethyl)-3-[(1,1,3,3-tetramethylbutyl)amino] propyl}carbamate (H45) | |
| 1,1-dimethylethyl [(1S,2R)-3-[(1,3-dimethylbutyl)amino]-2-hydroxy-1-(phenylmethyl)propyl]carbamate (H46) | |
| 1,1-dimethylethyl [(1S,2R)-3-({[4-fluoro-3-(trifluoromethyl)phenyl]methyl}amino)-2-hydroxy-1-(phenylmethyl)propyl]carbamate (H47) | |
| 1,1-dimethylethyl [(1S,2R)-3-[(1,1-dimethylhexyl)amino]-2-hydroxy-1-(phenylmethyl)propyl]carbamate (H48) | F48 |
| 1,1-dimethylethyl [(1S,2R)-2-hydroxy-3-({[2-methyl-5-(trifluoromethyl)phenyl] methyl}amino)-1-(phenylmethyl)propyl]carbamate (H49) | |
| 1,1-dimethylethyl [(1S,2R)-3-[(1S)-2,3-dihydro-1H-inden-1-ylamino]-2-hydroxy-1-(phenylmethyl)propyl] carbamate (H50) | |
| 1,1-dimethylethyl [(1S,2R)-2-hydroxy-3-{[(1S,2R)-2-hydroxy-2,3-dihydro-1H-inden-1-yl]amino}-1-(phenylmethyl)propyl]carbamate (H51) | |
| 1,1-dimethylethyl [(1S,2R)-2-hydroxy-3-{[6-(methyloxy)-2,3-dihydro-1H-inden-1-yl]amino}-1-(phenylmethyl)propyl]carbamate (H52) | F52 |
| 1,1-dimethylethyl [(1S,2R)-2-hydroxy-3-{[(1R,2S)-2-hydroxy-2,3-dihydro-1H-inden-1-yl]amino}-1-(phenylmethyl)propyl]carbamate (H53) | |
| 1,1-dimethylethyl [(1S,2R)-3-({1,1-dimethyl-2-[(2-methylpropyl)thio]ethyl}amino)-2-hydroxy-1-(phenylmethyl)propyl]carbamate (H54) | F54 |
| 1,1-dimethylethyl [(1S,2R)-3-{[1,1-dimethyl-2-(phenyloxy)ethyl] amino}-2-hydroxy-1-(phenylmethyl)propyl]carbamate (H55) | F55 |

-continued

| BOC-protected amine | Precursor |
|---|---|
| 1,1-dimethylethyl [(1S,2R)-3-({1,1-dimethyl-2-[(phenylmethyl)oxy] ethyl}amino)-2-hydroxy-1-(phenylmethyl)propyl]carbamate (H56) | F56 |
| 1,1-dimethylethyl [(1S,2R)-2-hydroxy-3-{[3-(methyloxy)phenyl] amino}-1-(phenylmethyl)propyl] carbamate (H57) | |
| 1,1-dimethylethyl [(1S,2R)-2-hydroxy-1-(phenylmethyl)-3-({2-[3-(trifluoromethyl)phenyl]ethyl}amino)propyl]carbamate (H58) | |
| 1,1-dimethylethyl [(1S,2R)-3-[(1,1-dimethyl-2-phenylethyl)amino]-2-hydroxy-1-(phenylmethyl)propyl] carbamate (H59) | |
| 1,1-dimethylethyl [(1S,2R)-2-hydroxy-3-{[2-(1-naphthalenyl) ethyl]amino}-1-(phenylmethyl) propyl]carbamate (H60) | |
| 1,1-dimethylethyl [(1S,2R)-3-({1,1-dimethyl-2-[3-(methyloxy)phenyl] ethyl}amino)-2-hydroxy-1-(phenylmethyl)propyl]carbamate (H61) | F61 |
| 1,1-dimethylethyl [(1S,2R)-2-hydroxy-3-(phenylamino)-1-(phenylmethyl)propyl]carbamate (H62) | |
| 1,1-dimethylethyl [(1S,2R)-3-({1-[3-(methyloxy) phenyl]cyclopropyl}amino)-1-(phenylmethyl)propyl]carbamate (H63) | F63 |
| 1,1-dimethylethyl [(1S,2R)-3-[(cyclohexylmethyl)amino]-2-hydroxy-1-(phenylmethyl)propyl] carbamate (H64) | |
| 1,1-dimethylethyl {(1S,2R)-2-hydroxy-1-(phenylmethyl)-3-[(tetrahydro-2H-pyran-4-ylmethyl)amino]propyl}carbamate (H65) | |
| 1,1-dimethylethyl [(1S,2R)-2-hydroxy-1-(phenylmethyl)-3-(tetrahydro-2H-thiopyran-4-ylamino)propyl]carbamate (H66) | |
| 1,1-dimethylethyl [(1S,2R)-2-hydroxy-3-[(1-methylpropyl)amino]-1-(phenylmethyl)propyl]carbamate (H67) | |
| 1,1-dimethylethyl [(1S,2R)-3-{[4-(1,1-dimethylethyl)cyclohexyl] amino}-2-hydroxy-1-(phenylmethyl)propyl]carbamate (H68) | |
| 1,1-dimethylethyl [(1S,2R)-3-[(1-ethylcyclobutyl)amino]-2-hydroxy-1-(phenylmethyl)propyl]carbamate (H69) | F69 |
| 1,1-dimethylethyl [(1S,2R)-3-({1,1-dimethyl-2-[(2-methylpropyl)oxy] ethyl}amino)-2-hydroxy-1-(phenylmethyl)propyl]carbamate (H70) | F70 |
| 1,1-dimethylethyl [(1S,2R)-3-({1,1-dimethyl-2-[(2-methyl-2-propen-1-yl)oxy]ethyl}amino)-2-hydroxy-1-(phenylmethyl)propyl]carbamate (H71) | F71 |
| 1,1-dimethylethyl [(1S,2R)-3-[(1R)-2,3-dihydro-1H-inden-1-ylamino]-2-hydroxy-1-(phenylmethyl)propyl]carbamate (H72) | |
| 1,1-dimethylethyl [(1S,2R)-2-hydroxy-3-{[1-(4-methylpentyl)cyclopropyl]amino}-1-(phenylmethyl)propyl]carbamate (H73) | F73 |
| 1,1-dimethylethyl [(1S,2R)-3-[(1-ethylcyclopropyl)amino]-2-hydroxy-1-(phenylmethyl)propyl]carbamate (H74) | F74 |
| 1,1-dimethylethyl [(1S,2R)-2-hydroxy-3-{[1-(1-methylethyl)cyclopropyl] amino}-1-(phenylmethyl)propyl]carbamate (H75) | F75 |
| 1,1-dimethylethyl [(1S,2R)-3-(butylamino)-2-hydroxy-1-(phenylmethyl)propyl]carbamate (H76) | |
| 1,1-dimethylethyl {(1S,2R)-2-hydroxy-1-(phenylmethyl)-3-[(1-propylcyclopropyl)amino]propyl} carbamate (H77) | F77 |
| 1,1-dimethylethyl [(1S,2R)-2-hydroxy-3-{[1-(3-methylbutyl) cyclopropyl]amino}-1-(phenylmethyl)propyl]carbamate (H78) | F78 |
| 1,1-dimethylethyl [(1S,2R)-2-hydroxy-3-{[1-(2-methylpropyl) cyclopropyl]amino}-1-(phenylmethyl)propyl]carbamate (H79) | F79 |
| 1,1-dimethylethyl [(1S,2R)-3-({1-[(3-chlorophenyl)methyl] cyclopropyl}amino)-2-hydroxy-1-(phenylmethyl)propyl]carbamate (H80) | F80 |
| 1,1-dimethylethyl [(1S,2R)-2-hydroxy-3-[(1-methylcyclohexyl) amino]-1-(phenylmethyl)propyl] carbamate (H81) | F81 |
| 1,1-dimethylethyl [(1S,2R)-3-[(2S)-bicyclo[2.2.1]hept-2-ylamino]-2-hydroxy-1-(phenylmethyl)propyl] carbamate (H82) | |
| 1,1-dimethylethyl [(1S,2R)-3-[(4,4-dimethylcyclohexyl)amino]-2-hydroxy-1-(phenylmethyl)propyl]carbamate (H83) | F83 |
| 1,1-dimethylethyl ((1S,2R)-2-hydroxy-1-(phenylmethyl)-3-{[(1R)-1,2,2-trimethylpropyl]amino} propyl)carbamate (H84) | |
| 1,1-dimethylethyl ((1S,2R)-2-hydroxy-1-(phenylmethyl)-3-{[(1S)-1,2,2-trimethylpropyl]amino} propyl)carbamate (H85) | |
| 1,1-dimethylethyl [(1S,2R)-3-[(2,2-dimethylcyclohexyl)amino]-2-hydroxy-1-(phenylmethyl)propyl] carbamate (H86) | F86 |
| 1,1-dimethylethyl [(1S,2R)-2-hydroxy-3-(pentylamino)-1-(phenylmethyl)propyl]carbamate (H87) | |
| 1,1-dimethylethyl [(1S,2R)-3-(hexylamino)-2-hydroxy-1-(phenylmethyl)propyl]carbamate (H88) | |
| 1,1-dimethylethyl [(1S,2R)-3-[(3,3-dimethylbutyl)amino]-2-hydroxy-1-(phenylmethyl)propyl]carbamate (H89) | |
| 1,1-dimethylethyl [(1S,2R)-3-[(1,1-dimethylpropyl)amino]-2-hydroxy-1-(phenylmethyl)propyl]carbamate (H90) | |
| 1,1-dimethylethyl [(1S,2R)-3-[(cyclopropylmethyl)amino]-2-hydroxy-1-(phenylmethyl)propyl]carbamate (H91) | |
| 1,1-dimethylethyl [(1S,2R)-3-[(3,3-dimethylcyclopentyl)amino]-2-hydroxy-1-(phenylmethyl)propyl]carbamate (H92) | F92 |
| 1,1-dimethylethyl [(1S,2R)-2-hydroxy-3-(methylamino)-1-(phenylmethyl)propyl]carbamate (H93) | |

| BOC-protected amine | Precursor |
|---|---|
| 1,1-dimethylethyl [(1S,2R)-2-hydroxy-1-(phenylmethyl)-3-(tricyclo[3.3.1.1³,⁷]dec-1-ylamino)propyl]carbamate (H94) | |
| 1,1-dimethylethyl [(1S,2R)-2-hydroxy-1-(phenylmethyl)-3-(1,2,3,4-tetrahydro-1-naphthalenylamino)propyl] carbamate (H95) | |
| 1,1-dimethylethyl [(1S,2R)-2-hydroxy-3-({2-[3-(methyloxy)phenyl]ethyl}amino)-1-(phenylmethyl)propyl]carbamate (H96) | |
| 1,1-dimethylethyl [(1S,2R)-2-hydroxy-3-({2-[4-(methyloxy)phenyl]ethyl}amino)-1-(phenylmethyl)propyl]carbamate (H97) | |
| 1,1-dimethylethyl [(1S,2R)-2-hydroxy-3-({2-[2-(methyloxy)phenyl]ethyl}amino)-1-(phenylmethyl)propyl]carbamate (H98) | |
| 1,1-dimethylethyl [(1S,2R)-3-{[2-(2-chlorophenyl)ethyl]amino}-2-hydroxy-1-(phenylmethyl)propyl]carbamate (H99) | |
| 1,1-dimethylethyl [(1S,2R)-3-{[2-(2-chlorophenyl)ethyl]amino}-2-hydroxy-1-(phenylmethyl)propyl]carbamate (H100) | |
| 1,1-dimethylethyl [(1S,2R)-3-{[2-(4-chlorophenyl)ethyl]amino}-2-hydroxy-1-(phenylmethyl)propyl]carbamate (H101) | |
| 1,1-dimethylethyl [(1S,2R)-2-hydroxy-3-{[2-(4-methylphenyl)ethyl]amino}-1-(phenylmethyl)propyl]carbamate (H102) | |
| 1,1-dimethylethyl [(1S,2R)-2-hydroxy-3-{[2-(2-methylphenyl)ethyl]amino}-1-(phenylmethyl)propyl]carbamate (H103) | |
| 1,1-dimethylethyl [(1S,2R)-3-{[2-(3,4-dichlorophenyl)ethyl]amino}-2-hydroxy-1-(phenylmethyl)propyl]carbamate (H104) | |
| 1,1-dimethylethyl [(1S,2R)-3-{[2-(2,4-dichlorophenyl)ethyl]amino}-2-hydroxy-1-(phenylmethyl)propyl]carbamate (H105) | |
| 1,1-dimethylethyl [(1S,2R)-3-({2-[3,5-bis(methyloxy)phenyl]ethyl}amino)-2-hydroxy-1-(phenylmethyl)propyl]carbamate (H106) | |
| 1,1-dimethylethyl [(1S,2R)-3-({2-[2,3-bis(methyloxy)phenyl] ethyl}amino)-2-hydroxy-1-(phenylmethyl)propyl]carbamate (H107) | |
| 1,1-dimethylethyl {(1S,2R)-2-hydroxy-1-(phenylmethyl)-3-[(phenylmethyl)amino]propyl} carbamate (H108) | |
| 1,1-dimethylethyl [(1S,2R)-2-hydroxy-3-[(2-phenylethyl)amino]-1-(phenylmethyl)propyl]carbamate (H109) | |
| 1,1-dimethylethyl [(1S,2R)-3-[(1-ethylcyclohexyl)amino]-2-hydroxy-1-(phenylmethyl)propyl]carbamate (H110) | F110 |
| 1,1-dimethylethyl [(1S,2R)-2-hydroxy-3-[(1-methylcyclopentyl)amino]-1-(phenylmethyl)propyl]carbamate (H111) | F111 |
| 1,1-dimethylethyl {(1S,2R)-2-hydroxy-1-(phenylmethyl)-3-[(1-propylcyclopentyl)amino]propyl} carbamate (H112) | F112 |
| 1,1-dimethylethyl {(1S,2R)-2-hydroxy-1-(phenylmethyl)-3-[(1-propylcyclohexyl)amino]propyl} carbamate (H113) | F113 |
| 1,1-dimethylethyl [(1S,2R)-3-{[2-(3-chlorophenyl)-1,1-dimethylethyl]amino}-2-hydroxy-1-(phenylmethyl)propyl]carbamate (H114) | F114 |

The following BOC-protected amines H115–H147 were prepared in an analogous manner to that described for BOC-protected amine H1, using the appropriate epoxide and the appropriate amine indicated in the table below (only non commercial amines are given):

| Boc-protected amine | Epoxide | Amine |
|---|---|---|
| 1,1-dimethylethyl [(1S,2R)-2-hydroxy-3-({[3-(methyloxy)phenyl]methyl}amino)-1-(3-pyridinylmethyl)propyl]carbamate (H115) | K13 | |
| 1,1-dimethylethyl [(1S,2R)-2-hydroxy-3-({[3-(methyloxy)phenyl]methyl}amino)-1-(1,3-thiazol-2-ylmethyl)propyl]carbamate (H116) | K11 | |
| 1,1-dimethylethyl [(1S,2R)-3-(cyclohexylamino)-2-hydroxy-1-(1,3-thiazol-2-ylmethyl)propyl]carbamate (H117) | K11 | |
| 1,1-dimethylethyl [(1S,2R)-3-[(1,5-dimethylhexyl)amino]-2-hydroxy-1-(1,3-thiazol-2-ylmethyl)propyl]carbamate (H118) | K11 | |
| 1,1-dimethylethyl [(1S,2R)-1-(2-furanylmethyl)-2-hydroxy-3-({[3-(methyloxy)phenyl]methyl}amino) propyl]carbamate (H119) | K9 | |
| 1,1-dimethylethyl [(1S,2R)-3-(cyclohexylamino)-1-(2-furanylmethyl)-2-hydroxypropyl]carbamate (H120) | K9 | |
| 1,1-dimethylethyl [(1S,2R)-3-[(1,5-dimethylhexyl)amino]-1-(2-furanylmethyl)-2-hydroxypropyl]carbamate (H121) | K9 | |
| 1,1-dimethylethyl {(1S,2R)-1-(2-furanylmethyl)-2-hydroxy-3-[(1,1,5-trimethylhexyl)amino]propyl} carbamate (H122) | K9 | F5 |
| 1,1-dimethylethyl [(1S,2R)-2-hydroxy-3-({[3-(methyloxy)phenyl]methyl}amino)-1-(2-pyridinylmethyl)propyl]carbamate (H123) | K10 | |
| 1,1-dimethylethyl [(1S,2R)-1-[(4-chlorophenyl)methyl]-3-(cyclohexylamino)-2-hydroxypropyl]carbamate (H124) | K6 | |

-continued

| Boc-protected amine | Epoxide | Amine |
|---|---|---|
| 1,1-dimethylethyl [(1S,2R)-1-[(4-chlorophenyl)methyl]-2-hydroxy-3-({[3-(methyloxy)phenyl]methyl} amino)propyl]carbamate (H125) | K6 | |
| 1,1-dimethylethyl [(1S,2R)-1-[(3,5-difluorophenyl)methyl]-2-hydroxy-3-({[3-(trifluoromethyl)phenyl] methyl}amino)propyl]carbamate (H126) | K1 | |
| 1,1-dimethylethyl [(1S,2R)-1-[(3,5-difluorophenyl)methyl]-2-hydroxy-3-({[3-(methyloxy)phenyl] methyl}amino)propyl]carbamate (H127) | K1 | |
| 1,1-dimethylethyl {(1S,2R)-1-[(3,5-difluorophenyl)methyl]-3-[(1,5-dimethylhexyl)amino]-2-hydroxypropyl}carbamate (H128) | K1 | |
| 1,1-dimethylethyl {(1S,2R)-3-(cyclohexylamino)-1-[(3,5-difluorophenyl)methyl]-2-hydroxypropyl}carbamate (H129) | K1 | |
| 1,1-dimethylethyl {(1S,2R)-1-[(3,5-difluorophenyl)methyl]-2-hydroxy-3-[(1,1,5-trimethylhexyl)amino]propyl} carbamate (H130) | K1 | F5 |
| 1,1-dimethylethyl [(1S,2R)-1-[(3,4-difluorophenyl)methyl]-2-hydroxy-3-({[3-(methyloxy)phenyl] methyl}amino)propyl]carbamate (H131) | K3 | |
| 1,1-dimethylethyl {(1S,2R)-3-(cyclohexylamino)-1-[(3,4-difluorophenyl)methyl]-2-hydroxypropyl}carbamate (H132) | K3 | |
| 1,1-dimethylethyl {(1S,2R)-1-[(3,4-difluorophenyl)methyl]-2-hydroxy-3-[(1,1,5-trimethylhexyl)amino] propyl}carbamate (H133) | K3 | F5 |
| 1,1-dimethylethyl [(1S,2R)-1-[(3-chlorophenyl)methyl]-2-hydroxy-3-({[3-(methyloxy)phenyl]methyl} amino)propyl]carbamate (H134) | K5 | |
| 1,1-dimethylethyl [(1S,2R)-1-[(3-chlorophenyl)methyl]-3-(cyclohexylamino)-2-hydroxypropyl]carbamate (H135) | K5 | |
| 1,1-dimethylethyl [(1S,2R)-1-[(2-chlorophenyl)methyl]-2-hydroxy-3-({[3-(methyloxy)phenyl]methyl} amino)propyl]carbamate (H136) | K4 | |
| 1,1-dimethylethyl [(1S,2R)-1-[(2-chlorophenyl)methyl]-3-(cyclohexylamino)-2-hydroxypropyl]carbamate (H137) | K4 | |
| 1,1-dimethylethyl {(1S,2R)-1-[(2-chlorophenyl)methyl]-3-[(1,5-dimethylhexyl)amino]-2-hydroxypropyl}carbamate (H138) | K4 | |
| 1,1-dimethylethyl {(1S,2R)-1-[(3-chlorophenyl)methyl]-3-[(1,5-dimethylhexyl)amino]-2-hydroxypropyl}carbamate (H139) | K5 | |
| 1,1-dimethylethyl [(1S,2R)-1-[(3-fluorophenyl)methyl]-2-hydroxy-3-({[3-(methyloxy)phenyl] methyl}amino)propyl]carbamate (H140) | K2 | |
| 1,1-dimethylethyl {(1S,2R)-3-[(1,5-dimethylhexyl)amino]-1-[(3-fluorophenyl)methyl]-2-hydroxypropyl}carbamate (H141) | K2 | |
| 1,1-dimethylethyl [(1S,2R)-2-hydroxy-3-({[3-(methyloxy)phenyl] methyl}amino)-1-(2-thienylmethyl)propyl]carbamate (H142) | K7 | |
| 1,1-dimethylethyl [(1S,2R)-3-[(1,5-dimethylhexyl)amino]-2-hydroxy-1-(2-thienylmethyl)propyl]carbamate (H143) | K7 | |
| 1,1-dimethylethyl [(1S,2R)-2-hydroxy-3-({[3-(methyloxy)phenyl] methyl}amino)-1-(1H-pyrazol-1-ylmethyl)propyl]carbamate (H144) | K12 | |
| 1,1-dimethylethyl [(1S,2R)-3-[(1,5-dimethylhexyl)amino]-2-hydroxy-1-(1H-pyrazol-1-ylmethyl)propyl]carbamate (H145) | K12 | |
| 1,1-dimethylethyl [(1S,2R)-2-hydroxy-3-({[3-(methyloxy)phenyl] methyl}amino)-1-(3-thienylmethyl)propyl]carbamate (H146) | K8 | |
| 1,1-dimethylethyl [(1S,2R)-3-[(1,5-dimethylhexyl)amino]-2-hydroxy-1-(3-thienylmethyl)propyl]carbamate (H147) | K8 | |

BOC-protected amines H148-H156 were prepared in an analogous manner to that described for BOC-protected amine H1, substituting cyclohexylamine with the amines indicated in the table below (if amines are not commercially available):

| BOC-protected amine | Precursor |
|---|---|
| 1,1-dimethylethyl {(1S,2R)-2-hydroxy-1-(phenylmethyl)-3-[(1-propylcyclobutyl)amino]propyl} carbamate (H148) | F148 |
| 1,1-dimethylethyl [(1S,2R)-2-hydroxy-3-{[1-(1-methylethyl)cyclobutyl]amino}-1-(phenylmethyl)propyl]carbamate (H149) | F149 |
| 1,1-dimethylethyl [(1S,2R)-3-({1-[(3-chlorophenyl) methyl]cyclobutyl} amino)-2-hydroxy-1-(phenylmethyl)propyl]carbamate (H150) | F150 |
| 1,1-dimethylethyl [(1S,2R)-2-hydroxy-1-(phenylmethyl)-3-(tricyclo[3.3.1.1$^{3,7}$]dec-2-ylamino)propyl]carbamate (H151) | |
| 1,1-dimethylethyl [(1S,2R)-3-[(1r,4R)-bicyclo[2.2.1]hept-1-ylamino]-2-hydroxy-1-(phenylmethyl)propyl]carbamate (H152) | |
| 1,1-dimethylethyl [(1S,2R)-3-(bicyclo[2.2.2]oct-1-ylamino)-2-hydroxy-1-(phenylmethyl)propyl]carbamate (H153) | |

-continued

| BOC-protected amine | Precursor |
|---|---|
| 1,1-dimethylethyl [(1S,2R)-3-{[(1-ethyl-1H-pyrazol-4-yl)methyl]amino}-2-hydroxy-1-(phenylmethyl)propyl]carbamate (H154) | |
| 1,1-dimethylethyl [(1S,2R)-3-[(4,4-difluorocyclohexyl)amino]-2-hydroxy-1-(phenylmethyl)propyl] carbamate (H155) | F155 |
| 1,1-dimethylethyl [(1S,2R)-3-({[3,4-bis(methyloxy)phenyl] methyl}amino)-2-hydroxy-1-(phenylmethyl)propyl]carbamate (H156) | |

BOC-protected Amine H157

1,1-Dimethylethyl [(1S,2R)-3-{[(3-ethyl-5-isoxazolyl)methyl]amino}-2-hydroxy-1-(phenylmethyl)propyl]carbamate (H157)

1,1-dimethylethyl [(1S,2R)-3-[[(3-ethyl-5-isoxazolyl)methyl]amino}-2-hydroxy-1-(phenylmethyl)propyl]carbamate (H157) was prepared from Description F157 in an analogous manner to the process described for BOC-protected amine H1.

Preparation of Acids

Acid 1

3-Methylsulfanyl-5-(2-oxo-pyrrolidin-1-yl)-benzoic acid (A1)

To a solution of 3-methylsulfanyl-5-(2-oxo-pyrrolidin-1-yl)-benzoic acid methyl ester (B1) (115 mg, 0.433 mmol, 1 equiv) in MeOH (8 ml) was added 2N aqueous NaOH solution (0.65 ml, 1.3 mmol, 3 equiv). The resulting mixture was stirred for 4 h, 2N aqueous NaOH solution (1 ml, mmol, equiv) was added and the resulting solution was stirred for 16 h then concentrated in vacuo. The residue was diluted with $H_2O$ and extracted with $Et_2O$. The aqueous layer was acidified using 2N aqueous HCl solution and the white precipitate formed was extracted twice with AcOEt. The combined organic solutions were dried over $Na_2SO_4$ and concentrated in vacuo to give 3-methylsulfanyl-5-(2-oxo-pyrrolidin-1-yl)-benzoic acid (A1) (109 mg, 100%) as a white solid. $[M+H]^+$=252.0, RT=2.61 min Acid 2

3-Ethylsulfanyl-5-(2-oxo-pyrrolidin-1-yl)-benzoic acid (A2)

Acid 2 was prepared from 125 mg (0.426 mmol) of 3-methylsulfanyl-5-(2-oxo-pyrrolidin-1-yl)-benzoic acid methyl ester (B2) in an analogous manner to that described for Acid 1 which yielded 11 mg (98%) of 3-methylsulfanyl-5-(2-oxo-pyrrolidin-1-yl)-benzoic acid (A2) as a white solid. $[M+H]^+$=266.1, RT=2.82 min Acid 3

3-(1,1-Dioxo-1/$^6$-isothiazolidin-2-yl)-5-methylsulfanyl-benzoic acid (A3)

To a solution of 3-(1,1-dioxo-1/$^6$-isothiazolidin-2-yl)-5-methylsulfanyl-benzoic acid methyl ester (B3) (144 mg, 0.48 mmol, 1 equiv) in MeOH (10 ml) was added 2N aqueous NaOH solution (2.4 ml, 4.8 mmol, 10 equiv). The resulting mixture was stirred at room temperature for 3.5 h and at 40° C. for 1 h, then cooled to room temperature and concentrated in vacuo. The residue was diluted with $H_2O$ and extracted with $Et_2O$. The aqueous layer was acidified with 2N aqueous HCl solution and the white precipitate formed was extracted twice with AcOEt. The combined organic solutions were dried over $Na_2SO_4$ and concentrated in vacuo to give 3-(1,1-dioxo-1/$^6$-isothiazolidin-2-yl)-5-methylsulfanyl-benzoic acid (A3) (136 mg, 100%) as a white solid. $[M+H]^+$=288.0, RT=2.63 min Acid 4

3-(1,1-Dioxo-1/$^6$-isothiazolidin-2-yl)-5-ethylsulfanyl-benzoic acid (A4)

To a solution of 3-(1,1-dioxo-1/$^6$-isothiazolidin-2-yl)-5-ethylsulfanyl-benzoic acid ethyl ester (B4) (145 mg, 0.44 mmol, 1 equiv) in MeOH (5 ml) was added 2N aqueous NaOH solution (2.2 ml, 4.4 mmol, 10 equiv). The resulting mixture was stirred at room temperature for 3 h then concentrated in vacuo. The residue was diluted with $H_2O$ and extracted with $Et_2O$. The aqueous layer was acidified with 2N aqueous HCl solution and the white precipitate formed extracted twice with AcOEt. The combined organic solutions were dried over $Na_2SO_4$ and concentrated in vacuo to give 3-(1,1-dioxo-1/$^6$-isothiazolidin-2-yl)-5-ethylsulfanyl-benzoic acid (A4) (133 mg, 100%) as a white solid. $[M+H]^+$=302.0, RT=2.83 min Acid 5

3-Methanesulfonyl-5-(2-oxo-pyrrolidin-1-yl)-benzoic acid (A5)

To a solution of 3-methylsulfanyl-5-(2-oxo-pyrrolidin-1-yl)-benzoic acid (A1) (59 mg, 0.235 mmol, 1 equiv) in MeOH/$H_2O$ (3:1, 24 ml) was added oxone (578 mg, 0.94 mol, 4 equiv). The resulting mixture was stirred at room temperature for 50 min and then concentrated in vacuo. The residue was partitioned between AcOEt and $H_2O$ and the layers separated. The organic layer was washed with $H_2O$ and brine, dried over $Na_2SO_4$ and concentrated in vacuo to give a solid which was triturated with $Et_2O$ to give 3-methanesulfonyl-5-(2-oxo-pyrrolidin-1-yl)-benzoic acid (A5) (57 mg, 86%) as a white solid. $[M+H]^+$=284.0, RT=2.05 min Acid 6

3-Ethanesulfonyl-5-(2-oxo-pyrrolidin-1-yl)-benzoic acid (A6)

Acid 6 was prepared from 59 mg (0.22 mmol) of 3-ethylsulfanyl-5-(2-oxo-pyrrolidin-1-yl)-benzoic acid (A2) in an analogous manner to that described for Acid 5 which yielded 59 mg (89%) of 3-ethanesulfonyl-5-(2-oxo-pyrrolidin-1-yl)-benzoic acid (A6) as a white solid. $[M+H]^+$=298.0, Rt=2.08 min Acid 7

3-(1,1-Dioxo-1/$^6$-isothiazolidin-2-yl)-5-methanesulfonyl-benzoic acid (A7)

Acid 7 was prepared from 78 mg (0.27 mmol) of 3-(1,1-dioxo-1/$^6$-isothiazolidin-2-yl)-5-methylsulfanyl-benzoic acid (A3) in an analogous manner to that described for Acid 6 which yielded 78 mg (90%) of 3-(1,1-dioxo-1/$^6$-isothiazolidin-2-yl)-5-methanesulfonyl-benzoic acid (A7) as a white solid. [M−H]=318.0, RT=2.07 min Acid 8

3-(1,1-Dioxo-1/$^6$-isothiazolidin-2-yl)-5-ethanesulfonyl-benzoic acid (A8)

Acid 8 was prepared from 72 mg (0.24 mmol) of 3-(1,1-dioxo-1/$^6$-isothiazolidin-2-yl)-5-ethylsulfanyl-benzoic acid (A4) 73 mg (91%) in an analogous manner to that described in Acid 7 which yielded 3-(1,1-dioxo-1/$^6$-isothiazolidin-2-yl)-5-ethanesulfonyl-benzoic acid A8 as a white solid. [M−H]$^−$=332.0, RT=2.14 min Acids A9-A15 were prepared from the corresponding ester indicated in the below table using a procedure analogous to that described in either A113 or A114 (indicated in the below table).

| Acid | Procedure | Ester |
|---|---|---|
| 3-Methoxy-5-(2-oxo-pyrrolidin-1-yl)-benzoic acid (A9) | A113 | B9 |
| 3-Propoxy-5-(2-oxo-pyrrolidin-1-yl)-benzoic acid (A10) | A113 | B10 |
| 3-Ethoxy-5-(2-oxo-pyrrolidin-1-yl)-benzoic acid (A11) | A113 | B11 |
| 3-Isopropoxy-5-(2-oxo-pyrrolidin-1-yl)-benzoic acid (A12) | A113 | B12 |
| 3-Pentoxy-5-(2-oxo-pyrrolidin-1-yl)-benzoic acid (A13) | A113 | B13 |
| 3-(2-Methoxy-ethoxy)-5-(2-oxo-pyrrolidin-1-yl)-benzoic acid (A14) | A113 | B14 |
| 3-(3-Hydroxy-propoxy)-5-(2-oxo-pyrrolidin-1-yl)-benzoic acid (A15) | A113 | B15 |

Acid 16

3-(2-Hydroxy-ethoxy)-5-(2-oxo-pyrrolidin-1-yl)-benzoic acid (A16)

Acid 16 was prepared in accordance with an analogous procedure to that described for Ester 15 from 3-(2-benzyloxy-ethoxy)-5-(2-oxo-pyrrolidin-1-yl)-benzoic acid (D40).

Acids A17-A22 and A24-A27 were prepared from the corresponding ester indicated in the below table using a procedure analogous to that described in either A113 or A114 (indicated in the below table).

| Acid | Procedure | Ester |
|---|---|---|
| 3-(3-Methoxy-propoxy)-5-(2-oxo-pyrrolidin-1-yl)-benzoic acid (A17) | A113 | B17 |
| 3-(1,1-Dioxo-1/$^6$-isothiazolidin-2-yl)-5-ethoxy-benzoic acid (A18) | A113 | B18 |
| 3-(1,1-Dioxo-1/$^6$-isothiazolidin-2-yl)-5-isopropoxy-benzoic acid (A19) | A113 | B19 |
| 3-(1,1-Dioxo-1/$^6$-isothiazolidin-2-yl)-5-methoxy-benzoic acid (A20) | A113 | B20 |
| 3-(1,1-Dioxo-1/$^6$-isothiazolidin-2-yl)-5-propoxy-benzoic acid (A21) | A113 | B21 |
| 3-(1,1-Dioxo-1/$^6$-isothiazolidin-2-yl)-5-pentoxy-benzoic acid (A22) | A113 | B22 |
| 3,5-Bis-(2-oxo-pyrrolidin-1-yl)-benzoic acid (A24) | A113 | B24 |
| 4-Chloro-3,5-bis-(2-oxo-pyrrolidin-1-yl)-benzoic acid (A25) | A113 | B25 |
| 4-Methoxy-3,5-bis-(2-oxo-pyrrolidin-1-yl)-benzoic acid (A26) | A113 | B26 |
| 3-Nitro-5-(2-oxo-pyrrolidin-1-yl)-benzoic acid (A27) | A113 | B27 |

Acid 27 (Alternative Procedure)

3-Nitro-5-(2-oxo-pyrrolidin-1-yl)-benzoic acid (A27)

A flask was charged under nitrogen with 3-bromo-5-nitrobenzoic acid (D5) (12.3 g, 50 mmol, 1 equiv), $Cs_2CO_3$ (24.4 g, 75 mmol, 1.5 equiv), tris(dibenzylideneacetone)dipalladium(0) (229 mg, 0.25 mmol, 0.005 equiv), Xantphos (433 mg, 0.75 mmol, 0.015 equiv) and dioxan (120 ml). 2-Pyrrolidin-2-one (5.7 ml, 75 mmol, 1.5 equiv) was then added via syringe and the resulting mixture was stirred at reflux for 60 h then cooled to room temperature and concentrated in vacuo. The residue was diluted with $H_2O$ and 1N aqueous NaOH solution and extracted twice with $Et_2O$. The aqueous phase was then acidified to pH 1 and extracted three times with AcOEt. The combined organic phases were dried over $MgSO_4$ and concentrated in vacuo to give 3-nitro-5-(2-oxo-pyrrolidin-1-yl)-benzoic acid (A27) (9.3 g, 75%) as a pale brown solid.

Acids A28-A74 were prepared from the corresponding ester indicated in the below table using a procedure analogous to that described in either A113 or A114 (indicated in the below table).

| Acid | Procedure | Ester |
|---|---|---|
| 3-(2-Oxo-pyrrolidin-1-yl)-5-piperidin-1-yl-benzoic acid (A28) | A113 | B28 |
| 3-Morpholin-4-yl-5-(2-oxo-pyrrolidin-1-yl)-benzoic acid (A29) | A113 | B29 |
| 3-(2-Oxo-pyrrolidin-1-yl)-5-phenylamino-benzoic acid (A30) | A113 | B30 |
| 3-Ethylamino-5-(2-oxo-pyrrolidin-1-yl)-benzoic acid (A31) | A114 | B31 |
| 3-Methylamino-5-(2-oxo-pyrrolidin-1-yl)-benzoic acid (A32) | A114 | B32 |
| 3-Diethylamino-5-(2-oxo-pyrrolidin-1-yl)-benzoic acid (A33) | A113 | B33 |
| 3-Dimethylamino-5-(2-oxo-pyrrolidin-1-yl)-benzoic acid (A34) | A113 | B34 |
| 3-(2-Oxo-pyrrolidin-1-yl)-5-pyropylamino-benzoic acid (A35) | A113 | B35 |
| 3-Isobutylamino-5-(2-oxo-pyrrolidin-1-yl)-benzoic acid (A36) | A113 | B36 |

-continued

| Acid | Procedure | Ester |
|---|---|---|
| 3-Benzylamino-5-(2-oxo-pyrrolidin-1-yl)-benzoic acid (A37) | A113 | B37 |
| 3-(3-Methyl-butylamino)-5-(2-oxo-pyrrolidin-1-yl)-benzoic acid (A38) | A113 | B38 |
| 3-Pentylamino-5-(2-oxo-pyrrolidin-1-yl)-benzoic acid (A39) | A113 | B39 |
| 3-Butylamino-5-(2-oxo-pyrrolidin-1-yl)-benzoic acid (A40) | A113 | B40 |
| 3-(2,2-Dimethyl-propylamino)-5-(2-oxo-pyrrolidin-1-yl)-benzoic acid (A41) | A113 | B41 |
| 3-(Cyclopropylmethyl-amino)-5-(2-oxo-pyrrolidin-1-yl)-benzoic acid (A42) | A113 | B42 |
| 3-(1-Ethyl-propylamino)-5-(2-oxo-pyrrolidin-1-yl)-benzoic acid (A43) | A113 | B43 |
| 3-Isopropylamino-5-(2-oxo-pyrrolidin-1-yl)-benzoic acid (A44) | A113 | B44 |
| 3-Cyclopentylamino-5-(2-oxo-pyrrolidin-1-yl)-benzoic acid (A45) | A113 | B45 |
| 3-Cyclohexylamino-5-(2-oxo-pyrrolidin-1-yl)-benzoic acid (A46) | A113 | B46 |
| 3-(Acetyl-methyl-amino)-5-(2-oxo-pyrrolidin-1-yl)-benzoic acid (A47) | A113 | B47 |
| 3-(Acetyl-propyl-amino)-5-(2-oxo-pyrrolidin-1-yl)-benzoic acid (A48) | A114 | B48 |
| 3-(Acetyl-isopropyl-amino)-5-(2-oxo-pyrrolidin-1-yl)-benzoic acid (A49) | A114 | B49 |
| 3-Acetylamino-5-(2-oxo-pyrrolidin-1-yl)-benzoic acid (A50) | A113 | B50 |
| 3-(Methanesulfonyl-methyl-amino)-5-(2-oxo-pyrrolidin-1-yl)-benzoic acid (A51) | A113 | B51 |
| 3-(Methanesulfonyl-propyl-amino)-5-(2-oxo-pyrrolidin-1-yl)-benzoic acid (A52) | A114 | B52 |
| 3-Methanesulfonylamino-5-(2-oxo-pyrrolidin-1-yl)-benzoic acid (A53) | A113 | B53 |
| 3-(2-Oxo-piperidin-1-yl)-5-pyrrolidin-1-yl-benzoic acid (A54) | A114 | B54 |
| 3-(2-Oxo-piperidin-1-yl)-5-piperidin-1-yl-benzoic acid (A55) | A114 | B55 |
| 3-Morpholin-4-yl-5-(2-oxo-piperidin-1-yl)-benzoic acid (A56) | A114 | B56 |
| 3-Methylamino-5-(2-oxo-piperidin-1-yl)-benzoic acid (A57) | A114 | B57 |
| 3-Propylamino-5-(2-oxo-piperidin-1-yl)-benzoic acid (A58) | A113 | B58 |
| 3-Ethylamino-5-(2-oxo-piperidin-1-yl)-benzoic acid (A59) | A114 | B59 |
| 3-Diethylamino-5-(2-oxo-piperidin-1-yl)-benzoic acid (A60) | A113 | B60 |
| 3-(1,1-Dioxo-1/$^6$-isothiazolidin-2-yl)-5-morpholin-4-yl-benzoic acid (A61) | A114 | B61 |
| 3-(1,1-Dioxo-1/$^6$-isothiazolidin-2-yl)-5-methylamino-benzoic acid (A62) | A114 | B62 |
| 3-Diethylamino-5-(1,1-dioxo-1/$^6$-isothiazolidin-2-yl)-benzoic acid (A63) | A113 | B63 |
| 3-Benzylamino-5-(1,1-dioxo-1/$^6$-isothiazolidin-2-yl)-benzoic acid (A64) | A113 | B64 |
| 3-Butylamino-5-(1,1-dioxo-1/$^6$-isothiazolidin-2-yl)-benzoic acid (A65) | A113 | B65 |
| 3-(1,1-Dioxo-1/$^6$-isothiazolidin-2-yl)-5-(3-methyl-butylamino)-benzoic acid (A66) | A113 | B66 |
| 3-(1,1-Dioxo-1/$^6$-isothiazolidin-2-yl)-5-phenethylamino-benzoic acid (A67) | A113 | B67 |
| 3-Pentylamino-5-(1,1-dioxo-1/$^6$-isothiazolidin-2-yl)-benzoic acid (A68) | A113 | B68 |
| 3-Propylamino-5-(1,1-dioxo-1/$^6$-isothiazolidin-2-yl)-benzoic acid (A69) | A113 | B69 |
| 3-Ethylamino-5-(1,1-dioxo-1/$^6$-isothiazolidin-2-yl)-benzoic acid (A70) | A113 | B70 |
| 3-(Cyclopropylmethyl-amino)-5-(1,1-dioxo-1/$^6$-isothiazolidin-2-yl)-benzoic acid (A71) | A113 | B71 |
| 3-(1,1-Dioxo-1/$^6$-isothiazolidin-2-yl)-5-isopropylamino-benzoic acid (A72) | A113 | B72 |
| 3-(1,1-Dioxo-1/$^6$-[1,2]thiazinan-2-yl)-5-ethylamino-benzoic acid (A73) | A114 | B73 |
| 3-tert-Butoxy-5-(2-oxo-pyrrolidin-1-yl)-benzoic acid (A74) | A113 | B74 |

Acids A75–A85 were prepared from the corresponding ester indicated in the below table using a procedure analogous to that described in either A113 or A114 (indicated in the below table).

| Acid | Procedure | Ester |
|---|---|---|
| 3-Methoxy-5-(2-oxo-pyrrolidin-1-yl)-benzoic acid (A75) | A114 | B74 |
| 3-Hydroxymethyl-5-(2-oxo-pyrrolidin-1-yl)-benzoic acid (A76) | A113 | B76 |
| 5-(2-Oxo-pyrrolidin-1-yl)-N-propyl-isophthalamic acid (A77) | A113 | B77 |
| N,N-Dimethyl-5-(2-oxo-pyrrolidin-1-yl)-isophthalamic acid (A78) | A113 | B78 |
| N-Methyl-5-(2-oxo-pyrrolidin-1-yl)-isophthalamic acid (A79) | A113 | B79 |
| 5-(2-Oxo-pyrrolidin-1-yl)-N,N-dipropyl-isophthalamic acid (A80) | A113 | B80 |
| 5-(2-Oxo-piperidin-1-yl)-N,N-dipropyl-isophthalamic acid (A81) | A113 | B81 |
| 3-Nitro-5-(2-oxo-piperidin-1-yl)-benzoic acid (A82) | A113 | B82 |
| 3-(1,1-Dioxo-1/$^6$-isothiazolidin-2-yl)-5-fluoromethyl-benzoic acid (A83) | A113 | B83 |
| 3-Dimethylaminomethyl-5-(dioxo-1/$^6$-isothiazolidin-2-yl)-benzoic acid (A84) | A113 | B84 |
| 3-Azidomethyl-5-(1,1-dioxo-1/$^6$-isothiazolidin-2-yl)-benzoic acid (A85) | A113 | B85 |

Acid 86

3-(1,1-Dioxo-1/$^6$-isothiazolidin-2-yl)-5-methoxymethyl-benzoic acid (A86)

A suspension of 3-(1,1-dioxo-1/$^6$-isothiazolidin-2-yl)-5-methanesulfonyloxymethyl-benzoic acid methyl ester (D85) (200 mg, 0.55 mmol, 1 equiv) in MeOH (100 ml) was treated with 2N aqueous NaOH solution (10 ml). The resulting mixture was stirred for 4 h at room temperature and then concentrated in vacuo. The residue was dissolved in AcOEt (100 ml) and the resulting solution was washed with 2N aqueous HCl solution (50 ml), dried over MgSO$_4$ and concentrated in vacuo. The residue was triturated with Et$_2$O to give 3-(1,1-dioxo-1/$^6$-isothiazolidin-2-yl)-5-methoxymethyl-benzoic acid (A86) (140 mg, 89%) as a white solid.

Acid 87

3-(1,1-Dioxo-1/$^6$-isothiazolidin-2-yl)-5-ethoxymethyl-benzoic acid (A87)

A suspension of 3-(1,1-dioxo-1/$^6$-isothiazolidin-2-yl)-5-methanesulfonyloxymethyl-benzoic acid methyl ester (D85) (200 mg, 0.55 mmol, 1 equiv) in EtOH (100 ml) was treated with 2N aqueous NaOH solution (10 ml). The resulting mixture was stirred for 4 h at room temperature and then concentrated in vacuo. The residue was dissolved in AcOEt (100 ml) and the resulting solution was washed with 2N aqueous HCl solution (50 ml), dried over MgSO$_4$ and concentrated in vacuo. The residue was triturated with Et$_2$O to give 3-(1,1-dioxo-1/$^6$-isothiazolidin-2-yl)-5-ethoxymethyl-benzoic acid (A87) (100 mg, 61%) as a white solid.

Acids A88-95 and A100-A102 were prepared from the corresponding ester indicated in the below table using a procedure analogous to that described in either A113 or A114 (indicated in the below table).

| Acid | Procedure | Ester |
| --- | --- | --- |
| 3-(1,1-Dioxo-1/$^6$-isothiazolidin-2-yl)-5-vinyl-benzoic acid (A88) | A113 | B88 |
| 3-(1,1-Dioxo-1/$^6$-isothiazolidin-2-yl)-5-(Z/E)-propenyl-benzoic acid (A89) | A113 | B89 |
| 3-(1,1-Dioxo-1/$^6$-isothiazolidin-2-yl)-5-(Z/E)-butenyl-benzoic acid (A90) | A113 | B90 |
| 3-(1,1-Dioxo-1/$^6$-isothiazolidin-2-yl)-5-(2-methyl-propenyl)-benzoic acid (A91) | A113 | B91 |
| 5-(1,1-Dioxo-1/$^6$-isothiazolidin-2-yl)-isophthalamic acid (A92) | A113 | B92 |
| 3-Cyano-5-(1,1-dioxo-1/$^6$-isothiazolidin-2-yl)-benzoic acid (A93) | A113 | B93 |
| 5-(1,1-Dioxo-1/$^6$-isothiazolidin-2-yl)-N,N-dipropyl-isophthalamic acid (A94) | A113 | B94 |
| 5-(1,1-Dioxo-1/$^6$-[1,2]thiazinan-2-yl)-N,N-dipropyl-isophthalamic acid (A95) | A113 | B95 |
| 2-Fluoro-3-(2-oxo-pyrrolidin-1-yl)-5-trifluoromethyl-benzoic acid (A100) | A113 | B100 |
| 3-(2-Oxo-pyrrolidin-1-yl)-(2-methyl-propenyl)-5-benzoic acid (A101) | A113 | B101 |
| 3-(2-Oxo-pyrrolidin-1-yl)-5-((E)-styryl)-benzoic acid (A102) | A113 | B102 |

| Acid | Alkene | [M + H]$^+$ | RT (min) |
| --- | --- | --- | --- |
| 3-(1,1-Dioxo-1/$^6$-[1,2]thiazinan-2-yl)-5-phenethyl-benzoic acid methyl ester (A103) | A102 | 310.0 | 3.12 |
| 3-Isobutyl-5-(2-Oxo-pyrrolidin-1-yl)-benzoic acid (A105) | A101 | 262.1 | 2.98 |

Acids A104, A106-A109 and A111-A112 were prepared from the corresponding ester indicated in the below table using a procedure analogous to that described in either A113 or A114 (indicated in the below table).

| Acid | Procedure | Ester |
| --- | --- | --- |
| 3-Isopropyl-5-(2-oxo-pyrrolidin-1-yl)-benzoic acid (A104) | A113 | B104 |
| 3-(2-Oxo-pyrrolidin-1-yl)-5-propyl-benzoic acid (A106) | A113 | B106 |
| 3-Cyclopentyl-5-(2-oxo-pyrrolidin-1-yl)-benzoic acid (A107) | A113 | B107 |
| 3-Cyclohexyl-5-(2-oxo-pyrrolidin-1-yl)-benzoic acid (A108) | A113 | B108 |
| 3-Ethynyl-5-(2-oxo-pyrrolidin-1-yl)-benzoic acid (A109) | A114 | B109 |
| 3-(1,1-Dioxo-1/$^6$-isothiazolidin-2-yl)-5-ethynyl-benzoic acid (A111) | A114 | B111 |
| 3-(1,1-Dioxo-1/$^6$-[1,2]thiazinan-2-yl)-5-propyl-benzoic acid (A112) | A114 | B112 |

Acid 113

3-(2-Oxo-pyrrolidin-1-yl)-5-pyrrolidin-1-yl-benzoic acid (A113)

To a solution 3-(2-oxo-pyrrolidin-1-yl)-5-pyrrolidin-1-yl-benzoic acid methyl ester (B113) (85 mg, 0.29 mmol, 11 equiv) in THF (5 ml) was added 1N aqueous NaOH solution The following compounds were prepared from the corresponding alkene in an analogous manner to the process described for 3-(2-oxo-piperidin-1-yl)-5-propyl-benzoic acid tert-butyl ester (B116):

(0.60 ml, 0.6 mmol, 2 equiv). The resulting mixture was stirred for 14 h then concentrated in vacuo. The residue was diluted with H$_2$O and extracted with Et$_2$O. The aqueous layer was acidified using 2N aqueous HCl solution and the white precipitate formed was extracted twice with AcOEt. The combined organic solutions were dried over MgSO$_4$ and concentrated in vacuo to give 3-(2-oxo-pyrrolidin-1-yl)-5-pyrrolidin-1-yl-benzoic acid (A113) (77 mg, 95%) as a white solid. [M+H]$^+$=275.0, RT=2.72 min Acid 114

3-(1,1-Dioxo-1/$^6$-isothiazolidin-2-yl)-5-pyrrolidin-1-yl-benzoic acid (A114)

A solution of 3-(1,1-dioxo-1/$^6$-isothiazolidin-2-yl)-5-pyrrolidin-1-yl-benzoic acid tert-butyl ester (B114) (106 mg, 0.29 mmol, 1 equiv) in DCM/TFA (1/1, 4 ml) was stirred at room temperature for 2 h then concentrated in vacuo. Traces of solvent were removed by azeotroping with toluene. The residue was triturated with Et$_2$O to give 3-(1,1-dioxo-1/$^6$-isothiazolidin-2-yl)-5-pyrrolidin-1-yl-benzoic acid (A114) (86 mg, 96%) as a pale brown solid. [M+H]$^+$=311.1, RT=2.75 min Acid 115

3-(4-Methyl-piperazin-1-yl)-5-(2-oxo-pyrrolidin-1-yl)-benzoic acid (A115)

To a solution 3-(4-methyl-piperazin-1-yl)-5-(2-oxo-pyrrolidin-1-yl)-benzoic acid methyl ester (B115) (296 mg, 0.93 mmol, 1 equiv) in THF (10 ml) was added 1N aqueous NaOH solution (1.8 ml, 1.8 mmol, 2 equiv). The resulting mixture was stirred for 14 h then concentrated in vacuo. The residual solid was extracted thoroughly with MeOH and the extracts were concentrated in vacuo to give 3-(4-methyl-piperazin-1-yl)-5-(2-oxo-pyrrolidin-1-yl)-benzoic acid (A115) (390 mg, 138%) as an off white solid. [M+H]$^+$=304.0, RT=1.64 min Acid 116

3-(2-Oxo-piperidin-1-yl)-5-propyl-benzoic acid (A116)

Acid 116 was prepared from Ester 116 in an analogous manner to the process described for Acid 114.

A117-A136, A138A154 and A156-A176 were prepared from esters B117-B136, B138-B154 and B156-B176, respectively using a procedure analogous to that described in either A113 or A114 (indicated in the below table).

| Acid | Procedure | [M + H]+ | RT (min) |
|---|---|---|---|
| 3-(1,1-Dioxido-6,7-dihydro-1,2-thiazepin-2(3H)-yl)-5-propylbenzoic acid (A117) | A113 | 308.0 ([M − H]$^−$) | 2.66 |
| 5-(Ethylamino)-2-fluoro-3-(2-oxo-1-pyrrolidinyl)benzoic acid (A118) | A113 | 267.2 | 1.62 |
| 3-(1,1-Dioxidotetrahydro-2H-1,2-thiazin-2-yl)-5-(ethylamino)-2-fluorobenzoic acid (A119) | A113 | 317.2 | 2.23 |
| 2-Fluoro-3-(2-oxo-1-pyrrolidinyl)-5-propylbenzoic acid (A120) | A113 | 266.2 | 2.71 |
| 3-(2-Oxo-5-phenyl-1-piperidinyl)-5-propylbenzoic acid (A121) | A114 | 338.2 | 3.37 |
| 3-(1,1-Dioxido-2-isothiazolidinyl)-5-(ethylamino)-2-fluorobenzoic acid (A122) | A113 | 303.1 | 1.98 |
| 3-(1,1-Dioxido-4-phenyltetrahydro-2H-1,2-thiazin-2-yl)-5-nitrobenzoic acid (A123) | A113 | 394.1 | 3.47 |
| 3-Amino-5-(1,1-dioxido-4-phenyltetrahydro-2H-1,2-thiazin-2-yl)benzoic acid (A124) | A113 | 347.2 | 2.83 |
| 3-(1,1-Dioxido-4-phenyltetrahydro-2H-1,2-thiazin-2-yl)-5-(ethylamino)benzoic acid (A125) | A113 | 375.2 | 3.17 |
| 3-Cyclopentyl-5-(1,1-dioxidotetrahydro-2H-1,2-thiazin-2-yl)benzoic acid (A126) | A113 | 324.0 | 0.88 |
| 3-(1,1-Dioxidotetrahydro-2H-1,2-thiazin-2-yl)-5-[(1-methylethyl)amino]benzoic acid (A127) | A113 | 313.2 | 2.38 |
| 3-[Ethyl(methyl)amino]-5-(2-oxo-1-pyrrolidinyl)benzoic acid (A128) | A114 | 263.3 | 2.15 |
| 3-(Ethylamino)-4-methyl-5-(2-oxo-1-pyrrolidinyl)benzoic acid (A129) | A113 | 263.1 | 2.30 |
| 3-(1,1-Dioxido-2-isothiazolidinyl)-5-(ethylamino)-4-methylbenzoic acid (A130) | A113 | 299.0 | 2.44 |
| 3-(1,1-Dioxidotetrahydro-2H-1,2-thiazin-2-yl)-5-(ethylamino)-4-methylbenzoic acid (A131) | A113 | 313.1 | 2.59 |
| 3-(1,1-Dioxidotetrahydro-2H-1,2-thiazin-2-yl)-5-(ethylamino)-4-(methyloxy)benzoic acid (A132) | A113 | 329.1 | 2.57 |
| 3-(Ethylamino)-4-(methyloxy)-5-(2-oxo-1-pyrrolidinyl)benzoic acid (A133) | A113 | 279.1 | 2.34 |
| 3-(1,1-Dioxido-2-isothiazolidinyl)-5-(ethylamino)-4-(methyloxy)benzoic acid (A134) | A113 | 315.1 | 2.45 |
| 3-(Diethylamino)-5-(1,1-dioxidotetrahydro-2H-1,2-thiazin-2-yl)-4-methylbenzoic acid (A135) | A113 | 341.1 | 2.05 |
| 3-(1,1-Dioxidotetrahydro-2H-1,2-thiazin-2-yl)-4-(methyloxy)-5-[(1E/Z)-1-propen-1-yl]benzoic acid (A136) | A113 | 326.0 | 2.87 |
| 3-(1,1-Dioxido-2-isothiazolidinyl)-5-(2-oxo-1-pyrrolidinyl)benzoic acid (A138) | A113 | 325.3 | 2.10 |
| 3-(1,1-Dioxidotetrahydro-2H-1,2-thiazin-2-yl)-5-(ethylamino)-2-(methyloxy)benzoic acid (A139) | A113 | 329.2 | 2.02 |

-continued

| Acid | Procedure | [M + H]+ | RT (min) |
|---|---|---|---|
| 1-Ethyl-4-(2-oxo-1-pyrrolidinyl)-1H-indole-6-carboxylic acid (A140) | A113 | 273.0 | 2.53 |
| 3-Ethyl-7-(2-oxo-1-pyrrolidinyl)-1H-indole-5-carboxylic acid (A141) | A113 | 273.1 | 2.68 |
| 3-Ethyl-1-methyl-7-(2-oxo-1-pyrrolidinyl)-1H-indole-5-carboxylic acid (A142) | A113 | 287.4 | 2.43 |
| 4-(1,1-Dioxido-2-isothiazolidinyl)-1-ethyl-1H-indole-6-carboxylic acid (A143) | A113 | 309.3 | 2.40 |
| 7-(1,1-Dioxido-2-isothiazolidinyl)-3-ethyl-1H-indole-5-carboxylic acid (A144) | A113 | 309.0 | 2.79 |
| 4-(1,1-Dioxidotetrahydro-2H-1,2-thiazin-2-yl)-1-ethyl-2,3-dihydro-1H-indole-6-carboxylic acid (A145) | A113 | 325.3 | 2.69 |
| 7-(1,1-Dioxido-2-isothiazolidinyl)-3-ethyl-1-methyl-1H-indole-5-carboxylic acid (A146) | A113 | | |
| 4-(1,1-Dioxidotetrahydro-2H-1,2-thiazin-2-yl)-1-ethyl-1H-indole-6-carboxylic acid (A147) | A113 | | |
| 7-(1,1-Dioxidotetrahydro-2H-1,2-thiazin-2-yl)-3-ethyl-1H-indole-5-carboxylic acid (A148) | A113 | 340.4 | 2.68 |
| 1-Ethyl-4-(2-oxo-1-pyrrolidinyl)-1H-benzimidazole-6-carboxylic acid (A149) | A113 | 274.4 | 1.55 |
| 4-(1,1-Dioxido-2-isothiazolidinyl)-1-ethyl-1H-benzimidazole-6-carboxylic acid (A150) | A113 | 310.2 | 1.98 |
| 4-(1,1-Dioxidotetrahydro-2H-1,2-thiazin-2-yl)-1-ethyl-1H-benzimidazole-6-carboxylic acid (A151) | A113 | 340.4 | 2.68 |
| 1-Ethyl-4-(2-oxo-1-pyrrolidinyl)-1H-indazole-6-carboxylic acid (A152) | A113 | 274.2 | 2.10 |
| 4-(1,1-Dioxido-2-isothiazolidinyl)-1-ethyl-1H-indazole-6-carboxylic acid (A153) | A113 | 310.3 | 2.15 |
| 4-(2-Oxo-1-pyrrolidinyl)-1H-indole-6-carboxylic acid (A154) | A113 | | |
| 1-Methyl-4-(2-oxo-1-pyrrolidinyl)-1H-indole-6-carboxylic acid (A156) | A113 | 259.4 | 2.20 |
| 1-Butyl-4-(2-oxo-1-pyrrolidinyl)-1H-indole-6-carboxylic acid (A157) | A113 | 301.0 | 2.88 |
| 4-(2-Oxo-1-pyrrolidinyl)-1-pentyl-1H-indole-6-carboxylic acid (A158) | A113 | 315.1 | 3.06 |
| 3-Methyl-7-(2-oxo-1-pyrrolidinyl)-1-benzofuran-5-carboxylic acid (A159) | A113 | 260.0 | 2.59 |
| 3-Methyl-7-(2-oxo-1-pyrrolidinyl)-1H-indole-5-carboxylic acid (A160) | A113 | 259.1 | 2.48 |
| 3-(1-Methylethyl)-7-(2-oxo-1-pyrrolidinyl)-1H-indole-5-carboxylic acid (A161) | A113 | 287.1 | 2.82 |
| 1-Methyl-3-(1-methylethyl)-7-(2-oxo-1-pyrrolidinyl)-1H-indole-5-carboxylic acid (A162) | A113 | 301.2 | 2.84 |
| 3-Ethyl-7-(2-oxo-1-pyrrolidinyl)-1-benzofuran-5-carboxylic acid (A163) | A113 | 274.1 | 2.81 |
| 4-Methyl-8-(2-oxo-1-pyrrolidinyl)-3,4-dihydro-2H-chromene-6-carboxylic acid (A164) | A113 | | |
| 3-Ethyl-7-(2-oxo-1-piperidinyl)-1H-indole-5-carboxylic acid (A165) | A113 | 287.4 | 2.56 |
| 3-Ethyl-7-(2-oxo-4-phenyl-1-pyrrolidinyl)-1H-indole-5-carboxylic acid (A166) | A113 | 349.2 | 3.21 |
| 1-Ethyl-4-(2-oxo-1-pyrrolidinyl)-1H-1,2,3-benzotriazole-6-carboxylic acid (A167) | A113 | 275.2 | 2.38 |
| 3-(1,1-Dioxidotetrahydro-2H-1,2-thiazin-2-yl)-5-[(1-methylethyl)oxy]benzoic acid (A168) | A113 | 314.15 | 0.77 |
| 3-Cyclopentyl-5-(1,1-dioxido-2-isothiazolidinyl)benzoic acid (A169) | A113 | 310.0 | 0.83 |
| 3-(1,1-Dioxidotetrahydro-2H-1,2-thiazin-2-yl)-5-(ethyloxy)benzoic acid (A170) | A113 | 300.12 | 0.73 |
| 4-Ethyl-8-(2-oxo-1-pyrrolidinyl)-1,2,3,4-tetrahydro-6-quinoxalinecarboxylic acid (A171) | A113 | 290.5 | 2.00 |
| 8-(1,1-Dioxido-2-isothiazolidinyl)-4-ethyl-1,2,3,4-tetrahydro-6-quinoxalinecarboxylic acid (A172) | A113 | 326.2 | 2.00 |
| 3-(1,1-Dioxidotetrahydro-2H-1,2-thiazin-2-yl)-2-fluoro-5-propylbenzoic acid (A173) | A113 | 316.1 | 2.49 |
| 3-(1,1-Dioxido-2-isothiazolidinyl)-2-fluoro-5-propylbenzoic acid (A174) | A113 | 302.1 | 2.48 |
| 3-(1,1-Dioxidotetrahydro-2H-1,2-thiazin-2-yl)-2-fluoro-5-[(1-methylethyl)amino]benzoic acid (A175) | A113 | 316.2 | 2.30 |
| 5-Cyclopentyl-3-(1,1-dioxidotetrahydro-2H-1,2-thiazin-2-yl)-2-fluorobenzoic acid (A176) | A113 | 342.2 | 2.89 |

Acid 137

3-(1,1-Dioxidotetrahydro-2H-1,2-thiazin-2-yl)-4-(methyloxy)-5-propylbenzoic acid (A137)

3-(1,1-Dioxidotetrahydro-2H-1,2-thiazin-2-yl)-4-(methyloxy)-5-propylbenzoic acid (A137) was prepared from 3-(1,1-dioxidotetrahydro-2H-1,2-thiazin-2-yl)-4-(methyloxy)-5-[(1E)-1-propen-1-yl]benzoic acid (A136) in an analogous manner to the process described for 3-(2-oxo-piperidin-1-yl)-5-propyl-benzoic acid tert-butyl ester (B116).

Acid 155

4-(1,1-Dioxidotetrahydro-2H-1,2-thiazin-2-yl)-1H-indole-6-carboxylic acid (A155)

To a solution of methyl 4-amino-1H-indole-6-carboxylate (D201) (1.0 g, 5.3 mmol, 1 equiv) in $CH_2Cl_2$ (50 ml) were added pyridine (0.55 g, 6.5 mmol, 1.2 equiv), 4-chloro-1-butanesulfonyl chloride (1.14 g, 6 mmol, 1.1 equiv) and DMAP (300 mg, 2.45 mmol, 0.5 equiv) and the resulting mixture was stirred at room temperature for 5 h. $NEt_3$ (1 ml, 7.2 mmol, 1.3 equiv) was added and the resulting solution stirred for 2 h then diluted with AcOEt, washed with a 2N aqueous solution, a saturated aqueous $NaHCO_3$ solution, dried over $MgSO_4$ and concentrated in vacuo. The residue was dissolved in MeOH (20 ml) and treated with a 2N aqueous NaOH solution (10 ml, 20 mmol, excess). The resulting solution was stirred at room temperature for 15 h then most of the MeOH was removed in vacuo. The residue was partitioned between AcOEt and a 2N aqueous HCl solution. The two layers were separated and the organic phase was dried over $MgSO_4$ and concentrated in vacuo. Purification of the residue by flash chromatography on silica gel ($CH_2Cl_2$/MeOH: 9/1) gave 4-(1,1-dioxidotetrahydro-2H-1,2-thiazin-2-yl)-1H-indole-6-carboxylic acid (A155) (320 mg, 20%) as a pale pink solid. [M+H]=295.0, RT=1.90 min.

Preparation of Amines

Amine 1 (C1)

(2R,3S)-3-Amino-1-cyclohexylamino-4-phenyl-butan-2-ol di-hydrogen chloride (C1)

((1S,2R)-1-Benzyl-3-cyclohexylamino-2-hydroxy-propyl)-carbamic acid tert-butyl ester (BOC-protected amine 1 (H1)) (9 g, 25 mmol, 1 equiv) was dissolved in MeOH (70 ml) and then a 4M solution of HCl in dioxane (60 ml, excess) was added. The resulting mixture was stirred for 3 h at room temperature and then the solvents were removed by evaporation in vacuo. The resulting residue was washed with AcOEt and then with $Et_2O$ before drying in vacuo to give the title compound (C1) as a white solid (7.4 g, 88%). $[M+H]^+$ 335.31.

Amines C2-C20, C24-C33 and C36 were prepared from their corresponding BOC-protected amines (H2-H20, H24-H33 and H36, respectively) in an analogous manner to that described in C1.

For amines C8-C19, C25-C26 and C29-C32, the 4M HCl in dioxane was replaced with 3 equivalents of p-toluene sulphonic acid to yield the tosic acid salts.

| Amine | $[M + H]^+$ | RT (min) |
|---|---|---|
| (2R,3S)-3-Amino-1-cyclobutylamino-4-phenyl-butan-2-ol di-hydrochloride (C2) | 235.1 | 0.32 |
| (2R,3S)-3-Amino-1-isobutylamino-4-phenyl-butan-2-ol di-hydrochloride (C3) | 237.1 | 0.86 |
| (2R,3S)-3-Amino-4-phenyl-1-propylamino-butan-2-ol di-hydrochloride (C4) | 223.1 | 0.43 |
| (2R,3S)-3-Amino-4-phenyl-1-(1,1,5-trimethyl-hexylamino)-butan-2-ol di-hydrochloride (C5) | 307.2 | 2.22 |
| (S)-2-((2R,3S)-3-Amino-2-hydroxy-4-phenyl-butylamino)-N-cyclohexyl-propionamide di-hydrochloride (C6) | F899 | — |
| (2R,3S)-3-Amino-1-[(R)-1-(3-methoxy-phenyl)-ethylamino]-4-phenyl-butan-2-ol di-hydrochloride (C7) | — | — |
| (2R,3S)-3-Amino-1-(1-methyl-1-phenyl-ethylamino)-4-phenyl-butan-2-ol di-tosylate (C8) | — | — |
| (2R,3S)-3-Amino-1-(3-methyl-butylamino)-4-phenyl-butan-2-ol di-tosylate (C9) | — | — |
| (2R,3S)-3-Amino-1-tert-butylamino-4-phenyl-butan-2-ol di-tosylate (C10) | — | — |
| (2R,3S)-3-Amino-4-phenyl-1-(3-trifluoromethoxy-benzylamino)-butan-2-ol di-tosylate (C11) | — | — |
| (2R,3S)-3-Amino-1-(2,2,3,3,3-pentafluoro-propylamino)-4-phenyl-butan-2-ol di-tosylate (C12) | — | — |
| (2R,3S)-3-Amino-1-(2,2,3,3,4,4,4-heptafluoro-butylamino)-4-phenyl-butan-2-ol di-tosylate (C13) | 362 | 2.9 |
| (2R,3S)-3-Amino-1-(3-methoxy-benzylamino)-4-phenyl-butan-2-ol di-tosylate (C14) | — | — |
| (2R,3S)-3-Amino-1-[1-(3-methoxy-phenyl)-1-methyl-ethylamino]-4-phenyl-butan-2-ol di-tosylate (C15) | 329.1 | 2.05 |
| (2R,3S)-3-Amino-4-phenyl-1-[3-(2,2,2-trifluoro-ethyl)-benzylamino]-butan-2-ol di-tosylate (C16) | — | — |
| (2R,3S)-3-Amino-1-[(S)-1-(3-methoxy-phenyl)-ethylamino]-4-phenyl-butan-2-ol di-tosylate (C17) | — | — |
| (2R,3S)-3-Amino-1-[(S)-1-(3-methoxy-phenyl)-ethylamino]-4-phenyl-butan-2-ol di-tosylate (C18) | — | — |
| (2R,3S)-3-Amino-1-(5-methyl-hexylamino)-4-phenyl-butan-2-ol di-tosylate (C19) | — | — |

-continued

| Amine | [M + H]+ | RT (min) |
|---|---|---|
| (2R,3S)-3-Amino-1-(1,5-dimethyl-hexylamino)-4-phenyl-butan-2-ol di-hydrochloride (C20) | 293.1 | 2.04 |
| (2R,3S)-3-Amino-1-ethylamino-4-phenyl-butan-2-ol di-hydrochloride (C24) | — | — |
| (2R,3S)-3-Amino-1-(bis-trifluoromethyl-benzylamino)-4-phenyl-butan-2-ol di-tosylate (C25) | — | — |
| (2R,3S)-3-Amino-1-cyclopropylamino-4-phenyl-butan-2-ol di-tosylate (C26) | — | — |
| (2R,3S)-3-Amino-1-(4-methoxy-benzylamino)-4-phenyl-butan-2-ol di-hydrochloride (C27) | — | — |
| (2R,3S)-3-Amino-1-isopropylamino-4-phenyl-butan-2-ol di-hydrochloride (C28) | — | — |
| (2R,3S)-3-Amino-1-(2-methoxy-benzylamino)-4-phenyl-butan-2-ol di-tosylate (C29) | 301.1 | 1.7 |
| (2R,3S)-3-Amino-4-phenyl-1-((S)-1-phenyl-ethylamino)-butan-2-ol di-tosylate (C30) | — | — |
| (2R,3S)-3-Amino-4-phenyl-1-((R)-1-phenyl-ethylamino)-butan-2-ol di-tosylate (C31) | — | — |
| (2R,3S)-3-Amino-1-(4-methyl-pentylamino)-4-phenyl-butan-2-ol di-tosylate (C32) | — | — |
| (R)-2-((2R,3S)-3-Amino-2-hydroxy-4-phenyl-butylamino)-3-hydroxy-hexanoic acid isobutyl-amide di-hydrochloride (C33) | — | — |
| (S)-2-((2R,3S)-3-Amino-2-hydroxy-4-phenyl-butylamino)-hexanoic acid isobutyl-amide di-hydrochloride (C36) | — | — |

Amines C40-C114 were prepared from their corresponding BOC-protected amines H40-H114, respectively) in an analogous manner to that described in C1.

| Amine | [M + H]+ | RT (min) |
|---|---|---|
| (2R,3S)-3-amino-1-({1-methyl-1-[3-(trifluoromethyl)phenyl]ethyl}amino)-4-phenyl-2-butanol di-tosylate (C40) | 367.2 | 2.44 |
| (2R,3S)-3-amino-1-({1-[3-(methyloxy)phenyl]cyclohexyl}amino)-4-phenyl-2-butanol di-hydrochloride (C41) | | |
| (2R,3S)-3-amino-1-{[(1-methyl-1H-pyrazol-4-yl)methyl]amino}-4-phenyl-2-butanol di-tosylate (C42) | | |
| (2R,3S)-3-amino-4-phenyl-1-(tetrahydro-2H-pyran-4-ylamino)-2-butanol di-tosylate (C43) | | |
| (2R,3S)-3-amino-1-[(3,3-dimethylbutyl)amino]-4-phenyl-2-butanol di-tosylate (C44) | 265.3 | 1.52 |
| (2R,3S)-3-amino-4-phenyl-1-[(1,1,3,3-tetramethylbutyl)amino]-2-butanol di-tosylate (C45) | 293.3 | 1.76 |
| (2R,3S)-3-amino-1-[(1,3-dimethylbutyl)amino]-4-phenyl-2-butanol di-tosylate (C46) | 265.3 | 1.53 |
| (2R,3S)-3-amino-1-({[4-fluoro-3-(trifluoromethyl)phenyl]methyl}amino)-4-phenyl-2-butanol di-tosylate (C47) | 357.3 | 1.79 |
| (2R,3S)-3-amino-1-[(1,1-dimethylhexyl)amino]-4-phenyl-2-butanol di-tosylate (C48) | 293.2 | 2.06 |
| (2R,3S)-3-amino-1-({[2-methyl-5-(trifluoromethyl)phenyl]methyl}amino)-4-phenyl-2-butanol di-tosylate (C49) | 353.1 | 2.09 |
| (2R,3S)-3-amino-1-[(1S)-2,3-dihydro-1H-inden-1-ylamino]-4-phenyl-2-butanol di-tosylate (C50) | | |
| (1S,2R)-1-{[(2R,3S)-3-amino-2-hydroxy-4-phenylbutyl]amino}-2,3-dihydro-1H-inden-2-ol di-tosylate (C51) | 313.1 | 1.83 |
| (2R,3S)-3-amino-1-{[6-(methyloxy)-2,3-dihydro-1H-inden-1-yl]amino}-4-phenyl-2-butanol di-tosylate (C52) | 327.5 | 1.82 |
| (1R,2S)-1-{[(2R,3S)-3-amino-2-hydroxy-4-phenylbutyl]amino}-2,3-dihydro-1H-inden-2-ol di-tosylate (C53) | 313.4 | 1.56 |
| (2R,3S)-3-amino-1-({1,1-dimethyl-2-[(2-methylpropyl)thio]ethyl}amino)-4-phenyl-2-butanol di-tosylate (C54) | | |
| (2R,3S)-3-amino-1-{[1,1-dimethyl-2-(phenyloxy)ethyl]amino}-4-phenyl-2-butanol di-tosylate (C55) | | |
| (2R,3S)-3-amino-1-({1,1-dimethyl-2-[(phenylmethyl)oxy]ethyl}amino)-4-phenyl-2-butanol di-tosylate (C56) | 343.5 | 1.92 |
| (2R,3S)-3-amino-1-{[3-(methyloxy)phenyl]amino}-4-phenyl-2-butanol di-tosylate (C57) | 287.4 | 2.11 |
| (2R,3S)-3-amino-4-phenyl-1-({2-[3-(trifluoromethyl)phenyl]ethyl}amino)-2-butanol di-tosylate (C58) | 353.4 | 2.00 |
| (2R,3S)-3-amino-1-[(1,1-dimethyl-2-phenylethyl)amino]-4-phenyl-2-butanol di-tosylate (C59) | 313.5 | 1.98 |

-continued

| Amine | [M + H]+ | RT (min) |
|---|---|---|
| (2R,3S)-3-amino-1-{[2-(1-naphthalenyl)ethyl]amino}-4-phenyl-2-butanol di-tosylate (C60) | 335.4 | 2.04 |
| (2R,3S)-3-amino-1-({1,1-dimethyl-2-[3-(methyloxy)phenyl]ethyl}amino)-4-phenyl-2-butanol di-tosylate (C61) | 343.3 | 1.93 |
| (2R,3S)-3-amino-4-phenyl-1-(phenylamino)-2-butanol di-tosylate (C62) | 257.4 | 2.06 |
| (2R,3S)-3-amino-1-({1-[3-(methyloxy)phenyl]cyclopropyl}amino)-4-phenyl-2-butanol di-tosylate (C63) | 327.5 | 1.90 |
| (2R,3S)-3-amino-1-[(cyclohexylmethyl)amino]-4-phenyl-2-butanol di-tosylate (C64) | | |
| (2R,3S)-3-amino-4-phenyl-1-[(tetrahydro-2H-pyran-4-ylmethyl)amino]-2-butanol di-tosylate (C65) | | |
| (2R,3S)-3-amino-4-phenyl-1-(tetrahydro-2H-thiopyran-4-ylamino)-2-butanol (C66) | | |
| (2R,3S)-3-amino-1-[(1-methylpropyl)amino]-4-phenyl-2-butanol di-tosylate (C67) | — | |
| (2R,3S)-3-amino-1-{[4-(1,1-dimethylethyl)cyclohexyl]amino}-4-phenyl-2-butanol di-tosylate (C68) | — | |
| (2R,3S)-3-amino-1-[(1-ethylcyclobutyl)amino]-4-phenyl-2-butanol di-hydrochloride (C69) | — | |
| (2R,3S)-3-amino-1-({1,1-dimethyl-2-[(2-methylpropyl)oxy]ethyl}amino)-4-phenyl-2-butanol di-tosylate (C70) | — | |
| (2R,3S)-3-amino-1-({1,1-dimethyl-2-[(2-methyl-2-propen-1-yl)oxy]ethyl}amino)-4-phenyl-2-butanol di-tosylate (C71) | | |
| (2R,3S)-3-amino-1-[(1R)-2,3-dihydro-1H-inden-1-ylamino]-4-phenyl-2-butanol di-tosylate (C72) | 577.2 | 2.67 |
| (2R,3S)-3-amino-1-{[1-(4-methylpentyl)cyclopropyl]amino}-4-phenyl-2-butanol di-hydrochloride (C73) | | |
| (2R,3S)-3-amino-1-[(1-ethylcyclopropyl)amino]-4-phenyl-2-butanol di-hydrochloride (C74) | | |
| (2R,3S)-3-amino-1-[(1-ethylcyclopropyl)amino]-4-phenyl-2-butanol di-hydrochloride (C75) | | |
| (2R,3S)-3-amino-1-(butylamino)-4-phenyl-2-butanol di-hydrochloride (C76) | | |
| (2R,3S)-3-amino-4-phenyl-1-[(1-propylcyclopropyl)amino]-2-butanol di-hydrochloride (C77) | | |
| (2R,3S)-3-amino-1-{[1-(3-methylbutyl)cyclopropyl]amino}-4-phenyl-2-butanol di-hydrochloride (C78) | | |
| (2R,3S)-3-amino-1-{[1-(2-methylpropyl)cyclopropyl]amino}-4-phenyl-2-butanol di-hydrochloride (C79) | | |
| (2R,3S)-3-amino-1-({1-[(3-chlorophenyl)methyl]cyclopropyl}amino)-4-phenyl-2-butanol di-hydrochloride (C80) | | |
| (2R,3S)-3-amino-1-[(1-methylcyclohexyl)amino]-4-phenyl-2-butanol di-hydrochloride (C81) | | |
| (2R,3S)-3-amino-1-[(2S)-bicyclo[2.2.1]hept-2-ylamino]-4-phenyl-2-butanol di-hydrochloride (C82) | | |
| (2R,3S)-3-amino-1-[(4,4-dimethylcyclohexyl)amino]-4-phenyl-2-butanol di-hydrochloride (C83) | | |
| (2R,3S)-3-amino-4-phenyl-1-{[(1R)-1,2,2-trimethylpropyl]amino}-2-butanol di-hydrochloride (C84) | | |
| (2R,3S)-3-amino-4-phenyl-1-{[(1S)-1,2,2-trimethylpropyl]amino}-2-butanol di-hydrochloride (C85) | | |
| (2R,3S)-3-amino-1-[(2,2-dimethylcyclohexyl)amino]-4-phenyl-2-butanol di-hydrochloride (C86) | | |
| (2R,3S)-3-amino-1-(pentylamino)-4-phenyl-2-butanol (C87) | | |
| (2R,3S)-3-amino-1-(hexylamino)-4-phenyl-2-butanol di-hydrochloride (C88) | | |
| (2R,3S)-3-amino-1-[(3,3-dimethylbutyl)amino]-4-phenyl-2-butanol di-hydrochloride (C89) | | |
| (2R,3S)-3-amino-1-[(1,1-dimethylpropyl)amino]-4-phenyl-2-butanol di-hydrochloride (C90) | | |
| (2R,3S)-3-amino-1-[(cyclopropylmethyl)amino]-4-phenyl-2-butanol di-hydrochloride (C91) | | |
| (2R,3S)-3-amino-1-[(3,3-dimethylcyclopentyl)amino]-4-phenyl-2-butanol di-hydrochloride (C92) | | |
| (2R,3S)-3-amino-1-(methylamino)-4-phenyl-2-butanol di-hydrochloride (C93) | | |
| (2R,3S)-3-amino-4-phenyl-1-(tricyclo[3.3.1.1$^{3,7}$]dec-1-ylamino)-2-butanol di-hydrochloride (C94) | | |
| (2R,3S)-3-amino-4-phenyl-1-(1,2,3,4-tetrahydro-1-naphthalenylamino)-2-butanol di-hydrochloride (C95) | | |
| (2R,3S)-3-amino-1-({2-[3-(methyloxy)phenyl]ethyl}amino)-4-phenyl-2-butanol di-hydrochloride (C96) | | |
| (2R,3S)-3-amino-1-({2-[4-(methyloxy)phenyl]ethyl}amino)-4-phenyl-2-butanol di-hydrochloride (C97) | | |
| (2R,3S)-3-amino-1-({2-[2-(methyloxy)phenyl]ethyl}amino)-4-phenyl-2-butanol di-hydrochloride (C98) | | |

| Amine | [M + H]⁺ | RT (min) |
|---|---|---|
| (2R,3S)-3-amino-1-{[2-(2-chlorophenyl)ethyl]amino}-4-phenyl-2-butanol di-hydrochloride (C99) | | |
| (2R,3S)-3-amino-1-{[2-(3-chlorophenyl)ethyl]amino}-4-phenyl-2-butanol di-hydrochloride (C100) | | |
| (2R,3S)-3-amino-1-{[2-(4-chlorophenyl)ethyl]amino}-4-phenyl-2-butanol di-hydrochloride (C101) | | |
| (2R,3S)-3-amino-1-{[2-(4-methylphenyl)ethyl]amino}-4-phenyl-2-butanol di-hydrochloride (C102) | | |
| (2R,3S)-3-amino-1-{[2-(2-methylphenyl)ethyl]amino}-4-phenyl-2-butanol di-hydrochloride (C103) | | |
| (2R,3S)-3-amino-1-{[2-(3,4-dichlorophenyl)ethyl]amino}-4-phenyl-2-butanol di-hydrochloride (C104) | | |
| (2R,3S)-3-amino-1-{[2-(2,4-dichlorophenyl)ethyl]amino}-4-phenyl-2-butanol di-hydrochloride (C105) | | |
| (2R,3S)-3-amino-1-({2-[3,5-bis(methyloxy)phenyl]ethyl}amino)-4-phenyl-2-butanol di-hydrochloride (C106) | | |
| (2R,3S)-3-amino-1-({2-[2,3-bis(methyloxy)phenyl]ethyl}amino)-4-phenyl-2-butanol di-hydrochloride (C107) | | |
| (2R,3S)-3-amino-4-phenyl-1-[(phenylmethyl)amino]-2-butanol di-hydrochloride (C108) | | |
| (2R,3S)-3-amino-4-phenyl-1-[(2-phenylethyl)amino]-2-butanol di-hydrochloride (C109) | | |
| (2R,3S)-3-amino-1-[(1-ethylcyclohexyl)amino]-4-phenyl-2-butanol di-hydrochloride (C110) | | |
| (2R,3S)-3-amino-1-[(1-methylcyclopentyl)amino]-4-phenyl-2-butanol di-hydrochloride (C111) | | |
| (2R,3S)-3-amino-4-phenyl-1-[(1-propylcyclopentyl)amino]-2-butanol di-hydrochloride (C112) | | |
| (2R,3S)-3-amino-4-phenyl-1-[(1-propylcyclohexyl)amino]-2-butanol di-hydrochloride (C113) | | |
| (2R,3S)-3-amino-1-{[2-(3-chlorophenyl)-1,1-dimethylethyl]amino}-4-phenyl-2-butanol di-hydrochloride (C114) | | |

Amines C115-C147 were prepared from their corresponding BOC-protected amines H115-H147, respectively in an analogous manner to that described in C1.

| Amine | [M + H]⁺ | RT (min) |
|---|---|---|
| (2R,3S)-3-amino-1-({[3-(methyloxy)phenyl]methyl}amino)-4-(3-pyridinyl)-2-butanol tri-hydrochloride (C115) | | |
| (2R,3S)-3-amino-1-({[3-(methyloxy)phenyl]methyl}amino)-4-(1,3-thiazol-2-yl)-2-butanol di-hydrochloride (C116) | | |
| (2R,3S)-3-amino-1-(cyclohexylamino)-4-(1,3-thiazol-2-yl)-2-butanol di-hydrochloride (C117) | | |
| (2R,3S)-3-amino-1-[(1,5-dimethylhexyl)amino]-4-(1,3-thiazol-2-yl)-2-butanol di-hydrochloride (C118) | | |
| (2R,3S)-3-amino-4-(2-furanyl)-1-({[3-(methyloxy)phenyl]methyl}amino)-2-butanol di-hydrochloride (C119) | | |
| (2R,3S)-3-amino-1-(cyclohexylamino)-4-(2-furanyl)-2-butanol di-hydrochloride (C120) | | |
| (2R,3S)-3-amino-1-[(1,5-dimethylhexyl)amino]-4-(2-furanyl)-2-butanol di-hydrochloride (C121) | | |
| (2R,3S)-3-amino-4-(2-furanyl)-1-[(1,1,5-trimethylhexyl)amino]-2-butanol di-hydrochloride (C122) | | |
| (2R,3S)-3-amino-1-({[3-(methyloxy)phenyl]methyl}amino)-4-(2-pyridinyl)-2-butanol tri-hydrochloride (C123) | | |
| (2R,3S)-3-amino-4-(4-chlorophenyl)-1-(cyclohexylamino)-2-butanol di-hydrochloride (C124) | | |
| (2R,3S)-3-amino-4-(4-chlorophenyl)-1-({[3-(methyloxy)phenyl]methyl}amino)-2-butanol di-hydrochloride (C125) | | |
| (2R,3S)-3-amino-4-(3,5-difluorophenyl)-1-({[3-(trifluoromethyl)phenyl]methyl} amino)-2-butanol di-hydrochloride (C126) | | |
| (2R,3S)-3-amino-4-(3,5-difluorophenyl)-1-({[3-(methyloxy)phenyl]methyl}amino)-2-butanol di-hydrochloride (C127) | | |
| (2R,3S)-3-amino-4-(3,5-difluorophenyl)-1-[(1,5-dimethylhexyl)amino]-2-butanol di-hydrochloride (C128) | | |

-continued

| Amine | [M + H]⁺ | RT (min) |
|---|---|---|
| (2R,3S)-3-amino-1-(cyclohexylamino)-4-(3,5-difluorophenyl)-2-butanol di-hydrochloride (C129) | | |
| (2R,3S)-3-amino-4-(3,5-difluorophenyl)-1-[(1,1,5-trimethylhexyl)amino]-2-butanol di-hydrochloride (C130) | | |
| (2R,3S)-3-amino-4-(3,4-difluorophenyl)-1-({[3-(methyloxy)phenyl]methyl}amino)-2-butanol di-hydrochloride (C131) | | |
| (2R,3S)-3-amino-1-(cyclohexylamino)-4-(3,4-difluorophenyl)-2-butanol di-hydrochloride (C132) | | |
| (2R,3S)-3-amino-4-(3,4-difluorophenyl)-1-[(1,1,5-trimethylhexyl)amino]-2-butanol di-hydrochloride (C133) | | |
| (2R,3S)-3-amino-4-(3-chlorophenyl)-1-({[3-(methyloxy)phenyl]methyl}amino)-2-butanol di-hydrochloride (C134) | | |
| (2R,3S)-3-amino-4-(3-chlorophenyl)-1-(cyclohexylamino)-2-butanol di-hydrocloride (C135) | | |
| (2R,3S)-3-amino-4-(2-chlorophenyl)-1-({[3-(methyloxy)phenyl]methyl}amino)-2-butanol di-hydrochloride (C136) | | |
| (2R,3S)-3-amino-4-(2-chlorophenyl)-1-(cyclohexylamino)-2-butanol di-hydrochloride (C137) | | |
| (2R,3S)-3-amino-4-(2-chlorophenyl)-1-[(1,5-dimethylhexyl)amino]-2-butanol di-hydrochloride (C138) | | |
| (2R,3S)-3-amino-4-(3-chlorophenyl)-1-[(1,5-dimethylhexyl)amino]-2-butanol di-hydrochloride (C139) | | |
| (2R,3S)-3-amino-4-(3-fluorophenyl)-1-({[3-(methyloxy)phenyl]methyl}amino)-2-butanol di-hydrochloride (C140) | | |
| (2R,3S)-3-amino-1-[(1,5-dimethylhexyl)amino]-4-(3-fluorophenyl)-2-butanol di-hydrochloride (C141) | | |
| (2R,3S)-3-amino-1-({[3-(methyloxy)phenyl]methyl}amino)-4-(2-thienyl)-2-butanol di-hydrochloride (C142) | | |
| (2R,3S)-3-amino-1-[(1,5-dimethylhexyl)amino]-4-(2-thienyl)-2-butanol di-hydrochloride (C143) | | |
| (2R,3S)-3-amino-1-({[3-(methyloxy)phenyl]methyl}amino)-4-(1H-pyrazol-1-yl)-2-butanol di-hydrochloride (C144) | | |
| (2R,3S)-3-amino-1-[(1,5-dimethylhexyl)amino]-4-(1H-pyrazol-1-yl)-2-butanol di-hydrochloride (C145) | | |
| (2R,3S)-3-amino-1-({[3-(methyloxy)phenyl]methyl}amino)-4-(3-thienyl)-2-butanol di-hydrochloride (C146) | | |
| (2R,3S)-3-amino-1-[(1,5-dimethylhexyl)amino]-4-(3-thienyl)-2-butanol di-hydrochloride (C147) | | |

Amines C148-C156 were prepared from their corresponding BOC-protected amines H148-H156, respectively) in an analogous manner to that described in C1

| Amine | [M + H]⁺ | RT (min) |
|---|---|---|
| (2R,3S)-3-amino-4-phenyl-1-[(1-propylcyclobutyl)amino]-2-butanol di-hydrochloride (C148) | | |
| (2R,3S)-3-amino-1-{[1-(1-methylethyl)cyclobutyl]amino}-4-phenyl-2-butanol di-hydrochloride (C149) | | |
| (2R,3S)-3-amino-1-({1-[(3-chlorophenyl)methyl]cyclobutyl}amino)-4-phenyl-2-butanol di-hydrochloride (C150) | | |
| (2R,3S)-3-amino-4-phenyl-1-(tricyclo[3.3.1.1³,⁷]dec-2-ylamino)-2-butanol di-hydrochloride (C151) | | |
| (2R,3S)-3-amino-1-[(1r,4R)-bicyclo[2.2.1]hept-1-ylamino]-4-phenyl-2-butanol di-hydrochloride (C152) | | |
| (2R,3S)-3-amino-1-(bicyclo[2.2.2]oct-1-ylamino)-4-phenyl-2-butanol di-hydrochloride (C153) | | |
| (2R,3S)-3-amino-1-{[(1-ethyl-1H-pyrazol-4-yl)methyl]amino}-4-phenyl-2-butanol di-hydrochloride (C154) | 289.5 | 1.13 |
| (2R,3S)-3-amino-1-[(4,4-difluorocyclohexyl)amino]-4-phenyl-2-butanol di-hydrochloride (C155) | 299.3 | 1.65 |
| (2R,3S)-3-amino-1-({[3,4-bis(methyloxy)phenyl]methyl}amino)-4-phenyl-2-butanol di-tosylate (C156) | | |

Amine 157

(2R,3S)-3-Amino-1-{[(3-ethyl-5-isoxazolyl)methyl]amino}4-phenyl-2-butanol di-hydrochloride (C157)

(2R,3S)-3-Amino-1-{[(3-ethyl-5-isoxazolyl)methyl]amino}-4-phenyl-2-butanol di-hydrochloride (C157) was obtained from BOC-protected amine H157 in an analogous manner to the process described for amine C1.

EXAMPLES

Example 1

N-[(1S,2R)-1-Benzyl-3-((S)-1-cyclohexylcarbamoylethylamino)-2-hydroxypropyl]-5-(2-oxopyrrolidin-1-yl)-N',N'-dipropylisophthalamide (E1)

To a solution of 5-(2-oxo-pyrrolidin-1-yl)-N,N-dipropyl-isophthalamic acid (A80) (66 mg, 0.2 mmol, 1 equiv) in DMF (5 ml) at room temperature was added EDAC.HCl (46 mg, 0.24 mmol, 1.2 equiv), HOBT (37 mg, 0.24 mmol, 1.2 equiv), 4-ethylmorpholine (153μ, 1.2 mmol, 6 equiv) and (S)-2-((2R,3S)-3-amino-2-hydroxy-4-phenyl-butylamino)-N-cyclohexyl-propionamide di-hydrochloride (C6) (82 mg, 0.2 mmol, 1 equiv). The resulting mixture was stirred for 3 h then concentrated in vacuo. The residue was diluted in CH$_2$Cl$_2$ and the organic phases washed with a saturated NaHCO$_3$ aqueous solution, dried over MgSO$_4$ and concentrated in vacuo. Purification of the residue by preparative LC/MS gave N-[(1S,2R)-1-benzyl-3-((S)-1-cyclohexylcarbamoylethylamino)-2-hydroxypropyl]-5-(2-oxopyrrolidin-1-yl)-N',N'-dipropylisophthalamide (E1) (78 mg, 60%) as a white foam. [M+H]$^+$=648.3 RT=2.70.

Examples 2-62

Examples 2-62 were prepared in an analogous manner to Example 1 from the appropriate acid and amines indicated in the below table:

| Example | Acid | Amine | [M + H]$^+$ | RT (min) |
|---|---|---|---|---|
| N-[(1S,2R)-1-Benzyl-3-((S)-1-cyclohexylcarbamoylethylamino)-2-hydroxypropyl]-5-(2-oxopyrrolidin-1-yl)-N',N'-dipropylisophthalamide (E2) | A80 | C6 | 648.3 | 2.7 |
| N-[(1S,2R)-1-Benzyl-3-((S)-1-cyclohexylcarbamoylethylamino)-2-hydroxypropyl]-5-(2-oxopyrrolidin-1-yl)-isophthalamic acid methyl ester (E3) | A75 | C6 | 579.2 | 2.47 |
| N-[(1S,2R)-1-Benzyl-3-((S)-1-cyclohexylcarbamoylethylamino)-2-hydroxypropyl]-5-(2-oxopyrrolidin-1-yl)-isophthalamic acid tert-butyl ester (E4) | A74 | C6 | 621.2 | 2.74 |
| N-[(1S,2R)-1-Benzyl-3-((S)-1-cyclohexylcarbamoylethylamino)-2-hydroxypropyl]-5-(2-oxopyrrolidin-1-yl)-N'-propylisophthalamide (E5) | A77 | C6 | 606.2 | 2.45 |
| N-[(1S,2R)-1-Benzyl-3-((S)-1-cyclohexylcarbamoylethylamino)-2-hydroxypropyl]-N',N'-dimethyl-5-(2-oxopyrrolidin-1-yl)-isophthalamide (E6) | A78 | C6 | 592.2 | 2.31 |
| N-[(1S,2R)-1-Benzyl-3-((S)-1-cyclohexylcarbamoylethylamino)-2-hydroxypropyl]-N'-methyl-5-(2-oxopyrrolidin-1-yl)-isophthalamide (E7) | A79 | C6 | 578.2 | 2.29 |
| N-[(1S,2R)-1-Benzyl-3-((S)-1-cyclohexylcarbamoylethylamino)-2-hydroxypropyl]-3-hydroxymethyl-5-(2-oxopyrrolidin-1-yl)benzamide (E8) | A76 | C6 | 551.2 | 2.28 |
| N-[(1S,2R)-1-Benzyl-2-hydroxy-3-(3-methoxybenzylamino)-propyl]-3-(2-oxopyrrolidin-1-yl)-5-((E)-styryl)benzamide (E9) | A102 | C14 | 590.2 | 2.83 |
| N-[(1S,2R)-1-Benzyl-2-hydroxy-3-(3-methoxybenzylamino)-propyl]-3-(2-oxopyrrolidin-1-yl)-5-phenethylbenzamide (E10) | A103 | C14 | 592.2 | 2.80 |
| N-[(1S,2R)-1-Benzyl-2-hydroxy-3-(3-methoxybenzylamino)-propyl]-3-cyclopentyl-5-(2-oxopyrrolidin-1-yl)benzamide (E11) | A107 | C14 | 556.3 | 2.75 |
| N-[(1S,2R)-1-Benzyl-3-((S)-1-cyclohexylcarbamoylethylamino)-2-hydroxypropyl]-3-cyclopentyl-5-(2-oxopyrrolidin-1-yl)benzamide (E12) | A107 | C6 | 589.3 | 2.78 |
| N-[(1S,2R)-1-Benzyl-3-((S)-1-cyclohexylcarbamoylethylamino)-2-hydroxypropyl]-3-cyclohexyl-5-(2-oxopyrrolidin-1-yl)benzamide (E13) | A108 | C6 | 603.3 | 2.86 |
| N-[(1S,2R)-1-Benzyl-2-hydroxy-3-(3-methoxybenzylamino)-propyl]-3-cyclohexyl-5-(2-oxopyrrolidin-1-yl)benzamide (E14) | A108 | C14 | 570.3 | 2.84 |
| N-[(1S,2R)-1-Benzyl-2-hydroxy-3-(3-methoxybenzylamino)propyl]-3-(2-oxopyrrolidin-1-yl)-5-propyl-benzamide (E15) | A108 | C14 | 530.2 | 2.64 |
| N-(1-Benzyl-3-cyclohexylamino-2-hydroxypropyl)-3-(2-oxopyrrolidin-1-yl)-5-propylbenzamide (E16) | A106 | C1 | 492.2 | 2.61 |
| N-[1-Benzyl-2-hydroxy-3-(3-methoxybenzylamino)propyl]-3-(2-methyl-propenyl)-5-(2-oxopyrrolidin-1-yl)benzamide (E17) | A101 | C14 | 542.3 | 2.69 |
| N-[1-Benzyl-2-hydroxy-3-(3-methoxybenzylamino)propyl]-3-isobutyl-5-(2-oxopyrrolidin-1-yl)benzamide (E18) | A105 | C14 | 544.3 | 2.73 |
| N-(1-Benzyl-3-cyclohexylamino-2-hydroxypropyl)-3-isopropyl-5-(2-oxopyrrolidin-1-yl)benzamide (E19) | A104 | C1 | 492.3 | 2.60 |
| N-(1-Benzyl-3-cyclohexylamino-2-hydroxypropyl)-3-isobutyl-5-(2-oxopyrrolidin-1-yl)benzamide (E20) | A105 | C1 | 506.3 | 2.71 |
| N-(1-Benzyl-3-cyclohexylamino-2-hydroxypropyl)-3-cyclopentyl-5-(2-oxopyrrolidin-1-yl)benzamide (E21) | A107 | C16 | 518.4 | 2.77 |

-continued

| Example | Acid | Amine | [M + H]+ | RT (min) |
|---|---|---|---|---|
| N-[1-Benzyl-2-hydroxy-3-(3-trifluoromethylbenzylamino)propyl]-3-cyclopentyl-5-(2-oxopyrrolidin-1-yl)benzamide (E22) | A107 | C16 | 594.4 | 2.97 |
| N-[1-Benzyl-2-hydroxy-3-(3-trifluoromethylbenzylamino)propyl]-3-(2-oxopyrrolidin-1-yl)-5-propylbenzamide (E23) | A106 | C16 | 568.3 | 2.69 |
| N-[1-Benzyl-3-(1,5-dimethylhexylamino)-2-hydroxypropyl]-3-(2-oxopyrrolidin-1-yl)-5-propylbenzamide formate salt (E24) | A106 | C20 | 522.4 | 2.67 |
| N-[1-Benzyl-2-hydroxy-3-(3-trifluoromethylbenzylamino)propyl]-3-ethynyl-5-(2-oxopyrrolidin-1-yl)benzamide (E25) | A109 | C16 | 550.3 | 2.47 |
| N-[1-Benzyl-3-(1-cyclohexylcarbamoylethylamino)-2-hydroxypropyl]-3-(2-oxopyrrolidin-1-yl)-5-propylbenzamide (E26) | A106 | C6 | 563.4 | 2.70 |
| N-[1-Benzyl-2-hydroxy-3-(3-trifluoromethylbenzylamino)propyl]-2-fluoro-3-(2-oxopyrrolidin-1-yl)-5-trifluoromethyl-benzamide formate salt (E27) | A100 | C16 | 612.0 | 2.76 |
| formic acid-5-cyclopentyl-3-(1,1-dioxidotetrahydro-2H-1,2-thiazin-2-yl)-2-fluoro-N-[(1S,2R)-2-hydroxy-1-(phenylmethyl)-3-({[3-trifluoromethyl)phenyl]methyl}amino)propyl]benzamide (1:1) (E28) | A176 | C16 | 662.5 | 3.00 |
| formic acid-5-cyclopentyl-3-(1,1-dioxidotetrahydro-2H-1,2-thiazin-2-yl)-2-fluoro-N-[(1S,2R)-2-hydroxy-3-({1-methyl-1-[3-(methyloxy)phenyl]ethyl}amino)-1-(phenylmethyl)propyl]benzamide (1:1) (E29) | A176 | C15 | 652.5 | 2.92 |
| formic acid-5-cyclopentyl-3-(1,1-dioxidotetrahydro-2H-1,2-thiazin-2-yl)-N-[(1S,2R)-3-{[(1-ethyl-1H-pyrazol-4-yl)methyl]amino}-2-hydroxy-1-(phenylmethyl)propyl]-2-fluorobenzamide (1:1) (E30) | A176 | C154 | 612.5 | 2.62 |
| formic acid-3-(1,1-dioxidotetrahydro-2H-1,2-thiazin-2-yl)-2-fluoro-N-[(1S,2R)-2-hydroxy-1-(phenylmethyl)-3-({[3-(trifluoromethyl)phenyl]methyl}amino)propyl]-5-[(1-methylethyl)amino]benzamide (1:1) (E31) | A175 | C16 | 651.5 | 2.78 |
| formic acid-3-(1,1-dioxidotetrahydro-2H-1,2-thiazin-2-yl)-2-fluoro-N-[(1S,2R)-2-hydroxy-3-({1-methyl-1-[3-(methyloxy)phenyl]ethyl}amino)-1-(phenylmethyl)propyl]-5-[(1-methylethyl)amino]benzamide (1:1) (E32) | A175 | C15 | 641.5 | 2.65 |
| formic acid-3-(1,1-dioxidotetrahydro-2H-1,2-thiazin-2-yl)-N-[(1S,2R)-3-{[(1-ethyl-1H-pyrazol-4-yl)methyl]amino}-2-hydroxy-1-(phenylmethyl)propyl]-2-fluoro-5-[(1-methylethyl)amino]benzamide (1:1) (E33) | A175 | C154 | 601.5 | 2.34 |
| formic acid-3-(1,1-dioxidotetrahydro-2H-1,2-thiazin-2-yl)-2-fluoro-N-{(1S,2R)-2-hydroxy-1-(phenylmethyl)-3-[(1,1,5-trimethylhexyl)amino]propyl}-5-[(1-methylethyl)amino]benzamide (1:1) (E34) | A175 | C5 | 619.6 | 2.94 |
| formic acid-3-(1,1-dioxidotetrahydro-2H-1,2-thiazin-2-yl)-2-fluoro-N-[(1S,2R)-2-hydroxy-1-(phenylmethyl)-3-(tetrahydro-2H-pyran-4-ylamino)propyl]-5-[(1-methylethyl)amino]benzamide (1:1) (E35) | A175 | C43 | 577.5 | 2.27 |
| N-[(1S,2R)-1-Benzyl-3-((S)-1-cyclohexylcarbamoylethylamino)-2-hydroxypropyl]-3,5-bis-(2-oxopyrrolidin-1-yl)benzamide (E36) | A24 | C6 | 604.2 | 2.02 |
| 3-Acetylamino-N-[(1S,2R)-1-benzyl-3-((S)-1-cyclohexylcarbamoylethylamino)-2-hydroxypropyl]-5-(2-oxopyrrolidin-1-yl)benzamide (E37) | A50 | C6 | 578.1 | 2.38 |
| N-[(1S,2R)-1-Benzyl-3-((S)-1-cyclohexylcarbamoylethylamino)-2-hydroxypropyl]-3-methanesulfonylamino-5-(2-oxopyrrolidin-1-yl)benzamide (E38) | A53 | C6 | 614.1 | 2.42 |
| N-[(1S,2R)-1-Benzyl-3-((S)-1-cyclohexylcarbamoylethylamino)-2-hydroxypropyl]-3-isopropylamino-5-(2-oxopyrrolidin-1-yl)benzamide (E39) | A44 | C6 | 578.2 | 2.59 |
| N-[(1S,2R)-1-Benzyl-3-((S)-1-cyclohexylcarbamoylethylamino)-2-hydroxypropyl]-3-(2-oxopyrrolidin-1-yl)-5-propylaminobenzamide (E40) | A35 | C6 | 578.3 | 2.62 |
| N-[(1S,2R)-1-Benzyl-3-((S)-1-cyclohexylcarbamoylethylamino)-2-hydroxypropyl]-3-cyclopentylamino-5-(2-oxopyrrolidin-1-yl)benzamide (E41) | A45 | C6 | 604.2 | 2.69 |
| N-[(1S,2R)-1-Benzyl-3-((S)-1-cyclohexylcarbamoylethylamino)-2-hydroxypropyl]-3-diethylamino-5-(2-oxopyrrolidin-1-yl)benzamide (E42) | A33 | C6 | 592.2 | 2.69 |
| N-[(1S,2R)-1-Benzyl-3-((S)-1-cyclohexylcarbamoylethylamino)-2-hydroxypropyl]-3-morpholin-4-yl-5-(2-oxopyrrolidin-1-yl)benzamide (E43) | A29 | C6 | 606.2 | 2.43 |
| N-[(1S,2R)-1-Benzyl-3-((S)-1-cyclohexylcarbamoylethylamino)-2-hydroxypropyl]-3-(4-methylpiperazin-1-yl)-5-(2-oxopyrrolidin-1-yl)benzamide (E44) | A115 | C6 | 619.2 | 2.05 |

-continued

| Example | Acid | Amine | [M + H]⁺ | RT (min) |
|---|---|---|---|---|
| N-[(1S,2R)-1-Benzyl-3-((S)-1-cyclohexylcarbamoylethylamino)-2-hydroxypropyl]-3-(2-oxopyrrolidin-1-yl)-5-piperidin-1-ylbenzamide (E45) | A28 | C6 | 604.2 | 2.64 |
| N-[(1S,2R)-1-Benzyl-3-((S)-1-cyclohexylcarbamoylethylamino)-2-hydroxypropyl]-3-(2-oxopyrrolidin-1-yl)-5-pyrrolidin-1-ylbenzamide (E46) | A113 | C6 | 590.2 | 2.65 |
| N-[(1S,2R)-1-Benzyl-3-((S)-1-cyclohexylcarbamoylethylamino)-2-hydroxypropyl]-3-(2-oxopyrrolidin-1-yl)-5-phenylaminobenzamide (E47) | A30 | C6 | 612.2 | 2.70 |
| N-[(1S,2R)-1-Benzyl-3-((S)-1-cyclohexylcarbamoylethylamino)-2-hydroxypropyl]-4-methoxy-3,5-bis-(2-oxopyrrolidin-1-yl)benzamide (E48) | A26 | C6 | 634.2 | 2.36 |
| N-[(1S,2R)-1-Benzyl-3-((S)-1-cyclohexylcarbamoylethylamino)-2-hydroxypropyl]-4-chloro-3,5-bis-(2-oxopyrrolidin-1-yl)benzamide (E49) | A25 | C6 | 638.1 | 2.41 |
| N-[(1S,2R)-1-Benzyl-3-((S)-1-cyclohexylcarbamoylethylamino)-2-hydroxypropyl]-3-ethylamino-5-(2-oxopyrrolidin-1-yl)benzamide (E50) | A31 | C6 | 564.2 | 2.48 |
| 3-Benzylamino-N-[(1S,2R)-1-benzyl-3-((S)-1-cyclohexylcarbamoylethylamino)-2-hydroxypropyl]-5-(2-oxopyrrolidin-1-yl)benzamide (E51) | A37 | C6 | 626.2 | 2.70 |
| N-[(1S,2R)-1-Benzyl-3-((S)-1-cyclohexylcarbamoylethylamino)-2-hydroxypropyl]-3-(3-methylbutylamino)-5-(2-oxopyrrolidin-1-yl)benzamide (E52) | A38 | C6 | 606.2 | 2.79 |
| N-[(1S,2R)-1-Benzyl-3-((S)-1-cyclohexylcarbamoylethylamino)-2-hydroxypropyl]-3-cyclohexylamino-5-(2-oxopyrrolidin-1-yl)benzamide (E53) | A46 | C6 | 618.2 | 2.77 |
| N-[(1S,2R)-1-Benzyl-3-((S)-1-cyclohexylcarbamoylethylamino)-2-hydroxypropyl]-3-(2-oxopyrrolidin-1-yl)-5-pentylaminobenzamide (E54) | A39 | C6 | 606.2 | 2.77 |
| N-[(1S,2R)-1-Benzyl-3-((S)-1-cyclohexylcarbamoylethylamino)-2-hydroxypropyl]-3-(1-ethylpropylamino)-5-(2-oxopyrrolidin-1-yl)benzamide (E55) | A43 | C6 | 606.2 | 2.77 |
| N-[(1S,2R)-1-Benzyl-3-((S)-1-cyclohexylcarbamoylethylamino)-2-hydroxypropyl]-3-butylamino-5-(2-oxopyrrolidin-1-yl)benzamide (E56) | A40 | C6 | 592.2 | 2.7 |
| N-[(1S,2R)-1-Benzyl-3-((S)-1-cyclohexylcarbamoylethylamino)-2-hydroxypropyl]-3-(2,2-dimethylpropylamino)-5-(2-oxopyrrolidin-1-yl)benzamide (E57) | A41 | C6 | 604.2 | 2.78 |
| N-[(1S,2R)-1-Benzyl-3-((S)-1-cyclohexylcarbamoylethylamino)-2-hydroxypropyl]-3-(cyclopropylmethylamino)-5-(2-oxopyrrolidin-1-yl)-benzamide (E58) | A42 | C6 | 590.2 | 2.60 |
| 3-(Acetylpropylamino)-N-[(1S,2R)-1-benzyl-3-((S)-1-cyclohexylcarbamoylethylamino)-2-hydroxypropyl]-5-(2-oxopyrrolidin-1-yl)benzamide (E59) | A48 | C6 | 620.2 | 2.47 |
| N-[(1S,2R)-1-Benzyl-3-(1,5-dimethylhexylamino)-2-hydroxypropyl]-3-isopropylamino-5-(2-oxopyrrolidin-1-yl)benzamide (E60) | A44 | C20 | 537.3 | 2.69 |
| N-[(1S,2R)-1-Benzyl-3-((S)-1-cyclohexylcarbamoylethylamino)-2-hydroxypropyl]-3-nitro-5-(2-oxopyrrolidin-1-yl)benzamide formate salt (E61) | A27 | C6 | 566.1 | 2.56 |
| N-[(1S,2R)-1-Benzyl-3-((S)-1-cyclohexylcarbamoylethylamino)-2-hydroxypropyl]-3-nitro-5-(2-oxopyrrolidin-1-yl)benzamide (E62) | A27 | C6 | 566.1 | 2.56 |

Example 63

3-Amino-N-[(1S,2R)-1-benzyl-3-((S)-1-cyclohexylcarbamoylethylamino)-2-hydroxypropyl]-5-(2-oxopyrrolidin-1-yl)benzamide (E63)

A mixture of N-[(1S,2R)-1-benzyl-3-((S)-1-cyclohexylcarbamoyl-ethylamino)-2-hydroxy-propyl]-3-nitro-5-(2-oxo-pyrrolidin-1-yl)-benzamide (E62) (40 mg, 0.07 mmol, 1 equiv), 10% Pd on charcoal (50% wet, 10 mg, 12.5% w/w), NH₄COOH (55 mg, 0.90 mmol, 13 equiv), EtOH (5 ml) and H₂O (2.5 ml) was stirred at 50° C. for 2 h, cooled to room temperature and the catalyst was filtered off through a pad of celite. Most of the EtOH was removed in vacuo and the residue was partitioned between AcOEt and saturated aqueous NaHCO₃ solution. The aqueous phase was extracted with AcOEt. The combined organic phases were dried over MgSO₄ and concentrated in vacuo. The residue was triturated with Et₂O to give 3-amino-N-[(1S,2R)-1-benzyl-3-((S)-1-cyclohexylcarbamoyl-ethylamino)-2-hydroxypropyl]-5-(2-oxo-pyrrolidin-1-yl)-benzamide (E63) (15 mg, 38%) as a pale yellow solid. [M+H]⁺=536.1 RT=2.27 min

Examples 64-65

Examples 64-65 were prepared in an analogous manner to Example 1 from the appropriate acid and amines indicated in the below table:

| Example | Acid | Amine | [M + H]+ | RT (min) |
| --- | --- | --- | --- | --- |
| 3-(Acetylisopropylamino)-N-[(1S,2R)-1-benzyl-3-((S)-1-cyclohexylcarbamoylethylamino)-2-hydroxypropyl]-5-(2-oxo-pyrrolidin-1-yl)benzamide (E64) | A49 | C6 | 620.2 | 2.44 |
| N-[(1S,2R)-1-Benzyl-3-((S)-1-cyclohexylcarbamoylethylamino)-2-hydroxypropyl]-3-(methanesulfonyl propylamino)-5-(2-oxopyrrolidin-1-yl)-benzamide (E65) | A52 | C6 | 656.2 | 2.56 |

Example 66

N-((1S,2R)-3-Amino-1-benzyl-2-hydroxypropyl)-3-ethylamino-5-(2-oxopyrrolidin-1-yl)benzamide (E66)

Example 66 (E66) was prepared in an analogous manner to Example 182 from [(2R,3S)-3-({1-[3-ethylamino-5-(2-oxo-pyrrolidin-1-yl)-phenyl]-methanoyl}amino)-2-hydroxy-4-phenyl-butyl]-carbamic acid benzyl ester (D106).

Examples 67-87

Examples 67-87 were prepared in an analogous manner to Example 1 from the appropriate acid and amines indicated in the below table:

| Example | Acid | Amine | [M + H]+ | RT (min) |
| --- | --- | --- | --- | --- |
| N-((1S,2R)-1-Benzyl-3-cyclopropylamino-2-hydroxypropyl)-3-ethylamino-5-(2-oxopyrrolidin-1-yl)benzamide (E67) | A31 | C26 | 451.2 | 2.23 |
| N-[(1S,2R)-1-Benzyl-2-hydroxy-3-(3-methoxybenzylamino)-propyl]-3-ethylamino-5-(2-oxopyrrolidin-1-yl)benzamide formate salt (E68) | A31 | C14 | 531.2 | 2.41 |
| N-((1S,2R)-1-Benzyl-3-cyclohexylamino-2-hydroxypropyl)-3-ethylamino-5-(2-oxopyrrolidin-1-yl)benzamide formate salt (E69) | A31 | C24 | 493.2 | 2.39 |
| N-((1S,2R)-1-Benzyl-3-ethylamino-2-hydroxypropyl)-3-ethylamino-5-(2-oxopyrrolidin-1-yl)benzamide formate salt (E70) | A31 | C24 | 439.2 | 2.20 |
| N-[(1S,2R)-1-Benzyl-2-hydroxy-3-(4-methoxybenzylamino)-propyl]-3-ethylamino-5-(2-oxopyrrolidin-1-yl)benzamide (E71) | A31 | C27 | 531.2 | 2.41 |
| N-((1S,2R)-1-Benzyl-2-hydroxy-3-isopropylaminopropyl)-3-ethylamino-5-(2-oxopyrrolidin-1-yl)benzamide (E72) | A31 | C28 | 453.2 | 2.20 |
| N-[((1S,2R)-1-Benzyl-2-hydroxy-3-(3-trifluoromethylbenzylamino)-propyl]-3-ethylamino-5-(2-oxopyrrolidin-1-yl)benzamide (E73) | A31 | C16 | 569.2 | 2.54 |
| N-[(1S,2R)-1-Benzyl-2-hydroxy-3-(2,2,3,3,3-pentafluoropropylamino)-propyl]-3-ethylamino-5-(2-oxopyrrolidin-1-yl)benzamide (E74) | A31 | C12 | 543.1 | 2.92 |
| N-[(1S,2R)-1-Benzyl-3-(2,2,3,3,4,4,4-heptafluorobutylamino)-2-hydroxypropyl]-3-ethylamino-5-(2-oxopyrrolidin-1-yl)benzamide (E75) | A31 | C13 | 593.1 | 3.13 |
| N-[(1S,2R)-1-Benzyl-2-hydroxy-3-(R)-1-phenylethylamino)propyl]-3-ethylamino-5-(2-oxopyrrolidin-1-yl)benzamide (E76) | A31 | C31 | 515.2 | 2.38 |
| N-[(1S,2R)-1-Benzyl-2-hydroxy-3-((S)-1-phenylethylamino)propyl]-3-ethylamino-5-(2-oxopyrrolidin-1-yl)benzamide (E77) | A31 | C30 | 515.2 | 2.38 |
| N-[(1S,2R)-1-Benzyl-2-hydroxy-3-(2-methoxybenzylamino)-propyl]-3-ethylamino-5-(2-oxopyrrolidin-1-yl)benzamide (E78) | A31 | C29 | 531.2 | 2.37 |
| N-[(1S,2R)-1-Benzyl-3-(3,5-bis-trifluoromethylbenzylamino)-2-hydroxypropyl]-3-ethylamino-5-(2-oxopyrrolidin-1-yl)benzamide (E79) | A31 | C25 | 637.1 | 2.74 |
| N-{(1S,2R)-1-Benzyl-2-hydroxy-3-[(R)-1-(3-methoxyphenyl)-ethylamino[-propyl]-3-ethylamino-5-(2-oxopyrrolidin-1-yl)benzamide (E80) | A31 | C7 | 545.2 | 2.41 |
| N-{(1S,2R)-1-Benzyl-2-hydroxy-3-[(S)-1-(3-methoxyphenyl)-ethylamino]-propyl}-3-ethylamino-5-(2-oxopyrrolidin-1-yl)benzamide (E81) | A31 | C17 | 545.2 | 2.43 |
| N-[(1S,2R)-1-Benzyl-3-((S)-1-cyclohexylcarbamoylethylamino)-2-hydroxypropyl]-3-isobutylamino-5-(2-oxopyrrolidin-1-yl)benzamide (E82) | A36 | C6 | 592.2 | 2.66 |
| N-[(1S,2R)-1-Benzyl-3-((S)-1-cyclohexylcarbamoylethylamino)-2-hydroxypropyl]-3-dimethylamino-5-(2-oxopyrrolidin-1-yl)benzamide (E83) | A34 | C6 | 564.2 | 2.47 |

-continued

| Example | Acid | Amine | [M + H]⁺ | RT (min) |
|---|---|---|---|---|
| N-[(1S,2R)-1-Benzyl-2-hydroxy-3-(1-methyl-1-phenylethylamino)-propyl]-3-ethylamino-5-(2-oxopyrrolidin-1-yl)benzamide (E84) | A31 | C8 | 529.3 | 2.44 |
| N-((1S,2R)-1-Benzyl-3-tert-butylamino-2-hydroxypropyl)-3-ethylamino-5-(2-oxopyrrolidin-1-yl)benzamide (E85) | A31 | C10 | 467.3 | 2.25 |
| N-[(1S,2R)-1-Benzyl-2-hydroxy-3-(3-trifluoromethoxybenzylamino)-propyl]-3-ethylamino-5-(2-oxopyrrolidin-1-yl)benzamide (E86) | A31 | C11 | 585.3 | 2.61 |
| N-[(1S,2R)-1-Benzyl-2-hydroxy-3-(3-methylbutylamino)-propyl]-3-ethylamino-5-(2-oxopyrrolidin-1-yl)benzamide (E87) | A31 | C9 | 481.3 | 2.38 |

Example 88

N-((1S,2R)-3-Amino-1-benzyl-2-hydroxypropyl)-3-isopropylamino-5-(2-oxopyrrolidin-1-yl)benzamide (E88)

Example 88 was prepared in an analogous manner to Example 182 from [(2R,3S)-3-({1-[3-isopropylamino-5-(2-oxo-pyrrolidin-1-yl)-phenyl]-methanoyl}-amino)-2-hydroxy-4-phenyl-butyl]-carbamic acid benzyl ester (D107). [M+H]⁺=425.2, RT=2.20 min

Examples 89-102

Examples 89-102 were prepared in an analogous manner to Example 1 from the appropriate acid and amines indicated in the below table:

| Example | Acid | Amine | [M + H]⁺ | RT (min) |
|---|---|---|---|---|
| N-[(1S,2R)-1-Benzyl-3-((S)-1-cyclohexylcarbamoylethylamino)-2-hydroxypropyl]-3-methylamino-5-(2-oxopyrrolidin-1-yl)benzamide (E89) | A32 | C6 | 550.3 | 2.37 |
| N-[(1S,2R)-1-Benzyl-3-((S)-1-cyclohexylcarbamoylethylamino)-2-hydroxypropyl]-3-(methanesulfonyl methylamino)-5-(2-oxopyrrolidin-1-yl)-benzamide (E90) | A51 | C6 | 628.2 | 2.41 |
| 3-(Acetylmethylamino)-N-[(1S,2R)-1-benzyl-3-((S)-1-cyclohexylcarbamoylethylamino)-2-hydroxypropyl]-5-(2-oxopyrrolidin-1-yl)-benzamide (E91) | A47 | C6 | 592.2 | 2.31 |
| N-((1S,2R)-1-Benzyl-3-cyclopentylamino-2-hydroxypropyl)-3-ethylamino-5-(2-oxopyrrolidin-1-yl)benzamide (E92) | A31 | C18 | 479.2 | 2.31 |
| N-[(1S,2R)-1-Benzyl-2-hydroxy-3-(4-methylpentylamino)-propyl]-3-ethylamino-5-(2-oxopyrrolidin-1-yl)benzamide (E93) | A31 | C32 | 495.3 | 2.51 |
| N-[(1S,2R)-1-Benzyl-2-hydroxy-3-(5-methylhexylamino)-propyl]-3-ethylamino-5-(2-oxopyrrolidin-1-yl)benzamide (E94) | A31 | C19 | 509.3 | 2.62 |
| N-[(1S,2R)-1-Benzyl-3-(1,5-dimethyl-hexylamino)-2-hydroxypropyl]-3-ethylamino-5-(2-oxopyrrolidin-1-yl)benzamide formate salt (E95) | A31 | C20 | 523.3 | 2.68 |
| N-((1S,2R)-1-Benzyl-3-cyclohexylamino-2-hydroxypropyl)-3-ethylamino-5-(2-oxopyrrolidin-1-yl)benzamide (E96) | A31 | C7 | 493.2 | 2.38 |
| N-(1-Benzyl-3-cyclobutylamino-2-hydroxypropyl)-3-ethylamino-5-(2-oxopyrrolidin-1-yl)benzamide (E97) | A31 | C2 | 465.4 | 2.29 |
| N-(1-Benzyl-3-cycloheptylamino-2-hydroxypropyl)-3-ethylamino-5-(2-oxopyrrolidin-1-yl)benzamide (E98) | A31 | C33 | 507.3 | 2.52 |
| N-(1-Benzyl-2-hydroxy-3-isobutylaminopropyl)-3-ethylamino-5-(2-oxopyrrolidin-1-yl)benzamide (E99) | A31 | C3 | 424.2 | 2.35 |
| N-[1-Benzyl-2-hydroxy-3-(1,1,5-trimethylhexylamino)propyl]-3-ethylamino-5-(2-oxopyrrolidin-1-yl)benzamide (E100) | A31 | C5 | 537.3 | 2.80 |
| N-(1-Benzyl-2-hydroxy-3-propylaminopropyl)-3-ethylamino-5-(2-oxopyrrolidin-1-yl)benzamide (E101) | A31 | C4 | 453.2 | 2.29 |
| N-{1-Benzyl-2-hydroxy-3-[1-(3-methoxyphenyl)-1-methylethylamino]propyl}-3-ethylamino-5-(2-oxopyrrolidin-1-yl)benzamide formate salt (E102) | A31 | C15 | 559.2 | 2.59 |

Examples 103-170

Examples 103-170 were prepared by reductive amination using N-((1S,2R)-3-amino-1-benzyl-2-hydroxypropyl)-3-ethylamino-5-(2-oxopyrrolidin-1-yl)benzamide (E66) in an analogous procedure to that described for E183.

| Example | [M + H]+ | RT (min) |
|---|---|---|
| N-[(1S,2R)-1-Benzyl-3-(3,4-dichloro-benzylamino)-2-hydroxy-propyl]-3-ethylamino-5-(2-oxo-pyrrolidin-1-yl)-benzamide (E103) | | |
| N-((1S,2R)-1-Benzyl-3-benzylamino-2-hydroxy-propyl)-3-ethylamino-5-(2-oxo-pyrrolidin-1-yl)-benzamide (E104) | | |
| N-[(1S,2R)-1-Benzyl-3-(4-fluoro-benzylamino)-2-hydroxy-propyl]-3-ethylamino-5-(2-oxo-pyrrolidin-1-yl)-benzamide (E105) | | |
| N-[(1S,2R)-1-Benzyl-2-hydroxy-3-(4-trifluoromethyl-benzylamino)-propyl]-3-ethylamino-5-(2-oxo-pyrrolidin-1-yl)-benzamide (E106) | | |
| N-{(1S,2R)-1-Benzyl-3-[(furan-2-ylmethyl)amino]-2-hydroxy-propyl}-3-ethylamino-5-(2-oxo-pyrrolidin-1-yl)-benzamide (E107) | | |
| N-{(1S,2R)-1-Benzyl-2-hydroxy-3-[(quinolin-4-ylmethyl)-amino]-propyl}-3-ethylamino-5-(2-oxo-pyrrolidin-1-yl)-benzamide (E108) | | |
| N-[(1S,2R)-1-Benzyl-2-hydroxy-3-(3-hydroxy-benzylamino)-propyl]-3-ethylamino-5-(2-oxo-pyrrolidin-1-yl)-benzamide (E109) | | |
| N-{(1S,2R)-1-Benzyl-2-hydroxy-3-[(thiophen-2-ylmethyl)-amino]-propyl}-3-ethylamino-5-(2-oxo-pyrrolidin-1-yl)-benzamide (E110) | | |
| N-{(1S,2R)-1-Benzyl-2-hydroxy-3-[(thiophen-3-ylmethyl)-amino]-propyl}-3-ethylamino-5-(2-oxo-pyrrolidin-1-yl)-benzamide (E111) | | |
| N-[(1S,2R)-1-Benzyl-3-(3-chloro-4-methoxy-benzylamino)-2-hydroxy-propyl]-3-ethylamino-5-(2-oxo-pyrrolidin-1-yl)-benzamide (E112) | | |
| N-[(1S,2R)-1-Benzyl-3-(2,3-dichloro-benzylamino)-2-hydroxy-propyl]-3-ethylamino-5-(2-oxo-pyrrolidin-1-yl)-benzamide (E113) | | |
| N-[(1S,2R)-3-(4-Acetylamino-benzylamino)-1-benzyl-2-hydroxy-propyl]-3-ethylamino-5-(2-oxo-pyrrolidin-1-yl)-benzamide (E114) | | |
| N-[(1S,2R)-1-Benzyl-3-(4-cyano-benzylamino)-2-hydroxy-propyl]-3-ethylamino-5-(2-oxo-pyrrolidin-1-yl)-benzamide (E115) | | |
| N-((1S,2R)-1-Benzyl-2-hydroxy-3-phenethylamino-propyl)-3-ethylamino-5-(2-oxo-pyrrolidin-1-yl)-benzamide (E116) | | |
| N-{(1S,2R)-1-Benzyl-2-hydroxy-3-[(1H-indol-3-ylmethyl)-amino]-propyl}-3-ethylamino-5-(2-oxo-pyrrolidin-1-yl)-benzamide (E117) | | |
| N-[(1S,2R)-1-Benzyl-2-hydroxy-3-(3-phenyl-butylamino)-propyl]-3-ethylamino-5-(2-oxo-pyrrolidin-1-yl)-benzamide (E118) | | |
| N-{(1S,2R)-3-[(1H-Benzoimidazol-5-ylmethyl)-amino]-1-benzyl-2-hydroxy-propyl}-3-ethylamino-5-(2-oxo-pyrrolidin-1-yl)-benzamide (E119) | | |
| N-{(1S,2R)-1-Benzyl-3-[(E)-3-(4-fluoro-phenyl)-allylamino]-2-hydroxy-propyl}-3-ethylamino-5-(2-oxo-pyrrolidin-1-yl)-benzamide (E120) | | |
| N-[(1S,2R)-1-Benzyl-2-hydroxy-3-(4-isopropoxy-benzylamino)-propyl]-3-ethylamino-5-(2-oxo-pyrrolidin-1-yl)-benzamide (E121) | | |
| N-[(1S,2R)-1-Benzyl-2-hydroxy-3-((E)-3-p-tolyl-allylamino)-propyl]-3-ethylamino-5-(2-oxo-pyrrolidin-1-yl)-benzamide (E122) | | |
| N-{(1S,2R)-1-Benzyl-3-[(2-ethyl-5-methyl-3H-imidazol-4-ylmethyl)-amino]-2-hydroxy-propyl}-3-ethylamino-5-(2-oxo-pyrrolidin-1-yl)-benzamide (E123) | | |
| N-[(1S,2R)-1-Benzyl-2-hydroxy-3-(2-methyl-3-phenyl-propylamino)-propyl]-3-ethylamino-5-(2-oxo-pyrrolidin-1-yl)-benzamide (E124) | | |
| N-[(1S,2R)-1-Benzyl-2-hydroxy-3-(3-methoxy-4-nitro-benzylamino)-propyl]-3-ethylamino-5-(2-oxo-pyrrolidin-1-yl)-benzamide (E125) | | |
| N-[(1S,2R)-1-Benzyl-3-(5-cyano-2-methoxy-benzylamino)-2-hydroxy-propyl]-3-ethylamino-5-(2-oxo-pyrrolidin-1-yl)-benzamide (E126) | | |
| N-{(1S,2R)-1-Benzyl-3-[(cyclohex-3-enylmethyl)-amino]-2-hydroxy-propyl}-3-ethylamino-5-(2-oxo-pyrrolidin-1-yl)-benzamide (E127) | | |
| N-[(1S,2R)-1-Benzyl-2-hydroxy-3-(2-phenyl-propylamino)-propyl]-3-ethylamino-5-(2-oxo-pyrrolidin-1-yl)-benzamide (E128) | | |
| N-[(1S,2R)-1-Benzyl-2-hydroxy-3-(3-methylsulfanyl-propylamino)-propyl]-3-ethylamino-5-(2-oxo-pyrrolidin-1-yl)-benzamide (E129) | | |
| N-[(1S,2R)-1-Benzyl-3-(3-cyano-benzylamino)-2-hydroxy-propyl]-3-ethylamino-5-(2-oxo-pyrrolidin-1-yl)-benzamide (E130) | | |
| N-{(1S,2R)-1-Benzyl-2-hydroxy-3-[(5-methyl-thiophen-2-ylmethyl)-amino]-propyl}-3-ethylamino-5-(2-oxo-pyrrolidin-1-yl)-benzamide (E131) | | |
| N-[(1S,2R)-1-Benzyl-2-hydroxy-3-(2-methoxy-5-methyl-benzylamino)-propyl]-3-ethylamino-5-(2-oxo-pyrrolidin-1-yl)-benzamide (E132) | | |
| N-{(1S,2R)-3-[(Benzofuran-2-ylmethyl)-amino]-1-benzyl-2-hydroxy-propyl}-3-ethylamino-5-(2-oxo-pyrrolidin-1-yl)-benzamide (E133) | | |
| N-[(1S,2R)-1-Benzyl-3-(3-fluoro-benzylamino)-2-hydroxy-propyl]-3-ethylamino-5-(2-oxo-pyrrolidin-1-yl)-benzamide (E134) | | |
| N-[(1S,2R)-1-Benzyl-2-hydroxy-3-(2-p-tolyl-ethylamino)-propyl]-3-ethylamino-5-(2-oxo-pyrrolidin-1-yl)-benzamide (E135) | | |
| N-[(1S,2R)-1-Benzyl-3-(dimethylamino-dimethyl-propylamino)-2-hydroxy-propyl]-3-ethylamino-5-(2-oxo-pyrrolidin-1-yl)-benzamide (E136) | | |

| Example | [M + H]+ | RT (min) |
|---|---|---|

-continued

N-{(1S,2R)-1-Benzyl-2-hydroxy-3-[(1H-indol-5-ylmethyl)-amino]-propyl}-3-ethylamino-5-(2-oxo-pyrrolidin-1-yl)-benzamide (E137)
N-{(1S,2R)-1-Benzyl-2-hydroxy-3-[(2-methyl-thiazol-4-ylmethyl)-amino]-propyl}-3-ethylamino-5-(2-oxo-pyrrolidin-1-yl)-benzamide (E138)
N-[(1S,2R)-1-Benzyl-3-(2-benzyloxy-ethylamino)-2-hydroxy-propyl]-3-ethylamino-5-(2-oxo-pyrrolidin-1-yl)-benzamide (E139)
N-[(1S,2R)-1-Benzyl-3-(3,4-dimethoxy-benzylamino)-2-hydroxy-propyl]-3-ethylamino-5-(2-oxo-pyrrolidin-1-yl)-benzamide (E140)
N-[(1S,2R)-1-Benzyl-2-hydroxy-3-(3-nitro-benzylamino)-propyl]-3-ethylamino-5-(2-oxo-pyrrolidin-1-yl)-benzamide (E141)
N-[(1S,2R)-1-Benzyl-3-(3-chloro-benzylamino)-2-hydroxy-propyl]-3-ethylamino-5-(2-oxo-pyrrolidin-1-yl)-benzamide (E142)
N-[(1S,2R)-1-Benzyl-3-(3-ethoxy-benzylamino)-2-hydroxy-propyl]-3-ethylamino-5-(2-oxo-pyrrolidin-1-yl)-benzamide (E143)
N-{(1S,2R)-1-Benzyl-3-[(5-chloro-thiophen-2-ylmethyl)-amino]-2-hydroxy-propyl}-3-ethylamino-5-(2-oxo-pyrrolidin-1-yl)-benzamide (E144)
N-{(1S,2R)-1-Benzyl-2-hydroxy-3-[(thiazol-2-ylmethyl)-amino]-propyl}-3-ethylamino-5-(2-oxo-pyrrolidin-1-yl)-benzamide (E145)
N-{(1S,2R)-1-Benzyl-2-hydroxy-3-[(pyridin-3-ylmethyl)-amino]-propyl}-3-ethylamino-5-(2-oxo-pyrrolidin-1-yl)-benzamide (E146)
N-[(1S,2R)-1-Benzyl-2-hydroxy-3-(4-hydroxy-3-methoxy-benzylamino)-propyl]-3-ethylamino-5-(2-oxo-pyrrolidin-1-yl)-benzamide (E147)
N-[(1S,2R)-1-Benzyl-2-hydroxy-3-(3-hydroxymethyl-benzylamino)-propyl]-3-ethylamino-5-(2-oxo-pyrrolidin-1-yl)-benzamide (E148)
N-{(1S,2R)-1-Benzyl-2-hydroxy-3-[3-(4-methoxy-phenyl)-propylamino]-propyl}-3-ethylamino-5-(2-oxo-pyrrolidin-1-yl)-benzamide (E149)
N-[(1S,2R)-1-Benzyl-3-(4-dimethylaminomethyl-benzylamino)-2-hydroxy-propyl]-3-ethylamino-5-(2-oxo-pyrrolidin-1-yl)-benzamide (E150)
N-[(1S,2R)-1-Benzyl-3-(3,4-difluoro-benzylamino)-2-hydroxy-propyl]-3-ethylamino-5-(2-oxo-pyrrolidin-1-yl)-benzamide (E151)
N-{(1S,2R)-1-Benzyl-2-hydroxy-3-[(5-methoxymethyl-furan-2-ylmethyl)-amino]-propyl}-3-ethylamino-5-(2-oxo-pyrrolidin-1-yl)-benzamide (E152)
N-[(1S,2R)-1-Benzyl-2-hydroxy-3-(3-propoxy-benzylamino)-propyl]-3-ethylamino-5-(2-oxo-pyrrolidin-1-yl)-benzamide (E153)
N-[(1S,2R)-1-Benzyl-3-(4-cyano-3-methoxy-benzylamino)-2-hydroxy-propyl]-3-ethylamino-5-(2-oxo-pyrrolidin-1-yl)-benzamide (E154)
N-[(1S,2R)-1-Benzyl-2-hydroxy-3-(3-imidazol-1-yl-benzylamino)-propyl]-3-ethylamino-5-(2-oxo-pyrrolidin-1-yl)-benzamide (E155)
N-[(1S,2R)-1-Benzyl-2-hydroxy-3-(3-pyrimidin-5-yl-benzylamino)-propyl]-3-ethylamino-5-(2-oxo-pyrrolidin-1-yl)-benzamide (E156)
N-{(1S,2R)-1-Benzyl-2-hydroxy-3-[(6-methoxy-pyridin-3-ylmethyl)-amino]-propyl}-3-ethylamino-5-(2-oxo-pyrrolidin-1-yl)-benzamide (E157)
N-{(1S,2R)-1-Benzyl-2-hydroxy-3-[(6-methoxy-pyridin-2-ylmethyl)-amino]-propyl}-3-ethylamino-5-(2-oxo-pyrrolidin-1-yl)-benzamide (E158)
N-[(1S,2R)-1-Benzyl-3-(3-tert-butoxymethyl-benzylamino)-2-hydroxy-propyl]-3-ethylamino-5-(2-oxo-pyrrolidin-1-yl)-benzamide (E159)
N-[(1S,2R)-1-Benzyl-2-hydroxy-3-(3-prop-2-ynyloxy-benzylamino)-propyl]-3-ethylamino-5-(2-oxo-pyrrolidin-1-yl)-benzamide (E160)
N-[(1S,2R)-3-(3-Acetylamino-benzylamino)-1-benzyl-2-hydroxy-propyl]-3-ethylamino-5-(2-oxo-pyrrolidin-1-yl)-benzamide (E161)
N-{(1S,2R)-1-Benzyl-2-hydroxy-3-[3-(3-methoxy-phenyl)-propylamino]-propyl}-3-ethylamino-5-(2-oxo-pyrrolidin-1-yl)-benzamide (E162)
N-{(1S,2R)-1-Benzyl-3-[3-(4-chloro-phenyl)-propylamino]-2-hydroxy-propyl}-3-ethylamino-5-(2-oxo-pyrrolidin-1-yl)-benzamide (E163)
N-[(1S,2R)-1-Benzyl-2-hydroxy-3-(3-p-tolyl-propylamino)-propyl]-3-ethylamino-5-(2-oxo-pyrrolidin-1-yl)-benzamide (E164)
N-{(1S,2R)-1-Benzyl-2-hydroxy-3-[3-(2H-tetrazol-5-yl)-benzylamino]-propyl}-3-ethylamino-5-(2-oxo-pyrrolidin-1-yl)-benzamide (E165)
N-{(1S,2R)-1-Benzyl-2-hydroxy-3-[3-(1H-pyrazol-3-yl)-benzylamino]-propyl}-3-ethylamino-5-(2-oxo-pyrrolidin-1-yl)-benzamide (E166)
N-{(1S,2R)-1-Benzyl-2-hydroxy-3-[3-(1H-imidazol-2-yl)-benzylamino]-propyl}-3-ethylamino-5-(2-oxo-pyrrolidin-1-yl)-benzamide (E167)
N-[(1S,2R)-1-Benzyl-3-(4-fluoro-3-methoxy-benzylamino)-2-hydroxy-propyl]-3-ethylamino-5-(2-oxo-pyrrolidin-1-yl)-benzamide (E168)
N-{(1S,2R)-1-Benzyl-3-[2,2-dimethyl-3-(2-oxo-pyrrolidin-1-yl)-propylamino]-2-hydroxy-propyl}-3-ethylamino-5-(2-oxo-pyrrolidin-1-yl)-benzamide (E169)
N-{(1S,2R)-3-[(Benzothiazol-6-ylmethyl)-amino]-1-benzyl-2-hydroxy-propyl}-3-ethylamino-5-(2-oxo-pyrrolidin-1-yl)-benzamide (E170)

Examples 171-181

Examples 171-181 were prepared in an analogous manner to Example 1 from the appropriate acid and amines indicated in the below table:

| Example | Acid | Amine | [M + H]$^+$ | RT (min) |
|---|---|---|---|---|
| N-[(1S,2R)-1-Benzyl-3-((S)-1-cyclohexylcarbamoylethylamino)-2-hydroxypropyl]-3-(2-oxopyrrolidin-1-yl)-5-propoxybenzamide formate salt (E171) | A10 | C6 | 579.4 | 2.34 |
| N-[(1S,2R)-1-Benzyl-3-((S)-1-cyclohexylcarbamoylethylamino)-2-hydroxypropyl]-3-methoxy-5-(2-oxopyrrolidin-1-yl)benzamide (E172) | A9 | C6 | 551.2 | 2.09 |
| N-[(1S,2R)-1-Benzyl-3-((S)-1-cyclohexylcarbamoylethylamino)-2-hydroxypropyl]-3-isopropoxy-5-(2-oxopyrrolidin-1-yl)benzamide (E173) | A12 | C6 | 579.2 | 2.68 |
| N-[(1S,2R)-1-Benzyl-3-((S)-1-cyclohexylcarbamoylethylamino)-2-hydroxypropyl]-3-(3-hydroxypropoxy)-5-(2-oxopyrrolidin-1-yl)benzamide (E174) | A15 | C6 | 595.2 | 2.40 |
| N-[(1S,2R)-1-Benzyl-3-((S)-1-cyclohexylcarbamoylethylamino)-2-hydroxypropyl]-3-(3-methoxypropoxy)-5-(2-oxopyrrolidin-1-yl)benzamide (E175) | A17 | C6 | 609.2 | 2.59 |
| N-[(1S,2R)-1-Benzyl-3-((S)-1-cyclohexylcarbamoylethylamino)-2-hydroxypropyl]-3-(2-hydroxyethoxy)-5-(2-oxopyrrolidin-1-yl)benzamide (E176) | A16 | C6 | 581.1 | 2.36 |
| N-[(1S,2R)-1-Benzyl-3-((S)-1-cyclohexylcarbamoylethylamino)-2-hydroxypropyl]-3-(2-methoxyethoxy)-5-(2-oxopyrrolidin-1-yl)benzamide (E177) | A14 | C6 | 595.2 | 2.50 |
| N-[(1S,2R)-1-Benzyl-3-((S)-1-cyclohexylcarbamoylethylamino)-2-hydroxypropyl]-3-(2-oxopyrrolidin-1-yl)-5-pentyloxybenzamide (E178) | A13 | C6 | 607.2 | 2.87 |
| N-[(1S,2R)-1-Benzyl-2-hydroxy-3-((S)-1-isobutylcarbamoylpentylamino)-propyl]-3-isopropoxy-5-(2-oxopyrrolidin-1-yl)benzamide (E179) | A12 | C36 | 595.2 | 2.75 |
| N-[(1S,2R)-1-Benzyl-2-hydroxy-3-(3-methoxybenzylamino)propyl]-3-isopropoxy-5-(2-oxopyrrolidin-1-yl)benzamide (E180) | A12 | C14 | 546.1 | 2.59 |
| N-[(1S,2R)-1-Benzyl-3-((S)-1-cyclohexylcarbamoylethylamino)-2-hydroxypropyl]-3-ethoxy-5-(2-oxopyrrolidin-1-yl)benzamide (E181) | A11 | C6 | 565.2 | 2.54 |

Example 182

N-((1S,2R)-3-Amino-1-benzyl-2-hydroxypropyl)-3-(2-oxopyrrolidin-1-yl)-5-pentyloxybenzamide (E182)

A mixture of [(2R,3S)-2-hydroxy-3-({1-[3-(2-oxo-pyrrolidin-1-yl)-5-pentyloxy-phenyl]-methanoyl}-amino)-4-phenyl-butyl]-carbamic acid benzyl ester (D105) (820 mg, 1.4 mmol, 1 equiv), 10% palladium on charcoal (50% wet, 100 mg, 6% w/w), NH$_4$CO$_2$H (800 mg, 12.7 mmol, 9 equiv), EtOH (25 ml) and H$_2$O (10 ml) was stirred at 60° C. for 1 h. The mixture was then cooled to room temperature and the catalyst was filtered off through a pad of celite. Most of the EtOH was removed in vacuo and the residue was partitioned between AcOEt and H$_2$O. The aqueous phase was extracted with AcOEt. The combined organic phases were dried over MgSO$_4$ and concentrated in vacuo to give N-((1S,2R)-3-amino-1-benzyl-2-hydroxy-propyl)-3-(2-oxo-pyrrolidin-1-yl)-5-pentyloxy-benzamide (420 mg, 66%) as a white solid. [M+H]$^+$=454.0, RT=2.63 min Example 183

N-[(1S,2R)-1-Benzyl-2-hydroxy-3-(1-propylbutylamino)-propyl]-3-(2-oxopyrrolidin-1-yl)-5-pentyloxybenzamide (E183)

To a solution of N-((1S,2R)-3-amino-1-benzyl-2-hydroxy-propyl)-3-(2-oxo-pyrrolidin-1-yl)-5-pentyloxy-benzamide (E182) (30 mg, 0.066 mmol, 1 equiv) in (CH$_2$Cl)$_2$ (5 ml) were added sodium triacetoxyborohydride (20 mg, 0.094 mmol, 1.4 equiv), 4-heptanone (10 μl, 0.070 mmol, 1.1 equiv) and CH$_3$COOH (4 μl, 0.070 mmol, 1,1 equiv). The resulting mixture was stirred at room temperature for 92 hours, diluted with CH$_2$Cl$_2$, washed with saturated aqueous NaHCO$_3$ solution, dried over MgSO$_4$ and concentrated in vacuo. Purification of the residue by flash chromatography on silica gel (iso-hexane/ethyl acetate: 3/2) gave N-[(1S,2R)-1-benzyl-2-hydroxy-3-(1-propyl-butylamino)-propyl]-3-(2-oxo-pyrrolidin-1-yl)-5-pentyloxy-benzamide (4.2 mg, 11%) as a colourless oil. [M+H]$^+$=552.2, RT=2.98 min

Examples 184-192

The following compounds were prepared in an analogous manner to Example 183 from 3-pentoxy-5-(2-oxo-pyrrolidin-1-yl)-benzoic acid (A13) and the appropriate aldehyde or ketone:

| Example | [M + H]$^+$ | RT (min) |
|---|---|---|
| N-[(1S,2R)-1-Benzyl-2-hydroxy-3-(3-methoxybenzylamino)-propyl]-3-(2-oxopyrrolidin-1-yl)-5-pentyloxybenzamide (E184) | 574.2 | 2.87 |
| N-((1S,2R)-1-Benzyl-3-benzylamino-2-hydroxypropyl)-3-(2-oxopyrrolidin-1-yl)-5-pentyloxybenzamide (E185) | 544.1 | 2.83 |
| N-((1S,2R)-1-Benzyl-3-ethylamino-2-hydroxypropyl)-3-(2-oxopyrrolidin-1-yl)-5-pentyloxy-benzamide (E186) | 482.2 | 2.70 |
| N-((1S,2R)-1-Benzyl-2-hydroxy-3-phenethylaminopropyl)-3-(2-oxopyrrolidin-1-yl)-5-pentyloxybenzamide (E187) | 558.2 | 2.91 |
| N-[(1S,2R)-1-Benzyl-2-hydroxy-3-(2-phenylpropylamino)-propyl]-3-(2-oxopyrrolidin-1-yl)-5-pentyloxybenzamide (E188) | 572.2 | 2.95 |
| N-((1S,2R)-1-Benzyl-3-cyclohexylamino-2-hydroxypropyl)-3-(2-oxopyrrolidin-1-yl)-5-pentyloxybenzamide (E189) | 536.2 | 2.84 |
| N-[(1S,2R)-1-Benzyl-2-hydroxy-3-(1-methylpiperidin-4-ylamino)-propyl]-3-(2-oxopyrrolidin-1-yl)-5-pentyloxybenzamide (E190) | 551.2 | 2.43 |
| N-[(1S,2R)-1-Benzyl-2-hydroxy-3-(3-methylbutylamino)-propyl]-3-(2-oxopyrrolidin-1-yl)-5-pentyloxybenzamide (E191) | 524.2 | 2.87 |
| N-[(1S,2R)-1-Benzyl-3-(1-ethylpropylamino)-2-hydroxypropyl]-3-(2-oxopyrrolidin-1-yl)-5-pentyloxybenzamide (E192) | 594.3 | 3.09 |

Examples 193-204

Examples 193-204 were prepared in an analogous manner to Example 1 from the appropriate acid and amines indicated in the below table:

| Example | Acid | Amine | [M + H]$^+$ | RT (min) |
|---|---|---|---|---|
| N-[(1S,2R)-1-Benzyl-3-(1,5-dimethylhexylamino)-2-hydroxy-propyl]-3-isopropoxy-5-(2-oxopyrrolidin-1-yl)benzamide (E193) | A11 | C20 | 538.3 | 2.81 |
| N-[1-Benzyl-2-hydroxy-3-(3-trifluoromethylbenzylamino)propyl]-3-ethoxy-5-(2-oxopyrrolidin-1-yl)benzamide (E194) | A11 | C16 | 570.3 | 2.64 |
| N-[1-Benzyl-3-(1,5-dimethylhexylamino)-2-hydroxypropyl]-3-ethoxy-5-(2-oxopyrrolidin-1-yl)benzamide formate salt (E195) | A11 | C20 | 524.3 | 2.74 |
| N-(1-Benzyl-3-cyclohexylamino-2-hydroxypropyl)-3-ethoxy-5-(2-oxopyrrolidin-1-yl)benzamide (E196) | A11 | C1 | 494.3 | 2.45 |
| N-[1-Benzyl-2-hydroxy-3-(3-methoxybenzylamino)propyl]-3-ethoxy-5-(2-oxopyrrolidin-1-yl)benzamide (E197) | A11 | C14 | 532.3 | 2.50 |
| N-[(1S,2R)-1-Benzyl-3-((S)-1-cyclohexyl carbamoylethylamino)-2-hydroxypropyl]-3-methanesulfonyl-5-(2-oxopyrrolidin-1-yl)benzamide (E198) | A5 | C6 | 599.1 | 2.41 |
| N-[1-Benzyl-2-hydroxy-3-(3-trifluoromethylbenzylamino)propyl]-3-methylsulfanyl-5-(2-oxopyrrolidin-1-yl)-benzamide (E199) | A1 | C16 | 572.2 | 2.72 |
| N-[1-Benzyl-2-hydroxy-3-(3-trifluoromethylbenzylamino)propyl]-3-ethylsulfanyl-5-(2-oxopyrrolidin-1-yl)benzamide (E200) | A2 | C16 | 586.2 | 2.80 |
| N-[1-Benzyl-2-hydroxy-3-(3-trifluoromethylbenzylamino)propyl]-3-ethanesulfonyl-5-(2-oxopyrrolidin-1-yl)-benzamide (E201) | A6 | C16 | 618.2 | 2.70 |
| N-[1-Benzyl-2-hydroxy-3-(3-trifluoromethylbenzylamino)propyl]-3-methanesulfonyl-5-(2-oxopyrrolidin-1-yl)-benzamide (E202) | A5 | C16 | 604.1 | 2.57 |
| N-[(1S,2R)-1-Benzyl-3-((S)-1-cyclohexylcarbamoylethylamino)-2- | A94 | C6 | 684.2 | 2.67 |

-continued

| Example | Acid | Amine | [M + H]+ | RT (min) |
|---|---|---|---|---|
| hydroxypropyl]-5-(1,1-dioxo-1/$^6$-isothiazolidin-2-yl)-N',N'-dipropylisophthalamide (E203) | | | | |
| 3-Azidomethyl-N-[(1S,2R)-1-benzyl-3-((S)-1-cyclohexylcarbamoylethylamino)-2-hydroxypropyl]-5-(1,1-dioxo-1/$^6$-isothiazolidin-2-yl)benzamide (E204) | A85 | C6 | 612.2 | 2.52 |

Example 205

3-Aminomethyl-N-[(1S,2R)-1-benzyl-3-((S)-1-cyclohexylcarbamoylethylamino)-2-hydroxypropyl]-5-(1,1-dioxo-1/$^6$-isothiazolidin-2-yl)benzamide (E205)

A mixture of 3-azidomethyl-N-[(1S,2R)-1-benzyl-3-((S)-1-cyclohexylcarbamoyl-ethylamino)-2-hydroxy-propyl]-5-(1,1-dioxo-1/$^6$-isothiazolidin-2-yl)-benzamide (E204) (70 mg, 0.12 mmol, 1 equiv), 10% palladium on charcoal (50% wet, 20 mg, 15% w/w), NH$_4$COOH (65 mg, 1 mmol, 9 equiv), EtOH (5 ml) and H$_2$O (2.5 ml) was stirred at 50° C. for 2 h, cooled to room temperature and the catalyst was filtered off through a pad of celite. Most of the EtOH was removed in vacuo and the residue was partitioned between AcOEt and saturated aqueous NaHCO$_3$ solution. The aqueous phase was extracted with AcOEt. The combined organic phases were dried over MgSO$_4$ and concentrated in vacuo. The residue was triturated with Et$_2$O to give 3-aminomethyl-N-[(1S,2R)-1-benzyl-3-((S)-1-cyclohexylcarbamoyl-ethylamino)-2-hydroxy-propyl]-5-(1,1-dioxo-1/$^6$-isothiazolidin-2-yl)-benzamide (20 mg, 30%) as a white solid. [M+H]$^+$= 586.2 RT=1.98 min

Examples 206-207

Examples 206-207 were prepared in an analogous manner to Example 1 from the appropriate acid and amines indicated in the below table:

| Example | Acid | Amine | [M + H]+ | RT (min) |
|---|---|---|---|---|
| N-[(1S,2R)-1-Benzyl-3-((S)-1-cyclohexylcarbamoylethylamino)-2-hydroxypropyl]-3-dimethylaminomethyl-5-(1,1-dioxo-1/$^6$-isothiazolidin-2-yl)-benzamide (E206) | A84 | C6 | 614.2 | 1.99 |
| N-[(1S,2R)-1-Benzyl-3-((S)-1-cyclohexylcarbamoylethylamino)-2-hydroxypropyl]-3-(1,1-dioxo-1/$^6$-isothiazolidin-2-yl)-5-vinyl-benzamide (E207) | A88 | C6 | 583.1 | 2.53 |

Example 208

N-[(1S,2R)-1-Benzyl-3-((S)-1-cyclohexylcarbamoylethylamino)-2-hydroxypropyl]-3-(1,1-dioxo-1/$^6$-isothiazolidin-2-yl)-5-ethyl-benzamide (E208)

Example 208 was prepared from Example 214 in an analogous manner to that described for Example 213. [M+H]$^+$=585.2, RT=2.56 min

Examples 209-212

Examples 209-212 were prepared in an analogous manner to Example 1 from the appropriate acid and amines indicated in the below table:

| Example | Acid | Amine | [M + H]+ | RT (min) |
|---|---|---|---|---|
| N-[(1S,2R)-1-Benzyl-3-((S)-1-cyclohexylcarbamoylethylamino)-2-hydroxypropyl]-3-(1,1-dioxo-1/$^6$-isothiazolidin-2-yl)-5-methoxymethylbenzamide (E209) | A86 | C6 | 601.2 | 2.41 |
| N-[(1S,2R)-1-Benzyl-3-((S)-1-cyclohexylcarbamoylethylamino)-2-hydroxypropyl]-3-(1,1-dioxo-1/$^6$-isothiazolidin-2-yl)-5-ethoxymethylbenzamide (E210) | A87 | C6 | 615.2 | 2.50 |
| N-[(1S,2R)-1-Benzyl-3-((S)-1-cyclohexylcarbamoylethylamino)-2-hydroxypropyl]-3-(1,1-dioxo-1/$^6$-isothiazolidin-2-yl)-5-(Z/E)-propenylbenzamide (E211) | A89 | C6 | 597.2 | 2.61 |

| Example | Acid | Amine | [M + H]⁺ | RT (min) |
|---|---|---|---|---|
| N-[(1S,2R)-1-Benzyl-3-((S)-1-cyclohexylcarbamoylethylamino)-2-hydroxypropyl]-3-(Z/E)-but-1-enyl-5-(1,1-dioxo-1/⁶-isothiazolidin-2-yl)benzamide (E212) | A90 | C6 | 611.2 | 2.70 |

Example 213

N-[(1S,2R)-1-Benzyl-3-((S)-1-cyclohexylcarbamoylethylamino)-2-hydroxypropyl]-3-(1,1-dioxo-1/⁶-isothiazolidin-2-yl)-5-propylbenzamide (E213)

A mixture of N-[(1S,2R)-1-benzyl-3-((S)-1-cyclohexylcarbamoyl-ethylamino)-2-hydroxy-propyl]-3-(1,1-dioxo-1/⁶-isothiazolidin-2-yl)-5-propenyl-benzamide (E211) (50 mg, 0.083 mmol, 1 equiv), 10% palladium on charcoal (50% wet, 15 mg, 15% w/w), NH₄COOH (50 mg, 0.79 mmol, 9 equiv) and EtOH (5 ml) was stirred at 60° C. for 1 h, cooled to room temperature and the catalyst was filtered off through a pad of celite. Most of the EtOH was removed in vacuo and the residue was partitioned between AcOEt and saturated aqueous NaHCO₃ solution. The aqueous phase was extracted with AcOEt. The combined organic phases were dried over MgSO₄ and concentrated in vacuo. The residue was triturated with Et₂O to give of N-[(1S,2R)-1-benzyl-3-((S)-1-cyclohexylcarbamoyl-ethylamino)-2-hydroxy-propyl]-3-(1,1-dioxo-1/⁶-isothiazolidin-2-yl)-5-propyl-benzamide (45 mg, 90%) as a white solid. [M+H]⁺=599.2, RT=2.63 min

Example 214

N-[(1S,2R)-1-Benzyl-3-((S)-1-cyclohexylcarbamoylethylamino)-2-hydroxypropyl]-3-butyl-5-(1,1-dioxo-1/⁶-isothiazolidin-2-yl)benzamide (E214)

Example 214 was prepared from N-[(1S,2R)-1-benzyl-3-((S)-1-cyclohexylcarbamoylethylamino)-2-hydroxypropyl]-3-(Z/E)-but-1-enyl-5-(1,1-dioxo-1/⁶-isothiazolidin-2-yl)benzamide (E212) in an analogous manner to that described in Example 213. [M+H]⁺=613.2, RT=2.75 min

Examples 215-216

Examples 215-216 were prepared in an analogous manner to Example 1 from the appropriate acid and amines indicated in the below table:

| Example | Acid | Amine | [M + H]⁺ | RT (min) |
|---|---|---|---|---|
| N-[(1S,2R)-1-Benzyl-3-((S)-1-cyclohexylcarbamoylethylamino)-2-hydroxypropyl]-3-(1,1-dioxo-1/⁶-isothiazolidin-2-yl)-5-(2-methylpropenyl)-benzamide (E215) | A91 | C6 | 611.2 | 2.70 |
| N-[(1S,2R)-1-Benzyl-3-((S)-1-cyclohexylcarbamoylethylamino)-2-hydroxypropyl]-3-(1,1-dioxo-1/⁶-isothiazolidin-2-yl)-5-fluoromethylbenzamide (E216) | A83 | C6 | 589.2 | 2.44 |

Example 217

N-[1-Benzyl-3-(1-cyclohexylcarbamoylethylamino)-2-hydroxy-propyl]-3-(1,1-dioxo-1/⁶-isothiazolidin-2-yl)-5-isobutylbenzamide (E217)

Example 217 was prepared from Example 215 in an analogous manner to that described in Example 213. [M+H]⁺=613.3, RT=2.72 min

Examples 218-220 and 222

Examples 218-220 and 222 were prepared in an analogous manner to Example 213 from the appropriate amine indicated in the table below:

| Example | Amine | [M + H]⁺ | RT (min) |
|---|---|---|---|
| N-[1-Benzyl-2-hydroxy-3-(3-trifluoromethylbenzylamino)propyl]-3-(1,1-dioxo-1/⁶-isothiazolidin-2-yl)-5-propylbenzamide (E218) | C16 | 604.3 | 2.76 |
| N-[1-Benzyl-3-(1,5-dimethylhexylamino)-2-hydroxypropyl]-3-(1,1-dioxo-1/⁶-isothiazolidin-2-yl)-5-propylbenzamide formate salt (E219) | C26 | 558.3 | 2.87 |

-continued

| Example | Amine | [M + H]⁺ | RT (min) |
|---|---|---|---|
| N-(1-Benzyl-3-cyclohexylamino-2-hydroxypropyl)-3-(1,1-dioxo-1/⁶-isothiazolidin-2-yl)-5-propylbenzamide (E220) | C6 | 528.3 | 2.61 |
| N-[1-Benzyl-2-hydroxy-3-(3-methoxybenzylamino)propyl]-3-(1,1-dioxo-1/⁶-isothiazolidin-2-yl)-5-propyl-benzamide (E222) | C14 | 566.2 | 2.64 |

Examples 221 and 223-226

Examples 221 and 223-226 were prepared in an analogous manner to Example 1 from the appropriate acid and amines indicated in the below table:

| Example | Acid | Amine | [M + H]⁺ | RT (min) |
|---|---|---|---|---|
| N-[1-Benzyl-3-(1-cyclohexylcarbamoylethylamino)-2-hydroxypropyl]-5-(1,1-dioxo-1/⁶-isothiazolidin-2-yl)isophthalamide (E221) | A92 | C6 | 600.2 | 2.23 |
| N-[1-Benzyl-3-(1-cyclohexylcarbamoylethylamino)-2-hydroxypropyl]-3-cyano-5-(1,1-dioxo-1/⁶-isothiazolidin-2-yl)benzamide (E223) | A93 | C6 | 582.2 | 2.47 |
| N-[1-Benzyl-2-hydroxy-3-(3-trifluoromethylbenzylamino)propyl]-3-cyano-5-(1,1-dioxo-1/⁶-isothiazolidin-2-yl)benzamide (E224) | A93 | C16 | 587.2 | 2.43 |
| N-[1-Benzyl-2-hydroxy-3-(3-trifluoromethylbenzylamino)propyl]-3-(1,1-dioxo-1/⁶-isothiazolidin-2-yl)-5-ethynyl-benzamide formate salt (E225) | A111 | C16 | 586.2 | 2.71 |
| N-[(1S,2R)-1-Benzyl-3-((S)-1-cyclohexylcarbamoylethylamino)-2-hydroxypropyl]-3-nitro-5-(2-oxopiperidin-1-yl)benzamide (E226) | A82 | C6 | 580.2 | 2.55 |

Example 227

3-Amino-N-[(1S,2R)-1-benzyl-3-((S)-1-cyclohexylcarbamoylethylamino)-2-hydroxypropyl]-5-(2-oxopiperidin-1-yl)benzamide (E227)

Example 227 was prepared from Example 226 in an analogous manner to the process described for Example 63. [M+H]⁺=550.1, RT=2.31 min

Examples 228-251

Examples 228-251 were prepared in an analogous manner to Example 1 from the appropriate acid and amines indicated in the below table:

| Example | Acid | Amine | [M + H]⁺ | RT (min) |
|---|---|---|---|---|
| N-[(1S,2R)-1-Benzyl-3-((S)-1-cyclohexylcarbamoylethylamino)-2-hydroxypropyl]-3-(2-oxopiperidin-1-yl)-5-propylaminobenzamide (E228) | A58 | C6 | 592.2 | 2.59 |
| N-[(1S,2R)-1-Benzyl-3-((S)-1-cyclohexylcarbamoylethylamino)-2-hydroxypropyl]-3-diethylamino-5-(2-oxopiperidin-1-yl)benzamide (E229) | A60 | C6 | 606.3 | 2.62 |
| N-[(1S,2R)-1-Benzyl-3-((S)-1-cyclohexylcarbamoylethylamino)-2-hydroxypropyl]-3-ethylamino-5-(2-oxopiperidin-1-yl)benzamide (E230) | A59 | C6 | 578.2 | 2.46 |
| N-[(1S,2R)-1-Benzyl-3-((S)-1-cyclohexylcarbamoylethylamino)-2-hydroxypropyl]-3-methylamino-5-(2-oxopiperidin-1-yl)benzamide (E231) | A57 | C6 | 564.3 | 2.40 |
| N-[(1S,2R)-1-Benzyl-3-((S)-1-cyclohexylcarbamoylethylamino)-2-hydroxypropyl]-3-(2-oxopiperidin-1-yl)-5-piperidin-1-ylbenzamide (E232) | A55 | C6 | 618.3 | 2.65 |
| N-[(1S,2R)-1-Benzyl-3-((S)-1-cyclohexylcarbamoylethylamino)-2-hydroxypropyl]-3-morpholin-4-yl-5-(2-oxopiperidin-1-yl)benzamide (E233) | A56 | C6 | 620.3 | 2.43 |
| N-[(1S,2R)-1-Benzyl-3-((S)-1-cyclohexylcarbamoylethylamino)-2-hydroxypropyl]-3-(2-oxopiperidinl-1-yl)-5-pyrrolidin-1-yl-benzamide (E234) | A54 | C6 | 604.3 | 2.64 |

-continued

| Example | Acid | Amine | [M + H]+ | RT (min) |
|---|---|---|---|---|
| N-[(1S,2R)-1-Benzyl-3-((S)-1-cyclohexylcarbamoylethylamino)-2-hydroxypropyl]-3-(1,1-dioxo-1/6-isothiazolidin-2-yl)-5-isopropylaminobenzamide (E235) | A72 | C6 | 614.2 | 2.58 |
| N-[(1S,2R)-1-Benzyl-2-hydroxy-3-((1S,2R)-2-hydroxy-1-isobutylcarbamoyl-pentylamino)-propyl]-3-(1,1-dioxo-1/6-isothiazolidin-2-yl)-5-isopropylaminobenzamide (E236) | A72 | C33 | 646.2 | 2.63 |
| 3-Benzylamino-N-[(1S,2R)-1-benzyl-3((S)-1-cyclohexylcarbamoylethylamino)-2-hydroxy-propyl]-5-(1,1-dioxo-1/6-isothiazolidin-2-yl)benzamide (E237) | A64 | C6 | 662.2 | 2.71 |
| N-[(1S,2R)-1-Benzyl-3-((S)-1-cyclohexylcarbamoylethylamino)-2-hydroxypropyl]-3-butylamino-5-(1,1-dioxo-1/6-isothiazolidin-2-yl)benzamide (E238) | A65 | C6 | 628.2 | 2.71 |
| N-[(1S,2R)-1-Benzyl-3-((S)-1-cyclohexlcarbamoylethylamino)-2-hydroxypropyl]-3-(1,1-dioxo-1/6-isothiazolidin-2-yl)-5-(3-methylbutylamino)-benzamide (E239) | A66 | C6 | 642.2 | 2.79 |
| N-[(1S,2R)-1-Benzyl-3-((S)-1-cyclohexylcarbamoylethylamino)-2-hydroxypropyl]-3-(1,1-dioxo-1/6-isothiazolidin-2-yl)-5-phenethylamino-benzamide (E240) | A67 | C6 | 676.2 | 2.80 |
| N-[(1S,2R)-1-Benzyl-3-((S)-1-cyclohexylcarbamoylethylamino)-2-hydroxypropyl]-3-(1,1-dioxo-1/6-isothiazolidin-2-yl)-5-pentylaminobenzamide (E241) | A68 | C6 | 642.2 | 2.79 |
| N-[(1S,2R)-1-Benzyl-3-((S)-1-cyclohexlcarbamoylethylamino)-2-hydroxypropyl]-3-(1,1-dioxo-1/6-isothiazolidin-2-yl)-5-propylaminobenzamide (E242) | A69 | C6 | 614.2 | 2.57 |
| N-[(1S,2R)-1-Benzyl-3-((S)-1-cyclohexylcarbamoylethylamino)-2-hydroxypropyl]-3-(1,1-dioxo-1/6-isothiazolidin-2-yl)-5-ethylaminobenzamide (E243) | A70 | C6 | 600.2 | 2.47 |
| N-[(1S,2R)-1-Benzyl-3-((S)-1-cyclohexylcarbamoylethylamino)-2-hydroxypropyl]-3-diethylamino-5-(1,1-dioxo-1/6-isothiazolidin-2-yl)benzamide (E244) | A63 | C6 | 628.2 | 2.63 |
| N-[(1S,2R)-1-Benzyl-3-(1,5-dimethylhexylamino)-2-hydroxypropyl]-3-(1,1-dioxo-1/6-isothiazolidin-2-yl)-5-ethylaminobenzamide (E245) | A70 | C20 | 559.2 | 2.68 |
| N-[(1S,2R)-1-Benzyl-3-(1,5-dimethylhexylamino)-2-hydroxypropyl]-3-(1,1-dioxo-1/6-isothiazolidin-2-yl)-5-isopropylaminobenzamide (E246) | A72 | C20 | 573.2 | 2.77 |
| N-[(1S,2R)-1-Benzyl-3-((S)-1-cyclohexylcarbamoylethylamino)-2-hydroxypropyl]-3-(cyclopropylmethylamino)-5-(1,1-dioxo-1/6-isothiazolidin-2-yl)benzamide (E247) | A71 | C6 | 626.2 | 2.59 |
| N-[(1S,2R)-1-Benzyl-2-hydroxy-3-(3-methoxybenzylamino)propyl]-3-(1,1-dioxo-1/6-isothiazolidin-2-yl)-5-ethylaminobenzamide formate salt (E248) | A70 | C14 | 567.2 | 2.44 |
| N-[(1S,2R)-1-Benzyl-2-hydroxy-3-(3-trifluoromethylbenzylamino)propyl]-3-(1,1-dioxo-1/6-isothiazolidin-2-yl)-5-ethylaminobenzamide formate salt (E249) | A70 | C16 | 605.1 | 2.60 |
| N-((1S,2R)-1-Benzyl-3-cyclohexylamino-2-hydroxypropyl)-3-(1,1-dioxo-1/6-isothiazolidin-2-yl)-5-ethylaminobenzamide (E250) | A70 | C1 | 529.3 | 2.40 |
| N-[1-Benzyl-2-hydroxy-3-(3-trifluoromethylbenzylamino)propyl]-3-(1,1-dioxo-1/6-isothiazolidin-2-yl)-5-morpholin-4-yl-benzamide formate salt (E251) | A61 | C16 | 647.3 | 2.39 |

Example 252

N-[(1S,2R)-1-Benzyl-2-hydroxy-3-(3-trifluoromethyl-benzylamino)-propyl]-3-(1,1-dioxo-1/$^6$-isothiazolidin-2-yl)-5-pyrrolidin-1-yl-benzamide formate salt (E252)

To a solution of 3-(1,1-dioxo-1/$^6$-isothiazolidin-2-yl)-5-pyrrolidin-1-yl-benzoic acid (A114) (62 mg, 0.2 mmol, 1 equiv) in DMF (5 ml) at room temperature was added (2R,3S)-3-amino-4-phenyl-1-(3-trifluoromethyl-benzylamino)-butan-2-ol (C16) (82 mg, 0.2 mmol, 1 equiv), 1-(3-dimethylaminopropyl)-3-ethyl-carbodiimide hydrochloride (46 mg, 0.24 mmol, 1.2 equiv), 1-hydroxybenzotriazole hydrate (37 mg, 0.24 mmol, 1.2 equiv) and 4-ethyl-morpholine (152 μl, 1.2 mmol, 6 equiv). The resulting mixture was stirred for 4 h then concentrated in vacuo. The residue was diluted with AcOEt and the organic phase washed with saturated aqueous NaHCO$_3$ solution, dried over MgSO$_4$ and concentrated in vacuo. The residue was purified by trituration with Et$_2$O to yield N-[(1S,2R)-1-benzyl-2-hydroxy-3-(3-trifluoromethyl-benzylamino)-propyl]-3-(1,1-dioxo-1/$^6$-isothiazolidin-2-yl)-5-pyrrolidin-1-yl-benzamide as a white solid (46 mg, 36%). [M+H]$^+$=631.2, RT=2.65 min

Examples 253-289

Examples 253-289 were prepared in an analogous manner to Example 1 from the appropriate acid and amines indicated in the below table:

| Example | Acid | Amine | [M + H]$^+$ | RT (min) |
| --- | --- | --- | --- | --- |
| N-[1-Benzyl-2-hydroxy-3-(3-trifluoromethylbenzylamino)propyl]-3-(1,1-dioxo-1-l6-isothiazolidin-2-yl)-5-methylaminobenzamide formate salt (E253) | A62 | C16 | 591.2 | 2.58 |
| N-[(1S,2R)-1-Benzyl-3-((S)-1-cyclohexylcarbamoylethylamino)-2-hydroxypropyl]-3-(1,1-dioxo-1/$^6$-isothiazolidin-2-yl)-5-ethoxybenzamide (E254) | A18 | C6 | 601.2 | 2.54 |
| N-[1-Benzyl-2-hydroxy-3-(3-trifluoromethylbenzylamino)propyl]-3-(1,1-dioxo-1/$^6$-isothiazolidin-2-yl)-5-ethoxy-benzamide (E255) | A18 | C16 | 606.2 | 2.66 |
| N-[1-Benzyl-3-(1,5-dimethylhexylamino)-2-hydroxypropyl]-3-(1,1-dioxo-1/$^6$-isothiazolidin-2-yl)-5-ethoxybenzamide formate salt (E256) | A18 | C20 | 560.3 | 2.74 |
| N-[1-Benzyl-2-hydroxy-3-(3-methoxybenzylamino)propyl]-3-(1,1-dioxo-1/$^6$-isothiazolidin-2-yl)-5-ethoxybenzamide (E257) | A18 | C14 | 568.3 | 2.50 |
| N-(1-Benzyl-3-cyclohexylamino-2-hydroxypropyl)-3-(1,1-dioxo-1/$^6$-isothiazolidin-2-yl)-5-ethoxybenzamide (E258) | A18 | C1 | 530.2 | 2.47 |
| N-[1-Benzyl-3-(1-cyclohexylcarbamoylethylamino)-2-hydroxypropyl]-3-(1,1-dioxo-1/$^6$-isothiazolidin-2-yl)-5-isopropoxybenzamide (E259) | A19 | C6 | 615.4 | 2.68 |
| N-[1-Benzyl-3-(1-cyclohexylcarbamoylethylamino)-2-hydroxypropyl]-3-(1,1-dioxo-1/$^6$-isothiazolidin-2-yl)-5-propoxybenzamide (E260) | A21 | C6 | 615.4 | 2.89 |
| N-[1-Benzyl-3-(1-cyclohexylcarbamoylethylamino)-2-hydroxypropyl]-3-(1,1-dioxo-1/$^6$-isothiazolidin-2-yl)-5-pentyloxybenzamide (E261) | A22 | C6 | 643.5 | 2.89 |
| N-[1-Benzyl-3-(1-cyclohexylcarbamoylethylamino)-2-hydroxypropyl]-3-(1,1-dioxo-1/$^6$-isothiazolidin-2-yl)-5-methoxybenzamide (E262) | A20 | C6 | 587.4 | 2.49 |
| N-(1-Benzyl-3-cyclopropylamino-2-hydroxypropyl)-3-(1,1-dioxo-1/$^6$-isothiazolidin-2-yl)-5-ethoxybenzamide (E263) | A18 | C26 | 488.2 | 2.37 |
| N-[1-Benzyl-2-hydroxy-3-(3-trifluoromethoxybenzylamino)propyl]-3-(1,1-dioxo-1/$^6$-isothiazolidin-2-yl)-5-ethoxybenzamide (E264) | A18 | C11 | 622.2 | 2.91 |
| N-[1-Benzyl-2-hydroxy-3-(3-trifluoromethylbenzylamino)propyl]-3-(1,1-dioxo-1/$^6$-isothiazolidin-2-yl)-5-methylsulfanylbenzamide (E265) | A3 | C16 | 608.2 | 2.73 |
| N-[1-Benzyl-2-hydroxy-3-(3-trifluoromethylbenzylamino)propyl]-3-(1,1-dioxo-1/$^6$-isothiazolidin-2-yl)-5-ethylsulfanylbenzamide (E266) | A4 | C16 | 622.2 | 2.82 |
| N-[1-Benzyl-2-hydroxy-3-(3-trifluoromethylbenzylamino)propyl]-3-(1,1-dioxo-1/$^6$-isothiazolidin-2-yl)-5-ethanesulfonylbenzamide (E267) | A8 | C16 | 654.1 | 2.65 |
| N-[1-Benzyl-2-hydroxy-3-(3-trifluoromethylbenzylamino)propyl]-3-(1,1-dioxo-1/$^6$-isothiazolidin-2-yl)-5-Methanesulfonylbenzamide (E268) | A7 | C16 | 640.2 | 2.62 |
| N-[(1S,2R)-1-Benzyl-3-((S)-1-cyclohexylcarbamoylethylamino)-2-hydroxypropyl]-5-(2-oxopiperidin-1-yl)-N',N'-dipropylisophthalamide (E269) | A81 | C6 | 662.3 | 2.63 |
| formic acid-3-(1,1-dioxidotetrahydro-2H-1,2-thiazin-2-yl)-2-fluoro-N-{(1S,2R)-2-hydroxy-1-(phenylmethyl)-3-[({3-[(trifluoromethyl)oxy]phenyl}methyl)amino]propyl}-5-[(1-methylethyl)amino]benzamide (1:1) (E270) | A175 | C11 | 667.4 | 2.82 |

-continued

| Example | Acid | Amine | [M + H]+ | RT (min) |
|---|---|---|---|---|
| 3-(1,1-dioxidotetrahydro-2H-1,2-thiazin-2-yl)-5-(ethylamino)-N-[(1S,2R)-3-{[(3-ethyl-5-isoxazolyl)methyl]amino}-2-hydroxy-1-(phenylmethyl)propyl]-2-fluorobenzamide (E271) | A119 | C157 | 588.4 | 2.30 |
| 4-(1,1-dioxidotetrahydro-2H-1,2-thiazin-2-yl)-1-ethyl-N-[(1S,2R)-2-hydroxy-1-(phenylmethyl)-3-(tetrahydro-2H-pyran-4-ylamino)propyl]-1H-benzimidazole-6-carboxamide (E272) | A151 | C43 | 570.4 | 1.91 |
| 8-(1,1-dioxido-2-isothiazolidinyl)-4-ethyl-N-[(1S,2R)-2-hydroxy-1-(phenylmethyl)-3-(tetrahydro-2H-pyran-4-ylamino)propyl]-1,2,3,4-tetrahydro-6-quinoxalinecarboxamide (E273) | A172 | C43 | 572.4 | 2.08 |
| 8-(1,1-dioxido-2-isothiazolidinyl)-4-ethyl-N-[(1S,2R)-3-{[(1-ethyl-1H-pyrazol-4-yl)methyl]amino}-2-hydroxy-1-(phenylmethyl)propyl]-1,2,3,4-tetrahydro-6-quinoxalinecarboxamide (E274) | A172 | C154 | 596.4 | 2.15 |
| 4-(1,1-dioxidotetrahydro-2H-1,2-thiazin-2-yl)-1-ethyl-N-[(1S,2R)-2-hydroxy-3-[(1-methylethyl)amino]-1-(phenylmethyl)propyl]-1H-benzimidazole-6-carboxamide (E275) | A151 | C28 | 528.4 | 1.92 |
| 8-(1,1-dioxido-2-isothiazolidinyl)-4-ethyl-N-[(1S,2R)-2-hydroxy-3-[(1-methylethyl)amino]-1-(phenylmethyl)propyl]-1,2,3,4-tetrahydro-6-quinoxalinecarboxamide (E276) | A172 | C28 | 530.4 | 2.11 |
| N-[(1S,2R)-1-Benzyl-3-((S)-1-cyclohexylcarbamoylethylamino)-2-hydroxypropyl]-5-(1,1-dioxo-1/$^6$-[1,2]thiazinan-2-yl)-N',N'-dipropylisophthalamide (E277) | A95 | C6 | 698.2 | 2.68 |
| N-[1-Benzyl-2-hydroxy-3-(3-trifluoromethylbenzylamino)propyl]-5-(1,1-dioxo-1/$^6$-[1,2]thiazinan-2-yl)-N',N'-dipropylisophthalamide (E278) | A95 | C16 | 703.3 | 2.87 |
| N-(1-Benzyl-3-cyclopropylamino-2-hydroxypropyl)-5-(1,1-dioxo-1/$^6$-[1,2]thiazinan-2-yl)-N',N'-dipropylisophthalamide (E279) | A95 | C26 | 585.3 | 2.55 |
| N-[1-Benzyl-2-hydroxy-3-(3-trifluoromethylbenzylamino)propyl]-3-(1,1-dioxo-1/$^6$-[1,2]thiazinan-2-yl)-5-propylbenzamide (E280) | A112 | C16 | 618.2 | 3.07 |
| N-[1-Benzyl-2-hydroxy-3-(3-methoxybenzylamino)propyl]-3-(1,1-dioxo-1/$^6$-[1,2]thiazinan-2-yl)-5-propylbenzamide formate salt (E281) | A112 | C14 | 580.3 | 2.77 |
| N-[1-Benzyl-3-(1,5-dimethylhexylamino)-2-hydroxypropyl]-3-(1,1-dioxo-1/$^6$-[1,2]thiazinan-2-yl)-5-propylbenzamide formate salt (E282) | A112 | C20 | 572.3 | 3.01 |
| N-[1-Benzyl-3-(1-cyclohexylcarbamoylethylamino)-2-hydroxypropyl]-3-(1,1-dioxo-1/$^6$-[1,2]thiazinan-2-yl)-5-propylbenzamide (E283) | A112 | C6 | 613.4 | 2.80 |
| N-[1-Benzyl-2-hydroxy-3-(3-methoxybenzylamino)propyl]-5-(1,1-dioxo-1/$^6$-[1,2]thiazinan-2-yl)-N',N'-dipropyl-isophthalamide (E284) | A95 | C14 | 665.3 | 2.85 |
| N-[1-Benzyl-2-hydroxy-3-(3-trifluoromethoxybenzylamino)propyl]-5-(1,1-dioxo-1/$^6$-[1,2]thiazinan-2-yl)-N',N'-dipropyl-isophthalamide formate salt (E285) | A95 | C11 | 719.2 | 3.02 |
| N-[1-Benzyl-2-hydroxy-3-(3-trifluoromethylbenzylamino)propyl]-3-(1,1-dioxo-1/$^6$-[1,2]thiazinan-2-yl)-5-ethylaminobenzamide formate salt (E286) | A73 | C16 | 619.2 | 2.73 |
| N-[1-Benzyl-2-hydroxy-3-(3-methoxybenzylamino)propyl]-3-(1,1-dioxo-1/$^6$-[1,2]thiazinan-2-yl)-5-ethylaminobenzamide formate salt (E287) | A73 | C14 | 581.2 | 2.72 |
| N-[1-Benzyl-3-(1,5-dimethylhexylamino)-2-hydroxypropyl]-3-(1,1-dioxo-1/$^6$-[1,2]thiazinan-2-yl)-5-ethylaminobenzamide formate salt (E288) | A73 | C20 | 573.3 | 2.99 |
| N-[1-Benzyl-3-(1-cyclohexylcarbamoylethylamino)-2-hydroxypropyl]-3-(1,1-dioxo-1/$^6$-[1,2]thiazinan-2-yl)-5-ethylaminobenzamide (E289) | A73 | C6 | 614.3 | 2.75 |

| Example | Precursor | [M + H]+ | RT (min) |
|---|---|---|---|
| formic acid-N-{(1S,2R)-1-Benzyl-3-[(3,5-dichlorobenzyl)amino]-2-hydroxypropyl}-3-(1,1-dioxido-1,2-thiazinan-2-yl)-5-(ethylamino)benzamide (1:1) (E290) | D120 | 619.3 | 2.69 |
| formic acid-N-{(1S,2R)-1-Benzyl-3-[(2-fluoro-5-methoxybenzyl)amino]-2-hydroxypropyl}-3-(1,1-dioxido-1,2-thiazinan-2-yl)-5-(ethylamino)benzamide (1:1) (E291) | D120 | 599.4 | 2.48 |
| formic acid-N-{(1S,2R)-1-Benzyl-3-[(4-fluoro-3-methoxybenzyl)amino]-2-hydroxypropyl}-3-(1,1-dioxido-1,2-thiazinan-2-yl)-5-(ethylamino)benzamide (1:1) (E292) | D120 | 599.4 | 2.52 |
| formic acid-N-{(1S,2R)-1-Benzyl-3-[(3,5-dimethylbenzyl)amino]-2-hydroxypropyl}-3-(1,1-dioxido-1,2-thiazinan-2-yl)-5-(ethylamino)benzamide (1:1) (E293) | D120 | 579.3 | 2.68 |
| N-{(1S,2R)-1-Benzyl-3-[(3,5-difluorobenzyl)amino]-2-hydroxypropyl}-3-(1,1-dioxido-1,2-thiazinan-2-yl)-5-(ethylamino)benzamide (E294) | D120 | 587.3 | 2.61 |
| N-((1S,2R)-1-Benzyl-2-hydroxy-3-{[3-nitro-5-(trifluoromethyl)benzyl]amino}propyl)-3-(1,1-dioxido-1,2-thiazinan-2-yl)-5-(ethylamino)benzamide (E295) | D120 | 664.2 | 2.78 |
| N-((1S,2R)-1-Benzyl-3-{[(5-cyanopyridin-3-yl)methyl]amino}-2-hydroxypropyl)-3-(1,1-dioxido-1,2-thiazinan-2-yl)-5-(ethylamino)benzamide (E296) | D120 | 577.3 | 2.42 |
| formic acid-N-{(1S,2R)-1-Benzyl-3-[(3-chloro-5-methoxybenzyl)amino]-2-hydroxypropyl}-3-(1,1-dioxido-1,2-thiazinan-2-yl)-5-(ethylamino)benzamide (1:1) (E297) | D120 | 615.3 | 2.70 |
| N-{(1S,2R)-1-Benzyl-3-[(3-bromo-5-fluorobenzyl)amino]-2-hydroxypropyl}-3-(1,1-dioxido-1,2-thiazinan-2-yl)-5-(ethylamino)benzamide (E298) | D120 | 649.2 | 2.70 |
| 5-{[((2R,3S)-3-{[3-(1,1-Dioxido-1,2-thiazinan-2-yl)-5-(ethylamino)benzoyl]amino}-2-hydroxy-4-phenylbutyl)amino]methyl}-N-methylnicotinamide (E299) | D120 | 609.3 | 2.34 |
| formic acid-N-{(1S,2R)-1-Benzyl-3-[(3-bromo-5-methoxybenzyl)amino]-2-hydroxypropyl}-3-(1,1-dioxido-1,2-thiazinan-2-yl)-5-(ethylamino)benzamide (1:1) (E300) | D120 | 661.2 | 2.71 |
| Methyl 5-{[((2R,3S)-3-{[3-(1,1-dioxido-1,2-thiazinan-2-yl)-5-(ethylamino)benzoyl] amino}-2-hydroxy-4-phenylbutyl)amino]methyl} nicotinate (E301) | D120 | 610.3 | 2.44 |
| N-{(1S,2R)-1-Benzyl-3-[(3,5-di-tert-butylbenzyl)amino]-2-hydroxypropyl}-3-(1,1-dioxido-1,2-thiazinan-2-yl)-5-(ethylamino)benzamide (E302) | D120 | 663.4 | 3.14 |
| N-((1S,2R)-1-Benzyl-2-hydroxy-3-{[3-methyl-5-(methylsulfonyl)benzyl]amino}propyl)-3-(1,1-dioxido-1,2-thiazinan-2-yl)-5-(ethylamino)benzamide (E303) | D120 | 643.3 | 2.53 |
| N-{(1S,2R)-1-Benzyl-2-hydroxy-3-[(3-methoxy-5-methylbenzyl)amino]propyl}-3-(1,1-dioxido-1,2-thiazinan-2-yl)-5-(ethylamino)benzamide (E304) | D120 | 595.3 | 2.65 |
| Dimethyl 5-{[((2R,3S)-3-{[3-(1,1-dioxido-1,2-thiazinan-2-yl)-5-(ethylamino)benzoyl] amino}-2-hydroxy-4-phenylbutyl)amino]methyl} isophthalate (E305) | D120 | 667.3 | 2.63 |
| N-{(1S,2R)-1-Benzyl-3-[(3,5-diisopropoxybenzyl)amino]-2-hydroxypropyl}-3-(1,1-dioxido-1,2-thiazinan-2-yl)-5-(ethylamino)benzamide (E306) | D120 | 667.4 | 2.91 |
| N-((1S,2R)-1-Benzyl-3-{[(4-bromo-2-thienyl)methyl]amino}-2-hydroxypropyl)-3-(1,1-dioxido-1,2-thiazinan-2-yl)-5-(ethylamino)benzamide (E307) | D120 | 637.3 | 2.56 |
| N-{(1S,2R)-1-Benzyl-3-[(2,3-dihydro-1-benzofuran-6-ylmethyl)amino]-2-hydroxypropyl}-3-(1,1-dioxido-1,2-thiazinan-2-yl)-5-(ethylamino)benzamide (E308) | D120 | 593.3 | 2.42 |
| formic acid-N-((1S,2R)-1-Benzyl-3-{[(4-chloro-1-methyl-1H-pyrazol-3-yl)methyl]amino}-2-hydroxypropyl)-3-(1,1-dioxido-1,2-thiazinan-2-yl)-5-(ethylamino)benzamide (1:1) (E309) | D120 | 589.3 | 2.26 |
| N-((1S,2R)-1-Benzyl-3-{[(2-bromo-1,3-thiazol-5-yl)methyl]amino}-2-hydroxypropyl)-3-(1,1-dioxido-1,2-thiazinan-2-yl)-5-(ethylamino)benzamide (E310) | D120 | 638.2 | 2.36 |
| N-((1S,2R)-1-Benzyl-3-{[(4-bromo-1H-pyrrol-2-yl)methyl]amino}-2-hydroxypropyl)-3-(1,1-dioxido-1,2-thiazinan-2-yl)-5-(ethylamino)benzamide (E311) | D120 | 618.2 | 2.54 |
| formic acid-N-((1S,2R)-1-Benzyl-3-{[(2-butyl-1H-imidazol-4-yl)methyl]amino}-2-hydroxypropyl)-3-(1,1-dioxido-1,2-thiazinan-2-yl)-5-(ethylamino)benzamide (1:1) (E312) | D120 | 597.4 | 2.11 |
| N-{(1S,2R)-1-Benzyl-3-[(3-bromobenzyl)amino]-2-hydroxypropyl}-3-(1,1-dioxido-1,2-thiazinan-2-yl)-5-(ethylamino)benzamide (E313) | D120 | 631.2 | 2.59 |
| N-{(1S,2R)-1-Benzyl-2-hydroxy-3-[(3-nitrobenzyl)amino]propyl}-3-(1,1-dioxido-1,2-thiazinan-2-yl)-5-(ethylamino)benzamide (E314) | D120 | 596.3 | 2.45 |
| N-{(1S,2R)-1-Benzyl-2-hydroxy-3-[(3-thienylmethyl) amino]propyl}-3-(1,1-dioxido-1,2-thiazinan-2-yl)-5-(ethylamino)benzamide (E315) | D120 | 557.3 | 2.36 |

| Example | Precursor | [M + H]+ | RT (min) |
|---|---|---|---|
| N-((1S,2R)-1-Benzyl-3-{[(4-bromo-1-methyl-1H-pyrazol-3-yl)methyl]amino}-2-hydroxypropyl)-3-(1,1-dioxido-1,2-thiazinan-2-yl)-5-(ethylamino)benzamide (E316) | D120 | 635.3 | 2.33 |
| N-((1S,2R)-1-Benzyl-3-{[3-fluoro-5-(trifluoromethyl)benzyl]amino}-2-hydroxypropyl)-3-(1,1-dioxido-1,2-thiazinan-2-yl)-5-(ethylamino)benzamide (E317) | D120 | 637.3 | 2.68 |
| formic acid-N-{(1S,2R)-1-Benzyl-2-hydroxy-3-[(3-vinylbenzyl)amino]propyl}-3-(1,1-dioxido-1,2-thiazinan-2-yl)-5-(ethylamino)benzamide (1:1) (E318) | D120 | 577.3 | 2.43 |
| formic acid-N-((1S,2R)-1-Benzyl-2-hydroxy-3-{[(4-methoxy-3-thienyl)methyl]amino}propyl)-3-(1,1-dioxido-1,2-thiazinan-2-yl)-5-(ethylamino)benzamide (1:1) (E319) | D120 | 587.3 | 2.31 |
| 3-{[((2R,3S)-3-{[3-(1,1-Dioxido-1,2-thiazinan-2-yl)-5-(ethylamino)benzoyl]amino}-2-hydroxy-4-phenylbutyl)amino]methyl}benzoic acid-formic acid (1:1) (E320) | D120 | 595.3 | 2.27 |
| formic acid-N-{(1S,2R)-1-Benzyl-3-[(3,4-dimethoxybenzyl)amino]-2-hydroxypropyl}-3-(1,1-dioxido-1,2-thiazinan-2-yl)-5-(ethylamino)benzamide (1:1) (E321) | D120 | 611.3 | 2.28 |
| formic acid-N-((1S,2R)-1-Benzyl-3-{[(5-ethyl-2-furyl)methyl]amino}-2-hydroxypropyl)-3-(1,1-dioxido-1,2-thiazinan-2-yl)-5-(ethylamino)benzamide (1:1) (E322) | D120 | 567.4 | 2.34 |
| formic acid-N-{(1S,2R)-1-Benzyl-3-[(2,3-dihydro-1,4-benzodioxin-6-ylmethyl)amino]-2-hydroxypropyl}-3-(1,1-dioxido-1,2-thiazinan-2-yl)-5-(ethylamino)benzamide (1:1) (E323) | D120 | 609.4 | 2.32 |
| formic acid-N-{(1S,2R)-1-Benzyl-3-[(3-ethoxy-4-methoxybenzyl)amino]-2-hydroxypropyl}-3-(1,1-dioxido-1,2-thiazinan-2-yl)-5-(ethylamino)benzamide (1:1) (E324) | D120 | 625.4 | 2.36 |
| formic acid-N-((1S,2R)-1-Benzyl-3-{[(5-ethyl-2-thienyl)methyl]amino}-2-hydroxypropyl)-3-(1,1-dioxido-1,2-thiazinan-2-yl)-5-(ethylamino)benzamide (1:1) (E325) | D120 | 585.3 | 2.46 |
| formic acid-N-{(1S,2R)-1-Benzyl-3-[(3-chloro-4-fluorobenzyl)amino]-2-hydroxypropyl}-3-(1,1-dioxido-1,2-thiazinan-2-yl)-5-(ethylamino)benzamide (1:1) (E326) | D120 | 603.3 | 2.49 |
| formic acid-N-((1S,2R)-1-Benzyl-3-{[(1-ethyl-1H-pyrazol-4-yl)methyl]amino}-2-hydroxypropyl)-3-(1,1-dioxido-1,2-thiazinan-2-yl)-5-(ethylamino)benzamide (1:1) (E327) | D120 | 569.4 | 2.13 |
| formic acid-N-((1S,2R)-1-Benzyl-3-{[(1-ethyl-3-methyl-1H-pyrazol-4-yl)methyl]amino}-2-hydroxypropyl)-3-(1,1-dioxido-1,2-thiazinan-2-yl)-5-(ethylamino)benzamide (1:1) (E328) | D120 | 583.4 | 2.17 |
| formic acid-N-((1S,2R)-1-Benzyl-3-{[(2,2-dimethyl-3,4-dihydro-2H-chromen-6-yl)methyl]amino}-2-hydroxypropyl)-3-(1,1-dioxido-1,2-thiazinan-2-yl)-5-(ethylamino)benzamide (1:1) (E329) | D120 | 635.4 | 2.60 |
| formic acid-N-((1S,2R)-1-Benzyl-3-{[4-chloro-3-(trifluoromethyl)benzyl]amino}-2-hydroxypropyl)-3-(1,1-dioxido-1,2-thiazinan-2-yl)-5-(ethylamino)benzamide (1:1) (E330) | D120 | 653.3 | 2.69 |
| formic acid-N-((1S,2R)-1-Benzyl-2-hydroxy-3-{[(6-methylpyridin-2-yl)methyl]amino}propyl)-3-(1,1-dioxido-1,2-thiazinan-2-yl)-5-(ethylamino)benzamide (1:1) (E331) | D120 | 566.3 | 2.22 |
| formic acid-N-{(1S,2R)-1-benzyl-3-[(3-ethylbenzyl)amino]-2-hydroxypropyl}-3-(1,1-dioxido-1,2-thiazinan-2-yl)-5-(ethylamino)benzamide (1:1) (E332) | D120 | 579.5 | 2.40 |
| N-((1S,2R)-1-benzyl-3-{[(1-ethyl-1H-pyrazol-4-yl)methyl]amino}-2-hydroxypropyl)-3-(1,1-dioxido-1,2-thiazinan-2-yl)-5-(ethylamino)-2-fluorobenzamide (E333) | D121 | 587.4 | 2.08 |
| formic acid-N-((1S,2R)-1-benzyl-3-{[(1-ethyl-1H-pyrazol-4-yl)methyl]amino}-2-hydroxypropyl)-3-(ethylamion)-5-(2-oxopyrrolidin-1-yl)benzamide (1:1) (E334) | E66 | 519.5 | 2.00 |
| formic acid-N-{(1S,2R)-1-benzyl-2-hydroxy-3-[(3-methoxy-4-methylbenzyl)amino]propyl}-3-(1,1-dioxido-1,2-thiazinan-2-yl)-5-(ethylamino)benzamide (1:1) (E335) | D120 | 595.2 | 2.65 |
| formic acid-N-{(1S,2R)-1-benzyl-2-hydroxy-3-[(3-methoxy-2-methylbenzyl)amino]propyl}-3-(1,1-dioxido-1,2-thiazinan-2-yl)-5-(ethylamino)benzamide (1:1) (E336) | D120 | 595.4 | 2.60 |
| 3-(1,1-dioxidotetrahydro-2H-1,2-thiazin-2-yl)-5-(ethylamino)-N-[(1S,2R)-2-hydroxy-3-[(1-methylbutyl)amino]-1-(phenylmethyl)propyl] benzamide (E337) | D120 | 531.5 | 0.75 |
| 3-(1,1-dioxidotetrahydro-2H-1,2-thiazin-2-yl)-5-(ethylamino)-N-{(1S,2R)-2-hydroxy-1-(phenylmethyl)-3-[(1-propylbutyl)amino]propyl} benzamide hydrochloride (E338) | D120 | 559.5 | 0.88 |
| 3-(1,1-dioxidotetrahydro-2H-1,2-thiazin-2-yl)-5-(ethylamino)-N-[(1S,2R)-2-hydroxy-3-[(1-methylpentyl)amino]-1-(phenylmethyl)propyl] benzamide hydrochloride (E339) | D120 | 545.5 | 0.84 |
| N-[(1S,2R)-3-[(1,4-dimethylpentyl)amino]-2-hydroxy-1-(phenylmethyl)propyl]-3-(1,1-dioxidotetrahydro-2H-1,2-thiazin-2-yl)-5-(ethylamino)benzamide hydrochloride (E340) | D120 | 559.5 | 0.88 |

-continued

| Example | Precursor | [M + H]+ | RT (min) |
|---|---|---|---|
| 3-(1,1-dioxidotetrahydro-2H-1,2-thiazin-2-yl)-5-(ethylamino)-N-[(1S,2R)-2-hydroxy-3-[(3-methylbutyl)amino]-1-(phenylmethyl)propyl] benzamide hydrochloride (E341) | D120 | 531.5 | 0.81 |
| 3-(1,1-dioxidotetrahydro-2H-1,2-thiazin-2-yl)-5-(ethylamino)-N-[(1S,2R)-2-hydroxy-1-(phenylmethyl)-3-(propylamino)propyl] benzamide hydrochloride E342) | D120 | 503.5 | 0.72 |
| N-[(1S,2R)-3-{[1-(3-chlorophenyl)propyl]amino}-2-hydroxy-1-(Phenylmethyl)propyl]-3-(ethylamino)-5-(2-oxo-1-pyrrolidinyl)benzamide hydrochloride (E343) | E66 | 563.5 | 0.84 |
| N-[(1S,2R)-3-{[1-(3-chlorophenyl)propyl]amino}-2-hydroxy-1-(Phenylmethyl)propyl]-3-cyclopentyl-5-(2-oxo-1-pyrrolidinyl)benzamide hydrochloride (E344) | D122 | 588.4 | 1.01 |
| 3-(1,1-dioxidotetrahydro-2H-1,2-thiazin-2-yl)-5-(ethylamino)-N-[(1S,2R)-2-hydroxy-3-[(4-methylpentyl)amino]-1-(phenylmethyl)propyl] benzamide hydrochloride (E345) | D120 | 545.5 | 0.85 |
| 3-(1,1-dioxidotetrahydro-2H-1,2-thiazin-2-yl)-5-(ethylamino)-N-[(1S,2R)-2-hydroxy-3-[(5-methylhexyl)amino]-1-(phenylmethyl)propyl] benzamide hydrochloride (E346) | D120 | 559.6 | 0.89 |
| 3-(1,1-dioxidotetrahydro-2H-1,2-thiazin-2-yl)-5-(ethylamino)-N-[(1S,2R)-2-hydroxy-3-[(1-methylpropyl)amino]-1-(phenylmethyl)propyl] benzamide hydrochloride (E347) | D120 | 517.5 | 0.74 |
| 3-(1,1-dioxidotetrahydro-2H-1,2-thiazin-2-yl)-5-(ethylamino)-N-[(1S,2R)-2-hydroxy-3-[(1-methylhexyl)amino]-1-(phenylmethyl)propyl] benzamide hydrochloride (E348) | D120 | 559.6 | 0.89 |
| N-[(1S,2R)-3-{[(3,5-dibromophenyl)methyl]amino}-2-hydroxy-1-(phenylmethyl)propyl]-3-[(1-methylethyl)oxy]-5-(2-oxo-1-pyrrolidinyl)benzamide (E349) | D123 | 672.3 | 0.89 |
| N-{(1S,2R)-2-hydroxy-1-(phenylmethyl)-3-[(phenylmethyl)amino]propyl}-3-[(1-methylethyl)oxy]-5-(2-oxo-1-pyrrolidinyl)benzamide (E350) | D123 | 516.5 | 0.78 |
| N-[(1S,2R)-3-{[(3-bromophenyl)methyl]amino}-2-hydroxy-1-(phenylmethyl)propyl]-3-[(1-methylethyl)oxy]-5-(2-oxo-1-pyrrolidinyl)benzamide (E351) | D123 | 596.2 | 0.83 |
| N-[(1S,2R)-3-({[3-(ethyloxy)phenyl]methyl} amino)-2-hydroxy-1-(phenylmethyl)propyl]-3-[(1-methylethyl)oxy]-5-(2-oxo-1-pyrrolidinyl)benzamide (E352) | D123 | 560.4 | 0.82 |
| N-[(1S-2R)-3-{[(3-chlorophenyl)methyl]amino}-2-hydroxy-1-(phenylmethyl)propyl]-3-[(1-methylethyl)oxy]-5-(2-oxo-1-pyrrolidinyl)benzamide (E353) | D123 | 550.3 | 0.82 |
| N-{(1S,2R)-2-hydroxy-1-(phenylmethyl)-3-[({3-[(trifluoromethyl)oxy]phenyl}methyl)amino]propyl}-3-[(1-methylethyl)oxy]-5-(2-oxo-1-pyrrolidinyl)benzamide (E354) | D123 | 600.3 | 0.87 |
| N-[(1S,2R)-3-({[3,5-bis(methyloxy)phenyl]methyl}amino)-2-hydroxy-1-(phenylmethyl)propyl]-3-[(1-methylethyl)oxy]-5-(2-oxo-1-pyrrolidinyl)benzamide (E355) | D123 | 576.4 | 0.81 |
| N-[(1S,2R)-3-{[(3,5-dichlorophenyl)methyl]amino}-2-hydroxy-1-(phenylmethyl)propyl]-3-[(1-methylethyl)oxy]-5-(2-oxo-1-pyrrolidinyl)benzamide (E356) | D123 | 584.2 | 0.87 |
| N-[(1S,2R)-3-{[(3,5-difluorophenyl)methyl]amino}-2-hydroxy-1-(phenylmethyl)propyl]-3-[(1-methylethyl)oxy]-5-(2-oxo-1-pyrrolidinyl)benzamide (E357) | D123 | 552.3 | 0.80 |
| N-[(1S,2R)-2-hydroxy-1-(phenylmethyl)-3-({[3-(trifluoromethyl)phenyl] methyl}amino)propyl]-3-[(1-methylethyl)oxy]-5-(2-oxo-1-pyrrolidinyl)benzamide (E358) | D123 | 584.3 | 0.85 |
| N-[(1S,2R)-3-({[3,5-bis(trifluoromethyl)phenyl] methyl}amino)-2-hydroxy-1-(phenylmethyl)propyl]-3-[(1-methylethyl)oxy]-5-(2-oxo-1-pyrrolidinyl)benzamide (E359) | D123 | 652.3 | 0.93 |
| N-[(1S,2R)-2-hydroxy-3-{[(3-methylphenyl)methyl]amino}-1-(phenylmethyl)propyl]-3-[(1-methylethyl)oxy]-5-(2-oxo-1-pyrrolidinyl)benzamide (E360) | D123 | 530.4 | 0.82 |
| 3-(1,1-dioxidotetrahydro-2H-1,2-thiazin-2-yl)-N-[(1S,2R)-2-hydroxy-1-(phenylmethyl)-3-({[3-(trifluoromethyl)phenyl] methyl}amino)propyl]-5-[(1-methylethyl)oxy]benzamide hydrochloride (E361) | D124 | 634.3 | 0.88 |
| 3-(1,1-dioxidotetrahydro-2H-1,2-thiazin-2-yl)-N-[(1S,2R)-2-hydroxy-3-({[3-(methyloxy)phenyl]methyl} amino)-1-(phenylmethyl)propyl]-5-[(1-methylethyl)oxy]benzamide hydrochloride (E362) | D124 | 596.3 | 0.82 |
| 3-(1,1-dioxidotetrahydro-2H-1,2-thiazin-2-yl)-N-{(1S,2R)-2-hydroxy-1-(phenylmethyl)-3-[({3-[(trifluoromethyl)oxy]phenyl}methyl)amino]propyl}-5-[(1-methylethyl)oxy]benzamide hydrochloride (E363) | D124 | 650.3 | 0.89 |
| N-[(1S,2R)-3-({[3,5-bis(trifluoromethyl)phenyl] methyl}amino)-2-hydroxy-1-(phenylmethyl)propyl]-3-(1,1-dioxidotetrahydro-2H-1,2-thiazin-2-yl)-5-[(1-methylethyl)oxy]benzamide hydrochloride (E364) | D124 | 702.3 | 0.96 |

-continued

| Example | Precursor | [M + H]+ | RT (min) |
|---|---|---|---|
| N-[(1S,2R)-3-({[3,5-bis(methyloxy)phenyl]methyl}amino)-2-hydroxy-1-(phenylmethyl)propyl]-3-(1,1-dioxidotetrahydro-2H-1,2-thiazin-2-yl)-5-[(1-methylethyl)oxy]benzamide hydrochloride (E365) | D124 | 626.3 | 0.82 |
| N-[(1S,2R)-3-{[(3,5-dibromophenyl)methyl]amino}-2-hydroxy-1-(phenylmethyl)propyl]-3-(1,1-dioxidotetrahydro-2H-1,2-thiazin-2-yl)-5-[(1-methylethyl)oxy]benzamide hydrochloride (E366) | D124 | 722.1 | 0.90 |
| 3-cyclopentyl-5-(1,1-dioxidotetrahydro-2H-1,2-thiazin-2-yl)-N-[(1S,2R)-2-hydroxy-1-(phenylmethyl)-3-({[3-(trifluoromethyl)phenyl] methyl}amino)propyl] benzamide hydrochloride (E367) | D125 | 644.4 | 0.94 |
| 3-cyclopentyl-5-(1,1-dioxidotetrahydro-2H-1,2-thiazin-2-yl)-N-[(1S,2R)-2-hydroxy-3-({[3-(methyloxy)phenyl]methyl} amino)-1-(phenylmethyl)propyl] benzamide hydrochloride (E368) | D125 | 606.4 | 0.88 |
| 3-cyclopentyl-5-(1,1-dioxidotetrahydro-2H-1,2-thiazin-2-yl)-N-{(1S,2R)-2-hydroxy-1-(phenylmethyl)-3-[({3-[(trifluoromethyl)oxy]phenyl}methyl)amino]propyl} benzamide hydrochloride (E369) | D125 | 660.4 | 0.95 |
| N-[(1S,2R)-3-({[3,5-bis(trifluoromethyl)phenyl] methyl}amino)-2-hydroxy-1-(Phenylmethyl)propyl]-3-cyclopentyl-5-(1,1-dioxidotetrahydro-2H-1,2-thiazin-2-yl)benzamide hydrochloride (E370) | D125 | 712.4 | 1.02 |
| N-[(1S,2R)-3-({[3,5-bis(methyloxy)phenyl]methyl}amino)-2-hydroxy-1-(phenylmethyl)propyl]-3-cyclopentyl-5-(1,1-dioxidotetrahydro-2H-1,2-thiazin-2-yl)benzamide hydrochloride (E371) | D125 | 636.4 | 0.90 |
| 3-cyclopentyl-N-[(1S,2R)-3-{[(3,5-dibromophenyl)methyl]amino}-2-hydroxy-1-(phenylmethyl)propyl]-5-(1,1-dioxidotetrahydro-2H-1,2-thiazin-2-yl)benzamide hydrochloride (E372) | D125 | 732.2 | 0.99 |
| 3-(1,1-dioxidotetrahydro-2H-1,2-thiazin-2-yl)-5-(ethylamino)-N-{(1S,2R)-2-hydroxy-1-(phenylmethyl)-3-[({3-[(trifluoromethyl)oxy]phenyl}methyl)amino]propyl} benzamide hydrochloride (E373) | D120 | 635.3 | 0.83 |
| N-[(1S,2R)-3-({[3,5-bis(trifluoromethyl)phenyl] methyl}amino)-2-hydroxy-1-(phenylmethyl)propyl]-3-(1,1-dioxidotetrahydro-2H-1,2-thiazin-2-yl)-5-(ethylamino)benzamide hydrochloride (E374) | D120 | 687.3 | 0.89 |
| N-[(1S,2R)-3-({[3,5-bis(methyloxy)phenyl]methyl}amino)-2-hydroxy-1-(phenylmethyl)propyl]-3-(1,1-dioxidotetrahydro-2H-1,2-thiazin-2-yl)-5-(ethylamino)benzamide hydrochloride (E375) | D120 | 611.4 | 0.77 |
| N-[(1S,2R)-3-{[(3,5-dibromophenyl)methyl]amino}-2-hydroxy-1-(phenylmethyl)propyl]-3-(1,1-dioxidotetrahydro-2H-1,2-thiazin-2-yl)-5-(ethylamino)benzamide hydrochloride (E376) | D120 | 707.2 | 0.85 |
| 3-(ethyloxy)-N-{(1S,2R)-2-hydroxy-1-(phenylmethyl)-3-[({3-[(trifluoromethyl)oxy]phenyl}methyl)amino]propyl}-5-(2-oxo-1-pyrrolidinyl)benzamide hydrochloride (E377) | D126 | 586.2 | 0.82 |
| N-[(1S,2R)-3-({[3,5-bis(trifluoromethyl)phenyl] methyl}amino)-2-hydroxy-1-(phenylmethyl)propyl]-3-(ethyloxy)-5-(2-oxo-1-pyrrolidinyl)benzamide hydrochloride (E378) | D126 | 638.2 | 0.88 |
| N-[(1S,2R)-3-({[3,5-bis(methyloxy)phenyl]methyl}amino)-2-hydroxy-1-(phenylmethyl)propyl]-3-(ethyloxy)-5-(2-oxo-1-pyrrolidinyl)benzamide hydrochloride (E379) | D126 | 562.3 | 0.75 |
| N-[(1S,2R)-3-{[(3,5-dibromophenyl)methyl]amino}-2-hydroxy-1-(phenylmethyl)propyl]-3-(ethyloxy)-5-(2-oxo-1-pyrrolidinyl)benzamide hydrochloride (E380) | D126 | 658.0 | 0.83 |
| 3-cyclopentyl-N-{(1S,2R)-2-hydroxy-1-(phenylmethyl)-3-[({3-[(trifluoromethyl)oxy]phenyl}methyl)amino]propyl}-5-(2-oxo-1-pyrrolidinyl)benzamide hydrochloride (E381) | D122 | 610.3 | 0.92 |
| N-[(1S,2R)-3-({[3,5-bis(trifluoromethyl)phenyl] methyl}amino)-2-hydroxy-1-(phenylmethyl)propyl]-3-cyclopentyl-5-(2-oxo-1-pyrrolidinyl)benzamide hydrochloride (E382) | D122 | 662.3 | 0.99 |
| N-[(1S,2R)-3-({[3,5-bis(methyloxy)phenyl]methyl}amino)-2-hydroxy-1-(phenylmethyl)propyl]-3-cyclopentyl-5-(2-oxo-1-pyrrolidinyl)benzamide hydrochloride (E383) | D122 | 586.3 | 0.86 |
| 3-cyclopentyl-N-[(1S,2R)-3-{[(3,5-dibromophenyl)methyl]amino}-2-hydroxy-1-(phenylmethyl)propyl]-5-(2-oxo-1-pyrrolidinyl)benzamide hydrochloride (E384) | D122 | 682.1 | 0.94 |
| N-[(1S,2R)-3-({[3,5-bis(methyloxy)phenyl]methyl}amino)-2-hydroxy-1-(phenylmethyl)propyl]-3-(ethylamino)-5-(2-oxo-1-pyrrolidinyl)benzamide hydrochloride (E385) | E66 | 561.3 | 0.73 |
| N-[(1S,2R)-3-{[(3,5-dibromophenyl)methyl]amino}-2-hydroxy-1-(phenylmethyl)propyl]-3-(ethylamino)-5-(2-oxo-1-pyrrolidinyl)benzamide hydrochloride (E386) | E66 | 657.1 | 0.80 |
| N-[(1S,2R)-3-({[3,5-bis(trifluoromethyl)phenyl] methyl}amino)-2-hydroxy-1-(phenylmethyl)propyl]-3-(1,1-dioxido-2-isothiazolidinyl)-5-(ethyloxy)benzamide hydrochloride (E387) | D127 | 674.2 | 0.88 |

| Example | Precursor | [M + H]+ | RT (min) |
|---|---|---|---|
| N-[(1S,2R)-3-({[3,5-bis(methyloxy)phenyl]methyl}amino)-2-hydroxy-1-(phenylmethyl)propyl]-3-(1,1-dioxido-2-isothiazolidinyl)-5-(ethyloxy)benzamide hydrochloride (E388) | D127 | 598.3 | 0.76 |
| N-[(1S,2R)-3-{[(3,5-dibromophenyl)methyl]amino}-2-hydroxy-1-(phenylmethyl)propyl]-3-(1,1-dioxido-2-isothiazolidinyl)-5-(ethyloxy)benzamide hydrochloride (E389) | D127 | 694.1 | 0.84 |
| 3-(1,1-dioxido-2-isothiazolidinyl)-N-[(1S,2R)-2-hydroxy-1-(phenylmethyl)-3-({[3-(trifluoromethyl)phenyl]methyl}amino)propyl]-5-[(1-methylethyl)oxy]benzamide hydrochloride (E390) | D128 | 620.2 | 0.84 |
| 3-(1,1-dioxido-2-isothiazolidinyl)-N-[(1S,2R)-2-hydroxy-3-({[3-(methyloxy)phenyl]methyl} amino)-1-(phenylmethyl)propyl]-5-[(1-methylethyl)oxy]benzamide hydrochloride (E391) | D128 | 582.3 | 0.77 |
| 3-(1,1-dioxido-2-isothiazolidinyl)-N-{(1S,2R)-2-hydroxy-3-(phenylmethyl)-3-[({3-[(trifluoromethyl)oxy]phenyl}methyl)amino]propyl}-5-[(1-methylethyl)oxy]benzamide hydrochloride (E392) | D128 | 636.2 | 0.85 |
| N-[(1S,2R)-3-({[3,5-bis(trifluoromethyl)phenyl] methyl}amino)-2-hydroxy-1-(phenylmethyl)propyl]-3-(1,1-dioxido-2-isothiazolidinyl)-5-[(1-methylethyl)oxy]benzamide hydrochloride (E393) | D128 | 688.2 | 0.91 |
| N-[(1S,2R)-3-({[3,5-bis(trifluoromethyl)phenyl] methyl}amino)-2-hydroxy-1-(phenylmethyl)propyl]-3-(1,1-dioxido-2-isothiazolidinyl)-5-[(1-methylethyl)oxy]benzamide hydrochloride (E394) | D128 | 612.2 | 0.80 |
| N-[(1S,2R)-3-{[(3,5-dibromophenyl)methyl]amino}-2-hydroxy-1-(phenylmethyl)propyl]-3-(1,1-dioxido-2-isothiazolidinyl)-5-[(1-methylethyl)oxy]benzamide hydrochloride (E395) | D128 | 708.1 | 0.87 |
| 3-cyclopentyl-5-(1,1-dioxido-2-isothiazolidinyl)-N-[(1S,2R)-2-hydroxy-1-(phenylmethyl)-3-({[3-(trifluoromethyl)phenyl]methyl}amino)propyl] benzamide hydrochloride (E396) | D129 | 630.2 | 0.90 |
| 3-cyclopentyl-5-(1,1-dioxido-2-isothiazolidinyl)-N-[(1S,2R)-2-hydroxy-3-({[3-(methyloxy)phenyl]methyl} amino)-1-(phenylmethyl)propyl] benzamide hydrochloride (E397) | D129 | 592.3 | 0.84 |
| 3-cyclopentyl-5-(1,1-dioxido-2-isothiazolidinyl)-N-{(1S,2R)-2-hydroxy-1-(phenylmethyl)-3-[({3-[(trifluoromethyl)oxy]phenyl}methyl)amino]propyl} benzamide hydrochloride (E398) | D129 | 646.3 | 0.91 |
| N-[(1S,2R)-3-({[3,5-bis(trifluoromethyl)phenyl] methyl}amino)-2-hydroxy-1-(phenylmethyl)propyl]-3-cyclopentyl-5-(1,1-dioxido-2-isothiazolidinyl)benzamide hydrochloride (E399) | D129 | 698.3 | 0.98 |
| N-[(1S,2R)-3-({[3,5-bis(methyloxy)phenyl]methyl}amino)-2-hydroxy-1-(phenylmethyl)propyl]-3-cyclopentyl-5-(1,1-dioxido-2-isothiazolidinyl)benzamide hydrochloride (E400) | D129 | 622.3 | 0.86 |
| 3-cyclopentyl-N-[(1S,2R)-3-{[(3,5-dibromophenyl)methyl]amino}-2-hydroxy-1-(phenylmethyl)propyl]-5-(1,1-dioxido-2-isothiazolidinyl)benzamide hydrochloride (E401) | D129 | 718.1 | 0.94 |
| 3-(1,1-dioxido-2-isothiazolidinyl)-5-(ethylamino)-N-{(1S,2R)-2-hydroxy-1-(phenylmethyl)-3-[({3-[(trifluoromethyl)oxy]phenyl}methyl)amino]propyl}benzamide hydrochloride (E402) | D130 | 621.3 | 0.80 |
| N-[(1S,2R)-3-({[3,5-bis(trifluoromethyl)phenyl] methyl}amino)-2-hydroxy-1-(phenylmethyl)propyl]-3-(1,1-dioxido-2-isothiazolidinyl)-5-(ethylamino)benzamide hydrochloride (E403) | D130 | 673.3 | 0.86 |
| N-[(1S,2R)-3-({[3,5-bis(methyloxy)phenyl]methyl}amino)-2-hydroxy-1-(phenylmethyl)propyl]-3-(1,1-dioxido-2-isothiazolidinyl)-5-(ethylamino)benzamide hydrochloride (E404) | D130 | 597.4 | 0.73 |
| N-[(1S,2R)-3-{[(3,5-dibromophenyl)methyl]amino}-2-hydroxy-1-(phenylmethyl)propyl]-3-(1,1-dioxido-2-isothiazolidinyl)-5-(ethylamino)benzamide hydrochloride (E405) | D130 | 693.2 | 0.82 |
| 3-(1,1-dioxidotetrahydro-2H-1,2-thiazin-2-yl)-5-(ethyloxy)-N-[(1S,2R)-2-hydroxy-1-(phenylmethyl)-3-({[3-(trifluoromethyl)phenyl] methyl}amino)propyl] benzamide hydrochloride (E406) | D131 | 620.3 | 0.83 |
| 3-(1,1-dioxidotetrahydro-2H-1,2-thiazin-2-yl)-5-(ethyloxy)-N-[(1S,2R)-2-hydroxy-3-({[3-(methyloxy)phenyl]methyl} amino)-1-(phenylmethyl)propyl] benzamide hydrochloride (E407) | D131 | 582.4 | 0.78 |
| 3-(1,1-dioxidotetrahydro-2H-1,2-thiazin-2-yl)-5-(ethyloxy)-N-{(1S,2R)-2-hydroxy-1-(phenylmethyl)-3-[({3-[(trifluoromethyl)oxy]phenyl}methyl)amino]propyl} benzamide hydrochloride (E408) | D131 | 636.3 | 0.86 |
| N-[(1S,2R)-3-({[3,5-bis(trifluoromethyl)phenyl] methyl}amino)-2-hydroxy-1-(phenylmethyl)propyl]-3-(1,1-dioxidotetrahydro-2H-1,2-thiazin-2-yl)-5-(ethyloxy)benzamide hydrochloride (E409) | D131 | 688.3 | 0.93 |
| N-[(1S,2R)-3-({[3,5-bis(methyloxy)phenyl]methyl}amino)-2-hydroxy-1-(phenylmethyl)propyl]-3-(1,1-dioxidotetrahydro-2H-1,2-thiazin-2-yl)-5-(ethyloxy)benzamide hydrochloride (E410) | D131 | 612.3 | 0.79 |

| Example | Precursor | [M + H]+ | RT (min) |
|---|---|---|---|
| N-[(1S,2R)-3-{[(3,5-dibromophenyl)methyl]amino}-2-hydroxy-1-(phenylmethyl)propyl]-3-(1,1-dioxidotetrahydro-2H-1,2-thiazin-2-yl)-5-(ethyloxy)benzamide hydrochloride (E411) | D131 | 708.1 | 0.88 |
| N-[(1S,2R)-3-{[1-(3-chlorophenyl)propyl]amino}-2-hydroxy-1-(phenylmethyl)propyl]-3-(1,1-dioxidotetrahydro-2H-1,2-thiazin-2-yl)-5-(ethylamino)benzamide hydrochloride (E412) | D120 | 613.3 | 0.92 |
| 3-cyclopentyl-5-(1,1-dioxidotetrahydro-2H-1,2-thiazin-2-yl)-N-[(1S,2R)-2-hydroxy-3-[(1-methylbutyl)amino]-1-(phenylmethyl)propyl] benzamide hydrochloride (E413) | D125 | 556.6 | 0.92 |
| N-[(1S,2R)-1-benzyl-2-hydroxy-3-(1,2,3,4-tetrahydronaphthalen-2-ylamino)propyl]-3-cyclopentyl-5-(2-oxopyrrolidin-1-yl)benzamide hydrochloride (E414) | D122 | 566.5 | 0.9 |
| N-[(1S,2R)-1-benzyl-3-(2,3-dihydro-1H-inden-2-ylamino)-2-hydroxypropyl]-3-cyclopentyl-5-(2-oxopyrrolidin-1-yl)benzamide hydrochloride (E415) | D122 | 552.6 | 0.9 |
| N-[(1S,2R)-1-benzyl-3-(2,3-dihydro-1H-inden-2-ylamino)-2-hydroxypropyl]-3-(1,1-dioxido-1,2-thiazinan-2-yl)-5-(ethylamino)benzamide hydrochloride (E416) | D120 | 577.5 | 0.8 |
| N-[(1S,2R)-1-benzyl-2-hydroxy-3-(1,2,3,4-tetrahydronaphthalen-2-ylamino)propyl]-3-(1,1-dioxido-1,2-thiazinan-2-yl)-5-(ethylamino)benzamide hydrochloride (E417) | D120 | 591.5 | 0.8 |
| N-{(1S,2R)-1-benzyl-2-hydroxy-3-[(7-methoxy-1,2,3,4-tetrahydronaphthalen-2-yl)amino]propyl}-3-cyclopentyl-5-(2-oxopyrrolidin-1-yl)benzamide hydrochloride (E418) | D122 | 596.6 | 0.9 |
| N-{(1S,2R)-1-benzyl-3-[(3,5-dichlorobenzyl)amino]-2-hydroxypropyl}-3-cyclopentyl-5-(2-oxopyrrolidin-1-yl)benzamide (E419) | D122 | 594.5 | 2.5 |
| N-{(1S,2R)-1-benzyl-3-[(3,5-dichlorobenzyl)amino]-2-hydroxypropyl}-3-(1,1-dioxidoisothiazolidin-2-yl)-5-ethoxybenzamide (E420) | D127 | 606.4 | 2.3 |
| N-{(1S,2R)-1-benzyl-3-[(3,5-dichlorobenzyl)amino]-2-hydroxypropyl}-3-(1,1-dioxidoisothiazolidin-2-yl)-5-isopropoxybenzamide (E421) | D128 | 620.4 | 2.3 |
| N-{(1S,2R)-1-benzyl-3-[(3,5-dichlorobenzyl)amino]-2-hydroxypropyl}-3-cyclopentyl-5-(1,1-dioxidoisothiazolidin-2-yl)benzamide (E422) | D129 | 630.4 | 2.5 |
| N-{(1S,2R)-1-benzyl-3-[(3,5-dichlorobenzyl)amino]-2-hydroxypropyl}-3-(1,1-dioxido-1,2-thiazinan-2-yl)-5-ethoxybenzamide (E423) | D131 | 620.3 | 2.3 |
| N-{(1S,2R)-1-benzyl-3-[(3,5-dichlorobenzyl)amino]-2-hydroxypropyl}-3-(1,1-dioxido-1,2-thiazinan-2-yl)-5-isopropoxybenzamide (E424) | D124 | 634.3 | 2.4 |
| N-{(1S,2R)-1-benzyl-3-[(3,5-dichlorobenzyl)amino]-2-hydroxypropyl}-3-cyclopentyl-5-(1,1-dioxido-1,2-thiazinan-2-yl)benzamide (E425) | D125 | 644.4 | 2.6 |
| N-{(1S,2R)-1-benzyl-3-[(3,5-dichlorobenzyl)amino]-2-hydroxypropyl}-3-(ethylamino)-5-(2-oxopyrrolidin-1-yl)benzamide hydrochloride (E426) | E66 | 568.8 | 2.2 |
| N-{(1S,2R)-1-benzyl-3-[(3,5-dichlorobenzyl)amino]-2-hydroxypropyl}-3-(1,1-dioxidoisothiazolidin-2-yl)-5-(ethylamino)benzamide hydrochloride (E427) | D130 | 604.9 | 2.2 |

Examples 428-570 (E428-E570)

Examples E428-E570 were prepared in an analogous manner to Example 1 from the appropriate acid and amines indicated in the below table:

| Example | Acid | Amine | [M + H]+ | RT (min) |
|---|---|---|---|---|
| 3-(1,1-dioxidotetrahydro-2H-1,2-thiazin-2-yl)-5-(ethylamino)-N-[(1S,2R)-2-hydroxy-3-{[1-(4-methylpentyl)cyclopropyl]amino}-1-(phenylmethyl)propyl] benzamide hydrochloride (E428) | A73 | C73 | 585.6 | 0.90 |
| 3-(1,1-dioxidotetrahydro-2H-1,2-thiazin-2-yl)-5-(ethylamino)-N-[(1S,2R)-3-[(1-ethylcyclopropyl)amino]-2-hydroxy-1-(phenylmethyl)propyl] benzamide hydrochloride (E429) | A73 | C74 | 529.5 | 0.73 |

-continued

| Example | Acid | Amine | [M + H]+ | RT (min) |
|---|---|---|---|---|
| 3-(1,1-dioxidotetrahydro-2H-1,2-thiazin-2-yl)-5-(ethylamino)-N-[(1S,2R)-2-hydroxy-3-{[1-(1-methylethyl)cyclopropyl]amino}-1-(phenylmethyl)propyl] benzamide hydrochloride (E430) | A73 | C75 | 543.4 | 0.77 |
| N-[(1S,2R)-3-(butylamino)-2-hydroxy-1-(phenylmethyl)propyl]-3-(1,1-dioxidotetrahydro-2H-1,2-thiazin-2-yl)-5-(ethylamino)benzamide hydrochloride (E431) | A73 | C76 | 517.4 | 0.75 |
| 3-(1,1-dioxidotetrahydro-2H-1,2-thiazin-2-yl)-5-(ethylamino)-N-{(1S,2R)-2-hydroxy-1-(phenylmethyl)-3-[(1-propylcyclopropyl)amino]propyl}benzamide hydrochloride (E432) | A73 | C77 | 543.5 | 0.79 |
| 3-(1,1-dioxidotetrahydro-2H-1,2-thiazin-2-yl)-5-(ethylamino)-N-[(1S,2R)-2-hydroxy-3-{[1-(3-methylbutyl)cyclopropyl]amino}-1-(phenylmethyl)propyl] benzamide hydrochloride (E433) | A73 | C78 | 571.6 | 0.88 |
| 3-(1,1-dioxidotetrahydro-2H-1,2-thiazin-2-yl)-5-(ethylamino)-N-[(1S,2R)-2-hydroxy-3-{[1-(2-methylpropyl)cyclopropyl]amino}-1-(phenylmethyl)propyl] benzamide hydrochloride (E434) | A73 | C79 | 557.5 | 0.84 |
| N-[(1S,2R)-3-({1-[(3-chlorophenyl)methyl]cyclopropyl}amino)-2-hydroxy-1-(phenylmethyl)propyl]-3-(1,1-dioxidotetrahydro-2H-1,2-thiazin-2-yl)-5-(ethylamino)benzamide hydrochloride (E435) | A73 | C80 | 625.4 | 0.90 |
| N-{(1S,2R)-1-benzyl-2-hydroxy-3-[(1-methylcyclohexyl)amino]propyl}-3-(1,1-dioxido-1,2-thiazinan-2-yl)-5-(ethylamino)benzamide hydrochloride (E436) | A73 | C81 | 557.5 | 0.78 |
| N-{(1S,2R)-1-benzyl-3-[(1S,2S,4R)-bicyclo[2.2.1]hept-2-ylamino]-2-hydroxypropyl}-3-(1,1-dioxido-1,2-thiazinan-2-yl)-5-(ethylamino)benzamide hydrochloride (E437) | A73 | C82 | 555.4 | 0.78 |
| N-{(1S,2R)-1-benzyl-3-[(4,4-dimethylcyclohexyl) amino]-2-hydroxypropyl}-3-(1,1-dioxido-1,2-thiazinan-2-yl)-5-(ethylamino)benzamide hydrochloride (E438) | A73 | C83 | 571.3 | 0.82 |
| N-((1S,2R)-1-benzyl-2-hydroxy-3-{[(1R)-1,2,2-trimethylpropyl]amino} propyl)-3-(1,1-dioxido-1,2-thiazinan-2-yl)-5-(ethylamino)benzamide hydrochloride (E439) | A73 | C84 | 545.6 | 0.8 |
| N-((1S,2R)-1-benzyl-2-hydroxy-3-{[(1S)-1,2,2-trimethylpropyl]amino} propyl)-3-(1,1-dioxido-1,2-thiazinan-2-yl)-5-(ethylamino)benzamide hydrochloride (E440) | A73 | C85 | 545.6 | 0.81 |
| N-{(1S,2R)-1-benzyl-3-[(2,2-dimethylcyclohexyl) amino]-2-hydroxypropyl}-3-(1,1-dioxido-1,2-thiazinan-2-yl)-5-(ethylamino)benzamide hydrochloride (E441) | A73 | C86 | 571.6 | 0.83 |
| N-[(1S,2R)-1-benzyl-2-hydroxy-3-(pentylamino)propyl]-3-(1,1-dioxido-1,2-thiazinan-2-yl)-5-(ethylamino)benzamide hydrochloride (E442) | A73 | C87 | 531.5 | 0.84 |
| N-[(1S,2R)-1-benzyl-3-(hexylamino)-2-hydroxypropyl]-3-(1-1-dioxido-1,2-thiazinan-2-yl)-5-(ethylamino)benzamide hydrochloride (E443) | A73 | C88 | 545.5 | 0.9 |
| N-{(1S,2R)-1-benzyl-3-[(3,3-dimethylbutyl)amino]-2-hydroxypropyl}-3-(1,1-dioxido-1,2-thiazinan-2-yl)-5-(ethylamino)benzamide hydrochloride (E444) | A73 | C89 | 545.5 | 0.86 |
| N-{(1S,2R)-1-benzyl-3-[(1,1-dimethylpropyl)amino]-2-hydroxypropyl}-3-(1,1-dioxido-1,2-thiazinan-2-yl)-5-(ethylamino)benzamide hydrochloride (E445) | A73 | C90 | 531.5 | 0.8 |
| N-{(1S,2R)-1-benzyl-3-[(cyclopropylmethyl) amino]-2-hydroxypropyl}-3-(1,1-dioxido-1,2-thiazinan-2-yl)-5-(ethylamino)benzamide hydrochloride (E446) | A73 | C91 | 515.5 | 0.76 |
| N-{(1S,2R)-1-benzyl-3-[(3,3-dimethylcyclopentyl) amino]-2-hydroxypropyl}-3-(1,1-dioxido-1,2-thiazinan-2-yl)-5-(ethylamino)benzamide hydrochloride (E447) | A73 | C92 | 557.6 | 0.81 |
| N-[(1S,2R)-1-benzyl-3-(ethylamino)-2-hydroxypropyl]-3-(1,1-dioxido-1,2-thiazinan-2-yl)-5-(ethylamino)benzamide hydrochloride (E448) | A73 | C24 | 489.5 | 0.7 |
| N-[(1S,2R)-1-benzyl-2-hydroxy-3-(methylamino)propyl]-3-(1,1-dioxido-1,2-thiazinan-2-yl)-5-(ethylamino)benzamide hydrochloride (E449) | A73 | C93 | 475.5 | 0.68 |
| N-[(1S,2R)-1-benzyl-3-(cyclopropylamino)-2-hydroxypropyl]-3-(1,1-dioxido-1,2-thiazinan-2-yl)-5-(ethylamino)benzamide hydrochloride (E450) | A73 | C26 | 501.5 | 0.71 |
| N-[(1S,2R)-3-(1-adamantylamino)-1-benzyl-2-hydroxypropyl]-3-(1,1-dioxido-1,2-thiazinan-2-yl)-5-(ethylamino)benzamide hydrochloride (E451) | A73 | C94 | 595.6 | 0.85 |
| N-[(1S,2R)-1-benzyl-2-hydroxy-3-(1,2,3,4-tetrahydronaphthalen-1-ylamino)propyl]-3-cyclopentyl-5-(2-oxopyrrolidin-1-yl)benzamide hydrochloride (E452) | A107 | C95 | 566.5 | 0.91 |

| Example | Acid | Amine | [M + H]+ | RT (min) |
|---|---|---|---|---|
| N-[(1S,2R)-1-benzyl-2-hydroxy-3-(1,2,3,4-tetrahydronaphthalen-1-ylamino)propyl]-3-(1,1-dioxido-1,2-thiazinan-2-yl)-5-(ethylamino)benzamide hydrochloride (E453) | A73 | C95 | 591.5 | 0.81 |
| N-((1S,2R)-1-benzyl-2-hydroxy-3-{[2-(3-methoxyphenyl)ethyl] amino}propyl)-3-(1,1-dioxido-1,2-thiazinan-2-yl)-5-(ethylamino)benzamide hydrochloride (E454) | A73 | C96 | 595.6 | 0.79 |
| N-((1S,2R)-1-benzyl-2-hydroxy-3-{[2-(4-methoxyphenyl)ethyl] amino}propyl)-3-(1,1-dioxido-1,2-thiazinan-2-yl)-5-(ethylamino)benzamide hydrochloride (E455) | A73 | C97 | 595.6 | 0.78 |
| N-((1S,2R)-1-benzyl-2-hydroxy-3-{[2-(2-methoxyphenyl)ethyl] amino}propyl)-3-(1,1-dioxido-1,2-thiazinan-2-yl)-5-(ethylamino)benzamide hydrochloride (E456) | A73 | C98 | 595.4 | 0.79 |
| N-((1S,2R)-1-benzyl-3-{[2-(2-chlorophenyl)ethyl]amino}-2-hydroxypropyl)-3-(1,1-dioxido-1,2-thiazinan-2-yl)-5-(ethylamino)benzamide hydrochloride (E457) | A73 | C99 | 599.5 | 0.81 |
| N-((1S,2R)-1-benzyl-3-{[2-(3-chlorophenyl)ethyl]amino}-2-hydroxypropyl)-3-(1,1-dioxido-1,2-thiazinan-2-yl)-5-(ethylamino)benzamide hydrochloride (E458) | A73 | C100 | 599.5 | 0.82 |
| N-((1S,2R)-1-benzyl-3-{[2-(4-chlorophenyl)ethyl]amino}-2-hydroxypropyl)-3-(1,1-dioxido-1,2-thiazinan-2-yl)-5-(ethylamino)benzamide hydrochloride (E459) | A73 | C101 | 599.5 | 0.82 |
| N-((1S,2R)-1-benzyl-2-hydroxy-3-{[2-(4-methylphenyl)ethyl]amino}propyl)-3-(1,1-dioxido-1,2-thiazinan-2-yl)-5-(ethylamino)benzamide hydrochloride (E460) | A73 | C102 | 579.5 | 2.02 |
| N-((1S,2R)-1-benzyl-2-hydroxy-3-{[2-(2-methylphenyl)ethyl]amino}propyl)-3-(1,1-dioxido-1,2-thiazinan-2-yl)-5-(ethylamino)benzamide hydrochloride (E461) | A73 | C103 | 580.5 | 2.02 |
| N-((1S,2R)-1-benzyl-3-{[2-(3,4-dichlorophenyl)ethyl] amino}-2-hydroxypropyl)-3-(1,1-dioxido-1,2-thiazinan-2-yl)-5-(ethylamino)benzamide hydrochloride (E462) | A73 | C104 | 633.4 | 2.15 |
| N-((1S,2R)-1-benzyl-3-{[2-(2,4-dichlorophenyl)ethyl] amino}-2-hydroxypropyl)-3-(1,1-dioxido-1,2-thiazinan-2-yl)-5-(ethylamino)benzamide hydrochloride (E463) | A73 | C105 | 633.4 | 0.86 |
| N-((1S,2R)-1-benzyl-3-{[2-(3,5-dimethoxyphenyl)ethyl] amino}-2-hydroxypropyl)-3-(1,1-dioxido-1,2-thiazinan-2-yl)-5-(ethylamino)benzamide hydrochloride (E464) | A73 | C106 | 625.5 | 0.8 |
| N-((1S,2R)-1-benzyl-3-{[2-(2,3-dimethoxyphenyl)ethyl] amino}-2-hydroxypropyl)-3-(1,1-dioxido-1,2-thiazinan-2-yl)-5-(ethylamino)benzamide hydrochloride (E465) | A73 | C107 | 625.4 | 0.79 |
| N-[(1S,2R)-1-benzyl-3-(benzylamino)-2-hydroxypropyl]-3-(1,1-dioxido-1,2-thiazinan-2-yl)-5-(ethylamino)benzamide hydrochloride (E466) | A73 | C108 | 551.5 | 0.75 |
| N-{(1S,2R)-1-benzyl-2-hydroxy-3-[(2-phenylethyl)amino]propyl}-3-(1,1-dioxido-1,2-thiazinan-2-yl)-5-(ethylamino)benzamide hydrochloride (E467) | A73 | C109 | 565.4 | 0.79 |
| N-{(1S,2R)-1-benzyl-3-[(1-ethylcyclohexyl)amino]-2-hydroxypropyl}-3-(1,1-dioxido-1,2-thiazinan-2-yl)-5-(ethylamino)benzamide hydrochloride (E468) | A73 | C110 | 571.6 | 0.82 |
| N-{(1S,2R)-1-benzyl-2-hydroxy-3-[(1-methylcyclopentyl)amino]propyl}-3-(1,1-dioxido-1,2-thiazinan-2-yl)-5-(ethylamino)benzamide hydrochloride (E469) | A73 | C111 | 544.5 | 1.81 |
| N-{(1S,2R)-1-benzyl-2-hydroxy-3-[(1-propylcyclopentyl)amino]propyl}-3-(1,1-dioxido-1,2-thiazinan-2-yl)-5-(ethylamino)benzamide hydrochloride (E470) | A73 | C112 | 571.7 | 0.83 |
| N-{(1S,2R)-1-benzyl-2-hydroxy-3-[(1-propylcyclohexyl)amino] propyl}-3-(1,1-dioxido-1,2-thiazinan-2-yl)-5-(ethylamino)benzamide hydrochloride (E471) | A73 | C113 | 585.6 | 0.88 |
| N-((1S,2R)-1-benzyl-3-{[2-(3-chlorophenyl)-1,1-dimethylethyl] amino}-2-hydroxypropyl)-3-(1,1-dioxido-1,2-thiazinan-2-yl)-5-(ethylamino)benzamide hydrochloride (E472) | A73 | C114 | 627.5 | 0.92 |
| 3-(1,1-dioxido-1,2-thiazinan-2-yl)-5-(ethylamino)-N-[(1S,2R)-2-hydroxy-3-[(3-methoxybenzyl)amino]-1-(pyridin-3-ylmethyl)propyl] benzamide hydrochloride (E473) | A73 | C115 | 582.0 | 1.75 |
| 3-(1,1-dioxido-1,2-thiazinan-2-yl)-5-(ethylamino)-N-[(1S,2R)-2-hydroxy-3-[(3-methoxybenzyl)amino]-1-(1,3-thiazol-2-ylmethyl)propyl] benzamide hydrochloride (E474) | A73 | C116 | 588.0 | 1.91 |
| N-[(1S,2R)-3-(cyclohexylamino)-2-hydroxy-1-(1,3-thiazol-2-ylmethyl)propyl]-3-(1,1-dioxido-1,2-thiazinan-2-yl)-5-(ethylamino)benzamide hydrochloride (E475) | A73 | C117 | 550.0 | 1.88 |

-continued

| Example | Acid | Amine | [M + H]+ | RT (min) |
|---|---|---|---|---|
| N-[(1S,2R)-3-[(1,5-dimethylhexyl)amino]-2-hydroxy-1-(1,3-thiazol-2-ylmethyl)propyl]-3-(1,1-dioxido-1,2-thiazinan-2-yl)-5-(ethylamino)benzamide hydrochloride (E476) | A73 | C118 | 580.1 | 2.21 |
| 3-(1,1-dioxido-1,2-thiazinan-2-yl)-5-(ethylamino)-N-{(1S,2R)-1-(2-furylmethyl)-2-hydroxy-3-[(3-methoxybenzyl)amino]propyl}benzamide hydrochloride (E477) | A73 | C119 | 571.0 | 2.02 |
| N-[(1S,2R)-3-(cyclohexylamino)-1-(2-furylmethyl)-2-hydroxypropyl]-3-(1,1-dioxido-1,2-thiazinan-2-yl)-5-(ethylamino)benzamide hydrochloride (E478) | A73 | C120 | 533.0 | 2.01 |
| N-[(1S,2R)-3-[(1,5-dimethylhexyl)amino]-1-(2-furylmethyl)-2-hydroxypropyl]-3-(1,1-dioxido-1,2-thiazinan-2-yl)-5-(ethylamino)benzamide hydrochloride (E479) | A73 | C121 | 563.1 | 2.32 |
| 3-(1,1-dioxido-1,2-thiazinan-2-yl)-5-(ethylamino)-N-{(1S,2R)-1-(2-furylmethyl)-2-hydroxy-3-[(1,1,5-trimethylhexyl)amino]propyl}benzamide hydrochloride (E480) | A73 | C122 | 577.2 | 2.39 |
| 3-(1,1-dioxido-1,2-thiazinan-2-yl)-5-(ethylamino)-N-[(1S)-2-hydroxy-3-[(3-methoxybenzyl)amino]-1-(pyridin-2-ylmethyl)propyl] benzamide (E481) | A73 | C123 | 581.9 | 1.84 |
| N-[(1S,2R)-1-[(4-chlorophenyl)methyl]-3-(cyclohexylamino)-2-hydroxypropyl]-3-(1,1-dioxidotetrahydro-2H-1,2-thiazin-2-yl)-5-(ethylamino)benzamide hydrochloride (E482) | A73 | C124 | 577.4 | 0.82 |
| N-[(1S,2R)-1-[(4-chlorophenyl)methyl]-2-hydroxy-3-({[3-(methyloxy)phenyl]methyl}amino)propyl]-3-(1,1-dioxidotetrahydro-2H-1,2-thiazin-2-yl)-5-(ethylamino)benzamide hydrochloride (E483) | A73 | C125 | 615.4 | 0.82 |
| 3-cyclopentyl-N-[(1S,2R)-1-[(3,5-difluorophenyl)methyl]-2-hydroxy-3-({[3-(trifluoromethyl)phenyl] methyl}amino)propyl]-5-(2-oxo-1-pyrrolidinyl)benzamide hydrochloride (E484) | A107 | C126 | 630.4 | 0.94 |
| N-[(1S,2R)-1-[(3,5-difluorophenyl)methyl]-2-hydroxy-3-({[3-(trifluoromethyl)phenyl] methyl}amino)propyl]-3-(1,1-dioxidotetrahydro-2H-1,2-thiazin-2-yl)-5-(ethylamino)benzamide hydrochloride (E485) | A73 | C126 | 655.4 | 0.85 |
| N-[(1S,2R)-1-[(3,5-difluorophenyl)methyl]-2-hydroxy-3-({[3-(methyloxy)phenyl]methyl}amino)propyl]-3-(1,1-dioxidotetrahydro-2H-1,2-thiazin-2-yl)-5-(ethylamino)benzamide hydrochloride (E486) | A73 | C127 | 617.3 | 0.8 |
| N-{(1S,2R)-1-[(3,5-difluorophenyl)methyl]-3-[(1,5-dimethylhexyl)amino]-2-hydroxypropyl}-3-(1,1-dioxidotetrahydro-2H-1,2-thiazin-2-yl)-5-(ethylamino)benzamide hydrochloride (E487) | A73 | C128 | 609.5 | 0.9 |
| N-{(1S,2R)-3-(cyclohexylamino)-1-[(3,5-difluorophenyl)methyl]-2-hydroxypropyl}-3-(1,1-dioxidotetrahydro-2H-1,2-thiazin-2-yl)-5-(ethylamino)benzamide hydrochloride (E488) | A73 | C129 | 579.4 | 0.8 |
| N-{(1S,2R)-1-[(3,5-difluorophenyl)methyl]-2-hydroxy-3-[(1,1,5-trimethylhexyl)amino] propyl}-3-(1,1-dioxidotetrahydro-2H-1,2-thiazin-2-yl)-5-(ethylamino)benzamide hydrochloride (E489) | A73 | C130 | 623.6 | 0.93 |
| N-[(1S,2R)-1-[(3,4-difluorophenyl)methyl]-2-hydroxy-3-({[3-(methyloxy)phenyl]methyl}amino)propyl]-3-(1,1-dioxidotetrahydro-2H-1,2-thiazin-2-yl)-5-(ethylamino)benzamide hydrochloride (E490) | A73 | C131 | 617.5 | 0.81 |
| N-{(1S,2R)-3-(cyclohexylamino)-1-[(3,4-difluorophenyl)methyl]-2-hydroxypropyl}-3-(1,1-dioxidotetrahydro-2H-1,2-thiazin-2-yl)-5-(ethylamino)benzamide hydrochloride (E491) | A73 | C132 | 579.5 | 0.79 |
| N-{(1S,2R)-1-[(3,4-difluorophenyl)methyl]-2-hydroxy-3-[(1,1,5-trimethylhexyl)amino] propyl}-3-(1,1-dioxidotetrahydro-2H-1,2-thiazin-2-yl)-5-(ethylamino)benzamide hydrochloride (E492) | A73 | C133 | 623.5 | 0.92 |
| N-[(1S,2R)-1-[(3-chlorophenyl)methyl]-2-hydroxy-3-({[3-(methyloxy)phenyl]methyl}amino)propyl]-3-(1,1-dioxidotetrahydro-2H-1,2-thiazin-2-yl)-5-(ethylamino)benzamide hydrochloride (E493) | A73 | C134 | 616.3 | 0.83 |
| N-[(1S,2R)-1-[(3-chlorophenyl)methyl]-3-(cyclohexylamino)-2-hydroxypropyl]-3-(1,1-dioxidotetrahydro-2H-1,2-thiazin-2-yl)-5-(ethylamino)benzamide hydrochloride (E494) | A73 | C135 | 578.3 | 0.83 |
| N-[(1S,2R)-1-[(2-chlorophenyl)methyl]-2-hydroxy-3-({[3-(methyloxy)phenyl]methyl}amino)propyl]-3-(1,1-dioxidotetrahydro-2H-1,2-thiazin-2-yl)-5-(ethylamino)benzamide hydrochloride (E495) | A73 | C136 | 616.4 | 0.86 |
| N-[(1S,2R)-1-[(2-chlorophenyl)methyl]-3-(cyclohexylamino)-2-hydroxypropyl]-3-(1,1-dioxidotetrahydro-2H-1,2-thiazin-2-yl)-5-(ethylamino)benzamide hydrochloride (E496) | A73 | C137 | 578.4 | 0.85 |
| N-{(1S,2R)-1-[(2-chlorophenyl)methyl]-3-[(1,5-dimethylhexyl)amino]-2-hydroxypropyl}-3-(1,1- | A73 | C138 | 608.5 | 0.98 |

-continued

| Example | Acid | Amine | [M + H]+ | RT (min) |
|---|---|---|---|---|
| dioxidotetrahydro-2H-1,2-thiazin-2-yl)-5-(ethylamino)benzamide hydrochloride (E497) | | | | |
| N-{(1S,2R)-1-[(3-chlorophenyl)methyl]-3-[(1,5-dimethylhexyl)amino]-2-hydroxypropyl}-3-(1,1-dioxidotetrahydro-2H-1,2-thiazin-2-yl)-5-(ethylamino)benzamide hydrochloride (E498) | A73 | C139 | 608.5 | 1 |
| 3-(1,1-dioxidotetrahydro-2H-1,2-thiazin-2-yl)-5-(ethylamino)-N-[(1S,2R)-1-[(3-fluorophenyl)methyl]-2-hydroxy-3-({[3-(methyloxy)phenyl]methyl}amino)propyl]benzamide hydrochloride (E499) | A73 | C140 | 599.4 | 0.82 |
| N-{(1S,2R)-3-[(1,5-dimethylhexyl)amino]-1-[(3-fluorophenyl)methyl]-2-hydroxypropyl}-3-(1,1-dioxidotetrahydro-2H-1,2-thiazin-2-yl)-5-(ethylamino)benzamide hydrochloride (E500) | A73 | C141 | 591.6 | 0.95 |
| 3-(1,1-dioxidotetrahydro-2H-1,2-thiazin-2-yl)-5-(ethylamino)-N-[(1S,2R)-2-hydroxy-3-({[3-(methyloxy)phenyl]methyl}amino)-1-(2-thienylmethyl)propyl] benzamide hydrochloride (E501) | A73 | C142 | 587.4 | 0.79 |
| N-[(1S,2R)-3-[(1,5-dimethylhexyl)amino]-2-hydroxy-1-(2-thienylmethyl)propyl]-3-(1,1-dioxidotetrahydro-2H-1,2-thiazin-2-yl)-5-(ethylamino)benzamide hydrochloride (E502) | A73 | C143 | 579.5 | 0.92 |
| 3-(1,1-dioxidotetrahydro-2H-1,2-thiazin-2-yl)-5-(ethylamino)-N-[(1S,2R)-2-hydroxy-3-({[3-(methyloxy)phenyl]methyl}amino)-1-(1H-pyrazol-1-ylmethyl)propyl] benzamide hydrochloride (E503) | A73 | C144 | 571.4 | 0.65 |
| N-[(1S,2R)-3-[(1,5-dimethylhexyl)amino]-2-hydroxy-1-(1H-pyrazol-1-ylmethyl)propyl]-3-(1,1-dioxidotetrahydro-2H-1,2-thiazin-2-yl)-5-(ethylamino)benzamide hydrochloride (E504) | A73 | C145 | 563.5 | 0.8 |
| 3-(1,1-dioxidotetrahydro-2H-1,2-thiazin-2-yl)-5-(ethylamino)-N-[(1S,2R)-2-hydroxy-3-({[3-(methyloxy)phenyl]methyl}amino)-1-(3-thienylmethyl)propyl] benzamide hydrochloride (E505) | A73 | C146 | 587.5 | 0.76 |
| N-[(1S,2R)-3-[(1,5-dimethylhexyl)amino]-2-hydroxy-1-(3-thienylmethyl)propyl]-3-(1,1-dioxidotetrahydro-2H-1,2-thiazin-2-yl)-5-(ethylamino)benzamide hydrochloride (E506) | A73 | C147 | 579.5 | 0.85 |
| formic acid-N-{(1S,2R)-1-benzyl-3-[(1,1-dimethylhexyl)amino]-2-hydroxypropyl}-3-(ethylamino)-5-(2-oxopyrrolidin-1-yl)benzamide (1:1) (E507) | A31 | C48 | 523.3 | 2.76 |
| formic acid-N-[(1S,2R)-1-benzyl-2-hydroxy-3-({1-methyl-1-[3-(trifluoromethyl)phenyl] ethyl}amino)propyl]-3-(ethylamino)-5-(2-oxopyrrolidin-1-yl)benzamide (1:1) (E508) | A31 | C40 | 597.3 | 3.03 |
| formic acid-N-((1S,2R)-1-benzyl-2-hydroxy-3-{[2-methyl-5-(trifluoromethyl)benzyl] amino}propyl)-3-(1,1-dioxido-1,2-thiazinan-2-yl)-5-(ethylamino)benzamide (1:1) (E509) | A73 | C49 | 633.2 | 2.84 |
| formic acid-N-{(1S,2R)-1-benzyl-3-[(1S)-2,3-dihydro-1H-inden-1-ylamino]-2-hydroxypropyl}-3-(1,1-dioxido-1,2-thiazinan-2-yl)-5-(ethylamino)benzamide (1:1) (E510) | A73 | C50 | 577.2 | 2.68 |
| formic acid-N-((1S,2R)-1-benzyl-2-hydroxy-3-{[(1S,2R)-2-hydroxy-2,3-dihydro-1H-inden-1-yl]amino}propyl)-3-(ethylamino)-5-(2-oxopyrrolidin-1-yl)benzamide (1:1) (E511) | A31 | C51 | 543.1 | 2.55 |
| N-{(1S,2R)-1-benzyl-2-hydroxy-3-[(6-methoxy-2,3-dihydro-1H-inden-1-yl)amino]propyl}-3-(1,1-dioxido-1,2-thiazinan-2-yl)-5-(ethylamino)benzamide (E512) | A73 | C52 | 607.5 | 2.55 |
| formic acid-N-((1S,2R)-1-benzyl-2-hydroxy-3-{[(1R,2S)-2-hydroxy-2,3-dihydro-1H-inden-1-yl]amino}propyl)-3-(1,1-dioxido-1,2-thiazinan-2-yl)-5-(ethylamino)benzamide (1:1) (E513) | A73 | C53 | 593.4 | 2.40 |
| N-((1S,2R)-1-benzyl-2-hydroxy-3-{[2-(isobutylthio)-1,1-dimethylethyl]amino} propyl)-3-(ethylamino)-5-(2-oxopyrrolidin-1-yl)benzamide (E514) | A31 | C54 | 555.4 | 2.62 |
| N-{(1S,2R)-1-benzyl-3-[(1,1-dimethyl-2-phenoxyethyl)amino]-2-hydroxypropyl}-3-(ethylamino)-5-(2-oxopyrrolidin-1-yl)benzamide (E515) | A31 | C55 | 559.4 | 2.56 |
| N-((1S,2R)-1-benzyl-3-{[2-(benzyloxy)-1,1-dimethylethyl]amino}-2-hydroxypropyl)-3-(ethylamino)-5-(2-oxopyrrolidin-1-yl)benzamide (E516) | A31 | C56 | 573.5 | 2.58 |
| N-{(1S,2R)-1-benzyl-2-hydroxy-3-[(3-methoxyphenyl)amino] propyl}-3-(ethylamino)-5-(2-oxopyrrolidin-1-yl)benzamide (E517) | A31 | C57 | 517.4 | 2.92 |
| formic acid-N-[(1S,2R)-1-benzyl-2-hydroxy-3-({2-[3-(trifluoromethyl)phenyl] ethyl}amino)propyl]-3-(ethylamino)-5-(2-oxopyrrolidin-1-yl)benzamide (1:1) (E518) | A31 | C58 | 583.4 | 2.62 |
| formic acid-N-{(1S,2R)-1-benzyl-3-[(1,1-dimethyl-2-phenylethyl)amino]-2-hydroxypropyl}-3-(ethylamino)-5-(2-oxopyrrolidin-1-yl)benzamide (1:1) (E519) | A31 | C59 | 543.5 | 2.55 |

-continued

| Example | Acid | Amine | [M + H]⁺ | RT (min) |
|---|---|---|---|---|
| formic acid-N-((1S,2R)-1-benzyl-2-hydroxy-3-{[2-(1-naphthyl)ethyl]amino} propyl)-3-(ethylamino)-5-(2-oxopyrrolidin-1-yl)benzamide (1:1) (E520) | A31 | C60 | 565.5 | 2.63 |
| formic acid-N-((1S,2R)-1-benzyl-2-hydroxy-3-{[2-(3-methoxyphenyl)-1,1-dimethylethyl]amino} propyl)-3-(ethylamino)-5-(2-oxopyrrolidin-1-yl)benzamide (1:1) (E521) | A31 | C61 | 573.5 | 2.57 |
| N-[(1S,2R)-3-anilino-1-benzyl-2-hydroxypropyl]-3-(ethylamino)-5-(2-oxopyrrolidin-1-yl)benzamide (E522) | A31 | C62 | 487.4 | 2.90 |
| N-((1S,2R)-1-benzyl-2-hydroxy-3-{[1-(3-methoxyphenyl)cyclopropyl]amino}propyl)-3-(ethylamino)-5-(2-oxopyrrolidin-1-yl)benzamide (E523) | A31 | C63 | 557.4 | 2.47 |
| formic acid-N-{(1S,2R)-1-benzyl-3-[(cyclohexylmethyl)amino]-2-hydroxypropyl}-3-(ethylamino)-5-(2-oxopyrrolidin-1-yl)benzamide (1:1) (E524) | A31 | C64 | 507.5 | 2.48 |
| formic acid-N-{(1S,2R)-1-benzyl-2-hydroxy-3-[(tetrahydro-2H-pyran-4-ylmethyl)amino]propyl}-3-(ethylamino)-5-(2-oxopyrrolidin-1-yl)benzamide (1:1) (E525) | A31 | C65 | 509.4 | 2.15 |
| N-[(1S,2R)-1-benzyl-2-hydroxy-3-(tetrahydro-2H-thiopyran-4-ylamino)propyl]-3-(ethylamino)-5-(2-oxopyrrolidin-1-yl)benzamide (E526) | A31 | C66 | 511.4 | 2.30 |
| formic acid-N-[(1S,2R)-1-benzyl-2-hydroxy-3-(isopropylamino)propyl]-3-ethyl-7-(2-oxopyrrolidin-1-yl)-1H-indole-5-carboxamide (1:1) (E527) | A141 | C28 | 478.5 | 2.04 |
| formic acid-N-[(1S,2R)-1-benzyl-3-(cyclohexylamino)-2-hydroxypropyl]-3-ethyl-7-(2-oxopyrrolidin-1-yl)-1H-indole-5-carboxamide (1:1) (E528) | A141 | C1 | 517.5 | 2.17 |
| formic acid-N-{(1S,2R)-1-benzyl-2-hydroxy-3-[(1,1,5-trimethylhexyl)amino]propyl}-3-ethyl-7-(2-oxopyrrolidin-1-yl)-1H-indole-5-carboxamide (1:1) (E529) | A141 | C5 | 561.5 | 2.56 |
| formic acid-N-{(1S,2R)-1-benzyl-2-hydroxy-3-[(3-methoxybenzyl)amino] propyl}-7-(1,1-dioxidoisothiazolidin-2-yl)-3-ethyl-1H-indole-5-carboxamide (1:1) (E530) | A144 | C14 | 591.4 | 2.36 |
| N-{(1S,2R)-1-benzyl-2-hydroxy-3-[(1,1,5-trimethylhexyl)amino] propyl}-7-(1,1-dioxidoisothiazolidin-2-yl)-3-ethyl-1H-indole-5-carboxamide (E531) | A144 | C5 | 597.5 | 2.72 |
| formic acid-N-[(1S,2R)-1-benzyl-3-(cyclohexylamino)-2-hydroxypropyl]-7-(1,1-dioxidoisothiazolidin-2-yl)-3-ethyl-1H-indole-5-carboxamide (1:1) (E532) | A144 | C1 | 554.5 | 2.33 |
| formic acid-N-[(1S,2R)-1-benzyl-2-hydroxy-3-(isopropylamino)propyl]-7-(1,1-dioxidoisothiazolidin-2-yl)-3-ethyl-1H-indole-5-carboxamide (1:1) (E533) | A144 | C28 | 514.4 | 2.14 |
| formic acid-N-((1S,2R)-1-benzyl-2-hydroxy-3-{[1-(3-methoxyphenyl)-1-methylethyl]amino}propyl)-7-(1,1-dioxidoisothiazolidin-2-yl)-3-ethyl-1H-indole-5-carboxamide (1:1) (E534) | A144 | C15 | 619.4 | 2.45 |
| formic acid-N-[(1S,2R)-1-benzyl-2-hydroxy-3-({1-methyl-1-[3-(trifluoromethyl)phenyl] ethyl}amino)propyl]-7-(1,1-dioxidoisothiazolidin-2-yl)-3-ethyl-1H-indole-5-carboxamide (1:1) (E535) | A144 | C40 | 657.4 | 2.62 |
| N-[(1S,2R)-1-benzyl-3-(sec-butylamino)-2-hydroxypropyl]-3-(ethylamino)-5-(2-oxopyrrolidin-1-yl)benzamide (E536) | A31 | C67 | 467.3 | 2.4 |
| N-{(1S,2R)-1-benzyl-3-[(4-tert-butylcyclohexyl)amino]-2-hydroxypropyl}-3-(ethylamino)-5-(2-oxopyrrolidin-1-yl)benzamide (E537) | A31 | C68 | 549.3 | 2.81 |
| N-{(1S,2R)-1-benzyl-3-[(1S)-2,3-dihydro-1H-inden-1-ylamino]-2-hydroxypropyl}-3-(ethylamino)-5-(2-oxopyrrolidin-1-yl)benzamide (E538) | A31 | C50 | 527.2 | 2.56 |
| N-{(1S,2R)-1-benzyl-2-hydroxy-3-[(2-isobutoxy-1,1-dimethylethyl)amino] propyl}-3-(ethylamino)-5-(2-oxopyrrolidin-1-yl)-benzamide (E539) | A31 | C70 | 539.2 | 2.64 |
| N-[(1S,2R)-1-benzyl-3-({1,1-dimethyl-2-[(2-methylprop-2-en-1-yl)oxy]ethyl}amino)-2-hydroxypropyl]-3-(ethylamino)-5-(2-oxopyrrolidin-1-yl)benzamide (E540) | A31 | C71 | 537.2 | 2.61 |
| N-{(1S,2R)-1-benzyl-3-[(1R)-2,3-dihydro-1H-inden-1-ylamino]-2-hydroxypropyl}-3-(ethylamino)-5-(2-oxopyrrolidin-1-yl)benzamide (E541) | A31 | C72 | 527.2 | 2.54 |
| N-{(1S,2R)-1-benzyl-3-[(1R)-2,3-dihydro-1H-inden-1-ylamino]-2-hydroxypropyl}-3-(1,1-dioxido-1,2-thiazinan-2-yl)-5-(ethylamino)benzamide (E542) | A73 | C72 | 577.2 | 2.64 |
| N-{(1S,2R)-1-benzyl-2-hydroxy-3-[(3-methoxybenzyl)amino] propyl}-3-[ethyl(methyl)amino]-5-(2-oxopyrrolidin-1-yl)benzamide (E543) | A128 | C14 | 546.5 | 2.49 |
| N-((1S,2R)-1-benzyl-2-hydroxy-3-{[1-(3-methoxyphenyl)-1-methylethyl]amino}propyl)-3-[ethyl(methyl)amino]-5-(2-oxopyrrolidin-1-yl)benzamide (E544) | A128 | C15 | 574.5 | 2.58 |

-continued

| Example | Acid | Amine | [M + H]+ | RT (min) |
|---|---|---|---|---|
| formic acid-N-((1S,2R)-1-benzyl-2-hydroxy-3-{[1-(3-methoxyphenyl) cyclohexyl]amino}propyl)-3-(ethylamino)-5-(2-oxopyrrolidin-1-yl)benzamide (1:1) (E545) | A31 | C41 | 599.5 | 2.60 |
| formic acid-N-((1S,2R)-1-benzyl-2-hydroxy-3-{[1-(3-methoxyphenyl) cyclohexyl]amino}propyl)-3-(1,1-dioxido-1,2-thiazinan-2-yl)-5-(ethylamino)benzamide (1:1) (E546) | A73 | C41 | 649.5 | 2.70 |
| formic acid-N-((1S,2R)-1-benzyl-2-hydroxy-3-{[(1-methyl-1H-pyrazol-4-yl)methyl]amino}propyl)-3-(1,1-dioxido-1,2-thiazinan-2-yl)-5-(ethylamino)benzamide (1:1) (E547) | A73 | C42 | 555.3 | 2.35 |
| formic acid-N-((1S,2R)-1-benzyl-2-hydroxy-3-{[(1-methyl-1H-pyrazol-4-yl)methyl]amino}propyl)-3-(ethylamino)-5-(2-oxopyrrolidin-1-yl)benzamide (1:1) (E548) | A31 | C42 | 505.3 | 2.27 |
| formic acid-N-[(1S,2R)-1-benzyl-3-(cyclohexylamino)-2-hydroxypropyl]-3-(1,1-dioxido-1,2-thiazinan-2-yl)-5-(ethylamino)benzamide (1:1) (E549) | A73 | C1 | 543.4 | 2.45 |
| formic acid-N-[(1S,2R)-1-benzyl-2-hydroxy-3-(tetrahydro-2H-pyran-4-ylamino)propyl]-3-(1,1-dioxido-1,2-thiazinan-2-yl)-5-(ethylamino)benzamide (1:1) (E550) | A73 | C43 | 545.4 | 2.28 |
| formic acid-N-[(1S,2R)-1-benzyl-3-(cyclohexylamino)-2-hydroxypropyl]-3-cyclopentyl-5-(1,1-dioxido-1,2-thiazinan-2-yl)benzamide (1:1) (E551) | A126 | C1 | 568.3 | 2.80 |
| formic acid-N-[(1S,2R)-1-benzyl-2-hydroxy-3-(tetrahydro-2H-pyran-4-ylamino)propyl]-3-cyclopentyl-5-(1,1-dioxido-1,2-thiazinan-2-yl)benzamide (1:1) (E552) | A126 | C43 | 570.3 | 2.61 |
| formic acid-N-{(1S,2R)-1-benzyl-3-[(3,3-dimethylbutyl)amino]-2-hydroxypropyl}-3-(1,1-dioxido-1,2-thiazinan-2-yl)-5-(ethylamino)-2-fluorobenzamide (1:1) (E553) | A119 | C44 | 563.4 | 2.53 |
| N-{(1S,2R)-1-benzyl-2-hydroxy-3-[(1,1,3,3-tetramethylbutyl)amino] propyl}-3-(1,1-dioxido-1,2-thiazinan-2-yl)-5-(ethylamino)-2-fluorobenzamide (E554) | A119 | C45 | 591.4 | 2.63 |
| formic acid-N-{(1S,2R)-1-benzyl-3-[(1,3-dimethylbutyl)amino]-2-hydroxypropyl}-3-(1,1-dioxido-1,2-thiazinan-2-yl)-5-(ethylamino)-2-fluorobenzamide (1:1) (E555) | A119 | C46 | 563.4 | 2.50 |
| formic acid-N-[(1S,2R)-1-benzyl-3-(cyclohexylamino)-2-hydroxypropyl]-3-(1,1-dioxido-1,2-thiazinan-2-yl)-5-(isopropylamino) benzamide (1:1) (E556) | A127 | C1 | 557.4 | 2.35 |
| formic acid-N-[(1S,2R)-1-benzyl-2-hydroxy-3-(isopropylamino)propyl]-3-(1,1-dioxido-1,2-thiazinan-2-yl)-5-(isopropylamino) benzamide (1:1) (E557) | A127 | C28 | 517.4 | 2.20 |
| formic acid-N-[(1S,2R)-1-benzyl-2-hydroxy-3-({1-methyl-1-[3-(trifluoromethyl)phenyl] ethyl}amino)propyl]-3-(1,1-dioxido-1,2-thiazinan-2-yl)-5-(isopropylamino) benzamide (1:1) (E558) | A127 | C40 | 661.4 | 2.70 |
| formic acid-N-{(1S,2R)-1-benzyl-2-hydroxy-3-[(3-methoxybenzyl)amino] propyl}-3-(1,1-dioxido-1,2-thiazinan-2-yl)-5-(isopropylamino) benzamide (1:1) (E559) | A127 | C14 | 595.4 | 2.41 |
| N-((1S,2R)-1-benzyl-2-hydroxy-3-{[3-(trifluoromethyl)benzyl] amino}propyl)-3-(1,1-dioxido-1,2-thiazinan-2-yl)-5-(isopropylamino) benzamide (E560) | A127 | C16 | 633.4 | 2.66 |
| formic acid-N-{(1S,2R)-1-benzyl-2-hydroxy-3-[(1,1,5-trimethylhexyl)amino] propyl}-3-(1,1-dioxido-1,2-thiazinan-2-yl)-5-(isopropylamino) benzamide (1:1) (E561) | A127 | C5 | 601.5 | 2.80 |
| formic acid-N-((1S,2R)-1-benzyl-3-{[4-fluoro-3-(trifluoromethyl)benzyl] amino}-2-hydroxypropyl)-3-(1,1-dioxido-1,2-thiazinan-2-yl)-5-(ethylamino)-2-fluorobenzamide (1:1) (E562) | A119 | C47 | 655.4 | 2.50 |
| formic acid-3-(ethylamino)-N-[(1S,2R)-2-hydroxy-3-({[3-(methyloxy)phenyl]methyl}amino)-1-(phenylmethyl)propyl]-5-(2-oxo-1-piperidinyl)benzamide (1:1) (E563) | A59 | C14 | 545.2 | 2.79 |
| formic acid-N-[(1S,2R)-3-[(1,5-dimethylhexyl)amino]-2-hydroxy-1-(phenylmethyl)propyl]-3-(ethylamino)-5-(2-oxo-1-piperidinyl)benzamide (1:1) (E564) | A59 | C20 | 537.3 | 2.81 |
| 3-(ethylamino)-N-[(1S,2R)-2-hydroxy-1-(phenylmethyl)-3-({[3-(trifluoromethyl)phenyl] methyl}amino)propyl]-5-(2-oxo-1-piperidinyl)benzamide (E565) | A59 | C16 | 583.2 | 2.69 |
| formic acid-N-[(1S,2R)-2-hydroxy-3-({[3-(methyloxy)phenyl]methyl}amino)-1-(phenylmethyl)propyl]-3-(2-oxo-1-piperidinyl)-5-propylbenzamide (1:1) (E566) | A116 | C14 | 544.3 | 2.74 |
| formic acid-N-[(1S,2R)-3-[(1,5-dimethylhexyl)amino]-2-hydroxy-1-(phenylmethyl)propyl]-3-(2-oxo-1-piperidinyl)-5-propylbenzamide (1:1) (E567) | A116 | C20 | 536.3 | 3.01 |
| N-[(1S,2R)-2-hydroxy-1-(phenylmethyl)-3-({[3-(trifluoromethyl)phenyl] methyl}amino)propyl]-3-(2-oxo-1-piperidinyl)-5-propylbenzamide (E568) | A116 | C16 | 582.2 | 2.88 |

| Example | Acid | Amine | [M + H]+ | RT (min) |
|---|---|---|---|---|
| N-[(1S,2R)-3-{[(1S)-2-(cyclohexylamino)-1-methyl-2-oxoethyl]amino}-2-hydroxy-1-(phenylmethyl)propyl]-3-(2-oxo-1-piperidinyl)-5-propylbenzamide (E569) | A116 | C6 | 577.3 | 2.76 |
| 3-(1,1-dioxido-2-isothiazolidinyl)-5-(ethylamino)-N-{(1S,2R)-2-hydroxy-1-(phenylmethyl)-3-[(1,1,5-trimethylhexyl)amino]propyl}benzamide (E570) | A70 | C5 | 573.5 | 2.67 |

Examples 571-572 (E571-E572)

The following compounds were prepared in an analogous manner to Example 183 from the appropriate amine and the appropriate aldehyde:

| Example | Precursor | [M + H]+ | RT (min) |
|---|---|---|---|
| formic acid-3-(1,1-dioxidotetrahydro-2H-1,2-thiazin-2-yl)-5-(ethylamino)-N-[(1S,2R)-2-hydroxy-3-({[1-(1-methylethyl)-1H-pyrazol-4-yl]methyl}amino)-1-(phenylmethyl)propyl]benzamide (1:1) (E571) | D120 | 583.5 | 2.24 |
| formic acid-3-(1,1-dioxidotetrahydro-2H-1,2-thiazin-2-yl)-5-(ethylamino)-N-[(1S,2R)-2-hydroxy-1-(phenylmethyl)-3-({[1-(2,2,2-trifluoroethyl)-1H-pyrazol-4-yl]methyl}amino)propyl]benzamide (1:1) (E572) | D120 | 623.4 | 2.28 |

Examples 573-695 (E573-E695)

Examples E573-695 were prepared in an analogous manner to Example 1 from the appropriate acid and amines indicated in the below table:

| Example | Acid | Amine | [M + H]+ | RT (min) |
|---|---|---|---|---|
| formic acid-5-(ethylamino)-2-fluoro-N-[(1S,2R)-2-hydroxy-3-({[3-(methyloxy)phenyl]methyl}amino)-1-(phenylmethyl)propyl]-3-(2-oxo-1-pyrrolidinyl)benzamide (1:1) (E573) | A118 | C14 | 549.3 | 2.42 |
| 3-(ethyloxy)-N-[(1S,2R)-2-hydroxy-3-({1-methyl-1-[3-(trifluoromethyl)phenyl] ethyl}amino)-1-(phenylmethyl)propyl]-5-(2-oxo-1-pyrrolidinyl)benzamide (E574) | A11 | C40 | 598.4 | 2.76 |
| 3-(1,1-dioxido-2-isothiazolidinyl)-5-(ethyloxy)-N-[(1S,2R)-2-hydroxy-3-({1-methyl-1-[3-(trifluoromethyl)phenyl] ethyl}amino)-1-(phenylmethyl)propyl] benzamide (E575) | A18 | C40 | 634.3 | 2.78 |
| 3-(1,1-dioxidotetrahydro-2H-1,2-thiazin-2-yl)-5-(ethylamino)-N-[(1S,2R)-2-hydroxy-3-({1-methyl-1-[3-(trifluoromethyl)phenyl] ethyl}amino)-1-(phenylmethyl)propyl] benzamide (E576) | A73 | C40 | 647.4 | 2.78 |
| 1-ethyl-N-[(1S,2R)-2-hydroxy-3-({1-methyl-1-[3-(trifluoromethyl)phenyl] ethyl}amino)-1-(phenylmethyl)propyl]-4-(2-oxo-1-pyrrolidinyl)-1H-indole-6-carboxamide (E577) | A140 | C40 | 621.4 | 2.75 |
| 3-(ethyloxy)-N-[(1S,2R)-2-hydroxy-3-({1-methyl-1-[3-(methyloxy)phenyl]ethyl}amino)-1-(phenylmethyl)propyl]-5-(2-oxo-1-pyrrolidinyl)benzamide (E578) | A11 | C15 | 560.4 | 2.62 |
| 1-ethyl-N-[(1S,2R)-2-hydroxy-3-({1-methyl-1-[3-(methyloxy)phenyl]ethyl}amino)-1-(phenylmethyl)propyl]-4-(2-oxo-1-pyrrodinyl)-1H-indole-6-carboxamide (E579) | A140 | C15 | 583.4 | 2.61 |
| 3-ethyl-N-[(1S,2R)-2-hydroxy-3-({1-methyl-1-[3-(trifluoromethyl)phenyl] ethyl}amino)-1-(phenylmethyl)propyl]-7-(2-oxo-1-pyrrolidinyl)-1H-indole-5-carboxamide (E580) | A141 | C40 | 621.4 | 2.81 |
| 3-(1,1-dioxido-2-isothiazolidinyl)-5-(ethyloxy)-N-[(1S,2R)-2-hydroxy-3-({1-methyl-1-[3-(methyloxy)phenyl]ethyl}amino)-1-(phenylmethyl)propyl] benzamide (E581) | A18 | C15 | 596.5 | 2.58 |
| 3-ethyl-N-[(1S,2R)-2-hydroxy-3-({1-methyl-1-[3-(methyloxy)phenyl]ethyl}amino)-1-(phenylmethyl)propyl]-7-(2-oxo-1-pyrrolidinyl)-1H-indole-5-carboxamide (E582) | A141 | C15 | 583.5 | 2.62 |

-continued

| Example | Acid | Amine | [M + H]+ | RT (min) |
|---|---|---|---|---|
| 3-(1,1-dioxidotetrahydro-2H-1,2-thiazin-2-yl)-5-(ethylamino)-2-fluoro-N-[(1S,2R)-2-hydroxy-3-({[3-(methyloxy)phenyl]methyl}amino)-1-(phenylmethyl)propyl] benzamide (E583) | A119 | C14 | 599.4 | 2.27 |
| 3-(1,1-dioxidotetrahydro-2H-1,2-thiazin-2-yl)-5-(ethylamino)-2-fluoro-N-[(1S,2R)-2-hydroxy-1-(phenylmethyl)-3-({[3-(trifluoromethyl)phenyl] methyl}amino)propyl] benzamide (E584) | A119 | C16 | 637.4 | 2.48 |
| 3-(1,1-dioxido-2-isothiazolidinyl)-5-(ethylamino)-N-[(1S,2R)-2-hydroxy-3-({1-methyl-1-[3-(trifluoromethyl)phenyl]ethyl}amino)-1-(phenylmethyl)propyl] benzamide (E585) | A70 | C40 | 633.3 | 2.73 |
| 3-(1,1-dioxido-2-isothiazolidinyl)-5-(ethylamino)-N-[(1S,2R)-2-hydroxy-3-({1-methyl-1-[3-(methyloxy)phenyl]ethyl}amino)-1-(phenylmethyl)propyl] benzamide (E586) | A70 | C15 | 595.3 | 2.57 |
| 5-(ethylamino)-2-fluoro-N-[(1S,2R)-2-hydroxy-1-(phenylmethyl)-3-({[3-(trifluoromethyl)phenyl] methyl}amino)propyl]-3-(2-oxo-1-pyrrolidinyl)benzamide (E587) | A118 | C16 | 587.3 | 2.60 |
| 2-fluoro-N-[(1S,2R)-2-hydroxy-3-({[3-(methyloxy)phenyl]methyl}amino)-1-(phenylmethyl)propyl]-3-(2-oxo-1-pyrrolidinyl)-5-propylbenzamide (E588) | A120 | C14 | 548.3 | 2.64 |
| 2-fluoro-N-[(1S,2R)-2-hydroxy-1-(phenylmethyl)-3-({[3-(trifluoromethyl)phenyl] methyl}amino)propyl]-3-(2-oxo-1-pyrrolidinyl)-5-propylbenzamide (E589) | A120 | C16 | 586.3 | 2.79 |
| N-[(1S,2R)-2-hydroxy-3-({[3-(methyloxy)phenyl]methyl}amino)-1-(phenylmethyl)propyl]-3-(2-oxo-5-phenyl-1-piperidinyl)-5-propylbenzamide (E590) | A121 | C14 | 620.5 | 3.02 |
| N-[(1S,2R)-2-hydroxy-3-[(1-methylethyl)amino]-1-(phenylmethyl)propyl]-3-(2-oxo-5-phenyl-1-piperidinyl)-5-propylbenzamide (E591) | A121 | C28 | 542.4 | 2.88 |
| N-[(1S,2R)-3-(cyclohexylamino)-2-hydroxy-1-(phenylmethyl)propyl]-3-(2-oxo-5-phenyl-1-piperidinyl)-5-propylbenzamide (E592) | A121 | C1 | 582.6 | 2.99 |
| 5-(ethylamino)-2-fluoro-N-[(1S,2R)-2-hydroxy-3-({1-methyl-1-[3-(trifluoromethyl)phenyl] ethyl}amino)-1-(phenylmethyl)propyl]-3-(2-oxo-1-pyrrolidinyl)benzamide (E593) | A118 | C40 | 615.3 | 2.61 |
| 5-(ethylamino)-2-fluoro-N-{(1S,2R)-2-hydroxy-1-(phenylmethyl)-3-[(1,1,5-trimethylhexyl)amino] propyl}-3-(2-oxo-1-pyrrolidinyl)benzamide (E594) | A118 | C5 | 555.4 | 2.71 |
| N-[(1S,2R)-3-(cyclohexylamino)-2-hydroxy-1-(phenylmethyl)propyl]-5-(ethylamino)-2-fluoro-3-(2-oxo-1-pyrrolidinyl)benzamide (E595) | A118 | C1 | 511.3 | 2.25 |
| 5-(ethylamino)-2-fluoro-N-[(1S,2R)-2-hydroxy-3-[(1-methylethyl)amino]-1-(phenylmethyl)propyl]-3-(2-oxo-1-pyrrolidinyl)benzamide (E596) | A118 | C28 | 471.3 | 2.05 |
| 5-(ethylamino)-2-fluoro-N-[(1S,2R)-2-hydroxy-3-({1-methyl-1-[3-(methyloxy)phenyl]ethyl}amino)-1-(phenylmethyl)propyl]-3-(2-oxo-1-pyrrolidinyl)benzamide (E597) | A118 | C15 | 577.4 | 2.42 |
| 3-(1,1-dioxidotetrahydro-2H-1,2-thiazin-2-yl)-5-(ethylamino)-2-fluoro-N-{(1S,2R)-2-hydroxy-1-(phenylmethyl)-3-[(1,1,5-trimethylhexyl)amino] propyl}benzamide (E598) | A119 | C5 | 605.4 | 2.87 |
| N-[(1S,2R)-3-(cyclohexylamino)-2-hydroxy-1-(phenylmethyl)propyl]-3-(1,1-dioxidotetrahydro-2H-1,2-thiazin-2-yl)-5-(ethylamino)-2-fluorobenzamide (E599) | A119 | C1 | 561.4 | 2.42 |
| 3-(1,1-dioxidotetrahydro-2H-1,2-thiazin-2-yl)-5-(ethylamino)-2-fluoro-N-[(1S,2R)-2-hydroxy-3-[(1-methylethyl)amino]-1-(phenylmethyl)propyl] benzamide (E600) | A119 | C28 | 521.3 | 2.20 |
| 4-(1,1-dioxido-2-isothiazolidinyl)-1-ethyl-N-[(1S,2R)-2-hydroxy-3-({[3-(methyloxy)phenyl]methyl}amino)-1-(phenylmethyl)propyl]-1H-indazole-6-carboxamide (E601) | A153 | C14 | 592.3 | 2.39 |
| 4-(1,1-dioxido-2-isothiazolidinyl)-1-ethyl-N-[(1S,2R)-2-hydroxy-1-(phenylmethyl)-3-({[3-(trifluoromethyl)phenyl] methyl}amino)propyl]-1H-indazole-6-carboxamide (E602) | A153 | C16 | 630.3 | 2.58 |
| 4-(1,1-dioxido-2-isothiazolidinyl)-1-ethyl-N-[(1S,2R)-2-hydroxy-3-({1-methyl-1-[3-(methyloxy)phenyl]ethyl}amino)-1-(phenylmethyl)propyl]-1H-indazole-6-carboxamide (E603) | A153 | C15 | 620.3 | 2.46 |
| 4-(1,1-dioxido-2-isothiazolidinyl)-1-ethyl-N-[(1S,2R)-2-hydroxy-3-({1-methyl-1-[3-(trifluoromethyl)phenyl] ethyl}amino)-1-(phenylmethyl)propyl]-1H-indazole-6-carboxamide (E604) | A153 | C40 | 658.3 | 2.65 |
| 4-(1,1-dioxido-2-isothiazolidinyl)-1-ethyl-N-{(1S,2R)-2-hydroxy-1-(phenylmethyl)-3-[(1,1,5-trimethylhexyl)amino] propyl}-1H-indazole-6-carboxamide (E605) | A153 | C5 | 598.5 | 2.47 |
| N-[(1S,2R)-3-(cyclohexylamino)-2-hydroxy-1-(phenylmethyl)propyl]-4-(1,1-dioxido-2-isothiazolidinyl)-1-ethyl-1H-indazole-6-carboxamide (E606) | A153 | C1 | 554.4 | 2.08 |

-continued

| Example | Acid | Amine | [M + H]+ | RT (min) |
|---|---|---|---|---|
| 4-(1,1-dioxido-2-isothiazolidinyl)-1-ethyl-N-[(1S,2R)-2-hydroxy-3-[(1-methylethyl)amino]-1-(phenylmethyl)propyl]-1H-indazole-6-carboxamide (E607) | A153 | C28 | 514.4 | 1.91 |
| 3-ethyl-N-[(1S,2R)-2-hydroxy-3-({[3-(methyloxy)phenyl] methyl}amino)-1-(phenylmethyl)propyl]-1-methyl-7-(2-oxo-1-pyrrolidinyl)-1H-indole-5-carboxamide (E608) | A142 | C14 | 569.5 | 2.38 |
| 3-ethyl-N-[(1S,2R)-2-hydroxy-3-({1-methyl-1-[3-(methyloxy) phenyl]ethyl}amino)-1-(phenylmethyl)propyl]-1-methyl-7-(2-oxo-1-pyrrolidinyl)-1H-indole-5-carboxamide (E609) | A142 | C15 | 597.5 | 2.45 |
| 3-ethyl-N-[(1S,2R)-2-hydroxy-3-({1-methyl-1-[3-(trifluoromethyl)phenyl] ethyl}amino)-1-(phenylmethyl)propyl]-1-methyl-7-(2-oxo-1-pyrrolidinyl)-1H-indole-5-carboxamide (E610) | A142 | C40 | 635.4 | 2.71 |
| N-[(1S,2R)-3-(cyclohexylamino)-2-hydroxy-1-(phenylmethyl)propyl]-3-ethyl-1-methyl-7-(2-oxo-1-pyrrolidinyl)-1H-indole-5-carboxamide (E611) | A142 | C1 | 531.5 | 2.33 |
| 3-ethyl-N-{(1S,2R)-2-hydroxy-1-(phenylmethyl)-3-[(1,1,5-trimethylhexyl)amino] propyl}-1-methyl-7-(2-oxo-1-pyrrolidinyl)-1H-indole-5-carboxamide (E612) | A142 | C5 | 575.4 | 2.80 |
| 3-ethyl-N-{(1S,2R)-2-hydroxy-1-(phenylmethyl)-3-[(1,1,5-trimethylhexyl)amino] propyl}-1-methyl-7-(2-oxo-1-pyrrolidinyl)-1H-indole-5-carboxamide formate salt (1:1) (E613) | A122 | C5 | 591.5 | 2.60 |
| formic acid-3-(1,1-dioxidotetrahydro-2H-1,2-thiazin-2-yl)-5-(ethylamino)-N-{(1S,2R)-2-hydroxy-1-(phenylmethyl)-3-[(1,1,5-trimethylhexyl)amino] propyl}benzamide (1:1) (E614) | A73 | C5 | 587.6 | 2.61 |
| N-[(1S,2R)-3-(cyclohexylamino)-2-hydroxy-1-(phenylmethyl)propyl]-3-(1,1-dioxido-2-isothiazolidinyl)-5-(ethylamino)-2-fluorobenzamide (E615) | A122 | C1 | 547.5 | 2.08 |
| 7-(1,1-dioxido-2-isothiazolidinyl)-3-ethyl-N-[(1S,2R)-2-hydroxy-3-({[3-(methyloxy)phenyl]methyl}amino)-1-(phenylmethyl)propyl]-1-methyl-1H-indole-5-carboxamide (E616) | A146 | C14 | 605.5 | 2.49 |
| 7-(1,1-dioxido-2-isothiazolidinyl)-3-ethyl-N-[(1S,2R)-2-hydroxy-1-(phenylmethyl)-3-({[3-(trifluoromethyl)phenyl]methyl}amino)propyl]-1-methyl-1H-indole-5-carboxamide (E617) | A146 | C16 | 643.4 | 2.68 |
| 7-(1,1-dioxido-2-isothiazolidinyl)-3-ethyl-N-[(1S,2R)-2-hydroxy-3-({1-methyl-1-[3-(methyloxy)phenyl]ethyl}amino)-1-(phenylmethyl)propyl]-1-methyl-1H-indole-5-carboxamide (E618) | A146 | C15 | 633.4 | 2.57 |
| 7-(1,1-dioxido-2-isothiazolidinyl)-3-ethyl-N-[(1S,2R)-2-hydroxy-3-({1-methyl-1-[3-(trifluoromethyl)phenyl] ethyl}amino)-1-(phenylmethyl)propyl]-1-methyl-1H-indole-5-carboxamide (E619) | A146 | C40 | 671.4 | 2.74 |
| 7-(1,1-dioxido-2-isothiazolidinyl)-3-ethyl-N-{(1S,2R)-2-hydroxy-1-(phenylmethyl)-3-[(1,1,5-trimethylhexyl)amino] propyl}-1-methyl-1H-indole-5-carboxamide (E620) | A146 | C5 | 611.5 | 2.84 |
| N-[(1S,2R)-3-(cyclohexylamino)-2-hydroxy-1-(phenylmethyl)propyl]-7-(1,1-dioxido-2-isothiazolidinyl)-3-ethyl-1-methyl-1H-indole-5-carboxamide (E621) | A146 | C1 | 567.5 | 2.46 |
| 3-(ethylamino)-N-[(1S,2R)-2-hydroxy-1-(phenylmethyl)-3-({[3-(trifluoromethyl)phenyl] methyl}amino)propyl]-4-methyl-5-(2-oxo-1-pyrrolidinyl)benzamide (E622) | A129 | C16 | 583.2 | 2.70 |
| 3-(1,1-dioxido-2-isothiazolidinyl)-5-(ethylamino)-N-[(1S,2R)-2-hydroxy-1-(phenylmethyl)-3-({[3-(trifluoromethyl)phenyl] methyl}amino)propyl]-4-methylbenzamide (E623) | A130 | C16 | 619.2 | 2.77 |
| 3-(1,1-dioxidotetrahydro-2H-1,2-thiazin-2-yl)-5-(ethylamino)-N-[(1S,2R)-2-hydroxy-1-(phenylmethyl)-3-({[3-(trifluoromethyl)phenyl] methyl}amino)propyl]-4-methylbenzamide (E624) | A131 | C16 | 633.2 | 2.84 |
| 3-(1,1-dioxidotetrahydro-2H-1,2-thiazin-2-yl)-5-(ethylamino)-N-[(1S,2R)-2-hydroxy-1-(phenylmethyl)-3-({[3-(trifluoromethyl)phenyl] methyl}amino)propyl]-4-(methyloxy)benzamide (E625) | A132 | C16 | 649.2 | 2.82 |
| 3-(ethylamino)-N-[(1S,2R)-2-hydroxy-1-(phenylmethyl)-3-({[3-(trifluoromethyl)phenyl] methyl}amino)propyl]-4-(methyloxy)-5-(2-oxo-1-pyrrolidinyl)benzamide (E626) | A133 | C16 | 599.2 | 2.71 |
| 3-(1,1-dioxido-2-isothiazolidinyl)-5-(ethylamino)-N-[(1S,2R)-2-hydroxy-1-(phenylmethyl)-3-({[3-(trifluoromethyl)phenyl] methyl}amino)propyl]-4-(methyloxy)benzamide (E627) | A134 | C16 | 635.2 | 2.76 |
| 3-(diethylamino)-5-(1,1-dioxidotetrahydro-2H-1,2-thiazin-2-yl)-N-[(1S,2R)-2-hydroxy-1-(phenylmethyl)-3-({[3-(trifluoromethyl)phenyl] methyl}amino)propyl]-4-methylbenzamide (E628) | A135 | C16 | 661.2 | 2.94 |

-continued

| Example | Acid | Amine | [M + H]⁺ | RT (min) |
|---|---|---|---|---|
| 3-(1,1-dioxidotetrahydro-2H-1,2-thiazin-2-yl)-N-[(1S,2R)-2-hydroxy-1-(phenylmethyl)-3-({[3-(trifluoromethyl)phenyl]methyl}amino)propyl]-4-(methyloxy)-5-[(1E)-1-propen-1-yl]benzamide (E629) | A136 | C16 | 646.1 | 2.95 |
| 3-(1,1-dioxidotetrahydro-2H-1,2-thiazin-2-yl)-N-[(1S,2R)-2-hydroxy-1-(phenylmethyl)-3-({[3-(trifluoromethyl)phenyl]methyl}amino)propyl]-4-(methyloxy)-5-propylbenzamide (E630) | A137 | C16 | 648.2 | 2.99 |
| N-[(1S,2R)-2-hydroxy-1-(phenylmethyl)-3-({[3-(trifluoromethyl)phenyl]methyl}amino)propyl]-4-(2-oxo-1-pyrrolidinyl)-1H-indole-6-carboxamide (E631) | A154 | C16 | 565.2 | 2.59 |
| 1-ethyl-N-[(1S,2R)-2-hydroxy-1-(phenylmethyl)-3-({[3-(trifluoromethyl)phenyl]methyl}amino)propyl]-4-(2-oxo-1-pyrrolidinyl)-1H-indole-6-carboxamide (E632) | A140 | C16 | 593.2 | 2.83 |
| 1-ethyl-N-[(1S,2R)-2-hydroxy-3-({[3-(methyloxy)phenyl]methyl}amino)-1-(phenylmethyl)propyl]-4-(2-oxo-1-pyrrolidinyl)-1H-indole-6-carboxamide (E633) | A140 | C14 | 555.2 | 2.36 |
| 4-(1,1-dioxidotetrahydro-2H-1,2-thiazin-2-yl)-N-[(1S,2R)-2-hydroxy-3-({[3-(methyloxy)phenyl]methyl}amino)-1-(phenylmethyl)propyl]-1H-indole-6-carboxamide (E634) | A155 | C14 | 577.1 | 2.31 |
| 4-(1,1-dioxidotetrahydro-2H-1,2-thiazin-2-yl)-1-ethyl-N-[(1S,2R)-2-hydroxy-3-({[3-(methyloxy)phenyl]methyl}amino)-1-(phenylmethyl)propyl]-1H-indole-6-carboxamide (E635) | A147 | C14 | 605.4 | 2.60 |
| N-[(1S,2R)-2-hydroxy-3-({[3-(methyloxy)phenyl]methyl}amino)-1-(phenylmethyl)propyl]-3-(1-methylethyl)-5-(2-oxo-1-pyrrolidinyl)benzamide (E636) | A104 | C14 | 530.5 | 2.60 |
| N-[(1S,2R)-2-hydroxy-3-({[3-(methyloxy)phenyl]methyl}amino)-1-(phenylmethyl)propyl]-1-methyl-4-(2-oxo-1-pyrrolidinyl)-1H-indole-6-carboxamide (E637) | A156 | C14 | 541.2 | 2.50 |
| 3-(1,1-dioxido-2-isothiazolidinyl)-N-[(1S,2R)-2-hydroxy-3-({[3-(methyloxy)phenyl]methyl}amino)-1-(phenylmethyl)propyl]-5-(2-oxo-1-pyrrolidinyl)benzamide (E638) | A138 | C14 | 607.2 | 2.43 |
| 1-butyl-N-[(1S,2R)-2-hydroxy-3-({[3-(methyloxy)phenyl]methyl}amino)-1-(phenylmethyl)propyl]-4-(2-oxo-1-pyrrolidinyl)-1H-indole-6-carboxamide (E639) | A157 | C14 | 583.2 | 2.78 |
| N-[(1S,2R)-2-hydroxy-3-({[3-(methyloxy)phenyl]methyl}amino)-1-(phenylmethyl)propyl]-4-(2-oxo-1-pyrrolidinyl)-1-pentyl-1H-indole-6-carboxamide (E640) | A158 | C14 | 597.2 | 2.90 |
| 3-(1,1-dioxido-2-isothiazolidinyl)-5-(ethylamino)-2-fluoro-N-[(1S,2R)-2-hydroxy-3-({[3-(methyloxy)phenyl]methyl}amino)-1-(phenylmethyl)propyl] benzamide (E641) | A122 | C14 | 585.3 | 2.47 |
| 3-(1,1-dioxido-2-isothiazolidinyl)-5-(ethylamino)-2-fluoro-N-[(1S,2R)-2-hydroxy-1-(phenylmethyl)-3-({[3-(trifluoromethyl)phenyl] methyl}amino)propyl] benzamide (E642) | A122 | C16 | 623.3 | 2.62 |
| 3-(1,1-dioxido-2-isothiazolidinyl)-5-(ethylamino)-2-fluoro-N-[(1S,2R)-2-hydroxy-3-({1-methyl-1-[3-(methyloxy)phenyl]ethyl}amino)-1-(phenylmethyl)propyl] benzamide (E643) | A122 | C15 | 613.3 | 2.56 |
| 3-(1,1-dioxido-2-isothiazolidinyl)-5-(ethylamino)-2-fluoro-N-[(1S,2R)-2-hydroxy-3-({1-methyl-1-[3-(trifluoromethyl)phenyl]ethyl}amino)-1-(phenylmethyl)propyl] benzamide (E644) | A122 | C40 | 651.3 | 2.70 |
| 3-(1,1-dioxidotetrahydro-2H-1,2-thiazin-2-yl)-5-(ethylamino)-2-fluoro-N-[(1S,2R)-2-hydroxy-3-({1-methyl-1-[3-(methyloxy)phenyl]ethyl}amino)-1-(phenylmethyl)propyl] benzamide (E645) | A119 | C15 | 627.3 | 2.63 |
| 3-(1,1-dioxidotetrahydro-2H-1,2-thiazin-2-yl)-5-(ethylamino)-2-fluoro-N-[(1S,2R)-2-hydroxy-3-({1-methyl-1-[3-(trifluoromethyl)phenyl]ethyl}amino)-1-(phenylmethyl)propyl] benzamide (E646) | A119 | C40 | 665.3 | 2.77 |
| 4-(1,1-dioxido-2-isothiazolidinyl)-1-ethyl-N-[(1S,2R)-2-hydroxy-3-({[3-(methyloxy)phenyl]methyl}amino)-1-(phenylmethyl)propyl]-1H-indole-6-carboxamide (E647) | A143 | C14 | 591.3 | 2.60 |
| 4-(1,1-dioxido-2-isothiazolidinyl)-1-ethyl-N-[(1S,2R)-2-hydroxy-1-(phenylmethyl)-3-({[3-(trifluoromethyl)phenyl]methyl}amino)propyl]-1H-indole-6-carboxamide (E648) | A143 | C16 | 629.3 | 2.75 |
| 4-(1,1-dioxido-2-isothiazolidinyl)-1-ethyl-N-[(1S,2R)-2-hydroxy-3-({1-methyl-1-[3-(methyloxy)phenyl]ethyl}amino)-1-(phenylmethyl)propyl]-1H-indole-6-carboxamide (E649) | A143 | C15 | 619.4 | 2.67 |
| 4-(1,1-dioxido-2-isothiazolidinyl)-1-ethyl-N-[(1S,2R)-2-hydroxy-3-({1-methyl-1-[3-(trifluoromethyl)phenyl]ethyl}amino)-1-(phenylmethyl)propyl]-1H-indole-6-carboxamide (E650) | A143 | C40 | 657.4 | 2.80 |
| 3-(1,1-dioxidotetrahydro-2H-1,2-thiazin-2-yl)-5-(ethylamino)-N-[(1S,2R)-2-hydroxy-3-({[3-(methyloxy)phenyl]methyl}amino)-1-(phenylmethyl)propyl]-2-(methyloxy)benzamide (E651) | A139 | C14 | 611.4 | 2.59 |

-continued

| Example | Acid | Amine | [M + H]+ | RT (min) |
|---|---|---|---|---|
| 3-(1,1-dioxidotetrahydro-2H-1,2-thiazin-2-yl)-5-(ethylamino)-N-[(1S,2R)-2-hydroxy-1-(phenylmethyl)-3-({[3-(trifluoromethyl)phenyl] methyl}amino)propyl]-2-(methyloxy)benzamide (E652) | A139 | C16 | 649.3 | 2.76 |
| 5-(1,1-dioxidotetrahydro-2H-1,2-thiazin-2-yl)-N'-[(1S,2R)-2-hydroxy-3-({1-methyl-1-[3-(methyloxy)phenyl]ethyl}amino)-1-(phenylmethyl)propyl]-N,N-dipropyl-1,3-benzenedicarboxamide (E653) | A95 | C15 | 693.5 | 2.82 |
| 5-(1,1-dioxidotetrahydro-2H-1,2-thiazin-2-yl)-N'-[(1S,2R)-2-hydroxy-3-({1-methyl-1-[3-(trifluoromethyl)phenyl] ethyl}amino)-1-(phenylmethyl)propyl]-N,N-dipropyl-1,3-benzenedicarboxamide (E654) | A95 | C40 | 731.4 | 2.94 |
| 1-ethyl-N-[(1S,2R)-2-hydroxy-3-({[3-(methyloxy)phenyl]methyl}amino)-1-(phenylmethyl)propyl]-4-(2-oxo-1-pyrrolidinyl)-1H-indazole-6-carboxamide (E655) | A152 | C14 | 556.3 | 2.33 |
| 1-ethyl-N-[(1S,2R)-2-hydroxy-1-(phenylmethyl)-3-({[3-(trifluoromethyl)phenyl] methyl}amino)propyl]-4-(2-oxo-1-pyrrolidinyl)-1H-indazole-6-carboxamide (E656) | A152 | C16 | 594.3 | 2.42 |
| 1-ethyl-N-[(1S,2R)-2-hydroxy-3-({1-methyl-1-[3-(methyloxy)phenyl]ethyl}amino)-1-(phenylmethyl)propyl]-4-(2-oxo-1-pyrrolidinyl)-1H-indazole-6-carboxamide (E657) | A152 | C15 | 584.4 | 2.42 |
| 1-ethyl-N-[(1S,2R)-2-hydroxy-3-({1-methyl-1-[3-(trifluoromethyl)phenyl] ethyl}amino)-1-(phenylmethyl)propyl]-4-(2-oxo-1-pyrrolidinyl)-1H-indazole-6-carboxamide (E658) | A152 | C40 | 622.4 | 2.61 |
| 4-(1,1-dioxidotetrahydro-2H-1,2-thiazin-2-yl)-1-ethyl-N-[(1S,2R)-2-hydroxy-3-({[3-(methyloxy)phenyl]methyl}amino)-1-(phenylmethyl)propyl]-2,3-dihydro-1H-indole-6-carboxamide (E659) | A145 | C14 | 607.4 | 2.61 |
| 4-(1,1-dioxidotetrahydro-2H-1,2-thiazin-2-yl)-1-ethyl-N-{(1S,2R)-2-hydroxy-1-(phenylmethyl)-3-[(1,1,5-trimethylhexyl)amino] propyl}-1H-indole-6-carboxamide (E660) | A147 | C5 | 611.5 | 2.92 |
| 4-(1,1-dioxido-2-isothiazolidinyl)-1-ethyl-N-{(1S,2R)-2-hydroxy-1-(phenylmethyl)-3-[(1,1,5-trimethylhexyl)amino] propyl}-1H-indole-6-carboxamide (E661) | A143 | C5 | 597.5 | 2.85 |
| 1-ethyl-N-{(1S,2R)-2-hydroxy-1-(phenylmethyl)-3-[(1,1,5-trimethylhexyl)amino] propyl}-4-(2-oxo-1-pyrrolidinyl)-1H-indole-6-carboxamide (E662) | A140 | C5 | 561.5 | 2.83 |
| N-[(1S,2R)-3-(cyclohexylamino)-2-hydroxy-1-(phenylmethyl)propyl]-4-(1,1-dioxidotetrahydro-2H-1,2-thiazin-2-yl)-1-ethyl-1H-indole-6-carboxamide (E663) | A147 | C1 | 567.5 | 2.62 |
| N-[(1S,2R)-3-(cyclohexylamino)-2-hydroxy-1-(phenylmethyl)propyl]-4-(1,1-dioxido-2-isothiazolidinyl)-1-ethyl-1H-indole-6-carboxamide (E664) | A143 | C1 | 553.5 | 2.54 |
| N-[(1S,2R)-3-(cyclohexylamino)-2-hydroxy-1-(phenylmethyl)propyl]-1-ethyl-4-(2-oxo-1-pyrrolidinyl)-1H-indole-6-carboxamide (E665) | A140 | C1 | 517.4 | 2.51 |
| 4-(1,1-dioxidotetrahydro-2H-1,2-thiazin-2-yl)-1-ethyl-N-[(1S,2R)-2-hydroxy-1-(phenylmethyl)-3-({[3-(trifluoromethyl)phenyl] methyl}amino)propyl]-1H-indole-6-carboxamide (E666) | A147 | C16 | 643.5 | 2.86 |
| 4-(1,1-dioxidotetrahydro-2H-1,2-thiazin-2-yl)-1-ethyl-N-[(1S,2R)-2-hydroxy-3-({1-methyl-1-[3-(methyloxy)phenyl]ethyl}amino)-1-(phenylmethyl)propyl]-1H-indole-6-carboxamide (E667) | A147 | C15 | 633.5 | 2.75 |
| 4-(1,1-dioxidotetrahydro-2H-1,2-thiazin-2-yl)-1-ethyl-N-[(1S,2R)-2-hydroxy-3-({1-methyl-1-[3-(trifluoromethyl)phenyl] ethyl}amino)-1-(phenylmethyl)propyl]-1H-indole-6-carboxamide (E668) | A147 | C40 | 671.5 | 2.92 |
| 7-[acetyl(ethyl)amino]-N-[(1S,2R)-2-hydroxy-1-(phenylmethyl)-3-({[3-trifluoromethyl)phenyl] methyl}amino) propyl]-3-methyl-1-benzofuran-5-carboxamide (E669) | A159 | C16 | 580.2 | 2.81 |
| formic acid-N-[(1S,2R)-2-hydroxy-1-(phenylmethyl)-3-({[3-(trifluoromethyl)phenyl] methyl}amino)propyl]-3-methyl-7-(2-oxo-1-pyrrolidinyl)-1H-indole-5-carboxamide (1:1) (E670) | A160 | C16 | 579.2 | 2.68 |
| N-[(1S,2R)-2-hydroxy-1-(phenylmethyl)-3-({[3-(trifluoromethyl)phenyl] methyl}amino)propyl]-3-(1-methylethyl)-7-(2-oxo-1-pyrrolidinyl)-1H-indole-5-carboxamide (E671) | A161 | C16 | 607.2 | 2.85 |
| formic acid-N-[(1S,2R)-2-hydroxy-1-(phenylmethyl)-3-({[3-(trifluoromethyl)phenyl] methyl}amino)propyl]-1-methyl-3-(1-methylethyl)-7-(2-oxo-1-pyrrolidinyl)-1H-indole-5-carboxamide (1:1) (E672) | A162 | C16 | 621.2 | 2.89 |

-continued

| Example | Acid | Amine | [M + H]+ | RT (min) |
|---|---|---|---|---|
| 3-ethyl-N-[(1S,2R)-2-hydroxy-1-(phenylmethyl)-3-({[3-(trifluoromethyl)phenyl] methyl}amino)propyl]-7-(2-oxo-1-pyrrolidinyl)-1-benzofuran-5-carboxamide (E673) | A163 | C16 | 594.2 | 2.90 |
| formic acid-N-[(1S,2R)-2-hydroxy-1-(phenylmethyl)-3-({[3-(trifluoromethyl)phenyl] methyl}amino)propyl]-4-methyl-8-(2-oxo-1-pyrrolidinyl)-3,4-dihydro-2H-chromene-6-carboxamide (1:1) (E674) | A164 | C16 | 596.2 | 2.81 |
| 3-ethyl-N-[1S,2R)-2-hydroxy-1-(phenylmethyl)-3-({[3-(trifluoromethyl)phenyl] methyl}amino)propyl]-7-(2-oxo-1-pyrrolidinyl)-1H-indole-5-carboxamide (E675) | A141 | C16 | 593.2 | 2.81 |
| 3-ethyl-N-[(1S,2R)-2-hydroxy-1-(phenylmethyl)-3-({[3-(trifluoromethyl)phenyl] methyl}amino)propyl]-1-methyl-7-(2-oxo-1-pyrrolidinyl)-1H-indole-5-carboxamide (E676) | A142 | C16 | 607.2 | 2.83 |
| 7-(1,1-dioxido-2-isothiazolidinyl)-3-ethyl-N-[(1S,2R)-2-hydroxy-1-(phenylmethyl)-3-({[3-(trifluoromethyl)phenyl] methyl}amino)propyl]-1H-indole-5-carboxamide (E677) | A144 | C16 | 629.1 | 2.87 |
| N-[(1S,2R)-2-hydroxy-3-({[3-(methyloxy)phenyl]methyl}amino)-1-(phenylmethyl)propyl]-3-(1-methylethyl)-7-(2-oxo-1-pyrrolidinyl)-1H-indole-5-carboxamide (E678) | A161 | C14 | 569.5 | 2.65 |
| formic acid-3-ethyl-N-[(1S,2R)-2-hydroxy-3-({[3-(methyloxy)phenyl]methyl}amino)-1-(phenylmethyl)propyl]-7-(2-oxo-1-pyrrolidinyl)-1H-indole-5-carboxamide (1:1) (E679) | A141 | C14 | 555.1 | 2.44 |
| formic acid-1-ethyl-N-[(1S,2R)-2-hydroxy-3-({[3-(methyloxy)phenyl]methyl}amino)-1-(phenylmethyl)propyl]-4-(2-oxo-1-pyrrolidinyl)-1H-benzimidazole-6-carboxamide (1:1) (E680) | A149 | C14 | 556.5 | 2.24 |
| formic acid-7-(1,1-dioxidotetrahydro-2H-1,2-thiazin-2-yl)-3-ethyl-N-[(1S,2R)-2-hydroxy-3-({[3-(methyloxy)phenyl]methyl}amino)-1-(phenylmethyl)propyl]-1H-indole-5-carboxamide (1:1) (E681) | A148 | C14 | 605.5 | 2.63 |
| formic acid-3-ethyl-N-[(1S,2R)-2-hydroxy-3-({[3-(methyloxy)phenyl]methyl}amino)-1-(phenylmethyl)propyl]-7-(2-oxo-1-piperidinyl)-1H-indole-5-carboxamide (1:1) (E682) | A165 | C14 | 569.2 | 2.68 |
| 3-(1,1-dioxido-4-phenyltetrahydro-2H-1,2-thiazin-2-yl)-N-[(1S,2R)-2-hydroxy-3-({[3-(methyloxy)phenyl]methyl}amino)-1-(phenylmethyl)propyl]-5-nitrobenzamide (E683) | A123 | C14 | 659.3 | 2.95 |
| 3-(1,1-dioxido-4-phenyltetrahydro-2H-1,2-thiazin-2-yl)-5-(ethylamino)-N-[(1S,2R)-2-hydroxy-3-({[3-(methyloxy)phenyl]methyl}amino)-1-(phenylmethyl)propyl] benzamide (E684) | A125 | C14 | 657.4 | 2.85 |
| 3-amino-5-(1,1-dioxido-4-phenyltetrahydro-2H-1,2-thiazin-2-yl)-N-[(1S,2R)-2-hydroxy-3-({[3-(methyloxy)phenyl]methyl}amino)-1-(phenylmethyl)propyl] benzamide (E685) | A124 | C14 | 629.4 | 2.67 |
| 3-ethyl-N-[(1S,2R)-2-hydroxy-3-({[3-(methyloxy)phenyl] methyl}amino)-1-(phenylmethyl)propyl]-7-(2-oxo-4-phenyl-1-pyrrolidinyl)-1H-indole-5-carboxamide (E686) | A166 | C14 | 631.4 | 2.92 |
| N-[(1S,2R)-3-(cyclohexylamino)-2-hydroxy-1-(phenylmethyl)propyl]-3-(1,1-dioxido-4-phenyltetrahydro-2H-1,2-thiazin-2-yl)-5-(ethylamino)benzamide (E687) | A125 | C1 | 619.4 | 2.89 |
| 3-(1,1-dioxido-4-phenyltetrahydro-2H-1,2-thiazin-2-yl)-5-(ethylamino)-N-[(1S,2R)-2-hydroxy-3-[(1-methylethyl)amino]-1-(phenylmethyl)propyl] benzamide (E688) | A125 | C28 | 579.4 | 2.76 |
| formic acid-1-ethyl-N-[(1S,2R)-2-hydroxy-1-(phenylmethyl)-3-({[3-(trifluoromethyl)phenyl] methyl}amino)propyl]-4-(2-oxo-1-pyrrolidinyl)-1H-1,2,3-benzotriazole-6-carboxamide (1:1) (E689) | A167 | C16 | 595.3 | 2.67 |
| formic acid-4-(1,1-dioxidotetrahydro-2H-1,2-thiazin-2-yl)-1-ethyl-N-[(1S,2R)-2-hydroxy-3-({[3-(methyloxy)phenyl]methyl}amino)-1-(phenylmethyl)propyl]-1H-benzimidazole-6-carboxamide (1:1) (E690) | A151 | C14 | 606.3 | 2.21 |
| 1-ethyl-N-[(1S,2R)-2-hydroxy-1-(phenylmethyl)-3-({[3-(trifluoromethyl)phenyl] methyl}amino)propyl]-4-(2-oxo-1-pyrrolidinyl)-1H-benzimidazole-6-carboxamide (E691) | A149 | C16 | 594.5 | 2.21 |
| 1-ethyl-N-[(1S,2R)-2-hydroxy-3-({1-methyl-1-[3-(trifluoromethyl)phenyl] ethyl}amino)-1-(phenylmethyl)propyl]-4-(2-oxo-1-pyrrolidinyl)-1H-benzimidazole-6-carboxamide (E692) | A149 | C40 | 622.5 | 2.24 |
| N-[(1S,2R)-3-(cyclohexylamino)-2-hydroxy-1-(phenylmethyl)propyl]-1-ethyl-4-(2-oxo-1-pyrrolidinyl)-1H-benzimidazole-6-carboxamide (E693) | A149 | C1 | 518.4 | 1.90 |
| 1-ethyl-N-{(1S,2R)-2-hydroxy-1-(phenylmethyl)-3-[(1,1,5-trimethylhexyl)amino] propyl}-4-(2-oxo-1-pyrrolidinyl)-1H-benzimidazole-6-carboxamide (E694) | A149 | C5 | 562.5 | 2.33 |

-continued

| Example | Acid | Amine | [M + H]⁺ | RT (min) |
|---|---|---|---|---|
| formic acid-1-ethyl-N-[(1S,2R)-2-hydroxy-3-({1-methyl-1-[3-(methyloxy)phenyl]ethyl}amino)-1-(phenylmethyl)propyl]-4-(2-oxo-1-pyrrolidinyl)-1H-benzimidazole-6-carboxamide (1:1) (E695) | A149 | C15 | 584.5 | 2.09 |

Example 696

3-(1,1-dioxidotetrahydro-1,2-thiazepin-2 (3H)-yl)-N-[(1S,2R)-2-hydroxy-3-({[3-(methyloxy)phenyl]methyl}amino)-1-(phenylmethyl)propyl]-5-propyl-benzamide (E696)

Example 696 was prepared from Description 313 in an analogous manner to that described for Example 213. [M+H]⁺=594.4, RT=2.77 min

Example 697

3-(1,1-dioxidotetrahydro-1,2-thiazepin-2 (3H)-yl)-N-[(1S,2R)-2-hydroxy-1-(phenylmethyl)-3-({[3-(trifluoromethyl)phenyl]methyl}amino)propyl]-5-propylbenzamide (E697)

Example 697 was prepared from Description 312 in an analogous manner to that described for Example 213. [M+H]⁺=632.1, RT=3.00 min

Examples 698-703 (E698-703)

The following compounds were prepared in an analogous manner to Example 183 from the appropriate amine and the appropriate aldehyde or ketone:

Example 704

Example E704 was prepared in an analogous manner to Example 1 from the appropriate acid and amine indicated in the below table:

| Example | Acid | Amine | [M + H]⁺ | RT (min) |
|---|---|---|---|---|
| N-[(1S,2R)-3-(bicyclo[2.2.2]oct-1-ylamino)-2-hydroxy-1-(phenylmethyl)propyl]-3-(1,1-dioxidotetrahydro-2H-1,2-thiazin-2-yl)-5-(ethylamino)benzamide hydrochloride (E704) | A73 | C153 | 569.5 | 2.02 |

Examples 705-709 (E705-709)

The following compounds were prepared in an analogous manner to Example 183 from the appropriate amine and the appropriate aldehyde or ketone:

| Example | Precursor | [M + H]⁺ | RT (min) |
|---|---|---|---|
| N-[(1S,2R)-3-{[2-(3-chlorophenyl)-1-methylethyl]amino}-2-hydroxy-1-(phenylmethyl)propyl]-3-(1,1-dioxidotetrahydro-2H-1,2-thiazin-2-yl)-5-(ethylamino)benzamide hydrochloride (E698) | D120 | 611.3 | 1.01 |
| N-[(1S,2R)-3-{[2-(3-chlorophenyl)-1-methylethyl]amino}-2-hydroxy-1-(phenylmethyl)propyl]-3-cyclopentyl-5-(1,1-dioxidotetrahydro-2H-1,2-thiazin-2-yl)benzamide hydrochloride (E699) | D125 | 638.4 | 1.00 |
| formic acid-3-(1,1-dioxidotetrahydro-2H-1,2-thiazin-2-yl)-5-(ethylamino)-N-[(1S,2R)-3-{[(5-ethyl-3-thienyl)methyl]amino}-2-hydroxy-1-(phenylmethyl)propyl] benzamide (1:1) (E700) | D120 | 585.5 | 2.57 |
| formic acid-3-(1,1-dioxidotetrahydro-2H-1,2-thiazin-2-yl)-5-(ethylamino)-N-[(1S,2R)-3-{[(4-ethyl-2-thienyl)methyl]amino}-2-hydroxy-1-(phenylmethyl)propyl] benzamide (1:1) (E701) | D120 | 585.5 | 2.45 |
| formic acid-3-(1,1-dioxidotetrahydro-2H-1,2-thiazin-2-yl)-5-(ethylamino)-N-[(1S,2R)-3-{[(1-ethyl-1H-pyrazol-3-yl)methyl]amino}-2-hydroxy-1-(phenylmethyl)propyl] benzamide (1:1) (E702) | D120 | 569.5 | 2.31 |
| formic acid-3-(1,1-dioxidotetrahydro-2H-1,2-thiazin-2-yl)-5-(ethylamino)-N-((1S,2R)-2-hydroxy-1-(phenylmethyl)-3-{[(1-propyl-1H-pyrazol-4-yl)methyl]amino}propyl) benzamide (1:1) (E703) | D120 | 583.5 | 2.29 |

| Example | Precursor | [M + H]⁺ | RT (min) |
|---|---|---|---|
| formic acid-3-(1,1-dioxidotetrahydro-2H-1,2-thiazin-2-yl)-N-[(1S,2R)-3-{[(5-ethenyl-3-thienyl)methyl]amino}-2-hydroxy-1-(phenylmethyl)propyl]-5-(ethylamino)benzamide (1:1) (E705) | D120 | 583.5 | 2.55 |
| formic acid-3-(1,1-dioxidotetrahydro-2H-1,2-thiazin-2-yl)-N-[(1S,2R)-3-{[(4-ethenyl-2-furanyl)methyl]amino}-2-hydroxy-1-(phenylmethyl)propyl]-5-(ethylamino)benzamide (1:1) (E706) | D120 | 567.5 | 2.44 |
| formic acid-3-(1,1-dioxidotetrahydro-2H-1,2-thiazin-2-yl)-5-(ethylamino)-N-[(1S,2R)-2-hydroxy-1-(phenylmethyl)-3-({[1-(2-propen-1-yl)-1H-pyrazol-4-yl]methyl}amino)propyl] benzamide (1:1) (E707) | D120 | 581.5 | 2.29 |
| formic acid-3-(1,1-dioxidotetrahydro-2H-1,2-thiazin-2-yl)-N-[(1S,2R)-3-{[(4-ethenyl-2-thienyl)methyl]amino}-2-hydroxy-1-(phenylmethyl)propyl]-5-(ethylamino)benzamide (1:1) (E708) | D120 | 583.5 | 2.52 |
| formic acid-3-(1,1-dioxidotetrahydro-2H-1,2-thiazin-2-yl)-5-(ethylamino)-N-[(1S,2R)-3-({[(1-(2-fluoroethyl)-1H-pyrazol-4-yl]methyl}amino)-2-hydroxy-1-(phenylmethyl)propyl] benzamide (1:1) (E709) | D120 | 587.5 | 2.22 |

Examples 710-744 (E710-744)

Examples E710-E744 were prepared in an analogous manner to Example 1 from the appropriate acid and amines indicated in the below table:

| Example | Acid | Amine | [M + H]⁺ | RT (min) |
|---|---|---|---|---|
| 3-cyclopentyl-N-[(1S,2R)-3-{[(1-ethyl-1H-pyrazol-4-yl)methyl]amino}-2-hydroxy-1-(phenylmethyl)propyl]-5-(2-oxo-1-pyrrolidinyl)benzamide (E710) | A107 | C154 | 544.7 | 2.51 |
| 3-(ethyloxy)-N-[(1S,2R)-3-{[(1-ethyl-1H-pyrazol-4-yl)methyl]amino}-2-hydroxy-1-(phenylmethyl)propyl]-5-2-oxo-1-pyrrolidinyl)benzamide (E711) | A11 | C154 | 520.7 | 2.20 |
| 3-(1,1-dioxidotetrahydro-2H-1,2-thiazin-2-yl)-5-(ethylamino)-N-[(1S,2R)-3-{[(1-ethyl-1H-pyrazol-4-yl)methyl]amino}-2-hydroxy-1-(phenylmethyl)propyl] benzamide (E712) | A73 | C154 | 569.6 | 2.19 |
| 3-(1,1-dioxidotetrahydro-2H-1,2-thiazin-2-yl)-N-[(1S,2R)-3-{[(1-ethyl-1H-pyrazol-4-yl)methyl]amino}-2-hydroxy-1-(phenylmethyl)propyl]-5-propylbenzamide (E713) | A112 | C154 | 568.6 | 2.46 |
| formic acid-N-[(1S,2R)-3-[(4,4-difluorocyclohexyl)amino]-2-hydroxy-1-(phenylmethyl) propyl]-3-(1,1-dioxidotetrahydro-2H-1,2-thiazin-2-yl)-5-(ethylamino)-2-fluorobenzamide (1:1) (E714) | A119 | C155 | 597.4 | 2.30 |
| 4-ethyl-N-[(1S,2R)-2-hydroxy-3-({[3-(methyloxy)phenyl]methyl}amino)-1-(phenylmethyl)propyl]-8-(2-oxo-1-pyrrolidinyl)-1,2,3,4-tetrahydro-6-quinoxalinecarboxamide (E715) | A171 | C14 | 572.5 | 2.61 |
| 4-(1,1-dioxido-2-isothiazolidinyl)-1-ethyl-N-[(1S,2R)-2-hydroxy-3-({[3-(methyloxy)phenyl]methyl}amino)-1-(phenylmethyl)propyl]-1H-benzimidazole-6-carboxamide (E716) | A150 | C14 | 592.4 | 2.21 |
| 4-(1,1-dioxido-2-isothiazolidinyl)-1-ethyl-N-[(1S,2R)-2-hydroxy-1-(phenylmethyl)-3-({[3-(trifluoromethyl)phenyl] methyl}amino)propyl]-1H-benzimidazole-6-carboxamide (E717) | A150 | C16 | 630.4 | 2.51 |
| 4-(1,1-dioxido-2-isothiazolidinyl)-1-ethyl-N-[(1S,2R)-2-hydroxy-3-({1-methyl-1-[3-(trifluoromethyl)phenyl]ethyl}amino)-1-(phenylmethyl)propyl]-1H-benzimidazole-6-carboxamide (E718) | A150 | C40 | 658.4 | 2.51 |
| 4-(1,1-dioxidotetrahydro-2H-1,2-thiazin-2-yl)-1-ethyl-N-[(1S,2R)-2-hydroxy-3-({1-methyl-1-[3-(trifluoromethyl)phenyl] ethyl}amino)-1-(phenylmethyl)propyl]-2,3-dihydro-1H-indole-6-carboxamide (E719) | A145 | C40 | 673.5 | 2.90 |
| 8-(1,1-dioxido-2-isothiazolidinyl)-4-ethyl-N-[(1S,2R)-2-hydroxy-1-(phenylmethyl)-3-({[3-(trifluoromethyl)phenyl] methyl}amino)propyl]-1,2,3,4-trtrahydro-6-quinoxalinecarboxamide (E720) | A172 | C16 | 646.5 | 2.65 |

-continued

| Example | Acid | Amine | [M + H]+ | RT (min) |
|---|---|---|---|---|
| formic acid-3-(1,1-dioxidotetrahydro-2H-1,2-thiazin-2-yl)-5-(ethylamino)-2-fluoro-N-{(1S,2R)-2-hydroxy-1-(phenylmethyl)-3[({3-[(trifluoromethyl)oxy]phenyl}methyl)amino] propyl}benzamide (1:1) (E721) | A119 | C11 | 653.5 | 2.54 |
| formic acid-3-(1,1-dioxido-2-isothiazolidinyl)-N-[(1S,2R)-3-{[(1-ethyl-1H-pyrazol-4-yl)methyl]amino}-2-hydroxy-1-(phenylmethyl)propyl]-2-fluoro-5-propylbenzamide (1:1) (E722) | A174 | C154 | 572.4 | 2.37 |
| 3-(1,1-dioxido-2-isothiazolidinyl)-2-fluoro-N-{(1S,2R)-2-hydroxy-1-(phenylmethyl)-3-[(1,1,5-trimethylhexyl)amino]propyl}-5-propylbenzamide (E723) | A174 | C5 | 590.5 | 2.92 |
| 3-(1,1-dioxido-2-isothiazolidinyl)-2-fluoro-N-[(1S,2R)-2-hydroxy-3-({1-methyl-1-[3-(methyloxy)phenyl]ethyl}amino)-1-(phenylmethyl)propyl]-5-propylbenzamide (E724) | A174 | C15 | 612.5 | 2.66 |
| 3-(1,1-dioxido-2-isothiazolidinyl)-2-fluoro-N-[(1S,2R)-2-hydroxy-1-(phenylmethyl)-3-({[3-(trifluoromethyl)phenyl]methyl}amino)propyl]-5-propylbenzamide (E725) | A174 | C16 | 622.4 | 2.68 |
| N-[(1S,2R)-3-[(1r,4R)-bicyclo[2.2.1]hept-1-ylamino]-2-hydroxy-1-(phenylmethyl)propyl]-3-(1,1-dioxidotetrahydro-2H-1,2-thiazin-2-yl)-5-(ethylamino)benzamide hydrochloride (E726) | A73 | C152 | 555.1 | 2.23 |
| formic acid-3-(1,1-dioxidotetrahydro-2H-1,2-thiazin-2-yl)-N-[(1S,2R)-3-{[(1-ethyl-1H-pyrazol-4-yl)methyl]amino}-2-hydroxy-1-(phenylmethyl)propyl]-2-fluoro-5-propylbenzamide (1:1) (E727) | A173 | C154 | 586.4 | 2.50 |
| 3-(1,1-dioxidotetrahydro-2H-1,2-thiazin-2-yl)-2-fluoro-N-[(1S,2R)-2-hydroxy-1-(phenylmethyl)-3-(tetrahydro-2H-pyran-4-ylamino)propyl]-5-propylbenzamide (E728) | A173 | C43 | 562.4 | 2.45 |
| formic acid-3-(1,1-dioxidotetrahydro-2H-1,2-thiazin-2-yl)-2-fluoro-N-[(1S,2R)-2-hydroxy-3-({1-methyl-1-[3-(trifluoromethyl)phenyl] ethyl}amino)-1-(phenylmethyl)propyl]-5-propylbenzamide (1:1) (E729) | A173 | C40 | 664.5 | 2.97 |
| 3-(1,1-dioxidotetrahydro-2H-1,2-thiazin-2-yl)-2-fluoro-N-[(1S,2R)-2-hydroxy-1-(phenylmethyl)-3-({[3-(trifluoromethyl)phenyl] methyl}amino)propyl]-5-propylbenzamide (E730) | A173 | C16 | 636.4 | 2.84 |
| 3-(1,1-dioxidotetrahydro-2H-1,2-thiazin-2-yl)-2-fluoro-N-[(1S,2R)-2-hydroxy-3-({[3-(methyloxy)phenyl]methyl}amino)-1-(phenylmethyl)propyl]-5-propylbenzamide (E731) | A173 | C14 | 598.4 | 2.70 |
| 2-fluoro-N-[(1S,2R)-2-hydroxy-1-(phenylmethyl)-3-(tetrahydro-2H-pyran-4-ylamino)propyl]-3-(2-oxo-1-pyrrolidinyl)-5-propylbenzamide (E732) | A120 | C43 | 512.5 | 2.32 |
| N-[(1S,2R)-3-{[(1-ethyl-1H-pyrazol-4-yl)methyl]amino}-2-hydroxy-1-(phenylmethyl)propyl]-2-fluoro-3-(2-oxo-1-pyrrolidinyl)-5-propylbenzamide (E733) | A120 | C154 | 536.5 | 2.36 |
| N-[(1S,2R)-3-({[3,4-bis(methyloxy)phenyl]methyl}amino)-2-hydroxy-1-(phenylmethyl)propyl]-2-fluoro-3-(2-oxo-1-pyrrolidinyl)-5-propylbenzamide (E734) | A120 | C156 | 578.5 | 2.40 |
| 2-fluoro-N-[(1S,2R)-2-hydroxy-3-[(1-methylethyl)amino]-1-(phenylmethyl)propyl]-3-(2-oxo-1-pyrrolidinyl)-5-propylbenzamide (E735) | A120 | C28 | 470.5 | 2.26 |
| N-[(1S,2R)-3-(cyclohexylamino)-2-hydroxy-1-(phenylmethyl)propyl]-2-fluoro-3-(2-oxo-1-pyrrolidinyl)-5-propylbenzamide (E736) | A120 | C1 | 510.5 | 2.44 |
| formic acid-2-fluoro-N-{(1S,2R)-2-hydroxy-1-(phenylmethyl)-3-[(1,1,5-trimethylhexyl)amino] propyl}-3-(2-oxo-1-pyrrolidinyl)-5-propylbenzamide (1:1) (E737) | A120 | C5 | 554.7 | 3.04 |
| formic acid-2-fluoro-N-[(1S,2R)-2-hydroxy-3-({1-methyl-1-[3-(trifluoromethyl)phenyl] ethyl}amino)-1-(phenylmethyl)propyl]-3-(2-oxo-1-pyrrolidinyl)-5-propylbenzamide (1:1) (E738) | A120 | C40 | 614.6 | 2.77 |
| formic acid-2-fluoro-N-[(1S,2R)-2-hydroxy-3-({1-methyl-1-[3-(methyloxy)phenyl]ethyl} amino)-1-(phenylmethyl)propyl]-3-(2-oxo-1-pyrrolidinyl)-5-propylbenzamide (1:1) (E739) | A120 | C15 | 576.6 | 2.66 |
| 3-(1,1-dioxidotetrahydro-2H-1,2-thiazin-2-yl)-5-(ethylamino)-N-[(1S,2R)-3-[(1-ethylcyclobutyl)amino]-2-hydroxy-1-(phenylmethyl)propyl] benzamide hydrochloride (E740) | A73 | C69 | 542.9 | 1.05 |
| 3-(1,1-dioxidotetrahydro-2H-1,2-thiazin-2-yl)-5-(ethylamino)-N-{(1S,2R)-2-hydroxy-1-(phenylmethyl)-3-[(1-propylcyclobutyl)amino] propyl}benzamide hydrochloride (E741) | A73 | C148 | 556.9 | 1.08 |

-continued

| Example | Acid | Amine | [M + H]+ | RT (min) |
|---|---|---|---|---|
| 3-(1,1-dioxidotetrahydro-2H-1,2-thiazin-2-yl)-5-(ethylamino)-N-[(1S,2R)-2-hydroxy-3-{[1-(1-methylethyl)cyclobutyl] amino}-1-(phenylmethyl)propyl] benzamide hydrochloride (E742) | A73 | C149 | 556.9 | 1.07 |
| N-[(1S,2R)-3-({1-[(3-chlorophenyl)methyl] cyclobutyl}amino)-2-hydroxy-1-(phenylmethyl)propyl]-3-(1,1-dioxidotetrahydro-2H-1,2-thiazin-2-yl)-5-(ethylamino)benzamide hydrochloride (E743) | A73 | C150 | 639.3 | 1.41 |
| 3-(1,1-dioxidotetrahydro-2H-1,2-thiazin-2-yl)-5-(ethylamino)-N-[(1S,2R)-2-hydroxy-1-(phenylmethyl)-3-(tricyclo[3.3.1.1~3,7~]dec-2-ylamino)propyl] benzamide hydrochloride (E744) | A73 | C151 | 595.7 | 2.12 |

Compounds of the invention may be tested for in vitro biological activity in accordance with the following assays:

(I) Asp-2 Inhibitory Assay

For each compound being assayed, in a 384 well plate, is added:

a) 1 µl of a DMSO solution of the test compound ($IC_{50}$ curve uses ten 1 in 2 serial dilutions from 500 µM).

b) 10 µl of substrate (FAM-SEVNLDAEFK-TAMRA) solution in buffer. This is prepared by diluting 2 ml of a 2 mM DMSO solution of the substrate into 400 ml of buffer (100 mM Sodium acetate pH=4.5, 1 l Milli-Q water, 0.06% Triton X-100 (0.5 ml/l), pH adjusted to 4.5 using glacial acetic acid). Aminomethyl fluorescein (FAM) and tetramethyl rhodamine (TAMRA) are fluorescent molecules which co-operate to emit fluorescence at 535 nm upon cleavage of the SEVNLDAEFK peptide.

c) 10 µl enzyme solution. This is prepared by diluting 16 ml of a 500 nM enzyme solution into 384 ml of buffer (prepared as above).

Blank wells (enzyme solution replaced by buffer) are included as controls on each plate. Wells are incubated for 1 h at room temperature and fluorescence read using a Tecan Ultra Fluorimeter/Spectrophotometer (485 nm excitation, 535 nm emission).

(II) Cathepsin D Inhibitory Assay

For each compound being assayed, in a 384 well plate, is added:

a) 1 µl of a DMSO solution of the test compound ($IC_{50}$ curve uses ten 1 in 2 serial dilutions from 500 µM).

b) 10 µl of substrate (FAM-SEVNLDAEFK-TAMRA) solution in buffer. This is prepared by diluting 2 ml of a 2 mM DMSO solution of the substrate into 400 ml of buffer (100 mM Sodium acetate pH=4.5, 1 l Milli-Q water, 0.06% Triton X-100 (0.5 ml/l), pH adjusted to 4.5 using glacial acetic acid).

c) 10 µl enzyme solution. This is prepared by diluting 1.6 ml of a 200 unit/ml (in 10 mM HCl) enzyme solution into 398.4 ml of buffer (prepared as above).

Blank wells (enzyme solution replaced by buffer) are included as controls on each plate, Wells are incubated for 1 h at room temperature and fluorescence read using a Tecan Ultra Fluorimeter/Spectrophotometer (485 nm excitation, 535 nm emission).

Pharmacological Data

The compounds of E1-E744 were tested in Assays (I) and (II) and exhibited inhibition within the following range: 1-10000 nM (Asp-2) and 10-10000 nM (CatD). More particularly, the compounds of E12, 22, 30, 31, 33, 50, 54-56, 60, 65, 86, 102, 179, 218, 222-223, 241, 245-246, 249, 255, 266, 270, 271, 277-278, 280-289, 296, 299, 303, 313-315, 317-318, 320-322, 325, 327, 329, 332-333, 361-363, 373, 375, 406-408, 559-560, 562, 583-584, 587, 632, 641-642, 647-648, 656, 680, 690-691, 694-695, 700, 703, 708, 713, 716-718, 720-721, 725, 727, 730-731 and 733 exhibited inhibition within the following range: 1-50 nM (Asp-2) and 100-10000 nM (CatD). Yet more particularly, the compounds of E30-31, 33, 270, 562, 584, 700 and 721 exhibited inhibition within the following range: 1-10 nM (Asp-2) and 500-10000 nM (CatD).

Abbreviations

| | |
|---|---|
| DMF | dimethylformamide |
| DMSO | dimethylsulfoxide |
| DMAP | dimethylaminophenol |
| DABCO | 1,4-diazabicyclo [2.2.2] octane |
| DME | dimethyl ether |
| EDAC | N-ethyl-N-(3-dimethylamino propyl)carbodiimide |
| THF | tetrahydrofuran |
| DEAD | diethylacetylene dicarboxylate |
| DCM | dichloromethane |
| TFA | trifluoroacetic acid |
| HOBT | N-hydroxybenzotriazole |
| FAM | carboxyfluorescein |
| TAMRA | carboxytetramethylrhodamine |
| [ ] | single amino acid letter code relating to peptide sequence |

What is claimed is:

1. A compound of formula (I):

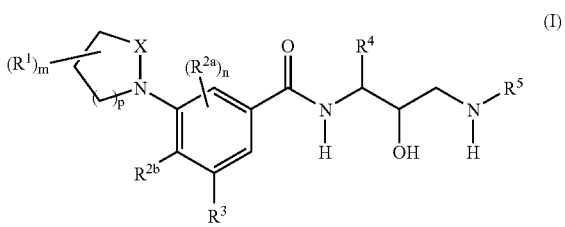

wherein $R^1$ represents $C_{1-6}$ alkyl, $C_{2-6}$ alkenyl, halogen, $C_{1-6}$ alkoxy, amino, cyano, hydroxy, aryl, heteroaryl or heterocyclyl;

$R^{2a}$ represents hydrogen, $C_{1-3}$ alkyl, $C_{1-3}$ alkoxy or halogen;

m and n independently represent 0, 1 or 2;

X represents CO, SO or $SO_2$;

p represents an integer from 1 to 3;

$R^{2b}$ represents hydrogen, $C_{1-6}$ alkyl, $C_{2-6}$ alkenyl, halogen, $C_{1-6}$ alkoxy, amino, cyano, hydroxy, aryl, heteroaryl or heterocyclyl;

$R^3$ represents halogen, $C_{1-6}$ alkyl, $C_{2-6}$ alkenyl, aryl, heteroaryl, heterocyclyl, —$C_{1-6}$ alkyl-aryl, —$C_{1-6}$ alkyl-heteroaryl, —$C_{1-6}$ alkyl-heterocyclyl, —$C_{2-6}$ alkenyl-aryl, —$C_{2-6}$ alkenyl-heteroaryl, —$C_{2-6}$ alkenyl-heterocyclyl, $C_{3-8}$ cycloalkyl, —$C_{1-6}$ alkyl-$C_{3-8}$ cycloalkyl, cyano, azido, nitro, —$NR^7R^8$, —$NR^9COR^{10}$, —$NR^{11}SO_2R^{12}$, —$OR^{13}$, —$SO_2R^{14}$, —$SR^{15}$, —C≡$CR^{16}$, —$C_{1-6}$ alkyl-$(CF_2)_qCF_3$, —$CONR^{17}R^{18}$, $COOR^{19}$, —$C_{1-6}$ alkyl-$NR^{20}R^{21}$ or —$C_{1-6}$ alkyl-$N_3$, or $R^3$ and $R^{2b}$ together with the phenyl group to which they are attached form a naphthyl or benzofused heterocyclic or heteroaryl ring optionally substituted by one or two $C_{1-6}$ alkyl groups;

$R^4$ represents —$C_{2-6}$ alkynyl, —$C_{1-6}$ alkyl-aryl, —$C_{1-6}$ alkyl-heteroaryl or —$C_{1-6}$ alkyl-heterocyclyl;

$R^5$ represents hydrogen, —$C_{1-10}$ alkyl, —$C_{3-10}$ cycloalkyl, —$C_{3-10}$ cycloalkenyl, aryl, heteroaryl, heterocyclyl, —$C_{1-6}$ alkyl-$C_{3-10}$ cycloalkyl, —$C_{3-10}$ cycloalkyl-$C_{1-10}$ alkyl, —$C_{3-10}$ cycloalkyl-$C_{1-6}$ alkyl-aryl, —$C_{3-10}$ cycloalkyl-aryl, —$C_{1-6}$ alkyl-aryl-heteroaryl, —$C(R^aR^b)$—CONH—$C_{1-6}$ alkyl, —$C(R^cR^d)$—CONH—$C_{3-10}$ cycloalkyl, —$C_{1-6}$ alkyl-S—$C_{1-6}$ alkyl, —$C_{1-6}$ alkyl-$NR^eR^f$, —$C_{1-6}$ alkyl-aryl, —$C_{1-6}$ alkyl-heteroaryl, —$C_{1-6}$ alkyl-heterocyclyl —$C_{1-6}$ alkyl-$C_{1-6}$ alkoxy-aryl, —$C_{1-6}$ alkyl-$C_{1-6}$ alkoxy-heteroaryl or —$C_{1-6}$ alkyl-$C_{1-6}$ alkoxy-heterocyclyl;

$R^7$, $R^8$, $R^9$, $R^{10}$, $R^{13}$, $R^{14}$, $R^{15}$, $R^{16}$, $R^{17}$, $R^{18}$, $R^{19}$, $R^{20}$ and $R^{21}$ independently represent hydrogen, $C_{1-6}$ alkyl, $C_{2-6}$ alkenyl, $C_{3-8}$ cycloalkyl, aryl, heteroaryl, heterocyclyl, —$C_{1-6}$ alkyl-$C_{3-8}$ cycloalkyl, —$C_{1-6}$ alkyl-aryl, —$C_{1-6}$ alkyl-heteroaryl, —$C_{1-6}$ alkyl-heterocyclyl or —CO—$C_{1-6}$ alkyl;

$R^{11}$, $R^{12}$, $R^a$, $R^c$, $R^e$ and $R^f$ independently represent hydrogen, $C_{1-6}$ alkyl or $C_{3-8}$ cycloalkyl;

$R^b$ and $R^d$ independently represent hydrogen, $C_{1-6}$ alkyl, $C_{3-8}$ cycloalkyl or —$C_{1-6}$ alkyl-$SO_2$—$C_{1-6}$ alkyl;

q represents 1 to 3;

wherein said alkyl groups may be optionally substituted by one or more halogen, $C_{1-6}$ alkyl, $C_{1-6}$ alkoxy, $C_{2-6}$ alkenoxy, $C_{3-8}$ cycloalkyl, amino, cyano or hydroxy groups;

and wherein said cycloalkyl, aryl, heteroaryl or heterocyclyl groups may be optionally substituted by one or more $C_{1-6}$ alkyl, $C_{2-6}$ alkenyl, $C_{2-6}$ alkynyl, halogen, halo$C_{1-6}$ alkyl, —$OCF_3$, oxo, $C_{1-6}$ alkoxy, —$C_{1-6}$ alkoxy-CN, amino, cyano, nitro, —$NR^{22}COR^{23}$, —$CONR^{22}R^{23}$, —$COOR^{22}$, —$SO_2R^{22}$, —$C_{1-6}$ alkyl-$NR^{22}R^{23}$ (wherein $R^{22}$ and $R^{23}$ independently represent hydrogen or $C_{1-6}$ alkyl), —$C_{1-6}$ alkyl-$C_{1-6}$ alkoxy, —$C_{1-6}$ alkanol or hydroxy groups;

or a pharmaceutically acceptable salt or solvate thereof.

2. A compound according to claim 1, wherein m is 0.

3. A compound according to claim 1, wherein n is 1.

4. A compound according to claim 1, wherein $R^{2a}$ represents $C_{1-3}$ alkoxy or halogen.

5. A compound according to claim 1, wherein X represents $SO_2$ and p is 2 or 3.

6. A compound according to claim 1, wherein X represents CO and p is 1 or 2.

7. A compound according to claim 1, wherein $R^{2b}$ represents hydrogen, halogen, $C_{1-6}$ alkyl, $C_{1-6}$ alkoxy or a heterocyclyl, which heterocyclyl is optionally substituted by an oxo group.

8. A compound according to claim 1, wherein $R^3$ represents $C_{1-6}$ alkyl, $C_{2-6}$ alkenyl, $C_{3-8}$ cycloalkyl, cyano, heterocyclyl, —$NR^7R^8$, —$OR^{13}$ —$SR^{15}$ or —$CONR^{17}R^{18}$, wherein said alkyl group is optionally substituted by one or more hydroxy, halogen or $C_{1-6}$ alkoxy groups and wherein said heterocyclyl group is optionally substituted by one or two oxo groups.

9. A compound according to claim 8, wherein $R^3$ represents $C_{1-6}$ alkyl, —$NR^7R^8$, $C_{3-8}$ cycloalkyl, —$OR^{13}$ or —$CONR^{17}R^{18}$.

10. A compound according to claim 1, wherein $R^4$ represents —$C_{1-6}$ alkyl-aryl or —$C_{1-6}$ alkyl-heteroaryl.

11. A compound according to claim 1, wherein $R^5$ represents:

—$C_{1-10}$ alkyl optionally substituted by one or more $C_{1-6}$ alkyl, $C_{1-6}$ alkoxy or $C_{2-6}$ alkenoxy groups;

—$C_{3-10}$ cycloalkyl optionally substituted by one or more $C_{1-6}$ alkyl or halogen groups;

—$C_{1-6}$ alkyl-$C_{3-10}$ cycloalkyl;

-aryl optionally substituted by one or more hydroxy or $C_{1-6}$ alkoxy groups;

—$C_{1-6}$ alkyl-aryl optionally substituted by one or more halogen, hydroxy, —$OCF_3$, halo$C_{1-6}$ alkyl, $C_{1-6}$ alkyl, $C_{2-6}$ alkenyl, $C_{2-6}$ alkynyl, $C_{1-6}$ alkoxy, cyano, nitro, —$COOR^{22}$, —$SO_2R^{22}$, —$NR^{22}COR^{23}$, —$C_{1-6}$ alkyl-$NR^{22}R^{23}$, —$C_{1-6}$ alkyl-$C_{1-6}$ alkoxy, —$C_{1-6}$ alkanol or —$C_{1-6}$ alkoxy-CN groups;

—$C_{1-6}$ alkyl-heteroaryl optionally substituted by one or more $C_{1-6}$ alkyl, $C_{2-6}$ alkenyl, $C_{2-6}$ alkynyl, halogen, halo$C_{1-6}$ alkyl, cyano, $C_{1-6}$ alkoxy, —$CONR^{22}R^{23}$ or —$COOR^{22}$ groups;

-heterocyclyl;

—$C_{1-6}$ alkyl-heterocyclyl;

—$C_{3-10}$ cycloalkyl-$C_{1-10}$ alkyl;

—$C_{3-10}$ cycloalkyl-$C_{1-6}$ alkyl-aryl optionally substituted by one or more halogen atoms;

—$C_{3-10}$ cycloalkyl-aryl optionally substituted by one or more halogen, hydroxy, —$OCF_3$, halo$C_{1-6}$ alkyl, $C_{1-6}$ alkyl, $C_{2-6}$ alkenyl, $C_{2-6}$ alkynyl, $C_{1-6}$ alkoxy, cyano, nitro, —$COOR^{22}$, —$SO_2R^{22}$, —$NR^{22}COR^{23}$, —$C_{1-6}$ alkyl-$NR^{22}R^{23}$, —$C_{1-6}$ alkyl-$C_{1-6}$ alkoxy, —$C_{1-6}$ alkanol or —$C_{1-6}$ alkoxy-CN groups;

—$C(R^aR^b)$—CONH—$C_{1-6}$ alkyl;

—$C(R^cR^d)$—CONH—$C_{3-10}$ cycloalkyl;

—$C_{1-6}$ alkyl-S—$C_{1-6}$ alkyl; or

—$C_{1-6}$ alkyl-$NR^eR^f$.

12. A compound according to claim 11, wherein $R^5$ represents:

—$C_{3-10}$ cycloalkyl;

—$C_{1-6}$ alkyl-aryl optionally substituted by one or more halogen, —$OCF_3$ or halo$C_{1-6}$ alkyl groups;

—$C_{1-6}$ alkyl-heteroaryl optionally substituted by one or more $C_{1-6}$ alkyl or halo$C_{1-6}$ alkyl groups; or -heterocyclyl.

13. A compound according to claim 1, wherein:

X represents CO or $SO_2$;

$R^{2a}$ represents hydrogen, $C_{1-3}$ alkyl or halogen;

$R^3$ and $R^{2b}$ together with the phenyl group which they are attached form an unsubstituted benzofused heterocyclic or heteroaryl ring;

$R^4$ represents —$C_{1-6}$ alkyl-aryl, —$C_{1-6}$ alkyl-heteroaryl or —$C_{1-6}$ alkyl-heterocyclyl;

R⁵ represents hydrogen, —C$_{1-10}$ alkyl, —C$_{3-8}$ cycloalkyl, —C$_{3-8}$ cycloalkenyl, aryl, heteroaryl, heterocyclyl, —C$_{1-6}$ alkyl-C$_{3-8}$ cycloalkyl, —C$_{1-6}$ alkyl-aryl-heteroaryl, —C(R$^a$R$^b$)—CONH—C$_{1-6}$ alkyl, —C(R$_c$R$^d$)—CONH—C$_{3-8}$ cycloalkyl, —C$_{1-6}$ alkyl-S—C$_{1-6}$ alkyl, —C$_{1-6}$ alkyl-NR$^e$R$^f$, —C$_{1-6}$ alkyl-aryl, —C$_{1-6}$ alkyl-heteroaryl, —C$_{1-6}$ alkyl-heterocyclyl —C$_{1-6}$ alkyl-C$_{1-6}$ alkoxy-aryl, —C$_{1-6}$ alkyl-C$_{1-6}$ alkoxy-heteroaryl or —C$_{1-6}$ alkyl-C$_{1-6}$ alkoxy-heterocyclyl;

wherein said alkyl groups may be optionally substituted by one or more halogen, C$_{1-6}$ alkoxy, amino, cyano or hydroxy groups; and wherein said aryl, heteroaryl or heterocyclyl groups may be optionally substituted by one or more C$_{1-6}$ alkyl, halogen, —OCF$_3$, oxo, C$_{1-6}$ alkoxy, amino, cyano, nitro, —NR$^{22}$COR$^{23}$—C$_{1-6}$ alkyl-NR$^{22}$R$^{23}$ (wherein R$^{22}$ and R$^{23}$ independently represent hydrogen or C$_{1-6}$ alkyl), —C$_{1-6}$ alkyl-C$_{1-6}$ alkoxy, —C$_{1-6}$ alkanol or hydroxy groups.

14. A compound according to claim 1 which is selected from the group consisting of:

N-[(1S,2R)-1-Benzyl-3-((S)-1-cyclohexylcarbamoyl-ethylamino)-2-hydroxypropyl]-5-(2-oxopyrrolidin-1-yl)-N',N'-dipropylisophthalamide;

N-[(1S,2R)-1-Benzyl-3-((S)-1-cyclohexylcarbamoyl ethylamino)-2-hydroxypropyl]-5-(2-oxopyrrolidin-1-yl)-N',N'-dipropylisophthalamide;

N-[(1S,2R)-1-Benzyl-3-((S)-1-cyclohexylcarbamoyl ethylamino)-2-hydroxypropyl]-5-(2-oxopyrrolidin-1-yl)-isophthalamic acid methyl ester;

N-[(1S,2R)-1-Benzyl-3-((S)-1-cyclohexylcarbamoyl ethylamino)-2-hydroxypropyl]-5-(2-oxopyrrolidin-1-yl)-isophthalamic acid tert-butyl ester;

N-[(1S,2R)-1-Benzyl-3-((S)-1-cyclohexylcarbamoyl ethylamino)-2-hydroxypropyl]-5-(2-oxopyrrolidin-1-yl)-N'-propylisophthalamide;

N-[(1S,2R)-1-Benzyl-3-((S)-1-cyclohexylcarbamoyl ethylamino)-2-hydroxypropyl]-N',N'-dimethyl-5-(2-oxopyrrolidin-1-yl)-isophthalamide;

N-[(1S,2R)-1-Benzyl-3-((S)-1-cyclohexylcarbamoyl ethylamino)-2-hydroxypropyl]-N'-methyl-5-(2-oxopyrrolidin-1-yl)-isophthalamide;

N-[(1S,2R)-1-Benzyl-3-((S)-1-cyclohexylcarbamoyl ethylamino)-2-hydroxypropyl]-3-hydroxymethyl-5-(2-oxopyrrolidin-1-yl)benzamide;

N-[(1S,2R)-1-Benzyl-2-hydroxy-3-(3-methoxybenzylamino)-propyl]-3-(2-oxopyrrolidin-1-yl)-5-((E)-styryl)benzamide;

N-[(1S,2R)-1-Benzyl-2-hydroxy-3-(3-methoxybenzylamino)-propyl]-3-(2-oxopyrrolidin-1-yl)-5-phenethylbenzamide;

N-[(1S,2R)-1-Benzyl-2-hydroxy-3-(3-methoxybenzylamino)-propyl]-3-cyclopentyl-5-(2-oxopyrrolidin-1-yl)benzamide;

N-[(1S,2R)-1-Benzyl-3-((S)-1-cyclohexylcarbamoyl ethylamino)-2-hydroxypropyl]-3-cyclopentyl-5-(2-oxopyrrolidin-1-yl)benzamide;

N-[(1S,2R)-1-Benzyl-3-((S)-1-cyclohexylcarbamoyl ethylamino)-2-hydroxypropyl]-3-cyclohexyl-5-(2-oxopyrrolidin-1-yl)benzamide;

N-[(1S,2R)-1-Benzyl-2-hydroxy-3-(3-methoxybenzylamino)-propyl]-3-cyclohexyl-5-(2-oxopyrrolidin-1-yl)benzamide;

N-[(1S,2R)-1-Benzyl-2-hydroxy-3-(3-methoxybenzylamino) propyl]-3-(2-oxopyrrolidin-1-yl)-5-propylbenzamide;

N-(1-Benzyl-3-cyclohexylamino-2-hydroxypropyl)-3-(2-oxopyrrolidin-1-yl)-5-propylbenzamide;

N-[1-Benzyl-2-hydroxy-3-(3-methoxybenzylamino)propyl]-3-(2-methyl-propenyl)-5-(2-oxopyrrolidin-1-yl)benzamide;

N-[1-Benzyl-2-hydroxy-3-(3-methoxybenzylamino)propyl]-3-isobutyl-5-(2-oxopyrrolidin-1-yl)benzamide;

N-(1-Benzyl-3-cyclohexylamino-2-hydroxypropyl)-3-isopropyl-5-(2-oxopyrrolidin-1-yl)benzamide;

N-(1-Benzyl-3-cyclohexylamino-2-hydroxypropyl)-3-isobutyl-5-(2-oxopyrrolidin-1-yl)benzamide;

N-(1-Benzyl-3-cyclohexylamino-2-hydroxypropyl)-3-cyclopentyl-5-(2-oxopyrrolidin-1-yl)benzamide;

N-[1-Benzyl-2-hydroxy-3-(3-trifluoromethylbenzylamino) propyl]-3-cyclopentyl-5-(2-oxopyrrolidin-1-yl)benzamide;

N-[1-Benzyl-2-hydroxy-3-(3-trifluoromethylbenzylamino) propyl]-3-(2-oxopyrrolidin-1-yl)-5-propylbenzamide;

N-[1-Benzyl-3-(1,5-dimethylhexylamino)-2-hydroxypropyl]-3-(2-oxopyrrolidin-1-yl)-5-propylbenzamide;

N-[1-Benzyl-2-hydroxy-3-(3-trifluoromethylbenzylamino)propyl]-3-ethynyl-5-(2-oxopyrrolidin-1-yl) benzamide;

N-[1-Benzyl-3-(1-cyclohexylcarbamoylethylamino)-2-hydroxypropyl]-3-(2-oxopyrrolidin-1-yl)-5-propylbenzamide;

N-[1-Benzyl-2-hydroxy-3-(3-trifluoromethylbenzylamino) propyl]-2-fluoro-3-(2-oxopyrrolidin-1-yl)-5-trifluoromethyl-benzamide;

5-cyclopentyl-3-(1,1-dioxidotetrahydro-2H-1,2-thiazin-2-yl)-2-fluoro-N-[(1S,2R)-2-hydroxy-1-(phenylmethyl)-3-({[3-trifluoromethyl)phenyl]methyl}amino) propyl]benzamide;

5-cyclopentyl-3-(1,1-dioxidotetrahydro-2H-1,2-thiazin-2-yl)-2-fluoro-N-[(1S,2R)-2-hydroxy-3-({1-methyl-1-[3-(methyloxy)phenyl]ethyl}amino)-1-(phenylmethyl) propyl]benzamide;

5-cyclopentyl-3-(1,1-dioxidotetrahydro-2H-1,2-thiazin-2-yl)-N-[(1S,2R)-3-{[(1-ethyl-1H-pyrazol-4-yl)methyl]amino}-2-hydroxy-1-(phenylmethyl)propyl]-2-fluorobenzamide;

3-(1,1-dioxidotetrahydro-2H-1,2-thiazin-2-yl)-2-fluoro-N-[(1S,2R)-2-hydroxy-1-(phenylmethyl)-3-({[3-(trifluoromethyl)phenyl]methyl}amino)propyl]-5-[(1-methylethyl)amino]benzamide;

3-(1,1-dioxidotetrahydro-2H-1,2-thiazin-2-yl)-2-fluoro-N-[(1S,2R)-2-hydroxy-3-({1-methyl-1-[3-(methyloxy)phenyl]ethyl}amino)-1-(phenylmethyl)propyl]-5-[(1-methylethyl)amino]benzamide;

3-(1,1-dioxidotetrahydro-2H-1,2-thiazin-2-yl)-N-[(1S,2R)-3-{[(1-ethyl-1H-pyrazol-4-yl)methyl]amino}-2-hydroxy-1-(phenylmethyl)propyl]-2-fluoro-5-[(1-methylethyl)amino]benzamide;

3-(1,1-dioxidotetrahydro-2H-1,2-thiazin-2-yl)-2-fluoro-N-{(1S,2R)-2-hydroxy-1-(phenylmethyl)-3-[(1,1,5-trimethylhexyl)amino]propyl}-5-[(1-methylethyl)amino] benzamide;

3-(1,1-dioxidotetrahydro-2H-1,2-thiazin-2-yl)-2-fluoro-N-[(1S,2R)-2-hydroxy-1-(phenylmethyl)-3-(tetrahydro-2H-pyran-4-ylamino)propyl]-5-[(1-methylethyl) amino]benzamide;

N-[(1S,2R)-1-Benzyl-3-((S)-1-cyclohexylcarbamoyl ethylamino)-2-hydroxypropyl]-3,5-bis-(2-oxopyrrolidin-1-yl)benzamide;

3-Acetylamino-N-[(1S,2R)-1-benzyl-3-((S)-1-cyclohexylcarbamoylethylamino)-2-hydroxypropyl]-5-(2-oxopyrrolidin-1-yl)benzamide;

N-[(1S,2R)-1-Benzyl-3-((S)-1-cyclohexylcarbamoyl ethylamino)-2-hydroxypropyl]-3-methanesulfonylamino-5-(2-oxopyrrolidin-1-yl)benzamide;

N-[(1S,2R)-1-Benzyl-3-((S)-1-cyclohexylcarbamoyl ethylamino)-2-hydroxypropyl]-3-isopropylamino-5-(2-oxopyrrolidin-1-yl)benzamide;

N-[(1S,2R)-1-Benzyl-3-((S)-1-cyclohexylcarbamoyl ethylamino)-2-hydroxypropyl]-3-(2-oxopyrrolidin-1-yl)-5-propylaminobenzamide;

N-[(1S,2R)-1-Benzyl-3-((S)-1-cyclohexylcarbamoylethyl amino)-2-hydroxypropyl]-3-cyclopentylamino-5-(2-oxopyrrolidin-1-yl)benzamide;

N-[(1S,2R)-1-Benzyl-3-((S)-1-cyclohexylcarbamoylethyl amino)-2-hydroxypropyl]-3-diethylamino-5-(2-oxopyrrolidin-1-yl)benzamide;

N-[(1S,2R)-1-Benzyl-3-((S)-1-cyclohexylcarbamoyl ethylamino)-2-hydroxypropyl]-3-morpholin-4-yl-5-(2-oxopyrrolidin-1-yl)benzamide;

N-[(1S,2R)-1-Benzyl-3-((S)-1-cyclohexylcarbamoyl ethylamino)-2-hydroxypropyl]-3-(4-methylpiperazin-1-yl)-5-(2-oxopyrrolidin-1-yl)benzamide;

N-[(1S,2R)-1-Benzyl-3-((S)-1-cyclohexylcarbamoyl ethylamino)-2-hydroxypropyl]-3-(2-oxopyrrolidin-1-yl)-5-piperidin-1-ylbenzamide;

N-[(1S,2R)-1-Benzyl-3-((S)-1-cyclohexylcarbamoyl ethylamino)-2-hydroxypropyl]-3-(2-oxopyrrolidin-1-yl)-5-pyrrolidin-1-ylbenzamide;

N-[(1S,2R)-1-Benzyl-3-((S)-1-cyclohexylcarbamoyl ethylamino)-2-hydroxypropyl]-3-(2-oxopyrrolidin-1-yl)-5-phenylaminobenzamide;

N-[(1S,2R)-1-Benzyl-3-((S)-1-cyclohexylcarbamoyl ethylamino)-2-hydroxypropyl]-4-methoxy-3,5-bis-(2-oxopyrrolidin-1-yl)benzamide;

N-[(1S,2R)-1-Benzyl-3-((S)-1-cyclohexylcarbamoyl ethylamino)-2-hydroxypropyl]-4-chloro-3,5-bis-(2-oxopyrrolidin-1-yl)benzamide;

N-[(1S,2R)-1-Benzyl-3-((S)-1-cyclohexylcarbamoyl ethylamino)-2-hydroxypropyl]-3-ethylamino-5-(2-oxopyrrolidin-1-yl)benzamide;

3-Benzylamino-N-[(1S,2R)-1-benzyl-3-((S)-1-cyclohexylcarbamoylethylamino)-2-hydroxypropyl]-5-(2-oxopyrrolidin-1-yl)benzamide;

N-[(1S,2R)-1-Benzyl-3-((S)-1-cyclohexylcarbamoyl ethylamino)-2-hydroxypropyl]-3-(3-methylbutylamino)-5-(2-oxopyrrolidin-1-yl)benzamide;

N-[(1S,2R)-1-Benzyl-3-((S)-1-cyclohexylcarbamoyl ethylamino)-2-hydroxypropyl]-3-cyclohexylamino-5-(2-oxopyrrolidin-1-yl)benzamide;

N-[(1S,2R)-1-Benzyl-3-((S)-1-cyclohexylcarbamoyl ethylamino)-2-hydroxypropyl]-3-(2-oxopyrrolidin-1-yl)-5-pentylaminobenzamide;

N-[(1S,2R)-1-Benzyl-3-((S)-1-cyclohexylcarbamoyl ethylamino)-2-hydroxypropyl]-3-(1-ethylpropylamino)-5-(2-oxopyrrolidin-1-yl)benzamide;

N-[(1S,2R)-1-Benzyl-3-((S)-1-cyclohexylcarbamoyl ethylamino)-2-hydroxypropyl]-3-butylamino-5-(2-oxopyrrolidin-1-yl)benzamide;

N-[(1S,2R)-1-Benzyl-3-((S)-1-cyclohexylcarbamoyl ethylamino)-2-hydroxypropyl]-3-(2,2-dimethylpropylamino)-5-(2-oxopyrrolidin-1-yl)benzamide;

N-[(1S,2R)-1-Benzyl-3-((S)-1-cyclohexylcarbamoyl ethylamino)-2-hydroxypropyl]-3-(cyclopropylmethylamino)-5-(2-oxopyrrolidin-1-yl)-benzamide;

3-(Acetylpropylamino)-N-[(1S,2R)-1-benzyl-3-((S)-1-cyclohexylcarbamoylethylamino)-2-hydroxypropyl]-5-(2-oxopyrrolidin-1-yl)benzamide;

N-[(1S,2R)-1-Benzyl-3-(1,5-dimethylhexylamino)-2-hydroxypropyl]-3-isopropylamino-5-(2-oxopyrrolidin-1-yl)benzamide;

N-[(1S,2R)-1-Benzyl-3-((S)-1-cyclohexylcarbamoyl ethylamino)-2-hydroxypropyl]-3-nitro-5-(2-oxopyrrolidin-1-yl)benzamide;

N-[(1S,2R)-1-Benzyl-3-((S)-1-cyclohexylcarbamoyl ethylamino)-2-hydroxypropyl]-3-nitro-5-(2-oxopyrrolidin-1-yl)benzamide;

3-Amino-N-[(1S,2R)-1-benzyl-3-((S)-1-cyclohexylcarbamoylethylamino)-2-hydroxypropyl]-5-(2-oxopyrrolidin-1-yl)benzamide;

3-(Acetylisopropylamino)-N-[(1S,2R)-1-benzyl-3-((S)-1-cyclohexylcarbamoylethylamino)-2-hydroxypropyl]-5-(2-oxo-pyrrolidin-1-yl)benzamide;

N-[(1S,2R)-1-Benzyl-3-((S)-1-cyclohexylcarbamoyl ethylamino)-2-hydroxypropyl]-3-(methanesulfonyl propylamino)-5-(2-oxopyrrolidin-1-yl)-benzamide;

N-((1S,2R)-3-Amino-1-benzyl-2-hydroxypropyl)-3-ethylamino-5-(2-oxopyrrolidin-1-yl)benzamide;

N-((1S,2R)-1-Benzyl-3-cyclopropylamino-2-hydroxypropyl)-3-ethylamino-5-(2-oxopyrrolidin-1-yl)benzamide;

N-[(1S,2R)-1-Benzyl-2-hydroxy-3-(3-methoxybenzylamino)-propyl]-3-ethylamino-5-(2-oxopyrrolidin-1-yl)benzamide;

N-((1S,2R)-1-Benzyl-3-cyclohexylamino-2-hydroxypropyl)-3-ethylamino-5-(2-oxopyrrolidin-1-yl)benzamide;

N-((1S,2R)-1-Benzyl-3-ethylamino-2-hydroxypropyl)-3-ethylamino-5-(2-oxopyrrolidin-1-yl)benzamide;

N-[(1S,2R)-1-Benzyl-2-hydroxy-3-(4-methoxybenzylamino)-propyl]-3-ethylamino-5-(2-oxopyrrolidin-1-yl)benzamide;

N-((1S,2R)-1-Benzyl-2-hydroxy-3-isopropylaminopropyl)-3-ethylamino-5-(2-oxopyrrolidin-1-yl)benzamide;

N-[(1S,2R)-1-Benzyl-2-hydroxy-3-(3-trifluoromethylbenzylamino)-propyl]-3-ethylamino-5-(2-oxopyrrolidin-1-yl)benzamide;

N-[(1S,2R)-1-Benzyl-2-hydroxy-3-(2,2,3,3,3-pentafluoro-propylamino)-propyl]-3-ethylamino-5-(2-oxopyrrolidin-1-yl)benzamide;

N-[(1S,2R)-1-Benzyl-3-(2,2,3,3,4,4,4-heptafluorobutylamino)-2-hydroxypropyl]-3-ethylamino-5-(2-oxopyrrolidin-1-yl)benzamide;

N-[(1S,2R)-1-Benzyl-2-hydroxy-3-(R)-1-phenylethylamino)propyl]-3-ethylamino-5-(2-oxopyrrolidin-1-yl)benzamide;

N-[(1S,2R)-1-Benzyl-2-hydroxy-3-((S)-1-phenylethylamino)propyl]-3-ethylamino-5-(2-oxopyrrolidin-1-yl)benzamide;

N-[(1S,2R)-1-Benzyl-2-hydroxy-3-(2-methoxybenzylamino)-propyl]-3-ethylamino-5-(2-oxopyrrolidin-1-yl)benzamide;

N-[(1S,2R)-1-Benzyl-3-(3,5-bis-trifluoromethylbenzyl amino)-2-hydroxypropyl]-3-ethylamino-5-(2-oxopyrrolidin-1-yl)benzamide;

N-{(1S,2R)-1-Benzyl-2-hydroxy-3-[(R)-1-(3-methoxyphenyl)-ethylamino]-propyl}-3-ethylamino-5-(2-oxopyrrolidin-1-yl)benzamide;

N-{(1S,2R)-1-Benzyl-2-hydroxy-3-[(S)-1-(3-methoxyphenyl)-ethylamino]-propyl}-3-ethylamino-5-(2-oxopyrrolidin-1-yl)benzamide;

N-[(1S,2R)-1-Benzyl-3-((S)-1-cyclohexylcarbamoyl-
ethylamino)-2-hydroxypropyl]-3-isobutylamino-5-(2-
oxopyrrolidin-1-yl)benzamide;
N-[(1S,2R)-1-Benzyl-3-((S)-1-cyclohexylcarbamoyl-
ethylamino)-2-hydroxypropyl]-3-dimethylamino-5-(2-
oxopyrrolidin-1-yl)benzamide;
N-[(1S,2R)-1-Benzyl-2-hydroxy-3-(1-methyl-1-phenyl-
ethylamino)-propyl]-3-ethylamino-5-(2-oxopyrrolidin-
1-yl)benzamide;
N-((1S,2R)-1-Benzyl-3-tert-butylamino-2-hydroxypro-
pyl)-3-ethylamino-5-(2-oxopyrrolidin-1-yl)benzamide;
N-[(1S,2R)-1-Benzyl-2-hydroxy-3-(3-trifluoromethoxy-
benzylamino)-propyl]-3-ethylamino-5-(2-oxopyrroli-
din-1-yl)benzamide;
N-[(1S,2R)-1-Benzyl-2-hydroxy-3-(3-methylbuty-
lamino)-propyl]-3-ethylamino-5-(2-oxopyrrolidin-1-
yl)benzamide;
N-((1S,2R)-3-Amino-1-benzyl-2-hydroxypropyl)-3-iso-
propylamino-5-(2-oxopyrrolidin-1-yl)benzamide;
N-[(1S,2R)-1-Benzyl-3-((S)-1-cyclohexylcarbamoyl
ethylamino)-2-hydroxypropyl]-3-methylamino-5-(2-
oxopyrrolidin-1-yl)benzamide; N-[(1S,2R)-1-Benzyl-
3-((S)-1-cyclohexylcarbamoyl ethylamino)-2-hydrox-
ypropyl]-3-(methanesulfonyl methylamino)-5-(2-
oxopyrrolidin-1-yl)-benzamide;
3-(Acetylmethylamino)-N-[(1S,2R)-1-benzyl-3-((S)-1-
cyclohexylcarbamoylethylamino)-2-hydroxypropyl]-
5-(2-oxopyrrolidin-1-yl)-benzamide;
N-((1S,2R)-1-Benzyl-3-cyclopentylamino-2-hydrox-
ypropyl)-3-ethylamino-5-(2-oxopyrrolidin-1-yl)benza-
mide;
N-[(1S,2R)-1-Benzyl-2-hydroxy-3-(4-methylpenty-
lamino)-propyl]-3-ethylamino-5-(2-oxopyrrolidin-1-
yl)benzamide;
N-[(1S,2R)-1-Benzyl-2-hydroxy-3-(5-methylhexy-
lamino)-propyl]-3-ethylamino-5-(2-oxopyrrolidin-1-
yl)benzamide;
N-[(1S,2R)-1-Benzyl-3-(1,5-dimethyl-hexylamino)-2-
hydroxypropyl]-3-ethylamino-5-(2-oxopyrrolidin-1-
yl)benzamide;
N-((1S,2R)-1-Benzyl-3-cyclohexylamino-2-hydroxypro-
pyl)-3-ethylamino-5-(2-oxopyrrolidin-1-yl)benzamide;
N-(1-Benzyl-3-cyclobutylamino-2-hydroxypropyl)-3-
ethylamino-5-(2-oxopyrrolidin-1-yl)benzamide;
N-(1-Benzyl-3-cycloheptylamino-2-hydroxypropyl)-3-
ethylamino-5-(2-oxopyrrolidin-1-yl)benzamide;
N-(1-Benzyl-2-hydroxy-3-isobutylaminopropyl)-3-ethy-
lamino-5-(2-oxopyrrolidin-1-yl)benzamide;
N-[1-Benzyl-2-hydroxy-3-(1,1,5-trimethylhexylamino)
propyl]-3-ethylamino-5-(2-oxopyrrolidin-1-yl)benza-
mide;
N-(1-Benzyl-2-hydroxy-3-propylaminopropyl)-3-ethy-
lamino-5-(2-oxopyrrolidin-1-yl)benzamide;
N-{1-Benzyl-2-hydroxy-3-[1-(3-methoxyphenyl)-1-me-
thylethylamino]propyl}-3-ethylamino-5-(2-oxopyrro-
lidin-1-yl)benzamide;
N-[(1S,2R)-1-Benzyl-3-(3,4-dichloro-benzylamino)-2-
hydroxy-propyl]-3-ethylamino-5-(2-oxo-pyrrolidin-1-
yl)-benzamide;
N-((1S,2R)-1-Benzyl-3-benzylamino-2-hydroxy-propyl)-
3-ethylamino-5-(2-oxo-pyrrolidin-1-yl)-benzamide;
N-[(1S,2R)-1-Benzyl-3-(4-fluoro-benzylamino)-2-hy-
droxy-propyl]-3-ethylamino-5-(2-oxo-pyrrolidin-1-
yl)-benzamide;
N-[(1S,2R)-1-Benzyl-2-hydroxy-3-(4-trifluoromethyl-
benzylamino)-propyl]-3-ethylamino-5-(2-oxo-pyrroli-
din-1-yl)-benzamide;

N-{(1S,2R)-1-Benzyl-3-[(furan-2-ylmethyl)-amino]-2-
hydroxy-propyl}-3-ethylamino-5-(2-oxo-pyrrolidin-1-
yl)-benzamide;
N-{(1S,2R)-1-Benzyl-2-hydroxy-3-[(quinolin-4-ylm-
ethyl)-amino]-propyl}-3-ethylamino-5-(2-oxo-pyrroli-
din-1-yl)-benzamide;
N-[(1S,2R)-1-Benzyl-2-hydroxy-3-(3-hydroxy-benzy-
lamino)-propyl]-3-ethylamino-5-(2-oxo-pyrrolidin-1-
yl)-benzamide;
N-{(1S,2R)-1-Benzyl-2-hydroxy-3-[(thiophen-2-ylm-
ethyl)-amino]-propyl}-3-ethylamino-5-(2-oxo-pyrroli-
din-1-yl)-benzamide;
N-{(1S,2R)-1-Benzyl-2-hydroxy-3-[(thiophen-3-ylm-
ethyl)-amino]-propyl}-3-ethylamino-5-(2-oxo-pyrroli-
din-1-yl)-benzamide;
N-[(1S,2R)-1-Benzyl-3-(3-chloro-4-methoxy-benzy-
lamino)-2-hydroxy-propyl]-3-ethylamino-5-(2-oxo-
pyrrolidin-1-yl)-benzamide;
N-[(1S,2R)-1-Benzyl-3-(2,3-dichloro-benzylamino)-2-
hydroxy-propyl]-3-ethylamino-5-(2-oxo-pyrrolidin-1-
yl)-benzamide;
N-[(1S,2R)-3-(4-Acetylamino-benzylamino)-1-benzyl-2-
hydroxy-propyl]-3-ethylamino-5-(2-oxo-pyrrolidin-1-
yl)-benzamide;
N-[(1S,2R)-1-Benzyl-3-(4-cyano-benzylamino)-2-hy-
droxy-propyl]-3-ethylamino-5-(2-oxo-pyrrolidin-1-
yl)-benzamide;
N-((1S,2R)-1-Benzyl-2-hydroxy-3-phenethylamino-pro-
pyl)-3-ethylamino-5-(2-oxo-pyrrolidin-1-yl)-benza-
mide;
N-{(1S,2R)-1-Benzyl-2-hydroxy-3-[(1H-indol-3-ylm-
ethyl)-amino]-propyl}-3-ethylamino-5-(2-oxo-pyrroli-
din-1-yl)-benzamide;
N-[(1S,2R)-1-Benzyl-2-hydroxy-3-(3-phenyl-buty-
lamino)-propyl]-3-ethylamino-5-(2-oxo-pyrrolidin-1-
yl)-benzamide;
N-{(1S,2R)-3-[(1H-Benzoimidazol-5-ylmethyl)-amino]-
1-benzyl-2-hydroxy-propyl}-3-ethylamino-5-(2-oxo-
pyrrolidin-1-yl)-benzamide;
N-{(1S,2R)-1-Benzyl-3-[(E)-3-(4-fluoro-phenyl)-ally-
lamino]-2-hydroxy-propyl}-3-ethylamino-5-(2-oxo-
pyrrolidin-1-yl)-benzamide;
N-[(1S,2R)-1-Benzyl-2-hydroxy-3-(4-isopropoxy-benzy-
lamino)-propyl]-3-ethylamino-5-(2-oxo-pyrrolidin-1-
yl)-benzamide;
N-[(1S,2R)-1-Benzyl-2-hydroxy-3-((E)-3-p-tolyl-ally-
lamino)-propyl]-3-ethylamino-5-(2-oxo-pyrrolidin-1-
yl)-benzamide;
N-{(1S,2R)-1-Benzyl-3-[(2-ethyl-5-methyl-3H-imidazol-
4-ylmethyl)-amino]-2-hydroxy-propyl}-3-ethylamino-
5-(2-oxo-pyrrolidin-1-yl)-benzamide;
N-[(1S,2R)-1-Benzyl-2-hydroxy-3-(2-methyl-3-phenyl-
propylamino)-propyl]-3-ethylamino-5-(2-oxo-pyrroli-
din-1-yl)-benzamide;
N-[(1S,2R)-1-Benzyl-2-hydroxy-3-(3-methoxy-4-nitro-
benzylamino)-propyl]-3-ethylamino-5-(2-oxo-pyrroli-
din-1-yl)-benzamide;
N-[(1S,2R)-1-Benzyl-3-(5-cyano-2-methoxy-benzy-
lamino)-2-hydroxy-propyl]-3-ethylamino-5-(2-oxo-
pyrrolidin-1-yl)-benzamide;
N-{(1S,2R)-1-Benzyl-3-[(cyclohex-3-enylmethyl)-
amino]-2-hydroxy-propyl}-3-ethylamino-5-(2-oxo-
pyrrolidin-1-yl)-benzamide;
N-[(1S,2R)-1-Benzyl-2-hydroxy-3-(2-phenyl-propy-
lamino)-propyl]-3-ethylamino-5-(2-oxo-pyrrolidin-1-
yl)-benzamide;

N-[(1S,2R)-1-Benzyl-2-hydroxy-3-(3-methylsulfanyl-propylamino)-propyl]-3-ethylamino-5-(2-oxo-pyrrolidin-1-yl)-benzamide;

N-[(1S,2R)-1-Benzyl-3-(3-cyano-benzylamino)-2-hydroxy-propyl]-3-ethylamino-5-(2-oxo-pyrrolidin-1-yl)-benzamide;

N-{(1S,2R)-1-Benzyl-2-hydroxy-3-[(5-methyl-thiophen-2-ylmethyl)-amino]-propyl}-3-ethylamino-5-(2-oxo-pyrrolidin-1-yl)-benzamide;

N-[(1S,2R)-1-Benzyl-2-hydroxy-3-(2-methoxy-5-methyl-benzylamino)-propyl]-3-ethylamino-5-(2-oxo-pyrrolidin-1-yl)-benzamide;

N-{(1S,2R)-3-[(Benzofuran-2-ylmethyl)-amino]-1-benzyl-2-hydroxy-propyl}-3-ethylamino-5-(2-oxo-pyrrolidin-1-yl)-benzamide;

N-[(1S,2R)-1-Benzyl-3-(3-fluoro-benzylamino)-2-hydroxy-propyl]-3-ethylamino-5-(2-oxo-pyrrolidin-1-yl)-benzamide;

N-[(1S,2R)-1-Benzyl-2-hydroxy-3-(2-p-tolyl-ethylamino)-propyl]-3-ethylamino-5-(2-oxo-pyrrolidin-1-yl)-benzamide;

N-[(1S,2R)-1-Benzyl-3-(dimethylamino-dimethyl-propylamino)-2-hydroxy-propyl]-3-ethylamino-5-(2-oxo-pyrrolidin-1-yl)-benzamide;

N-{(1S,2R)-1-Benzyl-2-hydroxy-3-[(1H-indol-5-ylmethyl)-amino]-propyl}-3-ethylamino-5-(2-oxo-pyrrolidin-1-yl)-benzamide;

N-{(1S,2R)-1-Benzyl-2-hydroxy-3-[(2-methyl-thiazol-4-ylmethyl)-amino]-propyl}-3-ethylamino-5-(2-oxo-pyrrolidin-1-yl)-benzamide;

N-[(1S,2R)-1-Benzyl-3-(2-benzyloxy-ethylamino)-2-hydroxy-propyl]-3-ethylamino-5-(2-oxo-pyrrolidin-1-yl)-benzamide;

N-[(1S,2R)-1-Benzyl-3-(3,4-dimethoxy-benzylamino)-2-hydroxy-propyl]-3-ethylamino-5-(2-oxo-pyrrolidin-1-yl)-benzamide;

N-[(1S,2R)-1-Benzyl-2-hydroxy-3-(3-nitro-benzylamino)-propyl]-3-ethylamino-5-(2-oxo-pyrrolidin-1-yl)-benzamide;

N-[(1S,2R)-1-Benzyl-3-(3-chloro-benzylamino)-2-hydroxy-propyl]-3-ethylamino-5-(2-oxo-pyrrolidin-1-yl)-benzamide;

N-[(1S,2R)-1-Benzyl-3-(3-ethoxy-benzylamino)-2-hydroxy-propyl]-3-ethylamino-5-(2-oxo-pyrrolidin-1-yl)-benzamide;

N-{(1S,2R)-1-Benzyl-3-[(5-chloro-thiophen-2-ylmethyl)-amino]-2-hydroxy-propyl}-3-ethylamino-5-(2-oxo-pyrrolidin-1-yl)-benzamide;

N-{(1S,2R)-1-Benzyl-2-hydroxy-3-[(thiazol-2-ylmethyl)-amino]-propyl}-3-ethylamino-5-(2-oxo-pyrrolidin-1-yl)-benzamide;

N-{(1S,2R)-1-Benzyl-2-hydroxy-3-[(pyridin-3-ylmethyl)-amino]-propyl}-3-ethylamino-5-(2-oxo-pyrrolidin-1-yl)-benzamide;

N-[(1S,2R)-1-Benzyl-2-hydroxy-3-(4-hydroxy-3-methoxy-benzylamino)-propyl]-3-ethylamino-5-(2-oxo-pyrrolidin-1-yl)-benzamide;

N-[(1S,2R)-1-Benzyl-2-hydroxy-3-(3-hydroxymethyl-benzylamino)-propyl]-3-ethylamino-5-(2-oxo-pyrrolidin-1-yl)-benzamide;

N-{(1S,2R)-1-Benzyl-2-hydroxy-3-[3-(4-methoxy-phenyl)-propylamino]-propyl}-3-ethylamino-5-(2-oxo-pyrrolidin-1-yl)-benzamide;

N-[(1S,2R)-1-Benzyl-3-(4-dimethylaminomethyl-benzylamino)-2-hydroxy-propyl]-3-ethylamino-5-(2-oxo-pyrrolidin-1-yl)-benzamide;

N-[(1S,2R)-1-Benzyl-3-(3,4-difluoro-benzylamino)-2-hydroxy-propyl]-3-ethylamino-5-(2-oxo-pyrrolidin-1-yl)-benzamide;

N-{(1S,2R)-1-Benzyl-2-hydroxy-3-[(5-methoxymethyl-furan-2-ylmethyl)-amino]-propyl}-3-ethylamino-5-(2-oxo-pyrrolidin-1-yl)-benzamide;

N-[(1S,2R)-1-Benzyl-2-hydroxy-3-(3-propoxy-benzylamino)-propyl]-3-ethylamino-5-(2-oxo-pyrrolidin-1-yl)-benzamide;

N-[(1S,2R)-1-Benzyl-3-(4-cyano-3-methoxy-benzylamino)-2-hydroxy-propyl]-3-ethylamino-5-(2-oxo-pyrrolidin-1-yl)-benzamide;

N-[(1S,2R)-1-Benzyl-2-hydroxy-3-(3-imidazol-1-yl-benzylamino)-propyl]-3-ethylamino-5-(2-oxo-pyrrolidin-1-yl)-benzamide;

N-[(1S,2R)-1-Benzyl-2-hydroxy-3-(3-pyrimidin-5-yl-benzylamino)-propyl]-3-ethylamino-5-(2-oxo-pyrrolidin-1-yl)-benzamide;

N-{(1S,2R)-1-Benzyl-2-hydroxy-3-[(6-methoxy-pyridin-3-ylmethyl)-amino]-propyl}-3-ethylamino-5-(2-oxo-pyrrolidin-1-yl)-benzamide;

N-{(1S,2R)-1-Benzyl-2-hydroxy-3-[(6-methoxy-pyridin-2-ylmethyl)-amino]-propyl}-3-ethylamino-5-(2-oxo-pyrrolidin-1-yl)-benzamide;

N-[(1S,2R)-1-Benzyl-3-(3-tert-butoxymethyl-benzylamino)-2-hydroxy-propyl]-3-ethylamino-5-(2-oxo-pyrrolidin-1-yl)-benzamide;

N-[(1S,2R)-1-Benzyl-2-hydroxy-3-(3-prop-2-ynyloxy-benzylamino)-propyl]-3-ethylamino-5-(2-oxo-pyrrolidin-1-yl)-benzamide;

N-[(1S,2R)-3-(3-Acetylamino-benzylamino)-1-benzyl-2-hydroxy-propyl]-3-ethylamino-5-(2-oxo-pyrrolidin-1-yl)-benzamide;

N-{(1S,2R)-1-Benzyl-2-hydroxy-3-[3-(3-methoxy-phenyl)-propylamino]-propyl}-3-ethylamino-5-(2-oxo-pyrrolidin-1-yl)-benzamide;

N-{(1S,2R)-1-Benzyl-3-[3-(4-chloro-phenyl)-propylamino]-2-hydroxy-propyl}-3-ethylamino-5-(2-oxo-pyrrolidin-1-yl)-benzamide;

N-[(1S,2R)-1-Benzyl-2-hydroxy-3-(3-p-tolyl-propylamino)-propyl]-3-ethylamino-5-(2-oxo-pyrrolidin-1-yl)-benzamide;

N-{(1S,2R)-1-Benzyl-2-hydroxy-3-[3-(2H-tetrazol-5-yl)-benzylamino]-propyl}-3-ethylamino-5-(2-oxo-pyrrolidin-1-yl)-benzamide;

N-{(1S,2R)-1-Benzyl-2-hydroxy-3-[3-(1H-pyrazol-3-yl)-benzylamino]-propyl}-3-ethylamino-5-(2-oxo-pyrrolidin-1-yl)-benzamide;

N-{(1S,2R)-1-Benzyl-2-hydroxy-3-[3-(1H-imidazol-2-yl)-benzylamino]-propyl}-3-ethylamino-5-(2-oxo-pyrrolidin-1-yl)-benzamide;

N-[(1S,2R)-1-Benzyl-3-(4-fluoro-3-methoxy-benzylamino)-2-hydroxy-propyl]-3-ethylamino-5-(2-oxo-pyrrolidin-1-yl)-benzamide;

N-{(1S,2R)-1-Benzyl-3-[2,2-dimethyl-3-(2-oxo-pyrrolidin-1-yl)-propylamino]-2-hydroxy-propyl}-3-ethylamino-5-(2-oxo-pyrrolidin-1-yl)-benzamide;

N-{(1S,2R)-3-[(Benzothiazol-6-ylmethyl)-amino]-1-benzyl-2-hydroxy-propyl}-3-ethylamino-5-(2-oxo-pyrrolidin-1-yl)-benzamide;

N-[(1S,2R)-1-Benzyl-3-((S)-1-cyclohexylcarbamoyl ethylamino)-2-hydroxypropyl]-3-(2-oxopyrrolidin-1-yl)-5-propoxybenzamide;

N-[(1S,2R)-1-Benzyl-3-((S)-1-cyclohexylcarbamoyl ethylamino)-2-hydroxypropyl]-3-methoxy-5-(2-oxopyrrolidin-1-yl)benzamide;

N-[(1S,2R)-1-Benzyl-3-((S)-1-cyclohexylcarbamoyl ethylamino)-2-hydroxypropyl]-3-isopropoxy-5-(2-oxopyrrolidin-1-yl)benzamide;

N-[(1S,2R)-1-Benzyl-3-((S)-1-cyclohexylcarbamoyl ethylamino)-2-hydroxypropyl]-3-(3-hydroxypropoxy)-5-(2-oxopyrrolidin-1-yl)benzamide;

N-[(1S,2R)-1-Benzyl-3-((S)-1-cyclohexylcarbamoyl ethylamino)-2-hydroxypropyl]-3-(3-methoxypropoxy)-5-(2-oxopyrrolidin-1-yl)benzamide;

N-[(1S,2R)-1-Benzyl-3-((S)-1-cyclohexylcarbamoyl ethylamino)-2-hydroxypropyl]-3-(2-hydroxyethoxy)-5-(2-oxopyrrolidin-1-yl)benzamide;

N-[(1S,2R)-1-Benzyl-3-((S)-1-cyclohexylcarbamoyl ethylamino)-2-hydroxypropyl]-3-(2-methoxyethoxy)-5-(2-oxopyrrolidin-1-yl)benzamide;

N-[(1S,2R)-1-Benzyl-3-((S)-1-cyclohexylcarbamoyl ethylamino)-2-hydroxypropyl]-3-(2-oxopyrrolidin-1-yl)-5-pentyloxybenzamide;

N-[(1S,2R)-1-Benzyl-2-hydroxy-3-((S)-1-isobutyl carbamoyl-pentylamino)-propyl]-3-isopropoxy-5-(2-oxopyrrolidin-1-yl)benzamide;

N-[(1S,2R)-1-Benzyl-2-hydroxy-3-(3-methoxybenzylamino)propyl]-3-isopropoxy-5-(2-oxopyrrolidin-1-yl)benzamide;

N-[(1S,2R)-1-Benzyl-3-((S)-1-cyclohexylcarbamoyl ethylamino)-2-hydroxypropyl]-3-ethoxy-5-(2-oxopyrrolidin-1-yl)benzamide;

N-((1S,2R)-3-Amino-1-benzyl-2-hydroxypropyl)-3-(2-oxopyrrolidin-1-yl)-5-pentyloxybenzamide;

N-[(1S,2R)-1-Benzyl-2-hydroxy-3-(1-propylbutylamino)-propyl]-3-(2-oxopyrrolidin-1-yl)-5-pentyloxybenzamide;

N-[(1S,2R)-1-Benzyl-2-hydroxy-3-(3-methoxybenzylamino)-propyl]-3-(2-oxopyrrolidin-1-yl)-5-pentyloxybenzamide;

N-((1S,2R)-1-Benzyl-3-benzylamino-2-hydroxypropyl)-3-(2-oxopyrrolidin-1-yl)-5-pentyloxybenzamide;

N-((1S,2R)-1-Benzyl-3-ethylamino-2-hydroxypropyl)-3-(2-oxopyrrolidin-1-yl)-5-pentyloxy-benzamide;

N-((1S,2R)-1-Benzyl-2-hydroxy-3-phenethylaminopropyl)-3-(2-oxopyrrolidin-1-yl)-5-pentyloxybenzamide;

N-[(1S,2R)-1-Benzyl-2-hydroxy-3-(2-phenylpropylamino)-propyl]-3-(2-oxopyrrolidin-1-yl)-5-pentyloxybenzamide;

N-((1S,2R)-1-Benzyl-3-cyclohexylamino-2-hydroxypropyl)-3-(2-oxopyrrolidin-1-yl)-5-pentyloxybenzamide;

N-[(1S,2R)-1-Benzyl-2-hydroxy-3-(1-methylpiperidin-4-ylamino)-propyl]-3-(2-oxopyrrolidin-1-yl)-5-pentyloxybenzamide;

N-[(1S,2R)-1-Benzyl-2-hydroxy-3-(3-methylbutylamino)-propyl]-3-(2-oxopyrrolidin-1-yl)-5-pentyloxybenzamide;

N-[(1S,2R)-1-Benzyl-3-(1-ethylpropylamino)-2-hydroxypropyl]-3-(2-oxopyrrolidin-1-yl)-5-pentyloxybenzamide;

N-[(1S,2R)-1-Benzyl-3-(1,5-dimethylhexylamino)-2-hydroxy-propyl]-3-isopropoxy-5-(2-oxopyrrolidin-1-yl)benzamide;

N-[1-Benzyl-2-hydroxy-3-(3-trifluoromethylbenzylamino)propyl]-3-ethoxy-5-(2-oxopyrrolidin-1-yl)benzamide;

N-[1-Benzyl-3-(1,5-dimethylhexylamino)-2-hydroxypropyl]-3-ethoxy-5-(2-oxopyrrolidin-1-yl)benzamide;

N-(1-Benzyl-3-cyclohexylamino-2-hydroxypropyl)-3-ethoxy-5-(2-oxopyrrolidin-1-yl)benzamide;

N-[1-Benzyl-2-hydroxy-3-(3-methoxybenzylamino)propyl]-3-ethoxy-5-(2-oxopyrrolidin-1-yl)benzamide;

N-[(1S,2R)-1-Benzyl-3-((S)-1-cyclohexyl carbamoylethylamino)-2-hydroxypropyl]-3-methanesulfonyl-5-(2-oxopyrrolidin-1-yl)benzamide;

N-[1-Benzyl-2-hydroxy-3-(3-trifluoromethylbenzylamino)propyl]-3-methylsulfanyl-5-(2-oxopyrrolidin-1-yl)-benzamide;

N-[1-Benzyl-2-hydroxy-3-(3-trifluoromethylbenzylamino)propyl]-3-ethylsulfanyl-5-(2-oxopyrrolidin-1-yl)benzamide;

N-[1-Benzyl-2-hydroxy-3-(3-trifluoromethylbenzylamino)propyl]-3-ethanesulfonyl-5-(2-oxopyrrolidin-1-yl)-benzamide;

N-[1-Benzyl-2-hydroxy-3-(3-trifluoromethylbenzylamino)propyl]-3-methanesulfonyl-5-(2-oxopyrrolidin-1-yl)-benzamide;

N-[(1S,2R)-1-Benzyl-3-((S)-1-cyclohexylcarbamoylethylamino)-2-hydroxypropyl]-5-(1,1-dioxo-1/$^6$-isothiazolidin-2-yl)-N',N'-dipropylisophthalamide;

3-Azidomethyl-N-[(1S,2R)-1-benzyl-3-((S)-1-cyclohexylcarbamoylethylamino)-2-hydroxypropyl]-5-(1,1-dioxo-1/$^6$-isothiazolidin-2-yl)benzamide;

3-Aminomethyl-N-[(1S,2R)-1-benzyl-3-((S)-1-cyclohexylcarbamoylethylamino)-2-hydroxypropyl]-5-(1,1-dioxo-1/$^6$-isothiazolidin-2-yl)benzamide;

N-[(1S,2R)-1-Benzyl-3-((S)-1-cyclohexylcarbamoyl ethylamino)-2-hydroxypropyl]-3-dimethylaminomethyl-5-(1,1-dioxo-1/$^6$-isothiazolidin-2-yl)-benzamide;

-[(1S,2R)-1-Benzyl-3-((S)-1-cyclohexylcarbamoyl ethylamino)-2-hydroxypropyl]-3-(1,1-dioxo-1/$^6$-isothiazolidin-2-yl)-5-vinyl-benzamide;

N-[(1S,2R)-1-Benzyl-3-((S)-1-cyclohexylcarbamoylethylamino)-2-hydroxypropyl]-3-(1,1-dioxo-1/$^6$-isothiazolidin-2-yl)-5-ethyl-benzamide;

N-[(1S,2R)-1-Benzyl-3-((S)-1-cyclohexylcarbamoyl ethylamino)-2-hydroxypropyl]-3-(1,1-dioxo-1/$^6$-isothiazolidin-2-yl)-5-methoxymethylbenzamide;

N-[(1S,2R)-1-Benzyl-3-((S)-1-cyclohexylcarbamoyl ethylamino)-2-hydroxypropyl]-3-(1,1-dioxo-1/$^6$-isothiazolidin-2-yl)-5-ethoxymethylbenzamide;

N-[(1S,2R)-1-Benzyl-3-((S)-1-cyclohexylcarbamoyl ethylamino)-2-hydroxypropyl]-3-(1,1-dioxo-1/$^6$-isothiazolidin-2-yl)-5-(Z/E)-propenylbenzamide;

N-[(1S,2R)-1-Benzyl-3-((S)-1-cyclohexylcarbamoyl ethylamino)-2-hydroxypropyl]-3-(Z/E)-but-1-enyl-5-(1,1-dioxo-1/$^6$-isothiazolidin-2-yl)benzamide;

N-[(1S,2R)-1-Benzyl-3-((S)-1-cyclohexylcarbamoylethylamino)-2-hydroxypropyl]-3-(1,1-dioxo-1/$^6$-isothiazolidin-2-yl)-5-propylbenzamide;

N-[(1S,2R)-1-Benzyl-3-((S)-1-cyclohexylcarbamoylethylamino)-2-hydroxypropyl]-3-butyl-5-(1,1-dioxo-1/$^6$-isothiazolidin-2-yl)benzamide;

N-[(1S,2R)-1-Benzyl-3-((S)-1-cyclohexylcarbamoyl ethylamino)-2-hydroxypropyl]-3-(1,1-dioxo-1/$^6$-isothiazolidin-2-yl)-5-(2-methylpropenyl)benzamide;

N-[(1S,2R)-1-Benzyl-3-((S)-1-cyclohexylcarbamoylethylamino)-2-hydroxypropyl]-3-(1,1-dioxo-1/$^6$-isothiazolidin-2-yl)-5-fluoromethylbenzamide;

N-[1-Benzyl-3-(1-cyclohexylcarbamoylethylamino)-2-hydroxy-propyl]-3-(1,1-dioxo-1/$^6$-isothiazolidin-2-yl)-5-isobutylbenzamide;

N-[1-Benzyl-2-hydroxy-3-(3-trifluoromethylbenzylamino)propyl]-3-(1,1-dioxo-1/$^6$-isothiazolidin-2-yl)-5-propylbenzamide;

N-[1-Benzyl-3-(1,5-dimethylhexylamino)-2-hydroxypropyl]-3-(1,1-dioxo-1/$^6$-isothiazolidin-2-yl)-5-propyl-benzamide;

N-(1-Benzyl-3-cyclohexylamino-2-hydroxypropyl)-3-(1,1-dioxo-1/$^6$-isothiazolidin-2-yl)-5-propylbenzamide;

N-[1-Benzyl-2-hydroxy-3-(3-methoxybenzylamino)propyl]-3-(1,1-dioxo-1/$^6$-isothiazolidin-2-yl)-5-propylbenzamide;

N-[1-Benzyl-3-(1-cyclohexylcarbamoylethylamino)-2-hydroxypropyl]-5-(1,1-dioxo-1/$^6$-isothiazolidin-2-yl) isophthalamide;

N-[1-Benzyl-3-(1-cyclohexylcarbamoylethylamino)-2-hydroxypropyl]-3-cyano-5-(1,1-dioxo-1/$^6$-isothiazolidin-2-yl)benzamide;

N-[1-Benzyl-2-hydroxy-3-(3-trifluoromethylbenzylamino)propyl]-3-cyano-5-(1,1-dioxo-1/$^6$-isothiazolidin-2-yl)benzamide;

N-[1-Benzyl-2-hydroxy-3-(3-trifluoromethylbenzyl amino)propyl]-3-(1,1-dioxo-1/$^6$-isothiazolidin-2-yl)-5-ethynyl-benzamide;

N-[(1S,2R)-1-Benzyl-3-((S)-1-cyclohexylcarbamoyl ethylamino)-2-hydroxypropyl]-3-nitro-5-(2-oxopiperidin-1-yl)benzamide;

3-Amino-N-[(1S,2R)-1-benzyl-3-((S)-1-cyclohexylcarbamoylethylamino)-2-hydroxypropyl]-5-(2-oxopiperidin-1-yl)benzamide;

N-[(1S,2R)-1-Benzyl-3-((S)-1-cyclohexylcarbamoyl ethylamino)-2-hydroxypropyl]-3-(2-oxopiperidin-1-yl)-5-propylaminobenzamide;

N-[(1S,2R)-1-Benzyl-3-((S)-1-cyclohexylcarbamoyl ethylamino)-2-hydroxypropyl]-3-diethylamino-5-(2-oxopiperidin-1-yl)benzamide;

N-[(1S,2R)-1-Benzyl-3-((S)-1-cyclohexylcarbamoyl ethylamino)-2-hydroxypropyl]-3-ethylamino-5-(2-oxopiperidin-1-yl)benzamide;

N-[(1S,2R)-1-Benzyl-3-((S)-1-cyclohexylcarbamoyl ethylamino)-2-hydroxypropyl]-3-methylamino-5-(2-oxopiperidin-1-yl)benzamide;

N-[(1S,2R)-1-Benzyl-3-((S)-1-cyclohexylcarbamoyl ethylamino)-2-hydroxypropyl]-3-(2-oxopiperidin-1-yl)-5-piperidin-1-ylbenzamide;

N-[(1S,2R)-1-Benzyl-3-((S)-1-cyclohexylcarbamoyl ethylamino)-2-hydroxypropyl]-3-morpholin-4-yl-5-(2-oxopiperidin-1-yl)benzamide;

N-[(1S,2R)-1-Benzyl-3-((S)-1-cyclohexylcarbamoyl ethylamino)-2-hydroxypropyl]-3-(2-oxopiperidin-1-yl)-5-pyrrolidin-1-yl-benzamide;

N-[(1S,2R)-1-Benzyl-3-((S)-1-cyclohexylcarbamoyl ethylamino)-2-hydroxypropyl]-3-(1,1-dioxo-1/$^6$-isothiazolidin-2-yl)-5-isopropylaminobenzamide;

N-[(1S,2R)-1-Benzyl-2-hydroxy-3-((1S,2R)-2-hydroxy-1-isobutylcarbamoyl-pentylamino)-propyl]-3-(1,1-dioxo-1/$^6$-isothiazolidin-2-yl)-5-isopropylamino-benzamide;

3-Benzylamino-N-[(1S,2R)-1-benzyl-3-((S)-1-cyclohexylcarbamoylethylamino)-2-hydroxy-propyl]-5-(1,1-dioxo-1/$^6$-isothiazolidin-2-yl)benzamide;

N-[(1S,2R)-1-Benzyl-3-((S)-1-cyclohexylcarbamoylethylamino)-2-hydroxypropyl]-3-butylamino-5-(1,1-dioxo-1/$^6$-isothiazolidin-2-yl)benzamide;

N-[(1S,2R)-1-Benzyl-3-((S)-1-cyclohexylcarbamoylethylamino)-2-hydroxypropyl]-3-(1,1-dioxo-1/$^6$-isothiazolidin-2-yl)-5-(3-methylbutylamino)-benzamide;

N-[(1S,2R)-1-Benzyl-3-((S)-1-cyclohexylcarbamoylethylamino)-2-hydroxypropyl]-3-(1,1-dioxo-1/$^6$-isothiazolidin-2-yl)-5-phenethylamino-benzamide;

N-[(1S,2R)-1-Benzyl-3-((S)-1-cyclohexylcarbamoylethylamino)-2-hydroxypropyl]-3-(1,1-dioxo-1/$^6$-isothiazolidin-2-yl)-5-pentylaminobenzamide;

N-[(1S,2R)-1-Benzyl-3-((S)-1-cyclohexylcarbamoylethylamino)-2-hydroxypropyl]-3-(1,1-dioxo-1/$^6$-isothiazolidin-2-yl)-5-propylaminobenzamide;

N-[(1S,2R)-1-Benzyl-3-((S)-1-cyclohexylcarbamoylethylamino)-2-hydroxypropyl]-3-(1,1-dioxo-1/$^6$-isothiazolidin-2-yl)-5-ethylaminobenzamide;

N-[(1S,2R)-1-Benzyl-3-((S)-1-cyclohexylcarbamoylethylamino)-2-hydroxypropyl]-3-diethylamino-5-(1,1-dioxo-1/$^6$-isothiazolidin-2-yl)benzamide;

N-[(1S,2R)-1-Benzyl-3-(1,5-dimethylhexylamino)-2-hydroxypropyl]-3-(1,1-dioxo-1/$^6$-isothiazolidin-2-yl)-5-ethylaminobenzamide;

N-[(1S,2R)-1-Benzyl-3-(1,5-dimethylhexylamino)-2-hydroxypropyl]-3-(1,1-dioxo-1/$^6$-isothiazolidin-2-yl)-5-isopropylaminobenzamide;

N-[(1S,2R)-1-Benzyl-3-((S)-1-cyclohexylcarbamoyl ethylamino)-2-hydroxypropyl]-3-(cyclopropylmethylamino)-5-(1,1-dioxo-1/$^6$-isothiazolidin-2-yl)benzamide;

N-[(1S,2R)-1-Benzyl-2-hydroxy-3-(3-methoxybenzylamino)propyl]-3-(1,1-dioxo-1/$^6$-isothiazolidin-2-yl)-5-ethylamino-benzamide;

N-[(1S,2R)-1-Benzyl-2-hydroxy-3-(3-trifluoromethylbenzylamino)propyl]-3-(1,1-dioxo-1/$^6$-isothiazolidin-2-yl)-5-ethylaminobenzamide;

N-((1S,2R)-1-Benzyl-3-cyclohexylamino-2-hydroxypropyl)-3-(1,1-dioxo-1/$^6$-isothiazolidin-2-yl)-5-ethylaminobenzamide;

N-[1-Benzyl-2-hydroxy-3-(3-trifluoromethylbenzylamino)propyl]-3-(1,1-dioxo-1/$^6$-isothiazolidin-2-yl)-5-morpholin-4-yl-benzamide;

N-[(1S,2R)-1-Benzyl-2-hydroxy-3-(3-trifluoromethylbenzylamino)-propyl]-3-(1,1-dioxo-1/$^6$-isothiazolidin-2-yl)-5-pyrrolidin-1-yl-benzamide;

N-[1-Benzyl-2-hydroxy-3-(3-trifluoromethylbenzylamino) propyl]-3-(1,1-dioxo-1/$^6$-isothiazolidin-2-yl)-5-methylaminobenzamide;

N-[(1S,2R)-1-Benzyl-3-((S)-1-cyclohexylcarbamoyl ethylamino)-2-hydroxypropyl]-3-(1,1-dioxo-1/$^6$-isothiazolidin-2-yl)-5-ethoxybenzamide;

N-[1-Benzyl-2-hydroxy-3-(3-trifluoromethylbenzylamino)propyl]-3-(1,1-dioxo-1/$^6$-isothiazolidin-2-yl)-5-ethoxy-benzamide;

N-[1-Benzyl-3-(1,5-dimethylhexylamino)-2-hydroxypropyl]-3-(1,1-dioxo-1/$^6$-isothiazolidin-2-yl)-5-ethoxy-benzamide;

N-[1-Benzyl-2-hydroxy-3-(3-methoxybenzylamino)propyl]-3-(1,1-dioxo-1/$^6$-isothiazolidin-2-yl)-5-ethoxybenzamide;

N-(1-Benzyl-3-cyclohexylamino-2-hydroxypropyl)-3-(1,1-dioxo-1/$^6$-isothiazolidin-2-yl)-5-ethoxybenzamide;

N-[1-Benzyl-3-(1-cyclohexylcarbamoylethylamino)-2-hydroxypropyl]-3-(1,1-dioxo-1/$^6$-isothiazolidin-2-yl)-5-isopropoxybenzamide;

N-[1-Benzyl-3-(1-cyclohexylcarbamoylethylamino)-2-hydroxypropyl]-3-(1,1-dioxo-1/$^6$-isothiazolidin-2-yl)-5-propoxybenzamide;

N-[1-Benzyl-3-(1-cyclohexylcarbamoylethylamino)-2-hydroxypropyl]-3-(1,1-dioxo-1/$^6$-isothiazolidin-2-yl)-5-pentyloxybenzamide;

N-[1-Benzyl-3-(1-cyclohexylcarbamoylethylamino)-2-hydroxypropyl]-3-(1,1-dioxo-1/$^6$-isothiazolidin-2-yl)-5-methoxybenzamide;

N-(1-Benzyl-3-cyclopropylamino-2-hydroxypropyl)-3-(1,1-dioxo-1/$^6$-isothiazolidin-2-yl)-5-ethoxybenzamide;

N-[1-Benzyl-2-hydroxy-3-(3-trifluoromethoxybenzylamino) propyl]-3-(1,1-dioxo-1/$^6$-isothiazolidin-2-yl)-5-ethoxybenzamide;

N-[1-Benzyl-2-hydroxy-3-(3-trifluoromethylbenzylamino)propyl]-3-(1,1-dioxo-1/$^6$-isothiazolidin-2-yl)-5-methylsulfanylbenzamide;

N-[1-Benzyl-2-hydroxy-3-(3-trifluoromethylbenzylamino)propyl]-3-(1,1-dioxo-1/$^6$-isothiazolidin-2-yl)-5-ethylsulfanylbenzamide;

N-[1-Benzyl-2-hydroxy-3-(3-trifluoromethylbenzylamino)propyl]-3-(1,1-dioxo-1/$^6$-isothiazolidin-2-yl)-5-ethanesulfonylbenzamide;

N-[1-Benzyl-2-hydroxy-3-(3-trifluoromethylbenzylamino)propyl]-3-(1,1-dioxo-1/$^6$-isothiazolidin-2-yl)-5-Methanesulfonylbenzamide;

N-[(1S,2R)-1-Benzyl-3-((S)-1-cyclohexylcarbamoyl ethylamino)-2-hydroxypropyl]-5-(2-oxopiperidin-1-yl)-N',N'-dipropylisophthalamide;

3-(1,1-dioxidotetrahydro-2H-1,2-thiazin-2-yl)-2-fluoro-N-{(1S,2R)-2-hydroxy-1-(phenylmethyl)-3-[({3-[(trifluoromethyl)oxy]phenyl}methyl)amino]propyl}-5-[(1-methylethyl)amino]benzamide;

3-(1,1-dioxidotetrahydro-2H-1,2-thiazin-2-yl)-5-(ethylamino)-N-[(1S,2R)-3-{[(3-ethyl-5-isoxazolyl)methyl]amino}-2-hydroxy-1-(phenylmethyl)propyl]-2-fluorobenzamide;

4-(1,1-dioxidotetrahydro-2H-1,2-thiazin-2-yl)-1-ethyl-N-[(1S,2R)-2-hydroxy-1-(phenylmethyl)-3-(tetrahydro-2H-pyran-4-ylamino)propyl]-1H-benzimidazole-6-carboxamide;

8-(1,1-dioxido-2-isothiazolidinyl)-4-ethyl-N-[(1S,2R)-2-hydroxy-1-(phenylmethyl)-3-(tetrahydro-2H-pyran-4-ylamino)propyl]-1,2,3,4-tetrahydro-6-quinoxalinecarboxamide;

8-(1,1-dioxido-2-isothiazolidinyl)-4-ethyl-N-[(1S,2R)-3-{[(1-ethyl-1H-pyrazol-4-yl)methyl]amino}-2-hydroxy-1-(phenylmethyl)propyl]-1,2,3,4-tetrahydro-6-quinoxalinecarboxamide;

4-(1,1-dioxidotetrahydro-2H-1,2-thiazin-2-yl)-1-ethyl-N-[(1S,2R)-2-hydroxy-3-[(1-methylethyl)amino]-1-(phenylmethyl)propyl]-1H-benzimidazole-6-carboxamide;

8-(1,1-dioxido-2-isothiazolidinyl)-4-ethyl-N-[(1S,2R)-2-hydroxy-3-[(1-methylethyl)amino]-1-(phenylmethyl)propyl]-1,2,3,4-tetrahydro-6-quinoxalinecarboxamide;

N-[(1S,2R)-1-Benzyl-3-((S)-1-cyclohexylcarbamoyl ethylamino)-2-hydroxypropyl]-5-(1,1-dioxo-1/$^6$-[1,2]thiazinan-2-yl)-N',N'-dipropylisophthalamide;

N-[1-Benzyl-2-hydroxy-3-(3-trifluoromethylbenzylamino)propyl]-5-(1,1-dioxo-1/$^6$-[1,2]thiazinan-2-yl)-N',N'-dipropylisophthalamide;

N-(1-Benzyl-3-cyclopropylamino-2-hydroxypropyl)-5-(1,1-dioxo-1/$^6$-[1,2]thiazinan-2-yl)-N',N'-dipropylisophthalamide;

N-[1-Benzyl-2-hydroxy-3-(3-trifluoromethylbenzylamino) propyl]-3-(1,1-dioxo-1/$^6$-[1,2]thiazinan-2-yl)-5-propylbenzamide;

N-[1-Benzyl-2-hydroxy-3-(3-methoxybenzylamino)propyl]-3-(1,1-dioxo-1/$^6$-[1,2]thiazinan-2-yl)-5-propylbenzamide;

N-[1-Benzyl-3-(1,5-dimethylhexylamino)-2-hydroxypropyl]-3-(1,1-dioxo-1/$^6$-[1,2]thiazinan-2-yl)-5-propylbenzamide;

N-[1-Benzyl-3-(1-cyclohexylcarbamoylethylamino)-2-hydroxypropyl]-3-(1,1-dioxo-1/$^6$-[1,2]thiazinan-2-yl)-5-propylbenzamide;

N-[1-Benzyl-2-hydroxy-3-(3-methoxybenzylamino)propyl]-5-(1,1-dioxo-1/$^6$-[1,2]thiazinan-2-yl)-N',N'-dipropyl-isophthalamide;

N-[1-Benzyl-2-hydroxy-3-(3-trifluoromethoxybenzylamino) propyl]-5-(1,1-dioxo-1/$^6$-[1,2]thiazinan-2-yl)-N',N'-dipropyl-isophthalamide;

N-[1-Benzyl-2-hydroxy-3-(3-trifluoromethylbenzylamino) propyl]-3-(1,1-dioxo-1/$^6$-[1,2]thiazinan-2-yl)-5-ethylaminobenzamide;

N-[1-Benzyl-2-hydroxy-3-(3-methoxybenzylamino)propyl]-3-(1,1-dioxo-1/$^6$-[1,2]thiazinan-2-yl)-5-ethylaminobenzamide;

N-[1-Benzyl-3-(1,5-dimethylhexylamino)-2-hydroxypropyl]-3-(1,1-dioxo-1/$^6$-[1,2]thiazinan-2-yl)-5-ethylaminobenzamide;

N-[1-Benzyl-3-(1-cyclohexylcarbamoylethylamino)-2-hydroxypropyl]-3-(1,1-dioxo-1/$^6$-[1,2]thiazinan-2-yl)-5-ethylaminobenzamide;

N-{(1S,2R)-1-Benzyl-3-[(3,5-dichlorobenzyl)amino]-2-hydroxypropyl}-3-(1,1-dioxido-1,2-thiazinan-2-yl)-5-(ethylamino)benzamide;

N-{(1S,2R)-1-Benzyl-3-[(2-fluoro-5-methoxybenzyl)amino]-2-hydroxypropyl}-3-(1,1-dioxido-1,2-thiazinan-2-yl)-5-(ethylamino)benzamide;

N-{(1S,2R)-1-Benzyl-3-[(4-fluoro-3-methoxybenzyl)amino]-2-hydroxypropyl}-3-(1,1-dioxido-1,2-thiazinan-2-yl)-5-(ethylamino)benzamide;

N-{(1S,2R)-1-Benzyl-3-[(3,5-dimethylbenzyl)amino]-2-hydroxypropyl}-3-(1,1-dioxido-1,2-thiazinan-2-yl)-5-(ethylamino)benzamide;

N-{(1S,2R)-1-Benzyl-3-[(3,5-difluorobenzyl)amino]-2-hydroxypropyl}-3-(1,1-dioxido-1,2-thiazinan-2-yl)-5-(ethylamino)benzamide;

N-((1S,2R)-1-Benzyl-2-hydroxy-3-{[3-nitro-5-(trifluoromethyl)benzyl]amino}propyl)-3-(1,1-dioxido-1,2-thiazinan-2-yl)-5-(ethylamino)benzamide;

N-((1S,2R)-1-Benzyl-3-{[(5-cyanopyridin-3-yl)methyl]amino}-2-hydroxypropyl)-3-(1,1-dioxido-1,2-thiazinan-2-yl)-5-(ethylamino)benzamide;

N-{(1S,2R)-1-Benzyl-3-[(3-chloro-5-methoxybenzyl)amino]-2-hydroxypropyl}-3-(1,1-dioxido-1,2-thiazinan-2-yl)-5-(ethylamino)benzamide;

N-{(1S,2R)-1-Benzyl-3-[(3-bromo-5-fluorobenzyl)amino]-2-hydroxypropyl}-3-(1,1-dioxido-1,2-thiazinan-2-yl)-5-(ethylamino)benzamide;

5-{[(((2R,3S)-3-{[3-(1,1-Dioxido-1,2-thiazinan-2-yl)-5-(ethylamino)benzoyl]amino}-2-hydroxy-4-phenylbutyl)amino]methyl}-N-methylnicotinamide;

N-{(1S,2R)-1-Benzyl-3-[(3-bromo-5-methoxybenzyl)amino]-2-hydroxypropyl}-3-(1,1-dioxido-1,2-thiazinan-2-yl)-5-(ethylamino)benzamide;

Methyl 5-{[(((2R,3S)-3-{[3-(1,1-dioxido-1,2-thiazinan-2-yl)-5-(ethylamino)benzoyl]amino}-2-hydroxy-4-phenylbutyl)amino]methyl}nicotinate;

N-{(1S,2R)-1-Benzyl-3-[(3,5-di-tert-butylbenzyl)amino]-2-hydroxypropyl}-3-(1,1-dioxido-1,2-thiazinan-2-yl)-5-(ethylamino)benzamide;

N-((1S,2R)-1-Benzyl-2-hydroxy-3-{[3-methyl-5-(methylsulfonyl)benzyl]amino}propyl)-3-(1,1-dioxido-1,2-thiazinan-2-yl)-5-(ethylamino)benzamide;

N-{(1S,2R)-1-Benzyl-2-hydroxy-3-[(3-methoxy-5-methylbenzyl)amino]propyl}-3-(1,1-dioxido-1,2-thiazinan-2-yl)-5-(ethylamino)benzamide;

Dimethyl 5-{[(((2R,3S)-3-{[3-(1,1-dioxido-1,2-thiazinan-2-yl)-5-(ethylamino)benzoyl]amino}-2-hydroxy-4-phenylbutyl)amino]methyl}isophthalate;

N-{(1S,2R)-1-Benzyl-3-[(3,5-diisopropoxybenzyl)amino]-2-hydroxypropyl}-3-(1,1-dioxido-1,2-thiazinan-2-yl)-5-(ethylamino)benzamide;

N-((1S,2R)-1-Benzyl-3-{[(4-bromo-2-thienyl)methyl]amino}-2-hydroxypropyl)-3-(1,1-dioxido-1,2-thiazinan-2-yl)-5-(ethylamino)benzamide;

N-{(1S,2R)-1-Benzyl-3-[(2,3-dihydro-1-benzofuran-6-ylmethyl)amino]-2-hydroxypropyl}-3-(1,1-dioxido-1,2-thiazinan-2-yl)-5-(ethylamino)benzamide;

N-((1S,2R)-1-Benzyl-3-{[(4-chloro-1-methyl-1H-pyrazol-3-yl)methyl]amino}-2-hydroxypropyl)-3-(1,1-dioxido-1,2-thiazinan-2-yl)-5-(ethylamino)benzamide;

N-((1S,2R)-1-Benzyl-3-{[(2-bromo-1,3-thiazol-5-yl)methyl]amino}-2-hydroxypropyl)-3-(1,1-dioxido-1,2-thiazinan-2-yl)-5-(ethylamino)benzamide;

N-((1S,2R)-1-Benzyl-3-{[(4-bromo-1H-pyrrol-2-yl)methyl]amino}-2-hydroxypropyl)-3-(1,1-dioxido-1,2-thiazinan-2-yl)-5-(ethylamino)benzamide;

N-((1S,2R)-1-Benzyl-3-{[(2-butyl-1H-imidazol-4-yl)methyl]amino}-2-hydroxypropyl)-3-(1,1-dioxido-1,2-thiazinan-2-yl)-5-(ethylamino)benzamide;

N-{(1S,2R)-1-Benzyl-3-[(3-bromobenzyl)amino]-2-hydroxypropyl}-3-(1,1-dioxido-1,2-thiazinan-2-yl)-5-(ethylamino)benzamide;

N-{(1S,2R)-1-Benzyl-2-hydroxy-3-[(3-nitrobenzyl)amino]propyl}-3-(1,1-dioxido-1,2-thiazinan-2-yl)-5-(ethylamino)benzamide;

N-{(1S,2R)-1-Benzyl-2-hydroxy-3-[(3-thienylmethyl)amino]propyl}-3-(1,1-dioxido-1,2-thiazinan-2-yl)-5-(ethylamino)benzamide;

N-((1S,2R)-1-Benzyl-3-{[(4-bromo-1-methyl-1H-pyrazol-3-yl)methyl]amino}-2-hydroxypropyl)-3-(1,1-dioxido-1,2-thiazinan-2-yl)-5-(ethylamino)benzamide;

N-((1S,2R)-1-Benzyl-3-{[3-fluoro-5-(trifluoromethyl)benzyl]amino}-2-hydroxypropyl}-3-(1,1-dioxido-1,2-thiazinan-2-yl)-5-(ethylamino)benzamide;

N-{(1S,2R)-1-Benzyl-2-hydroxy-3-[(3-vinylbenzyl)amino]propyl}-3-(1,1-dioxido-1,2-thiazinan-2-yl)-5-(ethylamino)benzamide;

N-((1S,2R)-1-Benzyl-2-hydroxy-3-{[(4-methoxy-3-thienyl)methyl]amino}propyl)-3-(1,1-dioxido-1,2-thiazinan-2-yl)-5-(ethylamino)benzamide;

3-{[((2R,3S)-3-{([3-(1,1-Dioxido-1,2-thiazinan-2-yl)-5-(ethylamino)benzoyl]amino}-2-hydroxy-4-phenylbutyl)amino]methyl}benzoic acid;

N-{(1S,2R)-1-Benzyl-3-[(3,4-dimethoxybenzyl)amino]-2-hydroxypropyl}-3-(1,1-dioxido-1,2-thiazinan-2-yl)-5-(ethylamino)benzamide;

N-((1S,2R)-1-Benzyl-3-{[(5-ethyl-2-furyl)methyl]amino}-2-hydroxypropyl)-3-(1,1-dioxido-1,2-thiazinan-2-yl)-5-(ethylamino)benzamide;

N-{(1S,2R)-1-Benzyl-3-[(2,3-dihydro-1,4-benzodioxin-6-ylmethyl)amino]-2-hydroxypropyl}-3-(1,1-dioxido-1,2-thiazinan-2-yl)-5-(ethylamino)benzamide;

N-{(1S,2R)-1-Benzyl-3-[(3-ethoxy-4-methoxybenzyl)amino]-2-hydroxypropyl}-3-(1,1-dioxido-1,2-thiazinan-2-yl)-5-(ethylamino)benzamide;

N-((1S,2R)-1-Benzyl-3-{[(5-ethyl-2-thienyl)methyl]amino}-2-hydroxypropyl)-3-(1,1-dioxido-1,2-thiazinan-2-yl)-5-(ethylamino)benzamide;

N-{(1S,2R)-1-Benzyl-3-[(3-chloro-4-fluorobenzyl)amino]-2-hydroxypropyl}-3-(1,1-dioxido-1,2-thiazinan-2-yl)-5-(ethylamino)benzamide;

N-((1S,2R)-1-Benzyl-3-{[(1-ethyl-1H-pyrazol-4-yl)methyl]amino}-2-hydroxypropyl)-3-(1,1-dioxido-1,2-thiazinan-2-yl)-5-(ethylamino)benzamide;

N-((1S,2R)-1-Benzyl-3-{[(1-ethyl-3-methyl-1H-pyrazol-4-yl)methyl]amino}-2-hydroxypropyl)-3-(1,1-dioxido-1,2-thiazinan-2-yl)-5-(ethylamino)benzamide;

N-((1S,2R)-1-Benzyl-3-{[(2,2-dimethyl-3,4-dihydro-2H-chromen-6-yl)methyl]amino}-2-hydroxypropyl)-3-(1,1-dioxido-1,2-thiazinan-2-yl)-5-(ethylamino)benzamide;

N-((1S,2R)-1-Benzyl-3-{[4-chloro-3-(trifluoromethyl)benzyl]amino}-2-hydroxypropyl)-3-(1,1-dioxido-1,2-thiazinan-2-yl)-5-(ethylamino)benzamide;

N-((1S,2R)-1-Benzyl-2-hydroxy-3-{([(6-methylpyridin-2-yl)methyl]amino}propyl)-3-(1,1-dioxido-1,2-thiazinan-2-yl)-5-(ethylamino)benzamide;

N-{(1S,2R)-1-benzyl-3-[(3-ethylbenzyl)amino]-2-hydroxypropyl}-3-(1,1-dioxido-1,2-thiazinan-2-yl)-5-(ethylamino)benzamide;

N-((1S,2R)-1-benzyl-3-{[(1-ethyl-1H-pyrazol-4-yl)methyl]amino}-2-hydroxypropyl)-3-(1,1-dioxido-1,2-thiazinan-2-yl)-5-(ethylamino)-2-fluorobenzamide;

N-((1S,2R)-1-benzyl-3-{[(1-ethyl-1H-pyrazol-4-yl)methyl]amino}-2-hydroxypropyl)-3-(ethylamino)-5-(2-oxopyrrolidin-1-yl)benzamide;

N-{(1S,2R)-1-benzyl-2-hydroxy-3-[(3-methoxy-4-methylbenzyl)amino]propyl}-3-(1,1-dioxido-1,2-thiazinan-2-yl)-5-(ethylamino)benzamide;

N-{(1S,2R)-1-benzyl-2-hydroxy-3-[(3-methoxy-2-methylbenzyl)amino]propyl}-3-(1,1-dioxido-1,2-thiazinan-2-yl)-5-(ethylamino)benzamide;

3-(1,1-dioxidotetrahydro-2H-1,2-thiazin-2-yl)-5-(ethylamino)-N-[(1S,2R)-2-hydroxy-3-[(1-methylbutyl)amino]-1-(phenylmethyl)propyl]benzamide;

3-(1,1-dioxidotetrahydro-2H-1,2-thiazin-2-yl)-5-(ethylamino)-N-{(1S,2R)-2-hydroxy-1-(phenylmethyl)-3-[(1-propylbutyl)amino]propyl}benzamide;

3-(1,1-dioxidotetrahydro-2H-1,2-thiazin-2-yl)-5-(ethylamino)-N-[(1S,2R)-2-hydroxy-3-[(1-methylpentyl)amino]-1-(phenylmethyl)propyl]benzamide;

N-[(1S,2R)-3-[(1,4-dimethylpentyl)amino]-2-hydroxy-1-(phenylmethyl)propyl]-3-(1,1-dioxidotetrahydro-2H-1,2-thiazin-2-yl)-5-(ethylamino)benzamide;

3-(1,1-dioxidotetrahydro-2H-1,2-thiazin-2-yl)-5-(ethylamino)-N-[(1S,2R)-2-hydroxy-3-[(3-methylbutyl)amino]-1-(phenylmethyl)propyl]benzamide;

3-(1,1-dioxidotetrahydro-2H-1,2-thiazin-2-yl)-5-(ethylamino)-N-[(1S,2R)-2-hydroxy-1-(phenylmethyl)-3-(propylamino)propyl]benzamide;

N-[(1S,2R)-3-{[1-(3-chlorophenyl)propyl]amino}-2-hydroxy-1-(phenylmethyl)propyl]-3-(ethylamino)-5-(2-oxo-1-pyrrolidinyl)benzamide;

N-[(1S,2R)-3-{[1-(3-chlorophenyl)propyl]amino}-2-hydroxy-1-(phenylmethyl)propyl]-3-cyclopentyl-5-(2-oxo-1-pyrrolidinyl)benzamide;

3-(1,1-dioxidotetrahydro-2H-1,2-thiazin-2-yl)-5-(ethylamino)-N-[(1S,2R)-2-hydroxy-3-[(4-methylpentyl)amino]-1-(phenylmethyl)propyl]benzamide;

3-(1,1-dioxidotetrahydro-2H-1,2-thiazin-2-yl)-5-(ethylamino)-N-[(1S,2R)-2-hydroxy-3-[(5-methylhexyl)amino]-1-(phenylmethyl)propyl]benzamide;

3-(1,1-dioxidotetrahydro-2H-1,2-thiazin-2-yl)-5-(ethylamino)-N-[(1S,2R)-2-hydroxy-3-[(1-methylpropyl)amino]-1-(phenylmethyl)propyl]benzamide;

3-(1,1-dioxidotetrahydro-2H-1,2-thiazin-2-yl)-5-(ethylamino)-N-[(1S,2R)-2-hydroxy-3-[(1-methylhexyl)amino]-1-(phenylmethyl)propyl]benzamide;

N-[(1S,2R)-3-{[(3,5-dibromophenyl)methyl]amino}-2-hydroxy-1-(phenylmethyl)propyl]-3-[(1-methylethyl)oxy]-5-(2-oxo-1-pyrrolidinyl)benzamide;

N-{(1S,2R)-2-hydroxy-1-(phenylmethyl)-3-[(phenylmethyl)amino]propyl}-3-[(1-methylethyl)oxy]-5-(2-oxo-1-pyrrolidinyl)benzamide;

N-[(1S,2R)-3-{([(3-bromophenyl)methyl]amino}-2-hydroxy-1-(phenylmethyl)propyl]-3-[(1-methylethyl)oxy]-5-(2-oxo-1-pyrrolidinyl)benzamide;

N-[(1S,2R)-3-({[3-(ethyloxy)phenyl]methyl}amino)-2-hydroxy-1-(phenylmethyl)propyl]-3-[(1-methylethyl)oxy]-5-(2-oxo-1-pyrrolidinyl)benzamide;

N-[(1S,2R)-3-{([(3-chlorophenyl)methyl]amino}-2-hydroxy-1-(phenylmethyl)propyl]-3-[(1-methylethyl)oxy]-5-(2-oxo-1-pyrrolidinyl)benzamide;

N-{(1S,2R)-2-hydroxy-1-(phenylmethyl)-3-[({3-[(trifluoromethyl)oxy]phenyl}methyl)amino]propyl}-3-[(1-methylethyl)oxy]-5-(2-oxo-1-pyrrolidinyl)benzamide;

N-[(1S,2R)-3-({[3,5-bis(methyloxy)phenyl]methyl}amino)-2-hydroxy-1-(phenylmethyl)propyl]-3-[(1-methylethyl)oxy]-5-(2-oxo-1-pyrrolidinyl)benzamide;

N-[(1S,2R)-3-{[(3,5-dichlorophenyl)methyl]amino}-2-hydroxy-1-(phenylmethyl)propyl]-3-[(1-methylethyl)oxy]-5-(2-oxo-1-pyrrolidinyl)benzamide;

N-[(1S,2R)-3-{[(3,5-difluorophenyl)methyl]amino}-2-hydroxy-1-(phenylmethyl)propyl]-3-[(1-methylethyl)oxy]-5-(2-oxo-1-pyrrolidinyl)benzamide;

N-[(1S,2R)-2-hydroxy-1-(phenylmethyl)-3-({[3-(trifluoromethyl)phenyl]methyl}amino)propyl]-3-[(1-methylethyl)oxy]-5-(2-oxo-1-pyrrolidinyl)benzamide;

N-[(1S,2R)-3-({[3,5-bis(trifluoromethyl)phenyl]methyl}amino)-2-hydroxy-1-(phenylmethyl)propyl]-3-[(1-methylethyl)oxy]-5-(2-oxo-1-pyrrolidinyl)benzamide;

N-[(1S,2R)-2-hydroxy-3-{[(3-methylphenyl)methyl]amino}-1-(phenylmethyl)propyl]-3-[(1-methylethyl)oxy]-5-(2-oxo-1-pyrrolidinyl)benzamide;

3-(1,1-dioxidotetrahydro-2H-1,2-thiazin-2-yl)-N-[(1S,2R)-2-hydroxy-1-(phenylmethyl)-3-({[3-(trifluoromethyl)phenyl]methyl}amino)propyl]-5-[(1-methylethyl)oxy]benzamide;

3-(1,1-dioxidotetrahydro-2H-1,2-thiazin-2-yl)-N-[(1S,2R)-2-hydroxy-3-({[3-(methyloxy)phenyl]methyl}amino)-1-(phenylmethyl)propyl]-5-[(1-methylethyl)oxy]benzamide;

3-(1,1-dioxidotetrahydro-2H-1,2-thiazin-2-yl)-N-{(1S,2R)-2-hydroxy-1-(phenylmethyl)-3-[({3-[(trifluoromethyl)oxy]phenyl}methyl)amino]propyl}-5-[(1-methylethyl)oxy]benzamide;

N-[(1S,2R)-3-({[3,5-bis(trifluoromethyl)phenyl]methyl}amino)-2-hydroxy-1-(phenylmethyl)propyl]-3-(1,1-dioxidotetrahydro-2H-1,2-thiazin-2-yl)-5-[(1-methylethyl)oxy]benzamide;

N-[(1S,2R)-3-({[3,5-bis(methyloxy)phenyl]methyl}amino)-2-hydroxy-1-(phenylmethyl)propyl]-3-(1,1-dioxidotetrahydro-2H-1,2-thiazin-2-yl)-5-[(1-methylethyl)oxy]benzamide;

N-[(1S,2R)-3-{[(3,5-dibromophenyl)methyl]amino}-2-hydroxy-1-(phenylmethyl)propyl]-3-(1,1-dioxidotetrahydro-2H-1,2-thiazin-2-yl)-5-[(1-methylethyl)oxy]benzamide;

3-cyclopentyl-5-(1,1-dioxidotetrahydro-2H-1,2-thiazin-2-yl)-N-[(1S,2R)-2-hydroxy-1-(phenylmethyl)-3-({[3-(trifluoromethyl)phenyl]methyl}amino)propyl]benzamide;

3-cyclopentyl-5-(1,1-dioxidotetrahydro-2H-1,2-thiazin-2-yl)-N-[(1S,2R)-2-hydroxy-3-({[3-(methyloxy)phenyl]methyl}amino)-1-(phenylmethyl)propyl]benzamide;

3-cyclopentyl-5-(1,1-dioxidotetrahydro-2H-1,2-thiazin-2-yl)-N-{(1S,2R)-2-hydroxy-1-(phenylmethyl)-3-[({3-[(trifluoromethyl)oxy]phenyl}methyl)amino]propyl}benzamide;

N-[(1S,2R)-3-({[3,5-bis(trifluoromethyl)phenyl]methyl}amino)-2-hydroxy-1-(phenylmethyl)propyl]-3-cyclopentyl-5-(1,1-dioxidotetrahydro-2H-1,2-thiazin-2-yl)benzamide;

N-[(1S,2R)-3-({[3,5-bis(methyloxy)phenyl]methyl}amino)-2-hydroxy-1-(phenylmethyl)propyl]-3-cyclopentyl-5-(1,1-dioxidotetrahydro-2H-1,2-thiazin-2-yl)benzamide;

3-cyclopentyl-N-[(1S,2R)-3-{[(3,5-dibromophenyl)methyl]amino}-2-hydroxy-1-(phenylmethyl)propyl]-5-(1,1-dioxidotetrahydro-2H-1,2-thiazin-2-yl)benzamide;

3-(1,1-dioxidotetrahydro-2H-1,2-thiazin-2-yl)-5-(ethylamino)-N-{(1S,2R)-2-hydroxy-1-(phenylmethyl)-3-[({3-[(trifluoromethyl)oxy]phenyl}methyl)amino]propyl}benzamide;

N-[(1S,2R)-3-({[3,5-bis(trifluoromethyl)phenyl]methyl}amino)-2-hydroxy-1-(phenylmethyl)propyl]-3-(1,1-dioxidotetrahydro-2H-1,2-thiazin-2-yl)-5-(ethylamino)benzamide;

N-[(1S,2R)-3-({[3,5-bis(methyloxy)phenyl]methyl}amino)-2-hydroxy-1-(phenylmethyl)propyl]-3-(1,1-dioxidotetrahydro-2H-1,2-thiazin-2-yl)-5-(ethylamino)benzamide;

N-[(1S,2R)-3-{[(3,5-dibromophenyl)methyl]amino}-2-hydroxy-1-(phenylmethyl)propyl]-3-(1,1-dioxidotetrahydro-2H-1,2-thiazin-2-yl)-5-(ethylamino)benzamide;

3-(ethyloxy)-N-{(1S,2R)-2-hydroxy-1-(phenylmethyl)-3-[({3-[(trifluoromethyl)oxy]phenyl}methyl)amino]propyl}-5-(2-oxo-1-pyrrolidinyl)benzamide;

N-[(1S,2R)-3-({[3,5-bis(trifluoromethyl)phenyl]methyl}amino)-2-hydroxy-1-(phenylmethyl)propyl]-3-(ethyloxy)-5-(2-oxo-1-pyrrolidinyl)benzamide;

N-[(1S,2R)-3-({[3,5-bis(methyloxy)phenyl]methyl}amino)-2-hydroxy-1-(phenylmethyl)propyl]-3-(ethyloxy)-5-(2-oxo-1-pyrrolidinyl)benzamide;

N-[(1S,2R)-3-{[(3,5-dibromophenyl)methyl]amino}-2-hydroxy-1-(phenylmethyl)propyl]-3-(ethyloxy)-5-(2-oxo-1-pyrrolidinyl)benzamide;

3-cyclopentyl-N-{(1S,2R)-2-hydroxy-1-(phenylmethyl)-3-[({3-[(trifluoromethyl)oxy]phenyl}methyl)amino]propyl}-5-(2-oxo-1-pyrrolidinyl)benzamide;

N-[(1S,2R)-3-({[3,5-bis(trifluoromethyl)phenyl]methyl}amino)-2-hydroxy-1-(phenylmethyl)propyl]-3-cyclopentyl-5-(2-oxo-1-pyrrolidinyl)benzamide;

N-[(1S,2R)-3-({[3,5-bis(methyloxy)phenyl]methyl}amino)-2-hydroxy-1-(phenylmethyl)propyl]-3-cyclopentyl-5-(2-oxo-1-pyrrolidinyl)benzamide;

3-cyclopentyl-N-[(1S,2R)-3-{[(3,5-dibromophenyl)methyl]amino}-2-hydroxy-1-(phenylmethyl)propyl]-5-(2-oxo-1-pyrrolidinyl)benzamide;

N-[(1S,2R)-3-({[3,5-bis(methyloxy)phenyl]methyl}amino)-2-hydroxy-1-(phenylmethyl)propyl]-3-(ethylamino)-5-(2-oxo-1-pyrrolidinyl)benzamide;

N-[(1S,2R)-3-{[(3,5-dibromophenyl)methyl]amino}-2-hydroxy-1-(phenylmethyl)propyl]-3-(ethylamino)-5-(2-oxo-1-pyrrolidinyl)benzamide;

N-[(1S,2R)-3-({[3,5-bis(trifluoromethyl)phenyl]methyl}amino)-2-hydroxy-1-(phenylmethyl)propyl]-3-(1,1-dioxido-2-isothiazolidinyl)-5-(ethyloxy)benzamide;

N-[(1S,2R)-3-({[3,5-bis(methyloxy)phenyl]methyl}amino)-2-hydroxy-1-(phenylmethyl)propyl]-3-(1,1-dioxido-2-isothiazolidinyl)-5-(ethyloxy)benzamide;

N-[(1S,2R)-3-{[(3,5-dibromophenyl)methyl]amino}-2-hydroxy-1-(phenylmethyl)propyl]-3-(1,1-dioxido-2-isothiazolidinyl)-5-(ethyloxy)benzamide;

3-(1,1-dioxido-2-isothiazolidinyl)-N-[(1S,2R)-2-hydroxy-1-(phenylmethyl)-3-({[3-(trifluoromethyl)phenyl]methyl}amino)propyl]-5-[(1-methylethyl)oxy]benzamide;

3-(1,1-dioxido-2-isothiazolidinyl)-N-[(1S,2R)-2-hydroxy-3-({[3-(methyloxy)phenyl]methyl}amino)-1-(phenylmethyl)propyl]-5-[(1-methylethyl)oxy]benzamide;

3-(1,1-dioxido-2-isothiazolidinyl)-N-{(1S,2R)-2-hydroxy-1-(phenylmethyl)-3-[({3-[(trifluoromethyl)oxy]phenyl}methyl)amino]propyl}-5-[(1-methylethyl)oxy]benzamide;

N-[(1S,2R)-3-({[3,5-bis(trifluoromethyl)phenyl]methyl}amino)-2-hydroxy-1-(phenylmethyl)propyl]-3-(1,1-dioxido-2-isothiazolidinyl)-5-[(1-methylethyl)oxy]benzamide;

N-[(1S,2R)-3-({[3,5-bis(trifluoromethyl)phenyl]methyl}amino)-2-hydroxy-1-(phenylmethyl)propyl]-3-(1,1-dioxido-2-isothiazolidinyl)-5-[(1-methylethyl)oxy]benzamide;

N-[(1S,2R)-3-{[(3,5-dibromophenyl)methyl]amino}-2-hydroxy-1-(phenylmethyl)propyl]-3-(1,1-dioxido-2-isothiazolidinyl)-5-[(1-methylethyl)oxy]benzamide;

3-cyclopentyl-5-(1,1-dioxido-2-isothiazolidinyl)-N-[(1S,2R)-2-hydroxy-1-(phenylmethyl)-3-({[3-(trifluoromethyl)phenyl]methyl}amino)propyl]benzamide;

3-cyclopentyl-5-(1,1-dioxido-2-isothiazolidinyl)-N-[(1S,2R)-2-hydroxy-3-({[3-(methyloxy)phenyl]methyl}amino)-1-(phenylmethyl)propyl]benzamide;

3-cyclopentyl-5-(1,1-dioxido-2-isothiazolidinyl)-N-{(1S,2R)-2-hydroxy-1-(phenylmethyl)-3-[({3-[(trifluoromethyl)oxy]phenyl}methyl)amino]propyl}benzamide;

N-[(1S,2R)-3-({[3,5-bis(trifluoromethyl)phenyl]methyl}amino)-2-hydroxy-1-(phenylmethyl)propyl]-3-cyclopentyl-5-(1,1-dioxido-2-isothiazolidinyl)benzamide;

N-[(1S,2R)-3-({[3,5-bis(methyloxy)phenyl]methyl}amino)-2-hydroxy-1-(phenylmethyl)propyl]-3-cyclopentyl-5-(1,1-dioxido-2-isothiazolidinyl)benzamide;

3-cyclopentyl-N-[(1S,2R)-3-{[(3,5-dibromophenyl)methyl]amino}-2-hydroxy-1-(phenylmethyl)propyl]-5-(1,1-dioxido-2-isothiazolidinyl)benzamide;

3-(1,1-dioxido-2-isothiazolidinyl)-5-(ethylamino)-N-{(1S,2R)-2-hydroxy-1-(phenylmethyl)-3-[({3-[(trifluoromethyl)oxy]phenyl}methyl)amino]propyl}benzamide;

N-[(1S,2R)-3-({[3,5-bis(trifluoromethyl)phenyl]methyl}amino)-2-hydroxy-1-(phenylmethyl)propyl]-3-(1,1-dioxido-2-isothiazolidinyl)-5-(ethylamino)benzamide;

N-[(1S,2R)-3-({[3,5-bis(methyloxy)phenyl]methyl}amino)-2-hydroxy-1-(phenylmethyl)propyl]-3-(1,1-dioxido-2-isothiazolidinyl)-5-(ethylamino)benzamide;

N-[(1S,2R)-3-{[(3,5-dibromophenyl)methyl]amino}-2-hydroxy-1-(phenylmethyl)propyl]-3-(1,1-dioxido-2-isothiazolidinyl)-5-(ethylamino)benzamide;

3-(1,1-dioxidotetrahydro-2H-1,2-thiazin-2-yl)-5-(ethyloxy)-N-[(1S,2R)-2-hydroxy-1-(phenylmethyl)-3-({[3-(trifluoromethyl)phenyl]methyl}amino)propyl]benzamide;

3-(1,1-dioxidotetrahydro-2H-1,2-thiazin-2-yl)-5-(ethyloxy)-N-[(1S,2R)-2-hydroxy-3-({[3-(methyloxy)phenyl]methyl}amino)-1-(phenylmethyl)propyl]benzamide;

3-(1,1-dioxidotetrahydro-2H-1,2-thiazin-2-yl)-5-(ethyloxy)-N-{(1S,2R)-2-hydroxy-1-(phenylmethyl)-3-[({3-[(trifluoromethyl)oxy]phenyl}methyl)amino]propyl}benzamide;

N-[(1S,2R)-3-({[3,5-bis(trifluoromethyl)phenyl]methyl}amino)-2-hydroxy-1-(phenylmethyl)propyl]-3-(1,1-dioxidotetrahydro-2H-1,2-thiazin-2-yl)-5-(ethyloxy)benzamide;

N-[(1S,2R)-3-({[3,5-bis(methyloxy)phenyl]methyl}amino)-2-hydroxy-1-(phenylmethyl)propyl]-3-(1,1-dioxidotetrahydro-2H-1,2-thiazin-2-yl)-5-(ethyloxy)benzamide;

N-[(1S,2R)-3-{[(3,5-dibromophenyl)methyl]amino}-2-hydroxy-1-(phenylmethyl)propyl]-3-(1,1-dioxidotetrahydro-2H-1,2-thiazin-2-yl)-5-(ethyloxy)benzamide;

N-[(1S,2R)-3-{[1-(3-chlorophenyl)propyl]amino}-2-hydroxy-1-(phenylmethyl)propyl]-3-(1,1-dioxidotetrahydro-2H-1,2-thiazin-2-yl)-5-(ethylamino)benzamide;

3-cyclopentyl-5-(1,1-dioxidotetrahydro-2H-1,2-thiazin-2-yl)-N-[(1S,2R)-2-hydroxy-3-[(1-methylbutyl)amino]-1-(phenylmethyl)propyl]benzamide;

N-[(1S,2R)-1-benzyl-2-hydroxy-3-(1,2,3,4-tetrahydronaphthalen-2-ylamino)propyl]-3-cyclopentyl-5-(2-oxopyrrolidin-1-yl)benzamide;

N-[(1S,2R)-1-benzyl-3-(2,3-dihydro-1H-inden-2-ylamino)-2-hydroxypropyl]-3-cyclopentyl-5-(2-oxopyrrolidin-1-yl)benzamide;

N-[(1S,2R)-1-benzyl-3-(2,3-dihydro-1H-inden-2-ylamino)-2-hydroxypropyl]-3-(1,1-dioxido-1,2-thiazinan-2-yl)-5-(ethylamino)benzamide;

N-[(1S,2R)-1-benzyl-2-hydroxy-3-(1,2,3,4-tetrahydronaphthalen-2-ylamino)propyl]-3-(1,1-dioxido-1,2-thiazinan-2-yl)-5-(ethylamino)benzamide;

N-{(1S,2R)-1-benzyl-2-hydroxy-3-[(7-methoxy-1,2,3,4-tetrahydronaphthalen-2-yl)amino]propyl}-3-cyclopentyl-5-(2-oxopyrrolidin-1-yl)benzamide;

N-{(1S,2R)-1-benzyl-3-[(3,5-dichlorobenzyl)amino]-2-hydroxypropyl}-3-cyclopentyl-5-(2-oxopyrrolidin-1-yl)benzamide;

N-{(1S,2R)-1-benzyl-3-[(3,5-dichlorobenzyl)amino]-2-hydroxypropyl}-3-(1,1-dioxidoisothiazolidin-2-yl)-5-ethoxybenzamide;

N-{(1S,2R)-1-benzyl-3-[(3,5-dichlorobenzyl)amino]-2-hydroxypropyl}-3-(1,1-dioxidoisothiazolidin-2-yl)-5-isopropoxybenzamide;

N-{(1S,2R)-1-benzyl-3-[(3,5-dichlorobenzyl)amino]-2-hydroxypropyl}-3-cyclopentyl-5-(1,1-dioxidoisothiazolidin-2-yl)benzamide;

N-{(1S,2R)-1-benzyl-3-[(3,5-dichlorobenzyl)amino]-2-hydroxypropyl}-3-(1,1-dioxido-1,2-thiazinan-2-yl)-5-ethoxybenzamide;

N-{(1S,2R)-1-benzyl-3-[(3,5-dichlorobenzyl)amino]-2-hydroxypropyl}-3-(1,1-dioxido-1,2-thiazinan-2-yl)-5-isopropoxybenzamide;

N-{(1S,2R)-1-benzyl-3-[(3,5-dichlorobenzyl)amino]-2-hydroxypropyl}-3-cyclopentyl-5-(1,1-dioxido-1,2-thiazinan-2-yl)benzamide;

N-{(1S,2R)-1-benzyl-3-[(3,5-dichlorobenzyl)amino]-2-hydroxypropyl}-3-(ethylamino)-5-(2-oxopyrrolidin-1-yl)benzamide;

N-{(1S,2R)-1-benzyl-3-[(3,5-dichlorobenzyl)amino]-2-hydroxypropyl}-3-(1,1-dioxidoisothiazolidin-2-yl)-5-(ethylamino)benzamide;

3-(1,1-dioxidotetrahydro-2H-1,2-thiazin-2-yl)-5-(ethylamino)-N-[(1S,2R)-2-hydroxy-3-{[1-(4-methylpentyl)cyclopropyl]amino}-1-(phenylmethyl)propyl]benzamide;

3-(1,1-dioxidotetrahydro-2H-1,2-thiazin-2-yl)-5-(ethylamino)-N-[(1S,2R)-3-[(1-ethylcyclopropyl)amino]-2-hydroxy-1-(phenylmethyl)propyl]benzamide;

3-(1,1-dioxidotetrahydro-2H-1,2-thiazin-2-yl)-5-(ethylamino)-N-[(1S,2R)-2-hydroxy-3-{[1-(1-methylethyl)cyclopropyl]amino}-1-(phenylmethyl)propyl]benzamide;

N-[(1S,2R)-3-(butylamino)-2-hydroxy-1-(phenylmethyl)propyl]-3-(1,1-dioxidotetrahydro-2H-1,2-thiazin-2-yl)-5-(ethylamino)benzamide;

3-(1,1-dioxidotetrahydro-2H-1,2-thiazin-2-yl)-5-(ethylamino)-N-{(1S,2R)-2-hydroxy-1-(phenylmethyl)-3-[(1-propyl cyclopropyl)amino]propyl}benzamide;

3-(1,1-dioxidotetrahydro-2H-1,2-thiazin-2-yl)-5-(ethylamino)-N-[(1S,2R)-2-hydroxy-3-{[1-(3-methylbutyl)cyclopropyl]amino}-1-(phenylmethyl)propyl]benzamide;

3-(1,1-dioxidotetrahydro-2H-1,2-thiazin-2-yl)-5-(ethylamino)-N-[(1S,2R)-2-hydroxy-3-{[1-(2-methylpropyl)cyclopropyl]amino}-1-(phenylmethyl)propyl]benzamide;

N-[(1S,2R)-3-({1-[(3-chlorophenyl)methyl]cyclopropyl}amino)-2-hydroxy-1-(phenylmethyl)propyl]-3-(1,1-dioxidotetrahydro-2H-1,2-thiazin-2-yl)-5-(ethylamino)benzamide;

N-{(1S,2R)-1-benzyl-2-hydroxy-3-[(1-methylcyclohexyl)amino]propyl}-3-(1,1-dioxido-1,2-thiazinan-2-yl)-5-(ethylamino)benzamide;

N-{(1S,2R)-1-benzyl-3-[(1S,2S,4R)-bicyclo[2.2.1]hept-2-ylamino]-2-hydroxypropyl}-3-(1,1-dioxido-1,2-thiazinan-2-yl)-5-(ethylamino)benzamide;

N-{(1S,2R)-1-benzyl-3-[(4,4-dimethylcyclohexyl)amino]-2-hydroxypropyl}-3-(1,1-dioxido-1,2-thiazinan-2-yl)-5-(ethylamino)benzamide;

N-((1S,2R)-1-benzyl-2-hydroxy-3-{[(1R)-1,2,2-trimethylpropyl]amino}propyl)-3-(1,1-dioxido-1,2-thiazinan-2-yl)-5-(ethylamino)benzamide;

N-((1S,2R)-1-benzyl-2-hydroxy-3-{[(1S)-1,2,2-trimethylpropyl]amino}propyl)-3-(1,1-dioxido-1,2-thiazinan-2-yl)-5-(ethylamino)benzamide;

N-{(1S,2R)-1-benzyl-3-[(2,2-dimethylcyclohexyl)amino]-2-hydroxypropyl}-3-(1,1-dioxido-1,2-thiazinan-2-yl)-5-(ethylamino)benzamide;

N-[(1S,2R)-1-benzyl-2-hydroxy-3-(pentylamino)propyl]-3-(1,1-dioxido-1,2-thiazinan-2-yl)-5-(ethylamino)benzamide;

N-[(1S,2R)-1-benzyl-3-(hexylamino)-2-hydroxypropyl]-3-(1,1-dioxido-1,2-thiazinan-2-yl)-5-(ethylamino)benzamide;

N-{(1S,2R)-1-benzyl-3-[(3,3-dimethylbutyl)amino]-2-hydroxypropyl}-3-(1,1-dioxido-1,2-thiazinan-2-yl)-5-(ethylamino)benzamide;

N-{(1S,2R)-1-benzyl-3-[(1,1-dimethylpropyl)amino]-2-hydroxypropyl}-3-(1,1-dioxido-1,2-thiazinan-2-yl)-5-(ethylamino)benzamide;

N-{(1S,2R)-1-benzyl-3-[(cyclopropylmethyl) amino]-2-hydroxypropyl}-3-(1,1-dioxido-1,2-thiazinan-2-yl)-5-(ethylamino)benzamide;

N-{(1S,2R)-1-benzyl-3-[(3,3-dimethylcyclopentyl)amino]-2-hydroxypropyl}-3-(1,1-dioxido-1,2-thiazinan-2-yl)-5-(ethylamino)benzamide;

N-[(1S,2R)-1-benzyl-3-(ethylamino)-2-hydroxypropyl]-3-(1,1-dioxido-1,2-thiazinan-2-yl)-5-(ethylamino)benzamide;

N-[(1S,2R)-1-benzyl-2-hydroxy-3-(methylamino)propyl]-3-(1,1-dioxido-1,2-thiazinan-2-yl)-5-(ethylamino)benzamide;

N-[(1S,2R)-1-benzyl-3-(cyclopropylamino)-2-hydroxypropyl]-3-(1,1-dioxido-1,2-thiazinan-2-yl)-5-(ethylamino)benzamide;

N-[(1S,2R)-3-(1-adamantylamino)-1-benzyl-2-hydroxypropyl]-3-(1,1-dioxido-1,2-thiazinan-2-yl)-5-(ethylamino)benzamide;

N-[(1S,2R)-1-benzyl-2-hydroxy-3-(1,2,3,4-tetrahydronaphthalen-1-ylamino)propyl]-3-cyclopentyl-5-(2-oxopyrrolidin-1-yl)benzamide;

N-[(1S,2R)-1-benzyl-2-hydroxy-3-(1,2,3,4-tetrahydronaphthalen-1-ylamino)propyl]-3-(1,1-dioxido-1,2-thiazinan-2-yl)-5-(ethylamino)benzamide;

N-((1S,2R)-1-benzyl-2-hydroxy-3-{[2-(3-methoxyphenyl)ethyl]amino}propyl)-3-(1,1-dioxido-1,2-thiazinan-2-yl)-5-(ethylamino)benzamide;

N-((1S,2R)-1-benzyl-2-hydroxy-3-{[2-(4-methoxyphenyl)ethyl]amino}propyl)-3-(1,1-dioxido-1,2-thiazinan-2-yl)-5-(ethylamino)benzamide;

N-((1S,2R)-1-benzyl-2-hydroxy-3-{[2-(2-methoxyphenyl)ethyl]amino}propyl)-3-(1,1-dioxido-1,2-thiazinan-2-yl)-5-(ethylamino)benzamide;

N-((1S,2R)-1-benzyl-3-{[2-(2-chlorophenyl)ethyl]amino}-2-hydroxypropyl)-3-(1,1-dioxido-1,2-thiazinan-2-yl)-5-(ethylamino)benzamide;

N-((1S,2R)-1-benzyl-3-{[2-(3-chlorophenyl)ethyl]amino}-2-hydroxypropyl)-3-(1,1-dioxido-1,2-thiazinan-2-yl)-5-(ethylamino)benzamide;

N-((1S,2R)-1-benzyl-3-{[2-(4-chlorophenyl)ethyl]amino}-2-hydroxypropyl)-3-(1,1-dioxido-1,2-thiazinan-2-yl)-5-(ethylamino)benzamide;

N-((1S,2R)-1-benzyl-2-hydroxy-3-{[2-(4-methylphenyl)ethyl]amino}propyl)-3-(1,1-dioxido-1,2-thiazinan-2-yl)-5-(ethylamino)benzamide;

N-((1S,2R)-1-benzyl-2-hydroxy-3-{[2-(2-methylphenyl)ethyl]amino}propyl)-3-(1,1-dioxido-1,2-thiazinan-2-yl)-5-(ethylamino)benzamide;

N-((1S,2R)-1-benzyl-3-{[2-(3,4-dichlorophenyl)ethyl]amino}-2-hydroxypropyl)-3-(1,1-dioxido-1,2-thiazinan-2-yl)-5-(ethylamino)benzamide;

N-((1S,2R)-1-benzyl-3-{[2-(2,4-dichlorophenyl)ethyl]amino}-2-hydroxypropyl)-3-(1,1-dioxido-1,2-thiazinan-2-yl)-5-(ethylamino)benzamide;

N-((1S,2R)-1-benzyl-3-{[2-(3,5-dimethoxyphenyl)ethyl]amino}-2-hydroxypropyl)-3-(1,1-dioxido-1,2-thiazinan-2-yl)-5-(ethylamino)benzamide;

N-((1S,2R)-1-benzyl-3-{[2-(2,3-dimethoxyphenyl)ethyl]amino}-2-hydroxypropyl)-3-(1,1-dioxido-1,2-thiazinan-2-yl)-5-(ethylamino)benzamide;

N-[(1S,2R)-1-benzyl-3-(benzylamino)-2-hydroxypropyl]-3-(1,1-dioxido-1,2-thiazinan-2-yl)-5-(ethylamino)benzamide;

N-{(1S,2R)-1-benzyl-2-hydroxy-3-[(2-phenylethyl)amino]propyl}-3-(1,1-dioxido-1,2-thiazinan-2-yl)-5-(ethylamino)benzamide;

N-{(1S,2R)-1-benzyl-3-[(1-ethylcyclohexyl)amino]-2-hydroxypropyl}-3-(1,1-dioxido-1,2-thiazinan-2-yl)-5-(ethylamino)benzamide;

N-{(1S,2R)-1-benzyl-2-hydroxy-3-[(1-methylcyclopentyl)amino]propyl}-3-(1,1-dioxido-1,2-thiazinan-2-yl)-5-(ethylamino)benzamide;

N-{(1S,2R)-1-benzyl-2-hydroxy-3-[(1-propylcyclopentyl)amino]propyl}-3-(1,1-dioxido-1,2-thiazinan-2-yl)-5-(ethylamino)benzamide;

N-{(1S,2R)-1-benzyl-2-hydroxy-3-[(1-propylcyclohexyl)amino]propyl}-3-(1,1-dioxido-1,2-thiazinan-2-yl)-5-(ethylamino)benzamide;

N-((1S,2R)-1-benzyl-3-{[2-(3-chlorophenyl)-1,1-dimethylethyl]amino}-2-hydroxypropyl)-3-(1,1-dioxido-1,2-thiazinan-2-yl)-5-(ethylamino)benzamide;

3-(1,1-dioxido-1,2-thiazinan-2-yl)-5-(ethylamino)-N-[(1S,2R)-2-hydroxy-3-[(3-methoxybenzyl)amino]-1-(pyridin-3-ylmethyl)propyl]benzamide;

3-(1,1-dioxido-1,2-thiazinan-2-yl)-5-(ethylamino)-N-[(1S,2R)-2-hydroxy-3-[(3-methoxybenzyl)amino]-1-(1,3-thiazol-2-ylmethyl)propyl]benzamide;

N-[(1S,2R)-3-(cyclohexylamino)-2-hydroxy-1-(1,3-thiazol-2-ylmethyl)propyl]-3-(1,1-dioxido-1,2-thiazinan-2-yl)-5-(ethylamino)benzamide;

N-[(1S,2R)-3-[(1,5-dimethylhexyl)amino]-2-hydroxy-1-(1,3-thiazol-2-ylmethyl)propyl]-3-(1,1-dioxido-1,2-thiazinan-2-yl)-5-(ethylamino)benzamide;

3-(1,1-dioxido-1,2-thiazinan-2-yl)-5-(ethylamino)-N-{(1S,2R)-1-(2-furylmethyl)-2-hydroxy-3-[(3-methoxybenzyl)amino]propyl}benzamide;

N-[(1S,2R)-3-(cyclohexylamino)-1-(2-furylmethyl)-2-hydroxypropyl]-3-(1,1-dioxido-1,2-thiazinan-2-yl)-5-(ethylamino)benzamide;

N-[(1S,2R)-3-[(1,5-dimethylhexyl)amino]-1-(2-furylmethyl)-2-hydroxypropyl]-3-(1,1-dioxido-1,2-thiazinan-2-yl)-5-(ethylamino)benzamide;

3-(1,1-dioxido-1,2-thiazinan-2-yl)-5-(ethylamino)-N-{(1S,2R)-1-(2-furylmethyl)-2-hydroxy-3-[(1,1,5-trimethylhexyl)amino]propyl}benzamide;

3-(1,1-dioxido-1,2-thiazinan-2-yl)-5-(ethylamino)-N-[(1S)-2-hydroxy-3-[(3-methoxybenzyl)amino]-1-(pyridin-2-ylmethyl)propyl]benzamide;

N-[(1S,2R)-1-[(4-chlorophenyl)methyl]-3-(cyclohexylamino)-2-hydroxypropyl]-3-(1,1-dioxidotetrahydro-2H-1,2-thiazin-2-yl)-5-(ethylamino)benzamide;

N-[(1S,2R)-1-[(4-chlorophenyl)methyl]-2-hydroxy-3-({[3-(methyloxy)phenyl]methyl}amino)propyl]-3-(1,1-dioxidotetrahydro-2H-1,2-thiazin-2-yl)-5-(ethylamino)benzamide;

3-cyclopentyl-N-[(1S,2R)-1-[(3,5-difluorophenyl)methyl]-2-hydroxy-3-({[3-(trifluoromethyl)phenyl]methyl}amino)propyl]-5-(2-oxo-1-pyrrolidinyl)benzamide;

N-[(1S,2R)-1-[(3,5-difluorophenyl)methyl]-2-hydroxy-3-({[3-(trifluoromethyl)phenyl]methyl}amino)propyl]-3-(1,1-dioxidotetrahydro-2H-1,2-thiazin-2-yl)-5-(ethylamino)benzamide;

N-[(1S,2R)-1-[(3,5-difluorophenyl)methyl]-2-hydroxy-3-({[3-(methyloxy)phenyl]methyl}amino)propyl]-3-(1,1-dioxidotetrahydro-2H-1,2-thiazin-2-yl)-5-(ethylamino)benzamide;

N-{(1S,2R)-1-[(3,5-difluorophenyl)methyl]-3-[(1,5-dimethylhexyl)amino]-2-hydroxypropyl}-3-(1,1-dioxidotetrahydro-2H-1,2-thiazin-2-yl)-5-(ethylamino)benzamide;

N-{(1S,2R)-3-(cyclohexylamino)-1-[(3,5-difluorophenyl)methyl]-2-hydroxypropyl}-3-(1,1-dioxidotetrahydro-2H-1,2-thiazin-2-yl)-5-(ethylamino)benzamide;

N-{(1S,2R)-1-[(3,5-difluorophenyl)methyl]-2-hydroxy-3-[(1,1,5-trimethylhexyl)amino]propyl}-3-(1,1-dioxidotetrahydro-2H-1,2-thiazin-2-yl)-5-(ethylamino)benzamide;

N-[(1S,2R)-1-[(3,4-difluorophenyl)methyl]-2-hydroxy-3-({[3-(methyloxy)phenyl]methyl}amino)propyl]-3-(1,1-dioxidotetrahydro-2H-1,2-thiazin-2-yl)-5-(ethylamino)benzamide;

N-{(1S,2R)-3-(cyclohexylamino)-1-[(3,4-difluorophenyl)methyl]-2-hydroxypropyl}-3-(1,1-dioxidotetrahydro-2H-1,2-thiazin-2-yl)-5-(ethylamino)benzamide;

N-{(1S,2R)-1-[(3,4-difluorophenyl)methyl]-2-hydroxy-3-[(1,1,5-trimethylhexyl)amino]propyl}-3-(1,1-dioxidotetrahydro-2H-1,2-thiazin-2-yl)-5-(ethylamino)benzamide;

N-[(1S,2R)-1-[(3-chlorophenyl)methyl]-2-hydroxy-3-({[3-(methyloxy)phenyl]methyl}amino)propyl]-3-(1,1-dioxidotetrahydro-2H-1,2-thiazin-2-yl)-5-(ethylamino)benzamide;

N-[(1S,2R)-1-[(3-chlorophenyl)methyl]-3-(cyclohexylamino)-2-hydroxypropyl]-3-(1,1-dioxidotetrahydro-2H-1,2-thiazin-2-yl)-5-(ethylamino)benzamide;

N-[(1S,2R)-1-[(2-chlorophenyl)methyl]-2-hydroxy-3-({[3-(methyloxy)phenyl]methyl}amino)propyl]-3-(1,1-dioxidotetrahydro-2H-1,2-thiazin-2-yl)-5-(ethylamino)benzamide;

N-[(1S,2R)-1-[(2-chlorophenyl)methyl]-3-(cyclohexylamino)-2-hydroxypropyl]-3-(1,1-dioxidotetrahydro-2H-1,2-thiazin-2-yl)-5-(ethylamino)benzamide;

N-{(1S,2R)-1-[(2-chlorophenyl)methyl]-3-[(1,5-dimethylhexyl)amino]-2-hydroxypropyl}-3-(1,1-dioxidotetrahydro-2H-1,2-thiazin-2-yl)-5-(ethylamino)benzamide;

N-{(1S,2R)-1-[(3-chlorophenyl)methyl]-3-[(1,5-dimethylhexyl)amino]-2-hydroxypropyl}-3-(1,1-dioxidotetrahydro-2H-1,2-thiazin-2-yl)-5-(ethylamino)benzamide;

3-(1,1-dioxidotetrahydro-2H-1,2-thiazin-2-yl)-5-(ethylamino)-N-[(1S,2R)-1-[(3-fluorophenyl)methyl]-2-hydroxy-3-({[3-(methyloxy)phenyl]methyl}amino)propyl]benzamide;

N-{(1S,2R)-3-[(1,5-dimethylhexyl)amino]-1-[(3-fluorophenyl) methyl]-2-hydroxypropyl}-3-(1,1-dioxidotetrahydro-2H-1,2-thiazin-2-yl)-5-(ethylamino)benzamide;

3-(1,1-dioxidotetrahydro-2H-1,2-thiazin-2-yl)-5-(ethylamino)-N-[(1S,2R)-2-hydroxy-3-({[3-(methyloxy)phenyl]methyl}amino)-1-(2-thienylmethyl)propyl]benzamide;

N-[(1S,2R)-3-[(1,5-dimethylhexyl)amino]-2-hydroxy-1-(2-thienylmethyl)propyl]-3-(1,1-dioxidotetrahydro-2H-1,2-thiazin-2-yl)-5-(ethylamino)benzamide;

3-(1,1-dioxidotetrahydro-2H-1,2-thiazin-2-yl)-5-(ethylamino)-N-[(1S,2R)-2-hydroxy-3-({[3-(methyloxy)phenyl]methyl}amino)-1-(1H-pyrazol-1-ylmethyl)propyl]benzamide;

N-[(1S,2R)-3-[(1,5-dimethylhexyl)amino]-2-hydroxy-1-(1H-pyrazol-1-ylmethyl)propyl]-3-(1,1-dioxidotetrahydro-2H-1,2-thiazin-2-yl)-5-(ethylamino)benzamide;

3-(1,1-dioxidotetrahydro-2H-1,2-thiazin-2-yl)-5-(ethylamino)-N-[(1S,2R)-2-hydroxy-3-({[3-(methyloxy)phenyl]methyl}amino)-1-(3-thienylmethyl)propyl]benzamide;

N-[(1S,2R)-3-[(1,5-dimethylhexyl)amino]-2-hydroxy-1-(3-thienylmethyl)propyl]-3-(1,1-dioxidotetrahydro-2H-1,2-thiazin-2-yl)-5-(ethylamino)benzamide;

N-{(1S,2R)-1-benzyl-3-[(1,1-dimethylhexyl)amino]-2-hydroxypropyl}-3-(ethylamino)-5-(2-oxopyrrolidin-1-yl)benzamide;

N-[(1S,2R)-1-benzyl-2-hydroxy-3-({1-methyl-1-[3-(trifluoromethyl)phenyl]ethyl}amino)propyl]-3-(ethylamino)-5-(2-oxopyrrolidin-1-yl)benzamide;

N-((1S,2R)-1-benzyl-2-hydroxy-3-{[2-methyl-5-(trifluoromethyl)benzyl]amino}propyl)-3-(1,1-dioxido-1,2-thiazinan-2-yl)-5-(ethylamino)benzamide;

N-{(1S,2R)-1-benzyl-3-[(1S)-2,3-dihydro-1H-inden-1-ylamino]-2-hydroxypropyl}-3-(1,1-dioxido-1,2-thiazinan-2-yl)-5-(ethylamino)benzamide;

N-((1S,2R)-1-benzyl-2-hydroxy-3-{[(1S,2R)-2-hydroxy-2,3-dihydro-1H-inden-1-yl]amino}propyl)-3-(ethylamino)-5-(2-oxopyrrolidin-1-yl)benzamide;

N-{(1S,2R)-1-benzyl-2-hydroxy-3-[(6-methoxy-2,3-dihydro-1H-inden-1-yl)amino]propyl}-3-(1,1-dioxido-1,2-thiazinan-2-yl)-5-(ethylamino)benzamide;

N-((1S,2R)-1-benzyl-2-hydroxy-3-{[(1R,2S)-2-hydroxy-2,3-dihydro-1H-inden-1-yl]amino}propyl)-3-(1,1-dioxido-1,2-thiazinan-2-yl)-5-(ethylamino)benzamide;

N-((1S,2R)-1-benzyl-2-hydroxy-3-{[2-(isobutylthio)-1,1-dimethylethyl]amino}propyl)-3-(ethylamino)-5-(2-oxopyrrolidin-1-yl)benzamide;

N-{(1S,2R)-1-benzyl-3-[(1,1-dimethyl-2-phenoxyethyl)amino]-2-hydroxypropyl}-3-(ethylamino)-5-(2-oxopyrrolidin-1-yl)benzamide;

N-((1S,2R)-1-benzyl-3-{[2-(benzyloxy)-1,1-dimethylethyl]amino}-2-hydroxypropyl)-3-(ethylamino)-5-(2-oxopyrrolidin-1-yl)benzamide;

N-{(1S,2R)-1-benzyl-2-hydroxy-3-[(3-methoxyphenyl)amino]propyl}-3-(ethylamino)-5-(2-oxopyrrolidin-1-yl)benzamide;

N-[(1S,2R)-1-benzyl-2-hydroxy-3-({2-[3-(trifluoromethyl)phenyl]ethyl}amino)propyl]-3-(ethylamino)-5-(2-oxopyrrolidin-1-yl)benzamide;

N-{(1S,2R)-1-benzyl-3-[(1,1-dimethyl-2-phenylethyl)amino]-2-hydroxypropyl}-3-(ethylamino)-5-(2-oxopyrrolidin-1-yl)benzamide;

N-((1S,2R)-1-benzyl-2-hydroxy-3-{[2-(1-naphthyl)ethyl]amino}propyl)-3-(ethylamino)-5-(2-oxopyrrolidin-1-yl)benzamide;

N-((1S,2R)-1-benzyl-2-hydroxy-3-{[2-(3-methoxyphenyl)-1,1-dimethylethyl]amino}propyl)-3-(ethylamino)-5-(2-oxopyrrolidin-1-yl)benzamide;

N-[(1S,2R)-3-anilino-1-benzyl-2-hydroxypropyl]-3-(ethylamino)-5-(2-oxopyrrolidin-1-yl)benzamide;

N-((1S,2R)-1-benzyl-2-hydroxy-3-{[1-(3-methoxyphenyl) cyclopropyl]amino}propyl)-3-(ethylamino)-5-(2-oxopyrrolidin-1-yl)benzamide;

N-{(1S,2R)-1-benzyl-3-[(cyclohexylmethyl)amino]-2-hydroxypropyl}-3-(ethylamino)-5-(2-oxopyrrolidin-1-yl)benzamide;

N-{(1S,2R)-1-benzyl-2-hydroxy-3-[(tetrahydro-2H-pyran-4-ylmethyl)amino]propyl}-3-(ethylamino)-5-(2-oxopyrrolidin-1-yl)benzamide;

N-[(1S,2R)-1-benzyl-2-hydroxy-3-(tetrahydro-2H-thiopyran-4-ylamino)propyl]-3-(ethylamino)-5-(2-oxopyrrolidin-1-yl)benzamide;

N-[(1S,2R)-1-benzyl-2-hydroxy-3-(isopropylamino)propyl]-3-ethyl-7-(2-oxopyrrolidin-1-yl)-1H-indole-5-carboxamide;

N-[(1S,2R)-1-benzyl-3-(cyclohexylamino)-2-hydroxypropyl]-3-ethyl-7-(2-oxopyrrolidin-1-yl)-1H-indole-5-carboxamide;

N-{(1S,2R)-1-benzyl-2-hydroxy-3-[(1,1,5-trimethylhexyl)amino]propyl}-3-ethyl-7-(2-oxopyrrolidin-1-yl)-1H-indole-5-carboxamide;

N-{(1S,2R)-1-benzyl-2-hydroxy-3-[(3-methoxybenzyl)amino]propyl}-7-(1,1-dioxidoisothiazolidin-2-yl)-3-ethyl-1H-indole-5-carboxamide;

N-{(1S,2R)-1-benzyl-2-hydroxy-3-[(1,1,5-trimethylhexyl)amino]propyl}-7-(1,1-dioxidoisothiazolidin-2-yl)-3-ethyl-1H-indole-5-carboxamide;

N-[(1S,2R)-1-benzyl-3-(cyclohexylamino)-2-hydroxypropyl]-7-(1,1-dioxidoisothiazolidin-2-yl)-3-ethyl-1H-indole-5-carboxamide;

N-[(1S,2R)-1-benzyl-2-hydroxy-3-(isopropylamino)propyl]-7-(1,1-dioxidoisothiazolidin-2-yl)-3-ethyl-1H-indole-5-carboxamide;

N-((1S,2R)-1-benzyl-2-hydroxy-3-{[1-(3-methoxyphenyl)-1-methylethyl]amino}propyl)-7-(1,1-dioxidoisothiazolidin-2-yl)-3-ethyl-1H-indole-5-carboxamide;

N-[(1S,2R)-1-benzyl-2-hydroxy-3-({1-methyl-1-[3-(trifluoromethyl)phenyl]ethyl}amino)propyl]-7-(1,1-dioxidoisothiazolidin-2-yl)-3-ethyl-1H-indole-5-carboxamide;

N-[(1S,2R)-1-benzyl-3-(sec-butylamino)-2-hydroxypropyl]-3-(ethylamino)-5-(2-oxopyrrolidin-1-yl)benzamide;

N-{(1S,2R)-1-benzyl-3-[(4-tert-butylcyclohexyl)amino]-2-hydroxypropyl}-3-(ethylamino)-5-(2-oxopyrrolidin-1-yl)benzamide;

N-{(1S,2R)-1-benzyl-3-[(1S)-2,3-dihydro-1H-inden-1-ylamino]-2-hydroxypropyl}-3-(ethylamino)-5-(2-oxopyrrolidin-1-yl)benzamide;

N-{(1S,2R)-1-benzyl-2-hydroxy-3-[(2-isobutoxy-1,1-dimethylethyl)amino]propyl}-3-(ethylamino)-5-(2-oxopyrrolidin-1-yl)benzamide;

N-[(1S,2R)-1-benzyl-3-({1,1-dimethyl-2-[(2-methylprop-2-en-1-yl)oxy]ethyl}amino)-2-hydroxypropyl]-3-(ethylamino)-5-(2-oxopyrrolidin-1-yl)benzamide;

N-{(1S,2R)-1-benzyl-3-[(1R)-2,3-dihydro-1H-inden-1-ylamino]-2-hydroxypropyl}-3-(ethylamino)-5-(2-oxopyrrolidin-1-yl)benzamide;

N-{(1S,2R)-1-benzyl-3-[(1R)-2,3-dihydro-1H-inden-1-ylamino]-2-hydroxypropyl}-3-(1,1-dioxido-1,2-thiazinan-2-yl)-5-(ethylamino)benzamide;

N-{(1S,2R)-1-benzyl-2-hydroxy-3-[(3-methoxybenzyl)amino]propyl}-3-[ethyl(methyl)amino]-5-(2-oxopyrrolidin-1-yl)benzamide;

N-((1S,2R)-1-benzyl-2-hydroxy-3-{[1-(3-methoxyphenyl)-1-methylethyl]amino}propyl)-3-[ethyl(methyl)amino]-5-(2-oxopyrrolidin-1-yl)benzamide;

N-((1S,2R)-1-benzyl-2-hydroxy-3-{[1-(3-methoxyphenyl) cyclohexyl]amino}propyl)-3-(ethylamino)-5-(2-oxopyrrolidin-1-yl)benzamide;

N-((1S,2R)-1-benzyl-2-hydroxy-3-{[1-(3-methoxyphenyl) cyclohexyl]amino}propyl)-3-(1,1-dioxido-1,2-thiazinan-2-yl)-5-(ethylamino)benzamide;

N-((1S,2R)-1-benzyl-2-hydroxy-3-{[(1-methyl-1H-pyrazol-4-yl)methyl]amino}propyl)-3-(1,1-dioxido-1,2-thiazinan-2-yl)-5-(ethylamino)benzamide;

N-((1S,2R)-1-benzyl-2-hydroxy-3-{[(1-methyl-1H-pyrazol-4-yl)methyl]amino}propyl)-3-(ethylamino)-5-(2-oxopyrrolidin-1-yl)benzamide;

N-[(1S,2R)-1-benzyl-3-(cyclohexylamino)-2-hydroxypropyl]-3-(1,1-dioxido-1,2-thiazinan-2-yl)-5-(ethylamino)benzamide;

N-[(1S,2R)-1-benzyl-2-hydroxy-3-(tetrahydro-2H-pyran-4-ylamino)propyl]-3-(1,1-dioxido-1,2-thiazinan-2-yl)-5-(ethylamino)benzamide;

N-[(1S,2R)-1-benzyl-3-(cyclohexylamino)-2-hydroxypropyl]-3-cyclopentyl-5-(1,1-dioxido-1,2-thiazinan-2-yl)benzamide;

N-[(1S,2R)-1-benzyl-2-hydroxy-3-(tetrahydro-2H-pyran-4-ylamino)propyl]-3-cyclopentyl-5-(1,1-dioxido-1,2-thiazinan-2-yl)benzamide;

N-{(1S,2R)-1-benzyl-3-[(3,3-dimethylbutyl) amino]-2-hydroxypropyl}-3-(1,1-dioxido-1,2-thiazinan-2-yl)-5-(ethylamino)-2-fluorobenzamide;

N-{(1S,2R)-1-benzyl-2-hydroxy-3-[(1,1,3,3-tetramethylbutyl)amino]propyl}-3-(1,1-dioxido-1,2-thiazinan-2-yl)-5-(ethylamino)-2-fluorobenzamide;

N-{(1S,2R)-1-benzyl-3-[(1,3-dimethylbutyl) amino]-2-hydroxypropyl}-3-(1,1-dioxido-1,2-thiazinan-2-yl)-5-(ethylamino)-2-fluorobenzamide;

N-[(1S,2R)-1-benzyl-3-(cyclohexylamino)-2-hydroxypropyl]-3-(1,1-dioxido-1,2-thiazinan-2-yl)-5-(isopropylamino) benzamide;

N-[(1S,2R)-1-benzyl-2-hydroxy-3-(isopropylamino)propyl]-3-(1,1-dioxido-1,2-thiazinan-2-yl)-5-(isopropylamino) benzamide;

N-[(1S,2R)-1-benzyl-2-hydroxy-3-({1-methyl-1-[3-(trifluoromethyl)phenyl]ethyl}amino)propyl]-3-(1,1-dioxido-1,2-thiazinan-2-yl)-5-(isopropylamino) benzamide;

N-{(1S,2R)-1-benzyl-2-hydroxy-3-[(3-methoxybenzyl) amino]propyl}-3-(1,1-dioxido-1,2-thiazinan-2-yl)-5-(isopropylamino) benzamide;

N-((1S,2R)-1-benzyl-2-hydroxy-3-{[3-(trifluoromethyl)benzyl]amino}propyl)-3-(1,1-dioxido-1,2-thiazinan-2-yl)-5-(isopropylamino) benzamide;

N-{(1S,2R)-1-benzyl-2-hydroxy-3-[(1,1,5-trimethylhexyl)amino]propyl}-3-(1,1-dioxido-1,2-thiazinan-2-yl)-5-(isopropylamino) benzamide;

N-((1S,2R)-1-benzyl-3-{[4-fluoro-3-(trifluoromethyl)benzyl]amino}-2-hydroxypropyl)-3-(1,1-dioxido-1,2-thiazinan-2-yl)-5-(ethylamino)-2-fluorobenzamide;

3-(ethylamino)-N-[(1S,2R)-2-hydroxy-3-({[3-(methyloxy)phenyl]methyl}amino)-1-(phenylmethyl)propyl]-5-(2-oxo-1-piperidinyl)benzamide;

N-[(1S,2R)-3-[(1,5-dimethylhexyl)amino]-2-hydroxy-1-(phenylmethyl)propyl]-3-(ethylamino)-5-(2-oxo-1-piperidinyl)benzamide;

3-(ethylamino)-N-[(1S,2R)-2-hydroxy-1-(phenylmethyl)-3-({[3-(trifluoromethyl)phenyl]methyl}amino)propyl]-5-(2-oxo-1-piperidinyl)benzamide;

N-[(1S,2R)-2-hydroxy-3-({[3-(methyloxy)phenyl]methyl}amino)-1-(phenylmethyl)propyl]-3-(2-oxo-1-piperidinyl)-5-propylbenzamide;

N-[(1S,2R)-3-[(1,5-dimethylhexyl)amino]-2-hydroxy-1-(phenylmethyl)propyl]-3-(2-oxo-1-piperidinyl)-5-propylbenzamide;

N-[(1S,2R)-2-hydroxy-1-(phenylmethyl)-3-({[3-(trifluoromethyl)phenyl]methyl}amino)propyl]-3-(2-oxo-1-piperidinyl)-5-propylbenzamide;

N-[(1S,2R)-3-{[(1S)-2-(cyclohexylamino)-1-methyl-2-oxoethyl]amino}-2-hydroxy-1-(phenylmethyl)propyl]-3-(2-oxo-1-piperidinyl)-5-propylbenzamide;

3-(1,1-dioxido-2-isothiazolidinyl)-5-(ethylamino)-N-{(1S,2R)-2-hydroxy-1-(phenylmethyl)-3-[(1,1,5-trimethylhexyl)amino]propyl}benzamide;

3-(1,1-dioxidotetrahydro-2H-1,2-thiazin-2-yl)-5-(ethylamino)-N-[(1S,2R)-2-hydroxy-3-({[1-(1-methylethyl)-1H-pyrazol-4-yl]methyl}amino)-1-(phenylmethyl)propyl]benzamide;

3-(1,1-dioxidotetrahydro-2H-1,2-thiazin-2-yl)-5-(ethylamino)-N-[(1S,2R)-2-hydroxy-1-(phenylmethyl)-3-({[1-(2,2,2-trifluoroethyl)-1H-pyrazol-4-yl]methyl}amino)propyl]benzamide;

5-(ethylamino)-2-fluoro-N-[(1S,2R)-2-hydroxy-3-({[3-(methyloxy)phenyl]methyl}amino)-1-(phenylmethyl)propyl]-3-(2-oxo-1-pyrrolidinyl)benzamide;

3-(ethyloxy)-N-[(1S,2R)-2-hydroxy-3-({1-methyl-1-[3-(trifluoromethyl)phenyl]ethyl}amino)-1-(phenylmethyl)propyl]-5-(2-oxo-1-pyrrolidinyl)benzamide;

3-(1,1-dioxido-2-isothiazolidinyl)-5-(ethyloxy)-N-[(1S,2R)-2-hydroxy-3-({1-methyl-1-[3-(trifluoromethyl)phenyl]ethyl}amino)-1-(phenylmethyl)propyl]benzamide;

3-(1,1-dioxidotetrahydro-2H-1,2-thiazin-2-yl)-5-(ethylamino)-N-[(1S,2R)-2-hydroxy-3-({1-methyl-1-[3-(trifluoromethyl)phenyl]ethyl}amino)-1-(phenylmethyl)propyl]benzamide;

1-ethyl-N-[(1S,2R)-2-hydroxy-3-({1-methyl-1-[3-(trifluoromethyl)phenyl]ethyl}amino)-1-(phenylmethyl)propyl]4-(2-oxo-1-pyrrolidinyl)-1H-indole-6-carboxamide;

3-(ethyloxy)-N-[(1S,2R)-2-hydroxy-3-({1-methyl-1-[3-(methyloxy)phenyl]ethyl}amino)-1-(phenylmethyl)propyl]-5-(2-oxo-1-pyrrolidinyl)benzamide;

1-ethyl-N-[(1S,2R)-2-hydroxy-3-({1-methyl-1-[3-(methyloxy)phenyl]ethyl}amino)-1-(phenylmethyl)propyl]-4-(2-oxo-1-pyrrolidinyl)-1H-indole-6-carboxamide;

3-ethyl-N-[(1S,2R)-2-hydroxy-3-({1-methyl-1-[3-(trifluoromethyl)phenyl]ethyl}amino)-1-(phenylmethyl)propyl]-7-(2-oxo-1-pyrrolidinyl)-1H-indole-5-carboxamide;

3-(1,1-dioxido-2-isothiazolidinyl)-5-(ethyloxy)-N-[(1S,2R)-2-hydroxy-3-({1-methyl-1-[3-(methyloxy)phenyl]ethyl}amino)-1-(phenylmethyl)propyl]benzamide;

3-ethyl-N-[(1S,2R)-2-hydroxy-3-({1-methyl-1-[3-(methyloxy)phenyl]ethyl}amino)-1-(phenylmethyl)propyl]-7-(2-oxo-1-pyrrolidinyl)-1H-indole-5-carboxamide;

3-(1,1-dioxidotetrahydro-2H-1,2-thiazin-2-yl)-5-(ethylamino)-2-fluoro-N-[(1S,2R)-2-hydroxy-3-({[3-(methyloxy)phenyl]methyl}amino)-1-(phenylmethyl)propyl]benzamide;

3-(1,1-dioxidotetrahydro-2H-1,2-thiazin-2-yl)-5-(ethylamino)-2-fluoro-N-[(1S,2R)-2-hydroxy-1-(phenylmethyl)-3-({[3-(trifluoromethyl)phenyl]methyl}amino)propyl]benzamide;

3-(1,1-dioxido-2-isothiazolidinyl)-5-(ethylamino)-N-[(1S,2R)-2-hydroxy-3-({1-methyl-1-[3-(trifluoromethyl)phenyl]ethyl}amino)-1-(phenylmethyl)propyl]benzamide;

3-(1,1-dioxido-2-isothiazolidinyl)-5-(ethylamino)-N-[(1S,2R)-2-hydroxy-3-({1-methyl-1-[3-(methyloxy)phenyl]ethyl}amino)-1-(phenylmethyl)propyl]benzamide;

5-(ethylamino)-2-fluoro-N-[(1S,2R)-2-hydroxy-1-(phenylmethyl)-3-({[3-(trifluoromethyl)phenyl]methyl}amino) propyl]-3-(2-oxo-1-pyrrolidinyl)benzamide;

2-fluoro-N-[(1S,2R)-2-hydroxy-3-({[3-(methyloxy)phenyl]methyl}amino)-1-(phenylmethyl)propyl]-3-(2-oxo-1-pyrrolidinyl)-5-propylbenzamide;

2-fluoro-N-[(1S,2R)-2-hydroxy-1-(phenylmethyl)-3-({[3-(trifluoromethyl)phenyl]methyl}amino)propyl]-3-(2-oxo-1-pyrrolidinyl)-5-propylbenzamide;

N-[(1S,2R)-2-hydroxy-3-({[3-(methyloxy)phenyl]methyl}amino)-1-(phenylmethyl)propyl]-3-(2-oxo-5-phenyl-1-piperidinyl)-5-propylbenzamide;

N-[(1S,2R)-2-hydroxy-3-[(1-methylethyl)amino]-1-(phenylmethyl)propyl]-3-(2-oxo-5-phenyl-1-piperidinyl)-5-propylbenzamide;

N-[(1S,2R)-3-(cyclohexylamino)-2-hydroxy-1-(phenylmethyl)propyl]-3-(2-oxo-5-phenyl-1-piperidinyl)-5-propylbenzamide;

5-(ethylamino)-2-fluoro-N-[(1S,2R)-2-hydroxy-3-({1-methyl-1-[3-(trifluoromethyl)phenyl]ethyl}amino)-1-(phenylmethyl) propyl]-3-(2-oxo-1-pyrrolidinyl)benzamide;

5-(ethylamino)-2-fluoro-N-{(1S,2R)-2-hydroxy-1-(phenylmethyl)-3-[(1,1,5-trimethylhexyl)amino]propyl}-3-(2-oxo-1-pyrrolidinyl)benzamide;

N-[(1S,2R)-3-(cyclohexylamino)-2-hydroxy-1-(phenylmethyl)propyl]-5-(ethylamino)-2-fluoro-3-(2-oxo-1-pyrrolidinyl)benzamide;

5-(ethylamino)-2-fluoro-N-[(1S,2R)-2-hydroxy-3-[(1-methylethyl)amino]-1-(phenylmethyl)propyl]-3-(2-oxo-1-pyrrolidinyl)benzamide;

5-(ethylamino)-2-fluoro-N-[(1S,2R)-2-hydroxy-3-({1-methyl-1-[3-(methyloxy)phenyl]ethyl}amino)-1-(phenylmethyl)propyl]-3-(2-oxo-1-pyrrolidinyl)benzamide;

3-(1,1-dioxidotetrahydro-2H-1,2-thiazin-2-yl)-5-(ethylamino)-2-fluoro-N-{(1S,2R)-2-hydroxy-1-(phenylmethyl)-3-[(1,1,5-trimethylhexyl)amino]propyl}benzamide;

N-[(1S,2R)-3-(cyclohexylamino)-2-hydroxy-1-(phenylmethyl)propyl]-3-(1,1-dioxidotetrahydro-2H-1,2-thiazin-2-yl)-5-(ethylamino)-2-fluorobenzamide;

3-(1,1-dioxidotetrahydro-2H-1,2-thiazin-2-yl)-5-(ethylamino)-2-fluoro-N-[(1S,2R)-2-hydroxy-3-[(1-methylethyl)amino]-1-(phenylmethyl)propyl]benzamide;

4-(1,1-dioxido-2-isothiazolidinyl)-1-ethyl-N-[(1S,2R)-2-hydroxy-3-({[3-(methyloxy)phenyl]methyl}amino)-1-(phenylmethyl)propyl]-1H-indazole-6-carboxamide;

4-(1,1-dioxido-2-isothiazolidinyl)-1-ethyl-N-[(1S,2R)-2-hydroxy-1-(phenylmethyl)-3-({[3-(trifluoromethyl)phenyl]methyl}amino)propyl]-1H-indazole-6-carboxamide;

4-(1,1-dioxido-2-isothiazolidinyl)-1-ethyl-N-[(1S,2R)-2-hydroxy-3-({1-methyl-1-[3-(methyloxy)phenyl]ethyl}amino)-1-(phenylmethyl)propyl]-1H-indazole-6-carboxamide;

4-(1,1-dioxido-2-isothiazolidinyl)-1-ethyl-N-[(1S,2R)-2-hydroxy-3-({1-methyl-1-[3-(trifluoromethyl)phenyl]ethyl}amino)-1-(phenylmethyl)propyl]-1H-indazole-6-carboxamide;

4-(1,1-dioxido-2-isothiazolidinyl)-1-ethyl-N-{(1S,2R)-2-hydroxy-1-(phenylmethyl)-3-[(1,1,5-trimethylhexyl)amino]propyl}-1H-indazole-6-carboxamide;

N-[(1S,2R)-3-(cyclohexylamino)-2-hydroxy-1-(phenylmethyl)propyl]-4-(1,1-dioxido-2-isothiazolidinyl)-1-ethyl-1H-indazole-6-carboxamide;

4-(1,1-dioxido-2-isothiazolidinyl)-1-ethyl-N-[(1S,2R)-2-hydroxy-3-[(1-methylethyl)amino]-1-(phenylmethyl)propyl]-1H-indazole-6-carboxamide;

3-ethyl-N-[(1S,2R)-2-hydroxy-3-({[3-(methyloxy)phenyl]methyl}amino)-1-(phenylmethyl)propyl]-1-methyl-7-(2-oxo-1-pyrrolidinyl)-1H-indole-5-carboxamide;

3-ethyl-N-[(1S,2R)-2-hydroxy-3-({1-methyl-1-[3-(methyloxy) phenyl]ethyl}amino)-1-(phenylmethyl)propyl]-1-methyl-7-(2-oxo-1-pyrrolidinyl)-1H-indole-5-carboxamide;

3-ethyl-N-[(1S,2R)-2-hydroxy-3-({1-methyl-1-[3-(trifluoromethyl)phenyl]ethyl}amino)-1-(phenylmethyl)propyl]-1-methyl-7-(2-oxo-1-pyrrolidinyl)-1H-indole-5-carboxamide;

N-[(1S,2R)-3-(cyclohexylamino)-2-hydroxy-1-(phenylmethyl)propyl]-3-ethyl-1-methyl-7-(2-oxo-1-pyrrolidinyl)-1H-indole-5-carboxamide;

3-ethyl-N-{(1S,2R)-2-hydroxy-1-(phenylmethyl)-3-[(1,1,5-trimethylhexyl)amino]propyl}-1-methyl-7-(2-oxo-1-pyrrolidinyl)-1H-indole-5-carboxamide;

3-ethyl-N-{((S,2R)-2-hydroxy-1-(phenylmethyl)-3-[(1,1,5-trimethylhexyl)amino]propyl}-1-methyl-7-(2-oxo-1-pyrrolidinyl)-1H-indole-5-carboxamide;

3-(1,1-dioxidotetrahydro-2H-1,2-thiazin-2-yl)-5-(ethylamino)-N-{(1S,2R)-2-hydroxy-1-(phenylmethyl)-3-[(1,1,5-trimethylhexyl)amino]propyl}benzamide;

N-[(1S,2R)-3-(cyclohexylamino)-2-hydroxy-1-(phenylmethyl)propyl]-3-(1,1-dioxido-2-isothiazolidinyl)-5-(ethylamino)-2-fluorobenzamide;

7-(1,1-dioxido-2-isothiazolidinyl)-3-ethyl-N-[(1S,2R)-2-hydroxy-3-({[3-(methyloxy)phenyl]methyl}amino)-1-(phenylmethyl)propyl]-1-methyl-1H-indole-5-carboxamide;

7-(1,1-dioxido-2-isothiazolidinyl)-3-ethyl-N-[(1S,2R)-2-hydroxy-1-(phenylmethyl)-3-({[3-(trifluoromethyl)phenyl]methyl}amino)propyl]-1-methyl-1H-indole-5-carboxamide;

7-(1,1-dioxido-2-isothiazolidinyl)-3-ethyl-N-[(1S,2R)-2-hydroxy-3-({1-methyl-1-[3-(methyloxy)phenyl]ethyl}amino)-1-(phenylmethyl)propyl]-1-methyl-1H-indole-5-carboxamide;

7-(1,1-dioxido-2-isothiazolidinyl)-3-ethyl-N-[(1S,2R)-2-hydroxy-3-({1-methyl-1-[3-(trifluoromethyl)phenyl]ethyl}amino)-1-(phenylmethyl)propyl]-1-methyl-1H-indole-5-carboxamide;

7-(1,1-dioxido-2-isothiazolidinyl)-3-ethyl-N-{(1S,2R)-2-hydroxy-1-(phenylmethyl)-3-[(1,1,5-trimethylhexyl)amino]propyl}-1-methyl-1H-indole-5-carboxamide;

N-[(1S,2R)-3-(cyclohexylamino)-2-hydroxy-1-(phenylmethyl)propyl]-7-(1,1-dioxido-2-isothiazolidinyl)-3-ethyl-1-methyl-1H-indole-5-carboxamide;

3-(ethylamino)-N-[(1S,2R)-2-hydroxy-1-(phenylmethyl)-3-({[3-(trifluoromethyl)phenyl]methyl}amino)propyl]-4-methyl-5-(2-oxo-1-pyrrolidinyl)benzamide;

3-(1,1-dioxido-2-isothiazolidinyl)-5-(ethylamino)-N-[(1S,2R)-2-hydroxy-1-(phenylmethyl)-3-({[3-(trifluoromethyl)phenyl]methyl}amino)propyl]-4-methylbenzamide;

3-(1,1-dioxidotetrahydro-2H-1,2-thiazin-2-yl)-5-(ethylamino)-N-[(1S,2R)-2-hydroxy-1-(phenylmethyl)-3-({([3-(trifluoromethyl)phenyl]methyl}amino)propyl]-4-methylbenzamide;

3-(1,1-dioxidotetrahydro-2H-1,2-thiazin-2-yl)-5-(ethylamino)-N-[(1S,2R)-2-hydroxy-1-(phenylmethyl)-3-({[3-(trifluoromethyl)phenyl]methyl}amino)propyl]-4-(methyloxy)benzamide;

3-(ethylamino)-N-[(1S,2R)-2-hydroxy-1-(phenylmethyl)-3-({[3-(trifluoromethyl)phenyl]methyl}amino)propyl]-4-(methyloxy)-5-(2-oxo-1-pyrrolidinyl)benzamide;

3-(1,1-dioxido-2-isothiazolidinyl)-5-(ethylamino)-N-[(1S,2R)-2-hydroxy-1-(phenylmethyl)-3-({[3-(trifluoromethyl)phenyl]methyl}amino)propyl]-4-(methyloxy)benzamide;

3-(diethylamino)-5-(1,1-dioxidotetrahydro-2H-1,2-thiazin-2-yl)-N-[(1S,2R)-2-hydroxy-1-(phenylmethyl)-3-({[3-(trifluoromethyl)phenyl]methyl}amino)propyl]-4-methylbenzamide;

3-(1,1-dioxidotetrahydro-2H-1,2-thiazin-2-yl)-N-[(1S,2R)-2-hydroxy-1-(phenylmethyl)-3-({[3-(trifluoromethyl)phenyl]methyl}amino)propyl]-4-(methyloxy)-5-[(1E)-1-propen-1-yl]benzamide;

3-(1,1-dioxidotetrahydro-2H-1,2-thiazin-2-yl)-N-[(1S,2R)-2-hydroxy-1-(phenylmethyl)-3-({[3-(trifluoromethyl)phenyl]methyl}amino)propyl]-4-(methyloxy)-5-propylbenzamide;

N-[(1S,2R)-2-hydroxy-1-(phenylmethyl)-3-({[3-(trifluoromethyl)phenyl]methyl}amino)propyl]-4-(2-oxo-1-pyrrolidinyl)-1H-indole-6-carboxamide;

1-ethyl-N-[(1S,2R)-2-hydroxy-1-(phenylmethyl)-3-({[3-(trifluoromethyl)phenyl]methyl}amino)propyl]-4-(2-oxo-1-pyrrolidinyl)-1H-indole-6-carboxamide;

1-ethyl-N-[(1S,2R)-2-hydroxy-3-({[3-(methyloxy)phenyl]methyl}amino)-1-(phenylmethyl)propyl]-4-(2-oxo-1-pyrrolidinyl)-1H-indole-6-carboxamide;

4-(1,1-dioxidotetrahydro-2H-1,2-thiazin-2-yl)-N-[(1S,2R)-2-hydroxy-3-({[3-(methyloxy)phenyl]methyl}amino)-1-(phenylmethyl)propyl]-1H-indole-6-carboxamide;

4-(1,1-dioxidotetrahydro-2H-1,2-thiazin-2-yl)-1-ethyl-N-[(1S,2R)-2-hydroxy-3-({[3-(methyloxy)phenyl]methyl}amino)-1-(phenylmethyl)propyl]-1H-indole-6-carboxamide;

N-[(1S,2R)-2-hydroxy-3-({[3-(methyloxy)phenyl]methyl}amino)-1-(phenylmethyl)propyl]-3-(1-methylethyl)-5-(2-oxo-1-pyrrolidinyl)benzamide;

N-[(1S,2R)-2-hydroxy-3-({[3-(methyloxy)phenyl]methyl}amino)-1-(phenylmethyl)propyl]-1-methyl-4-(2-oxo-1-pyrrolidinyl)-1H-indole-6-carboxamide;

3-(1,1-dioxido-2-isothiazolidinyl)-N-[(1S,2R)-2-hydroxy-3-({[3-(methyloxy)phenyl]methyl}amino)-1-(phenylmethyl) propyl]-5-(2-oxo-1-pyrrolidinyl)benzamide;

1-butyl-N-[(1S,2R)-2-hydroxy-3-({[3-(methyloxy)phenyl]methyl}amino)-1-(phenylmethyl)propyl]-4-(2-oxo-1-pyrrolidinyl)-1H-indole-6-carboxamide;

N-[(1S,2R)-2-hydroxy-3-({[3-(methyloxy)phenyl]methyl}amino)-1-(phenylmethyl)propyl]-4-(2-oxo-1-pyrrolidinyl)-1-pentyl-1H-indole-6-carboxamide;

3-(1,1-dioxido-2-isothiazolidinyl)-5-(ethylamino)-2-fluoro-N-[(1S,2R)-2-hydroxy-3-({[3-(methyloxy)phenyl]methyl}amino)-1-(phenylmethyl)propyl]benzamide;

3-(1,1-dioxido-2-isothiazolidinyl)-5-(ethylamino)-2-fluoro-N-[(1S,2R)-2-hydroxy-1-(phenylmethyl)-3-({[3-(trifluoromethyl) phenyl]methyl}amino)propyl] benzamide;

3-(1,1-dioxido-2-isothiazolidinyl)-5-(ethylamino)-2-fluoro-N-[(1S,2R)-2-hydroxy-3-({1-methyl-1-[3-(methyloxy)phenyl]ethyl}amino)-1-(phenylmethyl)propyl]benzamide;

3-(1,1-dioxido-2-isothiazolidinyl)-5-(ethylamino)-2-fluoro-N-[(1S,2R)-2-hydroxy-3-({1-methyl-1-[3-(trifluoromethyl)phenyl]ethyl}amino)-1-(phenylmethyl)propyl]benzamide;

3-(1,1-dioxidotetrahydro-2H-1,2-thiazin-2-yl)-5-(ethylamino)-2-fluoro-N-[(1S,2R)-2-hydroxy-3-({1-methyl-1-[3-(methyloxy)phenyl]ethyl}amino)-1-(phenylmethyl)propyl]benzamide;

3-(1,1-dioxidotetrahydro-2H-1,2-thiazin-2-yl)-5-(ethylamino)-2-fluoro-N-[(1S,2R)-2-hydroxy-3-({1-methyl-1-[3-(trifluoromethyl)phenyl]ethyl}amino)-1-(phenylmethyl)propyl]benzamide;

4-(1,1-dioxido-2-isothiazolidinyl)-1-ethyl-N-[(1S,2R)-2-hydroxy-3-({[3-(methyloxy)phenyl]methyl}amino)-1-(phenylmethyl)propyl]-1H-indole-6-carboxamide;

4-(1,1-dioxido-2-isothiazolidinyl)-1-ethyl-N-[(1S,2R)-2-hydroxy-1-(phenylmethyl)-3-({[3-(trifluoromethyl)phenyl]methyl}amino)propyl]-1H-indole-6-carboxamide;

4-(1,1-dioxido-2-isothiazolidinyl)-1-ethyl-N-[(1S,2R)-2-hydroxy-3-({1-methyl-1-[3-(methyloxy)phenyl]ethyl}amino)-1-(phenylmethyl)propyl]-1H-indole-6-carboxamide;

4-(1,1-dioxido-2-isothiazolidinyl)-1-ethyl-N-[(1S,2R)-2-hydroxy-3-({1-methyl-1-[3-(trifluoromethyl)phenyl]ethyl}amino)-1-(phenylmethyl)propyl]-1H-indole-6-carboxamide;

N-[(1S,2R)-2-hydroxy-3-({[3-(methyloxy)phenyl]methyl}amino)-1-(phenylmethyl)propyl]-2-(methyloxy)benzamide;

3-(1,1-dioxidotetrahydro-2H-1,2-thiazin-2-yl)-5-(ethylamino)-N-[(1S,2R)-2-hydroxy-1-(phenylmethyl)-3-({[3-(trifluoromethyl)phenyl]methyl}amino)propyl]-2-(methyloxy)benzamide;

5-(1,1-dioxidotetrahydro-2H-1,2-thiazin-2-yl)-N'-[(1S,2R)-2-hydroxy-3-({1-methyl-1-[3-(methyloxy)phenyl]ethyl}amino)-1-(phenylmethyl)propyl]-N,N-dipropyl-1,3-benzenedicarboxamide;

5-(1,1-dioxidotetrahydro-2H-1,2-thiazin-2-yl)-N'-[(1S,2R)-2-hydroxy-3-({1-methyl-1-[3-(trifluoromethyl)phenyl]ethyl}amino)-1-(phenylmethyl)propyl]-N,N-dipropyl-1,3-benzenedicarboxamide;

1-ethyl-N-[(1S,2R)-2-hydroxy-3-({[3-(methyloxy)phenyl]methyl}amino)-1-(phenylmethyl)propyl]-4-(2-oxo-1-pyrrolidinyl)-1H-indazole-6-carboxamide;

1-ethyl-N-[(1S,2R)-2-hydroxy-1-(phenylmethyl)-3-({[3-(trifluoromethyl)phenyl]methyl}amino)propyl]-4-(2-oxo-1-pyrrolidinyl)-1H-indazole-6-carboxamide;

1-ethyl-N-[(1S,2R)-2-hydroxy-3-({1-methyl-1-[3-(methyloxy)phenyl]ethyl}amino)-1-(phenylmethyl)propyl]-4-(2-oxo-1-pyrrolidinyl)-1H-indazole-6-carboxamide;

1-ethyl-N-[(1S,2R)-2-hydroxy-3-({1-methyl-1-[3-(trifluoromethyl)phenyl]ethyl}amino)-1-(phenylmethyl)propyl]-4-(2-oxo-1-pyrrolidinyl)-1H-indazole-6-carboxamide;

4-(1,1-dioxidotetrahydro-2H-1,2-thiazin-2-yl)-1-ethyl-N-[(1S,2R)-2-hydroxy-3-({[3-(methyloxy)phenyl]methyl}amino)-1-(phenylmethyl)propyl]-2,3-dihydro-1H-indole-6-carboxamide;

4-(1,1-dioxidotetrahydro-2H-1,2-thiazin-2-yl)-1-ethyl-N-{(1S,2R)-2-hydroxy-1-(phenylmethyl)-3-[(1,1,5-trimethylhexyl)amino]propyl}-1H-indole-6-carboxamide;

4-(1,1-dioxido-2-isothiazolidinyl)-1-ethyl-N-{(1S,2R)-2-hydroxy-1-(phenylmethyl)-3-[(1,1,5-trimethylhexyl)amino]propyl}-1H-indole-6-carboxamide;

1-ethyl-N-{(1S,2R)-2-hydroxy-1-(phenylmethyl)-3-[(1,1,5-trimethylhexyl)amino]propyl}-4-(2-oxo-1-pyrrolidinyl)-1H-indole-6-carboxamide;

N-[(1S,2R)-3-(cyclohexylamino)-2-hydroxy-1-(phenylmethyl)propyl]-4-(1,1-dioxidotetrahydro-2H-1,2-thiazin-2-yl)-1-ethyl-1H-indole-6-carboxamide;

N-[(1S,2R)-3-(cyclohexylamino)-2-hydroxy-1-(phenylmethyl)propyl]-4-(1,1-dioxido-2-isothiazolidinyl)-1-ethyl-1H-indole-6-carboxamide;

N-[(1S,2R)-3-(cyclohexylamino)-2-hydroxy-1-(phenylmethyl)propyl]-1-ethyl-4-(2-oxo-1-pyrrolidinyl)-1H-indole-6-carboxamide;

4-(1,1-dioxidotetrahydro-2H-1,2-thiazin-2-yl)-1-ethyl-N-[(1S,2R)-2-hydroxy-1-(phenylmethyl)-3-({[3-(trifluoromethyl)phenyl]methyl}amino)propyl]-1H-indole-6-carboxamide;

4-(1,1-dioxidotetrahydro-2H-1,2-thiazin-2-yl)-1-ethyl-N-[(1S,2R)-2-hydroxy-3-({1-methyl-1-[3-(methyloxy)phenyl]ethyl}amino)-1-(phenylmethyl)propyl]-1H-indole-6-carboxamide;

4-(1,1-dioxidotetrahydro-2H-1,2-thiazin-2-yl)-1-ethyl-N-[(1S,2R)-2-hydroxy-3-({1-methyl-1-[3-(trifluoromethyl)phenyl]ethyl}amino)-1-(phenylmethyl)propyl]-1H-indole-6-carboxamide;

7-[acetyl(ethyl)amino]-N-[(1S,2R)-2-hydroxy-1-(phenylmethyl)-3-({[3-(trifluoromethyl)phenyl]methyl}amino) propyl]-3-methyl-1-benzofuran-5-carboxamide;

N-[(1S,2R)-2-hydroxy-1-(phenylmethyl)-3-({[3-(trifluoromethyl)phenyl]methyl}amino)propyl]-3-methyl-7-(2-oxo-1-pyrrolidinyl)-1H-indole-5-carboxamide;

N-[(1S,2R)-2-hydroxy-1-(phenylmethyl)-3-({[3-(trifluoromethyl)phenyl]methyl}amino)propyl]-3-(1-methylethyl)-7-(2-oxo-1-pyrrolidinyl)-1H-indole-5-carboxamide;

N-[(1S,2R)-2-hydroxy-1-(phenylmethyl)-3-({[3-(trifluoromethyl)phenyl]methyl}amino)propyl]-1-methyl-3-(1-methylethyl)-7-(2-oxo-1-pyrrolidinyl)-1H-indole-5-carboxamide;

3-ethyl-N-[(1S,2R)-2-hydroxy-1-(phenylmethyl)-3-({[3-(trifluoromethyl)phenyl]methyl}amino)propyl]-7-(2-oxo-1-pyrrolidinyl)-1-benzofuran-5-carboxamide;

N-[(1S,2R)-2-hydroxy-1-(phenylmethyl)-3-({[3-(trifluoromethyl)phenyl]methyl}amino)propyl]-4-methyl-8-(2-oxo-1-pyrrolidinyl)-3,4-dihydro-2H-chromene-6-carboxamide;

3-ethyl-N-[(1S,2R)-2-hydroxy-1-(phenylmethyl)-3-({[3-(trifluoromethyl)phenyl]methyl}amino)propyl]-7-(2-oxo-1-pyrrolidinyl)-1H-indole-5-carboxamide;

3-ethyl-N-[(1S,2R)-2-hydroxy-1-(phenylmethyl)-3-({[3-(trifluoromethyl)phenyl]methyl}amino)propyl]-1-methyl-7-(2-oxo-1-pyrrolidinyl)-1H-indole-5-carboxamide;

7-(1,1-dioxido-2-isothiazolidinyl)-3-ethyl-N-[(1S,2R)-2-hydroxy-1-(phenylmethyl)-3-({[3-(trifluoromethyl)phenyl]methyl}amino)propyl]-1H-indole-5-carboxamide;

N-[(1S,2R)-2-hydroxy-3-({[3-(methyloxy)phenyl]methyl}amino)-1-(phenylmethyl)propyl]-3-(1-methylethyl)-7-(2-oxo-1-pyrrolidinyl)-1H-indole-5-carboxamide;

3-ethyl-N-[(1S,2R)-2-hydroxy-3-({[3-(methyloxy)phenyl]methyl}amino)-1-(phenylmethyl)propyl]-7-(2-oxo-1-pyrrolidinyl)-1H-indole-5-carboxamide;

1-ethyl-N-[(1S,2R)-2-hydroxy-3-({[3-(methyloxy)phenyl]methyl}amino)-1-(phenylmethyl)propyl]4-(2-oxo-1-pyrrolidinyl)-1H-benzimidazole-6-carboxamide;

7-(1,1-dioxidotetrahydro-2H-1,2-thiazin-2-yl)-3-ethyl-N-[(1S,2R)-2-hydroxy-3-({[3-(methyloxy)phenyl]methyl}amino)-1-(phenylmethyl)propyl]-1H-indole-5-carboxamide;

3-ethyl-N-[(1S,2R)-2-hydroxy-3-({[3-(methyloxy)phenyl]methyl}amino)-1-(phenylmethyl)propyl]-7-(2-oxo-1-piperidinyl)-1H-indole-5-carboxamide;

3-(1,1-dioxido-4-phenyltetrahydro-2H-1,2-thiazin-2-yl)-N-[(1S,2R)-2-hydroxy-3-({[3-(methyloxy)phenyl]methyl}amino)-1-(phenylmethyl)propyl]-5-nitrobenzamide;

3-(1,1-dioxido-4-phenyltetrahydro-2H-1,2-thiazin-2-yl)-5-(ethylamino)-N-[(1S,2R)-2-hydroxy-3-({[3-(methyloxy)phenyl]methyl}amino)-1-(phenylmethyl)propyl]benzamide;

3-amino-5-(1,1-dioxido-4-phenyltetrahydro-2H-1,2-thiazin-2-yl)-N-[(1S,2R)-2-hydroxy-3-({[3-(methyloxy)phenyl]methyl}amino)-1-(phenylmethyl)propyl]benzamide;

3-ethyl-N-[(1S,2R)-2-hydroxy-3-({[3-(methyloxy)phenyl]methyl}amino)-1-(phenylmethyl)propyl]-7-(2-oxo-4-phenyl-1-pyrrolidinyl)-1H-indole-5-carboxamide;

N-[(1S,2R)-3-(cyclohexylamino)-2-hydroxy-1-(phenylmethyl)propyl]-3-(1,1-dioxido-4-phenyltetrahydro-2H-1,2-thiazin-2-yl)-5-(ethylamino)benzamide;

3-(1,1-dioxido-4-phenyltetrahydro-2H-1,2-thiazin-2-yl)-5-(ethylamino)-N-[(1S,2R)-2-hydroxy-3-[(1-methylethyl)amino]-1-(phenylmethyl)propyl]benzamide;

1-ethyl-N-[(1S,2R)-2-hydroxy-1-(phenylmethyl)-3-({[3-(trifluoromethyl)phenyl]methyl}amino)propyl]-4-(2-oxo-1-pyrrolidinyl)-1H-1,2,3-benzotriazole-6-carboxamide;

4-(1,1-dioxidotetrahydro-2H-1,2-thiazin-2-yl)-1-ethyl-N-[(1S,2R)-2-hydroxy-3-({[3-(methyloxy)phenyl]methyl}amino)-1-(phenylmethyl)propyl]-1H-benzimidazole-6-carboxamide;

1-ethyl-N-[(1S,2R)-2-hydroxy-1-(phenylmethyl)-3-({[3-(trifluoromethyl)phenyl]methyl}amino)propyl]-4-(2-oxo-1-pyrrolidinyl)-1H-benzimidazole-6-carboxamide;

1-ethyl-N-[(1S,2R)-2-hydroxy-3-({1-methyl-1-[3-(trifluoromethyl)phenyl]ethyl}amino)-1-(phenylmethyl)propyl]4-(2-oxo-1-pyrrolidinyl)-1H-benzimidazole-6-carboxamide;

N-[(1S,2R)-3-(cyclohexylamino)-2-hydroxy-1-(phenylmethyl)propyl]-1-ethyl-4-(2-oxo-1-pyrrolidinyl)-1H-benzimidazole-6-carboxamide;

1-ethyl-N-{(1S,2R)-2-hydroxy-1-(phenylmethyl)-3-[(1,1,5-trimethylhexyl)amino]propyl}-4-(2-oxo-1-pyrrolidinyl)-1H-benzimidazole-6-carboxamide;

1-ethyl-N-[(1S,2R)-2-hydroxy-3-({1-methyl-1-[3-(methyloxy)phenyl]ethyl}amino)-1-(phenylmethyl)propyl]-4-(2-oxo-1-pyrrolidinyl)-1H-benzimidazole-6-carboxamide;

3-(1,1-dioxidotetrahydro-1,2-thiazepin-2 (3H)-yl)-N-[(1S,2R)-2-hydroxy-3-({[3-(methyloxy)phenyl]methyl}amino)-1-(phenylmethyl)propyl]-5-propylbenzamide;

3-(1,1-dioxidotetrahydro-1,2-thiazepin-2 (3H)-yl)-N-[(1S,2R)-2-hydroxy-1-(phenylmethyl)-3-({[3-(trifluoromethyl)phenyl]methyl}amino)propyl]-5-propylbenzamide;

N-[(1S,2R)-3-{([2-(3-chlorophenyl)-1-methylethyl]amino}-2-hydroxy-1-(phenylmethyl)propyl]-3-(1,1-dioxidotetrahydro-2H-1,2-thiazin-2-yl)-5-(ethylamino)benzamide;

N-[(1S,2R)-3-{[2-(3-chlorophenyl)-1-methylethyl]amino}-2-hydroxy-1-(phenylmethyl)propyl]-3-cyclopentyl-5-(1,1-dioxido tetrahydro-2H-1,2-thiazin-2-yl)benzamide;

3-(1,1-dioxidotetrahydro-2H-1,2-thiazin-2-yl)-5-(ethylamino)-N-[(1S,2R)-3-{[(5-ethyl-3-thienyl)methyl]amino}-2-hydroxy-1-(phenylmethyl)propyl]benzamide;

3-(1,1-dioxidotetrahydro-2H-1,2-thiazin-2-yl)-5-(ethylamino)-N-[(1S,2R)-3-{[(4-ethyl-2-thienyl)methyl]amino}-2-hydroxy-1-(phenylmethyl)propyl]benzamide;

3-(1,1-dioxidotetrahydro-2H-1,2-thiazin-2-yl)-5-(ethylamino)-N-[(1S,2R)-3-{[(1-ethyl-1H-pyrazol-3-yl)methyl]amino}-2-hydroxy-1-(phenylmethyl)propyl]benzamide;

3-(1,1-dioxidotetrahydro-2H-1,2-thiazin-2-yl)-5-(ethylamino)-N-((1S,2R)-2-hydroxy-1-(phenylmethyl)-3-{[(1-propyl-1H-pyrazol-4-yl)methyl]amino}propyl)benzamide;

N-[(1S,2R)-3-(bicyclo[2.2.2]oct-1-ylamino)-2-hydroxy-1-(phenylmethyl)propyl]-3-(1,1-dioxidotetrahydro-2H-1,2-thiazin-2-yl)-5-(ethylamino)benzamide;

3-(1,1-dioxidotetrahydro-2H-1,2-thiazin-2-yl)-N-[(1S,2R)-3-{[(5-ethenyl-3-thienyl)methyl]amino}-2-hydroxy-1-(phenylmethyl)propyl]-5-(ethylamino)benzamide;

3-(1,1-dioxidotetrahydro-2H-1,2-thiazin-2-yl)-N-[(1S,2R)-3-{[(4-ethenyl-2-furanyl)methyl]amino}-2-hydroxy-1-(phenylmethyl)propyl]-5-(ethylamino)benzamide;

3-(1,1-dioxidotetrahydro-2H-1,2-thiazin-2-yl)-5-(ethylamino)-N-[(1S,2R)-2-hydroxy-1-(phenylmethyl)-3-({[1-(2-propen-1-yl)-1H-pyrazol-4-yl]methyl}amino)propyl]benzamide;

3-(1,1-dioxidotetrahydro-2H-1,2-thiazin-2-yl)-N-[(1S,2R)-3-{[(4-ethenyl-2-thienyl)methyl]amino}-2-hydroxy-1-(phenylmethyl)propyl]-5-(ethylamino)benzamide;

3-(1,1-dioxidotetrahydro-2H-1,2-thiazin-2-yl)-5-(ethylamino)-N-[(1S,2R)-3-({[1-(2-fluoroethyl)-1H-pyrazol-4-yl]methyl}amino)-2-hydroxy-1-(phenylmethyl)propyl]benzamide;

3-cyclopentyl-N-[(1S,2R)-3-{[(1-ethyl-1H-pyrazol-4-yl)methyl]amino}-2-hydroxy-1-(phenylmethyl)propyl]-5-(2-oxo-1-pyrrolidinyl)benzamide;

3-(ethyloxy)-N-[(1S,2R)-3-{[(1-ethyl-1H-pyrazol-4-yl)methyl]amino}-2-hydroxy-1-(phenylmethyl)propyl]-5-(2-oxo-1-pyrrolidinyl)benzamide;

3-(1,1-dioxidotetrahydro-2H-1,2-thiazin-2-yl)-5-(ethylamino)-N-[(1S,2R)-3-{[(1-ethyl-1H-pyrazol-4-yl)methyl]amino}-2-hydroxy-1-(phenylmethyl)propyl]benzamide;

3-(1,1-dioxidotetrahydro-2H-1,2-thiazin-2-yl)-N-[(1S,2R)-3-{[(1-ethyl-1H-pyrazol-4-yl)methyl]amino}-2-hydroxy-1-(phenylmethyl)propyl]-5-propylbenzamide;

N-[(1S,2R)-3-[(4,4-difluorocyclohexyl)amino]-2-hydroxy-1-(phenylmethyl) propyl]-3-(1,1-dioxidotetrahydro-2H-1,2-thiazin-2-yl)-5-(ethylamino)-2-fluorobenzamide;

4-ethyl-N-[(1S,2R)-2-hydroxy-3-({[3-(methyloxy)phenyl]methyl}amino)-1-(phenylmethyl)propyl]-8-(2-oxo-1-pyrrolidinyl)-1,2,3,4-tetrahydro-6-quinoxalinecarboxamide;

4-(1,1-dioxido-2-isothiazolidinyl)-1-ethyl-N-[(1S,2R)-2-hydroxy-3-({[3-(methyloxy)phenyl]methyl}amino)-1-(phenylmethyl)propyl]-1H-benzimidazole-6-carboxamide;

4-(1,1-dioxido-2-isothiazolidinyl)-1-ethyl-N-[(1S,2R)-2-hydroxy-1-(phenylmethyl)-3-({[3-(trifluoromethyl)phenyl]methyl}amino)propyl]-1H-benzimidazole-6-carboxamide;

4-(1,1-dioxido-2-isothiazolidinyl)-1-ethyl-N-[(1S,2R)-2-hydroxy-3-({1-methyl-1-[3-(trifluoromethyl)phenyl]ethyl}amino)-1-(phenylmethyl)propyl]-1H-benzimidazole-6-carboxamide;

4-(1,1-dioxidotetrahydro-2H-1,2-thiazin-2-yl)-1-ethyl-N-[(1S,2R)-2-hydroxy-3-({1-methyl-1-[3-(trifluoromethyl) phenyl]ethyl}amino)-1-(phenylmethyl)propyl]-2,3-dihydro-1H-indole-6-carboxamide;

8-(1,1-dioxido-2-isothiazolidinyl)-4-ethyl-N-[(1S,2R)-2-hydroxy-1-(phenylmethyl)-3-({[3-(trifluoromethyl)phenyl]methyl}amino)propyl]-1,2,3,4-tetrahydro-6-quinoxalinecarboxamide;

3-(1,1-dioxidotetrahydro-2H-1,2-thiazin-2-yl)-5-(ethylamino)-2-fluoro-N-{(1S,2R)-2-hydroxy-1-(phenylmethyl)-3-[({3-[(trifluoromethyl)oxy]phenyl}methyl)amino]propyl}benzamide;

3-(1,1-dioxido-2-isothiazolidinyl)-N-[(1S,2R)-3-{[(1-ethyl-1H-pyrazol-4-yl)methyl]amino}-2-hydroxy-1-(phenylmethyl)propyl]-2-fluoro-5-propylbenzamide;

3-(1,1-dioxido-2-isothiazolidinyl)-2-fluoro-N-{(1S,2R)-2-hydroxy-1-(phenylmethyl)-3-[(1,1,5-trimethylhexyl)amino]propyl}-5-propylbenzamide;

3-(1,1-dioxido-2-isothiazolidinyl)-2-fluoro-N-[(1S,2R)-2-hydroxy-3-({1-methyl-1-[3-(methyloxy)phenyl]ethyl}amino)-1-(phenylmethyl)propyl]-5-propylbenzamide;

3-(1,1-dioxido-2-isothiazolidinyl)-2-fluoro-N-[(1S,2R)-2-hydroxy-1-(phenylmethyl)-3-({[3-(trifluoromethyl)phenyl]methyl}amino)propyl]-5-propylbenzamide;

N-[(1S,2R)-3-[(1r,4R)-bicyclo[2.2.1]hept-1-ylamino]-2-hydroxy-1-(phenylmethyl)propyl]-3-(1,1-dioxidotetrahydro-2H-1,2-thiazin-2-yl)-5-(ethylamino)benzamide;

3-(1,1-dioxidotetrahydro-2H-1,2-thiazin-2-yl)-N-[(1S,2R)-3-{[(1-ethyl-1H-pyrazol-4-yl)methyl]amino}-2-hydroxy-1-(phenylmethyl)propyl]-2-fluoro-5-propylbenzamide;

3-(1,1-dioxidotetrahydro-2H-1,2-thiazin-2-yl)-2-fluoro-N-[(1S,2R)-2-hydroxy-1-(phenylmethyl)-3-(tetrahydro-2H-pyran-4-ylamino)propyl]-5-propylbenzamide;

3-(1,1-dioxidotetrahydro-2H-1,2-thiazin-2-yl)-2-fluoro-N-[(1S,2R)-2-hydroxy-3-({1-methyl-1-[3-(trifluoromethyl)phenyl]ethyl}amino)-1-(phenylmethyl)propyl]-5-propylbenzamide;

3-(1,1-dioxidotetrahydro-2H-1,2-thiazin-2-yl)-2-fluoro-N-[(1S,2R)-2-hydroxy-1-(phenylmethyl)-3-({[3-(trifluoromethyl)phenyl]methyl}amino)propyl]-5-propylbenzamide;

3-(1,1-dioxidotetrahydro-2H-1,2-thiazin-2-yl)-2-fluoro-N-[(1S,2R)-2-hydroxy-3-({[3-(methyloxy)phenyl]methyl}amino)-1-(phenylmethyl)propyl]-5-propylbenzamide;

2-fluoro-N-[(1S,2R)-2-hydroxy-1-(phenylmethyl)-3-(tetrahydro-2H-pyran-4-ylamino)propyl]-3-(2-oxo-1-pyrrolidinyl)-5-propylbenzamide;

N-[(1S,2R)-3-{[(1-ethyl-1H-pyrazol-4-yl)methyl]amino}-2-hydroxy-1-(phenylmethyl)propyl]-2-fluoro-3-(2-oxo-1-pyrrolidinyl)-5-propylbenzamide;

N-[(1S,2R)-3-({[3,4-bis(methyloxy)phenyl]methyl}amino)-2-hydroxy-1-(phenylmethyl)propyl]-2-fluoro-3-(2-oxo-1-pyrrolidinyl)-5-propylbenzamide;

2-fluoro-N-[(1S,2R)-2-hydroxy-3-[(1-methylethyl)amino]-1-(phenylmethyl)propyl]-3-(2-oxo-1-pyrrolidinyl)-5-propylbenzamide;

N-[(1S,2R)-3-(cyclohexylamino)-2-hydroxy-1-(phenylmethyl)propyl]-2-fluoro-3-(2-oxo-1-pyrrolidinyl)-5-propylbenzamide;

2-fluoro-N-{(1S,2R)-2-hydroxy-1-(phenylmethyl)-3-[(1,1,5-trimethylhexyl)amino]propyl}-3-(2-oxo-1-pyrrolidinyl)-5-propylbenzamide;

2-fluoro-N-[(1S,2R)-2-hydroxy-3-({1-methyl-1-[3-(trifluoromethyl)phenyl]ethyl}amino)-1-(phenylmethyl)propyl]-3-(2-oxo-1-pyrrolidinyl)-5-propylbenzamide;

2-fluoro-N-[(1S,2R)-2-hydroxy-3-({1-methyl-1-[3-(methyloxy)phenyl]ethyl}amino)-1-(phenylmethyl)propyl]-3-(2-oxo-1-pyrrolidinyl)-5-propylbenzamide;

3-(1,1-dioxidotetrahydro-2H-1,2-thiazin-2-yl)-5-(ethylamino)-N-[(1S,2R)-3-[(1-ethylcyclobutyl)amino]-2-hydroxy-1-(phenylmethyl)propyl]benzamide;

3-(1,1-dioxidotetrahydro-2H-1,2-thiazin-2-yl)-5-(ethylamino)-N-{(1S,2R)-2-hydroxy-1-(phenylmethyl)-3-[(1-propylcyclobutyl)amino]propyl}benzamide;

3-(1,1-dioxidotetrahydro-2H-1,2-thiazin-2-yl)-5-(ethylamino)-N-[(1S,2R)-2-hydroxy-3-{[1-(1-methylethyl)cyclobutyl]amino}-1-(phenylmethyl)propyl]benzamide;

N-[(1S,2R)-3-({1-[(3-chlorophenyl)methyl]cyclobutyl}amino)-2-hydroxy-1-(phenylmethyl)propyl]-3-(1,1-dioxidotetrahydro-2H-1,2-thiazin-2-yl)-5-(ethylamino)benzamide;

3-(1,1-dioxidotetrahydro-2H-1,2-thiazin-2-yl)-5-(ethylamino)-N-[(1S,2R)-2-hydroxy-1-(phenylmethyl)-3-(tricyclo[3.3.1.1~3,7~]dec-2-ylamino)propyl]benzamide;

or a pharmaceutically acceptable salt thereof.

15. A pharmaceutical composition comprising a compound of formula (I) as defined in claim 1, or a pharmaceutically acceptable salt or solvate thereof in admixture with one or more pharmaceutically acceptable diluents or carriers.

16. A process for preparing a compound of formula (I) as defined in claim 1, which process comprises:
(a) reacting a compound of formula (II)

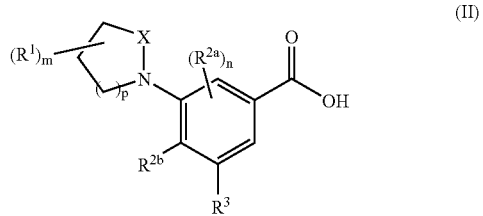

or an activated and optionally protected derivative thereof wherein $R^1$, m, X, p, $R^{2a}$, n, $R^{2b}$ and $R^3$ are as defined in claim 1, with a compound of formula (III)

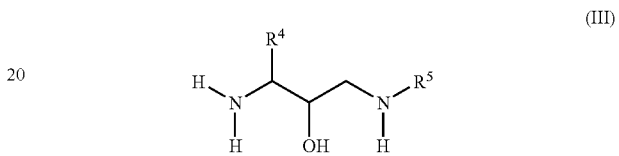

wherein $R^4$ and $R^5$ are as defined in claim 1; or
(b) preparing a compound of formula (I) which comprises reductive amination of a compound of formula (IV)

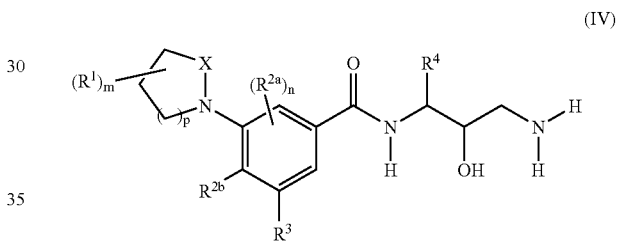

wherein $R^1$, m, X, p, $R^{2a}$, n, $R^{2b}$, $R^3$ and $R^4$ are as defined in claim 1, with an appropriate aldehyde or ketone; or
(c) deprotecting a compound of formula (I) which is protected; and optionally thereafter
(d) interconversion of compounds of formula (I) to other compounds of formula (I).

* * * * *

UNITED STATES PATENT AND TRADEMARK OFFICE
CERTIFICATE OF CORRECTION

PATENT NO.       : 7,253,198 B2
APPLICATION NO.  : 10/536303
DATED            : August 7, 2007
INVENTOR(S)      : Demont et al.

It is certified that error appears in the above-identified patent and that said Letters Patent is hereby corrected as shown below:

On the Title page:

A citation in Item (56) should be corrected as follows:

(56) References Cited
FOREIGN PATENT DOCUMENTS
"WO 9206691 A1" should read -- WO 9208691 A1 --

Claim 1 (Column 217, Line 26) should read as follows:

-- -C($R^c R^d$)-CONH-$C_{3-10}$ cycloalkyl, -$C_{1-6}$ alkyl- --

Claim 13 (Column 219, Line 5) should read as follows:

-- -C($R^c R^d$)-CONH-$C_{3-8}$ cycloalkyl, -$C_{1-6}$ alkyl- --

Claim 13 (Column 219, Line 17) should read as follows:

-- nitro, -$NR^{22}COR^{23}$, -$C_{1-6}$ alkyl-$NR^{22}R^{23}$ (wherein --

Claim 14 (Column 248, Lines 15-17) should read as follows:

-- 3-ethyl-N-{(1S,2R)-2-hydroxy-1-(phenylmethyl)-3-[(1,1,5-trimethylhexyl)amino]propyl}-1-methyl-7-(2-oxo-1-pyrrolidinyl)-1H-indole-5-carboxamide; --

Signed and Sealed this

Eleventh Day of December, 2007

JON W. DUDAS
*Director of the United States Patent and Trademark Office*